US011224600B2

(12) United States Patent
Blomgren et al.

(10) Patent No.: US 11,224,600 B2
(45) Date of Patent: Jan. 18, 2022

(54) COMPOUNDS FOR INHIBITION OF ALPHA 4 BETA 7 INTEGRIN

(71) Applicant: Gilead Sciences, Inc., Foster City, CA (US)

(72) Inventors: Peter A. Blomgren, Issaquah, WA (US); Taryn Campbell, Seattle, WA (US); Jayaraman Chandrasekhar, Redmond, WA (US); Christopher T. Clark, Seattle, WA (US); Julian A. Codelli, Seattle, WA (US); Kevin S. Currie, North Bend, WA (US); Jeffrey E. Kropf, Issaquah, WA (US); Yasamin Moazami, Seattle, WA (US); Nicole Nava, Seattle, WA (US); Leena Patel, Seattle, WA (US); Stephane Perreault, Brier, WA (US); Jason K. Perry, San Francisco, CA (US); Kassandra F. Sedillo, Princeton, NJ (US); Natalie Seeger, Seattle, WA (US); Kirk L. Stevens, Bothell, WA (US); Jennifer Anne Treiberg, Redmond, WA (US); Suet C. Yeung, Redmond, WA (US); Zhongdong Zhao, Bellevue, WA (US)

(73) Assignee: GILEAD SCIENCES, INC., Foster City, CA (US)

( * ) Notice: Subject to any disclaimer, the term of this patent is extended or adjusted under 35 U.S.C. 154(b) by 0 days.

(21) Appl. No.: 16/667,373

(22) Filed: Oct. 29, 2019

(65) Prior Publication Data

US 2020/0155563 A1 May 21, 2020

Related U.S. Application Data

(60) Provisional application No. 62/752,859, filed on Oct. 30, 2018.

(51) Int. Cl.
| | | |
|---|---|---|
| *C07D 413/14* | (2006.01) | |
| *A61K 31/5377* | (2006.01) | |
| *A61K 31/343* | (2006.01) | |
| *A61K 31/353* | (2006.01) | |
| *A61K 31/357* | (2006.01) | |
| *A61K 31/416* | (2006.01) | |
| *A61K 31/4375* | (2006.01) | |
| *A61K 31/4709* | (2006.01) | |
| *A61K 31/513* | (2006.01) | |
| *A61K 31/519* | (2006.01) | |
| *A61K 31/538* | (2006.01) | |

(Continued)

(52) U.S. Cl.
CPC ........ *A61K 31/5377* (2013.01); *A61K 31/343* (2013.01); *A61K 31/353* (2013.01); *A61K 31/357* (2013.01); *A61K 31/416* (2013.01); *A61K 31/4375* (2013.01); *A61K 31/4709* (2013.01); *A61K 31/513* (2013.01); *A61K 31/519* (2013.01); *A61K 31/538* (2013.01); *A61K 31/541* (2013.01); *A61K 45/06* (2013.01); *C07D 295/00* (2013.01); *C07D 307/87* (2013.01); *C07D 319/18* (2013.01); *C07D 405/10* (2013.01); *C07D 407/10* (2013.01); *C07D 413/14* (2013.01); *C07D 471/04* (2013.01)

(58) Field of Classification Search
CPC .......................... C07D 413/14; C07D 471/04; A61K 31/5377; A61K 31/519; A61P 29/00
USPC ............... 544/117, 279; 549/362; 514/234.2, 514/264.1, 456
See application file for complete search history.

(56) References Cited

U.S. PATENT DOCUMENTS

| | | | |
|---|---|---|---|
| 6,511,961 B1 | 1/2003 | Takahashi et al. | |
| 6,521,666 B1 | 2/2003 | Sircar et al. | |

(Continued)

FOREIGN PATENT DOCUMENTS

| | | | |
|---|---|---|---|
| CN | 105483206 A | 4/2016 | |
| CN | 106995439 A | 8/2017 | |

(Continued)

OTHER PUBLICATIONS

Notice of Allowance and Search Report dated Nov. 4, 2020 for Taiwanese Appl. No. 108139338.

(Continued)

*Primary Examiner* — Charanjit Aulakh

(57) ABSTRACT

The present disclosure provides a compound of Formula (I):

or a pharmaceutically acceptable salt thereof as described herein. The present disclosure also provides pharmaceutical compositions comprising a compound of Formula (I), processes for preparing compounds of Formula (I), and therapeutic methods for treating inflammatory disease.

21 Claims, No Drawings

(51) Int. Cl.
*A61K 31/541* (2006.01)
*A61K 45/06* (2006.01)
*C07D 295/00* (2006.01)
*C07D 307/87* (2006.01)
*C07D 319/18* (2006.01)
*C07D 405/10* (2006.01)
*C07D 407/10* (2006.01)
*C07D 471/04* (2006.01)

(56) References Cited

U.S. PATENT DOCUMENTS

| | | |
|---|---|---|
| 6,806,312 B2 | 10/2004 | Sasagawa et al. |
| 7,105,520 B2 | 9/2006 | Suzuki et al. |
| 7,335,673 B2 | 2/2008 | Hoshina et al. |
| 7,361,679 B2 | 4/2008 | Ikegami et al. |
| 7,566,724 B2 | 7/2009 | Hirano et al. |
| 8,546,610 B2 | 10/2013 | Kataoka et al. |
| 9,216,174 B2 | 12/2015 | Shen et al. |
| 9,533,985 B2 | 1/2017 | Ueno et al. |
| 9,822,110 B2 | 11/2017 | Ueno et al. |
| 2003/0114490 A1 | 6/2003 | Tanaka et al. |
| 2003/0130320 A1 | 7/2003 | Suzuki et al. |
| 2003/0149083 A1 | 8/2003 | Tanaka et al. |
| 2003/0220268 A1 | 11/2003 | Makino et al. |
| 2003/0220318 A1 | 11/2003 | Suzuki et al. |
| 2004/0039040 A1 | 2/2004 | Takahashi et al. |
| 2004/0077693 A1 | 4/2004 | Artis et al. |
| 2004/0087574 A1 | 5/2004 | Takahashi et al. |
| 2004/0110945 A1 | 6/2004 | Nakayama et al. |
| 2004/0132783 A1 | 7/2004 | Ono et al. |
| 2004/0235848 A1 | 11/2004 | Okuzumi et al. |
| 2004/0236147 A1 | 11/2004 | Chiba et al. |
| 2004/0259908 A1 | 12/2004 | Ikegami et al. |
| 2005/0101779 A1 | 5/2005 | Sagi et al. |
| 2005/0187284 A1 | 8/2005 | Artis et al. |
| 2005/0222141 A1 | 10/2005 | Sagi et al. |
| 2005/0261291 A1 | 11/2005 | Kawahara et al. |
| 2006/0009476 A1 | 1/2006 | Kataoka et al. |
| 2006/0204572 A1 | 9/2006 | Higuchi et al. |
| 2006/0204574 A1 | 9/2006 | Ogawa et al. |
| 2006/0223836 A1 | 10/2006 | Makino et al. |
| 2006/0241132 A1 | 10/2006 | Ishigaki et al. |
| 2007/0105936 A1 | 5/2007 | Ono et al. |
| 2007/0232601 A1 | 10/2007 | Yoneda et al. |
| 2007/0269835 A1 | 11/2007 | Katayama et al. |
| 2008/0075719 A1 | 3/2008 | Chan et al. |
| 2008/0108634 A1 | 5/2008 | Sagi et al. |
| 2008/0108637 A1 | 5/2008 | Fujita et al. |
| 2008/0161566 A1 | 7/2008 | Kotake et al. |
| 2008/0280909 A1 | 11/2008 | Okuzumi et al. |
| 2009/0048236 A1 | 2/2009 | Suzuki et al. |
| 2009/0163715 A1 | 6/2009 | Nagai et al. |
| 2009/0233901 A1 | 9/2009 | Machinaga et al. |
| 2009/0318688 A1 | 12/2009 | Kataoka et al. |
| 2009/0325962 A1 | 12/2009 | Jackson et al. |
| 2010/0022783 A1 | 1/2010 | Ono et al. |
| 2010/0137593 A1 | 6/2010 | Takahashi et al. |
| 2010/0204505 A1 | 8/2010 | Kataoka et al. |
| 2010/0267754 A1 | 10/2010 | Wakabayashi et al. |
| 2011/0009434 A1 | 1/2011 | Fujita et al. |
| 2011/0065918 A1 | 3/2011 | Makino et al. |
| 2011/0313154 A1 | 12/2011 | Kataoka et al. |
| 2012/0157437 A1 | 6/2012 | Machinaga et al. |
| 2012/0253041 A1 | 10/2012 | Makino et al. |
| 2013/0030013 A1 | 1/2013 | Aburatani et al. |
| 2013/0065882 A1 | 3/2013 | Machinaga et al. |
| 2013/0066072 A1 | 3/2013 | Kataoka et al. |
| 2014/0206705 A1 | 7/2014 | Kataoka et al. |
| 2015/0045435 A1 | 2/2015 | Scott et al. |
| 2015/0051395 A1 | 2/2015 | Ueno et al. |
| 2016/0367517 A1 | 12/2016 | Thompson |
| 2017/0196870 A1 | 7/2017 | Kageyama et al. |
| 2018/0244648 A1 | 8/2018 | Harrison et al. |
| 2018/0312498 A1 | 11/2018 | Biediger et al. |
| 2020/0155538 A1 | 5/2020 | Blomgren et al. |
| 2020/0163953 A1 | 5/2020 | Blomgren et al. |
| 2020/0165248 A1 | 5/2020 | Blomgren et al. |
| 2021/0053967 A1 | 2/2021 | Blomgren et al. |

FOREIGN PATENT DOCUMENTS

| | | |
|---|---|---|
| EP | 1209147 A1 | 5/2002 |
| EP | 1323711 A1 | 7/2003 |
| EP | 1889827 B1 | 8/2010 |
| EP | 3064491 A1 | 9/2016 |
| EP | 2842945 B1 | 10/2016 |
| IN | 2966/DEL/2005 | 7/2009 |
| JP | 2001089368 A | 4/2001 |
| JP | 2003048889 A | 2/2003 |
| JP | 2003277340 A | 10/2003 |
| JP | 2003321358 A | 11/2003 |
| JP | 2004277338 A | 10/2004 |
| JP | 2015083970 A | 4/2015 |
| JP | 201637467 A | 3/2016 |
| JP | 201637468 A | 3/2016 |
| JP | 2019031449 A | 2/2019 |
| WO | WO-94/012181 A1 | 6/1994 |
| WO | WO-96/000581 A1 | 1/1996 |
| WO | WO-97/003094 A1 | 1/1997 |
| WO | WO-97/005865 A1 | 2/1997 |
| WO | WO-98/004247 A1 | 2/1998 |
| WO | WO-98/042656 A1 | 10/1998 |
| WO | WO-98/053814 A1 | 12/1998 |
| WO | WO-98/053817 A1 | 12/1998 |
| WO | WO-98/053818 A1 | 12/1998 |
| WO | WO-98/058902 A1 | 12/1998 |
| WO | WO-99/006431 A1 | 2/1999 |
| WO | WO-99/006434 A1 | 2/1999 |
| WO | WO-99/006436 A1 | 2/1999 |
| WO | WO-99/006437 A1 | 2/1999 |
| WO | WO-99/010312 A1 | 3/1999 |
| WO | WO-99/010313 A1 | 3/1999 |
| WO | WO-99/013898 A1 | 3/1999 |
| WO | WO-99/025731 A1 | 5/1999 |
| WO | WO-99/026615 A1 | 6/1999 |
| WO | WO-99/026921 A1 | 6/1999 |
| WO | WO-99/030713 A1 | 6/1999 |
| WO | WO-99/036393 A1 | 7/1999 |
| WO | WO-99/052898 A1 | 10/1999 |
| WO | WO-99/061421 A1 | 12/1999 |
| WO | WO-99/062901 A1 | 12/1999 |
| WO | WO-99/064395 A1 | 12/1999 |
| WO | WO-99/067230 A1 | 12/1999 |
| WO | WO-2000/002903 A1 | 1/2000 |
| WO | WO-2000/005223 A2 | 2/2000 |
| WO | WO-2000/015612 A1 | 3/2000 |
| WO | WO-2000/035855 A1 | 6/2000 |
| WO | WO-2000/037444 A1 | 6/2000 |
| WO | WO-2000/043354 A2 | 7/2000 |
| WO | WO-2000/043369 A1 | 7/2000 |
| WO | WO-2000/043371 A2 | 7/2000 |
| WO | WO-2000/043372 A1 | 7/2000 |
| WO | WO-2000/043413 A2 | 7/2000 |
| WO | WO-2000/048994 A1 | 8/2000 |
| WO | WO-2000/051974 A1 | 9/2000 |
| WO | WO-2000/063234 A2 | 10/2000 |
| WO | WO-2000/064866 A1 | 11/2000 |
| WO | WO-2000/067746 A1 | 11/2000 |
| WO | WO-2000/071572 A1 | 11/2000 |
| WO | WO-2001/000206 A1 | 1/2001 |
| WO | WO-2001/007400 A1 | 2/2001 |
| WO | WO-2001/012183 A1 | 2/2001 |
| WO | WO-2001/012186 A1 | 2/2001 |
| WO | WO-2001/014328 A2 | 3/2001 |
| WO | WO-2001/021584 A1 | 3/2001 |
| WO | WO-2001/032610 A1 | 5/2001 |
| WO | WO-2001/042215 A1 | 6/2001 |
| WO | WO-2001/042225 A2 | 6/2001 |
| WO | WO-2001/043774 A1 | 6/2001 |
| WO | WO-2001/047868 A1 | 7/2001 |
| WO | WO-2001/047887 A1 | 7/2001 |
| WO | WO-2001/053279 A1 | 7/2001 |
| WO | WO-2001/053295 A1 | 7/2001 |

(56) References Cited

FOREIGN PATENT DOCUMENTS

| | | |
|---|---|---|
| WO | WO-2001/055121 A1 | 8/2001 |
| WO | WO-2001/056994 A1 | 8/2001 |
| WO | WO-2001/068586 A2 | 9/2001 |
| WO | WO-2001/070670 A1 | 9/2001 |
| WO | WO-2002/002556 A2 | 1/2002 |
| WO | WO-2002/008201 A2 | 1/2002 |
| WO | WO-2002/008203 A2 | 1/2002 |
| WO | WO-2002/008206 A1 | 1/2002 |
| WO | WO-2002/014262 A1 | 2/2002 |
| WO | WO-2002/016329 A1 | 2/2002 |
| WO | WO-2002/018320 A2 | 3/2002 |
| WO | WO-2002/022563 A1 | 3/2002 |
| WO | WO-2002/024697 A1 | 3/2002 |
| WO | WO-2002/028830 A1 | 4/2002 |
| WO | WO-2002/053534 A1 | 7/2002 |
| WO | WO-2002/057242 A2 | 7/2002 |
| WO | WO-2002/068393 A1 | 9/2002 |
| WO | WO-2003/008380 A1 | 1/2003 |
| WO | WO-2003/010135 A1 | 2/2003 |
| WO | WO-2003/011815 A1 | 2/2003 |
| WO | WO-2003/024933 A1 | 3/2003 |
| WO | WO-2003/048126 A1 | 6/2003 |
| WO | WO-2003/053926 A1 | 7/2003 |
| WO | WO-2003/070709 A1 | 8/2003 |
| WO | WO-2003/072536 A1 | 9/2003 |
| WO | WO-2003/080611 A1 | 10/2003 |
| WO | WO-2003/089410 A1 | 10/2003 |
| WO | WO-2003/093237 A1 | 11/2003 |
| WO | WO-2003/099231 A2 | 12/2003 |
| WO | WO-2003/099809 A1 | 12/2003 |
| WO | WO-2004/006918 A1 | 1/2004 |
| WO | WO-2004/007428 A1 | 1/2004 |
| WO | WO-2004/007494 A1 | 1/2004 |
| WO | WO-2004/014844 A2 | 2/2004 |
| WO | WO-2004/014859 A2 | 2/2004 |
| WO | WO-2004/062601 A2 | 7/2004 |
| WO | WO-2004/066931 A2 | 8/2004 |
| WO | WO-2004/066932 A2 | 8/2004 |
| WO | WO-2004/074264 A1 | 9/2004 |
| WO | WO-2004/099126 A1 | 11/2004 |
| WO | WO-2004/103967 A2 | 12/2004 |
| WO | WO-2005/000244 A2 | 1/2005 |
| WO | WO-2005/009992 A1 | 2/2005 |
| WO | WO-2005/014532 A1 | 2/2005 |
| WO | WO-2005/040135 A1 | 5/2005 |
| WO | WO-2005/042529 A1 | 5/2005 |
| WO | WO-2005/044817 A1 | 5/2005 |
| WO | WO-2005/061440 A1 | 7/2005 |
| WO | WO-2005/061466 A1 | 7/2005 |
| WO | WO-2005/063705 A1 | 7/2005 |
| WO | WO-2005/070921 A1 | 8/2005 |
| WO | WO-2005/077914 A1 | 8/2005 |
| WO | WO-2005/077915 A1 | 8/2005 |
| WO | WO-2005/087760 A1 | 9/2005 |
| WO | WO-2005/097162 A2 | 10/2005 |
| WO | WO-2005/107762 A2 | 11/2005 |
| WO | WO-2005/121135 A1 | 12/2005 |
| WO | WO-2006/010054 A2 | 1/2006 |
| WO | WO-2006/019632 A2 | 2/2006 |
| WO | WO-2006/023396 A2 | 3/2006 |
| WO | WO-2006/028393 A1 | 3/2006 |
| WO | WO-2006/052962 A2 | 5/2006 |
| WO | WO-2006/066780 A1 | 6/2006 |
| WO | WO-2006/068058 A1 | 6/2006 |
| WO | WO-2006/068213 A1 | 6/2006 |
| WO | WO-2006/081986 A1 | 8/2006 |
| WO | WO-2006/090234 A1 | 8/2006 |
| WO | WO-2006/096807 A1 | 9/2006 |
| WO | WO-2006/112738 A1 | 10/2006 |
| WO | WO-2006/113199 A1 | 10/2006 |
| WO | WO-2006/115918 A2 | 11/2006 |
| WO | WO-2006/126635 A1 | 11/2006 |
| WO | WO-2006/127584 A1 | 11/2006 |
| WO | WO-2006/131200 A1 | 12/2006 |
| WO | WO-2007/004958 A1 | 1/2007 |
| WO | WO-2007/069635 A1 | 6/2007 |
| WO | WO-2007/082809 A1 | 7/2007 |
| WO | WO-2007/100763 A2 | 9/2007 |
| WO | WO-2007/101165 A1 | 9/2007 |
| WO | WO-2008/062859 A1 | 5/2008 |
| WO | WO-2008/064830 A1 | 6/2008 |
| WO | WO-2008/125210 A1 | 10/2008 |
| WO | WO-2008/154642 A2 | 12/2008 |
| WO | WO-2009/075806 A1 | 6/2009 |
| WO | WO-2009/124755 A1 | 10/2009 |
| WO | WO-2009/140621 A2 | 11/2009 |
| WO | WO-2010/104306 A2 | 9/2010 |
| WO | WO-2010/105363 A1 | 9/2010 |
| WO | WO-2010/112865 A1 | 10/2010 |
| WO | WO-2010/126914 A1 | 11/2010 |
| WO | WO-2011/048091 A1 | 4/2011 |
| WO | WO-2011/094890 A1 | 8/2011 |
| WO | WO-2011/122619 A1 | 10/2011 |
| WO | WO-2011/143274 A1 | 11/2011 |
| WO | WO-2011/150499 A1 | 12/2011 |
| WO | WO-2011/159781 A2 | 12/2011 |
| WO | WO-2012/011123 A1 | 1/2012 |
| WO | WO-2012/068251 A2 | 5/2012 |
| WO | WO-2012/106343 A2 | 8/2012 |
| WO | WO-2013/070842 A1 | 5/2013 |
| WO | WO-2013/110680 A1 | 8/2013 |
| WO | WO-2013/110681 A1 | 8/2013 |
| WO | WO-2013/148978 A1 | 10/2013 |
| WO | WO-2013/161904 A1 | 10/2013 |
| WO | WO-2013/178816 A1 | 12/2013 |
| WO | WO-2014/051056 A1 | 4/2014 |
| WO | WO-2014/052605 A1 | 4/2014 |
| WO | WO-2015/064580 A1 | 5/2015 |
| WO | WO-2015/138882 A1 | 9/2015 |
| WO | WO-2015/172196 A1 | 11/2015 |
| WO | WO-2016/040505 A1 | 3/2016 |
| WO | WO-2016/051828 A1 | 4/2016 |
| WO | WO-2016/145258 A1 | 9/2016 |
| WO | WO-2017/006272 A1 | 1/2017 |
| WO | WO-2017/070518 A1 | 4/2017 |
| WO | WO-2017/126637 A1 | 7/2017 |
| WO | WO-2017/132620 A1 | 8/2017 |
| WO | WO-2017/135471 A1 | 8/2017 |
| WO | WO-2017/135472 A1 | 8/2017 |
| WO | WO-2018/049068 A1 | 3/2018 |
| WO | WO-2018/064119 A1 | 4/2018 |
| WO | WO-2018/085552 A1 | 5/2018 |
| WO | WO-2018/085574 A2 | 5/2018 |
| WO | WO-2018/089353 A1 | 5/2018 |
| WO | WO-2018/089355 A1 | 5/2018 |
| WO | WO-2018/089357 A1 | 5/2018 |
| WO | WO-2018/089358 A1 | 5/2018 |
| WO | WO-2018/089360 A1 | 5/2018 |
| WO | WO-2018/160522 A1 | 9/2018 |
| WO | WO-2018/200625 A1 | 11/2018 |
| WO | WO-2018/201167 A2 | 11/2018 |
| WO | WO-2019/085441 A1 | 5/2019 |
| WO | WO-2019/094319 A1 | 5/2019 |
| WO | WO-2019/173653 A1 | 9/2019 |
| WO | WO-2019/178248 A1 | 9/2019 |
| WO | WO-2019/200202 A1 | 10/2019 |
| WO | WO-2020/033724 A1 | 2/2020 |
| WO | WO-2020/043533 A1 | 3/2020 |
| WO | WO-2020/047207 A1 | 3/2020 |
| WO | WO-2020/047208 A1 | 3/2020 |
| WO | WO-2020/047239 A1 | 3/2020 |
| WO | WO-2020/092375 A1 | 5/2020 |
| WO | WO-2020/092383 A1 | 5/2020 |
| WO | WO-2020/092394 A1 | 5/2020 |
| WO | WO-2020/092401 A1 | 5/2020 |
| WO | WO-2021/030438 A1 | 2/2021 |

OTHER PUBLICATIONS

Hatley R J D et al. (2019), "The Design of Potent, Selective and Drug-Like RGD αvβ1 Small-Molecule Inhibitors Derived from non-RGD α4β1 Antagonists", Chem MedChem, 14, 1-7.

(56) References Cited

OTHER PUBLICATIONS

Intl. Search Report-Written Opinion dated Jan. 14, 2020 for Intl. Appl. No. PCT/US2019/058610.
Intl. Search Report-Written Opinion dated Jan. 21, 2020 for Intl. Appl. No. PCT/US2019/058573.
Intl. Search Report-Written Opinion dated Jan. 23, 2020 for Intl. Appl. No. PCT/US2019/058583.
Intl. Search Report-Written Opinion dated Jan. 28, 2020 for Intl. Appl. No. PCT/US2019/058599.
Li H et al. (2018), "$\alpha 4\beta 7$ integrin inhibitors: a patent review", Expert Opinion on Therapeutic Patents, 28:12, 903-917.
Sircar Ila et al. (2002), "Synthesis and SAR of N-Benzoyl-L-Biphenylalanine Derivatives: Discovery of TR-14035, A Dual $\alpha 4\beta 7$/$\alpha 4\beta 1$ Integrin Antagonist", Bioorganic & Medicinal Chemistry, vol. 10, No. 6, pp. 2051-2066.
Xu Y-Z et al. (2013), "Orally available and efficacious $\alpha 4\beta 1$/$\alpha 4\beta 7$ integrin inhibitors", Bioorganic & Medicinal Chemistry Letters 23:4370-4373.
Office Action dated Aug. 4, 2020 for Taiwanese Appl. No. 108139359.
Office Action dated Sep. 11, 2020 for Taiwanese Appl. No. 108139358.
Office Action dated Sep. 18, 2020 for Taiwanese Appl. No. 108139336.
Intl. Preliminary Report on Patentability dated May 4, 2021 for Intl. Appl. No. PCT/US2019/058573.
Intl. Preliminary Report on Patentability dated May 4, 2021 for Intl. Appl. No. PCT/US2019/058583.
Intl. Preliminary Report on Patentability dated May 4, 2021 for Intl. Appl. No. PCT/US2019/058599.
Intl. Preliminary Report on Patentability dated May 4, 2021 for Intl. Appl. No. PCT/US2019/058610.
Intl. Search Report-Written Opinion dated Jan. 21, 2021 for Intl. Appl. No. PCT/US2020/045938.
Non-Final Office Action dated Mar. 19, 2021 for U.S. Appl. No. 16/667,532.
Notice of Allowance dated Mar. 26, 2021 for Taiwanese Appl. No. 108139358.
Notice of Allowance and Fees Due dated Feb. 24, 2021 for U.S. Appl. No. 16/667,306.
Notice of Allowance and Fees Due dated Mar. 12, 2021 for U.S. Appl. No. 16/667,373.
Notice of Allowance and Fees Due dated Mar. 19, 2021 for U.S. Appl. No. 16/667,572.
Notice of Allowance and Fees Due dated Jun. 14, 2021 for U.S. Appl. No. 16/667,306.

COMPOUNDS FOR INHIBITION OF ALPHA 4 BETA 7 INTEGRIN

CROSS REFERENCE TO RELATED APPLICATION

This application claims priority to U.S. Provisional Application No. 62/752,859, filed Oct. 30, 2018, which is incorporated herein in its entirety for all purposes.

FIELD

The present disclosure relates generally to novel compounds that have α4β7 integrin inhibitory action, prodrugs of compounds having α4β7 integrin inhibitory action, and methods of use and manufacture thereof.

BACKGROUND

Integrins are heterodimeric cell surface proteins involved in numerous cellular processes including cell-cell and cell-extracellular matrix interactions. Upon binding of an extracellular ligand, integrins mediate signal transduction to the cell interior resulting in lymphocyte cell capture, adhesion, and infiltration into the tissue.

Integrins are heterodimeric proteins consisting of an alpha and a beta subunit. There are 18 known alpha subunits and 8 known beta subunits. The α4β7 integrin is expressed on the surface of lymphocytes and recognizes the extracellular ligand mucosal addressing cell adhesion molecule-1 (MAdCAM-1). α4β7 integrin governs lymphocyte trafficking to and retention in gut tissues through its interaction with MAdCAM-1, which is expressed on venules in the intestinal mucosa and high endothelial venules (HEV) in the gut-associated lymphoid tissues (GALT). Inhibiting the interactions of integrins with their respective ligands has been proposed as an effective method of treating a variety of autoimmune and inflammatory diseases, and blocking the α4β7-MAdCAM-1 interaction has shown therapeutic benefit in inflammatory bowel disease (Crohn's disease and ulcerative colitis).

There is a need to for improved α4β7 integrin antagonist molecules for the treatment of autoimmune and inflammatory diseases, including, but not limited to, inflammatory bowel disease.

SUMMARY

The present disclosure provides compounds that are inhibitors for α4β7 integrin. The disclosure also provides compositions, including pharmaceutical compositions, kits that include the compounds, and methods of using (or administering) and making the compounds. The compounds provided herein are useful in treating diseases, disorders, or conditions that are mediated, at least in part, by α4β7 integrin. The disclosure also provides compounds for use in therapy. The disclosure further provides compounds for use in a method of treating a disease, disorder, or condition that is mediated, at least in part, by α4β7 integrin. Moreover, the disclosure provides uses of the compounds in the manufacture of a medicament for the treatment of a disease, disorder or condition that is mediated, at least in part, by α4β7 integrin.

The present disclosure provides a compound of formula (I):

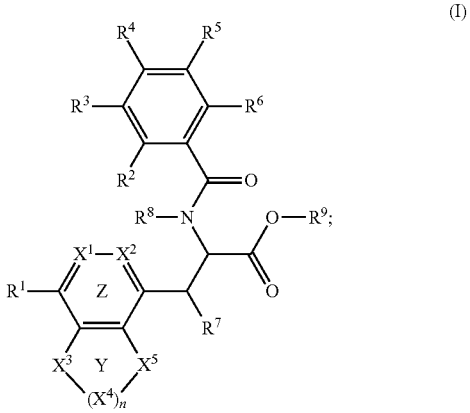

or a pharmaceutically acceptable salt thereof; wherein:
$X^1$ and $X^2$ are each independently selected from $CR^{10}$ and N;
$X^3$ and $X^5$ are each independently selected from $NR^{11}$, O, S, C(O), and $C(R^{10})_2$;
each $X^4$ is independently selected from $NR^{11}$, O, S, C(O), and $C(R^{10})_2$;
$R^1$ is selected from -L-$A^1$, -L-$A^2$, -L-$A^3$, and -L-$A^4$;
L is selected from a bond, —O—, —O—C(O)—*, —NH—, —C(O)—N(H)—*, and —N(H)—C(O)—*; wherein * indicates a point of attachment of L to $A^1$, $A^2$, $A^3$, or $A^4$;
$A^1$ is $C_{6-10}$aryl optionally substituted with one to six $R^a$;
$A^2$ is 5-10 membered heteroaryl containing one to five heteroatoms independently selected from S, N, and O, and optionally one or two C(O); wherein $A^2$ is optionally substituted with one to six $R^a$;
$A^3$ is 5-10 membered cycloalkyl or 5-14 membered heterocyclyl; wherein $A^3$ is optionally substituted with one to six $R^a$; and
$A^4$ is —$NR^{a1}R^{a2}$;
wherein each $R^a$ is independently selected from halo, cyano, hydroxyl, —$NR^{a1}R^{a2}$, $C_{1-6}$alkyl, $C_{2-6}$alkenyl, $C_{2-6}$alkynyl, $C_{1-6}$alkoxyl, $C_{1-6}$haloalkyl, $C_{1-6}$haloalkoxyl, —$S(O)_m$—$C_{1-6}$alkyl, $C_{3-8}$cycloalkyl, 3-6 membered heterocyclyl, $C_{6-10}$aryl, 5-6 membered heteroaryl, —O-(3-6 membered heterocyclyl), —O—$C_{1-4}$alkylene-$C_{3-8}$cycloalkyl, —O-phenyl, and —O—$C_{3-8}$cycloalkyl;
each $C_{1-6}$alkyl, $C_{2-6}$alkenyl, $C_{2-6}$alkynyl, $C_{1-6}$alkoxyl, $C_{1-6}$haloalkyl, $C_{1-6}$haloalkoxyl, and —$S(O)_m$—$C_{1-6}$alkyl of $R^a$ are optionally substituted with one to three $R^{a3}$; wherein each $R^{a3}$ is independently selected from hydroxyl, cyano, —$NR^{a1}R^{a2}$, $C_{1-6}$alkoxyl, $C_{3-8}$cycloalkyl, phenyl, and 3-6 membered heterocyclyl; wherein each $C_{3-8}$cycloalkyl, phenyl, and 3-6 membered heterocyclyl of $R^{a3}$ is independently optionally substituted with one to three $R^{a4}$; wherein each $R^{a4}$ is independently selected from halo, cyano, hydroxyl, —$NR^{a1}R^{a2}$, $C_{1-6}$alkyl, $C_{1-6}$haloalkyl, $C_{1-6}$alkoxyl, $C_{1-6}$haloalkoxyl, $C_{3-8}$cycloalkyl, and 3-6 membered heterocyclyl; and
each $C_{3-8}$cycloalkyl, 3-6 membered heterocyclyl, $C_{6-10}$aryl, 5-6 membered heteroaryl, —O-(3-6 membered heterocyclyl), —O—$C_{1-4}$alkylene-$C_{3-8}$cycloalkyl, —O-phenyl, and —O—$C_{3-8}$cycloalkyl of $R^a$ is independently optionally substituted with one to three groups independently selected from halo, cyano, hydroxyl, —NR$^{a1}$R$^{a2}$, C$_{1-6}$alkyl, C$_{1-6}$haloalkyl, C$_{1-6}$alkoxyl, and C$_{1-6}$haloalkoxyl;

each R$^2$, R$^3$, R$^4$, R$^5$, and R$^6$ is independently selected from H, halo, cyano, hydroxyl, C$_{1-6}$alkyl, C$_{2-6}$alkenyl, C$_{2-6}$alkynyl, C$_{1-6}$alkoxyl, C$_{1-8}$haloalkyl, C$_{1-8}$haloalkoxyl, —NR$^{b1}$R$^{b2}$, —R$^{b3}$S(O)$_m$R$^{b4}$, —S(O)$_m$R$^{b4}$, —NR$^{b1}$S(O)$_v$R$^{b4}$, —COOR$^{b1}$, —CONR$^{b1}$R$^{b2}$, —NR$^{b1}$COOR$^{b2}$, —NR$^{b1}$COR$^{b4}$, —R$^{b3}$NR$^{b1}$R$^{b2}$, —S(O)$_v$NR$^{b1}$R$^{b2}$, C$_{3-12}$cycloalkyl, C$_{6-10}$aryl, 5-6 membered heteroaryl, and 3-12 membered heterocyclyl;

each C$_{1-6}$alkyl, C$_{2-6}$alkenyl, C$_{2-6}$alkynyl, C$_{1-6}$alkoxyl, C$_{1-8}$haloalkyl, and C$_{1-8}$haloalkoxyl of R$^2$, R$^3$, R$^4$, R$^5$, and R$^6$ is independently optionally substituted with one to two R$^c$; wherein each R$^c$ is independently selected from azido, oxo, cyano, halo, hydroxyl, —NR$^{a1}$R$^{a2}$, C$_{1-4}$alkoxyl, C$_{3-8}$cycloalkyl, C$_{6-10}$aryl, 5-6 membered heteroaryl, and 4-6 membered heterocyclyl; wherein each C$_{3-8}$cycloalkyl, C$_{6-10}$aryl, 5-6 membered heteroaryl, and 4-6 membered heterocyclyl of R$^c$ is independently optionally substituted with one to three groups independently selected from halo, hydroxyl, cyano, —NR$^{a1}$R$^{a2}$, C$_{1-4}$alkyl, C$_{1-6}$haloalkyl, C$_{1-4}$alkoxyl, and C$_{3-6}$cycloalkyl;

each C$_{6-10}$aryl and 5-6 membered heteroaryl of R$^2$, R$^3$, R$^4$, R$^5$, and R$^6$ is independently optionally substituted with one to five R$^b$; and each C$_{3-12}$cycloalkyl and 3-12 membered heterocyclyl of R$^2$, R$^3$, R$^4$, R$^5$, and R$^6$ is independently optionally substituted with one to six groups independently selected from =CR$^{b1}$R$^{b2}$, and R$^b$;

wherein each R$^b$ is independently selected from azido, cyano, halo, hydroxyl, —NR$^{a1}$R$^{a2}$, C$_{1-6}$alkyl, C$_{1-8}$haloalkyl, C$_{1-6}$alkoxyl, C$_{3-6}$cycloalkyl, C$_{6-10}$aryl, 5-6 membered heteroaryl, and 4-6 membered heterocyclyl; wherein each C$_{3-6}$cycloalkyl, C$_{6-10}$aryl, 5-6 membered heteroaryl, and 4-6 membered heterocyclyl of R$^b$ is independently optionally substituted with one to three groups independently selected from halo, hydroxyl, cyano, —NR$^{a1}$R$^{a2}$, C$_{1-4}$alkyl, C$_{1-4}$haloalkyl, and C$_{1-4}$alkoxyl;

each R$^{b1}$ and R$^{b2}$ is independently selected from H, C$_{1-8}$alkyl, C$_{1-8}$haloalkyl, C$_{3-8}$cycloalkyl, C$_{6-10}$aryl, 5-6 membered heteroaryl, and 3-8 membered heterocyclyl;

each C$_{1-8}$alkyl and C$_{1-6}$haloalkyl of R$^{b1}$ and R$^{b2}$ is optionally substituted with one to two R$^{b5}$; and each C$_{3-8}$cycloalkyl, C$_{6-10}$aryl, 5-6 membered heteroaryl, and 3-8 membered heterocyclyl of R$^{b1}$ and R$^{b2}$ is independently optionally substituted with one to three groups independently selected from halo, cyano, hydroxyl, —NR$^{a1}$R$^{a2}$, C$_{1-8}$alkyl, C$_{1-8}$haloalkyl, C$_{1-6}$alkoxyl, C$_{3-6}$cycloalkyl, C$_{6-10}$aryl, 5-6 membered heteroaryl, and 4-6 membered heterocyclyl;

R$^{b3}$ is C$_{1-4}$alkylene;

R$^{b4}$ is selected from C$_{1-4}$alkyl, C$_{1-4}$haloalkyl, C$_{3-6}$cycloalkyl, C$_{6-10}$aryl, 5-6 membered heteroaryl, and 4-6 membered heterocyclyl; wherein each C$_{1-4}$alkyl, C$_{1-4}$haloalkyl, C$_{3-8}$cycloalkyl, C$_{6-10}$aryl, 5-6 membered heteroaryl, and the 4-6 membered heterocyclyl of R$^{b4}$ is optionally substituted with one to three R$^{b6}$;

each R$^{b5}$ is independently selected from cyano, hydroxyl, C$_{1-4}$alkoxyl, C$_{3-8}$cycloalkyl, C$_{6-10}$aryl, 5-6 membered heteroaryl, and 4-6 membered heterocyclyl; wherein each C$_{3-8}$cycloalkyl, C$_{6-10}$aryl, 5-6 membered heteroaryl, and 4-6 membered heterocyclyl of R$^{b5}$ is optionally substituted with one to three groups independently selected from halo, cyano, hydroxyl, —NR$^{a1}$R$^{a2}$, C$_{1-4}$alkyl, C$_{1-4}$haloalkyl, C$_{1-4}$alkoxyl, and phenyl; and each R$^{b6}$ is independently selected from halo, cyano, C$_{1-4}$alkyl, C$_{1-4}$haloalkyl, C$_{1-4}$alkoxyl, C$_{3-6}$cycloalkyl, phenyl, 4-6 membered heterocyclyl, and 5-6 membered heteroaryl; wherein each C$_{3-6}$cycloalkyl, 4-6 membered heterocyclyl, and 5-6 membered heteroaryl of R$^{b6}$ is independently optionally substituted with one to three groups independently selected from halo, cyano, —NR$^{a1}$R$^{a2}$, C$_{1-4}$alkyl, C$_{1-4}$haloalkyl, and C$_{1-4}$alkoxyl; or R$^2$ and R$^3$, R$^3$ and R$^4$, or R$^5$ and R$^6$ together with the atoms to which they are attached may form a C$_{6-10}$aryl, 5-6 membered heteroaryl, C$_{3-6}$cycloalkyl, or 5-6 membered heterocyclyl; wherein each C$_{6-10}$aryl, 5-6 membered heteroaryl, C$_{3-6}$cycloalkyl, or 5-6 membered heterocyclyl is optionally substituted with one to three groups independently selected from halo, cyano, —NR$^{a1}$R$^{a2}$, C$_{1-6}$alkyl, C$_{1-6}$alkoxyl, C$_{1-6}$haloalkyl, C$_{3-8}$cycloalkyl, 3-6 membered heterocyclyl, C$_{6-10}$aryl, 5-6 membered heteroaryl, C$_{1-4}$alkylene-C$_{3-8}$cycloalkyl, C$_{1-4}$alkylene-C$_{6-10}$ aryl, and C$_{1-4}$alkylene-(5-6 membered heteroaryl);

R$^7$ is selected from H, C$_{1-4}$alkyl, and C$_{1-4}$haloalkyl;

R$^8$ is selected from H, C$_{1-4}$alkyl, and C$_{1-4}$haloalkyl;

R$^9$ is selected from H, C$_{1-6}$alkyl, —C$_{1-4}$alkylene-NR$^{a1}$R$^{a2}$, —C$_{1-4}$alkylene-C(O)NR$^{a1}$R$^{a2}$, —C$_{1-4}$alkylene-O—C(O)—C$_{1-4}$alkyl, —C$_{1-4}$alkylene-O—C(O)—O—C$_{1-4}$alkyl, —C$_{1-4}$alkylene-O—C(O)—C$_{1-4}$alkylene-NR$^{a1}$R$^{a2}$, —C$_{1-4}$alkylene-O—C$_{1-4}$alkyl, C$_{3-8}$cycloalkyl, —C$_{1-4}$alkylene-C$_{3-8}$cycloalkyl, 4-6 membered heterocyclyl, and —C$_{1-4}$alkylene-(4-6 membered heterocyclyl);

wherein each C$_{3-8}$cycloalkyl, —C$_{1-4}$alkylene-C$_{3-8}$cycloalkyl, 4-6 membered heterocyclyl and —C$_{1-4}$alkylene-(4-6 membered heterocyclyl) of R$^9$ is optionally substituted with one to three groups independently selected from halo, C$_{1-4}$alkyl, C$_{1-4}$alkoxyl, and C$_{1-4}$haloalkyl; or R$^9$ together with the N that attaches to R$^8$ forms a 5 membered heterocyclyl; wherein the 5 membered heterocyclyl is optionally substituted with one to two groups independently selected from halo, C$_{1-6}$alkyl, C$_{1-6}$alkoxyl, C$_{1-6}$haloalkyl, and C$_{6-10}$aryl; wherein C$_{6-10}$aryl is optionally substituted with one to three groups independently selected from halo, C$_{1-6}$alkyl, C$_{1-6}$alkoxyl, and C$_{1-6}$haloalkyl;

each R$^{10}$ is independently selected from H, halo, cyano, hydroxyl, —C(O)R$^{b1}$, —NR$^{a1}$R$^{a2}$, C$_{1-4}$alkyl, C$_{1-4}$alkoxyl, C$_{1-4}$haloalkyl, C$_{1-4}$haloalkoxyl, C$_{3-10}$cycloalkyl, 3-8 membered heterocyclyl, C$_{6-10}$aryl, and 5-6 membered heteroaryl; wherein each C$_{1-4}$alkyl, C$_{1-4}$alkoxyl, C$_{1-4}$haloalkyl, C$_{1-4}$haloalkoxyl, C$_{3-10}$cycloalkyl, 3-8-membered heterocyclyl, C$_{6-10}$aryl, and 5-6 membered heteroaryl is independently optionally substituted with one to three groups independently selected from halo, hydroxyl, cyano, —NR$^{a1}$R$^{a2}$, C$_{1-4}$alkyl, C$_{1-4}$haloalkyl, C$_{1-4}$alkoxyl, and C$_{3-6}$cycloalkyl;

or two R$^{10}$ either attached to the same or adjacent atoms form C$_{3-12}$cycloalkyl or 3-10 membered heterocyclyl; wherein each C$_{3-12}$cycloalkyl and 3-10 membered heterocyclyl is optionally substituted with one to three groups independently selected from H, halo, C$_{1-4}$ alkyl, C$_{1-4}$alkoxyl, C$_{1-4}$haloalkyl, and C$_{1-4}$haloalkoxyl;

each R$^{11}$ is independently selected from H, C$_{1-4}$alkyl, and C$_{1-4}$haloalkyl; wherein each C$_{1-4}$ alkyl, —C(O)R$^{b1}$, and C$_{1-4}$haloalkyl of R$^{11}$ is independently optionally substituted with one to three groups independently selected from halo, hydroxyl, cyano, —NR$^{a1}$R$^{a2}$, C$_{1-4}$alkyl, C$_{1-4}$ haloalkyl, C$_{1-4}$alkoxyl, and C$_{3-6}$cycloalkyl; or R$^{10}$ and R$^{11}$, or two R$^{11}$ together with the atoms to which they are attached to form 3-12 membered heterocyclyl; wherein 3-12 membered heterocyclyl is optionally substituted with one to three groups independently selected from H, halo, C$_{1-4}$alkyl, C$_{1-4}$alkoxyl, C$_{1-4}$haloalkyl, and C$_{1-4}$haloalkoxyl;

each R$^{a1}$ and R$^{a2}$ is independently selected from H, C$_{1-6}$alkyl, and C$_{1-6}$haloalkyl;

n is selected from 1, 2, and 3;

m is selected from 0, 1, and 2; and v is selected from 1 and 2.

Also provided herein is a pharmaceutical composition comprising a compound of formula (I), or any formula described herein, or a pharmaceutically acceptable salt, stereoisomer, mixture of stereoisomers, tautomer, or deuterated analog thereof, and at least one pharmaceutically acceptable carrier.

Also provided herein is a pharmaceutical composition comprising a compound of formula (I), or any formula described herein, or a pharmaceutically acceptable salt, stereoisomer, mixture of stereoisomers, tautomer, or deuterated analog thereof, and further comprising a second therapeutic agent.

In some embodiments, provided is a method for treating a disease or condition mediated, at least in part, by α4β7 integrin comprising administrating to a subject an effective amount of a pharmaceutical composition comprising a compound of formula (I), or any formula described herein, or a pharmaceutically acceptable salt, stereoisomer, mixture of stereoisomers, tautomer, or deuterated analog thereof, and at least one pharmaceutically acceptable carrier.

In some embodiments, provided is a method for treating a disease or condition mediated, at least in part, by α4β7 integrin comprising administrating to a subject an effective amount of a pharmaceutical composition comprising a compound of formula (I), or any formula described herein, or a pharmaceutically acceptable salt, stereoisomer, mixture of stereoisomers, tautomer, or deuterated analog thereof, and further comprising a second therapeutic agent.

In some embodiments, provided is a method for treating an inflammatory disease comprising administrating to a subject an effective amount of a pharmaceutical composition comprising a compound of formula (I), or any formula described herein, or a pharmaceutically acceptable salt, stereoisomer, mixture of stereoisomers, tautomer, or deuterated analog thereof.

DETAILED DESCRIPTION

Definitions and General Parameters

The following description sets forth exemplary methods, parameters and the like. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —CONH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

A squiggly line on a chemical group as shown below, for example,

indicates a point of attachment, i.e., it shows the broken bond by which the group is connected to another described group.

The prefix "C$_{n1-n2}$" indicates that the following group has from n1 to n2 carbon atoms. For example, "C$_{1-8}$alkyl" indicates that the alkyl group has from 1 to 8 carbon atoms.

Reference to "about" a value or parameter herein includes (and describes) embodiments that are directed to that value or parameter per se. In some embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., C$_{1-20}$ alkyl), 1 to 8 carbon atoms (i.e., C$_{1-8}$ alkyl), 1 to 6 carbon atoms (i.e., C$_{1-6}$ alkyl), or 1 to 4 carbon atoms (i.e., C$_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —(CH$_2$)$_3$CH$_3$), sec-butyl (i.e. —CH(CH$_3$)CH$_2$CH$_3$), isobutyl (i.e. —CH$_2$CH(CH$_3$)$_2$) and tert-butyl (i.e. —C(CH$_3$)$_3$); and "propyl" includes n-propyl (i.e. —(CH$_2$)$_2$CH$_3$) and isopropyl (i.e. —CH(CH$_3$)$_2$).

"Alkenyl" refers to an aliphatic group containing at least one carbon-carbon double bond and having from 2 to 20 carbon atoms (i.e., C$_{2-20}$ alkenyl), 2 to 8 carbon atoms (i.e., C$_{2-8}$ alkenyl), 2 to 6 carbon atoms (i.e., C$_{2-6}$ alkenyl), or 2 to 4 carbon atoms (i.e., C$_{2-4}$ alkenyl). Examples of alkenyl groups include ethenyl, propenyl, butadienyl (including 1,2-butadienyl and 1,3-butadienyl).

"Alkynyl" refers to an aliphatic group containing at least one carbon-carbon triple bond and having from 2 to 20 carbon atoms (i.e., C$_{2-20}$ alkynyl), 2 to 8 carbon atoms (i.e., C$_{2-8}$ alkynyl), 2 to 6 carbon atoms (i.e., C$_{2-6}$ alkynyl), or 2 to 4 carbon atoms (i.e., C$_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, isopropoxy, n-butoxy, tert-butoxy, sec-butoxy, n-pentoxy, n-hexoxy, and 1,2-dimethylbutoxy.

"Alkylene" (including those which are part of other groups) refers to branched and unbranched divalent "alkyl" groups. As used herein, alkylene has 1 to 20 carbon atoms (i.e., $C_{1-20}$alkylene), 1 to 8 carbon atoms (i.e., $C_{1-8}$ alkylene), 1 to 6 carbon atoms (i.e., $C_{1-6}$ alkylene), or 1 to 4 carbon atoms (i.e., $C_{1-4}$ alkylene). Examples include: methylene, ethylene, propylene, 1-methylethylene, butylene, 1-methylpropylene, 1,1-dimethylethylene or 1,2-dimethylethylene. Unless stated otherwise, the definitions propylene and butylene include all the possible isomeric forms of the groups in question with the same number of carbons. Thus, for example, propyl also includes 1-methylethylene and butylene includes 1-methylpropylene, 1,1-dimethylethylene, and 1,2-dimethylethylene.

"Acyl" refers to a group refers to a group —C(O)$R^y$, wherein $R^y$ is hydrogen, alkyl, alkenyl, alkynyl, cycloalkyl, heterocyclyl, aryl, heteroalkyl or heteroaryl; each of which may be optionally substituted, as defined herein. Examples of acyl include, e.g., formyl, acetyl, cyclohexylcarbonyl, cyclohexylmethyl-carbonyl and benzoyl.

"Amido" refers to both a "C-amido" group which refers to the group —C(O)N$R^y R^z$ and an "N-amido" group which refers to the group —N$R^y$C(O)$R^z$, wherein $R^y$ and $R^z$ are independently selected from the group consisting of hydrogen, alkyl, aryl, haloalkyl, or heteroaryl; each of which may be optionally substituted.

"Amino" refers to the group —N$R^y R^z$ wherein $R^y$ and $R^z$ are independently selected from the group consisting of hydrogen, alkyl, haloalkyl, aryl, or heteroaryl; each of which may be optionally substituted.

"Amidino" refers to —C(NH)(NH$_2$).

"Carbamoyl" refers to both an "O-carbamoyl" group which refers to the group —O—C(O)N$R^y R^z$ and an "N-carbamoyl" group which refers to the group —N$R^y$C(O)O$R^z$, wherein $R^y$ and $R^z$ are independently selected from the group consisting of hydrogen, alkyl, aryl, haloalkyl, or heteroaryl; each of which may be optionally substituted.

"Carboxyl" refers to —C(O)OH.

"Carboxyl ester" refers to both —OC(O)R and —C(O)OR, wherein R is alkyl, cycloalkyl, heterocyclyl, aryl, heteroalkyl, or heteroaryl; each of which may be optionally substituted, as defined herein.

"Guanidino" refers to —NHC(NH)(NH$_2$).

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where R is H, alkyl, aryl, cycloalkyl, heteroalkyl, heteroaryl or heterocyclyl, each of which may be optionally substituted. Examples of heteroalkyl groups include —OCH$_3$, —CH$_2$OCH$_3$, —SCH$_3$, —CH$_2$SCH$_3$, —NRCH$_3$, and —CH$_2$NRCH$_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Alkylsulfonyl" refers to the group —S(O)$_2$R, where R is alkyl.

"Alkylsulfinyl" refers to the group —S(O)R, where R is alkyl.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl ring, the resulting ring system is heteroaryl.

"Azido" refers to the group —N$_3$.

"Cyano" or "carbonitrile" refers to the group —CN.

"Cycloalkyl" refers to a saturated or partially saturated cyclic alkyl group having a single ring or multiple rings including fused, bridged, and spiro ring systems. The term "cycloalkyl" includes cycloalkenyl groups (e.g. the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include, but are not limited to, cyclopropyl, cyclobutyl, cyclopentyl, and cyclohexyl. Cycloalkyl groups also include partially unsaturated ring systems containing one or more double bonds, including fused ring systems with one aromatic ring and one non-aromatic ring, but not fully aromatic ring systems.

"Bridged" refers to a ring fusion wherein non-adjacent atoms on a ring are joined by a divalent substituent, such as an alkylenyl or heteroalkylenyl group or a single heteroatom. Quinuclidinyl and admantanyl are examples of bridged ring systems.

The term "fused" refers to a ring which is bound to an adjacent ring.

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents.

"Spiro" also refers to a bicyclic portion, wherein the two rings are connected through a single common atom. Spiro compounds may be fully carbocyclic or heterocyclic. Examples of spiro groups include 5-oxa-8-azaspiro[3.5]nonane, 7-oxa-4-azaspiro[2.5]octane, and 5$\lambda^2$-azaspiro[2.4]heptane.

"Halogen" or "halo" includes fluoro, chloro, bromo, and iodo.

"Haloalkyl" refers to an unbranched or branched alkyl group as defined above, wherein one or more hydrogen atoms, up to the total number of possible hydrogen atoms in a group, are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$) and trifluoromethyl (—CF$_3$).

"Haloalkoxyl" or "haloalkoxy" refers to an alkoxy group as defined above, wherein one or more hydrogen atoms, up to the total number of possible hydrogen atoms in a group, are replaced by a halogen. Examples of haloalkoxyl include, but are not limited to, difluoromethoxyl (—OCHF$_2$), and trifluoromethoxyl (—OCF$_3$).

The term "heterocyclyl" or "heterocycle" as used herein refers to a single saturated or partially unsaturated non-aromatic ring or a non-aromatic multiple ring system that has at least one heteroatom in the ring, i.e., at least one annular heteroatom selected from oxygen, nitrogen, and sulfur, wherein the nitrogen or sulfur may be oxidized. Thus, the term includes rings having one or more annular O, N, S, S(O), S(O)$_2$, and N-oxide groups. The term includes rings having one or more annular C(O) groups. Unless otherwise specified, a heterocyclyl group has from 5 to about 20 annular atoms, for example from 3 to 12 annular atoms, for example from 3 to 10 annular atoms, for example from 5 to 10 annular atoms or for example from 5 to 6 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms independently selected from the group consisting of oxygen, nitrogen and sulfur in the ring. The rings of the multiple condensed ring (e.g. bicyclic heterocyclyl) system can be connected to each other via fused, spiro and bridged bonds when allowed by valency requirements. Heterocycles include, but are not limited to, groups derived from azetidine, aziridine, imidazolidine, morpholine, oxirane (epoxide), oxetane, piperazine, piperidine, pyrazolidine, pyrrolidine, pyrrolidinone, tetrahydrofuran, tetrahydrothiophene, dihydropyridine, tetrahydropyridine, tetrahydro-2H-thiopyran 1,1-dioxide, quinuclidine, N-bromopyrrolidine, N-chloropiperidine, and the like. Heterocycles include spirocycles, such as, for example, aza or oxo-spiroheptanes. Heterocyclyl groups also include partially unsaturated ring systems containing one or more double bonds, including fused ring systems with one aromatic ring and one non-aromatic ring, but not fully aromatic ring systems. Examples include dihydroquinolines, e.g. 3,4-dihydroquinoline, dihydroisoquinolines, e.g. 1,2-dihydroisoquinoline, dihydroimidazole, tetrahydroimidazole, etc., indoline, isoindoline, isoindolones (e.g. isoindolin-1-one), isatin, dihydrophthalazine, quinolinone, spiro[cyclopropane-1,1'-isoindolin]-3'-one, and the like. Additional examples of heterocycles include 3,8-diazabicyclo[3.2.1] octanyl, 2,5-diazabicyclo [2.2.1]heptanyl, 3,6-diazabicyclo [3.1.1]heptanyl, 3-oxa-7,9-diazabicyclo[3.3.1]nonanyl, and hexahydropyrazino[2,1-c][1,4]oxazinyl, for example.

"Hydroxyl" and "hydroxy" are used interchangeably and refer to —OH.

"Oxo" refers to the group (=O) or (O). Where tautomeric forms of the compound exist, hydroxyl and oxo groups may be interchangeable.

"Heteroaryl" refers to an aromatic group, including groups having an aromatic tautomer or resonance structure, having a single ring, multiple rings, or multiple fused rings, with at least one heteroatom in the ring, i.e., one or more ring heteroatoms independently selected from nitrogen, oxygen, and sulfur, wherein the nitrogen or sulfur may be oxidized. Thus, the term includes rings having one or more annular O, N, S, S(O), S(O)$_2$, and N-oxide groups. The term includes rings having one or more annular C(O) groups. As used herein, heteroaryl include 3 to 20 ring atoms (i.e., 3-20 membered heteroaryl), 3 to 12 ring atoms (i.e., 3-12 membered heteroaryl), or 5 to 10 ring atoms (i.e., 5-10 membered heteroaryl), and 1 to 5 heteroatoms independently selected from nitrogen, oxygen, and sulfur, and oxidized forms of the heteroatoms. Examples of heteroaryl groups include pyridin-2(1H)-one, pyridazin-3(2H)-one, pyrimidin-4(3H)-one, quinolin-2(1H)-one, pyrimidinyl, purinyl, pyridyl, pyridazinyl, benzothiazolyl, and pyrazolyl. Heteroaryl does not encompass or overlap with aryl as defined above.

"Sulfonyl" refers to the group —S(O)$_2$R, where R is alkyl, haloalkyl, heterocyclyl, cycloalkyl, heteroaryl, or aryl. Examples of sulfonyl are methylsulfonyl, ethylsulfonyl, phenylsulfonyl, and toluenesulfonyl.

Whenever the graphical representation of a group terminates in a singly bonded nitrogen atom, that group represents an —NH group unless otherwise indicated. Similarly, unless otherwise expressed, hydrogen atom(s) are implied and deemed present where necessary in view of the knowledge of one of skill in the art to complete valency or provide stability.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted.

In some embodiments, the term "substituted alkyl" refers to an alkyl group having one or more substituents including hydroxyl, halo, alkoxy, cycloalkyl, heterocyclyl, aryl, and heteroaryl. In additional embodiments, "substituted cycloalkyl" refers to a cycloalkyl group having one or more substituents including alkyl, haloalkyl, cycloalkyl, heterocyclyl, aryl, heteroaryl, alkoxy, halo, oxo, and hydroxyl; "substituted heterocyclyl" refers to a heterocyclyl group having one or more substituents including alkyl, haloalkyl, heterocyclyl, cycloalkyl, aryl, heteroaryl, alkoxy, halo, oxo, and hydroxyl; "substituted aryl" refers to an aryl group having one or more substituents including halo, alkyl, haloalkyl, cycloalkyl, heterocyclyl, heteroaryl, alkoxy, and cyano; "substituted heteroaryl" refers to an heteroaryl group having one or more substituents including halo, alkyl, haloalkyl, heterocyclyl, heteroaryl, alkoxy, and cyano and "substituted sulfonyl" refers to a group —S(O)$_2$R, in which R is substituted with one or more substituents including alkyl, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

Some of the compounds exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes compounds in which from 1 to n hydrogens attached to a carbon atom is/are replaced by deuterium, in which n is the number of hydrogens in the molecule. Such compounds exhibit increased resistance to metabolism and are thus useful for increasing the half-life of any compound provided herein when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, mono, di or tri cycloalkyl amines, mono, di or tri arylamines or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Provided are also compounds described herein or pharmaceutically acceptable salts, isomer, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts.

A "solvate" is formed by the interaction of a solvent and a compound. Solvates of salts of the compounds described herein are also provided. Hydrates of the compounds described herein are also provided.

A "prodrug" is a biologically inactive derivative of a drug that upon administration to the human body is converted to the biologically active parent drug according to some chemical or enzymatic pathway.

In some embodiments, provided are optical isomers, racemates, or other mixtures thereof of the compounds described herein or pharmaceutically acceptable salts or a mixture thereof. In those situations, the single enantiomer or diastereomer, i.e., optically active form, can be obtained by asymmetric synthesis or by resolution of the racemate. Resolution of racemates can be accomplished, for example, by conventional methods such as crystallization in the presence of a resolving agent, or chromatography, using, for example a chiral high pressure liquid chromatography (HPLC) column. In addition, provided are also Z- and E-forms (or cis- and trans-forms) of the hydroxyamidine compounds described herein. Specifically, Z- and E-forms are included even if only one designation is named for both carbon-carbon double bonds as well as the hydroxyamidine bond.

Where chirality is not specified but is present, it is understood that the embodiment is directed to either the specific diastereomerically or enantiomerically enriched form; or a racemic or scalemic mixture of such compound(s).

"Enantiomers" are a pair of stereoisomers that are non-superimposable mirror images of each other. A 1:1 mixture of a pair of enantiomers is a "racemic" mixture. A mixture of enantiomers at a ratio other than 1:1 is a "scalemic" mixture.

"Diastereoisomers" are stereoisomers that have at least two asymmetric atoms, but which are not mirror-images of each other.

"Atropisomers" are stereoisomers arising due to hindered rotation about a single bond, where the barrier to rotation about the bond is high enough to allow for isolation of individual stereoisomers.

Compositions provided herein that include a compound described herein or pharmaceutically acceptable salts, isomer, or a mixture thereof may include racemic mixtures, or mixtures containing an enantiomeric excess of one enantiomer or single diastereomers or diastereomeric mixtures. All such isomeric forms of these compounds are expressly included herein the same as if each and every isomeric form were specifically and individually listed.

In some embodiments, provided are also chelates, non-covalent complexes, and mixtures thereof, of the compounds described herein or pharmaceutically acceptable salts, isomer, or a mixture thereof. A "chelate" is formed by the coordination of a compound to a metal ion at two (or more) points. A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding).

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In some embodiments, the subject is a human.

The term "therapeutically effective amount" or "effective amount" of a compound described herein or pharmaceutically acceptable salts, isomer, or a mixture thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of α4β7 integrin activity. The therapeutically effective amount may vary depending on the subject, and disease or condition being treated, the weight and age of the subject, the severity of the disease or condition, and the manner of administering, which can readily be determined by one or ordinary skill in the art.

The term "inhibition" indicates a decrease in the baseline activity of a biological activity or process. "Inhibition of activity of α4β7 integrin" or variants thereof refers to a decrease in activity of α4β7 integrin as a direct or indirect response to the presence of a compound of the present application relative to the activity of α4β7 integrin in the absence of the compound of the present application. "Inhibition of α4β7 integrin" refers to a decrease in α4β7 integrin activity as a direct or indirect response to the presence of a compound described herein relative to the activity of α4β7 integrin in the absence of the compound described herein. In some embodiments, the inhibition of α4β7 integrin activity may be compared in the same subject prior to treatment, or other subjects not receiving the treatment.

Compounds

Provided herein are compounds that function as inhibitors of α4β7 integrin. In some embodiments, provided is a compound of formula (I):

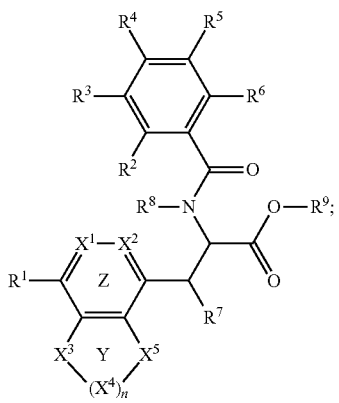

or a pharmaceutically acceptable salt thereof; wherein:
$X^1$ and $X^2$ are each independently selected from $CR^{10}$ and N;
$X^3$ and $X^5$ are each independently selected from $NR^{11}$, O, S, C(O), and $C(R^{10})_2$;
each $X^4$ is independently selected from $NR^{11}$, O, S, C(O), and $C(R^{10})_2$;
$R^1$ is selected from -L-$A^1$, -L-$A^2$, -L-$A^3$, and -L-$A^4$;
L is selected from a bond, —O—, —O—C(O)—*, —NH—, —C(O)—N(H)—*, and —N(H)—C(O)—*; wherein * indicates a point of attachment of L to $A^1$, $A^2$, $A^3$, or $A^4$;
$A^1$ is $C_{6-10}$aryl optionally substituted with one to six $R^a$;
$A^2$ is 5-10 membered heteroaryl containing one to five heteroatoms independently selected from S, N, and O, and optionally one or two C(O); wherein $A^2$ is optionally substituted with one to six $R^a$;
$A^3$ is 5-10 membered cycloalkyl or 5-14 membered heterocyclyl; wherein $A^3$ is optionally substituted with one to six $R^a$; and
$A^4$ is —$NR^{a1}R^{a2}$;
wherein each $R^a$ is independently selected from halo, cyano, hydroxyl, —$NR^{a1}R^{a2}$, $C_{1-6}$alkyl, $C_{2-6}$alkenyl, $C_{2-6}$alkynyl, $C_{1-6}$alkoxyl, $C_{1-6}$haloalkyl, $C_{1-6}$haloalkoxyl, —$S(O)_m$—$C_{1-6}$alkyl, $C_{3-8}$cycloalkyl, 3-6 membered heterocyclyl, $C_{6-10}$aryl, 5-6 membered heteroaryl, —O-(3-6 membered heterocyclyl), —O—$C_{1-4}$alkylene-$C_{3-8}$cycloalkyl, —O-phenyl, and —O—$C_{3-8}$cycloalkyl;
each $C_{1-6}$alkyl, $C_{2-6}$alkenyl, $C_{2-6}$alkynyl, $C_{1-6}$alkoxyl, $C_{1-6}$haloalkyl, $C_{1-6}$haloalkoxyl, and —$S(O)_m$—$C_{1-6}$alkyl of $R^a$ are optionally substituted with one to three $R^{a3}$; wherein each $R^{a3}$ is independently selected from hydroxyl, cyano, —$NR^{a1}R^{a2}$, $C_{1-6}$alkoxyl, $C_{3-8}$cycloalkyl, phenyl, and 3-6 membered heterocyclyl; wherein each $C_{3-8}$cycloalkyl, phenyl, and 3-6 membered heterocyclyl of $R^{a3}$ is independently optionally substituted with one to three $R^{a4}$; wherein each $R^{a4}$ is independently selected from halo, cyano, hydroxyl, —$NR^{a1}R^{a2}$, $C_{1-6}$alkyl, $C_{1-6}$haloalkyl, $C_{1-6}$alkoxyl, $C_{1-6}$haloalkoxyl, $C_{3-8}$cycloalkyl, and 3-6 membered heterocyclyl; and
each $C_{3-8}$cycloalkyl, 3-6 membered heterocyclyl, $C_{6-10}$aryl, 5-6 membered heteroaryl, —O-(3-6 membered heterocyclyl), —O—$C_{1-4}$alkylene-$C_{3-8}$cycloalkyl, —O-phenyl, and —O—$C_{3-8}$cycloalkyl of $R^a$ is independently optionally substituted with one to three groups independently selected from halo, cyano, hydroxyl, —$NR^{a1}R^{a2}$, $C_{1-6}$alkyl, $C_{1-6}$haloalkyl, $C_{1-6}$alkoxyl, and $C_{1-6}$haloalkoxyl;
each $R^2$, $R^3$, $R^4$, $R^5$, and $R^6$ is independently selected from H, halo, cyano, hydroxyl, $C_{1-6}$ alkyl, $C_{2-6}$alkenyl, $C_{2-6}$alkynyl, $C_{1-6}$alkoxyl, $C_{1-8}$haloalkyl, $C_{1-8}$haloalkoxyl, —$NR^{b1}R^{b2}$, —$R^{b3}S(O)_mR^{b4}$, —$S(O)_mR^{b4}$, —$NR^{b1}S(O)_vR^{b4}$, —$COOR^{b1}$, —$CONR^{b1}R^{b2}$, —$NR^{b1}COOR^{b2}$, —$NR^{b1}COR^{b4}$, —$R^{b3}NR^{b1}R^{b2}$, —$S(O)_vNR^{b1}R^{b2}$, $C_{3-12}$cycloalkyl, $C_{6-10}$aryl, 5-6 membered heteroaryl, and 3-12 membered heterocyclyl;
each $C_{1-6}$alkyl, $C_{2-6}$alkenyl, $C_{2-6}$alkynyl, $C_{1-6}$alkoxyl, $C_{1-8}$haloalkyl, and $C_{1-8}$haloalkoxyl of $R^2$, $R^3$, $R^4$, $R^5$, and $R^6$ is independently optionally substituted with one to two $R^c$; wherein each $R^c$ is independently selected from azido, oxo, cyano, halo, hydroxyl, —$NR^{a1}R^{a2}$, $C_{1-4}$alkoxyl, $C_{3-8}$cycloalkyl, $C_{6-10}$aryl, 5-6 membered heteroaryl, and 4-6 membered heterocyclyl; wherein each $C_{3-8}$cycloalkyl, $C_{6-10}$aryl, 5-6 membered heteroaryl, and 4-6 membered heterocyclyl of $R^c$ is independently optionally substituted with one to three groups independently selected from halo, hydroxyl, cyano, —$NR^{a1}R^{a2}$, $C_{1-4}$alkyl, $C_{1-6}$haloalkyl, $C_{1-4}$alkoxyl, and $C_{3-6}$cycloalkyl;
each $C_{6-10}$aryl and 5-6 membered heteroaryl of $R^2$, $R^3$, $R^4$, $R^5$, and $R^6$ is independently optionally substituted with one to five $R^b$; and
each $C_{3-12}$cycloalkyl and 3-12 membered heterocyclyl of $R^2$, $R^3$, $R^4$, $R^5$, and $R^6$ is independently optionally substituted with one to six groups independently selected from =$CR^{b1}R^{b2}$, and $R^b$;
wherein each $R^b$ is independently selected from azido, cyano, halo, hydroxyl, —$NR^{a1}R^{a2}$, $C_{1-6}$alkyl, $C_{1-8}$haloalkyl, $C_{1-6}$alkoxyl, $C_{3-6}$cycloalkyl, $C_{6-10}$aryl, 5-6 membered heteroaryl, and 4-6 membered heterocyclyl; wherein each $C_{3-6}$cycloalkyl, $C_{6-10}$aryl, 5-6 membered heteroaryl, and 4-6 membered heterocyclyl of $R^b$ is independently optionally substituted with one to three groups independently selected from halo, hydroxyl, cyano, $-NR^{a1}R^{a2}$, $C_{1-4}$alkyl, $C_{1-4}$haloalkyl, and $C_{1-4}$alkoxyl;

each $R^{b1}$ and $R^{b2}$ is independently selected from H, $C_{1-8}$alkyl, $C_{1-8}$haloalkyl, $C_{3-8}$cycloalkyl, $C_{6-10}$aryl, 5-6 membered heteroaryl, and 3-8 membered heterocyclyl;
 each $C_{1-8}$alkyl and $C_{1-6}$haloalkyl of $R^{b1}$ and $R^{b2}$ is optionally substituted with one to two $R^{b5}$; and
 each $C_{3-8}$cycloalkyl, $C_{6-10}$aryl, 5-6 membered heteroaryl, and 3-8 membered heterocyclyl of $R^{b1}$ and $R^{b2}$ is independently optionally substituted with one to three groups independently selected from halo, cyano, hydroxyl, $-NR^{a1}R^{a2}$, $C_{1-8}$alkyl, $C_{1-8}$haloalkyl, $C_{1-6}$alkoxyl, $C_{3-6}$cycloalkyl, $C_{6-10}$aryl, 5-6 membered heteroaryl, and 4-6 membered heterocyclyl;

$R^{b3}$ is $C_{1-4}$alkylene;

$R^{b4}$ is selected from $C_{1-4}$alkyl, $C_{1-4}$haloalkyl, $C_{3-6}$cycloalkyl, $C_{6-10}$aryl, 5-6 membered heteroaryl, and 4-6 membered heterocyclyl; wherein each $C_{1-4}$alkyl, $C_{1-4}$haloalkyl, $C_{3-8}$cycloalkyl, $C_{6-10}$aryl, 5-6 membered heteroaryl, and the 4-6 membered heterocyclyl of $R^{b4}$ is optionally substituted with one to three $R^{b6}$;

each $R^{b5}$ is independently selected from cyano, hydroxyl, $C_{1-4}$alkoxyl, $C_{3-8}$cycloalkyl, $C_{6-10}$aryl, 5-6 membered heteroaryl, and 4-6 membered heterocyclyl; wherein each $C_{3-8}$cycloalkyl, $C_{6-10}$aryl, 5-6 membered heteroaryl, and 4-6 membered heterocyclyl of $R^{b5}$ is optionally substituted with one to three groups independently selected from halo, cyano, hydroxyl, $-NR^{a1}R^{a2}$, $C_{1-4}$alkyl, $C_{1-4}$haloalkyl, $C_{1-4}$alkoxyl, and phenyl; and each $R^{b6}$ is independently selected from halo, cyano, $C_{1-4}$alkyl, $C_{1-4}$haloalkyl, $C_{1-4}$alkoxyl, $C_{3-6}$cycloalkyl, phenyl, 4-6 membered heterocyclyl, and 5-6 membered heteroaryl; wherein each $C_{3-6}$cycloalkyl, 4-6 membered heterocyclyl, and 5-6 membered heteroaryl of $R^{b6}$ is independently optionally substituted with one to three groups independently selected from halo, cyano, $-NR^{a1}R^{a2}$, $C_{1-4}$alkyl, $C_{1-4}$haloalkyl, and $C_{1-4}$ alkoxyl;
or
$R^2$ and $R^3$, $R^3$ and $R^4$, or $R^5$ and $R^6$ together with the atoms to which they are attached may form a $C_{6-10}$aryl, 5-6 membered heteroaryl, $C_{3-6}$cycloalkyl, or 5-6 membered heterocyclyl; wherein each $C_{6-10}$aryl, 5-6 membered heteroaryl, $C_{3-6}$cycloalkyl, or 5-6 membered heterocyclyl is optionally substituted with one to three groups independently selected from halo, cyano, $-NR^{a1}R^{a2}$, $C_{1-6}$alkyl, $C_{1-6}$alkoxyl, $C_{1-6}$haloalkyl, $C_{3-8}$cycloalkyl, 3-6 membered heterocyclyl, $C_{6-10}$aryl, 5-6 membered heteroaryl, $C_{1-4}$alkylene-$C_{3-8}$cycloalkyl, $C_{1-4}$alkylene-$C_{6-10}$aryl, and $C_{1-4}$alkylene-(5-6 membered heteroaryl);

$R^7$ is selected from H, $C_{1-4}$alkyl, and $C_{1-4}$haloalkyl;

$R^8$ is selected from H, $C_{1-4}$alkyl, and $C_{1-4}$haloalkyl;

$R^9$ is selected from H, $C_{1-6}$alkyl, $-C_{1-4}$alkylene-$NR^{a1}R^{a2}$, $-C_{1-4}$alkylene-$C(O)NR^{a1}R^{a2}$, $-C_{1-4}$alkylene-$O-C(O)-C_{1-4}$alkyl, $-C_{1-4}$alkylene-$O-C(O)-O-C_{1-4}$alkyl, $-C_{1-4}$alkylene-$O-C(O)-C_{1-4}$alkylene-$NR^{a1}R^{a2}$, $-C_{1-4}$alkylene-$O-C_{1-4}$alkyl, $C_{3-8}$cycloalkyl, $-C_{1-4}$alkylene-$C_{3-8}$cycloalkyl, 4-6 membered heterocyclyl, and $-C_{1-4}$alkylene-(4-6 membered heterocyclyl);
 wherein each $C_{3-8}$cycloalkyl, $-C_{1-4}$alkylene-$C_{3-8}$cycloalkyl, 4-6 membered heterocyclyl and $-C_{1-4}$alkylene-(4-6 membered heterocyclyl) of $R^9$ is optionally substituted with one to three groups independently selected from halo, $C_{1-4}$alkyl, $C_{1-4}$alkoxyl, and $C_{1-4}$haloalkyl; or $R^9$ together with the N that attaches to $R^8$ forms a 5 membered heterocyclyl; wherein the 5 membered heterocyclyl is optionally substituted with one to two groups independently selected from halo, $C_{1-6}$alkyl, $C_{1-6}$alkoxyl, $C_{1-6}$haloalkyl, and $C_{6-10}$aryl; wherein $C_{6-10}$aryl is optionally substituted with one to three groups independently selected from halo, $C_{1-6}$alkyl, $C_{1-6}$alkoxyl, and $C_{1-6}$haloalkyl;

each $R^{10}$ is independently selected from H, halo, cyano, hydroxyl, $-C(O)R^{b1}$, $-NR^{a1}R^{a2}$, $C_{1-4}$alkyl, $C_{1-4}$alkoxyl, $C_{1-4}$haloalkyl, $C_{1-4}$haloalkoxyl, $C_{3-10}$cycloalkyl, 3-8 membered heterocyclyl, $C_{6-10}$aryl, and 5-6 membered heteroaryl; wherein each $C_{1-4}$alkyl, $C_{1-4}$alkoxyl, $C_{1-4}$haloalkyl, $C_{1-4}$haloalkoxyl, $C_{3-10}$cycloalkyl, 3-8-membered heterocyclyl, $C_{6-10}$aryl, and 5-6 membered heteroaryl is independently optionally substituted with one to three groups independently selected from halo, hydroxyl, cyano, $-NR^{a1}R^{a2}$, $C_{1-4}$alkyl, $C_{1-4}$haloalkyl, $C_{1-4}$alkoxyl, and $C_{3-6}$cycloalkyl;
 or two $R^{10}$ either attached to the same or adjacent atoms form $C_{3-12}$cycloalkyl or 3-10 membered heterocyclyl; wherein each $C_{3-12}$cycloalkyl and 3-10 membered heterocyclyl is optionally substituted with one to three groups independently selected from H, halo, $C_{1-4}$alkyl, $C_{1-4}$alkoxyl, $C_{1-4}$haloalkyl, and $C_{1-4}$haloalkoxyl;

each $R^{11}$ is independently selected from H, $C_{1-4}$alkyl, and $C_{1-4}$haloalkyl; wherein each $C_{1-4}$alkyl, $-C(O)R^{b1}$, and $C_{1-4}$haloalkyl of $R^{11}$ is independently optionally substituted with one to three groups independently selected from halo, hydroxyl, cyano, $-NR^{a1}R^{a2}$, $C_{1-4}$alkyl, $C_{1-4}$haloalkyl, $C_{1-4}$alkoxyl, and $C_{3-6}$cycloalkyl; or $R^{10}$ and $R^{11}$, or two $R^{11}$ together with the atoms to which they are attached to form 3-12 membered heterocyclyl; wherein 3-12 membered heterocyclyl is optionally substituted with one to three groups independently selected from H, halo, $C_{1-4}$alkyl, $C_{1-4}$alkoxyl, $C_{1-4}$haloalkyl, and $C_{1-4}$haloalkoxyl;

each $R^{a1}$ and $R^{a2}$ is independently selected from H, $C_{1-6}$alkyl, and $C_{1-6}$haloalkyl;

n is selected from 1, 2, and 3;

m is selected from 0, 1, and 2; and v is selected from 1 and 2.

In some embodiments, provided is a compound of formula (I), or a pharmaceutically acceptable salt thereof, wherein:

$X^1$ and $X^2$ are each independently selected from $CR^{10}$ and N;

$X^3$ and $X^5$ are each independently selected from $NR^{11}$, O, S, C(O), and $C(R^{10})_2$;

each $X^4$ is independently selected from $NR^{11}$, O, S, C(O), and $C(R^{10})_2$;

$R^1$ is selected from $A^1$, $A^2$, and $A^3$;

$A^1$ is $C_{6-10}$aryl optionally substituted with one to six $R^a$;

$A^2$ is 5-10 membered heteroaryl containing one to five heteroatoms independently selected from S, N, and O, and optionally one or two C(O); wherein $A^2$ is optionally substituted with one to six $R^a$; and $A^3$ is 5-10 membered cycloalkyl or 5-14 membered heterocyclyl; wherein $A^3$ is optionally substituted with one to four $R^a$;
 wherein each $R^a$ is independently selected from halo, cyano, hydroxyl, $C_{1-6}$ alkyl, $C_{2-6}$alkenyl, $C_{2-6}$alkynyl, $C_{1-6}$alkoxyl, $C_{1-6}$haloalkyl, $C_{1-6}$haloalkoxyl, $C_{3-8}$cycloalkyl, and $-O-C_{3-8}$cycloalkyl;
 each $C_{1-6}$alkyl, $C_{2-6}$alkenyl, $C_{2-6}$alkynyl, $C_{1-6}$alkoxyl, $C_{1-6}$haloalkyl, $C_{1-6}$haloalkoxyl, $C_{3-8}$cycloalkyl, and $-O-C_{3-8}$cycloalkyl of $R^a$ is optionally substituted with one to three $R^{a3}$;

wherein each $R^{a3}$ is independently selected from hydroxyl, $C_{1-6}$alkoxyl, $C_{1-6}$haloalkyl, and $C_{1-6}$haloalkoxyl;

each $R^2$ and $R^6$ is independently selected from H, halo, $C_{1-6}$alkyl, and $C_{1-6}$haloalkyl;

each $R^3$ and $R^5$ is H;

$R^4$ is selected from H, halo, $C_{1-6}$alkyl, $C_{1-6}$alkoxyl, $C_{1-6}$haloalkyl, $C_{1-6}$haloalkoxyl, —$NR^{b1}R^{b2}$, —$R^{b3}S(O)_m R^{b4}$, —$S(O)_m R^{b4}$, —$NR^{b1}S(O)_v R^{b4}$, —$COOR^{b1}$, —$CONR^{b1}R^{b2}$, —$NR^{b1}COOR^{b2}$, —$NR^{b1}COR^{b4}$, —$R^{b3}NR^{b1}R^{b2}$, —$S(O)_v NR^{b1}R^{b2}$, $C_{6-10}$aryl, $C_{3-10}$cycloalkyl, 5-6 membered heteroaryl, and 4-10 membered heterocyclyl;

each $C_{1-6}$alkyl, $C_{1-6}$haloalkyl, $C_{1-6}$alkoxyl, and $C_{1-6}$haloalkoxyl of $R^4$ is independently optionally substituted with one to two $R^c$; wherein each $R^c$ is independently selected from cyano, azido, oxo, hydroxyl, —$NR^{a1}R^{a2}$, $C_{1-4}$alkoxyl, $C_{3-6}$cycloalkyl, and 4-6 membered heterocyclyl; and wherein each $C_{3-6}$cycloalkyl, and 4-6 membered heterocyclyl of $R^c$ is independently optionally substituted with one to three groups independently selected from halo, hydroxyl, cyano, —$NR^{a1}R^{a2}$, $C_{1-4}$alkyl, $C_{1-4}$haloalkyl, $C_{1-4}$alkoxyl, and $C_{3-6}$cycloalkyl;

each $C_{6-10}$aryl, $C_{3-10}$cycloalkyl, 5-6 membered heteroaryl, and 4-10 membered heterocyclyl of $R^4$ is independently optionally substituted with one to three $R^b$; wherein each $R^b$ is independently selected from halo, hydroxyl, cyano, —$NR^{a1}R^{a2}$, $C_{1-6}$alkyl, $C_{1-6}$haloalkyl, $C_{1-6}$alkoxyl, $C_{3-6}$cycloalkyl, phenyl, and 4-6 membered heterocyclyl; wherein each $C_{3-6}$cycloalkyl, phenyl, and 4-6 membered heterocyclyl of $R^b$ is optionally substituted with one to two groups independently selected from halo, hydroxyl, cyano, —$NR^{a1}R^{a2}$, $C_{1-4}$alkyl, $C_{1-4}$haloalkyl, and $C_{1-4}$alkoxyl;

each $R^{b1}$ and $R^{b2}$ is independently selected from H, $C_{1-8}$alkyl, $C_{1-8}$haloalkyl, $C_{3-6}$cycloalkyl, phenyl, and 4-6 membered heterocyclyl;

each $C_{1-8}$alkyl and $C_{1-6}$haloalkyl of $R^{b1}$ and $R^{b2}$ is independently optionally substituted with one to two $R^{b5}$; wherein each $R^{b5}$ is independently selected from hydroxyl, $C_{1-4}$alkoxyl, $C_{3-6}$cycloalkyl, phenyl, and 4-6 membered heterocyclyl; wherein each $C_{3-6}$cycloalkyl, phenyl, and 4-6 membered heterocyclyl of $R^{b5}$ is optionally substituted with one to three groups independently selected from halo, cyano, hydroxyl, —$NR^{a1}R^{a2}$, $C_{1-4}$alkyl, $C_{1-4}$haloalkyl, $C_{1-4}$alkoxyl, and phenyl; and each $C_{3-6}$cycloalkyl, phenyl, and 4-6 membered heterocyclyl of $R^{b1}$ and $R^{b2}$ is independently optionally substituted with one to three groups independently selected from halo, hydroxyl, cyano, —$NR^{a1}R^{a2}$, $C_{1-6}$-alkyl, $C_{1-6}$haloalkyl, $C_{1-6}$alkoxyl, $C_{3-6}$cycloalkyl, phenyl, and 4-6 membered heterocyclyl;

$R^{b3}$ is $C_{1-4}$alkylene;

$R^{b4}$ is selected from $C_{1-4}$alkyl, $C_{1-4}$haloalkyl, $C_{3-6}$cycloalkyl, phenyl, and 4-6 membered heterocyclyl; wherein each $C_{3-6}$cycloalkyl, phenyl, and 4-6 membered heterocyclyl of $R^{b4}$ is optionally substituted with one to three $R^{b6}$; wherein each $R^{b6}$ is independently 4-6 membered heterocyclyl, and 5-6 membered heteroaryl; and wherein each $C_{3-6}$cycloalkyl, 4-6 membered heterocyclyl, and 5-6 membered heteroaryl of $R^{b6}$ is independently optionally substituted with one to three groups independently selected from halo, cyano, —$NR^{a1}R^{a2}$, $C_{1-4}$alkyl, $C_{1-4}$haloalkyl, and $C_{1-4}$alkoxyl;

each $R^{a1}$ and $R^{a2}$ is independently selected from H, $C_{1-6}$alkyl, and $C_{1-6}$haloalkyl;

$R^7$ is H;

$R^8$ is H;

$R^9$ is H;

each $R^{10}$ is independently selected from H, halo, $C_{1-4}$alkyl, $C_{1-4}$alkoxyl, $C_{1-4}$haloalkyl, and $C_{1-4}$haloalkoxyl;

or two $R^{10}$ either attached to the same or adjacent atoms form a $C_{3-10}$cycloalkyl; and each $R^{11}$ is independently selected from H, —$C(O)R^{b1}$, $C_{1-4}$alkyl, and $C_{1-4}$haloalkyl, wherein each $C_{1-4}$alkyl and $C_{1-4}$haloalkyl, is independently optionally substituted with one to three groups independently selected from halo, hydroxyl, $C_{1-4}$alkyl, $C_{1-4}$haloalkyl, $C_{1-4}$alkoxyl, and $C_{3-6}$cycloalkyl;

m is selected from 0, 1, and 2;

n is selected from 1, 2, and 3; and v is selected from 1 and 2.

In some embodiments, $R^4$ is selected from H, —$NR^{b1}R^{b2}$, —$NR^{b1}S(O)_v R^{b4}$, and 4-10 membered heterocyclyl containing one to two heteroatoms independently selected from N and O;

the 4-10 membered heterocyclyl of $R^4$ is independently optionally substituted with one to three $R^b$; wherein each $R^b$ is independently selected from halo, $C_{1-6}$alkyl, and $C_{1-6}$haloalkyl;

each $R^{b1}$ and $R^{b2}$ is independently selected from H, $C_{1-8}$alkyl, and $C_{1-8}$haloalkyl;

each $C_{1-8}$alkyl and $C_{1-8}$haloalkyl of $R^{b1}$ and $R^{b2}$ is independently optionally substituted with one to two $R^{b5}$; wherein each $R^{b5}$ is independently selected from $C_{1-4}$alkoxyl, $C_{3-6}$cycloalkyl, phenyl, and 4-6 membered heterocyclyl containing at least one heteroatom selected from N and O; and wherein each $C_{3-6}$cycloalkyl, phenyl, and 4-6 membered heterocyclyl of $R^{b5}$ is optionally substituted with one to three groups independently selected from halo, $C_{1-4}$alkyl, and $C_{1-4}$haloalkyl; and $R^{b4}$ is selected from $C_{1-4}$alkyl, $C_{1-4}$haloalkyl, $C_{3-6}$cycloalkyl, and phenyl; wherein each $C_{3-6}$cycloalkyl and phenyl of $R^{b4}$ is independently optionally substituted with one to three $R^{b6}$; wherein each $R^{b6}$ is independently selected from halo, $C_{1-4}$alkyl, $C_{1-4}$haloalkyl, and 5-6 membered heteroaryl containing one to three heteroatoms independently selected from S, N and O; and wherein each 5-6 membered heteroaryl of $R^{b6}$ is independently optionally substituted with one to three groups independently selected from halo, $C_{1-4}$alkyl, and $C_{1-4}$haloalkyl.

In some embodiments, the ring formed by Y and Z is selected from:

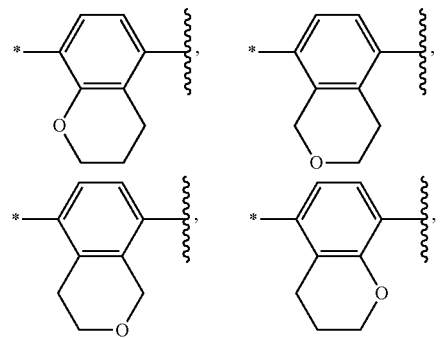

-continued

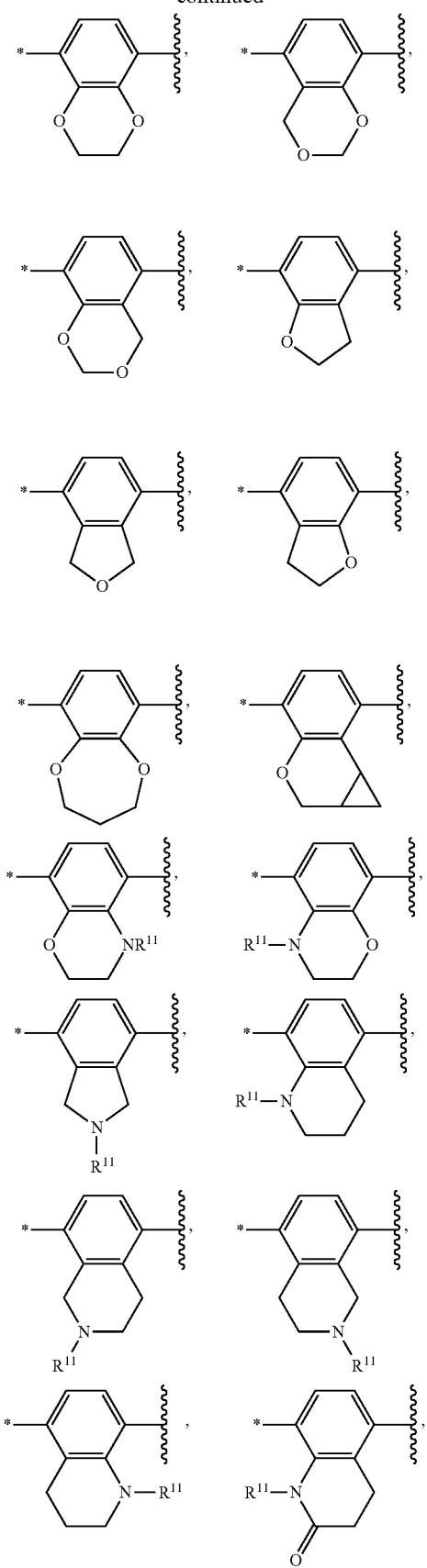

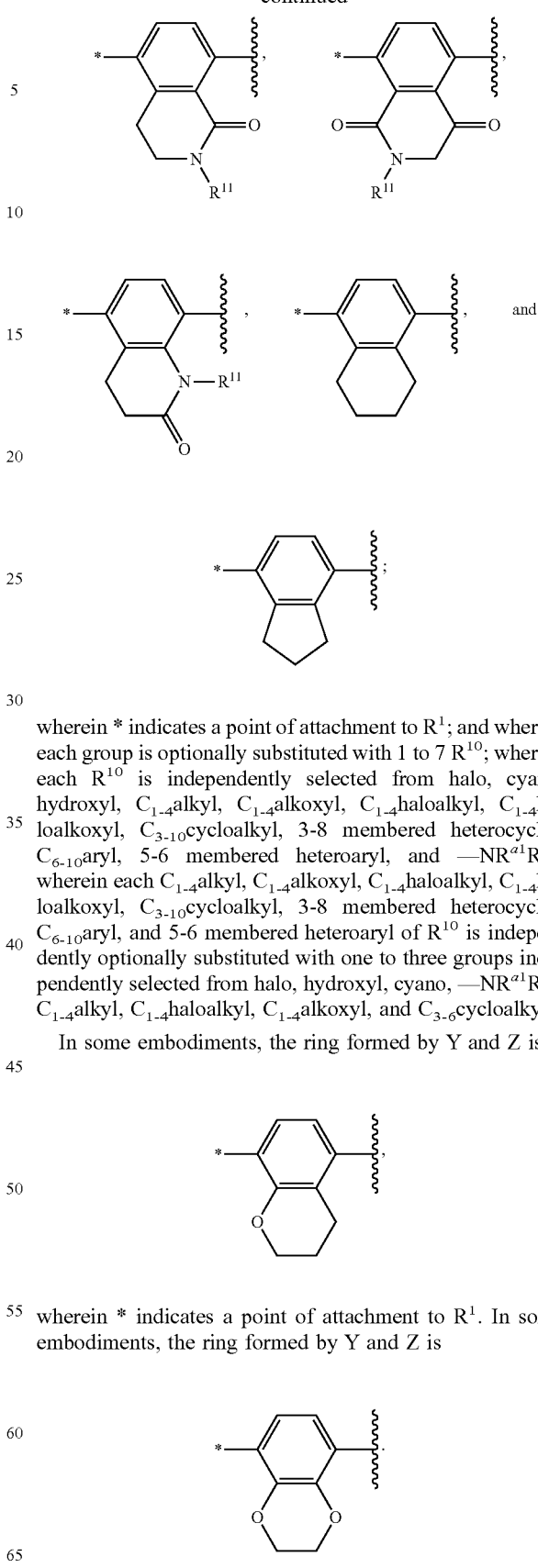

wherein * indicates a point of attachment to $R^1$; and wherein each group is optionally substituted with 1 to 7 $R^{10}$; wherein each $R^{10}$ is independently selected from halo, cyano, hydroxyl, $C_{1-4}$alkyl, $C_{1-4}$alkoxyl, $C_{1-4}$haloalkyl, $C_{1-4}$haloalkoxyl, $C_{3-10}$cycloalkyl, 3-8 membered heterocyclyl, $C_{6-10}$aryl, 5-6 membered heteroaryl, and —$NR^{a1}R^{a2}$; wherein each $C_{1-4}$alkyl, $C_{1-4}$alkoxyl, $C_{1-4}$haloalkyl, $C_{1-4}$haloalkoxyl, $C_{3-10}$cycloalkyl, 3-8 membered heterocyclyl, $C_{6-10}$aryl, and 5-6 membered heteroaryl of $R^{10}$ is independently optionally substituted with one to three groups independently selected from halo, hydroxyl, cyano, —$NR^{a1}R^{a2}$, $C_{1-4}$alkyl, $C_{1-4}$haloalkyl, $C_{1-4}$alkoxyl, and $C_{3-6}$cycloalkyl.

In some embodiments, the ring formed by Y and Z is wherein * indicates a point of attachment to $R^1$. In some embodiments, the ring formed by Y and Z is Also provided are compounds of Formula (Ia):

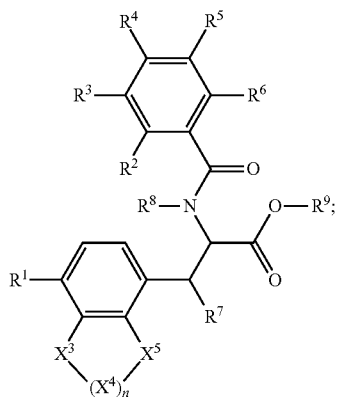

or a pharmaceutically acceptable salt thereof. $X^3$, $X^4$, $X^5$, n, $R^1$, $R^2$, $R^3$, $R^4$, $R^5$, $R^6$, $R^7$, $R^8$, and $R^9$ are defined as above.

Also provided are compounds of Formula (Ib):

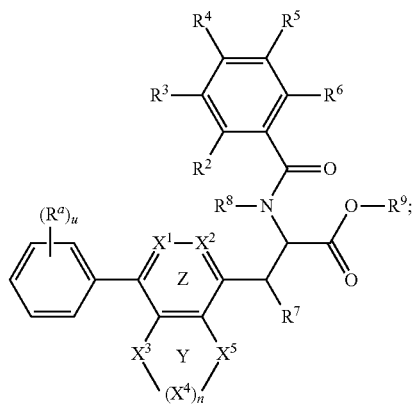

or a pharmaceutically acceptable salt thereof, wherein u is selected from 0, 1, 2, 3, 4, and 5. Y, Z, $X^1$, $X^2$, $X^3$, $X^4$, $X^5$, n, $R^a$, $R^2$, $R^3$, $R^4$, $R^5$, $R^6$, $R^7$, $R^8$, and $R^9$ are defined as above.

Also provided are compounds of Formula (Ic):

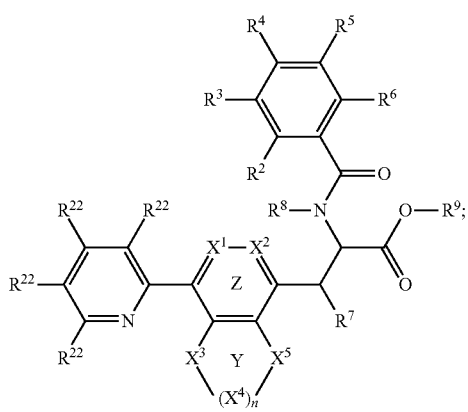

or a pharmaceutically acceptable salt thereof; wherein each $R^{22}$ is independently selected from H and $R^a$. Y, Z, $X^1$, $X^2$, $X^3$, $X^4$, $X^5$, n, $R^a$, $R^2$, $R^3$, $R^4$, $R^5$, $R^6$, $R^7$, $R^8$, and $R^9$ are defined as above.

Also provided are compounds of Formula (Id):

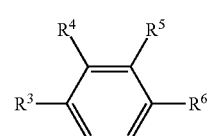
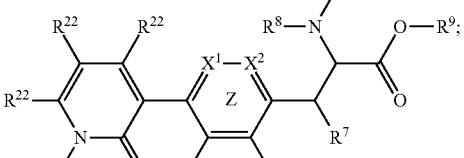

or a pharmaceutically acceptable salt thereof; wherein each $R^{22}$ is independently selected from H and $R^a$. Y, Z, $X^1$, $X^2$, $X^3$, $X^4$, $X^5$, n, $R^a$, $R^2$, $R^3$, $R^4$, $R^5$, $R^6$, $R^7$, $R^8$, and $R^9$ are defined as above.

Also provided are compounds of Formula (Ie):

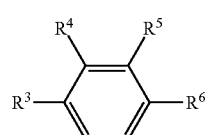
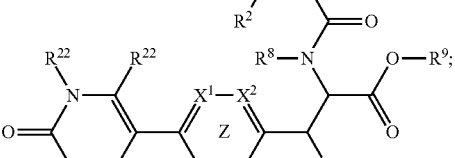

or a pharmaceutically acceptable salt thereof; wherein each $R^{22}$ is independently selected from H and $R^a$. Y, Z, $X^1$, $X^2$, $X^3$, $X^4$, $X^5$, n, $R^a$, $R^2$, $R^3$, $R^4$, $R^5$, $R^6$, $R^7$, $R^8$, and $R^9$ are defined as above.

Also provided are compounds of Formula (If):

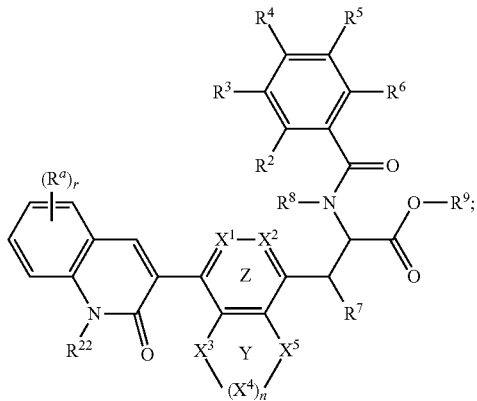

(If)

or a pharmaceutically acceptable salt thereof; wherein each $R^{22}$ is independently selected from H and $R^a$; and wherein r is selected from 0, 1, 2, 3, 4 and 5. Y, Z, $X^1$, $X^2$, $X^3$, $X^4$, $X^5$, n, $R^a$, $R^2$, $R^3$, $R^4$, $R^5$, $R^6$, $R^7$, $R^8$, and $R^9$ are defined as above.

Also provided are compounds of Formula (Ig):

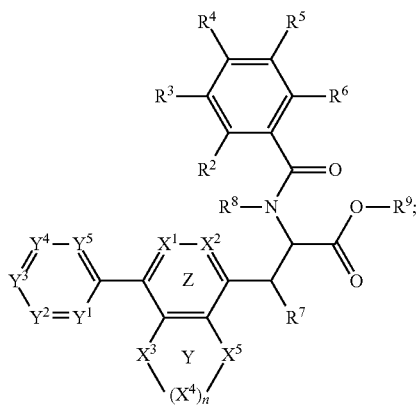

(Ig)

or a pharmaceutically acceptable salt thereof; wherein each $Y^1$, $Y^2$, $Y^3$, $Y^4$, and $Y^5$ is independently selected from $CR^{22}$ and N, provided that at least one of $Y^1$, $Y^2$, $Y^3$, $Y^4$, and $Y^5$ is $CR^{22}$; and wherein $R^{22}$ is selected from H and $R^a$. Y, Z, $X^1$, $X^2$, $X^3$, $X^4$, $X^5$, n, $R^a$, $R^2$, $R^3$, $R^4$, $R^5$, $R^6$, $R^7$, $R^8$, and $R^9$ are defined as above.

Also provided are compounds of Formula (Ih):

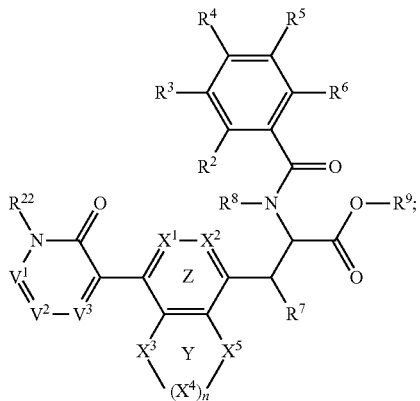

(Ih)

or a pharmaceutically acceptable salt thereof; wherein each $V^1$, $V^2$, and $V^3$ is independently selected from $CR^{22}$ and N, provided that at least one of $V^1$, $V^2$, and $V^3$ is $CR^{22}$; and wherein $R^{22}$ is selected from H and $R^a$. Y, Z, $X^1$, $X^2$, $X^3$, $X^4$, $X^5$, n, $R^a$, $R^2$, $R^3$, $R^4$, $R^5$, $R^6$, $R^7$, $R^8$, and $R^9$ are defined as above.

Also provided are compounds of Formula (Ii):

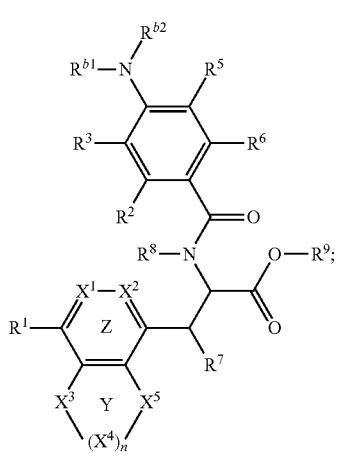

(Ii)

or a pharmaceutically acceptable thereof. $R^{b1}$, $R^{b2}$, Y, Z, $X^1$, $X^2$, $X^3$, $X^4$, $X^5$, n, $R^1$, $R^2$, $R^3$, $R^5$, $R^6$, $R^7$, $R^8$, and $R^9$ are defined as above.

Also provided are compounds of Formula (Ij):

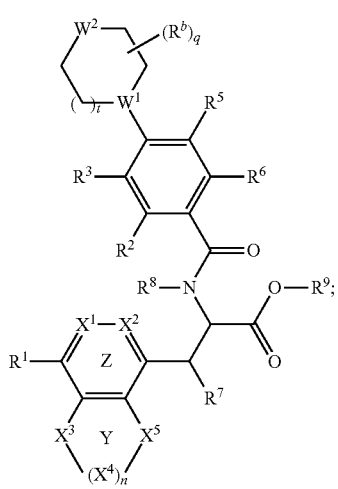

(Ij)

or a pharmaceutically acceptable salt thereof, wherein $W^1$ is selected from $CR^{31}$ and N; $W^2$ is selected from $CR^{31}R^{31}$, $NR^{32}$, O, and $S(O)_2$; each $R^{31}$ is independently selected from H and $R^b$; and $R^{32}$ is selected from H, $C_{1-4}$alkyl, and $C_{1-4}$haloalkyl; q is selected from 0, 1, 2, and 3; and t is 0 or 1. $R^b$, Y, Z, $X^1$, $X^2$, $X^3$, $X^4$, $X^5$, n, $R^1$, $R^2$, $R^3$, $R^5$, $R^6$, $R^7$, $R^8$, and $R^9$ are defined as above.

Also provided are compounds of Formula (Ik):

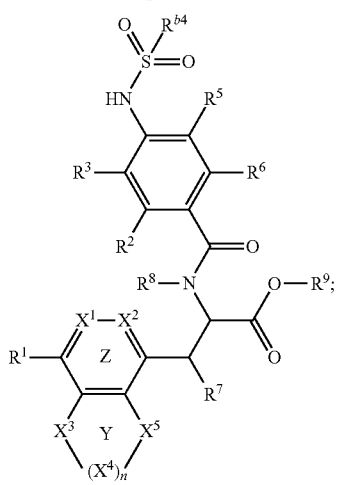

(Ik)

or a pharmaceutically acceptable salt thereof. $R^{b4}$, Y, Z, $X^1$, $X^2$, $X^3$, $X^4$, $X^5$, n, $R^1$, $R^2$, $R^3$, $R^5$, $R^6$, $R^7$, $R^8$, and $R^9$ are defined as above.

Also provided are compounds of Formula (Im):

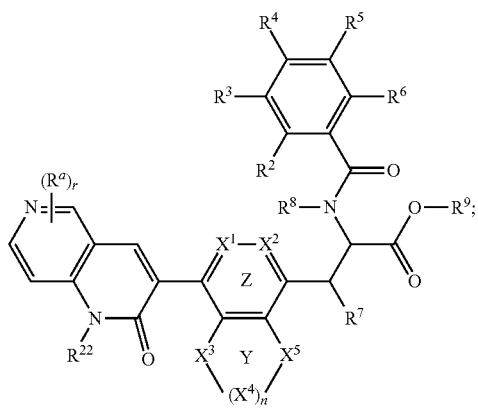

(Im)

or a pharmaceutically acceptable salt thereof. Y, Z, $X^1$, $X^2$, $X^3$, $X^4$, $X^5$, n, $R^a$, $R^2$, $R^3$, $R^4$, $R^5$, $R^6$, $R^7$, $R^8$, $R^9$, $R^{22}$, and r are defined as above.

Also provided are compounds of Formula (II):

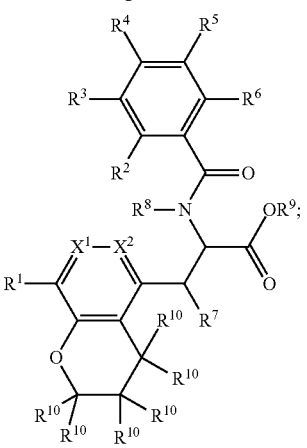

(II)

or a pharmaceutically acceptable salt thereof; wherein $X^1$, $X^2$, $R^1$, $R^2$, $R^3$, $R^4$, $R^5$, $R^6$, $R^7$, $R^8$, $R^9$, and $R^{10}$ are as defined above.

Also provided are compounds of Formula (IIa):


(IIa)

or a pharmaceutically acceptable salt thereof. $R^{b1}$, $R^{b2}$, $R^1$, $R^2$, $R^3$, $R^5$, $R^6$, $R^9$, and $R^{10}$ are as defined above.

Also provided are compounds of Formula (IIb):

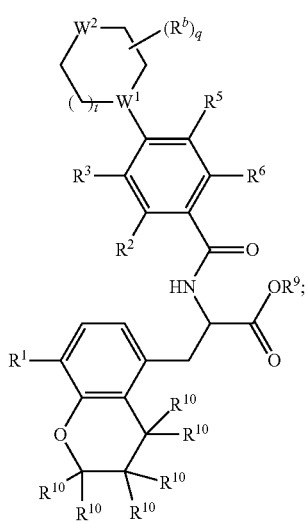

(IIb)

or a pharmaceutically acceptable salt thereof; wherein $W^1$ is selected from $CR^{31}$, and N; $W^2$ is selected from $CR^{31}R^{31}$, $NR^{32}$, O, and $S(O)_2$; each $R^{31}$ is independently selected from H, and $R^b$; $R^{32}$ is selected from H, $C_{1-4}$alkyl, and $C_{1-4}$haloalkyl; q is selected from 0, 1, 2, and 3; and t is 0 or 1. $R^b$, $R^1$, $R^2$, $R^3$, $R^5$, $R^6$, $R^9$, and $R^{10}$ are as defined above.

Also provided are compounds of Formula (IIc):

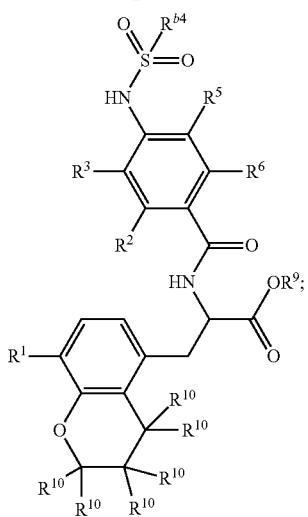
(IIc)

or a pharmaceutically acceptable salt thereof. $R^{b4}$, $R^1$, $R^2$, $R^3$, $R^5$, $R^6$, $R^9$, and $R^{10}$ are as defined above.

Also provided are compounds of Formula (IId):

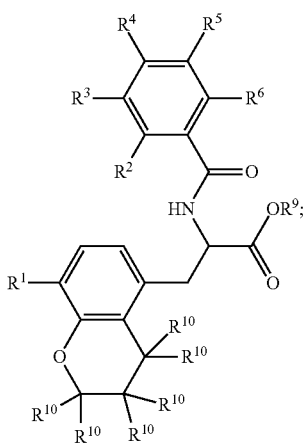
(IId)

or a pharmaceutically acceptable salt thereof. $R^1$, $R^2$, $R^3$, $R^4$, $R^5$, $R^6$, $R^9$, and $R^{10}$ are as defined above.

Also provided are compounds of Formula (III):

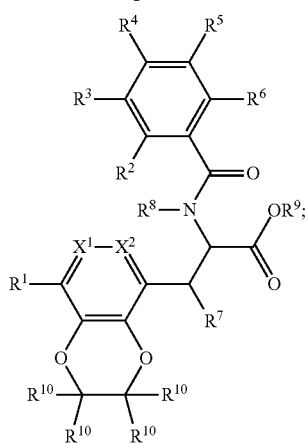
(III)

or a pharmaceutically acceptable salt thereof; wherein $X^1$, $X^2$, $R^1$, $R^2$, $R^3$, $R^4$, $R^5$, $R^6$, $R^7$, $R^8$, $R^9$, and $R^{10}$ are as defined above.

Also provided are compounds of Formula (IIIa):

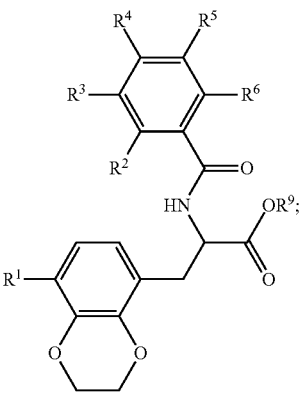
(IIIa)

or a pharmaceutically acceptable salt thereof; wherein $R^1$, $R^2$, $R^3$, $R^4$, $R^5$, $R^6$, and $R^9$ are as defined above.

Also provided are compounds of Formula (IV):

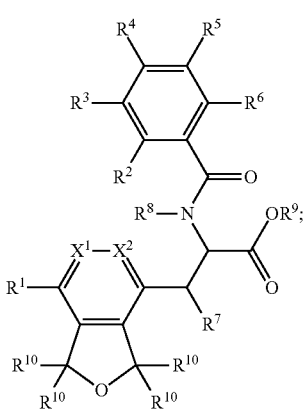
(IV)

or a pharmaceutically acceptable salt thereof; wherein $X^1$, $X^2$, $R^1$, $R^2$, $R^3$, $R^4$, $R^5$, $R^6$, $R^7$, $R^8$, $R^9$, and $R^{10}$ are as defined above.

Also provided are compounds of Formula (V):

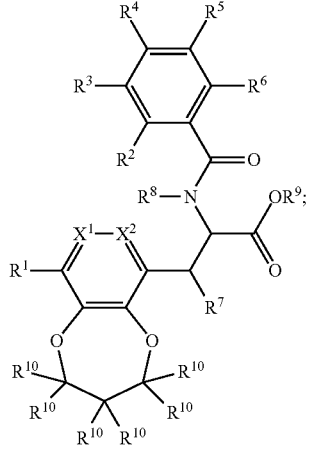
(V)

or a pharmaceutically acceptable salt thereof; wherein $X^1$, $X^2$, $R^1$, $R^2$, $R^3$, $R^4$, $R^5$, $R^6$, $R^7$, $R^8$, $R^9$, and $R^{10}$ are as defined above.

Also provided are compounds of Formula (VI):

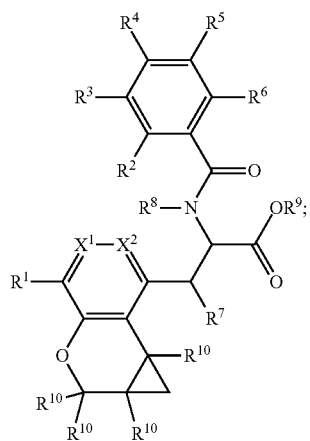

(VI)

or a pharmaceutically acceptable salt thereof; wherein $X^1$, $X^2$, $R^1$, $R^2$, $R^3$, $R^4$, $R^5$, $R^6$, $R^7$, $R^8$, $R^9$, and $R^{10}$ are as defined above.

Also provided are compounds of Formula (VII):

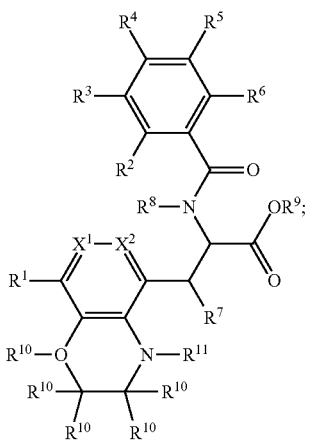

(VII)

or a pharmaceutically acceptable salt thereof; wherein $X^1$, $X^2$, $R^1$, $R^2$, $R^3$, $R^4$, $R^5$, $R^6$, $R^7$, $R^8$, $R^9$, $R^{10}$, and $R^{11}$ are as defined above.

Also provided are compounds of Formula (VIII):

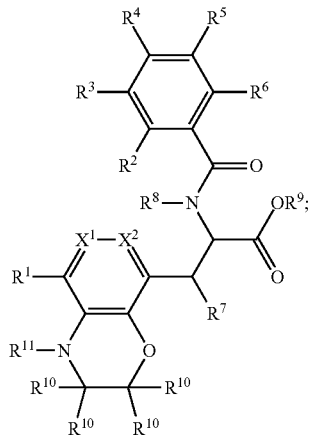

(VIII)

or a pharmaceutically acceptable salt thereof; wherein $X^1$, $X^2$, $R^1$, $R^2$, $R^3$, $R^4$, $R^5$, $R^6$, $R^7$, $R^8$, $R^9$, $R^{10}$, and $R^{11}$ are as defined above.

Also provided are compounds of Formula (IX):

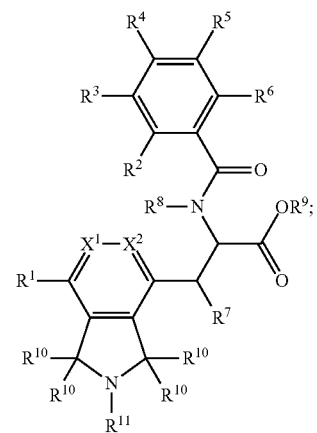

(IX)

or a pharmaceutically acceptable salt thereof; wherein $X^1$, $X^2$, $R^1$, $R^2$, $R^3$, $R^4$, $R^5$, $R^6$, $R^7$, $R^8$, $R^9$, $R^{10}$, and $R^{11}$ are as defined above.

Also provided are compounds of Formula (X):

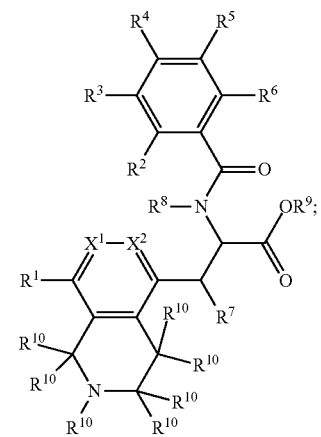

(X)

or a pharmaceutically acceptable salt thereof; wherein $X^1$, $X^2$, $R^1$, $R^2$, $R^3$, $R^4$, $R^5$, $R^6$, $R^7$, $R^8$, $R^9$, $R^{10}$, and $R^{11}$ are as defined above.

Also provided are compounds of Formula (XI):

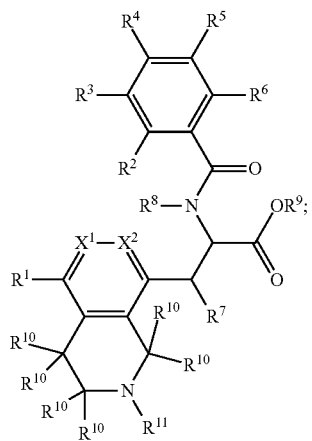

(XI)

or a pharmaceutically acceptable salt thereof; wherein $X^1$, $X^2$, $R^1$, $R^2$, $R^3$, $R^4$, $R^5$, $R^6$, $R^7$, $R^8$, $R^9$, $R^{10}$, and $R^{11}$ are as defined above.

Also provided are compounds of Formula (XII):

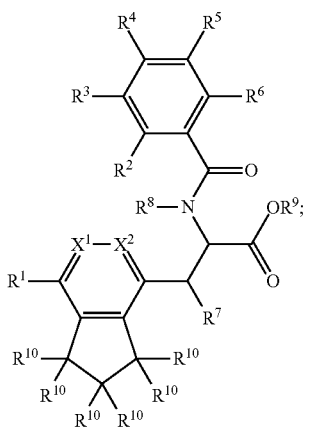

(XII)

or a pharmaceutically acceptable salt thereof; wherein $X^1$, $X^2$, $R^1$, $R^2$, $R^3$, $R^4$, $R^5$, $R^6$, $R^7$, $R^8$, $R^9$, and $R^{10}$ are as defined above.

Also provided are compounds of Formula (XIII):

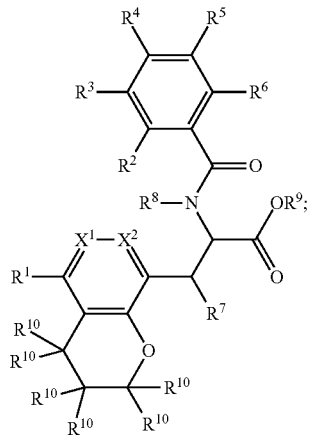

(XIII)

or a pharmaceutically acceptable salt thereof; wherein $X^1$, $X^2$, $R^1$, $R^2$, $R^3$, $R^4$, $R^5$, $R^6$, $R^7$, $R^8$, $R^9$, and $R^{10}$ are as defined above.

Also provided are compounds of Formula (XIV):

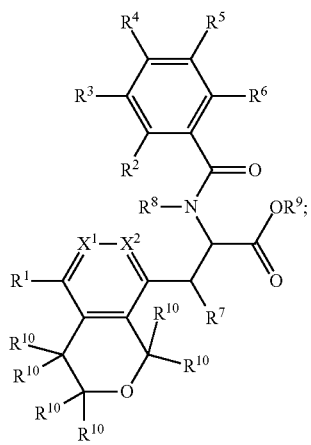

(XIV)

or a pharmaceutically acceptable salt thereof; wherein $X^1$, $X^2$, $R^1$, $R^2$, $R^3$, $R^4$, $R^5$, $R^6$, $R^7$, $R^8$, $R^9$, and $R^{10}$ are as defined above.

Also provided are compounds of Formula (XV):

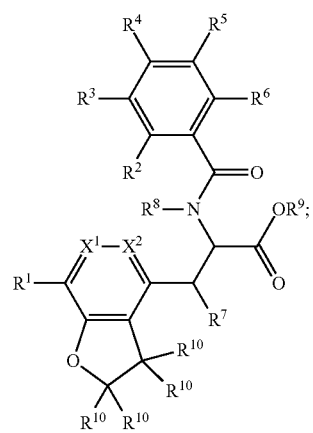

(XV)

or a pharmaceutically acceptable salt thereof; wherein $X^1$, $X^2$, $R^1$, $R^2$, $R^3$, $R^4$, $R^5$, $R^6$, $R^7$, $R^8$, $R^9$, and $R^{10}$ are as defined above.

In some embodiments, each $X^1$ and $X^2$ is independently $CR^{10}$. In some embodiments, $X^1$ is $CR^{10}$ and $X^2$ is N. In some embodiments, $X^1$ is N and $X^2$ is $CR^{10}$. In some embodiments, each $X^1$ and $X^2$ is independently $CR^{10}$ and each $R^{10}$ is independently selected from H, halo, hydroxyl, $C_{1-4}$alkyl, $C_{1-4}$alkoxyl, $C_{1-4}$haloalkyl, and $C_{1-4}$haloalkoxyl, wherein each $C_{1-4}$alkyl, $C_{1-4}$alkoxyl, $C_{1-4}$haloalkyl, $C_{1-4}$haloalkoxyl is independently optionally substituted with one to three groups independently selected from halo, hydroxyl, cyano, $-NR^{a1}R^{a2}$, $C_{1-4}$alkyl, $C_{1-4}$haloalkyl, $C_{1-4}$alkoxyl, and $C_{3-6}$cycloalkyl. In some embodiments, each $X^1$ and $X^2$ is independently $CR^{10}$ and each $R^{10}$ is independently selected from H, F, Cl, cyano, hydroxyl, $-CH_3$, $-CH_2F$, $-CHF_2$, $-CF_3$, $-OCH_3$, and $-OCF_3$.

In some embodiments, $X^3$, $X^4$, and $X^5$ are each independently selected from O, $NR^{11}$, S, and $C(R^{10})_2$, provided that at least one of $X^3$, $X^4$, and $X^5$ is $C(R^{10})_2$.

In some embodiments, two $R^{10}$ form cyclopropyl fused to Y ring. In some embodiments, two $R^{10}$ form 7-8 membered bridged cycloalkyl or heterocyclyl. In some embodiments, $R^{10}$ and $R^{11}$ form 7-8 membered bridged cycloalkyl or heterocyclyl.

In some embodiments, each $X^1$ and $X^2$ is CH.

In some embodiments, L is a bond and $R^1$ is selected from $-L-A^1$, $-L-A^2$, and $-L-A^3$. In some embodiments, when $R^1$ is $-L-A^4$, then L is a bond.

In some embodiments, $A^1$, $A^2$, or $A^3$ is selected from phenyl, naphthyl, pyridinyl, pyridazinyl, pyrazinyl, pyrimidinyl, quinolinyl, isoquinolinyl, isoxazolyl, triazolyl, pyrazolyl, benzothiazolyl, pyridinonyl, quinolinonyl, isoquinolinonyl, quinazolindionyl, pyrazinonyl, pyrimidinonyl, pyrimidinedionyl, pyridazinonyl, quinazolinonyl, benzofuranyl, tetrahydrocyclopenta[b]pyridinonyl, naphthyridinonyl, chromanyl, isochromanyl, and chromenonyl, and wherein each of which is independently optionally substituted with one to four $R^a$.

In some embodiments, $R^1$ is

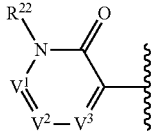

wherein each $V^1$, $V^2$, and $V^3$ is independently selected from $CR^{22}$ and N, provided that at least one of $V^1$, $V^2$, and $V^3$ is $CR^{22}$; and wherein $R^{22}$ is selected from H, and $R^a$.

In some embodiments, $R^1$ is

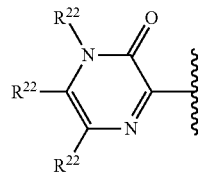

wherein $R^{22}$ is selected from H, and $R^a$.

In some embodiments, $R^1$ is

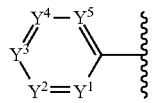

wherein each of $Y^1$, $Y^2$, $Y^3$, $Y^4$, and $Y^5$ is independently selected from $CR^{22}$, and N, provided that at least one of $Y^1$, $Y^2$, $Y^3$, $Y^4$, and $Y^5$ is $CR^{22}$; and wherein $R^{22}$ is selected from H, and $R^a$.

In some embodiments, $R^1$ is

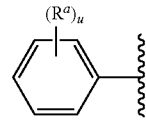

wherein u is selected from 0, 1, 2, 3, 4, and 5.

In some embodiments, $R^1$ is

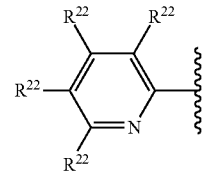

wherein $R^{22}$ is selected from H, and $R^a$.

In some embodiments, $R^1$ is

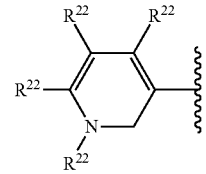

wherein $R^{22}$ is selected from H, and $R^a$.

In some embodiments, $R^1$ is

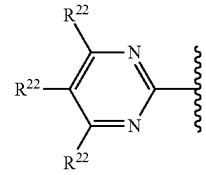

wherein $R^{22}$ is selected from H, and $R^a$.

In some embodiments, $R^1$ is

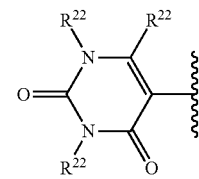

wherein $R^{22}$ is selected from H, and $R^a$.

In some embodiments, $R^1$ is
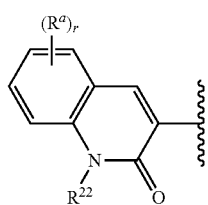
wherein r is selected from 0, 1, 2, 3, 4 and 5, and $R^{22}$ is selected from H, and $R^a$.
In some embodiments, $R^1$ is selected from
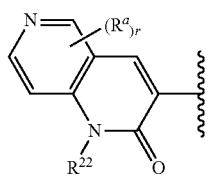
wherein r is selected from 0, 1, 2, 3, 4 and 5, and $R^{22}$ is selected from H, and $R^a$.
In some embodiments, $R^1$ is selected from:
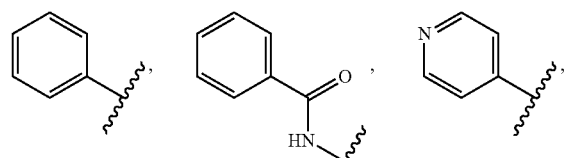
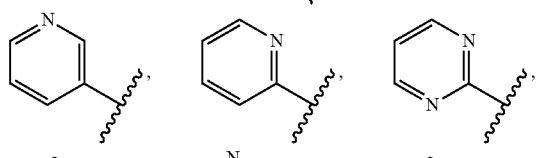
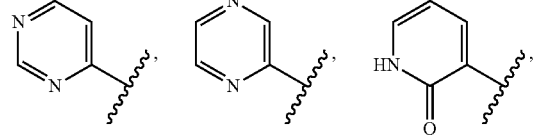
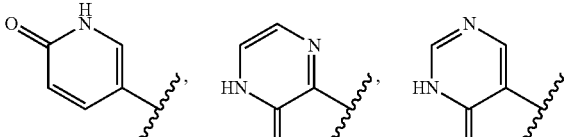
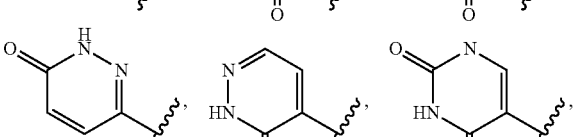
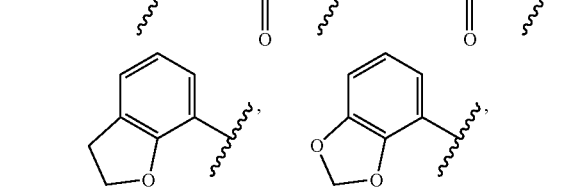
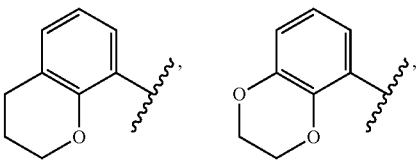
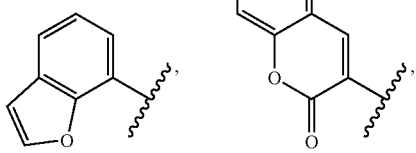
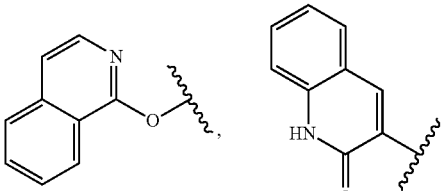
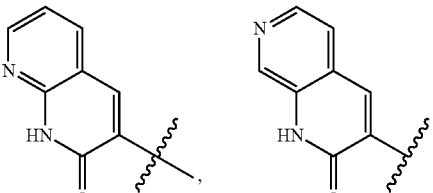
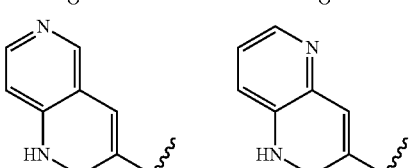
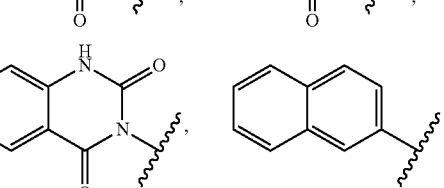
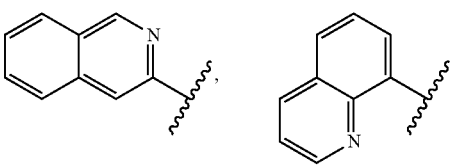
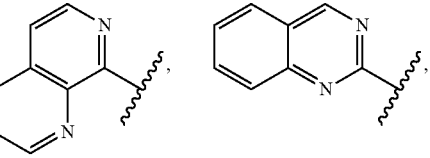
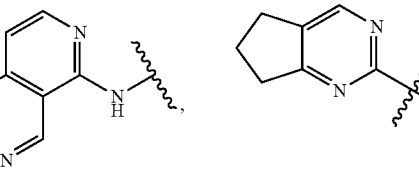

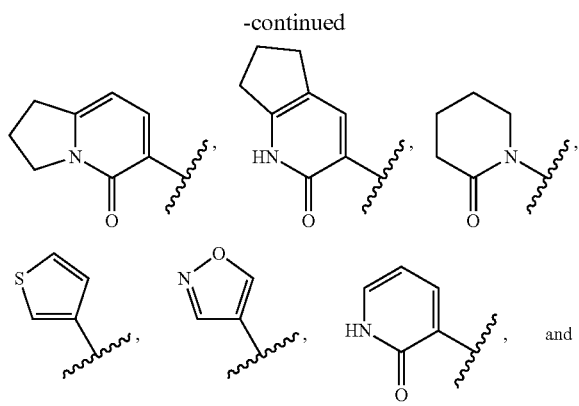

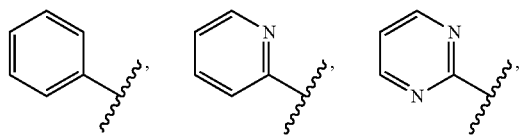

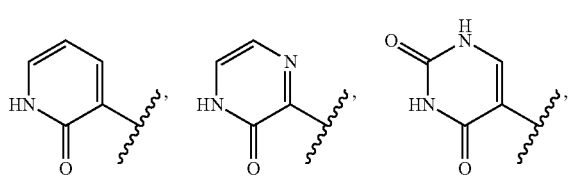

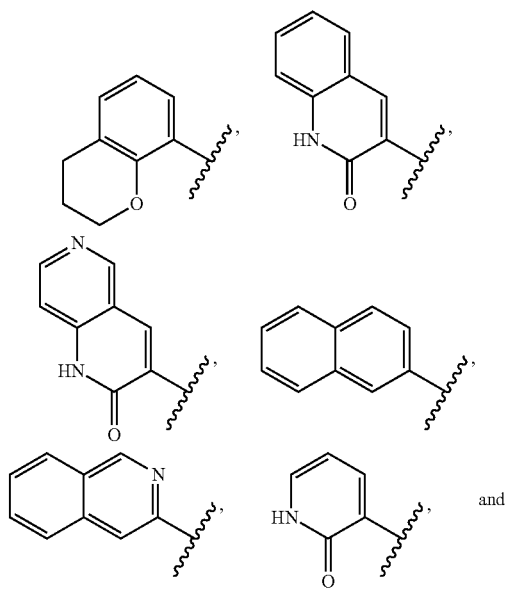

wherein each R¹ is optionally substituted with one to four Rᵃ.

In some embodiments, R¹ is selected from

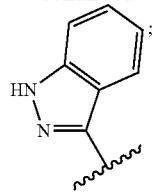

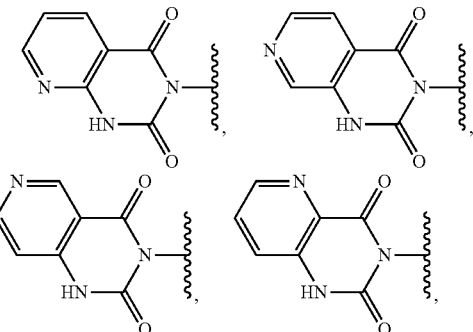

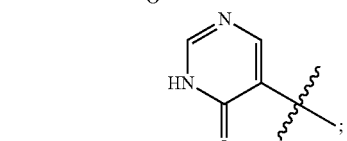

wherein each R¹ is optionally substituted with one to four Rᵃ.

In some embodiments, R¹ is selected from each R¹ is optionally substituted with one to four Rᵃ. In some embodiments, each Rᵃ is independently selected from halo, CN, —OH, NR^{a1}R^{a2}, C_{1-4}alkyl, C_{1-4}alkoxyl, C_{1-4}haloalkyl, C_{1-4}haloalkoxyl, C_{3-6}cycloalkyl, —O—C_{3-6}cycloalkyl, and phenyl. In some embodiments, each Rᵃ is independently selected from F, Cl, OH, CN, —NH₂, —NH(CH₃), —N(CH₃)₂, —CH₃, —CH₂F, —CHF₂, —CF₃, —OCH₃, and —OCF₃. In some embodiments, each Rᵃ is independently selected from F, Cl, —N(CH₃)₂, —CH₃, —OCH₃, and —CF₃.

In some embodiments, R¹ is substituted with one to four Rᵃ, and each Rᵃ is independently selected from halo, cyano, hydroxyl, —NR^{a1}R^{a2}, C_{1-4}alkyl, C_{2-6}alkenyl, C_{2-6}alkynyl, C_{1-4}alkoxyl, C_{1-4}haloalkyl, C_{1-4}haloalkoxyl, —S(O)₂—C_{1-6}alkyl, C_{3-6}cycloalkyl, 3-6 membered heterocyclyl, —O—C_{3-6}cycloalkyl, —O-(3-6 membered heterocyclyl), and phenyl. In some embodiments, each Rᵃ is independently selected from halo, cyano, hydroxyl, —NR^{a1}R^{a2}, C_{1-4}alkyl, C_{1-4}alkoxyl, C_{1-4}haloalkyl, C_{1-4}haloalkoxyl, C_{3-6}cycloalkyl, phenyl, and —O—C_{3-6}cycloalkyl.

In some embodiments, R¹ is substituted with one to three Rᵃ, and each Rᵃ is independently selected from F, Cl, Br, cyano, hydroxyl, —NH₂, —N(CH₃)₂, —CH₃, —CH₂CH₃, —CH(CH₃)₂, —C(CH₃)₃, —CH₂CN, —CH₂CH₂CN, —CH₂OH, —CH₂CH₂OH, —OCH₃, —OCD₃, —OCH₂CH₃, —OCH(CH₃)₂, —OC(CH₃)₃, —CH₂OCH₃, —CH₂OCH₂CH₃, —CH₂OCH(CH₃)₂, —CH₂F, —CHF₂, —CF₃, —CH₂CH₂F, —CH₂CHF₂, —CH₂CF₃, —OCH₂F, —OCHF₂, —OCF₃, —OCH₂CH₂F, —OCH₂CHF₂, —OCH₂CF₃, —SO₂CH₃, —SO₂CH₂CH₃,

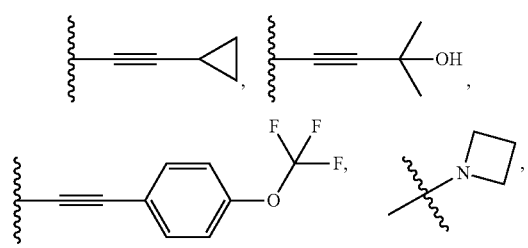
cyclopropyl, cyclobutyl, cyclopentyl, cyclohexyl, phenyl, —O-cyclopropyl, —O—CH$_2$-cyclopropyl, —O-cyclobutyl, —O—CH$_2$cyclobutyl, —O-cyclopentyl, —O—CH$_2$cyclopentyl, —O-cyclohexyl, —O—CH$_2$cyclohexyl, and —O-phenyl.
In some embodiments, R$^1$ is selected from
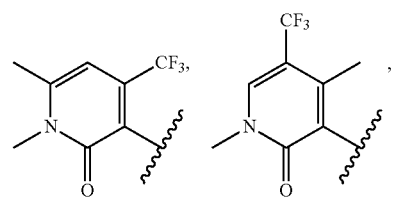
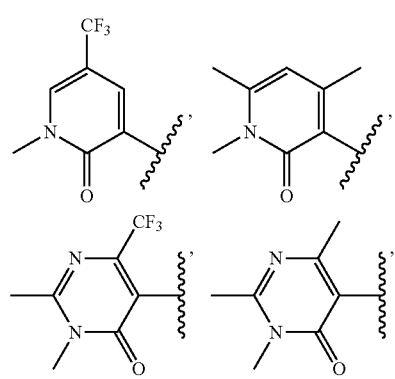
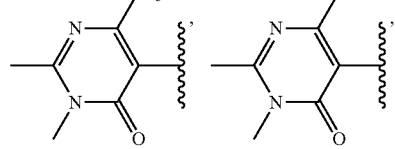
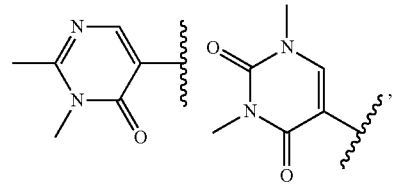
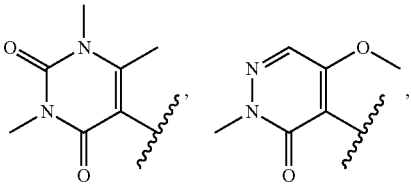
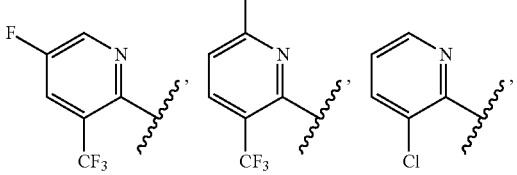
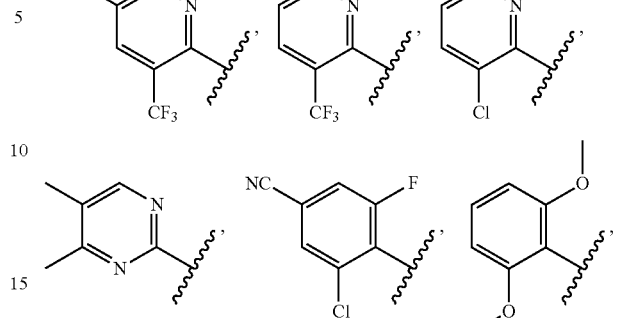
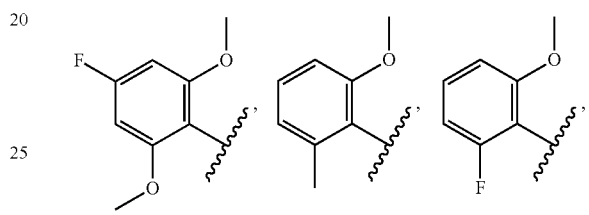
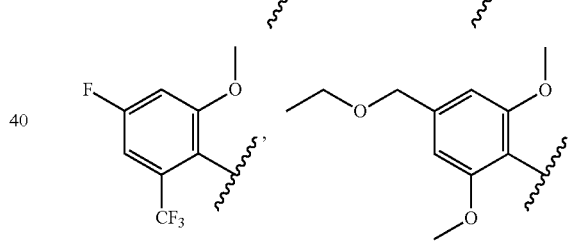
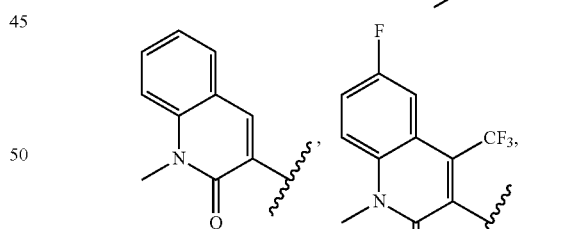
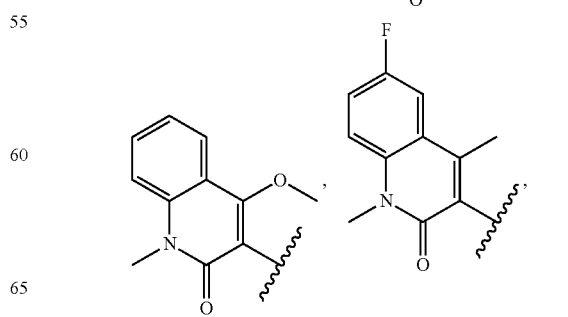

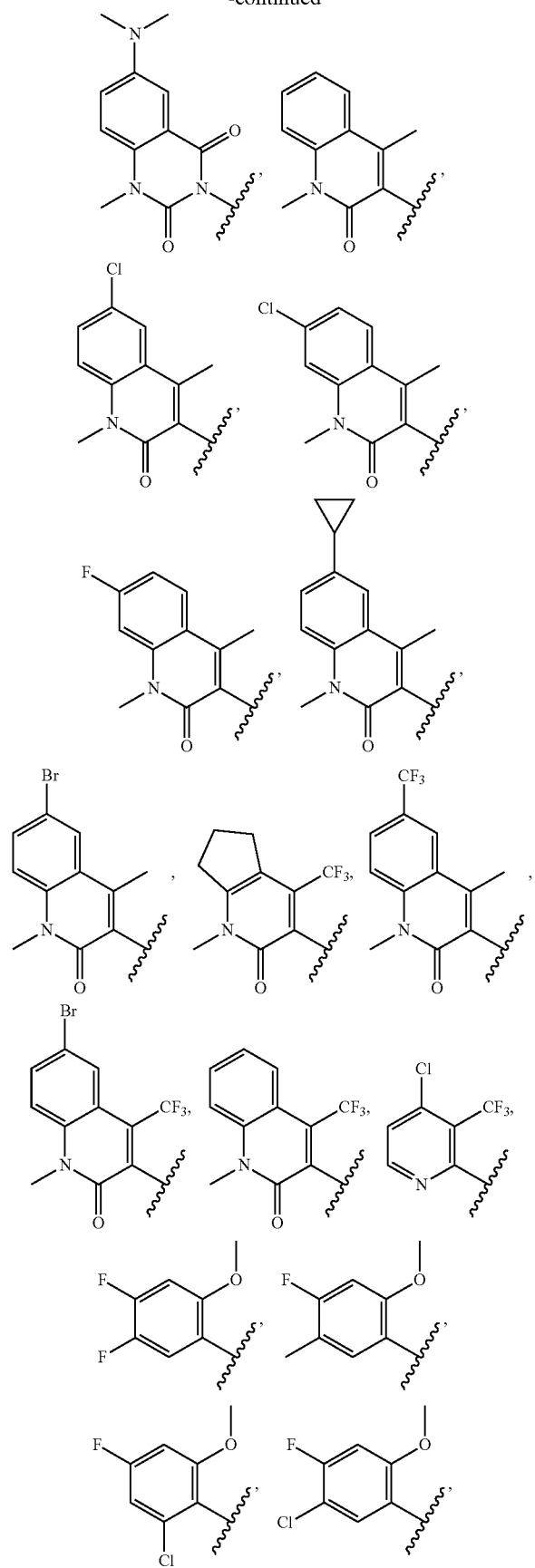
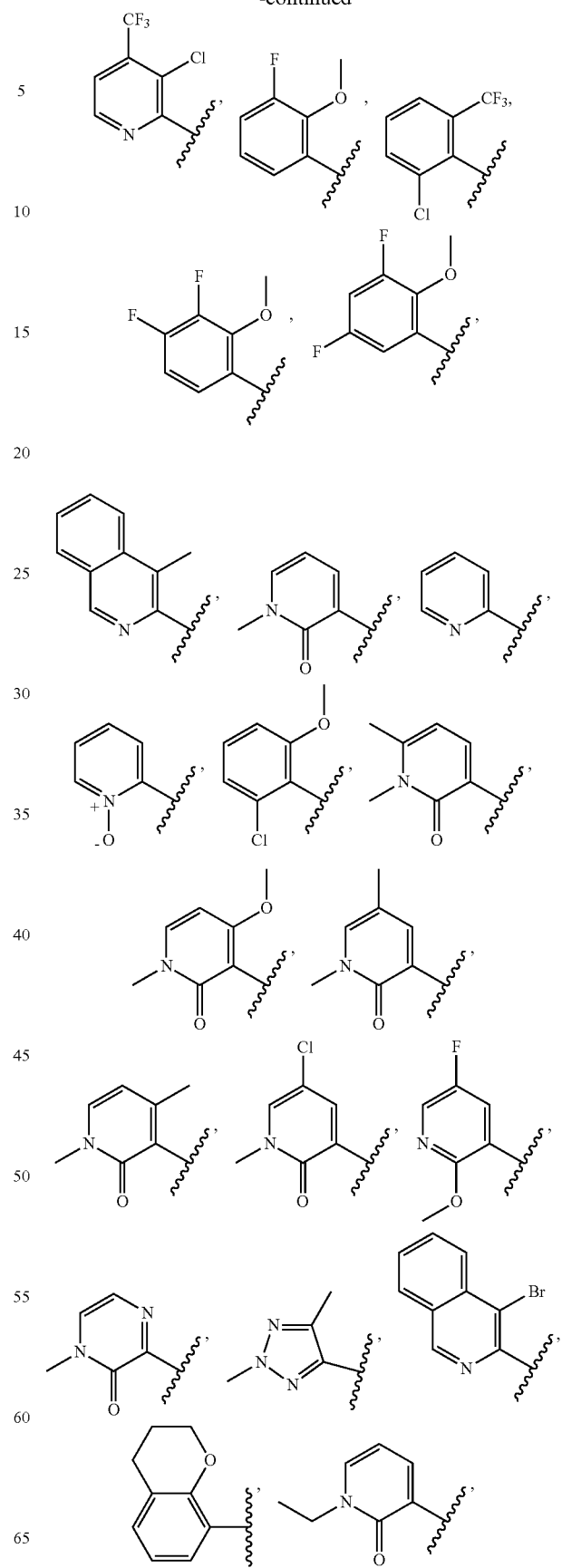

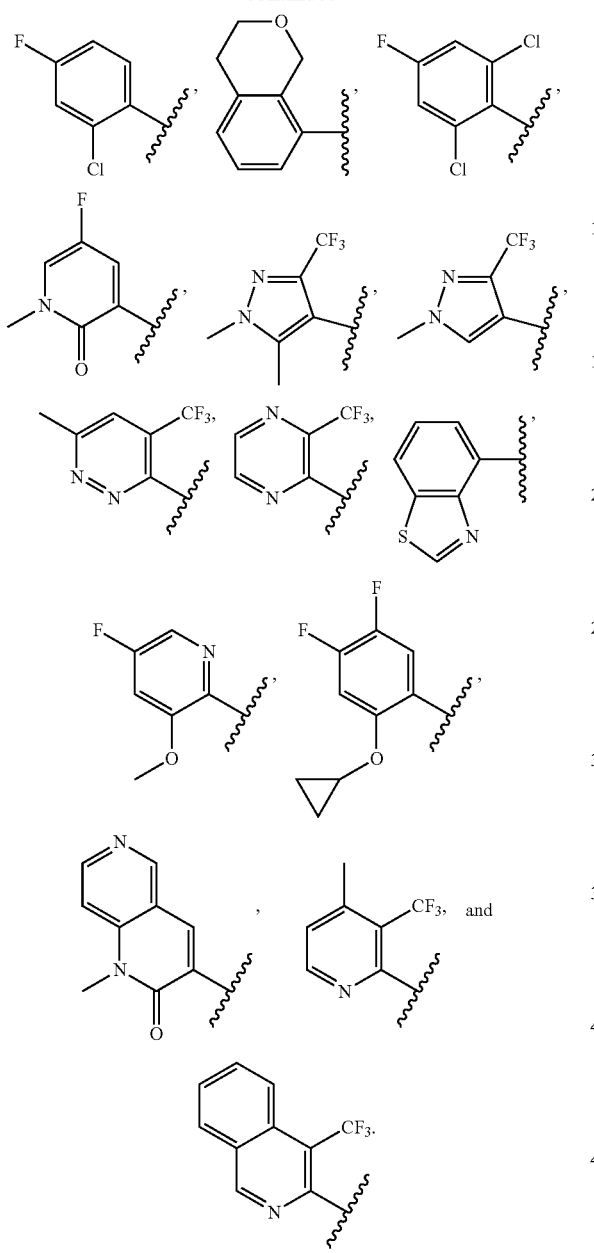
In some embodiments, $R^1$ is selected from
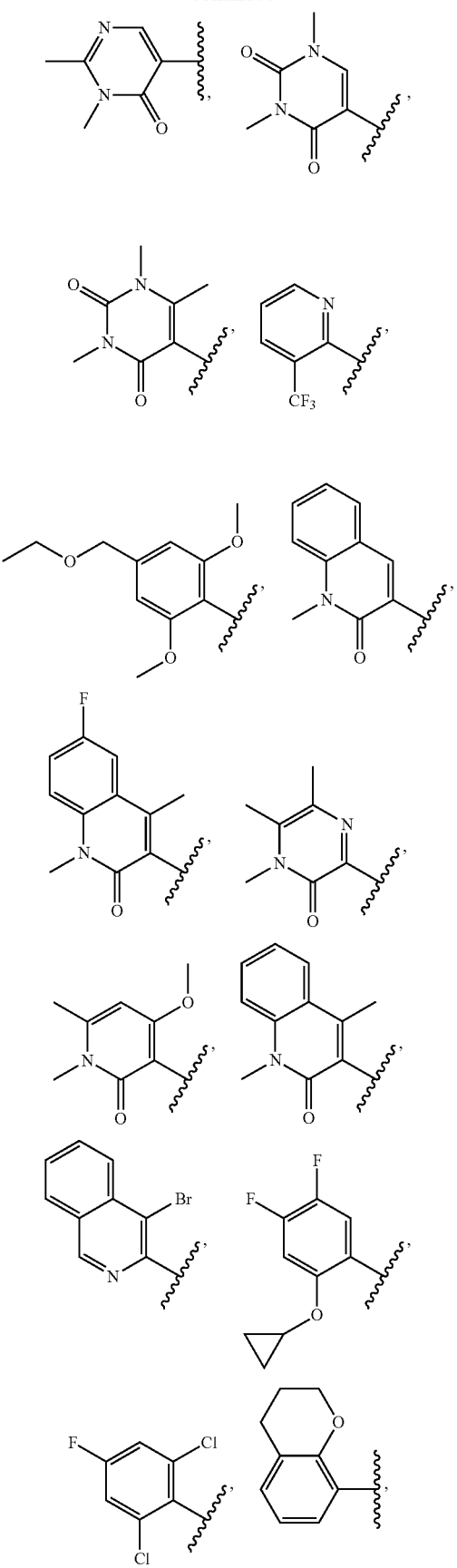

-continued

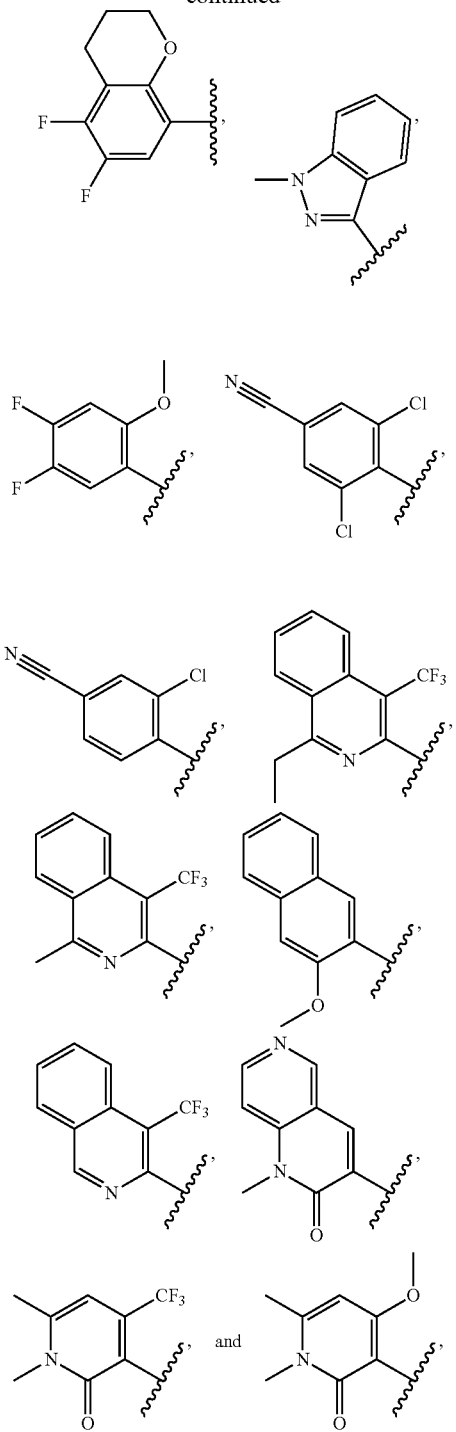

In some embodiments, $R^1$ is selected from:

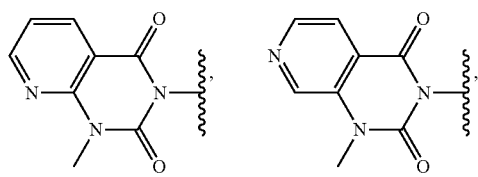

-continued

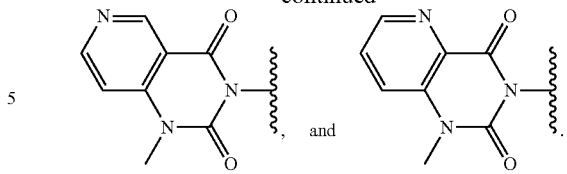, and 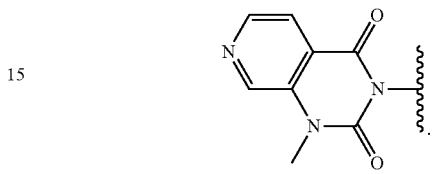.

In some embodiments, $R^1$ is

[structure]

In some embodiments, each $R^a$ is selected from halo, cyano, $C_{1-6}$alkyl, $C_{1-6}$alkoxyl, $C_{1-6}$haloalkyl, $C_{1-6}$haloalkoxyl, $C_{3-8}$cycloalkyl, and —O—$C_{3-8}$cycloalkyl. In some embodiments, each $R^a$ is selected from F, Cl, Br, cyano, —$CH_3$, —$CH_2CH_3$, —$CH_2F$, —$CHF_2$, —$CF_3$, —$OCH_3$, —$OCD_3$, —$OCH_2CH_3$, $OCF_3$, —$CH_2OCH_3$, —$CH_2OCH_2CH_3$, cyclopropyl, and —O-cyclopropyl.

In some embodiments, each $R^2$ and $R^6$ is independently selected from H, halo, cyano, hydroxyl, —$NR^{b1}R^{b2}$, $C_{1-4}$alkyl, $C_{1-4}$alkoxyl, $C_{1-4}$haloalkyl, and $C_{1-4}$haloalkoxyl. In some embodiments, each $R^2$ and $R^6$ is independently selected from F, Cl, cyano, hydroxyl, —$CH_3$, —$CD_3$, —$CH_2CH_3$, —$CH(CH_3)_2$, —$C(CH_3)_3$, cyclopropyl, —$OCH_3$, —$OCH_2CH_3$, —$CH_2F$, —$CHF_2$, —$CF_3$, —$CH_2CH_2F$, —$CH_2CHF_2$, —$CH_2CF_3$, —$NH_2$, and —$N(CH_3)_2$. In some embodiments, each $R^2$ and $R^6$ is independently selected from —$CH_3$, —$CD_3$, F, and Cl. In some embodiments, each $R^2$ and $R^6$ is independently F or Cl. In some embodiments, each $R^2$ and $R^6$ is F. In some embodiments, each $R^2$ and $R^6$ is Cl.

In some embodiments, each $R^3$ and $R^5$ is independently selected from H, $C_{1-4}$alkyl, $C_{1-4}$alkoxyl, $C_{1-4}$haloalkyl, and $C_{1-4}$haloalkoxyl. In some embodiments, each $R^3$ and $R^5$ is H.

In some embodiments, $R^4$ is selected from H, —$NR^{b1}R^{b2}$, —$NR^{b1}S(O)_xR^{b4}$, and 4-6 membered heterocyclyl containing one to two heteroatoms or groups independently selected from N, O, S, and $S(O)_2$.

In some embodiments, $R^4$ is —$NR^{b1}R^{b2}$. In some embodiments, $R^4$ is —$NHR^{b2}$, wherein $R^{b2}$ is selected from $C_{1-6}$alkyl, $C_{1-6}$haloalkyl, $C_{3-6}$cycloalkyl, and 4-6 membered saturated or partially unsaturated heterocyclyl.

In some embodiments each $R^{b1}$ and $R^{b2}$ is independently selected from H, $C_{1-8}$alkyl, $C_{1-6}$haloalkyl, $C_{3-6}$cycloalkyl, phenyl, and 4-6 membered heterocyclyl containing one to two atoms independently selected from N and O. In some embodiments, $R^{b1}$ is selected from H, and $C_{1-4}$alkyl. In some embodiments, $R^{b1}$ is selected from H, and $CH_3$. In some embodiments, $R^{b2}$ is selected from $C_{1-6}$alkyl, $C_{1-6}$haloalkyl, and 4-6 membered heterocyclyl. In some embodiments, $R^{b1}$ is H, and $R^{b2}$ is selected from $C_{1-6}$alkyl, $C_{1-6}$haloalkyl, and 5-6 membered heterocyclyl. In some embodiments, $R^{b1}$ is H, and $R^{b2}$ is $C_{1-6}$haloalkyl. In some embodiments, $R^{b2}$ is —$C_{1-5}$alkylene-$CF_3$. In some embodiments, $R^{b2}$ is selected from -methylene-$CF_3$, -ethylene-$CF_3$, -propylene-$CF_3$, -butylene-$CF_3$, and -pentylene-$CF_3$. In some embodiments, $R^{b2}$ is —$C_{1-5}$alkylene-$CF_3$ substituted with one or two $R^{b5}$. In some embodiments, each $R^{b5}$ is independently selected from hydroxyl, $C_{1-4}$alkoxyl, $C_{3-6}$cycloalkyl, phenyl, and 4-6 membered heterocyclyl. In some embodiments, each $R^{b5}$ is independently selected from $C_{3-6}$cycloalkyl, 4-6 membered heterocyclyl, and phenyl. Each $C_{3-6}$cycloalkyl, 4-6 membered heterocyclyl, and phenyl of $R^{b5}$ is independently optionally substituted with one or three groups independently selected from halo, hydroxyl, cyano, —$NR^{b1}R^{b2}$, $C_{1-4}$alkyl, $C_{1-4}$alkoxyl, and $C_{1-4}$haloalkyl. In some embodiments, $R^{b5}$ is selected from phenyl, cyclobutyl, cyclopentyl, tetrahydropyranyl, and tetrahydrofuranyl; and each $R^{b5}$ is optionally substituted with one group selected from F, Cl, CN, —$CH_3$, —$CH_2F$, —$CHF_2$, and —$CF_3$. In some embodiments, $R^{b5}$ is phenyl. In some embodiments, $R^{b5}$ is phenyl substituted with one or two groups independently selected from F, Cl, CN, —$CH_3$, —$CH_2F$, —$CHF_2$, and —$CF_3$. In some embodiments, $R^{b5}$ is phenyl substituted with one or two groups independently selected from F, Cl, CN, and —$CF_3$. In some embodiments, $R^{b5}$ is unsubstituted phenyl.

In some embodiments, $R^4$ is H.

In some embodiments, $R^4$ is selected from

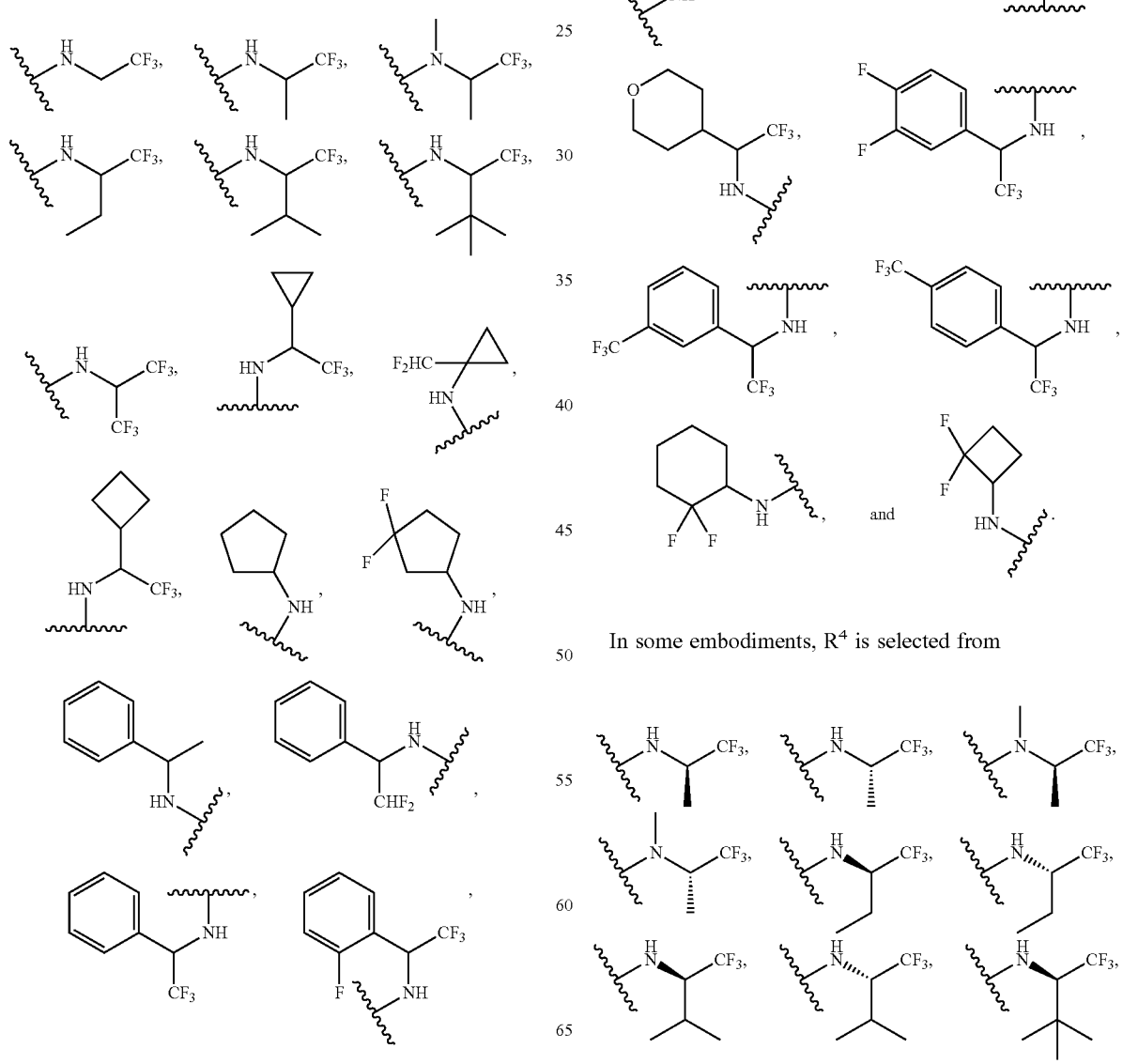

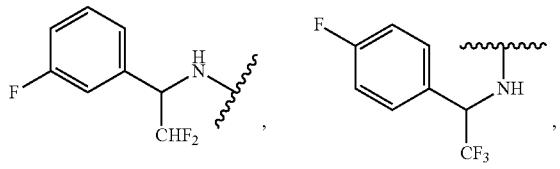

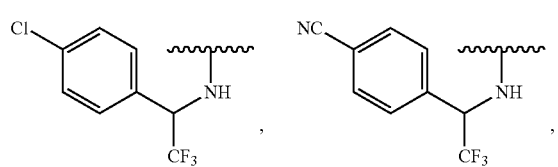

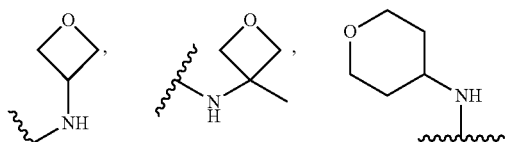

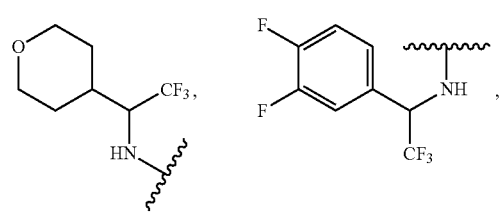

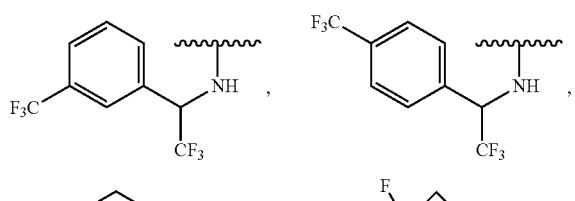

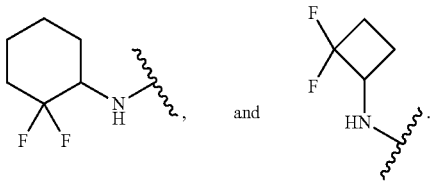

In some embodiments, $R^4$ is selected from

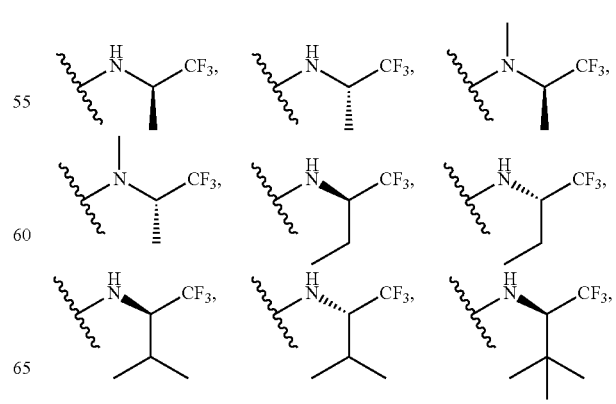

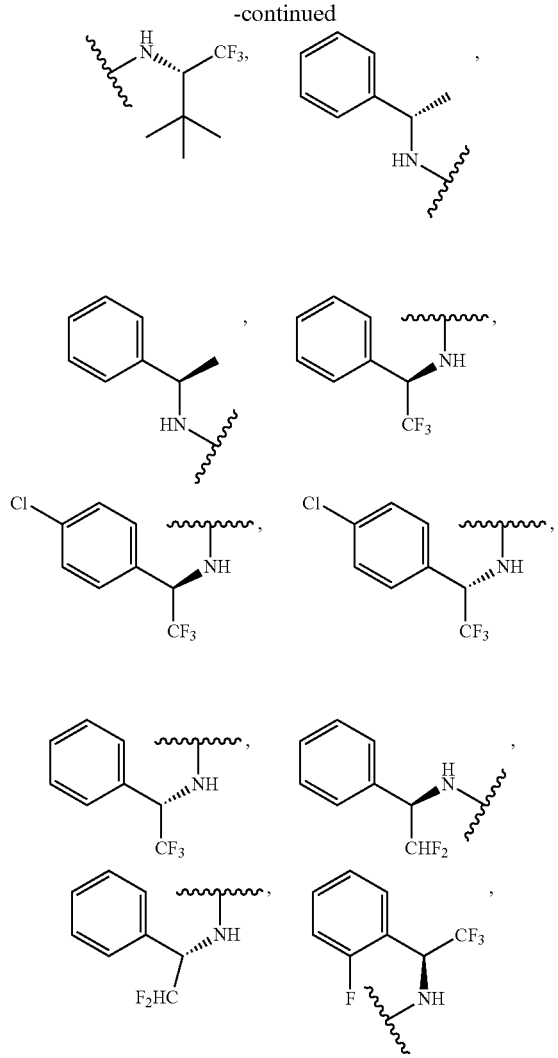

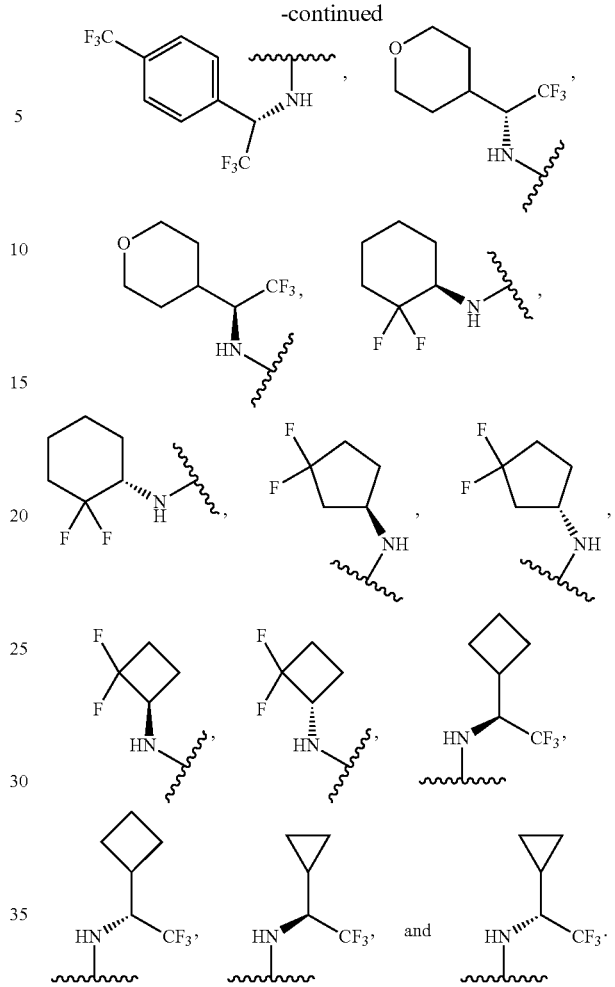

In some embodiments, R⁴ is selected from

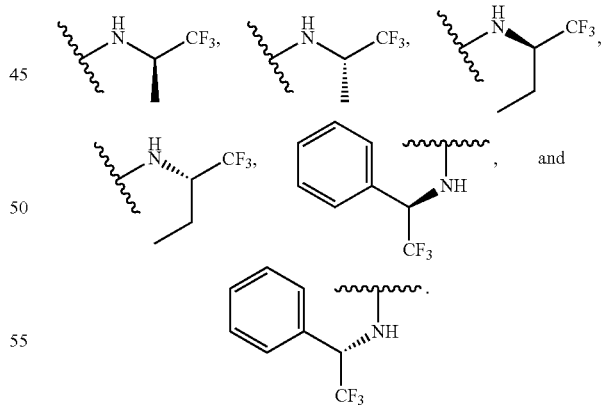

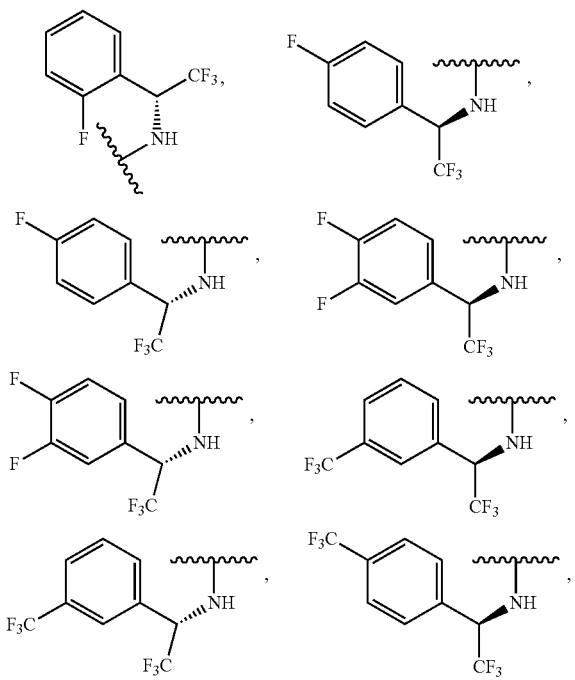

In some embodiments, R⁴ is 5-6 membered heterocyclyl optionally substituted with one to three $R^b$; and each $R^b$ is independently selected from halo, hydroxyl, cyano, —$NR^{a1}R^{a2}$, $C_{1-4}$alkyl, $C_{1-4}$alkoxyl, and $C_{1-4}$haloalkyl.

In some embodiments, R⁴ is 4-6 membered heterocyclyl containing one to two heteroatoms or groups independently selected from N, O, S, and $S(O)_2$. In some embodiments, R⁴ is a 4-10 membered saturated ring

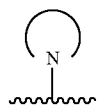 [SMILES: *N]

containing zero to two additional heteroatoms or groups independently selected from N, O, S, and S(O)$_2$.

In some embodiments, R$^4$ is selected from morpholinyl, piperidinyl, tetrahydropyranyl, and pyrrolidinyl. In some embodiments, R$^4$ is 5-6 membered heterocyclyl optionally substituted with one to two groups independently selected from F, Cl, CN, —OH, —CH$_3$, —CH(CH$_3$)$_2$, and —CF$_3$.

In some embodiments, R$^4$ is selected from

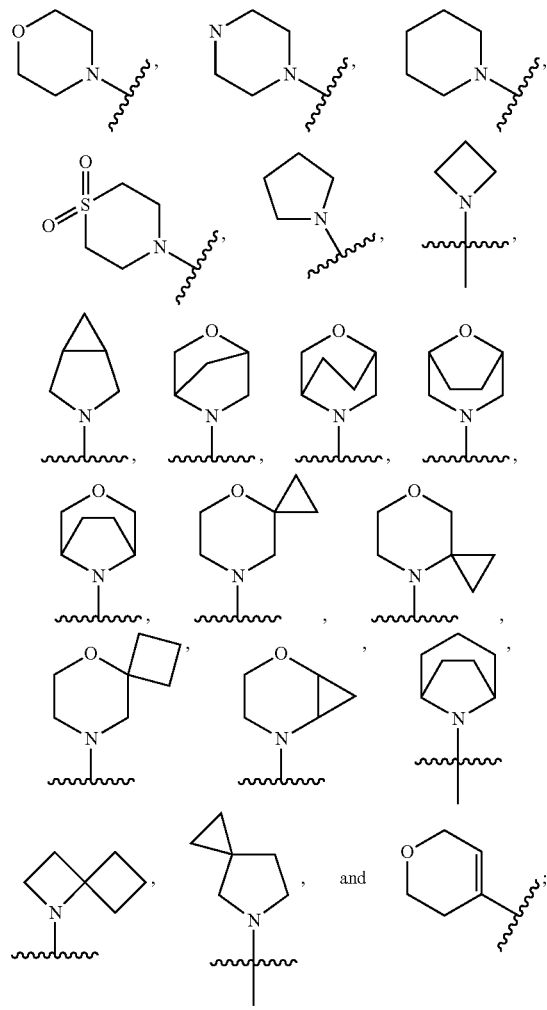

and each R$^4$ is optionally substituted with one to three groups independently selected from halo, OH, CN, —NR$^{a1}$R$^{a2}$, C$_{1-4}$alkyl, C$_{1-4}$alkoxyl, and C$_{1-4}$haloalkyl.

In some embodiments, R$^4$ is selected from

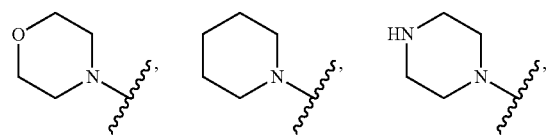

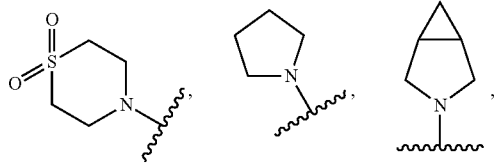

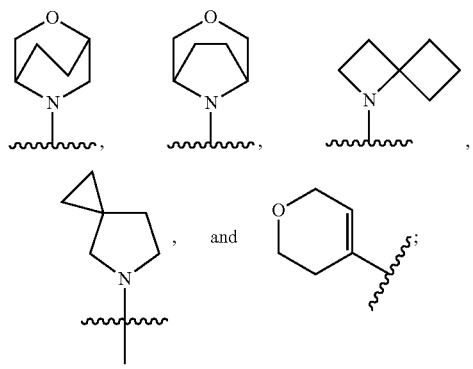

and each R$^4$ is optionally substituted with one to two R$^b$ independently selected from halo, hydroxyl, cyano, —NR$^{a1}$R$^{a2}$, C$_{1-4}$alkyl, C$_{1-4}$alkoxyl, and C$_{1-4}$haloalkyl.

In some embodiments, R$^4$ is selected from

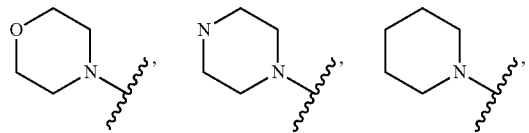

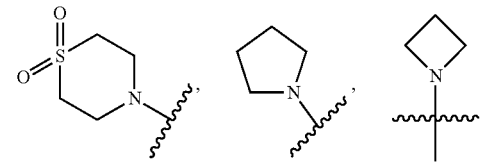

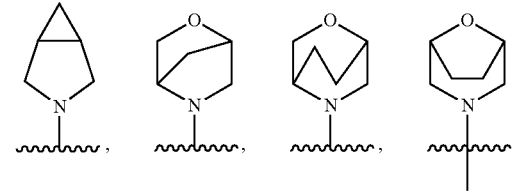

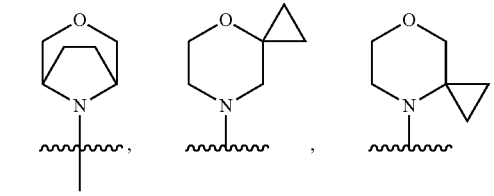

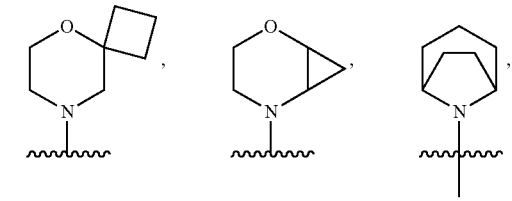

-continued

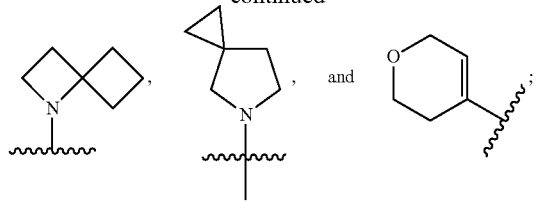

and each R⁴ is optionally substituted with one to three groups independently selected from F, Cl, OH, CN, NH₂, —CH₃, —CH(CH₃)₂, —CH₂F, —CHF₂, —CF₃, —CH₂CH₂F, —CH₂CHF₂, —CH₂CF₃, C₃₋₆cycloalkyl, and —CH₂C₃₋₆cycloalkyl.

In some embodiments, R⁴ is selected from

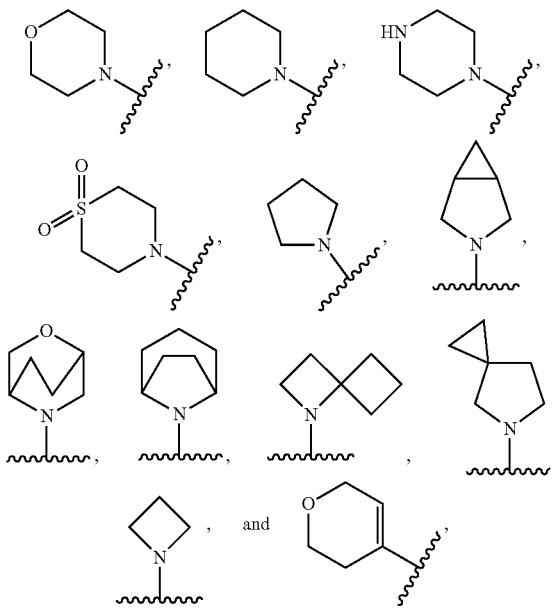

wherein each R⁴ is optionally substituted with one to two groups independently selected from F, Cl, hydroxyl, cyano, —CH₃, —CH(CH₃)₂, CH₂CF₃, and —CF₃.

In some embodiments, R⁴ is selected from

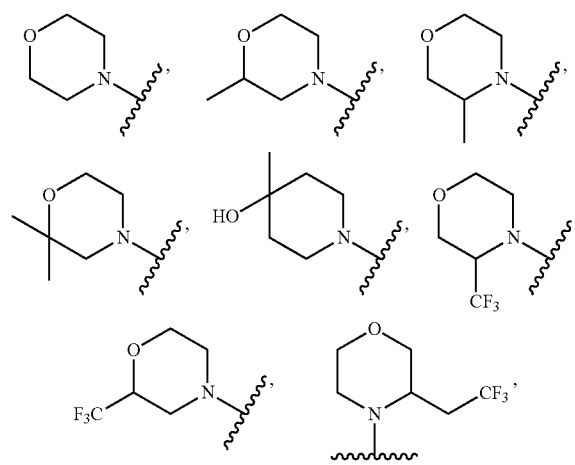

-continued

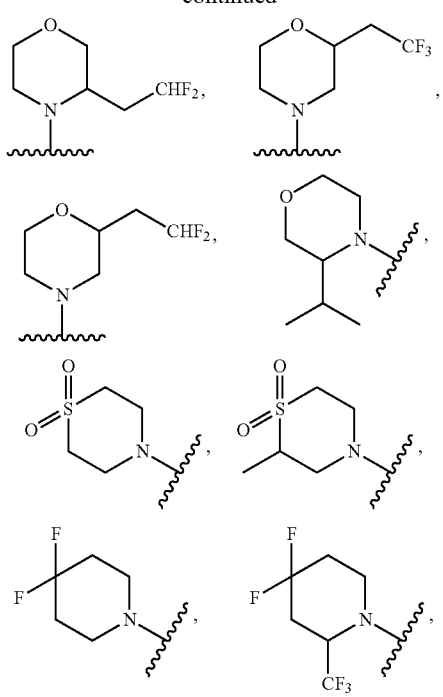

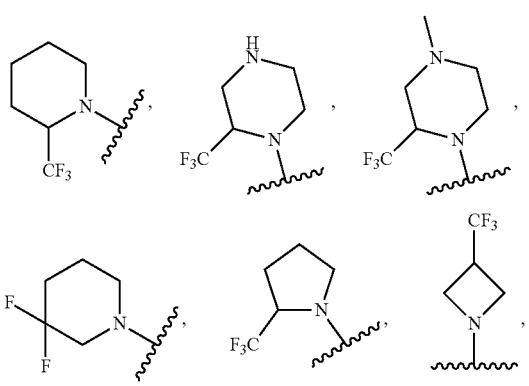

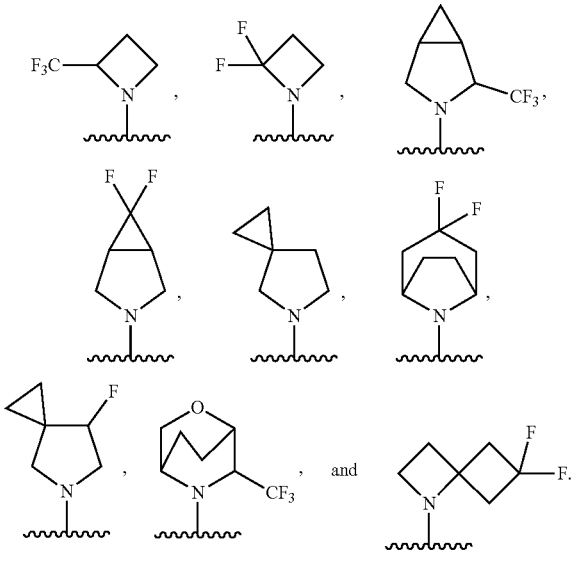

In some embodiments, R⁴ is selected from

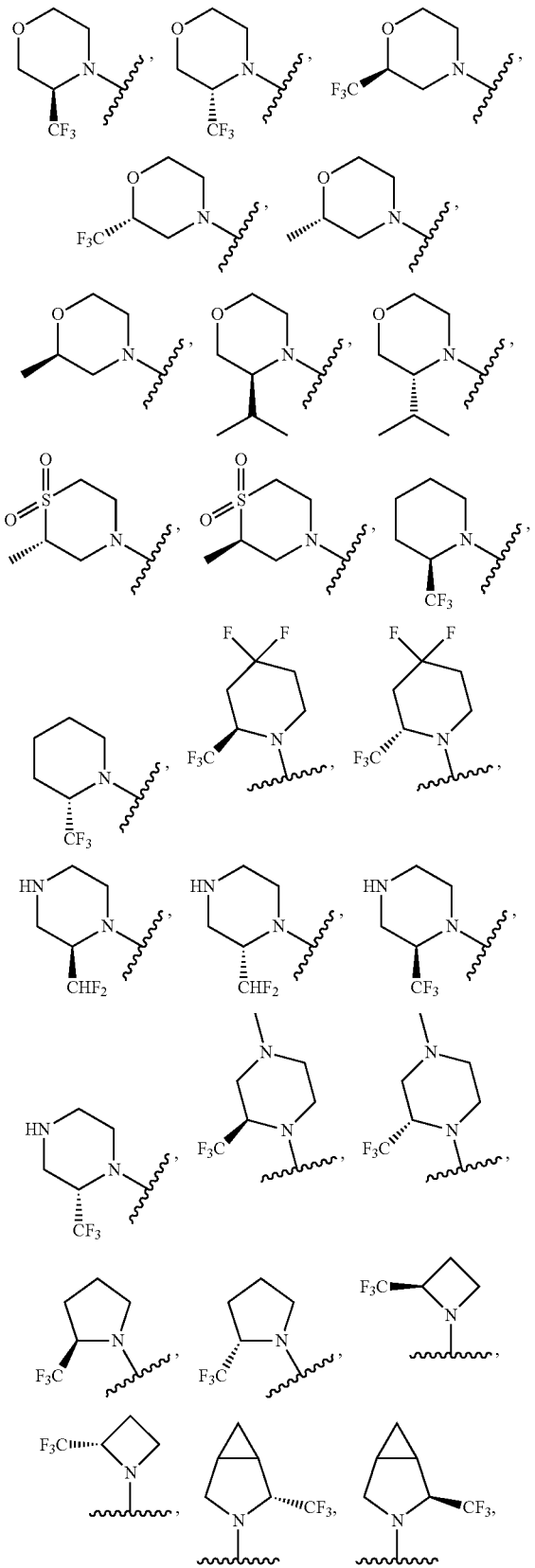

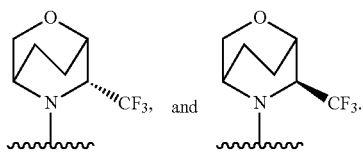

-continued

In some embodiments, R⁴ is

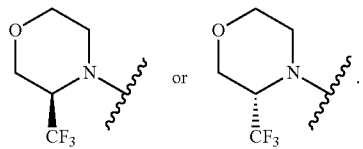 [SMILES: *N1CCOC[C@@H]1C(F)(F)F ; *N1CCOC[C@H]1C(F)(F)F]

In some embodiments, R⁴ is —NR$^{b1}$S(O)$_v$R$^{b4}$. In some embodiments R⁴ is —NHS(O)$_2$R$^{b4}$, and R$^{b4}$ is selected from C$_{1-4}$alkyl, C$_{1-4}$haloalkyl, C$_{3-6}$cycloalkyl, and phenyl. In some embodiments, R$^{b4}$ is selected from —CH$_3$, —CH$_2$F, —CHF$_2$, —CF$_3$, and phenyl. The phenyl is optionally substituted with pyridinyl that is optionally substituted with one or two groups independently selected from halo, and C$_{1-4}$alkyl. In some embodiments, the pyridinyl is optionally substituted with one or two groups independently selected from F, and —CH$_3$. In some embodiments, R⁴ is —NHS(O)$_2$R$^{b4}$, R$^{b4}$ is selected from —CH$_3$, —CH$_2$F, —CHF$_2$, —CF$_3$, and phenyl; and wherein the phenyl is optionally substituted with pyridinyl or triazolyl that is optionally substituted with one or two groups independently selected from halo, and C$_{1-4}$alkyl.

In some embodiments, R⁴ is selected from

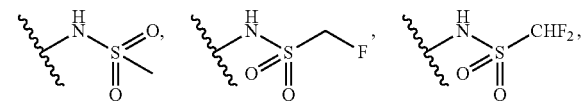

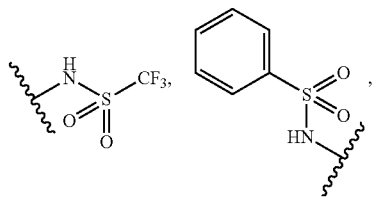

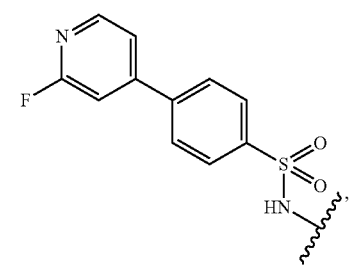

-continued

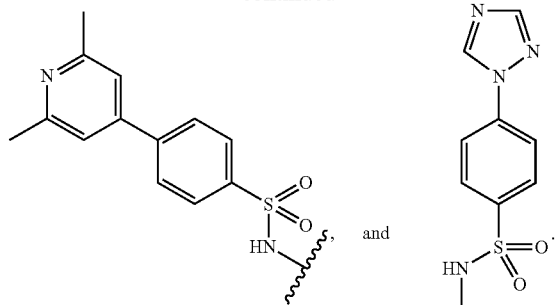

In some embodiments, $R^4$ is selected from

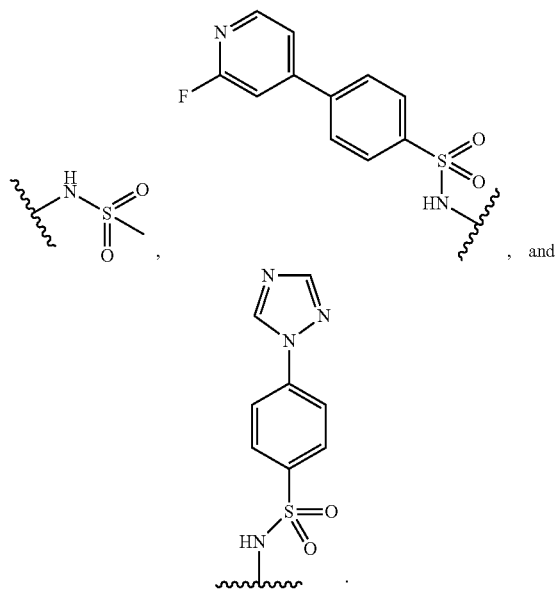

In some embodiments, $R^4$ is selected from

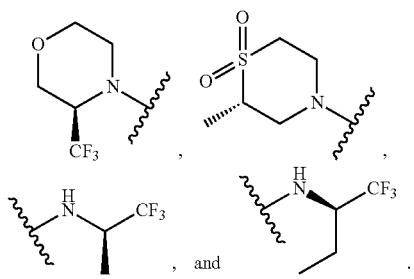

In some embodiments, each $R^7$ and $R^8$ is H. In some embodiments, each $R^7$, $R^8$, $R^{10}$ and $R^{11}$ is H.

In some embodiments, $R^9$ is selected from H, methyl, ethyl, propyl, butyl, —CH$_2$C(O)N(CH$_3$)$_2$, —(CH$_2$)$_2$N(CH$_2$CH$_3$)$_2$, —CH$_2$—O—C(O)CH$_3$, —(CH$_2$)$_2$—O—C(O)CH$_3$, —CH$_2$—O—C(O)C(CH$_3$)$_3$, —(CH$_2$)$_2$—O—C(O)C(CH$_3$)$_3$, —CH$_2$—O—C(O)—O—CH$_3$, —CH(CH$_3$)—O—C(O)—O—CH$_3$, —CH$_2$—O—C(O)—O—CH$_2$CH$_3$, —CH$_2$—O—C(O)—O—CH(CH$_3$)$_2$, —CH$_2$—O—C(O)—O—C(CH$_3$)$_3$, —(CH$_2$)$_2$C(O)CH$_3$,

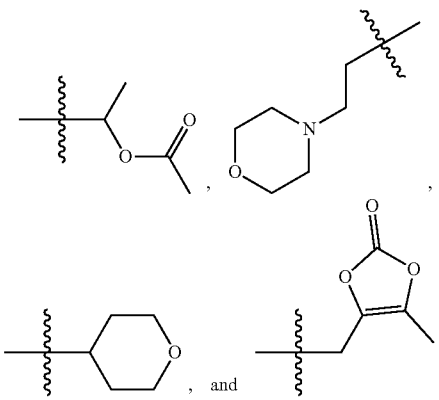

In some embodiments, $R^9$ is selected from H, —CH$_2$—O—C(O)C(CH$_3$)$_3$, —CH(CH$_3$)—O—C(O)—O—CH$_3$,

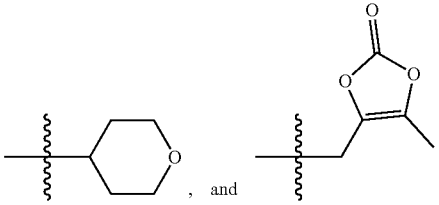

In some embodiments, $R^9$ is H.

In some embodiments, $R^9$ is methyl. In some embodiments, $R^9$ is ethyl. In some embodiments, $R^9$ is propyl.

In some embodiments, $R^9$ is H. In some embodiments, $R^9$ is selected from $C_{1-6}$alkyl, $C_{3-8}$cycloalkyl, and 4-6 membered heterocyclyl, wherein the $C_{1-6}$alkyl of $R^9$ is optionally substituted with one to three groups independently selected from halo, —NR$^{a1}$R$^{a2}$, —C(O)NR$^{a1}$R$^{a2}$, —O—C(O)—C$_{1-4}$alkyl, —O—C(O)—O—C$_{1-4}$alkyl, —O—C(O)—C$_{1-4}$alkylene-NR$^{a1}$R$^{a2}$, —O—C$_{1-4}$alkyl, C$_{3-8}$cycloalkyl, and 4-6 membered heterocyclyl containing at least one heteroatom selected from N and O, and wherein the $C_{3-8}$cycloalkyl, and 4-6 membered heterocyclyl of $R^9$ is optionally substituted with one to three groups independently selected from halo, $C_{1-4}$alkyl, and $C_{1-4}$haloalkyl. In some embodiments, when administered to a patient, an $R^9$ ester generates a compound wherein $R^9$ is H, as a result of chemical reaction(s), enzyme catalyzed chemical reaction(s), and/or metabolic chemical reaction(s). In some embodiments, a compound in which $R^9$ is not H may be a prodrug.

In some embodiments, $R^9$ together with the N that attaches to $R^8$ forms a 5 membered heterocyclyl. In some embodiments, the 5 membered heterocyclyl is substituted with one to two groups independently selected from $C_{1-6}$alkyl, $C_{1-6}$alkoxyl, $C_{1-6}$haloalkyl, and $C_{6-10}$aryl. In some embodiments, the 5 membered heterocyclyl is substituted with one to two groups independently selected from CH$_3$, CH$_2$CH$_3$, —OCH$_3$, —OCH$_2$CH$_3$, and phenyl. In some embodiments, the 5 membered heterocyclyl is substituted with phenyl, and phenyl is optionally substituted with one to three groups independently selected from halo, $C_{1-6}$alkyl, $C_{1-6}$alkoxyl, and $C_{1-6}$haloalkyl.

In some embodiments, each $R^{10}$ is independently selected from H, halo, $C_{1-4}$alkyl, $C_{1-4}$haloalkyl, and $C_{1-4}$alkoxyl. In some embodiments, each $R^{10}$ is independently selected from H, F, Cl, —CH₃, —CH₂F, —CHF₂, —CF₃, —OCH₃, and —OCF₃. In some embodiments, each $R^{10}$ is H.

In some embodiments, each $R^{11}$ is independently selected from H, —C(O)CH₃, —CH₃, —CH₂F, —CHF₂, and —CF₃. In some embodiments, each $R^{11}$ is independently selected from H, —CH₃, and —C(O)CH₃.

In some embodiments, q is 1. In some embodiments, q is 2.

In some embodiments, r is selected from 1, 2, and 3. In some embodiments, r is 3.

In some embodiments, t is 0. In some embodiments, t is 1.

In some embodiments, u is selected from 1, 2, and 3. In some embodiments, u is 3.

In some embodiments, v is 2.

In some embodiments, each $V^1$, $V^2$ and $V^3$ is independently $CR^{22}$ or N, wherein each $R^{22}$ is independently selected from H, halo, $C_{1-4}$alkyl, $C_{1-4}$haloalkyl, and $C_{1-4}$alkoxyl. In some embodiments, each $V^1$, $V^2$ and $V^3$ is independently $CR^{22}$ or N, wherein each $R^{22}$ is independently selected from H, F, Cl, —CH₃, —CH₂F, —CHF₂, —CF₃, —OCH₃, and —OCF₃. In some embodiments, $V^1$ is N, and each $V^2$ and $V^3$ is independently $CR^{22}$. In some embodiments, $V^1$ is N, and each $V^2$ and $V^3$ is independently $CR^{22}$, wherein each $R^{22}$ is independently selected from H, halo, $C_{1-4}$alkyl, $C_{1-4}$haloalkyl, and $C_{1-4}$alkoxyl. In some embodiments, $V^1$ is N, and each $V^2$ and $V^3$ is independently $CR^{22}$, wherein each $R^{22}$ is independently selected from H, F, Cl, —CH₃, —CH₂F, —CHF₂, —CF₃, —OCH₃, and —OCF₃.

In some embodiments, $W^1$ is N, and $W^2$ is O. In some embodiments, $W^1$ is N, and $W^2$ is CH₂. In some embodiments, $W^1$ is N, and $W^2$ is S(O)₂. In some embodiments, each $R^b$ is independently selected from F, OH, —CH₃, —CH(CH₃)₂, —CH₂F, —CHF₂, and —CF₃.

In some embodiments, at least one of $Y^1$, $Y^2$, $Y^3$, $Y^4$, and $Y^5$ is N. In some embodiments, $Y^1$ is N; and each $Y^2$, $Y^3$, $Y^4$, and $Y^5$ is independently $CR^{22}$. In some embodiments, $Y^2$ is N; and each $Y^1$, $Y^3$, $Y^4$, and $Y^5$ is independently $CR^{22}$. In some embodiments, $Y^3$ is N; and each $Y^1$, $Y^2$, $Y^4$, and $Y^5$ is independently $CR^{22}$. In some embodiments, $Y^4$ is N; and each $Y^1$, $Y^2$, $Y^3$, and $Y^5$ is independently $CR^{22}$. In some embodiments, $Y^1$ and $Y^5$ are N; and each $Y^1$, $Y^2$, and $Y^3$ is independently $CR^{22}$.

In some embodiments, the compound of the present disclosure is selected from examples 1-113.

In some embodiments, the compound of the present disclosure is selected from examples 114-205.

In some embodiments, the compound of the present disclosure is selected from:

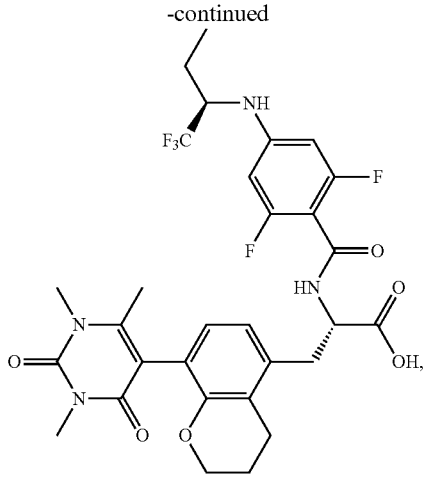

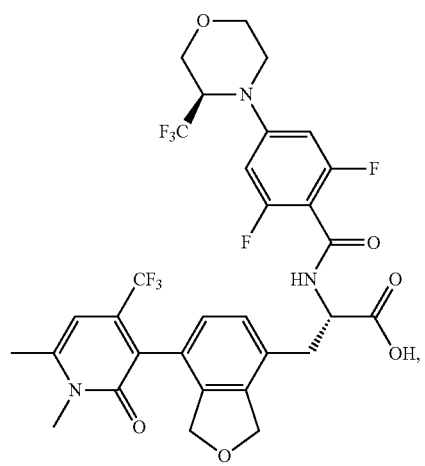

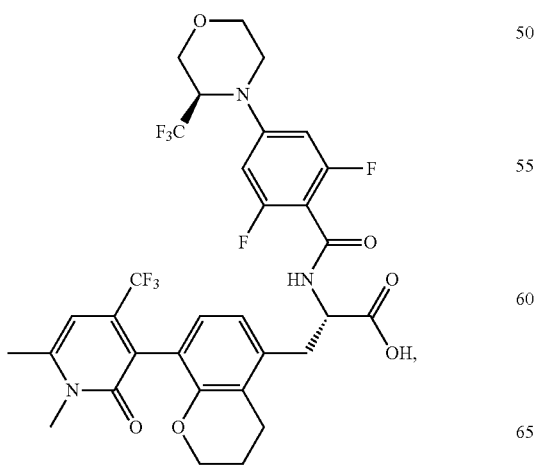

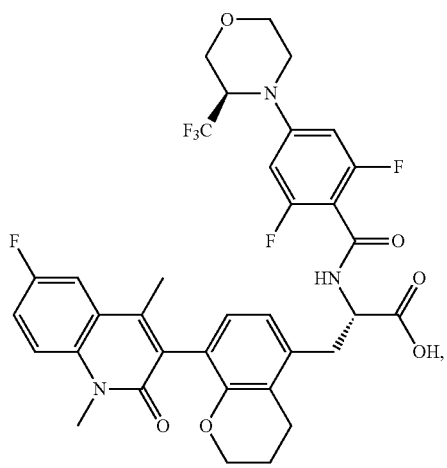

63
-continued
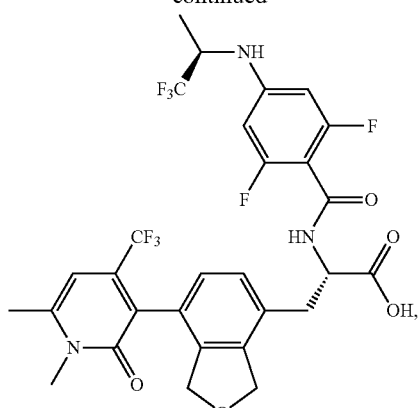
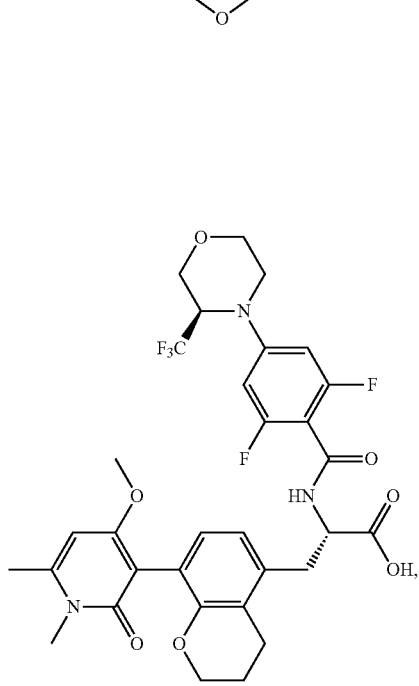
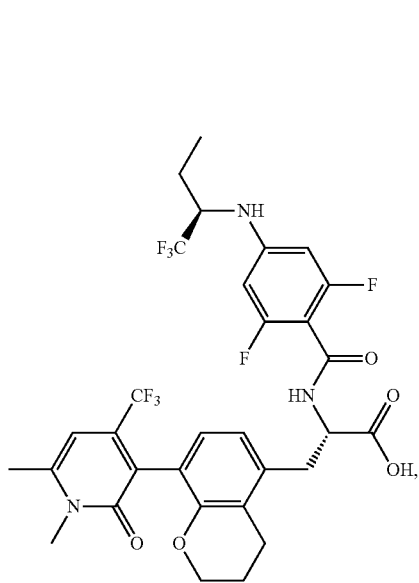
64
-continued
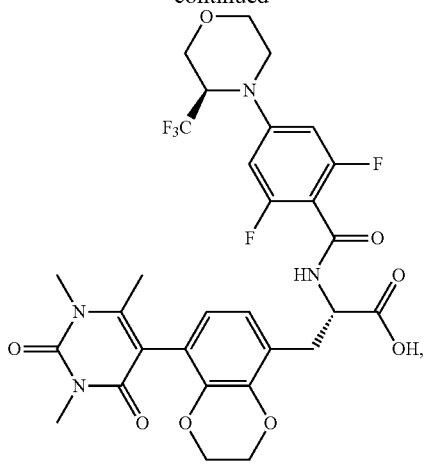
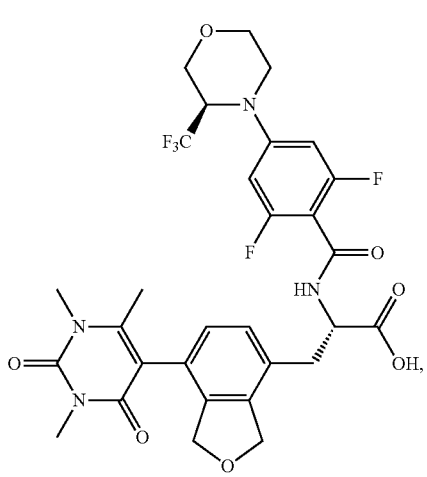
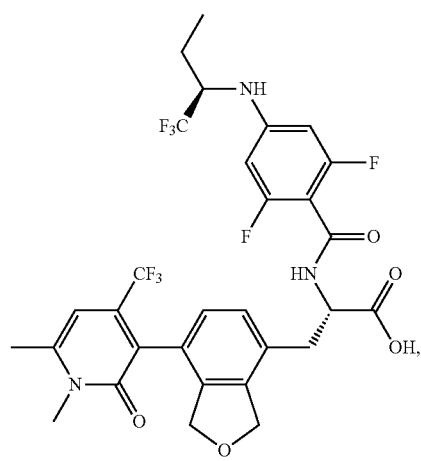

65
-continued
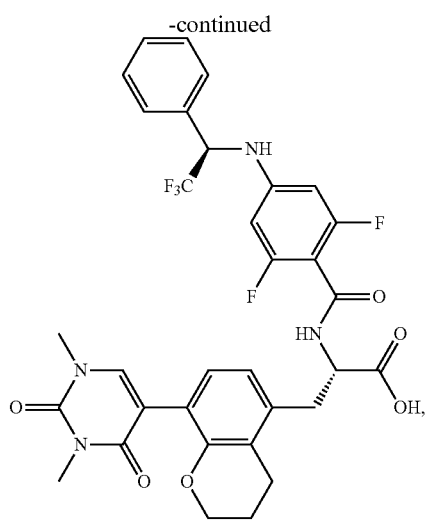
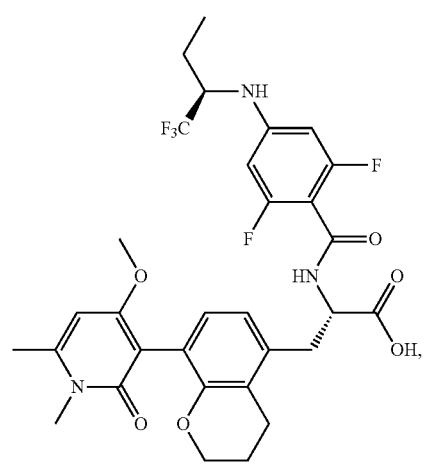
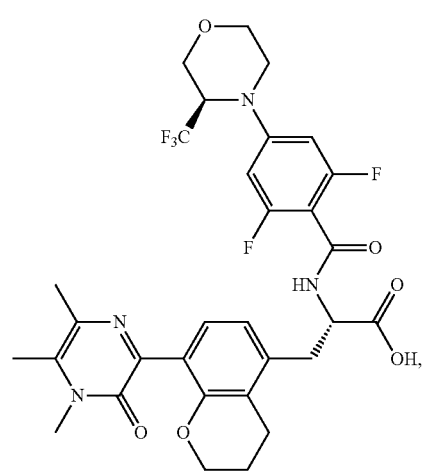
66
-continued
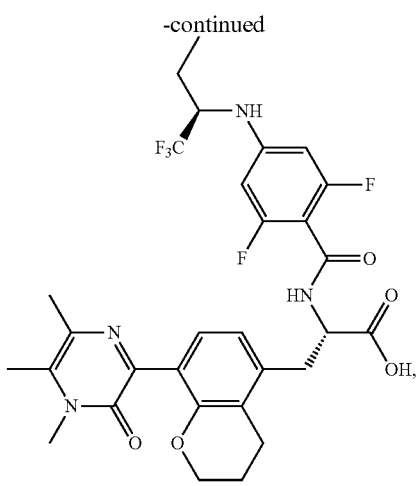
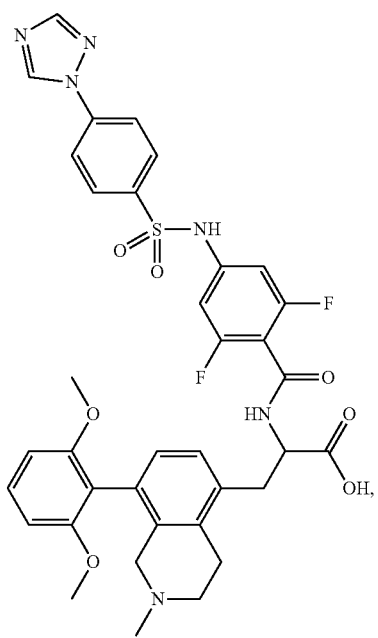

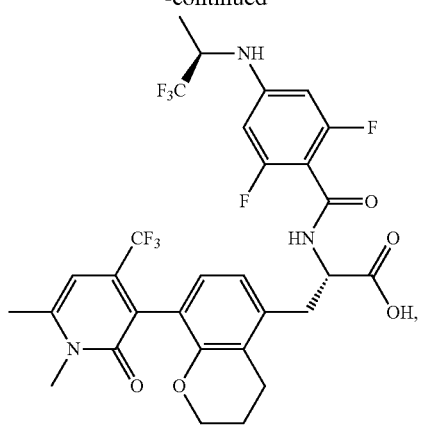
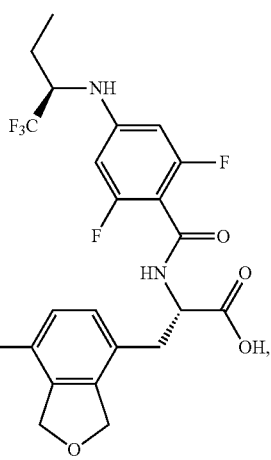
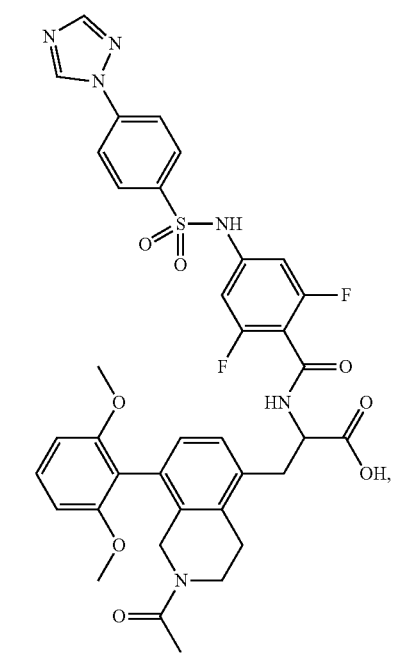
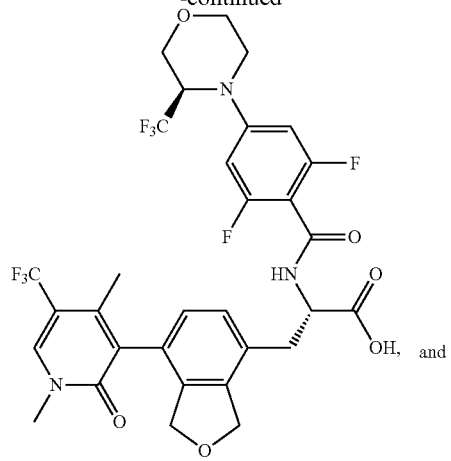
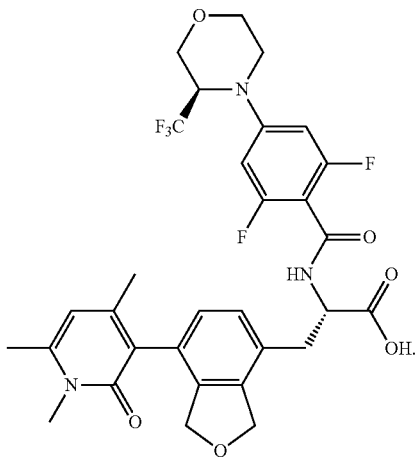
In some embodiments, the compound of the present disclosure is selected from:
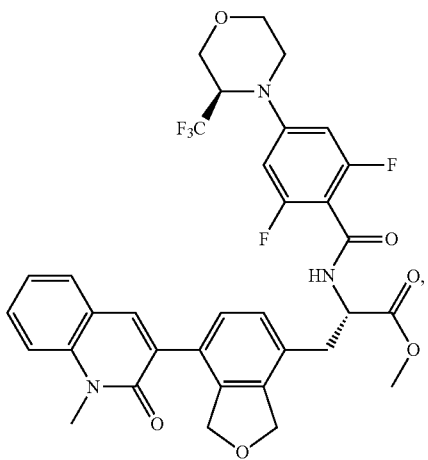

69
-continued
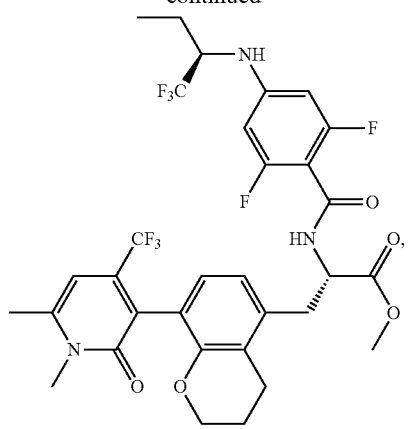
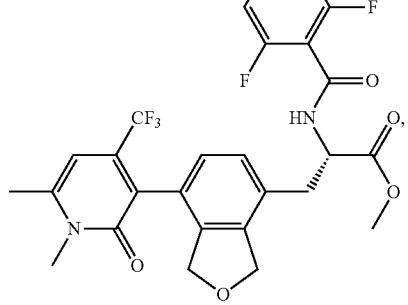
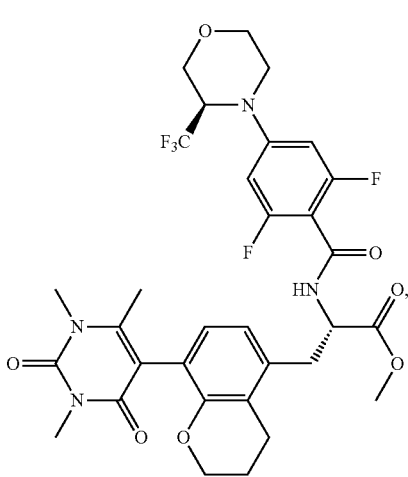
70
-continued
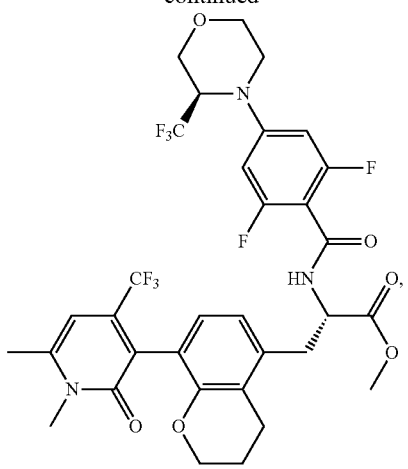
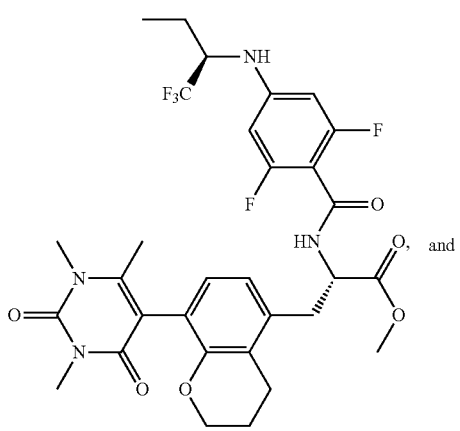
, and
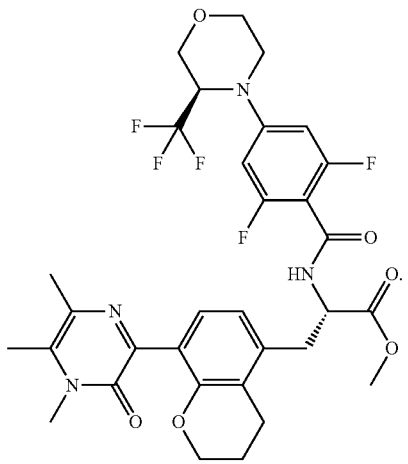

In some embodiments, the compound of the present disclosure is

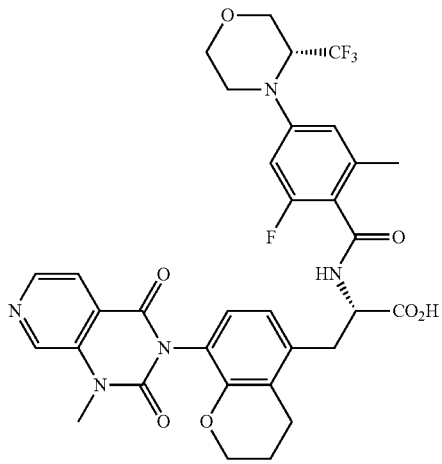 [SMILES: Cc1cc(N2CCOC[C@@H]2C(F)(F)F)cc(F)c1C(=O)N[C@@H](Cc1ccc(-n2c(=O)c3ccncc3n(C)c2=O)c2c1CCCO2)C(=O)O]

In some embodiments, the compound of the present disclosure is

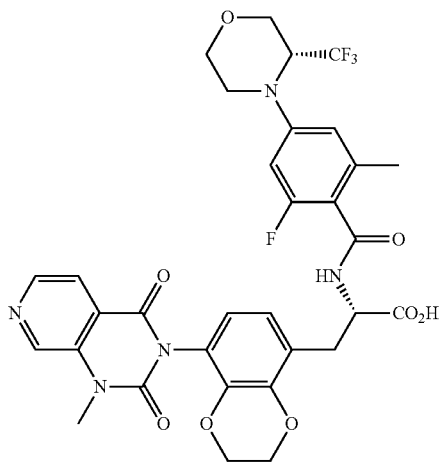 [SMILES: Cc1cc(N2CCOC[C@@H]2C(F)(F)F)cc(F)c1C(=O)N[C@@H](Cc1ccc(-n2c(=O)c3ccncc3n(C)c2=O)c2c1OCCO2)C(=O)O]

One of skill in the art is aware that each and every embodiment of a group (e.g., $R^1$) disclosed herein may be combined with any other embodiment of each of the remaining groups (e.g., $R^4$, $R^9$, $X^3$, etc.) to generate a complete compound of formula (I), or any formula described herein or a pharmaceutically acceptable salt, stereoisomer, mixture of stereoisomers, solvate, or tautomer thereof, each of which is deemed within the ambit of the present disclosure.

| List of Abbreviations and Acronyms | |
|---|---|
| Abbreviation | Meaning |
| % | Percent |
| ° C. | Degree Celsius |
| Ac | Acetyl |
| AcOH | Acetic acid |
| ACN/CH$_3$CN/MeCN | Acetonitrile |
| ADME | Absorption, distribution, metabolism and excretion |
| AIBN | 2,2'-Azobis(2-methylpropionitrile) |
| Aq. | Aqueous |
| ASK | Apoptosis signal-regulating kinase |
| Bicarb | Bicarbonate |
| Bn | Benzyl |
| BOC/Boc | Tert-butyloxycarbonyl |
| Bpin | Pinacolborane |
| br | Broad |
| CAS | Chemical Abstract Service |
| cataCXium A | Di(1-adamantyl)-n-butylphosphine |
| CNS | Central nervous system |
| COPD | Chronic obstructive pulmonary disease |
| CREST | Calcinosis, Raynaud's syndrome, esophageal dysmotility, sclerodactyly and telangiectasia |
| CVP | Cyclophosphamide, vincristine, prednisone |
| d | Doublet |
| D/d | Deuterium |
| DAST | Diethylaminosulfur trifluoride |
| DABCO ® | 1,4-Diazabicyclo[2.2.2]octane |
| DCC | N,N'-Dicyclohexylcarbodiimide |
| DCE | Dichloroethane |
| DCM | Dichloromethane/methylene chloride |
| dd | Doublet of doublets |
| DIEA | N,N-Diisopropylethylamine |
| DIPEA | N,N-Diisopropylethylamine |
| DMA | N,N-Dimethylacetamide |
| DMAP | 4-Dimethylaminopyridine |
| DME | Dimethoxy ethane |
| DMF | Dimethylformamide |
| DMPK | Drug metabolism and pharmacokinetics |
| DMSO | Dimethylsulfoxide |
| dppf | 1,1'-Bis(diphenylphosphino)ferrocene |
| dppp | 1,3-Bis(diphenylphosphino)propane |
| EC$_{50}$ | The half maximal effective concentration |
| equiv/eq | Equivalents |
| EA | Ethyl acetate |
| Et | Ethyl |
| Et$_2$O | Diethyl ether |
| EtOAc/AcOEt | Ethyl acetate |
| EtOH | Ethanol |
| F | Fahrenheit |
| FBS | Fetal bovine serum |
| g | Grams |
| Gp | Glycoprotein |
| h/hr | Hours |
| HATU | (1-[Bis(dimethylamino)methylene]-1H-1,2,3-triazolo[4,5-b]pyridinium 3-oxid hexafluorophosphate) |
| hex | Hexanes |
| HPLC | High pressure liquid chromatography |
| Hz | Hertz |
| IL | Interleukin |
| IUPAC | International Union of Pure and Applied Chemistry |
| J | Coupling constant (MHz) |
| JAK | Janus kinase |
| Kg/kg | Kilogram |
| KOAc | Potassium acetate |
| L | Liter |
| LCMS/LC-MS | Liquid chromatography-mass spectrometry |
| LHMDS | Lithium hexamethyl disilazide |
| LiMg-TMP | 2,2,6,6-Tetramethylpiperidinylmagnesium chloride lithium chloride complex |
| M | Molar |
| m | multiplet |
| M+ | Mass peak |
| M + H | Mass peak plus hydrogen |
| m-CPBA | Meta-Chloroperbenzoic acid |
| Me | Methyl |
| Me$_2$N | Dimethylamine |
| MeI | Methyl Iodide |
| MeOH | Methanol |
| MeOTs | Methyl Tosylate |
| mg | Milligram |
| MHz | Megahertz |
| min/m | Minute |
| ml/mL | Milliliter |

List of Abbreviations and Acronyms

| Abbreviation | Meaning |
|---|---|
| mM | Millimolar |
| mmol | Millimole |
| mol | Mole |
| MS | Mass spectroscopy |
| MS | Multiple sclerosis |
| MsCl | Methanesulfonyl chloride |
| MTBE | Methyl tert-Butyl ether |
| M/Z | Mass/Charge |
| N | Normal |
| NADH | Nicotinamide adenine dinucleotide in reduced form |
| NaOH | Sodium hydroxide |
| NBS | N-Bromosuccinimide |
| ng | Nanograms |
| NIS | N-Iodosuccinimide |
| nM | Nanomolar |
| NMR | Nuclear magnetic resonance |
| ON | Overnight |
| PEG | Polyethylene glycol |
| PET | Positron emission tomography |
| Ph | Phenyl |
| PhMe | Toluene |
| $PhNO_2$ | Nitrobenzene |
| $PhNTf_2$ | N-Phenyl triflamide |
| pH | Expressing the acidity or alkalinity of a solution |
| prep | Preparative |
| RA | Rheumatoid arthritis |
| Rf | Retention factor |
| RPM | Revolutions per minute |
| RT/r | Room temperature |
| RuPhos | 2-Dicyclohexylphosphino-2',6'-diisopropoxybiphenyl |
| s | Second |
| s | Singlet |
| sat. | Saturated |
| SFC | Super-critical fluid chromatography |
| SLE | Systemic lupus erythematosus |
| SPECT | Single-photon emission computed tomography |
| SPhos Pd G3 | (2-Dicyclohexylphosphino-2',6'-dimethoxybiphenyl) [2-(2'-amino-1,1'-biphenyl)]palladium(II) methanesulfonate |
| SYK | Spleen tyrosine kinase |
| t | Triplet |
| TBACl | Tetrabutylammonium chloride |
| TBS/TBDMS | Tert-butyldimethylsilyl |
| tBuOH | Tert-Butanol |
| tBuBrettPhos Pd G3 | [(2-Di-tert-butylphosphino-3,6-dimethoxy-2',4',6'-triisopropyl-1,1'-biphenyl)-2-(2'-amino-1,1'-biphenyl)]palladium(II) methanesulfonate |
| TCA | Trichloroacetic acid |
| TEA/NEt₃ | Triethylamine |
| temp. | Temperature |
| TES | Triethylsilane |
| TFA | Trifluoroacetic acid |
| TFAA | Trifluoroacetic acid anhydride |
| THF | Tetrahydrofuran |
| TLC | Thin-layer chromatography |
| TMP | Tetramethyl piperidine |
| TMS | Trimethylsilyl |
| Tol | Toluene |
| TPL2 | Tumor Progression Locus 2 Kinase |
| Trityl | Triphenylmethyl |
| Vac | Vacuum |
| w/v | Weight/volume |
| w/w | Weight/weight |
| XPhos Pd G3 | (2-Dicyclohexylphosphino-2',4',6'-triisopropyl-1,1'-biphenyl)[2-(2'-amino-1,1'-biphenyl)]palladium(II) methanesulfonate |
| σ | Chemical shift (ppm) |
| μg | Microgram |
| μL/μl | Microliter |
| μM | Micromolar |
| μm | Micrometer |
| μmol | Micromole |

Therapeutic Uses of the Compounds

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. Exemplary tissue samples include tumors and biopsies thereof. In this context, the compounds may be used for a variety of purposes, including therapeutic and experimental purposes. For example, the compounds may be used ex vivo to determine the optimal schedule and/or dosing of administration of an α4β7 integrin inhibitor for a given indication, cell type, individual, and other parameters. Information gleaned from such use may be used for experimental purposes or in the clinic to set protocols for in vivo treatment. Other ex vivo uses for which the compounds may be suited are described below or will become apparent to those skilled in the art. The selected compounds may be further characterized to examine the safety or tolerance dosage in human or non-human subjects. Such properties may be examined using commonly known methods to those skilled in the art.

In some embodiments, compounds described herein, for example, compounds of formula (I), formula (Ia), formula (Ib), formula (Ic), formula (Id), formula (Ie), formula (If), formula (Ig), formula (Ih), formula (Ii), formula (Ij), formula (Ik), formula (Im), formula (II), formula (IIa), formula (IIb), formula (IIc), formula (IId), formula (III), formula (IV), formula (V), formula (VI), formula (VII), formula (VIII), formula (IX), formula (X), formula (XI), formula (XII), formula (XIII), formula (XIV), or formula (XV), or a pharmaceutically acceptable salt, stereoisomer, mixture of stereoisomers, tautomer, or deuterated analog thereof, may be used to treat subjects who have or are suspected of having disease states, disorders, and conditions (also collectively referred to as "indications") responsive or believed to be responsive to the inhibition of α4β7 integrin activity. In some embodiments, the compounds described herein may be used to inhibit the activity of α4β7 integrin. In some embodiments, the compounds described herein may be used to inhibit excessive or destructive immune reactions or growth or a proliferation of a cell, such as a cancer cell, or inhibit immunosuppression.

Methods

In some embodiments, the present disclosure provides a compound described herein useful as an inhibitor of α4β7 integrin. In some embodiments, the present disclosure provides a method of treating an inflammatory disease or condition mediated, at least in part, by α4β7 integrin, comprising administering a compound described herein.

In some embodiments, the present disclosure provides a pharmaceutical composition comprising a compound described herein and a pharmaceutically acceptable carrier.

In some embodiments, the present disclosure provides a pharmaceutical composition comprising a compound described herein and at least one additional therapeutic agent and at least one pharmaceutically acceptable excipient.

The present disclosure provides a compound described herein for use in therapy.

In another embodiment, the present disclosure provides a compound described herein for use in the manufacture of a medicament for treating a disease or condition provided herein.

In some embodiments, provided is a compound described herein useful for the treatment of a disease or condition in a patient that is amenable to treatment by inhibiting α4β7 integrin. Diseases or conditions that may be treated with the compounds described herein include a solid tumor, diabetes, an inflammatory disease, graft versus host disease, primary sclerosing cholangitis, HIV, an autoimmune disease, inflammatory bowel disease (IBD), alcoholic hepatitis, systemic lupus erythematosus (SLE), and lupus nephritis.

In some embodiments, provided is a compound described herein useful for the treatment of an inflammatory disease or condition in a patient that is mediated, at least in part, by α4β7 integrin.

"Administering" or "administration" refers to the delivery of one or more therapeutic agents to a patient. In some embodiments, the administration is a monotherapy wherein a compound described herein is the only active ingredient administered to the patient in need of therapy. In another embodiment, the administration is co-administration such that two or more therapeutic agents are delivered together during the course of the treatment. In some embodiments, two or more therapeutic agents may be co-formulated into a single dosage form or "combined dosage unit", or formulated separately and subsequently combined into a combined dosage unit, as is typically for intravenous administration or oral administration as a mono or bilayer tablet or capsule.

In some embodiments, the compound described herein is administered to a human patient in need thereof in an effective amount, such as, from about 0.1 mg to about 1000 mg per dose of said compound. In some embodiments, the effective amount is from about 0.1 mg to about 200 mg per dose. In some embodiments, the effective amount is from about 1 mg to about 100 mg per dose. In other embodiments, the effective amount is about 1 mg, about 3 mg, about 5 mg, about 10 mg, about 15 mg, about 18 mg, about 20 mg, about 30 mg, about 40 mg, about 60 mg, about 80 mg, or about 100 mg per dose.

In some embodiments, the compound described herein and at least one additional therapeutic agent is administered to a human patient in need thereof in an effective amount of each agent, independently from about 0.1 mg to about 1000 mg per dose of a compound or formulation per dose per compound. In some embodiments, the effective amount of the combination treatment of a compound described herein and an additional compound is independently from about 0.1 mg to about 200 mg per compound per dose. In some embodiments, the effective amount of the combination treatment of a compound described herein and an additional compound is independently from about 1 mg to about 100 mg per compound per dose. In other embodiments, the effective amount of the combination treatment of a compound described herein and an additional compound is for each component, about 1 mg, about 3 mg, about 5 mg, about 10 mg, about 15 mg, about 18 mg, about 20 mg, about 30 mg, about 40 mg, about 60 mg, about 80 mg, about 100 mg, about 200 mg, or about 500 mg each per dose.

In some embodiments, the dose of a compound described herein and/or a combination of the dose of the compound described herein and/or the dose of an additional therapeutic agent is administered once per day, twice per day, or thrice per day. In yet another embodiment, the dose of a compound described herein and/or the dose of an additional therapeutic agent is administered as a loading dose of from about 0.1 mg to about 1000 mg per compound on the first day and each day or on alternate days or weekly for up to a month followed by a regular regimen of a compound described herein and/or one or more additional therapeutic agents or therapies. The maintenance dose may be about 0.1 mg to about 1000 mg once per day, twice per day, thrice per day, or weekly, for each component of a multi component drug regimen. A qualified care giver or treating physician is aware of what dose regimen is best for a particular patient or particular presenting conditions and will make appropriate treating regimen decisions for that patient. Thus, in another embodiment, the qualified caregiver is able to tailor a dose regimen of the compound described herein and/or an additional therapeutic agent(s) as disclosed herein to fit with the particular needs of the patient. Thus, it will be understood that the amount of the dose of a compound described herein and the amount of the dose of an additional therapeutic agent actually administered will usually be determined by a physician, in light of the relevant circumstances, including the condition(s) to be treated, the chosen route of administration, the actual compound (e.g., salt or free base) administered and its relative activity, the age, weight, and response of the individual patient, the severity of the patient's symptoms, and the like.

Co-administration may also include administering a dose of component drugs e.g., a dose of one or more compounds described herein and a dose of one or more additional (e.g., a second, third, fourth or fifth) therapeutic agent(s). Such combination of a dose of one on more compounds described herein and a dose of one or more additional therapeutic agent(s) may be administered simultaneously or in sequence (one after the other) within a reasonable period of time of each administration (e.g., about 1 minute to 24 hours) depending on the pharmacokinetic and/or pharmacodynamics properties of each agent or the combination. Co-administration may also involve treatment with a fixed combination wherein agents of the treatment regimen are combinable in a fixed dosage or combined dosage medium e.g., solid, liquid or aerosol. In some embodiments, a kit may be used to prepare and/or administer the drug or drug components.

Thus, some embodiments of the present disclosure is a method of treating a disease or condition mediated, at least in part, by α4β7 integrin, comprising administering therapeutically effective amounts of formulations of one on more compounds described herein and one or more additional therapeutic agents, including for example, via a kit to a patient in need thereof. It will be understood that a qualified care giver will administer or direct the administration of a therapeutically effective amount of any of the compound(s) or combinations of compounds of the present disclosure.

"Intravenous administration" is the administration of substances directly into a vein, or "intravenously." Compared with other routes of administration, the intravenous (IV) route is a faster way to deliver fluids and medications throughout the body. An infusion pump can allow precise control over the flow rate and total amount of medication delivered. However, in cases where a change in the flow rate would not have serious consequences, or if pumps are not available, the drip is often left to flow simply by placing the bag above the level of the patient and using the clamp to regulate the rate. Alternatively, a rapid infuser can be used if the patient requires a high flow rate and the IV access device is of a large enough diameter to accommodate it. This is either an inflatable cuff placed around the fluid bag to force the fluid into the patient or a similar electrical device that may also heat the fluid being infused. When a patient requires medications only at certain times, intermittent infusion is used which does not require additional fluid. It can use the same techniques as an intravenous drip (pump or gravity drip), but after the complete dose of medication has been given, the tubing is disconnected from the IV access device. Some medications are also given by IV push or bolus, meaning that a syringe is connected to the IV access device and the medication is injected directly (slowly, if it might irritate the vein or cause a too-rapid effect). Once a medicine has been injected into the fluid stream of the IV tubing there must be some means of ensuring that it gets from the tubing to the patient. Usually this is accomplished by allowing the fluid stream to flow normally and thereby carry the medicine into the bloodstream; however, a second fluid injection is sometimes used, as a "flush", following the injection to push the medicine into the bloodstream more quickly. Thus, in some embodiments, compound(s) or combination of compounds described herein may be administered by IV administration alone or in combination with administration of certain components of the treatment regimen by oral or parenteral routes.

"Oral administration" is a route of administration where a substance is taken through the mouth, and includes buccal, sub labial, and sublingual administration, as well as enteral administration and that through the respiratory tract, unless made through e.g., tubing so the medication is not in direct contact with any of the oral mucosa. Typical form for the oral administration of therapeutic agents includes the use of tablets or capsules. Thus in some embodiments, compound(s) or combination of compounds described herein may be administered by oral route alone or in combination with administration of certain components of the treatment regimen by IV or parenteral routes.

The compounds disclosed herein are useful for the treatment of diseases or conditions mediated, at least in part, by α4β7 integrin. Non-limiting examples of diseases or conditions mediated, at least in part, by α4β7 integrin include, without limitation, acne, acid-induced lung injury, Addison's disease, adrenal hyperplasia, adrenocortical insufficiency, adult-onset Still's disease, adult respiratory distress syndrome (ARDS), age-related macular degeneration, aging, alcoholic hepatitis, alcoholic liver disease, allergen-induced asthma, allergic bronchopulmonary, allergic conjunctivitis, allergic contact dermatitis, allergies, allergic encephalomyelitis, allergic neuritis, allograft rejection, alopecia, alopecia areata, Alzheimer's disease, amyloidosis, amyotrophic lateral sclerosis, angina pectoris, angioedema, angiofibroma, anhidrotic ectodermal dysplasia-ill, antiglomerular basement membrane disease, antigen-antibody complex mediated diseases, ankylosing spondylitis, antiphospholipid syndrome, aphthous stomatitis, appendicitis, arthritis, ascites, aspergillosis, asthma, atherosclerosis, atherosclerotic plaques, atopic dermatitis, atrophic thyroiditis, autoimmune diseases, autoimmune hemolytic anemia (immune pancytopenia, paroxysmal nocturnal hemoglobinuria), autoimmune polyendocrinopathies, autoimmune thrombocytopenia (idiopathic thrombocytopenic purpura, immune-mediated thrombocytopenia), autoimmune hepatitis, autoimmune thyroid disorders, autoinflammatory diseases, back pain, *Bacillus anthracis* infection, Bechet's disease, bee sting-induced inflammation, Behçet's syndrome, Bell's palsy, berylliosis, Blau syndrome, bone pain, bronchiolitis, bullous pemphigoid (BP) asthma, burns, bursitis, cardiac hypertrophy, carpal tunnel syndrome, Castleman's disease, catabolic disorders, cataracts, Celiac disease, cerebral aneurysm, chemical irritant-induced inflammation, chorioretinitis, chronic atypical neutrophilic dermatosis with lipodystrophy and elevated temperature (CANDLE) syndrome, chronic heart failure, chronic lung disease of prematurity, chronic obstructive pulmonary disease (COPD), chronic pancreatitis, chronic prostatitis, chronic recurrent multifocal osteomyelitis, cicatricial alopecia, colitis, complex regional pain syndrome, complications of organ transplantation, conjunctivitis, connective tissue disease, contact dermatitis, corneal graft neovascularization, corneal ulcer, Crohn's disease, cryopyrin-associated periodic syndromes, cutaneous lupus erythematosus (CLE), cryptococcosis, cystic fibrosis, deficiency of the interleukin-1 receptor antagonist (DIRA), dermatitis, dermatitis endotoxemia, dermatomyositis, diabetic macular edema, diverticulitis, eczema, encephalitis, endometriosis, endotoxemia, eosinophilic pneumonias, epicondylitis, epidermolysis bullosa, erythema multiforme, erythroblastopenia, esophagitis, familial amyloidotic polyneuropathy, familial cold urticarial, familial Mediterranean fever, fetal growth retardation, fibromyalgia, fistulizing Crohn's disease, food allergies, giant cell arteritis, glaucoma, glioblastoma, glomerular disease, glomerular nephritis, glomerulonephritis, gluten-sensitive enteropathy, gout, gouty arthritis, graft-versus-host disease (GVHD), granulomatous hepatitis, Graves' disease, growth plate injuries, Guillain-Barre syndrome. gut diseases, hair loss, Hashimoto's thyroiditis, head injury, headache, hearing loss, heart disease, hemangioma, hemolytic anemia, hemophilic joints, Henoch-Scholein purpura, hepatitis, hereditary periodic fever syndrome, heritable disorders of connective tissue, herpes zoster and simplex, hidradenitis suppurativa (HS), hip replacement, Hodgkin's disease, Huntington's disease, hyaline membrane disease, hyperactive inflammatory response, hyperammonemia, hypercalcemia, hypercholesterolemia, hypereosinophilic syndrome (HES), hyperimmunoglobulinemia D with recurrent fever (HIDS), hypersensitivity pneumonitis, hypertropic bone formation, hypoplastic and other anemias, hypoplastic anemia, ichthyosis, idiopathic demyelinating polyneuropathy, Idiopathic inflammatory myopathies (dermatomyositis, polymyositis), idiopathic pulmonary fibrosis, idiopathic thrombocytopenic purpura, immunoglobulin nephropathies, immune complex nephritis, immune thrombocytopenic purpura (ITP), incontinentia pigmenti (IP, Bloch-Siemens syndrome), infectious mononucleosis, infectious diseases including viral diseases such as AIDS (HIV infection), hepatitis A, B, C, D, and E, herpes; inflammation, inflammation of the CNS, inflammatory bowel disease (IBD), inflammatory disease of the lower respiratory tract including bronchitis or chronic obstructive pulmonary diseases, inflammatory disease of the upper respiratory tract including the nose and sinuses such as rhinitis or sinusitis, inflammatory diseases of the respiratory tract, inflammatory ischemic event such as stroke or cardiac arrest, inflammatory lung disease, inflammatory myopathy such as myocarditis, inflammatory liver disease, inflammatory neuropathy, inflammatory pain, insect bite-induced inflammation, interstitial cystitis, interstitial lung disease, iritis, irritant-induced inflammation, ischemia/reperfusion, joint replacement, juvenile arthritis, juvenile rheumatoid arthritis, keratitis, kidney injury caused by parasitic infections, kidney transplant rejection, leptospirosis, leukocyte adhesion deficiency, lichen sclerosus (LS), Lambert-Eaton myasthenic syndrome, Loeffler's syndrome, lupus, lupus nephritis, Lyme disease, Marfan syndrome (MFS), mast cell activation syndrome, mastocytosis, meningitis, meningioma, mesothelioma, mixed connective tissue disease, Muckle-Wells syndrome (urticaria deafness amyloidosis), mucositis, multiple organ injury syndrome, multiple sclerosis, muscle wasting, muscular dystrophy, myasthenia gravis (MG), myelodysplastic syndrome, myocarditis, myositis, nasal sinusitis, necrotizing enterocolitis, neonatal onset multisystem inflammatory disease (NOMID), neovascular glaucoma, nephrotic syndrome, neuritis, neuropathological diseases, non-allergen induced asthma, obesity, ocular allergy, optic neuritis, organ transplant rejection, Osier-Weber syndrome, osteoarthritis, osteogenesis imperfecta, osteonecrosis, osteoporosis, osterarthritis, otitis, pachyonychia congenita, Paget's disease, Paget's disease of bone, pancreatitis, Parkinson's disease, pediatric rheumatology, pelvic inflammatory disease, pemphigus, pemphigus vulgaris (PV), bullous pemphigoid (BP), pericarditis, periodic fever, periodontitis, peritoneal endometriosis, pernicious anemia (Addison's disease), pertussis, PFAPA (periodic fever aphthous pharyngitis and cervical adenopathy), pharyngitis and adenitis (PFAPA syndrome), plant irritant-induced inflammation, pneumocystis infection, pneumonia, pneumonitis, poison ivy/urushiol oil-induced inflammation, polyarthritis nodosa, polychondritis, polycystic kidney disease, polymyalgia rheumatic, giant cell arteritis, polymyositis, pouchitis, reperfusion injury and transplant rejection, primary biliary cirrhosis, primary pulmonary hypertension, primary sclerosing cholangitis (PSC), proctitis, psoriasis, psoriasis vulgaris, psoriatic arthritis, psoriatic epidermis, psychosocial stress diseases, pulmonary disease, pulmonary fibrosis, pulmonary hypertension, pyoderma gangrenosum, pyogenic granuloma retrolental fibroplasias, pyogenic sterile arthritis, Raynaud's syndrome, Reiter's disease, reactive arthritis, renal disease, renal graft rejection, reperfusion injury, respiratory distress syndrome, retinal disease, retrolental fibroplasia, Reynaud's syndrome, rheumatic carditis, rheumatic diseases, rheumatic fever, rheumatoid arthritis, rhinitis, rhinitis psoriasis, rosacea, sarcoidosis, Schnitzler syndrome, scleritis, sclerosis, scleroderma, scoliosis, seborrhea, sepsis, septic shock, severe pain, Sézary syndrome, sickle cell anemia, silica-induced disease (Silicosis), Sjogren's syndrome, skin diseases, skin irritation, skin rash, skin sensitization (contact dermatitis or allergic contact dermatitis), sleep apnea, spinal cord injury, spinal stenosis, spondyloarthropathies, sports injuries, sprains and strains, Stevens-Johnson syndrome (SJS), stroke, subarachnoid hemorrhage, sunburn, synovial inflammation, systemic inflammatory response syndrome (SIRS), systemic lupus erythematosus, systemic mast cell disease (SMCD), systemic vasculitis, systemic-onset juvenile idiopathic arthritis, temporal arteritis, tendinitis, tenosynovitis, thrombocytopenia, thyroiditis, thyroiditis, tissue transplant, toxoplasmosis, trachoma, transplantation rejection, traumatic brain injury, tuberculosis, tubulointerstitial nephritis, tumor necrosis factor (TNF) receptor associated periodic syndrome (TRAPS), type 1 diabetes, type 2 diabetes, complications from type 1 or type 2 diabetes, ulcerative colitis, urticaria, uterine fibroids, uveitis, uveoretinitis, vascular restenosis, vasculitis, vasculitis (NHLBI), vitiligo, Wegener's granulomatosis, and Whipple's disease.

In further embodiments, the methods are provided for alleviating a symptom of a disease or disorder mediated, at least in part, by $\alpha 4\beta 7$ integrin. In some embodiments, the methods include identifying a mammal having a symptom of a disease or disorder mediated, at least in part, by $\alpha 4\beta 7$ integrin, and providing to the mammal an amount of a compound as described herein effective to ameliorate (i.e., lessen the severity of) the symptom.

In some embodiments, the disease or condition mediated, at least in part, by $\alpha 4\beta 7$ integrin is an inflammatory disease or LPS induced endotoxin shock. In some embodiments, the disease is an autoimmune disease. In particular embodiments, the autoimmune disease is systemic lupus erythematosus (SLE), myestenia gravis, rheumatoid arthritis (RA), acute disseminated encephalomyelitis, idiopathic thrombocytopenic purpura, multiple sclerosis (MS), inflammatory bowel disease (IBD), sepsis, psoriasis, Sjoegren's syndrome, autoimmune hemolytic anemia, asthma, or chronic obstructive pulmonary disease (COPD), ankylosing spondylitis, acute gout and ankylosing spondylitis, reactive arthritis, monoarticular arthritis, osteoarthritis, gouty arthritis, juvenile arthritis, juvenile onset rheumatoid arthritis, juvenile rheumatoid arthritis or psoriatic arthritis. In other embodiments, the disease is inflammation. In yet other embodiments, the disease is excessive or destructive immune reactions, such as asthma, rheumatoid arthritis, multiple sclerosis, chronic obstructive pulmonary disease (COPD), and lupus.

In some embodiments, the disease or condition mediated, at least in part, by $\alpha 4\beta 7$ integrin is inflammatory bowel disease (IBD). The term "inflammatory bowel disease" or "IBD" as used herein is a collective term describing inflammatory disorders of the gastrointestinal tract, the most common forms of which are ulcerative colitis and Crohn's disease. Other forms of IBD that can be treated with the presently disclosed compounds, compositions and methods include diversion colitis, ischemic colitis, infectious colitis, chemical colitis, microscopic colitis (including collagenous colitis and lymphocytic colitis), atypical colitis, pseudomembranous colitis, fulminant colitis, autistic enterocolitis, indeterminate colitis, Behçet's disease, gastroduodenal CD, jejunoileitis, ileitis, ileocolitis, Crohn's (granulomatous) colitis, irritable bowel syndrome, mucositis, radiation induced enteritis, short bowel syndrome, celiac disease, stomach ulcers, diverticulitis, pouchitis, proctitis, and chronic diarrhea.

Treating or preventing IBD also includes ameliorating or reducing one or more symptoms of IBD. As used herein, the term "symptoms of IBD" refers to detected symptoms such as abdominal pain, diarrhea, rectal bleeding, weight loss, fever, loss of appetite, and other more serious complications, such as dehydration, anemia and malnutrition. A number of such symptoms are subject to quantitative analysis (e.g. weight loss, fever, anemia, etc.). Some symptoms are readily determined from a blood test (e.g. anemia) or a test that detects the presence of blood (e.g. rectal bleeding). The term "wherein said symptoms are reduced" refers to a qualitative or quantitative reduction in detectable symptoms, including but not limited to a detectable impact on the rate of recovery from disease (e.g. rate of weight gain). The diagnosis is typically determined by way of an endoscopic observation of the mucosa, and pathologic examination of endoscopic biopsy specimens.

The course of IBD varies, and is often associated with intermittent periods of disease remission and disease exacerbation. Various methods have been described for characterizing disease activity and severity of IBD as well as response to treatment in subjects having IBD. Treatment according to the present methods is generally applicable to a subject having IBD of any level or degree of disease activity.

In some embodiments, the disease or condition treated by the administration of a compound of composition described herein includes acute gout and ankylosing spondylitis, allergic disorders, Alzheimer's disease, Amyotrophic lateral sclerosis (ALS), Amyotrophic lateral sclerosis and multiple sclerosis, atherosclerosis, bacterial infections, bone cancer pain and pain due to endometriosis, BRAF resistant melanoma, brain stem glioma or pituitary adenomas, burns, bursitis, cancer of the anal region, cancer of the endocrine system, cancer of the kidney or ureter (e.g. renal cell carcinoma, and carcinoma of the renal pelvis), cancer of the penis, cancer of the small intestine, cancer of the thyroid, cancer of the urethra, cancers of the blood such as acute myeloid leukemia, cancers of the tongue, carcinoma of the cervix, carcinoma of the endometrium, carcinoma of the fallopian tubes, carcinoma of the renal pelvis, carcinoma of the vagina or carcinoma of the vulva, chronic myeloid leukemia, chronic or acute leukemia, chronic pain, classic Bartter syndrome, common cold conjunctivitis, coronary heart disease, cutaneous or intraocular melanoma, dermatitis, dysmenorrhea, eczema, endometriosis, familial adenomatous polyposis, fibromyalgia, fungal infections, gout, gynecologic tumors, uterine sarcomas, carcinoma of the fallopian tubes, headache, hemophilic arthropathy, Parkinson's disease, AIDS, herpes zoster, Hodgkin's disease, Huntington's, hyperprostaglandin E syndrome, influenza, iritis, juvenile arthritis, juvenile onset rheumatoid arthritis, juvenile rheumatoid arthritis, low back and neck pain, lymphocytic lymphomas, myofascial disorders, myositis, neuralgia, neurodegenerative disorders such as Alzheimer's disease, neuroinflammatory disorders, neuropathic pain, carcinoma of the vulva, Parkinson's disease, pediatric malignancy, pulmonary fibrosis rectal cancer, rhinitis, sarcoidosis, sarcomas of soft tissues, scleritis, skin cancer, solid tumors of childhood, spinal axis tumors, sprains and strains, stomach cancer, stroke, subacute and chronic musculoskeletal pain syndromes such as bursitis, surgical or dental procedures, symptoms associated with influenza or other viral infections, synovitis, toothache, ulcers, uterine cancer, uterine sarcomas, uveitis, vasculitis, viral infections, viral infections {e.g. influenza) and wound healing.

Criteria useful for assessment of disease activity in subjects with ulcerative colitis can be found in, e.g., Truelove et al. (1955) Br Med J 2:1041-1048.) Using these criteria, disease activity can be characterized in a subject having IBD as mild disease activity or severe disease activity. Subjects who do not meet all the criteria for severe disease activity, and who exceed the criteria for mild disease activity are classified as having moderate disease activity.

The presently disclosed treatment methods can also be applied at any point in the course of the disease. In some embodiments, the methods are applied to a subject having IBD during a time period of remission (i.e., inactive disease). In such embodiments, the present methods provide benefit by extending the time period of remission (e.g., extending the period of inactive disease) or by preventing, reducing, or delaying the onset of active disease. In other embodiments, methods may be applied to a subject having IBD during a period of active disease. Such methods provide benefit by reducing the duration of the period of active disease, reducing or ameliorating one or more symptoms of IBD, or treating IBD.

Measures for determining efficacy of treatment of IBD in clinical practice have been described and include, for example, the following: symptom control; fistula closure; extent of corticosteroid therapy required; and, improvement in quality of life. Heath-related quality of life (HRQL) can be assessed using the Inflammatory Bowel Disease Questionnaire (IBDQ), which is extensively used in clinical practice to assess quality of life in a subject with IBD. (See Guyatt et al. (1989) Gastroenterology 96:804-810.) In some embodiments, the disease or condition is immune-mediated liver injury, disease or condition.

In some embodiments, the disease or condition mediated, at least in part, by $\alpha 4\beta 7$ integrin is alcoholic hepatitis. Alcoholic hepatitis is a clinical syndrome characterized by jaundice and liver failure that develops in subjects with chronic and active alcohol abuse. (See Akriviadis E. et. al, Ann Gastroenterol. 2016 April-June; 29(2): 236-237). Alcoholic hepatitis can cause cirrhosis and fibrosis of the liver cells. Glucocorticoids, (e.g. prednisolone) and phosphodiesterase inhibitors (e.g. pentoxifylline) can be used to treat alcoholic hepatitis. The compounds herein can be used as stand-alone treatments or in combination with the current treatments for alcoholic hepatitis.

In one aspect, the present disclosure provides methods of treating or preventing a human immunodeficiency virus (HIV) infection in a subject in need thereof, comprising administering to the subject a therapeutically effective amount of a compound provided herein, or a pharmaceutically acceptable salt thereof, or a pharmaceutical composition provided herein.

In some embodiments, the disease or condition mediated, at least in part, by $\alpha 4\beta 7$ integrin is systemic lupus erythematosus (SLE), lupus nephritis, lupus-related, or other autoimmune disorders or a symptom of SLE. Symptoms of systemic lupus erythematosus include joint pain, joint swelling, arthritis, fatigue, hair loss, mouth sores, swollen lymph nodes, sensitivity to sunlight, skin rash, headaches, numbness, tingling, seizures, vision problems, personality changes, abdominal pain, nausea, vomiting, abnormal heart rhythms, coughing up blood and difficulty breathing, patchy skin color and Raynaud's phenomenon.

Combination Therapy

Also provided are methods of treatment in which a compound described herein is given to a patient in combination with one or more additional active agents or therapy.

Thus in some embodiments, a method of treating diseases or conditions mediated, at least in part, by $\alpha 4\beta 7$ integrin and/or diseases or symptoms that co-present or are exacerbated or triggered by the diseases or conditions mediated, at least in part, by $\alpha 4\beta 7$ integrin, e.g., an allergic disorder and/or an autoimmune and/or inflammatory disease, and/or an acute inflammatory reaction, comprises administering to a patient in need thereof an effective amount of a compound described herein optionally in combination with an additional agent (e.g., a second, third, fourth or fifth active agent) which can be useful for treating diseases or conditions mediated, at least in part, by $\alpha 4\beta 7$, an allergic disorder and/or an autoimmune and/or inflammatory disease, and/or an acute inflammatory reaction incident to or co-presenting with diseases or conditions mediated, at least in part, by $\alpha 4\beta 7$ integrin. Treatment with the second, third, fourth or fifth active agent may be prior to, concomitant with, or following treatment with a compound described herein. In some embodiments, a compound described herein is combined with another active agent in a single dosage form. Suitable therapeutics that may be used in combination with a compound described herein include, but are not limited to, therapeutic agents provided herein, or a combination comprising at least one therapeutic agent provided herein.

Included herein are methods of treatment in which a compound described herein is administered in combination with an agent for treatment of an inflammatory disease or condition. Examples of agents for treatment of an inflammatory disease or condition that can be used in combination with compounds described herein, include alpha-fetoprotein modulators; adenosine A3 receptor antagonist; adrenomedullin ligands; AKT1 gene inhibitors; antibiotics; antifungals; ASK1 inhibitors; ATPase inhibitors; beta adrenoceptor antagonists; BTK inhibitors; calcineurin inhibitors; carbohydrate metabolism modulators; cathepsin S inhibitors; CCR9 chemokine antagonists; CD233 modulators; CD29 modulators; CD3 antagonists; CD40 ligand inhibitors; CD40 ligand receptor antagonists; chemokine CXC ligand inhibitors; CHST15 gene inhibitors; collagen modulators; CSF-1 antagonists; CX3CR1 chemokine modulators; ecobiotics; eotaxin ligand inhibitors; EP4 prostanoid receptor agonists; F1F0 ATP synthase modulators; farnesoid X receptor (FXR and NR1H4) agonists or modulators; fecal microbiota transplantation (FMT); fractalkine ligand inhibitors; free fatty acid receptor 2 antagonists; GATA 3 transcription factor inhibitors; glucagon-like peptide 2 agonists; glucocorticoid agonists; Glucocorticoid receptor modulators; guanylate cyclase receptor agonists; HIF prolyl hydroxylase inhibitors; histone deacetylase inhibitors; HLA class II antigen modulators; hypoxia inducible factor-1 stimulator; ICAM1 gene inhibitors; IL-1 beta ligand modulators; IL-12 antagonists; IL-13 antagonists; IL-18 antagonists; IL-22 agonists; IL-23 antagonists; IL-23A inhibitors; IL-6 antagonists; IL-7 receptor antagonists; IL-8 receptor antagonists; integrin alpha-4/beta-1 antagonists; integrin alpha-4/beta-7 antagonists; integrin antagonists; interleukin ligand inhibitors; interleukin receptor 17A antagonists; interleukin-1 beta ligands; interleukin 1 like receptor 2 inhibitors; IL-6 receptor modulators; JAK tyrosine kinase inhibitors; Jak1 tyrosine kinase inhibitors; Jak3 tyrosine kinase inhibitors; lactoferrin stimulators; LanC like protein 2 modulators; leukocyte elastate inhibitors; leukocyte proteinase-3 inhibitors; MAdCAM inhibitors; melanin concentrating hormone (MCH-1) antagonist; melanocortin agonists; metalloprotease-9 inhibitors; microbiome-targeting therapeutics; natriuretic peptide receptor C agonists; neuregulin-4 ligands; NLPR3 inhibitors; NKG2 D activating NK receptor antagonists; nuclear factor kappa B inhibitors; opioid receptor antagonists; OX40 ligand inhibitors; oxidoreductase inhibitors; P2X7 purinoceptor modulators; PDE 4 inhibitors; Pellino homolog 1 inhibitors; PPAR alpha/delta agonists; PPAR gamma agonists; protein fimH inhibitors; P-selectin glycoprotein ligand-1 inhibitors; Ret tyrosine kinase receptor inhibitors; RIP-1 kinase inhibitors; RIP-2 kinase inhibitors; RNA polymerase inhibitors; sphingosine 1 phosphate phosphatase 1 stimulators; sphingosine-1-phosphate receptor-1 agonists; sphingosine-1-phosphate receptor-5 agonists; sphingosine-1-phosphate receptor-1 antagonists; sphingosine-1-phosphate receptor-1 modulators; stem cell antigen-1 inhibitors; superoxide dismutase modulators; SYK inhibitors; tissue transglutaminase inhibitor; TLR-3 antagonists; TLR-4 antagonists; Toll-like receptor 8 (TLR8) inhibitors; TLR-9 agonists; TNF alpha ligand inhibitors; TNF ligand inhibitors; TNF alpha ligand modulators; TNF antagonists; TPL-2 inhibitors; tumor necrosis factor 14 ligand modulators; tumor necrosis factor 15 ligand inhibitors; Tyk2 tyrosine kinase inhibitors; type I IL-1 receptor antagonists; vanilloid VR1 agonists; and zonulin inhibitors, and combinations thereof.

Adenosine A3 receptor antagonists include PBF-677.
Adrenomedullin ligands include adrenomedullin.

Antibiotics include ciprofloxacin, clarithromycin, metronidazole, vancomycin, rifamycin, rifaximin, and tosufloxacin.

ASK1 inhibitors include GS-4997.
Alpha-fetoprotein modulators include ACT-101.
Anti-CD28 inhibitors include JNJ-3133 and abatacept.
Beta adrenoceptor antagonists include NM-001.
BTK inhibitors include GS-4059.
Calcineurin inhibitors: include tacrolimus, and ciclosporin.
Carbohydrate metabolism modulators include ASD-003.
Cathepsin S inhibitors include VBY-129.
CCR9 chemokine antagonists include CCX-507.
CD233 modulators include GSK-2831781.
CD29 modulators include PF-06687234.
CD3 antagonists include NI-0401.
CD4 antagonists include IT-1208.
CD40 ligand inhibitors include SAR-441344, and letolizumab.
CD40 gene inhibitors include NJA-730.
CD40 ligand receptor antagonists include FFP-104, BI-655064.
Chaperonin binding immunoglobulin protein includes IRL-201805.
Chemokine CXC ligand inhibitors include LY-3041658.
CHST15 gene inhibitors include STNM-01.
Collagen modulators include ECCS-50 (DCCT-10).
COT protein kinase inhibitors include GS-4875.
CSF-1 antagonists include JNJ-40346527 (PRV-6527), and SNDX-6352.
CX3CR1 chemokine modulators include E-6130.
Ecobiotics include SER-287.
Eotaxin ligand inhibitors include bertilimumab.
EP4 prostanoid receptor agonists include KAG-308.
F1F0 ATP synthase modulators include LYC-30937 EC.
Fractalkine ligand inhibitors include quetmolimab (E-6011).
Free fatty acid receptor 2 antagonists include GLPG-0974.
GATA 3 transcription factor inhibitors include SB-012.
Glucagon-like peptide 2 agonists include teduglutide, and apraglutide.
Glucocorticoid receptor agonists include budesonide, beclomethasone dipropionate, and dexamethasone sodium phosphate.
Glucocorticoid receptor modulators/TNF ligand inhibitors include ABBV-3373.
Guanylate cyclase receptor agonists include dolcanatide.
HIF prolyl hydroxylase inhibitors include DS-1093, and AKB-4924.
HIF prolyl hydroxylase-2 inhibitors/hypoxia inducible factor-1 stimulators include GB-004.
Histone deacetylase inhibitors include givinostat.
Histone deacetylase-6 inhibitors include CKD-506.
HLA class II antigen modulators include HLA class II protein modulators.
ICAM1 gene inhibitors include alicaforsen.
IL-12 antagonists include ustekinumab (IL12/IL23).
IL-13 antagonists include tralokinumab.
IL-18 antagonists include GSK-1070806
IL-22 agonists include RG-7880.
IL-23 antagonists include tildrakizumab, risankizumab (BI-655066), mirikizumab (LY-3074828), brazikumab (AMG-139), and PTG-200.
IL-23A inhibitors include guselkumab.
IL-6 antagonists include olokizumab.
IL-7 receptor antagonists include OSE-127.

IL-8 receptor antagonists include clotrimazole.

Integrin alpha-4/beta-1 antagonists include natalizumab.

Integrin alpha-4/beta-7 antagonists include etrolizumab (a4b7/aEb7), vedolizumab, carotegast methyl, TRK-170 (a4b7/a4b1), PN-10943, and PTG-100.

Integrin antagonists include E-6007.

Interleukin ligand inhibitors include bimekizumab (IL-17A/IL-17F).

Interleukin receptor 17A antagonists include brodalumab.

Interleukin-1 beta ligands include K(D)PT.

Interleukin 1 like receptor 2 inhibitors include BI-655130.

IL-6 receptor modulators include olamkicept.

JAK tyrosine kinase inhibitors include tofacitinib (1/3), peficitinib (1/3), TD-3504, an TD-1473. Jak1 tyrosine kinase inhibitors include a compound disclosed in WO2008/109943. Examples of other JAK inhibitors include, but are not limited to, AT9283, AZD1480, baricitinib, BMS-911543, fedratinib, filgotinib (GLPG0634), gandotinib (LY2784544), INCB039110, lestaurtinib, momelotinib (CYT0387), NS-018, pacritinib (SB1518), peficitinib (ASP015K), ruxolitinib, tofacitinib (formerly tasocitinib), XL019, upadacitinib (ABT-494), filgotinib, GLPG-0555, SHR-0302, and brepocitinib (PF-06700841) (JAK1/Tyk2).

Jak3 tyrosine kinase inhibitors include PF-06651600.

Lactoferrin stimulators include recombinant human lactoferrin (VEN-100).

LanC like protein 2 modulators include BT-11.

Leukocyte elastase inhibitors/Leukocyte proteinase-3 inhibitors include tiprelestat.

MAdCAM inhibitors include SHP-647 (PF-547659).

Melanin concentrating hormone (MCH-1) antagonists include CSTI-100.

Melanocortin MC1 receptor agonists include ASP-3291, and PL-8177.

Metalloprotease-9 inhibitors include GS-5745.

Microbiome modulator include ABI-M201.

Natriuretic peptide receptor C agonists include plecanatide.

Neuregulin-4 ligands include NRG-4.

NKG2 D activating NK receptor antagonists include JNJ-4500.

NLPR3 inhibitors include dapansutrile, BMS-986299, SB-414, MCC-950, IFM-514, JT-194, PELA-167, and NBC-6.

Farnesoid X receptor (FXR and NR1H4) agonists or modulators include AGN-242266, cilofexor tromethamine (GS-9674), EDP-305, EYP-001, GNF-5120, MET-409, nidufexor (LMB-763), obeticholic acid, TERN-101, and tropifexor.

Nuclear factor kappa B inhibitors include Thetanix.

Opioid receptor antagonists include naltrexone, and IRT-103.

OX40 ligand inhibitors include KHK-4083.

Oxidoreductase inhibitors include olsalazine.

Pellino homolog 1 inhibitors include BBT-401.

P2X7 purinoceptor modulators include SGM-1019.

PDE 4 inhibitors include apremilast.

PPAR alpha/delta agonists include elafibranor (GFT-1007).

PPAR gamma agonists include GED-0507-34-Levo.

Protein fimH inhibitors include sibofimloc (EB-8018).

P-selectin glycoprotein ligand-1 inhibitors include SEL-K2, AbGn-168H, and neihulizumab.

Ret tyrosine kinase receptor inhibitors include GSK-3179106.

RIP-1 kinase inhibitors include GSK-2982772.

RIP-2 kinase inhibitors include GSK-2983559.

Sphingosine 1 phosphate phosphatase 1 stimulators include etrasimod.

Sphingosine-1-phosphate receptor-1 agonists include ozanimod, mocravimod (KRP-203), and BMS-986166.

Sphingosine-1-phosphate receptor-1 agonists/Sphingosine-1-phosphate receptor-5 agonists include ozanimod.

Sphingosine-1-phosphate receptor-1 antagonists include amiselimod (MT-1303).

Sphingosine-1-phosphate receptor-1 modulators include OPL-002.

Stem cell antigen-1 inhibitors include Ampion (DMI-9523).

Superoxide dismutase modulators include midismase.

Syk inhibitors include GS-9876.

Tissue transglutaminase inhibitor includes zampilimab.

TLR-3 antagonists include PRV-300.

TLR-4 antagonists include JKB-122.

Toll-like receptor 8 (TLR8) inhibitors include E-6887, IMO-4200, IMO-8400, IMO-9200, MCT-465, MEDI-9197, motolimod, resiquimod, VTX-1463, and VTX-763.

TLR-9 agonists include cobitolimod, IMO-2055, IMO-2125, lefitolimod, litenimod, MGN-1601, and PUL-042.

TNF alpha ligand inhibitors include adalimumab, certolizumab pegol, infliximab, golimumab, DLX-105, Debio-0512, HMPL-004, CYT-020-TNFQb, Hemay-007 and V-565.

TNF antagonists include AVX-470, tulinercept, and etanercept.

TPL-2 inhibitors include GS-4875.

Tumor necrosis factor 14 ligand modulators include AEVI-002.

Tumor necrosis factor 15 ligand inhibitors include PF-06480605.

Tyk2 tyrosine kinase inhibitors include PF-06826647, and BMS-986165.

TrkA receptor antagonist includes SNA-125.

Type I IL-1 receptor antagonists include anakinra.

Zonulin inhibitors include larazotide acetate.

Included herein are methods of treatment in which a compound described herein is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor receptor (TNF) receptors antagonists, immunosuppressants and methotrexate.

Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an $IC_{50}$ that is at least 50-fold lower than the $IC_{50}$ for COX-1) such as celecoxib, valdecoxib, lumiracoxib, etoricoxib and/or rofecoxib.

In a further embodiment, the anti-inflammatory agent is a salicylate. Salicylates include but are not limited to acetylsalicylic acid or aspirin, sodium salicylate, and choline and magnesium salicylates.

The anti-inflammatory agent may also be a corticosteroid. For example, the corticosteroid may be chosen from cortisone, dexamethasone, methylprednisolone, prednisolone, prednisolone sodium phosphate, and prednisone.

In some embodiments, the anti-inflammatory therapeutic agent is a gold compound such as gold sodium thiomalate or auranofin.

In some embodiments, the anti-inflammatory agent is a metabolic inhibitor such as a dihydrofolate reductase inhibitor, such as methotrexate or a dihydroorotate dehydrogenase inhibitor, such as leflunomide.

In some embodiments, the anti-inflammatory compound is an anti-C5 monoclonal antibody (such as eculizumab or pexelizumab), a TNF antagonist, such as entanercept, or infliximab, which is an anti-TNF alpha monoclonal antibody.

Included herein are methods of treatment in which a compound described herein, is administered in combination with an immunosuppressant. In some embodiments, the immunosuppressant is methotrexate, leflunomide, cyclosporine, tacrolimus, azathioprine, or mycophenolate mofetil.

Included herein are methods of treatment in which a compound described herein, is administered in combination with a class of agent for treatment of IBD. Examples of classes of agents for treatment of IBD that can be used in combination with a compound described herein include ASK1 inhibitors, beta adrenoceptor antagonists, BTK inhibitors, beta-glucuronidase inhibitors, bradykinin receptor modulators, calcineurin inhibitors, calcium channel inhibitors, cathepsin S inhibitors, CCR3 chemokine antagonists, CD40 ligand receptor antagonists, chemokine CXC ligand inhibitors, CHST15 gene inhibitors, collagen modulators, CSF-1 antagonists, cyclooxygenase inhibitors, cytochrome P450 3A4 inhibitors, eotaxin ligand inhibitors, EP4 prostanoid receptor agonists, erythropoietin receptor agonists, fractalkine ligand inhibitors, free fatty acid receptor 2 antagonists, GATA 3 transcription factor inhibitors, glucagon-like peptide 2 agonists, glucocorticoid agonists, guanylate cyclase receptor agonists, histone deacetylase inhibitors, HLA class II antigen modulators, IL-12 antagonists, IL-13 antagonists, IL-23 antagonists, IL-6 antagonists, IL-6 receptor modulators, interleukin-7 receptor modulators, IL-7 antagonists, IL-8 antagonists, integrin alpha-4/beta-1 antagonists, integrin alpha-4/beta-7 antagonists, integrin alpha-E antagonists, integrin antagonists, integrin beta-7 antagonists, interleukin ligand inhibitors, interleukin-2 ligand, interleukin receptor 17A antagonists, interleukin-1 beta ligands, interleukin-1 beta ligand modulators, IRAK4 inhibitors, JAK tyrosine kinase inhibitors, Jak1 tyrosine kinase inhibitors, Jak3 tyrosine kinase inhibitors, LanC like protein 2 modulators, lipoxygenase modulators, MAdCAM inhibitors, matrix metalloprotease inhibitors, melanocortin agonists, metalloprotease-9 inhibitors, natriuretic peptide receptor C agonists, neuregulin-4 ligands, NKG2 D activating NK receptor antagonists, opioid receptor antagonists, opioid receptor delta antagonists, oxidoreductase inhibitors, P2X7 purinoceptor agonists, PDE 4 inhibitors, phagocytosis stimulating peptide modulators, potassium channel inhibitors, PPAR alpha agonists, PPAR delta agonists, PPAR gamma agonists, protein fimH inhibitors, P-selectin glycoprotein ligand-1 inhibitors, RNA polymerase inhibitors, sphingosine 1 phosphate phosphatase 1 stimulators, sphingosine 1 phosphate phosphatase modulators, sphingosine-1-phosphate receptor-1 agonists, sphingosine-1-phosphate receptor-1 inhibitors, sphingosine-1-phosphate receptor-1 modulators, sphingosine-1-phosphate receptor-5 modulators, STAT3 gene inhibitors, stem cell antigen-1 inhibitors, superoxide dismutase modulators, superoxide dismutase stimulators, SYK inhibitors, TGF beta 1 ligand inhibitors, thymulin agonists, TLR antagonists, TLR agonists, TNF alpha ligand inhibitors, TNF antagonists, tumor necrosis factor 14 ligand modulators, type II TNF receptor modulators, Tpl 2 inhibitors, and Zonulin inhibitors.

Included herein are methods of treatment in which a compound described herein is administered in combination with an agent for treatment of IBD. Examples of agents for treatment of IBD that can be used in combination with a compound described herein, or a pharmaceutically acceptable salt, stereoisomer, mixture of stereoisomers, tautomer, or deuterated analog thereof, include those provided herein for the treatment of an inflammatory disease or condition, and ABX-464, adalimumab; alicaforsen, ALLO-ASC-CD, AMG-966, anakinra, apremilast; Alequel; AMG-139; amiselimod, ASD-003, ASP-3291, AX-1505, BBT-401, balsalazide; beclomethasone dipropionate; BI-655130, BMS-986184; budesonide; CEQ-508; certolizumab; ChAdOx2-HAV, dexamethasone sodium phosphate, DNVX-078, etanercept; cibinetide; *Clostridium butyricum*; ETX-201, golimumab; GS-4997, GS-9876, GS-4875, GS-4059, infliximab; mesalazine, HLD-400, LYC-30937 EC; IONIS-JBI1-2.5Rx, JNJ-64304500, JNJ-4447, naltrexone; natalizumab; neihulizumab, olsalazine; PH-46-A, propionyl-L-carnitine; PTG-100; remestemcel-L; tacrolimus; teduglutide; tofacitinib; ASP-1002; ustekinumab; vedolizumab; AVX-470; INN-108; SGM-1019; PF-06480605; PF-06651600; PF-06687234; RBX-8225, SER-287; Thetanix; TOP-1288; VBY-129; 99mTc-annexin V-128; bertilimumab; DLX-105; dolcanatide; FFP-104; filgotinib; foralumab; GED-0507-34-Levo; givinostat; GLPG-0974; iberogast; JNJ-40346527; K(D)PT; KAG-308; KHK-4083; KRP-203; larazotide acetate; LY-3074828, midismase; olokizumab; OvaSave; P-28-GST; PF-547659; prednisolone; QBECO; RBX-2660, RG-7835; JKB-122; SB-012; STNM-01; Debio-0512; TRK-170; zucapsaicin; ABT-494; Ampion; BI-655066; carotegast methyl; cobitolimod; elafibranor; etrolizumab; GS-5745; HMPL-004; LP-02, ozanimod; peficitinib; quetmolimab (E-6011); RHB-104; rifaximin; tildrakizumab; tralokinumab; brodalumab; laquinimod; plecanatide; vidofludimus; and AZD-058.

Included herein are methods of treatment in which a compound described herein is administered in combination with an agent for treatment of graft versus host disease. Examples of agents for treatment of graft versus host disease that can be used in combination with a compound described herein include those provided herein for the treatment of an inflammatory disease or condition, and [18F]F-AraG, AM-01, Alpha 1 antitrypsin stimulator: AAT-IV and CSL-964; Allocetra, efavaleukin alfa (AMG-592), arsenic trioxide, ATIR-101, belatacept, belimumab, beta lactamase modulator: ribaxamase, bortezomib, brentuximab vedotin, brimonidine, brimonidine tartrate, cannabidiol, ciclosporin, CYP-001, um, dilanubicel, dornase alfa, DSM-9843, eculizumab, EDP-1066, everolimus, Furestem, GL-101, ibrutinib, IMSUT-CORD, IRX-4204, itolizumab, KD-025, MaaT-013, milatuzumab, mizoribine, mycophenolate mofetil, MSCTC-0010, nalotimagene carmaleucel, MET-2, nilotinib, narsoplimab (OMS-721), pacritinib, PF-05285401, ProTmune, QPI-1002, remestemcel-L, RGI-2001, saratin, SCM-CGH, sirolimus, T-allo10, telmisartan, TOP-1288, TZ-101, voclosporin; CCR5 chemokine antagonist: leronlimab (PRO-140); CD40 ligand receptor antagonist: iscalimab; Complement Cis subcomponent inhibitor: CE-1145, sutimlimab, Cinryze, BIVV-009; B-lymphocyte antigen CD20 inhibitor: obinutuzumab, rituximab; CASP9 gene stimulator: rivogenlecleucel; CD3 antagonist or CD7 inhibitor: T-Guard; Complement C5a factor inhibitor: olendalizumab; Dipeptidyl peptidase IV inhibitor: begelomab;

JAK1/2 tyrosine kinase inhibitor: ruxolitinib; Jak1 tyrosine kinase inhibitor: itacitinib; Interleukin-2 ligand: aldesleukin; Interleukin 22 ligand: F-652; IL-2 receptor alpha subunit inhibitor: basiliximab and inolimomab; IL-6 receptor agonist: PLX-1; IL-6 receptor antagonist: clazakizumab; OX40 ligand inhibitor: KY-1005; An example of such OX40 inhibitor is a compound disclosed in U.S. Pat. No. 8,450,460, the entire contents of which are incorporated herein by reference; Signal transducer CD24 modulator: CD24-IgFc; Somatostatin receptor agonist: Thymoglobulin; and sphingosine-1-phosphate receptor-1 agonist: ponesimod.

Included herein are methods of treatment in which a compound described herein is administered in combination with an agent for treatment of primary sclerosing cholangitis. Examples of agents for treatment of primary sclerosing cholangitis that can be used in combination with compounds described herein include those provided herein for the treatment of an inflammatory disease or condition, and BTT-1023, CM-101, Doconexent, GRI-0124, HTD-1801, HTD-2802, hymecromone, IDN-7314, NGM-282, norursodeoxycholic acid, ORBCEL-C, integrin alpha-V/beta-1 and beta-6 antagonist: PLN-74809; PPAR delta agonist: seladelpar lysine; SCT-5-27, PTGS2 gene and TGF beta 1 gene inhibitor: SCT-5-27, and STP-705; Farnesoid X receptor (FXR, NR1H4) agonists or modulators: AGN-242266, cilofexor tromethamine (GS-9674), EDP-305, EYP-001, GNF-5120, MET-409, nidufexor (LMB-763), obeticholic acid, TERN-101, tropifexor; liver X receptor antagonist: DUR-928; and CCR5/CCR2 chemokine antagonist: cenicriviroc.

In some embodiments, the one or more additional therapeutic agents is selected from the group consisting of: combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or a pharmaceutically acceptable salt of any of the foregoing, or any combinations thereof.

In some embodiments, the one or more additional therapeutic agents is selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, or a pharmaceutically acceptable salt of any of the foregoing, or any combinations thereof.

In some embodiments, the one or more additional therapeutic agent is an immune modulating agent, e.g., an immunostimulant or an immunosuppressant. In certain other embodiments, an immune modulating agent is an agent capable of altering the function of immune checkpoints, including the CTLA-4, LAG-3, B7-H3, B7-H4, Tim3, BTLA, KIR, A2aR, CD200 and/or PD-1 pathways. In other embodiments, the immune modulating agent is immune checkpoint modulating agents. Exemplary immune checkpoint modulating agents include anti-CTLA-4 antibody (e.g., ipilimumab), anti-LAG-3 antibody, anti-B7-H3 antibody, anti-B7-H4 antibody, anti-Tim3 antibody, anti-BTLA antibody, anti-KIR antibody, anti-A2aR antibody, anti CD200 antibody, anti-PD-1 antibody, anti-PD-L1 antibody, anti-CD28 antibody, anti-CD80 or -CD86 antibody, anti-B7RP1 antibody, anti-B7-H3 antibody, anti-HVEM antibody, anti-CD137 or -CD137L antibody, anti-OX40 or -OX40L antibody, anti-CD40 or -CD40L antibody, anti-GAL9 antibody, anti-IL-10 antibody and A2aR drug. For certain such immune pathway gene products, the use of either antagonists or agonists of such gene products is contemplated, as are small molecule modulators of such gene products. In some embodiments, immune modulating agents include those agents capable of altering the function of mediators in cytokine mediated signaling pathways.

In some embodiments, a compound as disclosed herein (e.g., a compound described herein may be combined with one or more (e.g., one, two, three, four, one or two, one to three, or one to four) additional therapeutic agents in any dosage amount of the compound described herein (e.g., from 10 mg to 1000 mg of compound).

A compound described herein may be combined with the agents provided herein in any dosage amount of the compound (e.g., from 50 mg to 500 mg of compound) the same as if each combination of dosages were specifically and individually listed.

In some embodiments, provided are kits comprising a pharmaceutical composition comprising a compound described herein or a compound described herein and at least one additional therapeutic agent, or a pharmaceutically acceptable salt thereof, and at least one pharmaceutically acceptable carrier. In some embodiments, kits comprising a compound disclosed herein, or a pharmaceutically acceptable salt, stereoisomer, mixture of stereoisomers, tautomer, or deuterated analog thereof, in combination with one or more (e.g., one, two, three, four, one or two, or one to three, or one to four) additional therapeutic agents are provided. Any pharmaceutical composition provided in the present disclosure may be used in the kits, the same as if each and every composition were specifically and individually listed for use in a kit. In some embodiments, the kit comprises instructions for use in the treatment of an inflammatory disease or condition. In some embodiments, the instructions in the kit are directed to use of the pharmaceutical composition for the treatment of IBD.

Articles of Manufacture

Articles of manufacture comprising a container in which a compound described herein and at least one pharmaceutically acceptable carrier are contained are provided. The article of manufacture may be a bottle, vial, ampoule, single-use disposable applicator, or the like, containing the pharmaceutical composition provided in the present disclosure. The container may be formed from a variety of materials, such as glass or plastic and in one aspect also contains a label on, or associated with, the container which indicates directions for use in the treatment of cancer or inflammatory conditions.

It should be understood that the active ingredient may be packaged in any material capable of providing reasonable chemical and physical stability, such as an aluminum foil bag.

Unit dosage forms of the pharmaceutical composition comprising a compound described herein and at least one pharmaceutically acceptable carrier are also provided.

Any pharmaceutical composition provided in the present disclosure may be used in the articles of manufacture, the same as if each and every composition were specifically and individually listed for use an article of manufacture.

Also provided is a kit that includes a compound described herein; a label, and/or instructions for use of the compound in the treatment of a disease or condition mediated, at least in part, by α4β7 integrin.

Also provided is an article of manufacture which includes a compound described herein; and a container. In some embodiments, the container may be a vial, jar, ampoule, preloaded syringe, or an intravenous bag.

Formulations of compound(s) of the present disclosure i.e., a compound described herein or the combination of a compound described herein and an additional agent may be accomplished by admixing said compounds or salt thereof with one or more non-toxic, pharmaceutically acceptable vehicles, carriers and/or diluents and/or adjuvants collectively referred to herein as excipients or carrier materials. The compounds of the disclosure may be administered by any suitable route, preferably in the form of a pharmaceutical composition adapted to such route, and in a therapeutically effective dose. The compounds or the combination of compounds for the disclosure may be delivered orally, mucosally, parenterally, including intravascularly, intravenously, intraperitoneally, subcutaneously, intramuscularly, and intranasally in dosage formulations containing conventional pharmaceutical excipients.

In some embodiments, the combination of a compound described herein, and an additional therapeutic agent may be formulated in a fixed dose or combined dose formulation in a tablet, capsule or premixed IV solution. In another embodiment, the fixed dose combination preferably comprises of a compound described herein, and an additional anti-inflammatory agent. Other fixed dose formulations may include premixed liquids, suspensions, elixirs, aerosolized sprays or patch presentations. As used herein fixed dose or combined dose formulations are synonymous with simultaneous co-administration of the active ingredients of the compound described herein and at least one additional therapeutic agent.

Also provided herein are methods for treating a subject who is undergoing one or more standard therapies for treatment of an inflammatory disease or condition comprising administering or co-administering a compound described herein to said subject. Accordingly, one or more compounds described herein may be administered before, during, or after administration of another therapeutic agent for treatment of an inflammatory disease or condition, or combination thereof.

In some embodiments, the subject may be a human who is (i) substantially refractory to at least one treatment of an inflammatory disease or condition, or (ii) in relapse after treatment with treatment of an inflammatory disease or condition, or both (i) and (ii). In some of embodiments, the subject is refractory to at least two, at least three, or at least four treatment of an inflammatory disease or condition (including standard or experimental treatments of an inflammatory disease or condition).

The above therapeutic agents when employed in combination with a compound(s) disclosed herein, may be used, for example, in those amounts indicated in the referenced manuals e.g., Physicians' Desk Reference or in amounts generally known to a qualified care giver, i.e., one of ordinary skill in the art. In the methods of the present disclosure, such other therapeutic agent(s) may be administered prior to, simultaneously with, or following the administration of the compound described herein. Certain other therapeutic agents may be combined into a single formulation or kit when amenable to such. For example, tablet, capsule or liquid formulations may be combined with other tablet, capsule or liquid formulations into one fixed or combined dose formulation or regimen. Other combinations may be given separately, contemporaneously or otherwise.

Improvements in any of the foregoing response criteria are specifically provided by the methods of the present disclosure.

Synthesis

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of typical compounds of formula (I), e.g., compounds having structures described by one or more of formula (I), or other formulas or compounds disclosed herein, or a pharmaceutically acceptable salt, stereoisomer, mixture of stereoisomers, tautomer, or deuterated analog thereof, may be accomplished as described in the following examples.

General Syntheses

Typical embodiments of compounds in accordance with the present disclosure may be synthesized using the general reaction schemes and/or examples described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Starting materials are typically obtained from commercial sources or synthesized using published methods for synthesizing compounds which are embodiments of the present disclosure, inspection of the structure of the compound to be synthesized will provide the identity of each substituent group. The identity of the final product will generally render apparent the identity of the necessary starting materials by a simple process of inspection, given the examples herein. Group labels (e.g., $R^1$, $R^a$) used in the reaction schemes herein are for illustrative purposes only and unless otherwise specified do not necessarily match by name or function the labels used elsewhere to describe compounds of formula (I), or any formula described herein, or aspects or fragments thereof.

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis,* 3rd Edition, Wiley, New York, and references cited therein.

Furthermore, the compounds of this disclosure may contain one or more asymmetric ("chiral") centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The term "q.s." means adding a quantity sufficient to achieve a stated function, e.g., to bring a solution to the desired volume (i.e., 100%).

Compounds as provided herein may be synthesized according to the general schemes provided below. In the Schemes below, it should be appreciated that each of the compounds shown therein may have protecting groups as required present at any step. Standard protecting groups are well within the pervue of one skilled in the art.

Scheme 1 shows an exemplary synthetic route for the synthesis of compounds provided herein (e.g., compounds of Formula I). The compounds of Formula I, or other formulas or compounds disclosed herein, are typically prepared by first providing the molecular core 503 and then attaching the desired $R^1$ substituents using suitable coupling conditions (e.g., Suzuki coupling) and the desired phenyl-amide substituents (substituted at the phenyl by $R^2$—$R^6$) using suitable amide coupling conditions. In Scheme 1, Y, Z, p, $R^1$, $R^2$, $R^3$, $R^4$, $R^5$, $R^6$, $R^7$, $R^8$, $R^9$, $X^1$, $X^2$, $X^3$, $X^4$, $X^5$, $X^6$, and $X^7$ are as defined herein, ring Y' optionally includes one or two double bonds between $X^3$, $X^4$, and $X^5$, $R^{51}$ is a leaving group (e.g., halo); $R^{52}$ is $C_{1-6}$ alkyl; $R^{53}$ is hydroxy or a leaving group (e.g., halo); $R^{54}$ is a moiety suitable for undergoing a coupling reaction (e.g., a boronic acid or halo); $R^{55}$ is O (i.e., oxo) or N, where if $R^{55}$ is N then $R^{55}$ is a constituent of optional ring to $E^1$; $E^1$ is a double bonded N-auxiliary that is optionally cyclized at $R^{55}$, or $E^1$ may be a single bonded N-protecting group and $R^8$; and $R^{56}$ is a moiety suitable for undergoing a metal-catalyzed coupling reaction (e.g., halo, or a boronic acid or an ester thereof).

In Scheme 1, compound 501 is reacted with compound 502 under standard nucleophilic displacement conditions (e.g., using a base) in a suitable solvent (e.g., THF etc.), optionally under an inert atmosphere, to provide compound 503. In general, compound 502 is deprotonated using a strong base, such as potassium hydroxide or butyllithium, and then contacted with compound 501. The reaction is carried out in an inert solvent, for example dichloromethane or THF. The reaction is typically conducted at a temperature of about −78 to 0° C., for about 5 minutes to about 1 hour, or at a temperature of about 0 to 50° C., for about 1 hour to about 12 hours. When the reaction is substantially complete, the product compound 503 is isolated by conventional means.

Compound 503 is coupled with compound 507 under standard metal-catalyzed coupling conditions (e.g., using a palladium catalyst) in a suitable solvent (e.g., dioxane, water, etc.), optionally under an inert atmosphere, to provide compound 508. Compound 507 is an appropriate derivative of formula $R^1$—$R^{54}$. If $R^{54}$ is a boronic acid —$B(OH)_2$, or an ester thereof, compound 507 is coupled to compound 503 where $R^{56}$ is a halogen (e.g., Br). If $R^{54}$ is a halogen, compound 503 may first be coupled with a suitable source of boron, e.g., bis(pinacolato)diboron, to provide a boronic acid, or an ester thereof, at $R^{56}$. The coupling reaction is carried out in an inert solvent, for example aqueous N,N-dimethylformamide, in the Scheme 1
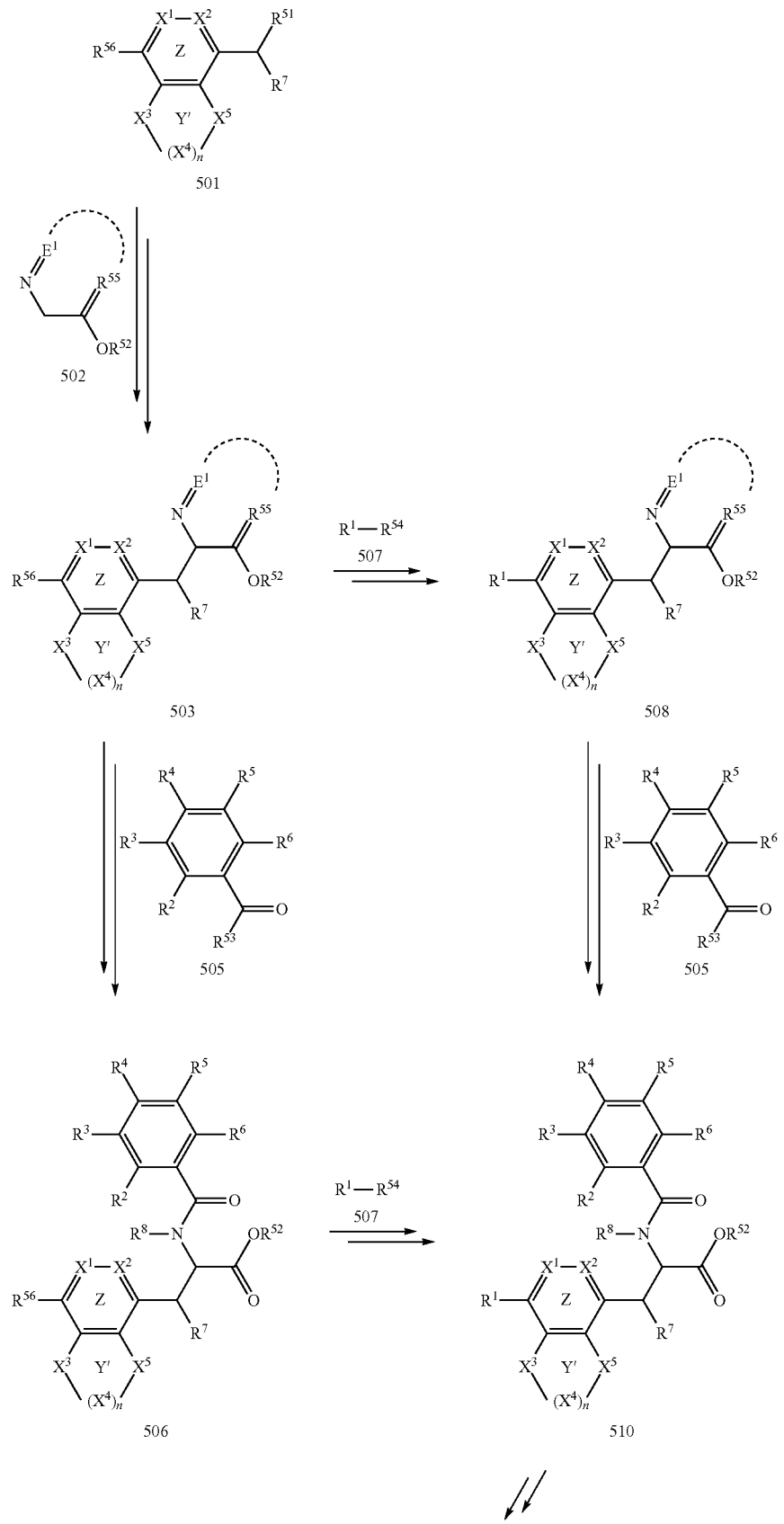

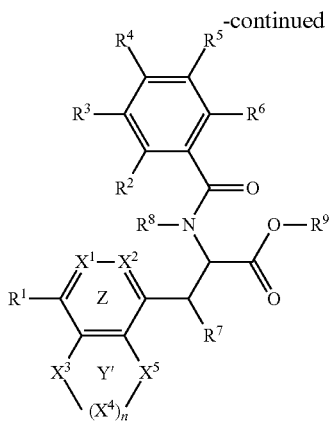

511 presence of a mild base, for example potassium acetate, potassium carbonate, sodium bicarbonate. The reaction is typically conducted in the presence of a metal catalyst with an appropriate ligand, for example dichlorobis(triphenylphosphine) palladium(II) or dichloro 1,1'-bis(diphenylphosphino)ferrocene palladium(II), at a temperature of about 60 to 150° C., for about 10 minutes to about 12 hours. When the reaction is substantially complete, the product compound 508 is isolated by conventional means.

Compound 508 is reacted under acidic conditions sufficient to remove $E^1$. For example, compound 508 may be contacted with an acid in the presence of water or an alcohol, if $E^1$ is double bonded to N, such as when $E^1$ is a diphenylmethine. For example, compound 508 may be contacted with HCl in a suitable solvent, such as methanol/dioxane. Alternatively, compound 508 may be contacted with an acid (e.g., HCl or trifluoroacetic acid) in an inert solvent (e.g., dioxane or dichloromethane), if $E^1$ is single bonded to N, such as when $E^1$ is a trityl or tert-butoxycarbonyl. Following removal of $E^1$, N—H derivative of compound 508 is reacted with compound 505 under standard amide coupling conditions in a suitable solvent (e.g., THF etc.), optionally under an inert atmosphere, to provide compound 510. In compound 505, $R^{53}$ may be a leaving group (e.g., halo), or —OH. Where $R^{53}$ is —OH, compound 505 is activated using a suitable agent, such as HATU, and contacted with compound 508 in the presence of a base (e.g., an organic base such as triethylamine or diisopropylethylamine). The reaction is carried out in an inert solvent, for example dichloromethane, DMF or THF. Where $R^{53}$ is a leaving group, compound 505 is contacted with compound 508 in the presence of a base (e.g., an organic base such as triethylamine or diisopropylethylamine) in an inert solvent, for example dichloromethane or THF. The reaction is typically conducted at a temperature of about 0 to 30° C., for about 5 minutes to about 12 hours. When the reaction is substantially complete, the product compound 510 is isolated by conventional means.

Alternatively, in Scheme 1, compound 503 is reacted under acidic conditions sufficient to remove $E^1$. For example, compound 503 may be contacted with an acid in the presence of water or an alcohol, if $E^1$ is double bonded to N, such as when $E^1$ is a diphenylmethine. For example, compound 503 may be contacted with HCl in a suitable solvent, such as methanol/dioxane. Alternatively, compound 503 may be contacted with an acid (e.g., HCl or trifluoroacetic acid) in an inert solvent (e.g., dioxane or dichloromethane), if $E^1$ is single bonded to N, such as when $E^1$ is a trityl or tert-butoxycarbonyl. Following removal of $E^1$, N—H derivative of compound 503 is reacted with compound 505 under standard amide coupling conditions in a suitable solvent (e.g., THF etc.), optionally under an inert atmosphere, to provide compound 506. In compound 505, $R^{53}$ may be a leaving group (e.g., halo), or —OH. Where $R^{53}$ is —OH, compound 505 is activated using a suitable agent, such as HATU, and contacted with compound 503 in the presence of a base (e.g., an organic base such as triethylamine or diisopropylethylamine). The reaction is carried out in an inert solvent, for example dichloromethane, DMF or THF. Where $R^{53}$ is a leaving group, compound 505 is contacted with compound 503 in the presence of a base (e.g., an organic base such as triethylamine or diisopropylethylamine) in an inert solvent, for example dichloromethane or THF. The reaction is typically conducted at a temperature of about 0 to 30° C., for about 5 minutes to about 24 hours. When the reaction is substantially complete, the product compound 506 is isolated by conventional means.

Compound 506 is coupled with compound 507 under standard metal-catalyzed coupling conditions (e.g., using a palladium catalyst) in a suitable solvent (e.g., dioxane, water, etc.), optionally under an inert atmosphere, to provide compound 510. Compound 507 is an appropriate derivative of formula $R^1$—$R^{54}$. If $R^{54}$ is a boronic acid —$B(OH)_2$, or an ester thereof, compound 507 is coupled to compound 506 where $R^{56}$ is a halogen (e.g., Br). If $R^{54}$ is a halogen, compound 506 may first be coupled with a suitable source of boron, e.g., bis(pinacolato)diboron, to provide a boronic acid, or an ester thereof, at $R^{56}$. The coupling reaction is carried out in an inert solvent, for example aqueous N,N-dimethylformamide, in the presence of a mild base, for example potassium acetate, potassium carbonate, sodium bicarbonate. The reaction is typically conducted in the presence of a metal catalyst with an appropriate ligand, for example dichlorobis(triphenylphosphine) palladium(II) or dichloro 1,1'-bis(diphenylphosphino)ferrocene palladium (II), at a temperature of about 60 to 150° C., for about 10 minutes to about 12 hours. When the reaction is substantially complete, the product compound 510 is isolated by conventional means.

Compound 510 is optionally reduced at Y'—Z to form a ring Y—Z as in compound 511. Compound 510 is reduced at Y'—Z under suitable conditions including a reducing agent (e.g., hydrogen), and a metal catalyst, optionally in an inert solvent. For example, compound 510 is contacted with pressurized hydrogen gas (e.g., 20 to 5000 psi) and platinum oxide in an inert solvent (e.g., THF, ethyl acetate, methanol) at 0 to 30° C. for about 30 minutes to about 12 hours. In general, compound 510 is hydrolyzed under standard aqueous hydrolysis conditions (e.g., using a base or acid) in a suitable aqueous medium (e.g., THF and water, ethanol and water, etc.), optionally under an inert atmosphere, to provide compound 511. The reaction is typically conducted at a temperature of about 0 to 30° C., for about 10 minutes to about 1 hour or at a higher temperature, i.e., 30 to 100° C. for about 10 minutes to about 1 hour. When the reaction is substantially complete, the product of Formula I is isolated by conventional means.

It will be appreciated that the $R^1$ substituent can be added either before (as shown in Scheme 1) or after the removal of the $E^1$ moiety. Thus, the $R^1$ moiety may be coupled to the core-$E^1$ compound 503 under coupling reaction conditions with an appropriate reagent of formula $R^1$—$R^{54}$ as shown in Scheme 1. Alternatively, the $R^1$ moiety may be coupled to the core compound 506 with an appropriate reagent of formula $R^1$—$R^{54}$, following reaction with compound 505 as shown in Scheme 1.

Optional Synthesis

In some embodiments, compound 501 may be synthesized by routes illustrated in Scheme 2. For example, an alternative route for the synthesis of compound 501-1 is shown in Scheme 2. In the embodiment of scheme 2, $R^{57}$ is H, alkoxy, or OH, and $R^{51}$ is halo, for example, bromo or chloro. Compound 515 is reduced under conditions suitable for reduction of a carbonyl containing moiety such as an aldehyde, ester, or carboxylic acid, in a suitable solvent (e.g., THF, etc.), optionally under an inert atmosphere, to provide compound 516. The reduction reaction is carried out in an inert solvent, for example THF, in which compound 515 is contacted with reducing agent, e.g., lithium borohydride, lithium aluminum hydride, or borane. The reaction is typically conducted at a temperature of about 0 to 100° C., for about 10 minutes to about 24 hours. When the reaction is substantially complete, the product compound 516 is isolated by conventional means. Compound 516 is halogenated to provide compound 501-1. The halogenation reaction is carried out in an inert solvent, for example dichloromethane, in which compound 516 is contacted with a suitable dehydrohalogenation agent, for example, carbon tetrabromide and triphenylphosphine, or HCl. The reaction is typically conducted at a temperature of about 0 to 50° C., for about 10 minutes to about 24 hours. When the reaction is substantially complete, the product compound 501-1 is isolated by conventional means.

Scheme 2

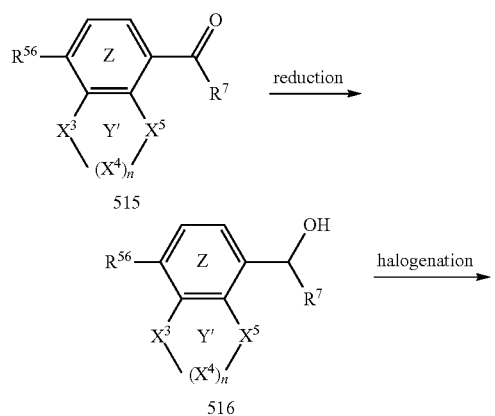

In some embodiments, compound 508 may be synthesized by routes illustrated in Scheme 3. For example, an alternative route for the synthesis of compound 508-1 is shown in Scheme 3, wherein the ring Y—Z forms a tetrahydroisoquinolinyl. In the embodiment of scheme 3, $R^{54}$ is a boronic acid —$B(OH)_2$, $R^{55}$ is O, $E^1$ is a protecting group (e.g., tert-butoxycarbonyl), and the optional ring between $E^1$ and $R^{55}$ is absent. $R^{52}$ is as defined above. Compound 520 is coupled with compound 507 under standard metal-catalyzed coupling conditions (e.g., using a palladium catalyst) in a suitable solvent (e.g., acetonitrile, water, etc.), optionally under an inert atmosphere, to provide compound 521. The coupling reaction is carried out in an inert solvent, for example aqueous N,N-dimethylformamide, in the presence of a mild base, for example sodium carbonate. The reaction is typically conducted in the presence of a metal catalyst with an appropriate ligand, for example dichlorobis(triphenylphosphine) palladium(II), at a temperature of about 60 to 150° C., for about 10 minutes to about 12 hours. When the reaction is substantially complete, the product compound 521 is isolated by conventional means. Compound 521 is coupled with compound 522 under Heck metal-catalyzed coupling conditions (e.g., using a palladium catalyst) in a suitable solvent (e.g., DMF, etc.), optionally under an inert atmosphere, to provide compound 523. Compound 522 is an appropriate acrylate derivative. The coupling reaction is carried out in an inert solvent, for example aqueous N,N-dimethylformamide, in the presence of a mild base, for example triethylamine. The reaction is typically conducted in the presence of a metal catalyst, for example palladium(II) acetate, at a temperature of about 60 to 150° C., for about 10 minutes to about 12 hours. Compound 523 is reduced under suitable conditions including a reducing agent (e.g., hydrogen), and a metal catalyst, optionally in an inert solvent. For example, compound 523 is contacted with pressurized hydrogen gas (e.g., 20 to 5000 psi) and palladium on carbon (e.g., 10% Pd/C) in an inert solvent (e.g., methanol and THF) at 0 to 100° C. for about 30 minutes to about 12 hours. When the reaction is substantially complete, the product compound 508-1 is isolated by conventional means.

Scheme 3

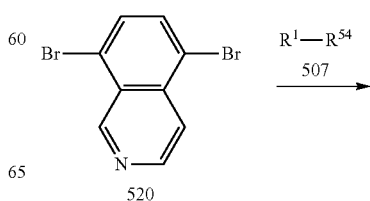

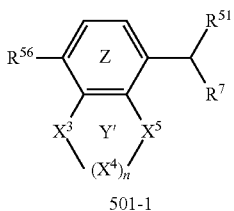

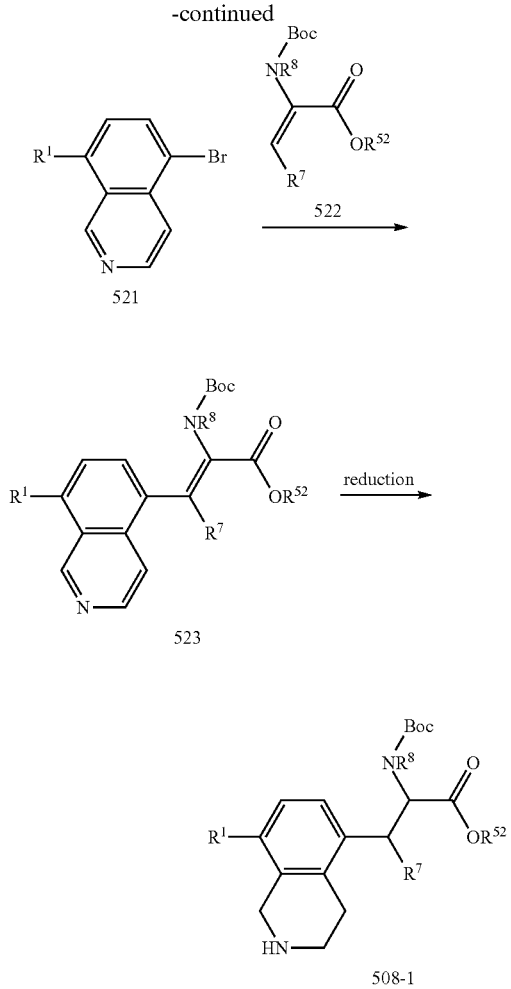

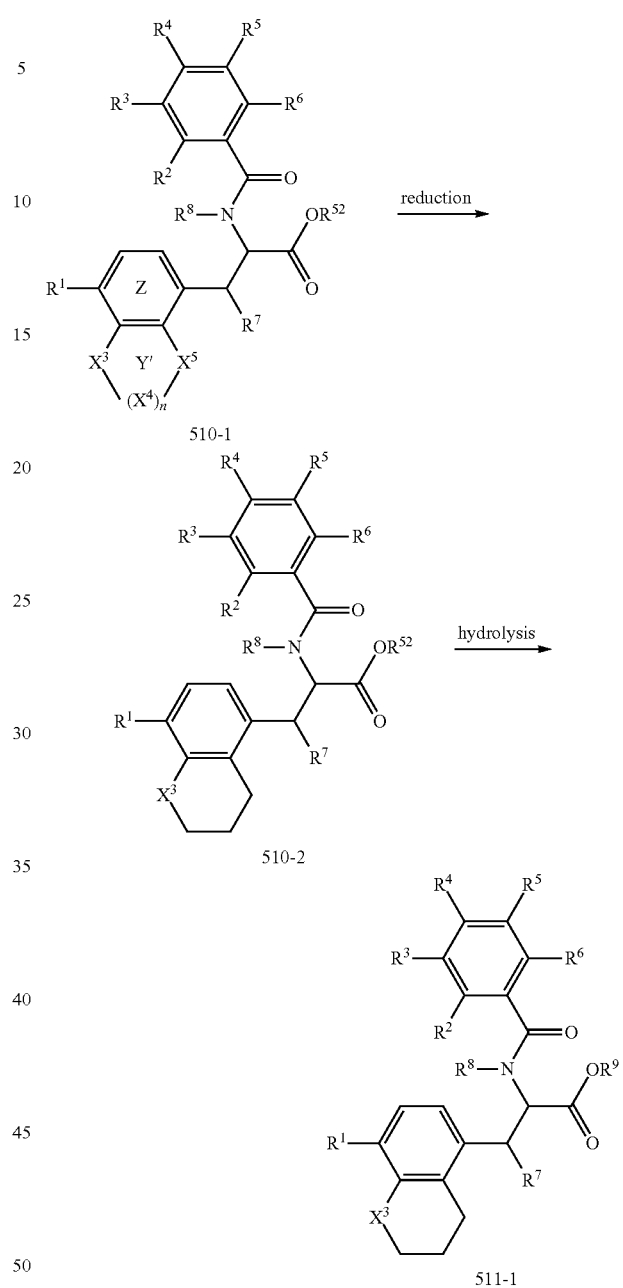

In some embodiments, compound 511 may be synthesized by routes illustrated in Scheme 4. For example, an alternative route for the synthesis of compound 510-1 is shown in Scheme 4, wherein the ring Y—Z forms a tetrahydroquinolinyl or a chromane. In Scheme 4, $X^3$ is O or N, and Y'—Z forms a chromenyl or quinolinyl. $R^{52}$ is as described above. The reaction of compound 510-1 is carried out under standard reduction conditions to provide compound 510-2. Compound 510-1 is reduced under suitable conditions including a reducing agent (e.g., hydrogen), and a metal catalyst, optionally in an inert solvent. For example, compound 510-1 is contacted with pressurized hydrogen gas (e.g., 20 to 5000 psi) and platinum oxide in an inert solvent (e.g., THF, ethyl acetate, methanol) at 0 to 30° C. for about 30 minutes to about 12 hours. The product compound 510-2 is isolated by conventional means. Compound 510-2 is hydrolyzed under standard aqueous hydrolysis conditions (e.g., using a base or acid) in a suitable aqueous medium (e.g., THF and water, ethanol and water, etc.), optionally under an inert atmosphere, to provide compound 511-1. The reaction is typically conducted at a temperature of about 0 to 30° C., for about 10 minutes to about 1 hour or at a higher temperature, i.e., 30 to 100° C. for about 10 minutes to about 1 hour. When the reaction is substantially complete, compound 511-1 is isolated by conventional means.

In some embodiments, compound 515 may be synthesized by routes illustrated in Scheme 5. For example, an alternative route for the synthesis of compound 515-1 is shown in Scheme 5, wherein the ring Y'—Z forms a chromenyl. In Scheme 5, $R^{56}$ is as described above, and $R^{57}$ is methoxy. The reaction of compound 525 to form compound 527 is carried out by contacting compound 525 with an alkyne 526 and a metal catalyst (e.g., copper(II) chloride) in an inert solvent (e.g., acetonitrile). The reaction is typically conducted at a temperature of about 0 to 30° C., for about 10 minutes to about 24 hours. When the reaction is substantially complete, the product compound 527 is isolated by conventional means. Compound 527 is then cyclized under standard conditions (e.g., using a gold catalyst) in a suitable solvent (e.g., dichloromethane), optionally under an inert atmosphere, to provide compound 515-1. The reaction is typically conducted in the presence of a metal catalyst (e.g., (CH₃CN)[(2-biphenyl)di-tert-butylphosphine]gold(I) hexafluoroantimonate), at a temperature of about 0 to 30° C., for about 10 minutes to about 12 hours. When the reaction is substantially complete, the product compound 515-1 is isolated by conventional means.

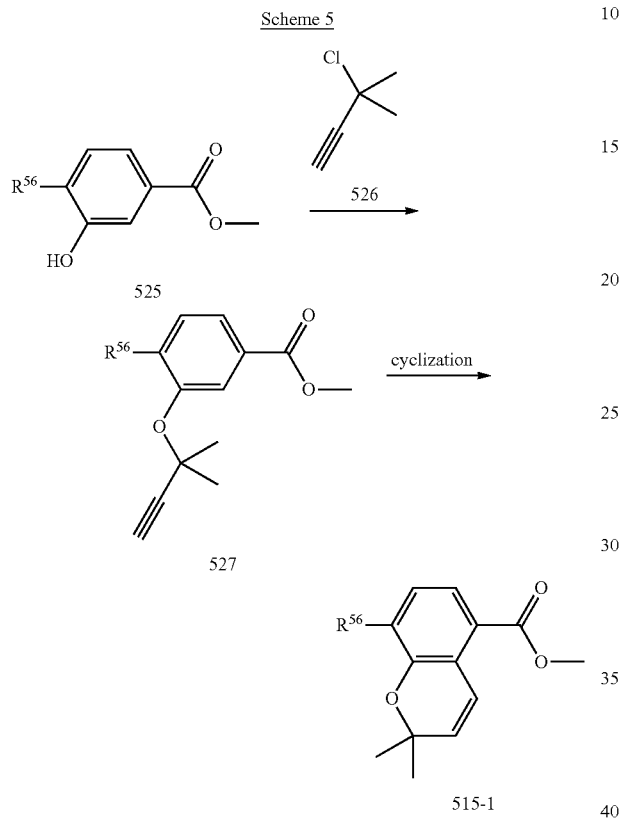

Suitably substituted compounds for use in the methods provided herein can be purchased from commercial sources or synthesized by known methods. Resolution of the isomers of compound 511 can be performed as needed using standard chiral separation/resolution conditions (e.g., chromatography, crystallization, etc.).

EXAMPLES

Methods for preparing the novel compounds described herein will be apparent to those of skill in the art with suitable procedures being described, for example, in the reaction schemes and examples below.

Example 1

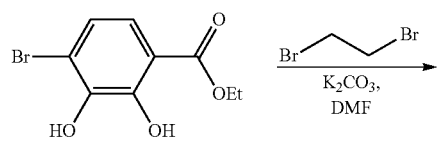

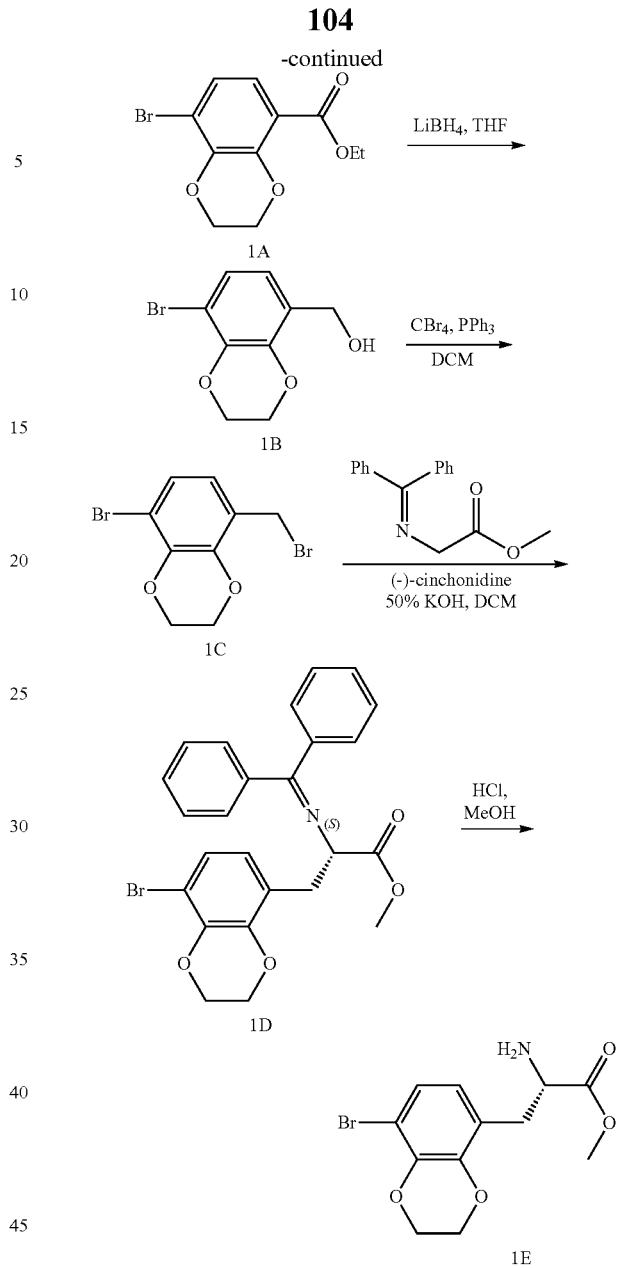

Synthesis of ethyl 8-bromo-2,3-dihydrobenzo[1,4]dioxine-5-carboxylate (1A): To a stirred solution of ethyl 4-bromo-2,3-dihydroxybenzoate (16.8 g, 64.4 mmol) in DMF (168 mL) were added K₂CO₃ (44.5 g, 322 mmol) and dibromoethane (18.3 g, 96.5 mmol) and at RT and the reaction was heated to 120° C. for 6 h. The mixture was cooled to RT, diluted with EtOAc, washed with water and brine. The combined organic layer was dried over Na₂SO₄ and concentrated under vacuum to afford the crude material. The material was purified by 100-200 mesh silica gel column chromatography and eluted with 30% EtOAc in hexanes to afford compound 1A.

Synthesis of (8-bromo-2,3-dihydrobenzo[1,4]dioxin-5-yl)methanol (1B): To a stirred solution of compound 1A (16.0 g, 55.7 mmol) in THF (160 mL) was added a solution of 2M LiBH₄ in THF (167 mL, 334 mmol) at 0° C. The reaction mixture was heated at 40° C. and stirred for 4 h. Upon completion, the mixture was cooled to 0° C., quenched with ice-water and stirred for 30 min. The mixture was acidified with aq. 2N HCl (pH~4-5) and heated to 40° C. for 2 h. The mixture was cooled to RT and the pH was adjusted with sat. NaHCO₃ solution (pH~8-9) and extracted with EtOAc. The organic layer was dried over Na₂SO₄ and concentrated under vacuum to afford the crude material. The material was purified by 230-400 mesh silica gel column chromatography and eluted with 50% EtOAc in hexane to afford compound 1B.

Synthesis of 5-bromo-8-(bromomethyl)-2,3-dihydrobenzo[1,4]dioxine (1C): To a stirred solution of 1B (12.0 g, 49.0 mmol) in dichloromethane (240 mL) was added triphenylphosphine (19.2 g, 73.4 mmol) and carbon tetrabromide (24.4 g, 73.4 mol) at 0° C. and mixture was stirred at RT for 1 h. The mixture was concentrated under vacuum to afford the crude material. The material was purified by 100-200 mesh silica gel column chromatography and eluted with 4-10% EtOAc in hexane to afford compound 1C.

Synthesis of methyl (S)-3-(8-bromo-2,3-dihydrobenzo[b][1,4]dioxin-5-yl)-2-((diphenylmethylene)amino)propanoate (1D): To a stirred solution of -((diphenylmethylene) amino) acetate (9.70 g, 38.4 mmol) in dichloromethane (291 mL) was added (−)-cinchonidine (1.14 g, 3.83 mmol) at RT. The reaction mixture was cooled to 0° C., KOH (78 mL, 50% aq) was added followed by compound 1C (13.0 g, 42.2 mmol). The reaction mixture was allowed to stir at RT for 6 h. The reaction mixture was diluted with water and stirred for 15 minute. DCM was added and the organic layer was washed with brine, dried over anhydrous Na₂SO₄, and concentrated under reduced pressure to afford crude material. The crude compound 1D was used without any purification.

Synthesis of methyl (S)-2-amino-3-(8-bromo-2,3-dihydrobenzo[1,4]dioxin-5-yl)propanoate (1E): To a stirred solution of 1D (22.0 g, 45.8 mmol) in MeOH (110 mL) was added HCl in 1,4-dioxane (154 mL, 4N). The reaction mixture was allowed to stir at RT for 72 h. The reaction mixture was concentrated under reduced pressure, dissolved in water, and washed with EtOAc. The aqueous layer was adjusted to pH~8 using Sat. NaHCO₃ and extracted with EtOAc. The combined organic layer was washed with brine, dried over anhydrous Na₂SO₄, and concentrated under reduced pressure to afford the crude material. The material was purified using 230-400 mesh silica gel column chromatography and eluted with 2% MeOH in DCM to afford a 60:40 mixture of racemic 1E. The mixture of isomers was purified by SFC to obtain compound 1E. To a solution of compound 1E (7.00 g, 22.1 mmol) in dichloromethane (70.0 mL) was added HCl in 1,4-dioxane (22.1 mL, 4 N) at 0° C. and the reaction mixture was allowed to stir at room temperature for 1 h. The reaction mixture was concentrated under vacuum to afford compound 1E.

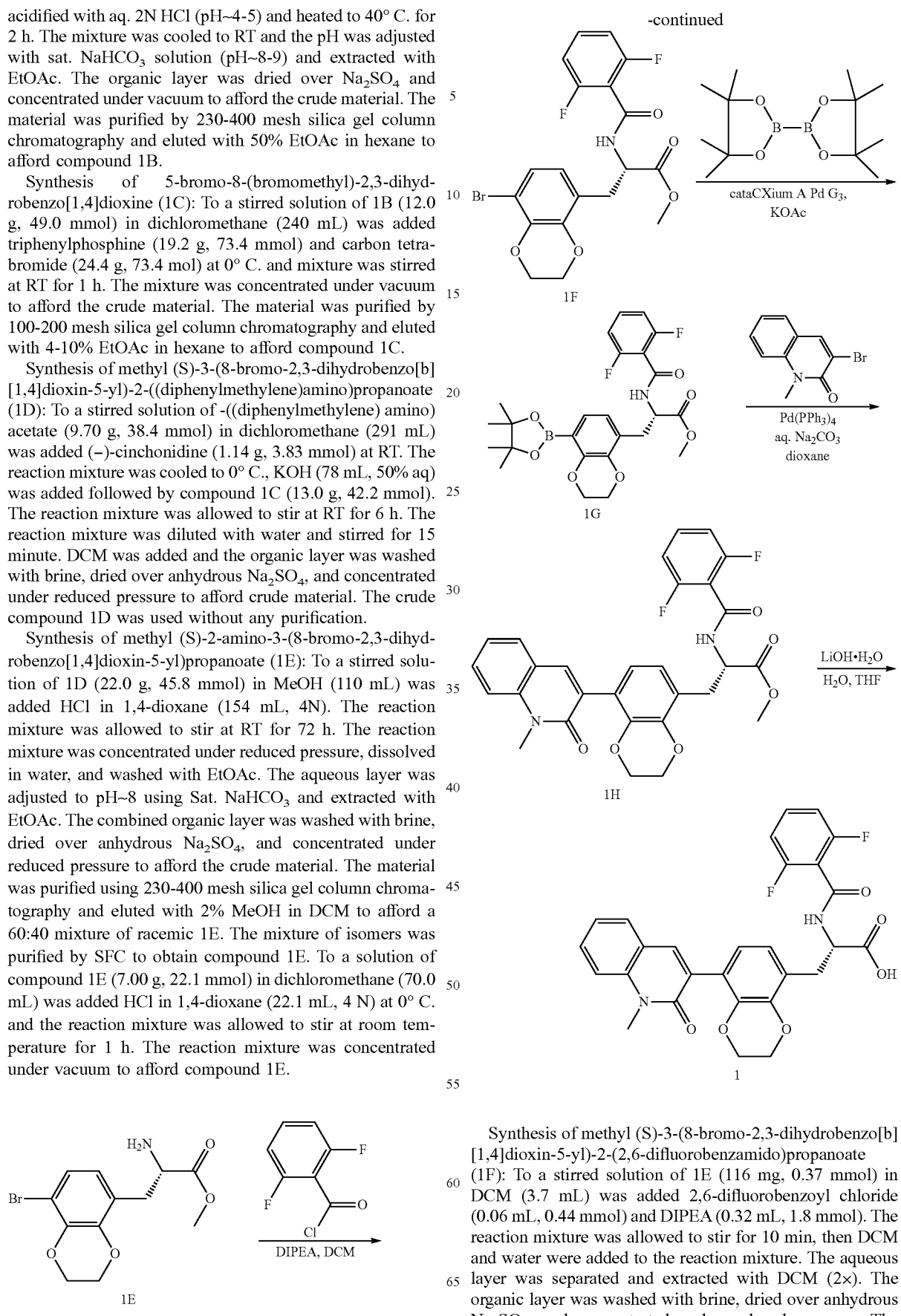

Synthesis of methyl (S)-3-(8-bromo-2,3-dihydrobenzo[b][1,4]dioxin-5-yl)-2-(2,6-difluorobenzamido)propanoate (1F): To a stirred solution of 1E (116 mg, 0.37 mmol) in DCM (3.7 mL) was added 2,6-difluorobenzoyl chloride (0.06 mL, 0.44 mmol) and DIPEA (0.32 mL, 1.8 mmol). The reaction mixture was allowed to stir for 10 min, then DCM and water were added to the reaction mixture. The aqueous layer was separated and extracted with DCM (2×). The organic layer was washed with brine, dried over anhydrous Na₂SO₄, and concentrated under reduced pressure. The material was purified on silica gel eluting with EtOAc in Hex (0-50%) to give the title compound.

Synthesis of methyl (S)-2-(2,6-difluorobenzamido)-3-(8-(4,4,5,5-tetramethyl-1,3,2-dioxaborolan-2-yl)-2,3-dihydrobenzo[b][1,4]dioxin-5-yl)propanoate (1G): To a stirred solution of 1F (154 mg, 0.34 mmol) in DMA was added bis(pinacolato)diboron (171 mg, 0.68 mmol), followed by KOAc (99 mg, 1.0 mmol) and cataCXium A Pd G3 (12 mg, 0.02 mmol). The reaction vessel was flushed with nitrogen then heated to 90° C. for 1 hr. EtOAc and water was added to the reaction mixture. The aqueous layer was separated and extracted with EtOAc (2×). The organic layer was washed with water (4×) and brine, dried over anhydrous $Na_2SO_4$, and concentrated under reduced pressure. The material was purified on silica gel eluting with EtOAc in hex (0-50%) to give the title compound.

Synthesis of methyl (S)-2-(2,6-difluorobenzamido)-3-(8-(1-methyl-2-oxo-1,2-dihydroquinolin-3-yl)-2,3-dihydrobenzo[b][1,4]dioxin-5-yl)propanoate (1H): To a microwave vial was added 1G (47 mg, 0.09 mmol), 3-bromo-1-methylquinolin-2(1H)-one (19 mg, 0.08 mmol), $Pd(PPh_3)_4$ (4.5 mg, 0.004 mmol), and aq. $Na_2CO_3$ (0.12 mL, 2 M) in dioxane (0.6 mL). The reaction mixture was allowed to stir at 130° C. for 30 min. EA and water was added, and the mixture was acidified to pH 3-4. The organic layer was dried over anhydrous $Na_2SO_4$, and concentrated under reduced pressure to give the title compound along with hydrolyzed ester and used without further purification.

Synthesis of (S)-2-(2,6-difluorobenzamido)-3-(8-(1-methyl-2-oxo-1,2-dihydroquinolin-3-yl)-2,3-dihydrobenzo[b][1,4]dioxin-5-yl)propanoic acid (1): To a stirred solution of 1H (42 mg, 0.08 mmol) in THF (0.5 mL) and water (0.5 mL) was added $LiOH \cdot H_2O$ (33 mg, 0.78 mmol). The reaction mixture was allowed to stir for 15 min then concentrated under reduced pressure. The material was purified via reverse phase HPLC to afford the title compound. MS (m/z) 521.1 $[M+H]^+$. 1H NMR (400 MHz, DMSO-d6) δ 12.76 (s, 1H), 9.10 (d, J=8.0 Hz, 1H), 7.85 (s, 1H), 7.74 (dd, J=7.9, 1.6 Hz, 1H), 7.63 (ddd, J=8.6, 7.1, 1.6 Hz, 1H), 7.56-7.45 (m, 2H), 7.28 (td, J=7.5, 1.0 Hz, 1H), 7.19-7.09 (m, 2H), 6.82-6.72 (m, 2H), 4.64 (td, J=8.8, 5.2 Hz, 1H), 4.30-4.26 (m, 2H), 4.20-4.15 (m, 2H), 3.67 (s, 3H), 3.20 (dd, J=13.9, 5.2 Hz, 1H), 2.87 (dd, J=14.0, 9.6 Hz, 1H).

Example 2

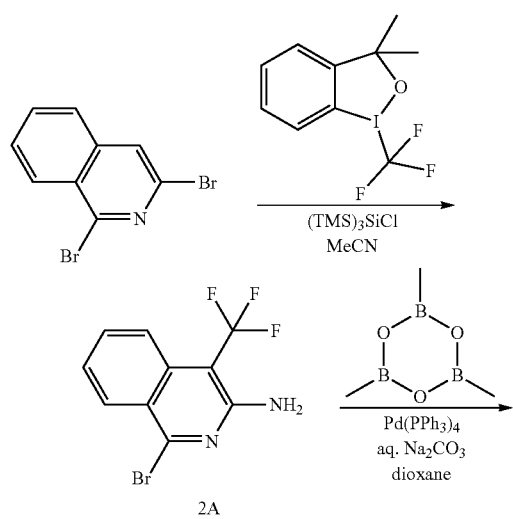

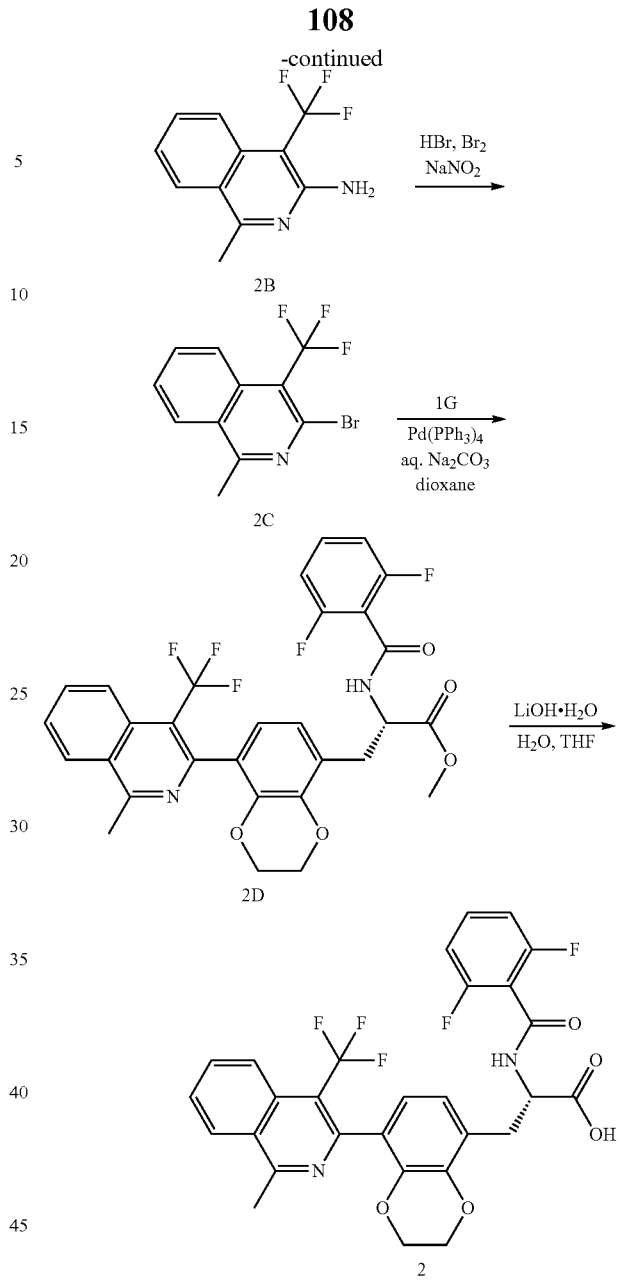

Synthesis of 1-bromo-4-(trifluoromethyl)isoquinolin-3-amine (2A): To a stirred solution of 1-bromoisoquinolin-3-amine (1.56 g, 6.5 mmol) in MeCN was added 3,3-dimethyl-1-(trifluoromethyl)-1,2-benziodoxole (2.22 g, 7.8 mmol) and tris(trimethylsilyl)silyl chloride (2.2 ml, 7.8 mmol). This mixture was heated to 80° C. for 1 h. EtOAc and water was added to the reaction mixture. The aqueous layer was separated and extracted with EtOAc (2×). The organic layer was washed with water (4×) and brine, dried over anhydrous $Na_2SO_4$, and concentrated under reduced pressure. The material was purified on silica gel eluting with EtOAc in Hex (0-20%) to give the title compound.

Synthesis of 1-methyl-4-(trifluoromethyl)isoquinolin-3-amine (2B): The title compound was prepared according to the method presented for the synthesis of compound 1H of Example 1 starting with trimethylboroxine and 2A.

Synthesis of 3-bromo-1-methyl-4-(trifluoromethyl)isoquinoline (2C): To a stirred solution of 2B (54 mg, 0.24 mmol) in HBr (2.5 mL, 48% soln) was added Br$_2$ (0.07 ml, 1.4 mmol). The reaction mixture was kept at 0° C. for 10 minutes at which time NaNO$_2$ (82 mg, 1.2 mmol) was added as a solution in water (2 mL). The reaction mixture was allowed to stir 2 h while allowing to slowly warm to RT. The reaction was quenched with sodium bicarbonate, extracted with EtOAc, concentrated under reduced pressure. The material was purified by silica gel chromatography eluting EtOAc in Hex (0-10%) to give the title compound.

Synthesis of methyl (S)-2-(2,6-difluorobenzamido)-3-(8-(1-methyl-4-(trifluoromethyl) isoquinolin-3-yl)-2,3-dihydrobenzo[b][1,4]dioxin-5-yl)propanoate (2D): The title compound was prepared according to the method presented for the synthesis of compound 1H of Example 1 starting with 1G and 2C.

Synthesis of (S)-2-(2,6-difluorobenzamido)-3-(8-(1-methyl-4-(trifluoromethyl) isoquinolin-3-yl)-2,3-dihydrobenzo[b][1,4]dioxin-5-yl)propanoic acid (2): The title compound was prepared according to the method presented for the synthesis of compound 1 of Example 1 starting with 2D. MS (m/z) 573.2 [M+H]$^+$. 1H NMR (400 MHz, DMSO-d6) δ 9.10 (dd, J=16.5, 8.0 Hz, 1H), 8.42 (dd, J=8.4, 1.1 Hz, 1H), 8.15 (d, J=8.4 Hz, 1H), 8.00 (ddd, J=8.6, 6.9, 1.3 Hz, 1H), 7.92-7.77 (m, 1H), 7.51 (td, J=8.5, 6.0 Hz, 1H), 7.14 (q, J=7.9 Hz, 2H), 6.93-6.76 (m, 2H), 4.79-4.57 (m, 1H), 4.41-3.96 (m, 4H), 3.21 (ddd, J=38.1, 13.9, 5.4 Hz, 1H), 2.98 (s, 3H), 2.95-2.84 (m, 1H).

Example 3

Synthesis of bisboc-1-bromo-4-(trifluoromethyl)isoquinolin-3-amine (3A): To a stirred solution of 2A (955 mg, 3.3 mmol) and trimethylamine (1.14 mL, 8.2 mmol) in DCM (22 mL) was added di-tert-butyl dicarbonate (1.79 g, 122 mmol) and 4-(dimethylamino)pyridine (40 mg, 0.33 mmol). The reaction mixture was heated to reflux and allowed to stir for 90 min. Then DCM and water was added to the reaction mixture. The aqueous layer was separated and extracted with DCM (2×). The organic layer was washed with brine, dried over anhydrous Na$_2$SO$_4$, and concentrated under reduced pressure. The material was purified on silica gel eluting with EtOAc in Hex (0-10%) to give the title compound.

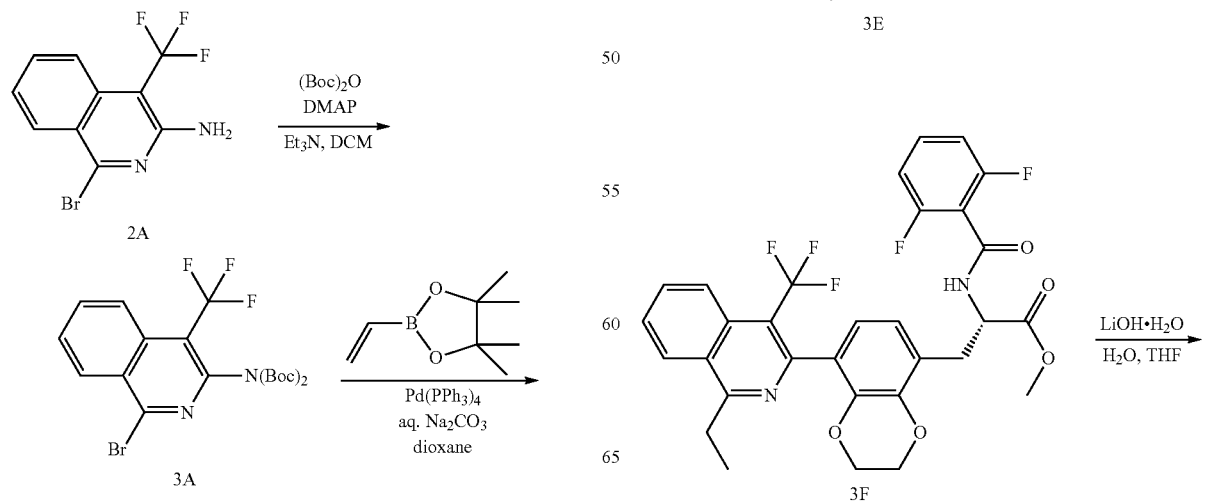

-continued

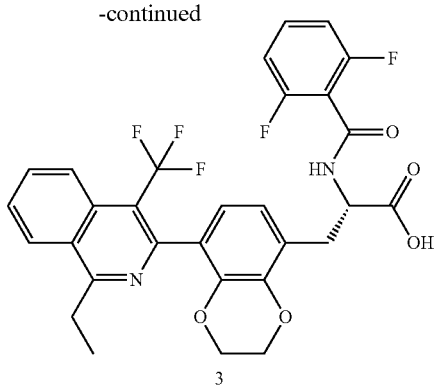

3

Synthesis of bis(boc)-4-(trifluoromethyl)-1-vinylisoquinolin-3-amine (3B): The title compound was prepared according to the method presented for the synthesis of compound 1H of Example 1 starting with vinylboronic acid pinacol ester and 3A.

Synthesis of bisBoc-1-ethyl-4-(trifluoromethyl)isoquinolin-3-amine (3C): To a stirred solution of 3B (57 mg, 0.13 mmol) in EtOH (5 mL) was added 10% Pd on carbon (15 mg). The reaction was placed under $H_2$ gas using a balloon. After vigorous stirring for 1 hr, the mixture was filtered through Celite and concentrated under reduced pressure to give the title compound which was used without further purification.

Synthesis of 1-ethyl-4-(trifluoromethyl)isoquinolin-3-amine (3D): To a stirred solution of 3C (57 mg, 0.12 mmol) in DCM (1.3 mL) at rt was added TFA (0.3 mL, 114 mmol). The reaction mixture was allowed to stir for 16 h and then concentrated. Then DCM and sat. aq. $NaHCO_3$ were added. The aqueous layer was separated and extracted with DCM (3×). The organic layer was dried over anhydrous $Na_2SO_4$, and concentrated under reduced pressure. The resulting crude material of the title compound was used with no further purification.

Synthesis of 3-bromo-1-ethyl-4-(trifluoromethyl)isoquinoline (3E): The title compound was prepared according to the method presented for the synthesis of compound 2C of Example 2 starting with 3D.

Synthesis of methyl (S)-2-(2,6-difluorobenzamido)-3-(8-(1-ethyl-4-(trifluoromethyl)isoquinolin-3-yl)-2,3-dihydrobenzo[b][1,4]dioxin-5-yl)propanoate (3F): The title compound was prepared according to the method presented for the synthesis of compound 1H of Example 1 starting with 1G and 3E.

Synthesis of ((S)-2-(2,6-difluorobenzamido)-3-(8-(1-ethyl-4-(trifluoromethyl) isoquinolin-3-yl)-2,3-dihydrobenzo[b][1,4]dioxin-5-yl)propanoic acid (3): The title compound was prepared according to the method presented for the synthesis of compound 1 of Example 1 starting with 3F. MS (m/z) 588.4 $[M+H]^+$. 1H NMR (400 MHz, DMSO-d6) δ 9.10 (dd, J=15.2, 8.0 Hz, 1H), 8.46 (dd, J=8.3, 1.2 Hz, 1H), 8.15 (d, J=8.5 Hz, 1H), 7.98 (ddd, J=8.5, 6.9, 1.3 Hz, 1H), 7.84 (ddd, J=8.2, 6.8, 1.1 Hz, 1H), 7.51 (ddd, J=14.6, 8.4, 6.3 Hz, 1H), 7.19-7.07 (m, 2H), 6.92-6.77 (m, 2H), 4.81-4.59 (m, 1H), 4.38-4.01 (m, 2H), 3.38 (q, J=7.5 Hz, 2H), 3.21 (ddd, J=30.6, 13.9, 5.4 Hz, 1H), 2.91 (ddd, J=17.6, 13.9, 9.5 Hz, 1H), 1.34 (td, J=7.5, 2.0 Hz, 3H).

Example 4

Synthesis of (2S,5R)-2-((8-bromo-2,3-dihydrobenzo[b][1,4]dioxin-5-yl)methyl)-5-isopropyl-3,6-dimethoxy-2,5-dihydropyrazine (4A): To a stirred solution of (R)-2,5-dihydro-3,6-dimethoxy-2-isopropylpyrazine (0.44 mL, 184 mmol) in 2-MeTHF (8.1 mL) was added n-BuLi (1.6 mL, 1.6M solution in hexanes) dropwise at −78° C. After stirring for 25 min, a solution of 1C (500 mg, 1.6 mmol) in 2-MeTHF (13 mL) was added dropwise. The reaction mixture was allowed to stir at −78° C. for 45 min. $H_2O$ was added and the reaction mixture was warmed to RT. The aqueous layer was separated and extracted with EtOAc (2×). The organic layer was washed with brine, dried over anhydrous $Na_2SO_4$, and concentrated under reduced pressure. The material was purified by silica gel chromatography using 0-40% EtOAc in hexanes to give the title compound.

Synthesis of (2S,5R)-2-((8-(2,6-dichloro-4-fluorophenyl)-2,3-dihydrobenzo[b][1,4]dioxin-5-yl)methyl)-5-isopropyl-3,6-dimethoxy-2,5-dihydropyrazine (4B): To a stirred solution of 4A (303 mg, 0.74 mmol), (2,6-dichloro-4-fluorophenyl)boronic acid (308 mg, 1.47 mmol), $K_3PO_4$ (547 mg, 2.58 mmol), SPhos Pd G3 (575 mg, 0.74 mmol) were dissolved in toluene (5.8 mL) and heated to 100° C. for 2 hours. After cooling to RT, EtOAc and water were added to the reaction mixture. The aqueous layer was separated and extracted with EtOAc (2×). The organic layer was washed with brine, dried over anhydrous $Na_2SO_4$, and concentrated under reduced pressure. The material was purified on silica gel eluting with EtOAc in Hex (0-50%) to give the title compound.

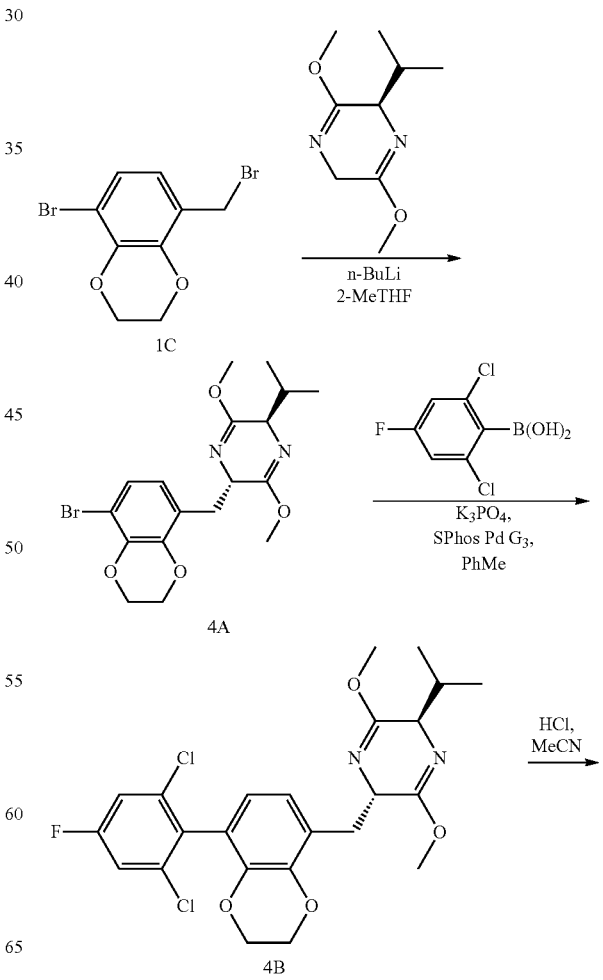

-continued

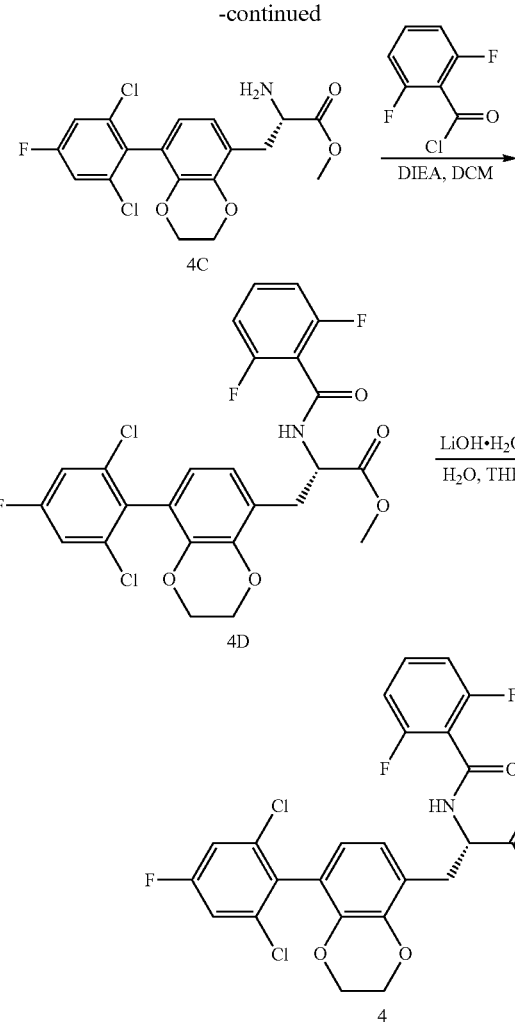

1H), 6.58 (d, J=7.8 Hz, 1H), 4.73 (ddd, J=10.1, 8.2, 5.0 Hz, 1H), 4.29 (dd, J=4.9, 3.0 Hz, 2H), 4.18 (q, J=3.9, 3.4 Hz, 2H), 3.21 (dd, J=14.1, 5.0 Hz, 1H), 2.87 (dd, J=14.1, 10.1 Hz, 1H).

Example 5

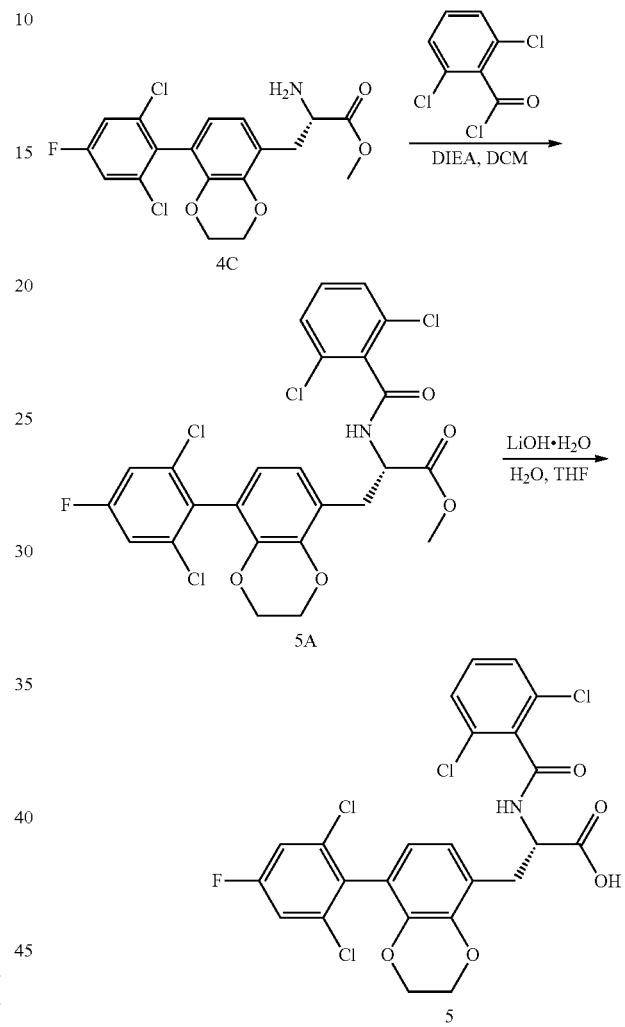

Synthesis of methyl (S)-2-amino-3-(8-(2,6-dichloro-4-fluorophenyl)-2,3-dihydrobenzo[b][1,4]dioxin-5-yl)propanoate (4C): To a stirred solution of 4B (100 mg, 0.2 mmol) in MeCN (2 mL) at rt was added aq. HCl (0.5 mL, 2M). The reaction mixture was allowed to stir for 2 h and then carefully poured into sat aq. NaHCO$_3$. EtOAc was then added to the mixture. The aqueous layer was separated and extracted with EtOAc (2×, ~10 mL) and 2-MeTHF (1×, ~10 mL). The organic layers were combined, dried over anhydrous Na$_2$SO$_4$, and concentrated under reduced pressure. The material was purified on silica gel eluting with DCM in MeOH (0-5%) to give the title compound.

Synthesis of methyl (S)-3-(8-(2,6-dichloro-4-fluorophenyl)-2,3-dihydrobenzo[b][1,4]dioxin-5-yl)-2-(2,6-difluorobenzamido)propanoate (4D): The title compound was prepared according to the method presented for the synthesis of compound 1F of Example 1 starting with 2,6-difluorobenzoyl chloride and 4C.

Synthesis of (S)-3-(8-(2,6-dichloro-4-fluorophenyl)-2,3-dihydrobenzo[b][1,4]dioxin-5-yl)-2-(2,6-difluorobenzamido)propanoic acid (4): The title compound was prepared according to the method presented for the synthesis of compound 1 of Example 1 starting with 4D. MS (m/z) 526.0 [M+H]$^+$. 1H NMR (400 MHz, DMSO-d6) δ 12.76 (s, 1H), 9.05 (d, J=8.1 Hz, 1H), 7.59 (d, J=8.6 Hz, 2H), 7.49 (tt, J=8.4, 6.5 Hz, 1H), 7.18-7.05 (m, 2H), 6.86 (d, J=7.9 Hz, Synthesis of methyl (S)-3-(8-(2,6-dichloro-4-fluorophenyl)-2,3-dihydrobenzo[b][1,4]dioxin-5-yl)-2-(2,6-dichlorobenzamido)propanoate (5A): The title compound was prepared according to the method presented for the synthesis of compound 1F of Example 1 starting with 2,6-dichlorobenzoyl chloride and 4C.

Synthesis of (S)-3-(8-(2,6-dichloro-4-fluorophenyl)-2,3-dihydrobenzo[b][1,4]dioxin-5-yl)-2-(2,6-dichlorobenzamido)propanoic acid (5): The title compound was prepared according to the method presented for the synthesis of compound 1 of Example 1 starting with 5A. MS (m/z) 560.0 [M+H]$^+$. 1H NMR (400 MHz, DMSO-d6) δ 12.71 (s, 1H), 9.03 (d, J=8.5 Hz, 1H), 7.59 (d, J=8.6 Hz, 2H), 7.53-7.32 (m, 3H), 6.91 (d, J=7.8 Hz, 1H), 6.56 (d, J=7.8 Hz, 1H), 4.81 (ddd, J=10.8, 8.4, 4.3 Hz, 1H), 4.30 (q, J=3.9 Hz, 2H), 4.18 (t, J=4.1 Hz, 2H), 3.20 (dd, J=14.0, 4.3 Hz, 1H), 2.86 (dd, J=14.1, 10.8 Hz, 1H).

Example 6

Synthesis of methyl (S)-3-(8-(2,6-dichloro-4-fluorophenyl)-2,3-dihydrobenzo[b][1,4]dioxin-5-yl)-2-(2-(difluoromethoxy)-6-fluorobenzamido)propanoate (6A): To a stirred solution of 2-(difluoromethoxy)-6-fluorobenzoic acid (28 mg, 0.14 mmol) in DMF (2 mL) was added 4C (55 mg, 0.14 mmol), HATU (63 mg, 0.16 mmol) and DIPEA (0.14 mL, 0.83 mmol). The reaction mixture was stirred for 2 hrs at RT. EtOAc and water was added to the reaction mixture. The aqueous layer was separated and extracted with EtOAc (2×). The organic layer was washed with brine, dried over anhydrous Na$_2$SO$_4$, and concentrated under reduced pressure. The material was purified on silica gel eluting with EtOAc in Hex (0-100%) to give the title compound.

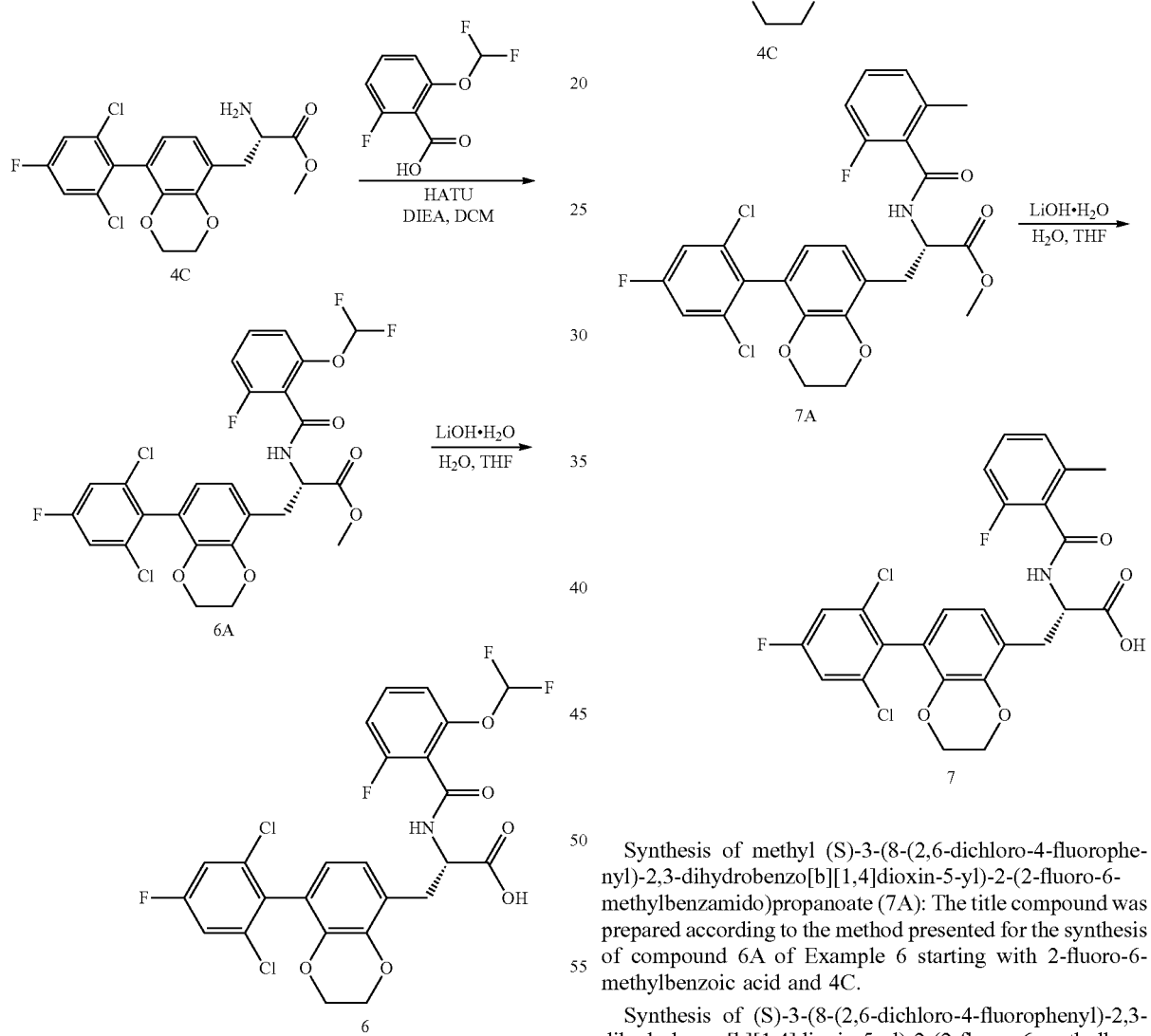

Synthesis of (S)-3-(8-(2,6-dichloro-4-fluorophenyl)-2,3-dihydrobenzo[b][1,4]dioxin-5-yl)-2-(2-(difluoromethoxy)-6-fluorobenzamido)propanoic acid (6): The title compound was prepared according to the method presented for the synthesis of compound 1 of Example 1 starting with 6A. MS (m/z) 574.0 [M+H]$^+$. 1H NMR (400 MHz, DMSO-d6) δ 9.00 (d, J=8.0 Hz, 1H), 7.58 (d, J=8.6 Hz, 1H), 7.48 (td, J=8.4, 6.5 Hz, 1H), 7.30-6.88 (m, 3H), 6.85 (d, J=7.8 Hz, 1H), 6.56 (d, J=7.8 Hz, 1H), 4.69 (ddd, J=9.7, 8.0, 5.2 Hz, 1H), 4.32-4.21 (m, 2H), 4.16 (q, J=3.2 Hz, 2H), 3.15 (dd, J=14.4, 5.3 Hz, 1H), 2.87 (dd, J=14.4, 9.7 Hz, 1H).

Example 7

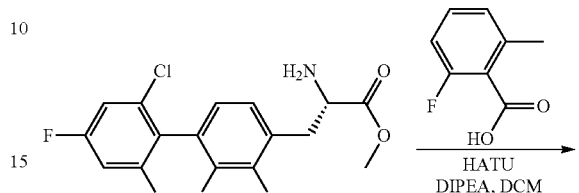

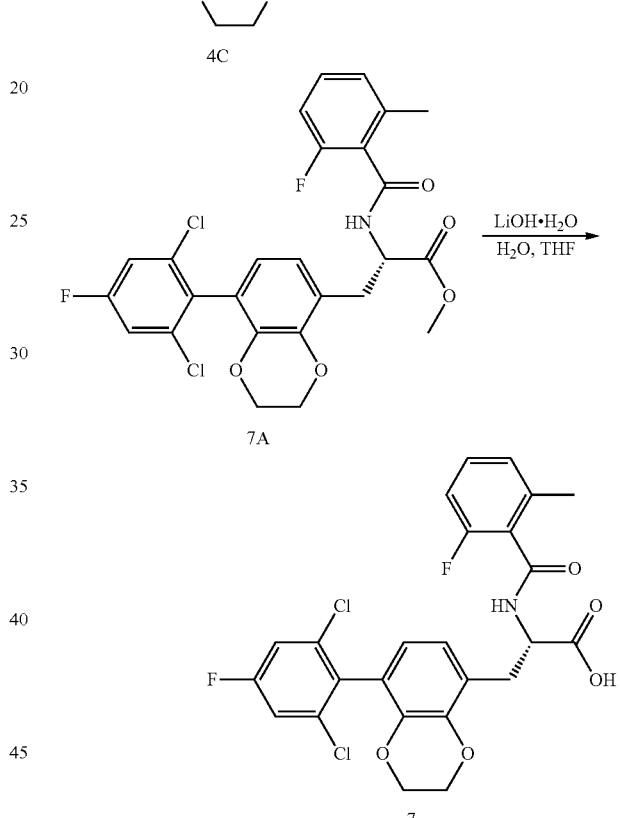

Synthesis of methyl (S)-3-(8-(2,6-dichloro-4-fluorophenyl)-2,3-dihydrobenzo[b][1,4]dioxin-5-yl)-2-(2-fluoro-6-methylbenzamido)propanoate (7A): The title compound was prepared according to the method presented for the synthesis of compound 6A of Example 6 starting with 2-fluoro-6-methylbenzoic acid and 4C.

Synthesis of (S)-3-(8-(2,6-dichloro-4-fluorophenyl)-2,3-dihydrobenzo[b][1,4]dioxin-5-yl)-2-(2-fluoro-6-methylbenzamido)propanoic acid (7): The title compound was prepared according to the method presented for the synthesis of compound 1 of Example 1 starting with 7A. MS (m/z) 522.1 [M+H]$^+$. 1H NMR (400 MHz, DMSO-d6) δ 8.83 (d, J=8.3 Hz, 1H), 7.58 (d, J=8.6 Hz, 2H), 7.33-7.20 (m, 1H), 7.08-6.90 (m, 2H), 6.87 (d, J=7.8 Hz, 1H), 6.56 (d, J=7.8 Hz, 1H), 4.77 (ddd, J=11.0, 8.3, 4.2 Hz, 1H), 4.28 (q, J=3.5 Hz, 2H), 4.17 (d, J=3.1 Hz, 2H), 3.22 (dd, J=14.0, 4.3 Hz, 1H), 2.82 (dd, J=14.1, 11.0 Hz, 1H), 2.06 (s, 3H).

Example 8

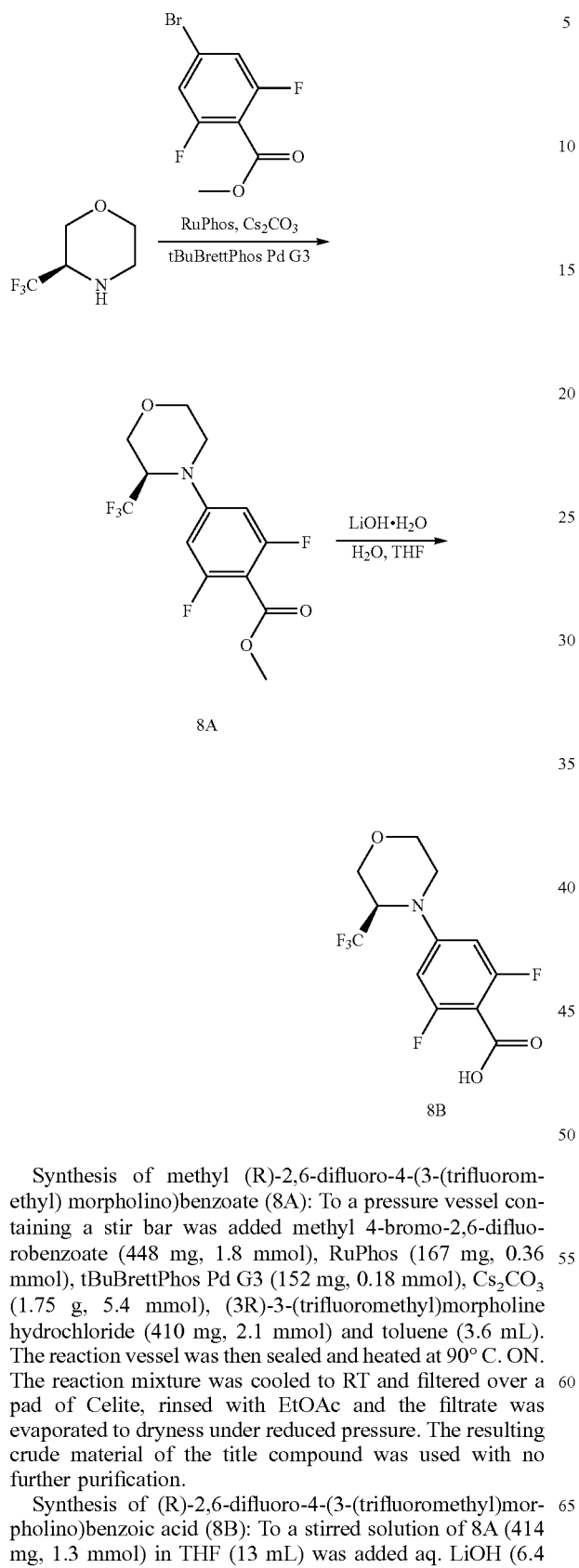

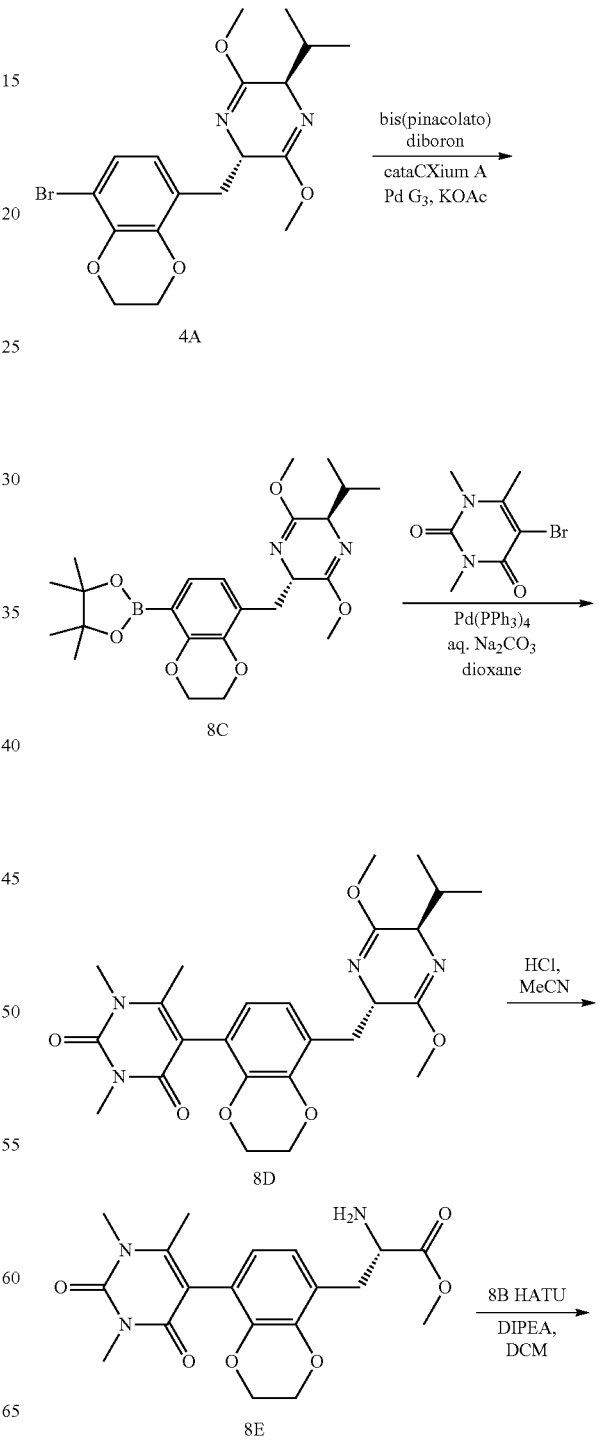

Synthesis of methyl (R)-2,6-difluoro-4-(3-(trifluoromethyl) morpholino)benzoate (8A): To a pressure vessel containing a stir bar was added methyl 4-bromo-2,6-difluorobenzoate (448 mg, 1.8 mmol), RuPhos (167 mg, 0.36 mmol), tBuBrettPhos Pd G3 (152 mg, 0.18 mmol), Cs$_2$CO$_3$ (1.75 g, 5.4 mmol), (3R)-3-(trifluoromethyl)morpholine hydrochloride (410 mg, 2.1 mmol) and toluene (3.6 mL). The reaction vessel was then sealed and heated at 90° C. ON. The reaction mixture was cooled to RT and filtered over a pad of Celite, rinsed with EtOAc and the filtrate was evaporated to dryness under reduced pressure. The resulting crude material of the title compound was used with no further purification.

Synthesis of (R)-2,6-difluoro-4-(3-(trifluoromethyl)morpholino)benzoic acid (8B): To a stirred solution of 8A (414 mg, 1.3 mmol) in THF (13 mL) was added aq. LiOH (6.4 mL, 1M). The reaction mixture was heated to 50° C. and allowed to stir for 16 hrs. The mixture was then cooled to RT and the pH was adjusted to 2-3 using 1M HCl. The reaction was concentrated under reduced pressure, then EtOAc and water was added. The aqueous layer was separated and extracted with EtOAc (2×). The organic layer was dried over anhydrous Na$_2$SO$_4$, and concentrated under reduced pressure to give the title compound which was used without further purification.

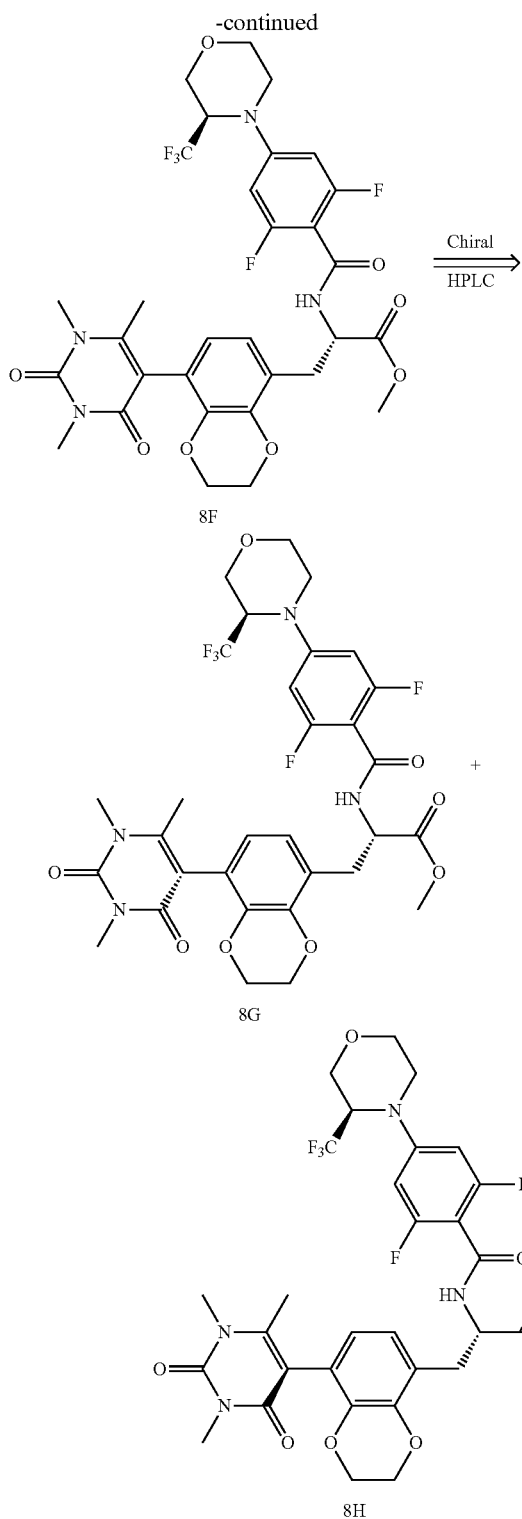

8F

8G

8H

Synthesis of methyl (2R,5S)-2-isopropyl-3,6-dimethoxy-5-((8-(4,4,5,5-tetramethyl-1,3,2-dioxaborolan-2-yl)-2,3-dihydrobenzo[b][1,4]dioxin-5-yl)methyl)-2,5-dihydropyrazine (8C): The title compound was prepared according to the method presented for the synthesis of compound 1G of Example 1 starting with 4A.

Synthesis of 5-(8-(((2S,5R)-5-isopropyl-3,6-dimethoxy-2,5-dihydropyrazin-2-yl) methyl)-2,3-dihydrobenzo[b][1,4] dioxin-5-yl)-1,3,6-trimethylpyrimidine-2,4(1H,3H)-dione (8D): The title compound was prepared according to the method presented for the synthesis of compound 1H of Example 1 starting with 5-bromo-1,3,6-trimethylpyrimidine-2,4(1H,3H)-dione and 8C.

Synthesis of methyl (S)-2-amino-3-(8-(1,3,6-trimethyl-2,4-dioxo-1,2,3,4-tetrahydropyrimidin-5-yl)-2,3-dihydrobenzo[b][1,4]dioxin-5-yl)propanoate (8E): To a stirred solution of 8D (139 mg, 0.29 mmol) in MeCN (2.9 mL) at rt was added aq. HCl (0.72 mL, 2M). The reaction mixture was allowed to stir for 2 h and then concentrated. The material was purified on silica gel eluting with DCM in MeOH (0-20%) to give the title compound.

Synthesis of methyl (S)-2-(2,6-difluoro-4-((R)-3-(trifluoromethyl)morpholino) benzamido)-3-(8-(1,3,6-trimethyl-2,4-dioxo-1,2,3,4-tetrahydropyrimidin-5-yl)-2,3-dihydrobenzo[b][1,4]dioxin-5-yl)propanoate (8F): To a stirred solution of 8E (42 mg, 0.1 mmol), 8B (28 mg, 0.1 mmol), DIPEA (0.12 mL, 0.69 mmol) in DCM (0.8 mL) and DMF (0.8 mL) was added HATU (41 mg, 0.11 mmol). The reaction mixture was allowed to stir for 45 min and then concentrated. DCM and water was added and extracted with DCM. The organic layer was washed with brine, dried over anhydrous $Na_2SO_4$, and concentrated under reduced pressure. The material was purified by silica gel chromatography eluting with EtOAc in hexanes (0-100%) to give the title compound.

Preparation of methyl (S)-2-(2,6-difluoro-4-((R)-3-(trifluoromethyl)morpholino) benzamido)-3-(8-(1,3,6-trimethyl-2,4-dioxo-1,2,3,4-tetrahydropyrimidin-5-yl)-2,3-dihydrobenzo[b][1,4]dioxin-5-yl)propanoate atropisomer 1 (8G) and methyl (S)-2-(2,6-difluoro-4-((R)-3-(trifluoromethyl)morpholino)benzamido)-3-(8-(1,3,6-trimethyl-2,4-dioxo-1,2,3,4-tetrahydropyrimidin-5-yl)-2,3-dihydrobenzo[b][1,4]dioxin-5-yl)propanoate atropisomer 2 (8H): 8F was separated into its 2 diastereomeric atropisomers by supercritical fluid chromatography using 50% MeOH/TFA co-solvent, at a flow rate of 3 mL/min, using an IC 5 μm 4.6×100 mm column. The title compounds were identified as 8G and 8H corresponding to the first and second eluting peaks.

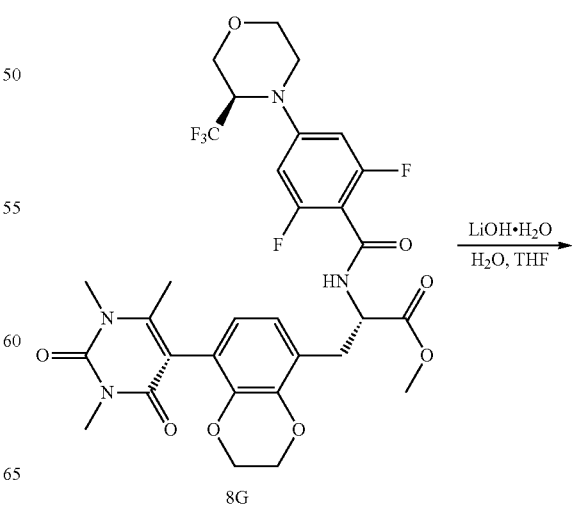

8G

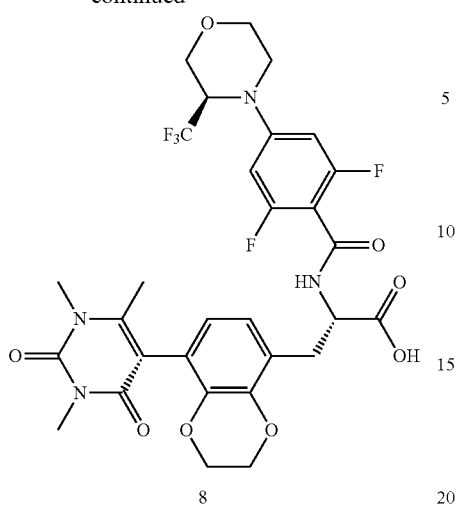

8

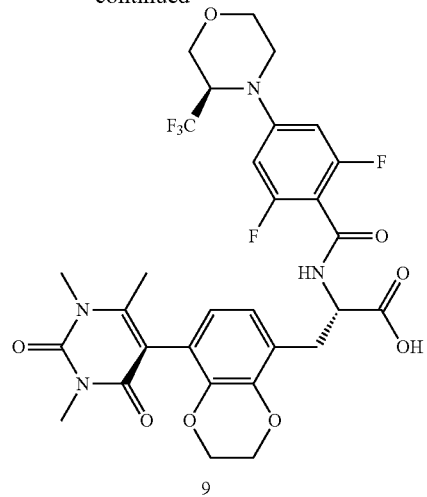

9

Synthesis of (S)-2-(2,6-difluoro-4-((R)-3-(trifluoromethyl)morpholino)benzamido)-3-(8-(1,3,6-trimethyl-2,4-dioxo-1,2,3,4-tetrahydropyrimidin-5-yl)-2,3-dihydrobenzo[b][1,4]dioxin-5-yl)propanoic acid atropisomer 1 (8): The title compound was prepared according to the method presented for the synthesis of compound 1 of Example 1 starting with the first eluting peak from chiral HPLC, 8G. MS (m/z) 669.3 [M+H]$^+$. 1H NMR (400 MHz, DMSO-d6) δ 8.72 (dd, J=17.5, 7.9 Hz, 1H), 6.76 (t, J=11.3 Hz, 3H), 6.51 (dd, J=12.1, 7.7 Hz, 1H), 4.91 (t, J=8.6 Hz, 1H), 4.74-4.48 (m, 1H), 4.25 (d, J=4.3 Hz, 2H), 4.21-4.11 (m, 2H), 3.99-3.92 (m, 1H), 3.66 (s, 48H), 3.40 (s, 3H), 3.20 (s, 3H), 3.11 (dd, J=13.9, 5.4 Hz, 0H), 2.85 (ddd, J=47.7, 14.0, 9.9 Hz, 1H), 2.03 (d, J=2.3 Hz, 3H).

Example 9

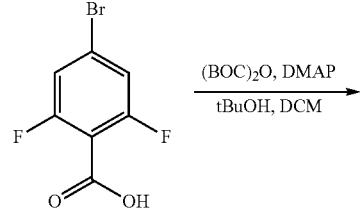

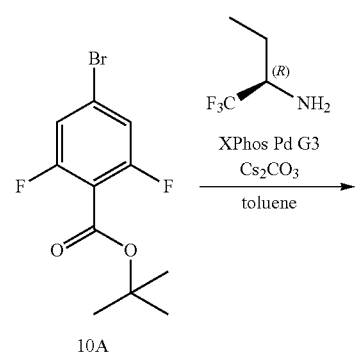

10A

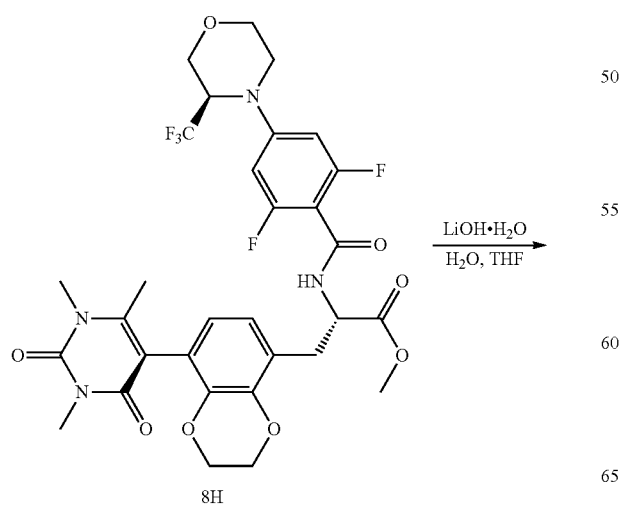

8H

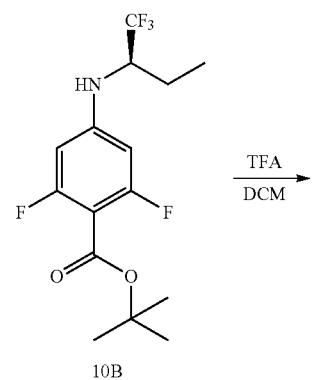

10B

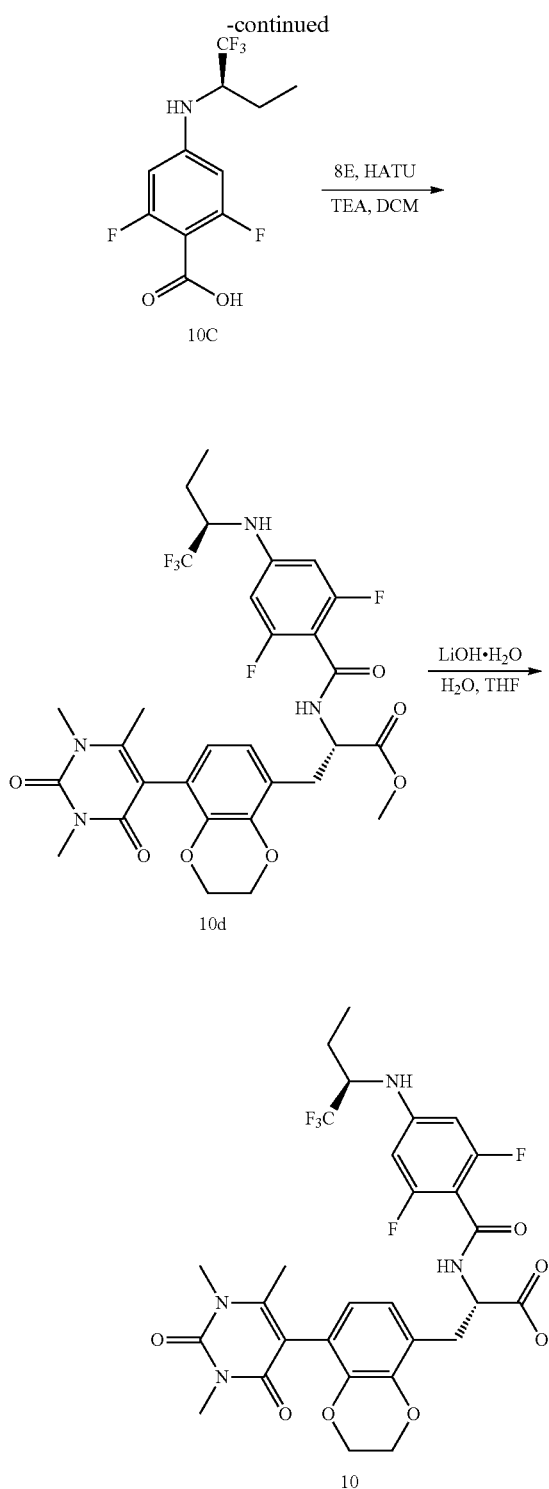

Synthesis of (S)-2-(2,6-difluoro-4-((R)-3-trifluoromethyl)morpholino)benzamido)-3-(8-(1,3,6-trimethyl-2,4-dioxo-1,2,3,4-tetrahydropyrimidin-5-yl)-2,3-dihydrobenzo[b][1,4]dioxin-5-yl)propanoic acid atropisomer 2 (9): The title compound was prepared according to the method presented for the synthesis of compound 1 of Example 1 starting with the second eluting peak from chiral HPLC, 8H. MS (m/z) 669.2 [M+H]$^+$. 1H NMR (400 MHz, DMSO-d6) δ 8.73 (dd, J=17.6, 7.9 Hz, 1H), 6.76 (dd, J=12.6, 9.8 Hz, 3H), 6.51 (dd, J=12.1, 7.8 Hz, 1H), 4.99-4.83 (m, 1H), 4.74-4.48 (m, 1H), 4.25 (q, J=3.9 Hz, 2H), 4.21-4.11 (m, 3H), 3.96 (dd, J=11.5, 3.6 Hz, 1H), 3.69 (s, 49H), 3.40 (s, 3H), 3.20 (s, 4H), 3.11 (ddd, J=13.9, 5.3 Hz, 0H), 2.85 (ddd, J=47.6, 13.9, 9.9 Hz, 1H), 2.04 (d, J=2.3 Hz, 3H).

Synthesis of tert-butyl 4-bromo-2,6-difluorobenzoate (10A): To a stirred solution of 4-bromo-2,6-difluorobenzoic acid (5 g, 21.1 mmol) in dichloromethane (50 mL) and tert-butyl alcohol (50 mL) was added di-tert-butyl dicarbonate (9.2 g, 42.2 mol) followed by 4-dimethyl aminopyridine (0.8 g, 6.3 mmol). The reaction mixture was allowed to stir at RT for 12 h. The reaction mixture was concentrated under reduced pressure, dissolved in EtOAc (100 mL) and washed with a 10% aq. solution of citric acid (100 mL). The organic layer was washed with brine, dried over anhydrous Na$_2$SO$_4$, and concentrated under reduced pressure to afford crude material. This material was suspended in hexanes, the solid was filtered off and the filtrate was evaporated under reduced pressure to afford compound 10A. MS (m/z) 236.6 [M+H—C$_4$H$_8$]$^+$. $^1$H NMR (400 MHz, DMSO-d6) δ 7.69-7.56 (m, 2H), 1.50 (s, 9H).

Synthesis of tert-butyl (R)-2,6-difluoro-4-((1,1,1-trifluorobutan-2-yl)amino)benzoate (10B): To a stirred suspension of tert-butyl 4-bromo-2,6-difluorobenzoate (10A) (250 mg, 0.55 mmol), (R)-1,1,1-trifluorobutan-2-amine (85 mg, 0.67 mmol), and cesium carbonate (904 mg, 2.8 mmol) in toluene (5 mL) was added XPhos Pd G3 (42 mg, 0.06 mmol). The reaction mixture was sparged with nitrogen and then heated to 90° C. for 12 h. The mixture was cooled to RT and diluted with EtOAc (50 mL). The resultant suspension was filtered through a pad of celite, and the filtrate was evaporated under reduced pressure to afford compound 10B. MS (m/z) 284.1 [M+H—C$_4$H$_8$]$^+$.

Synthesis of (R)-2,6-difluoro-4-((1,1,1-trifluorobutan-2-yl)amino)benzoic acid (10C): To a stirred solution of tert-butyl (R)-2,6-difluoro-4-((1,1,1-trifluorobutan-2-yl)amino) benzoate (10B) (188 mg, 0.55 mmol) in dichloromethane (1 mL) was added trifluoroacetic acid (1 mL). The reaction mixture was allowed to stir at RT for 20 mins. The reaction mixture was concentrated under reduced pressure to afford crude material. This material was purified by silica gel column chromatography and eluted EtOAc in hexane to afford compound 10C. MS (m/z) 338.1 [M+H]$^+$.

Synthesis of methyl (S)-2-(2,6-difluoro-4-(((R)-1,1,1-trifluorobutan-2-yl)amino) benzamido)-3-(8-(1,3,6-trimethyl-2,4-dioxo-1,2,3,4-tetrahydropyrimidin-5-yl)-2,3-dihydrobenzo[b][1,4]dioxin-5-yl)propanoate (10D): The title compound was prepared according to the method presented for the synthesis of compound 8F of Example 8 starting with 10C and 8E.

Synthesis of (S)-2-(2,6-difluoro-4-(((R)-1,1,1-trifluorobutan-2-yl)amino)benzamido)-3-(8-(1,3,6-trimethyl-2,4-dioxo-1,2,3,4-tetrahydropyrimidin-5-yl)-2,3-dihydrobenzo[b][1,4]dioxin-5-yl)propanoic acid (10): The title compound was prepared according to the method presented for the synthesis of compound 1 of Example 1 starting with 10D. MS (m/z) 641.2 [M+H]$^+$. 1H NMR (400 MHz, DMSO-d6) δ 8.56 (dd, J=14.0, 7.9 Hz, 1H), 6.84-6.70 (m, 2H), 6.59-6.36 (m, 3H), 4.73-4.44 (m, 1H), 4.30 (s, 2H), 4.29-4.09 (m, 4H), 3.40 (s, 3H), 3.20 (s, 3H), 3.18-3.04 (m, 1H), 2.83 (ddd, J=45.4, 13.9, 9.8 Hz, 1H), 2.03 (d, J=2.2 Hz, 3H), 1.84-1.45 (m, 0H), 0.93 (td, J=7.4, 1.7 Hz, 3H).

Example 11

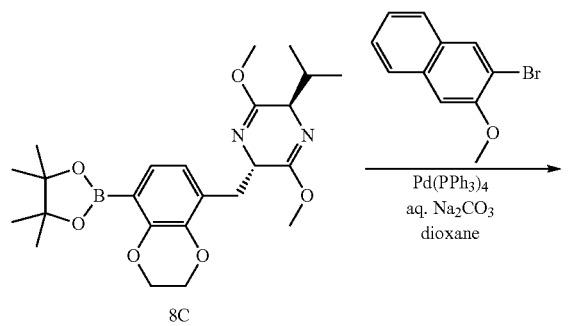

8C

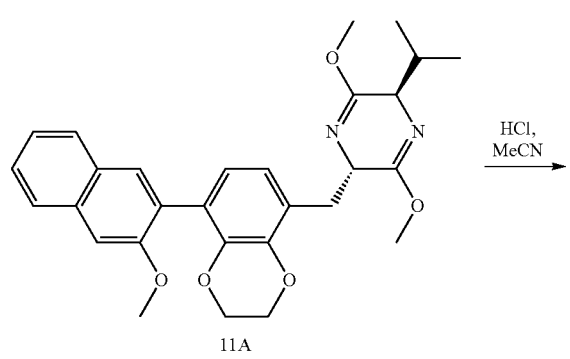

11A

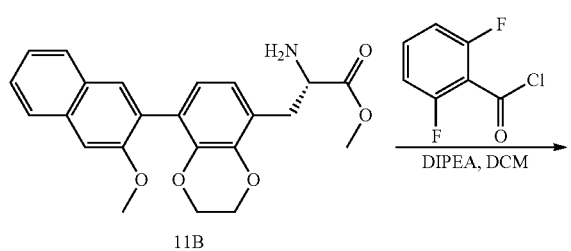

11B

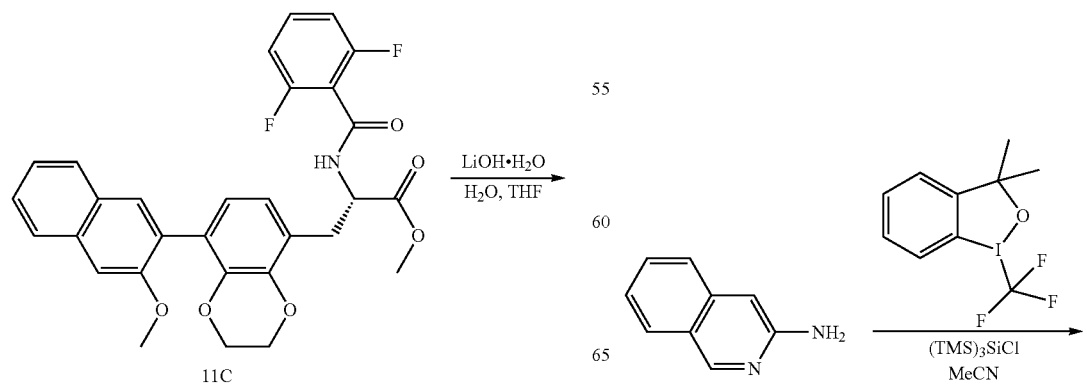

11C

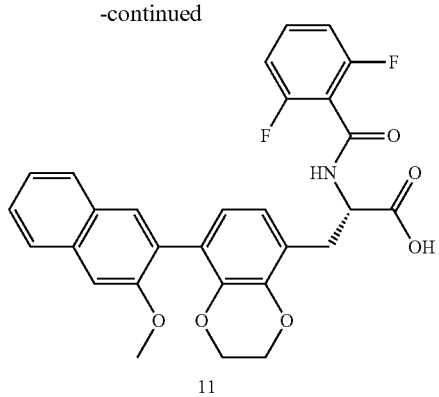

11

Synthesis of methyl (2R,5S)-2-isopropyl-3,6-dimethoxy-5-((8-(3-methoxynaphthalen-2-yl)-2,3-dihydrobenzo[b][1,4]dioxin-5-yl)methyl)-2,5-dihydropyrazine (11A): The title compound was prepared according to the method presented for the synthesis of compound 1H of Example 1 starting with 2-bromo-3-methoxynaphthalene and 8C.

Synthesis of methyl (2R,5S)-2-isopropyl-3,6-dimethoxy-5-((8-(3-methoxynaphthalen-2-yl)-2,3-dihydrobenzo[b][1,4]dioxin-5-yl)methyl)-2,5-dihydropyrazine (11B): The title compound was prepared according to the method presented for the synthesis of compound 8D of Example 8 starting with 11A.

Synthesis of methyl (S)-2-(2,6-difluorobenzamido)-3-(8-(3-methoxynaphthalen-2-yl)-2,3-dihydrobenzo[b][1,4]dioxin-5-yl)propanoate (11C): The title compound was prepared according to the method presented for the synthesis of compound 1F of Example 1 starting with 11B.

Synthesis of (S)-2-(2,6-difluorobenzamido)-3-(8-(3-methoxynaphthalen-2-yl)-2,3-dihydrobenzo[b][1,4]dioxin-5-yl)propanoic acid (11): The title compound was prepared according to the method presented for the synthesis of compound 1 of Example 1 starting with 11C. MS (m/z) 520.2 [M+H]$^+$. 1H NMR (400 MHz, DMSO-d6) δ 12.76 (s, 1H), 9.11 (d, J=8.0 Hz, 1H), 7.91-7.76 (m, 2H), 7.66 (s, 1H), 7.57-7.41 (m, 2H), 7.39-7.30 (m, 2H), 7.21-7.09 (m, 2H), 6.81 (d, J=7.8 Hz, 1H), 6.70 (d, J=7.7 Hz, 1H), 4.72-4.62 (m, 1H), 4.29 (t, J=4.2 Hz, 2H), 4.16 (q, J=3.4 Hz, 2H), 3.83 (s, 3H), 3.21 (dd, J=14.0, 5.1 Hz, 1H), 2.88 (dd, J=14.0, 9.7 Hz, 1H).

Example 12

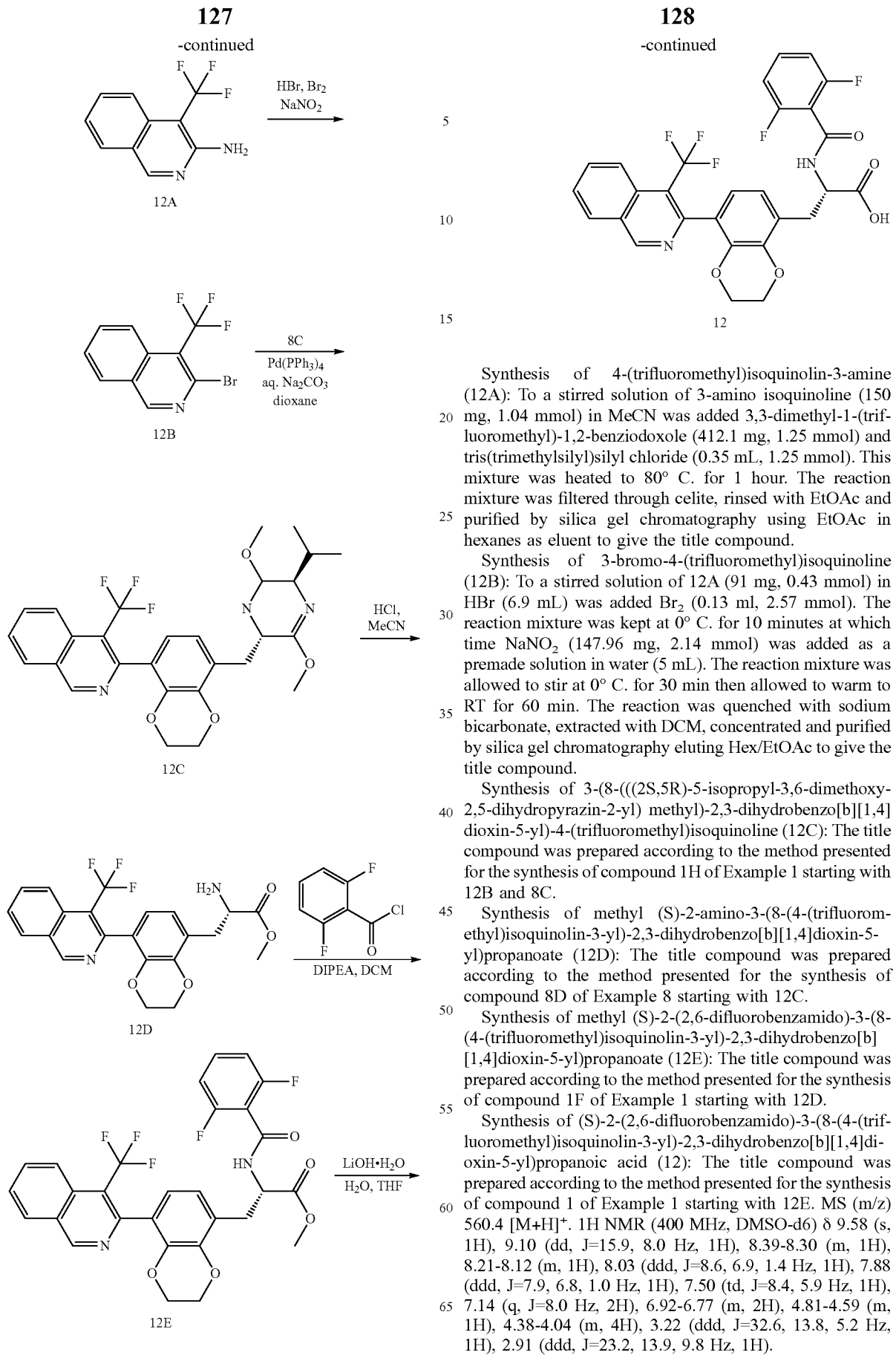

Synthesis of 4-(trifluoromethyl)isoquinolin-3-amine (12A): To a stirred solution of 3-amino isoquinoline (150 mg, 1.04 mmol) in MeCN was added 3,3-dimethyl-1-(trifluoromethyl)-1,2-benziodoxole (412.1 mg, 1.25 mmol) and tris(trimethylsilyl)silyl chloride (0.35 mL, 1.25 mmol). This mixture was heated to 80° C. for 1 hour. The reaction mixture was filtered through celite, rinsed with EtOAc and purified by silica gel chromatography using EtOAc in hexanes as eluent to give the title compound.

Synthesis of 3-bromo-4-(trifluoromethyl)isoquinoline (12B): To a stirred solution of 12A (91 mg, 0.43 mmol) in HBr (6.9 mL) was added $Br_2$ (0.13 ml, 2.57 mmol). The reaction mixture was kept at 0° C. for 10 minutes at which time $NaNO_2$ (147.96 mg, 2.14 mmol) was added as a premade solution in water (5 mL). The reaction mixture was allowed to stir at 0° C. for 30 min then allowed to warm to RT for 60 min. The reaction was quenched with sodium bicarbonate, extracted with DCM, concentrated and purified by silica gel chromatography eluting Hex/EtOAc to give the title compound.

Synthesis of 3-(8-(((2S,5R)-5-isopropyl-3,6-dimethoxy-2,5-dihydropyrazin-2-yl) methyl)-2,3-dihydrobenzo[b][1,4]dioxin-5-yl)-4-(trifluoromethyl)isoquinoline (12C): The title compound was prepared according to the method presented for the synthesis of compound 1H of Example 1 starting with 12B and 8C.

Synthesis of methyl (S)-2-amino-3-(8-(4-(trifluoromethyl)isoquinolin-3-yl)-2,3-dihydrobenzo[b][1,4]dioxin-5-yl)propanoate (12D): The title compound was prepared according to the method presented for the synthesis of compound 8D of Example 8 starting with 12C.

Synthesis of methyl (S)-2-(2,6-difluorobenzamido)-3-(8-(4-(trifluoromethyl)isoquinolin-3-yl)-2,3-dihydrobenzo[b][1,4]dioxin-5-yl)propanoate (12E): The title compound was prepared according to the method presented for the synthesis of compound 1F of Example 1 starting with 12D.

Synthesis of (S)-2-(2,6-difluorobenzamido)-3-(8-(4-(trifluoromethyl)isoquinolin-3-yl)-2,3-dihydrobenzo[b][1,4]dioxin-5-yl)propanoic acid (12): The title compound was prepared according to the method presented for the synthesis of compound 1 of Example 1 starting with 12E. MS (m/z) 560.4 [M+H]$^+$. 1H NMR (400 MHz, DMSO-d6) δ 9.58 (s, 1H), 9.10 (dd, J=15.9, 8.0 Hz, 1H), 8.39-8.30 (m, 1H), 8.21-8.12 (m, 1H), 8.03 (ddd, J=8.6, 6.9, 1.4 Hz, 1H), 7.88 (ddd, J=7.9, 6.8, 1.0 Hz, 1H), 7.50 (td, J=8.4, 5.9 Hz, 1H), 7.14 (q, J=8.0 Hz, 2H), 6.92-6.77 (m, 2H), 4.81-4.59 (m, 1H), 4.38-4.04 (m, 4H), 3.22 (ddd, J=32.6, 13.8, 5.2 Hz, 1H), 2.91 (ddd, J=23.2, 13.9, 9.8 Hz, 1H).

Example 13

Synthesis of 1,4-dibromo-2,3-bis(bromomethyl)benzene (13A): To a stirred solution of 1,4-dibromo-2,3-dimethylbenzene (700.0 g, 2.652 mol) in carbon tetrachloride (5.6 L) were added N-bromo succinimide (944.0 g, 5.304 mol) and benzoyl peroxide (10.92 g, 0.045 mol) at RT. The reaction mixture was allowed to stir at 85° C. for 16 h. The reaction mixture was cooled to RT, filtered through a pad of celite, and the pad was washed with EA. The filtrate was collected, concentrated under reduced pressure, and purified via 100-200 mesh silica gel chromatography eluting 2% EA in petroleum ether to afford the title compound.

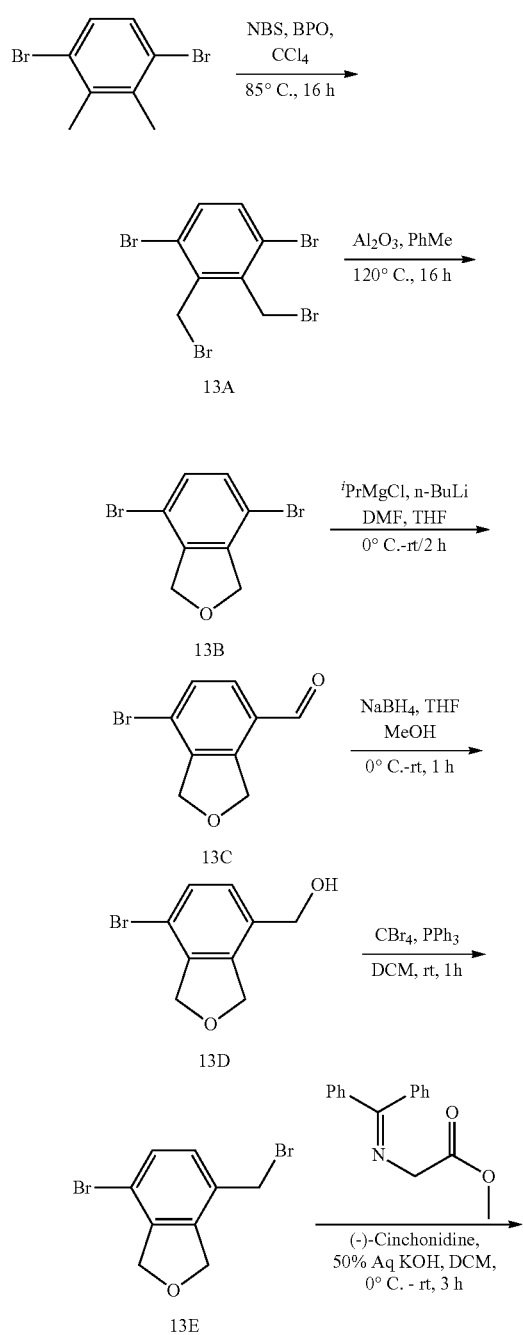

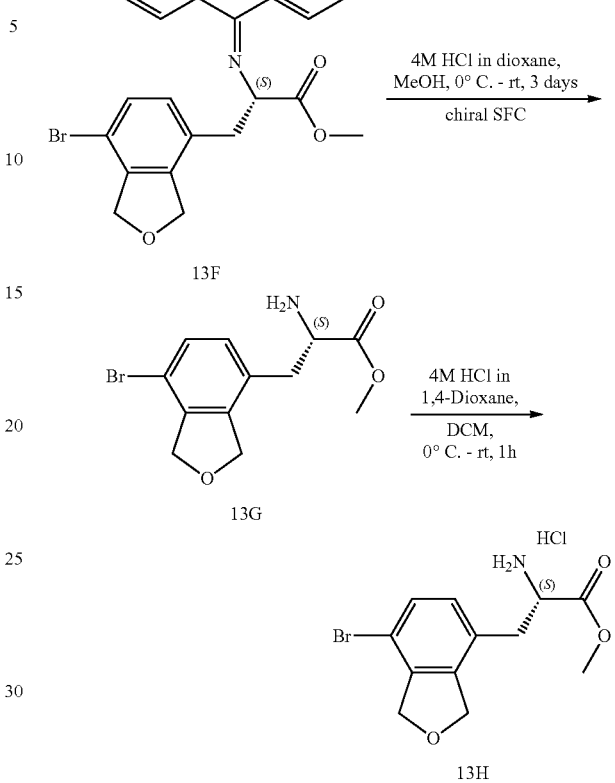

Synthesis of 4,7-dibromo-1,3-dihydroisobenzofuran (13B): To a stirred solution of compound 13A (100.0 g, 0.237 mol) in toluene (1 L) were added activated alumina (18.13 g, 5.453 mol) at RT. The reaction mixture was allowed to stir at 120° C. for 16 hrs. The reaction mixture was cooled to RT, filtered through a pad of celite, and the pad was washed with EA. The filtrate was collected, concentrated under reduced pressure, and purified via 100-200 mesh silica gel chromatography eluting 8% EA in petroleum ether to afford the title compound.

Synthesis of 7-bromo-1,3-dihydroisobenzofuran-4-carbaldehyde (13C): To a stirred solution of compound 13B (30 g, 0.108 mol) in THF (1 L) was added isopropyl magnesium chloride (18.13 g, 0.216 mol) at 0° C. The reaction mixture was allowed to stir at 0° C. for 10 min. n-BuLi (1.6 M in THF, 74.2 mL, 0.119 mol) was added and the reaction mixture was allowed to stir at 0° C. for 1 hr. DMF (12.5 mL, 0.162 mol) was added at 0° C. and the reaction was warmed to RT and allowed to stir for 16 hr. The reaction was quenched with the addition of water (0.200 L) and extracted with EA (0.500 L, 2×). The organic layer was dried over anhydrous $Na_2SO_4$ and concentrated under reduced pressure to afford the title compound without further purification.

Synthesis of (7-bromo-1,3-dihydroisobenzofuran-4-yl) methanol (13D): To a stirred solution of compound 13C (22 g, 96.89 mmol) in THF (0.484 L) and MeOH (0.660 L) was added sodium borohydride (5.04 g, 96.89 mmol) keeping the temperature below 0° C. The reaction mixture was allowed to stir while warming to RT over 1 hr. The reaction was quenched with an ice/water slurry and extracted with EA (0.500 L, 2×). The organic layer was dried over anhydrous $Na_2SO_4$, concentrated under reduced pressure, and purified via 100-200 mesh silica gel chromatography eluting 20% EA in hexane to afford title compound.

Synthesis of 4-bromo-7-(bromomethyl)-1,3-dihydroisobenzofuran (13E): To a solution of compound 13D (20.0 g, 87.30 mmol) in DCM (0.180 L) were added triphenyl phosphine (34.31 g, 130.9 mmol) and carbontetrabromide (43.4 g, 130.9 mmol) at room temperature. The reaction mixture was allowed to stir at RT for 1 hr. The reaction mixture was concentrated under reduced pressure and purified via 100-200 mesh silica gel chromatography eluting 2-6% EA in hexane to afford the title compound.

Synthesis of methyl (S)-3-(7-bromo-1,3-dihydroisobenzofuran-4-yl)-2-((diphenyl methylene)amino)propanoate (13F): To a stirred solution of methyl 2-((diphenylmethylene) amino)acetate (18.0 g, 71.06 mmol) in DCM (0.540 L) was added (−)-cinchonidine (2.091 g, 7.106 mmol) at RT. The reaction mixture was cooled to 0° C. and potassium hydroxide (50%, 0.144 L), compound 13E (19.71 g, 67.50 mmol) were added. The reaction mixture was allowed to stir while warming to RT for 3 hrs. The reaction was quenched with water (0.150 L) and stirred at RT for 15 min. The aqueous layer was extracted with DCM (0.300 L, 2×) and combined organics dried over anhydrous $Na_2SO_4$. The organic layer was concentrated under reduced pressure to afford the title compound used without further purification.

Synthesis of methyl (S)-2-amino-3-(7-bromo-1,3-dihydroisobenzofuran-4-yl) propanoate (13G): To a stirred solution of crude compound 13F (38.0 g, 81.83 mmol) in MeOH (0.190 L) at 0° C. was added 4 M HCl in dioxane (0.266 L) [Note: becomes uniform solution after addition of HCl]. The reaction mixture was allowed to stir while warming to RT for 3 days. The reaction mixture was concentrated under reduced pressure, dissolved in water (0.400 L), and washed with EA (0.400 L, 2×). The aqueous layer was isolated, pH adjusted to (~8) with saturated $NaHCO_3$, and extracted with EA (0.400 L, 2×). The combined organics were dried over anhydrous $Na_2SO_4$, concentrated under reduced pressure, and purified via 100-200 mesh silica gel chromatography eluting 2% MeOH in DCM to afford compound 13G as a 60:40 mixture of isomers. The mixture of isomers was further purified via chiral SFC to afford the title compound (Peak 2). SFC conditions: Chiralpak IA (30×250 mm) 5μ, 65% $CO_2$, 35% cosolvent (0.5% DEA in MeOH), 90.0 g/min, 90.0 bar, UV 225.0 nm, stack time 5.40 min, 110 mg injection.

Synthesis of methyl (S)-2-amino-3-(7-bromo-1,3-dihydroisobenzofuran-4-yl)propanoate hydrochloride (13H): To a solution of compound G (SFC peak 2, 10.2 g, 33.98 mmol) in DCM (0.102 L) at 0° C. was added 4M HCl in dioxane (0.041 L, 135.9 mmol). The reaction mixture was allowed to stir while warming to room temperature for 1 hr. The reaction mixture was concentrated under reduced pressure to afford the title compound.

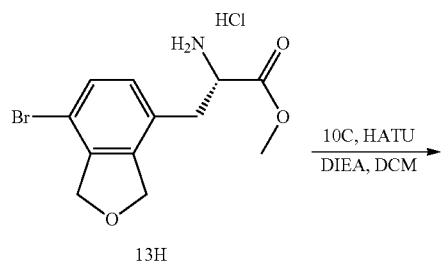

13H

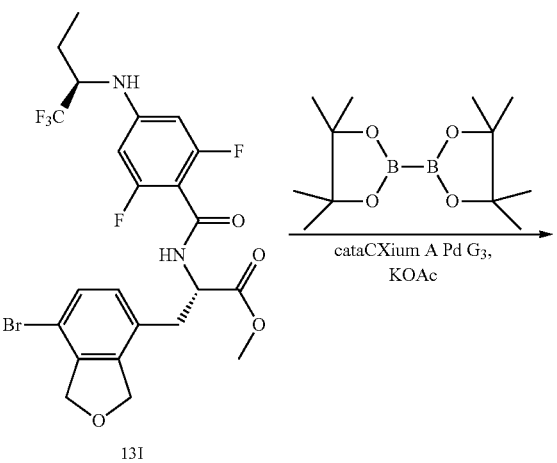

13I

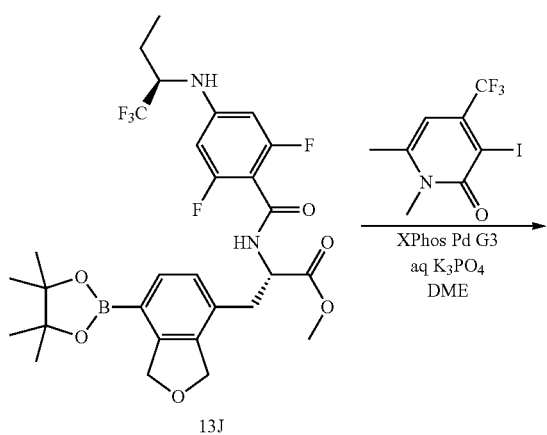

13J

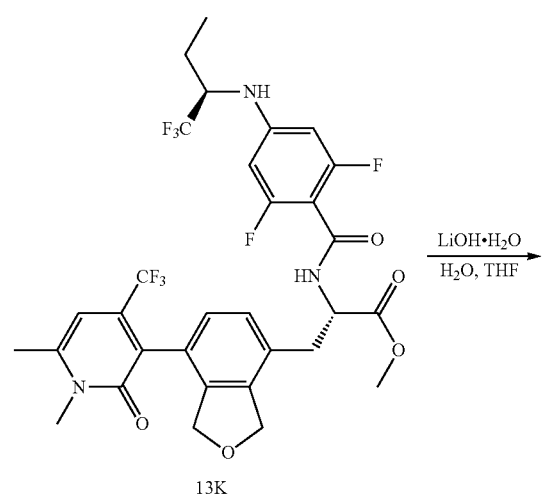

13K

Example 14

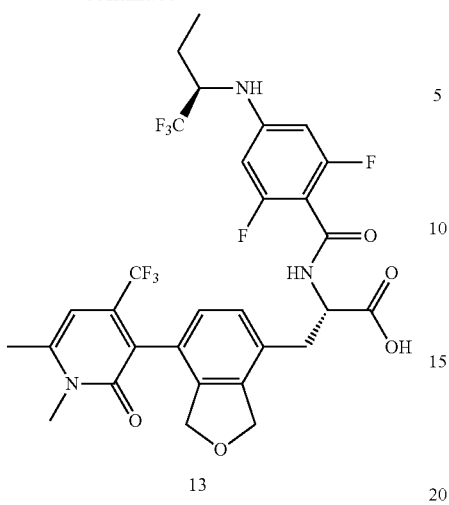

13

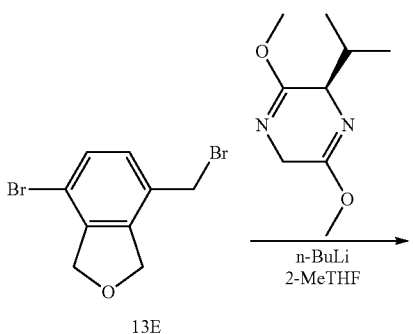

Synthesis of methyl (S)-3-(7-bromo-1,3-dihydroisobenzofuran-4-yl)-2-(2,6-difluoro-4-(((R)-1,1,1-trifluorobutan-2-yl)amino)benzamido)propanoate (13I): The title compound was prepared according to the method presented for the synthesis of compound 8F of Example 8 starting with 10C and 13H.

Synthesis of methyl (S)-2-(2,6-difluoro-4-(((R)-1,1,1-trifluorobutan-2-yl)amino) benzamido)-3-(7-(4,4,5,5-tetramethyl-1,3,2-dioxaborolan-2-yl)-1,3-dihydroisobenzofuran-4-yl)propanoate (13J): The title compound was prepared according to the method presented for the synthesis of compound 1G of Example 1 starting with 13I.

Synthesis of methyl (S)-2-(2,6-difluoro-4-(((R)-1,1,1-trifluorobutan-2-yl)amino) benzamido)-3-(7-(1,6-dimethyl-2-oxo-4-(trifluoromethyl)-1,2-dihydropyridin-3-yl)-1,3-dihydroisobenzofuran-4-yl)propanoate (13K): To a stirred solution 13I (196 mg, 0.32 mmol) in DME (4.9 mL) was added 3-iodo-1,6-dimethyl-4-(trifluoromethyl)pyridin-2(1H)-one (122 mg, 0.38 mmol), XPhos Pd G3 (14 mg, 0.016 mmol) and aq. $K_3PO_4$ (1.1 mL, 1 M). The reaction was degassed with nitrogen and heated at 90° C. for 15 min. EtOAc and water was added to the reaction mixture. The aqueous layer was separated and extracted with EtOAc (2×). The combined organics were dried over anhydrous $Na_2SO_4$, and concentrated under reduced pressure. The material was purified on silica gel eluting with EtOAc in Hex (0-100%) to give the title compound.

Synthesis of (S)-2-(2,6-difluoro-4-(((R)-1,1,1-trifluorobutan-2-yl)amino)benzamido)-3-(7-(1,6-dimethyl-2-oxo-4-(trifluoromethyl)-1,2-dihydropyridin-3-yl)-1,3-dihydroisobenzofuran-4-yl)propanoic acid (13): The title compound was prepared according to the method presented for the synthesis of compound 1 of Example 1 starting with 13K. MS (m/z) 662.2 [M+H]+. 1H NMR (400 MHz, DMSO-d6) δ 12.72 (s, 1H), 8.70 (d, J=7.9 Hz, 1H), 7.18 (t, J=8.2 Hz, 1H), 6.91 (d, J=7.8 Hz, 1H), 6.75 (d, J=9.4 Hz, 1H), 6.52 (s, 1H), 6.45 (d, J=11.9 Hz, 2H), 5.12 (t, J=10.3 Hz, 2H), 4.76 (d, J=12.2 Hz, 1H), 4.69-4.54 (m, 2H), 4.31 (d, J=9.0 Hz, 1H), 3.49 (s, 3H), 3.07 (dt, J=12.2, 5.7 Hz, 1H), 2.91 (dd, J=14.6, 9.9 Hz, 1H), 2.48 (s, 3H), 1.76 (dd, J=14.3, 6.9 Hz, 1H), 1.53 (dp, J=21.0, 7.4 Hz, 1H), 0.93 (t, J=7.3 Hz, 3H).

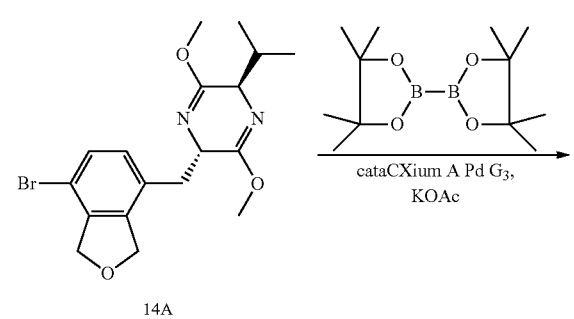

14A

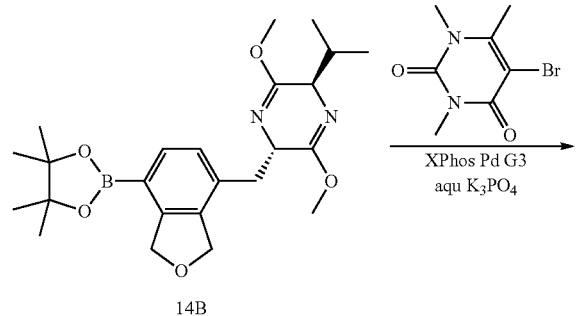

14B

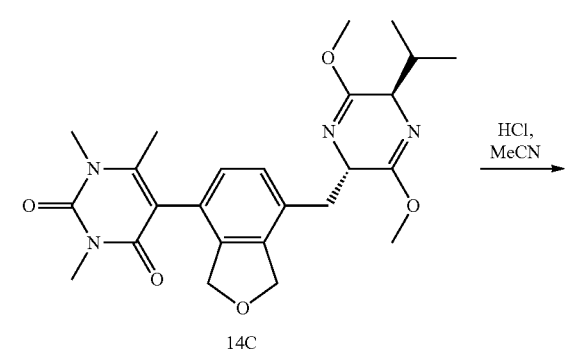

14C

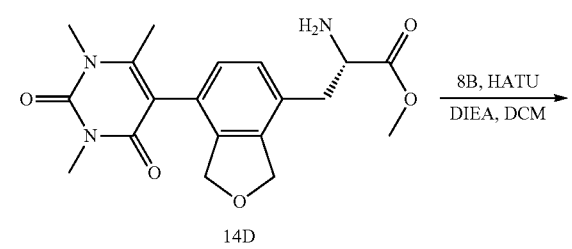

14D

-continued

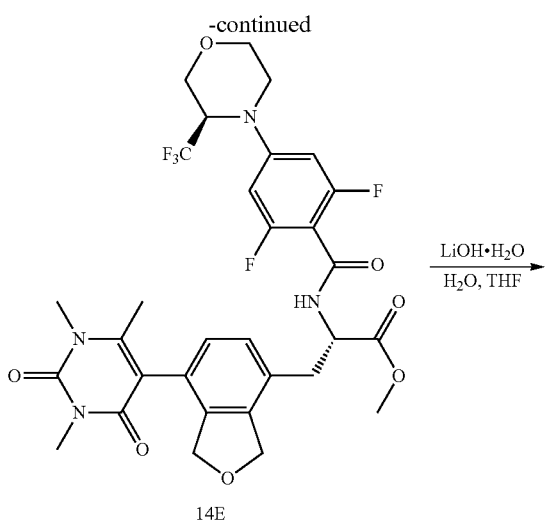

14E

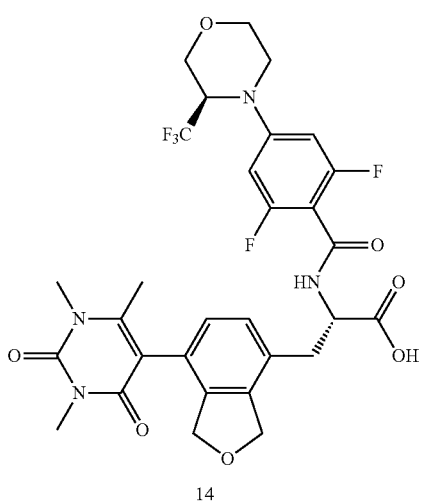

14

Synthesis of (2S,5R)-2-((7-bromo-1,3-dihydroisobenzofuran-4-yl)methyl)-5-isopropyl-3,6-dimethoxy-2,5-dihydropyrazine (14A): The title compound was prepared according to the method presented for the synthesis of compound 4A of Example 4 starting with 13E.

Synthesis of (2R,5S)-2-isopropyl-3,6-dimethoxy-5-((7-(4,4,5,5-tetramethyl-1,3,2-dioxaborolan-2-yl)-1,3-dihydroisobenzofuran-4-yl)methyl)-2,5-dihydropyrazine (14B): The title compound was prepared according to the method presented for the synthesis of compound 1G of Example 1 starting with 14A.

Synthesis of 5-(7-(((2S,5R)-5-isopropyl-3,6-dimethoxy-2,5-dihydropyrazin-2-yl) methyl)-1,3-dihydroisobenzofuran-4-yl)-1,3,6-trimethylpyrimidine-2,4(1H,3H)-dione (14C): The title compound was prepared according to the method presented for the synthesis of compound 13K of Example 13 starting with 5-bromo-1,3,6-trimethylpyrimidine-2,4(1H,3H)-dione and 14B.

Synthesis of methyl (S)-2-amino-3-(7-(1,3,6-trimethyl-2,4-dioxo-1,2,3,4-tetrahydropyrimidin-5-yl)-1,3-dihydroisobenzofuran-4-yl)propanoate (14D): The title compound was prepared according to the method presented for the synthesis of compound 4C of Example 4 starting with 14C.

Synthesis of methyl (S)-2-(2,6-difluoro-4-((R)-3-(trifluoromethyl)morpholino) benzamido)-3-(7-(1,3,6-trimethyl-2,4-dioxo-1,2,3,4-tetrahydropyrimidin-5-yl)-1,3-dihydroisobenzofuran-4-yl)propanoate (14E): The title compound was prepared according to the method presented for the synthesis of compound 8F of Example 8 starting with 8B and 14D.

Synthesis of (S)-2-(2,6-difluoro-4-((R)-3-(trifluoromethyl)morpholino)benzamido)-3-(7-(1,3,6-trimethyl-2,4-dioxo-1,2,3,4-tetrahydropyrimidin-5-yl)-1,3-dihydroisobenzofuran-4-yl) propanoic acid (14): The title compound was prepared according to the method presented for the synthesis of compound 1 of Example 1 starting with 14E. MS (m/z) 653.2 [M+H]+. 1H NMR (400 MHz, DMSO-d6) δ 12.84 (s, 1H), 8.86 (t, J=7.8 Hz, 1H), 7.20 (dd, J=11.8, 7.7 Hz, 1H), 6.95 (t, J=7.0 Hz, 1H), 6.75 (dd, J=11.6, 3.0 Hz, 2H), 5.10 (d, J=15.1 Hz, 2H), 4.91 (d, J=9.6 Hz, 1H), 4.78 (s, 2H), 4.63 (dtd, J=18.4, 9.2, 4.6 Hz, 1H), 4.16 (d, J=12.7 Hz, 1H), 3.95 (dd, J=11.6, 3.7 Hz, 1H), 3.74 (d, J=13.0 Hz, 1H), 3.55 (t, J=10.9 Hz, 1H), 3.40 (s, 4H), 3.20 (s, 4H), 3.13-3.04 (m, 1H), 2.90 (dt, J=14.5, 9.6 Hz, 1H), 2.05 (d, J=7.9 Hz, 3H).

Example 15

Synthesis of methyl (S)-2-(2,6-difluoro-4-(((R)-1,1,1-trifluorobutan-2-yl)amino) benzamido)-3-(7-(1,3,6-trimethyl-2,4-dioxo-1,2,3,4-tetrahydropyrimidin-5-yl)-1,3-dihydroisobenzofuran-4-yl)propanoate (15A): The title compound was prepared according to the method presented for the synthesis of compound 8F of Example 8 starting with 10C and 14D.

Synthesis of (S)-2-(2,6-difluoro-4-(((R)-1,1,1-trifluorobutan-2-yl)amino)benzamido)-3-(7-(1,3,6-trimethyl-2,4-dioxo-1,2,3,4-tetrahydropyrimidin-5-yl)-1,3-dihydroisobenzofuran-4-yl)propanoic acid (15): The title compound was prepared according to the method presented for the synthesis of compound 1 of Example 1 starting with 15A. MS (m/z) 625.2 [M+H]+. 1H NMR (400 MHz, DMSO-d6) δ 8.71 (t, J=7.6 Hz, 1H), 7.19 (dd, J=10.8, 7.7 Hz, 1H), 6.95 (dd, J=7.7, 5.4 Hz, 1H), 6.77 (dd, J=9.7, 2.5 Hz, 1H), 6.44 (dd, J=11.3, 2.8 Hz, 2H), 5.17-5.03 (m, 2H), 4.77 (d, J=3.2 Hz, 2H), 4.61 (dddd, J=15.5, 10.1, 8.1, 4.8 Hz, 1H), 4.30 (d, J=8.7 Hz, 1H), 3.39 (d, J=1.1 Hz, 3H), 3.20 (s, 3H), 3.07 (dd, J=14.4, 4.8 Hz, 1H), 2.89 (dt, J=14.4, 9.5 Hz, 1H), 2.05 (d, J=7.4 Hz, 3H), 1.77 (ddd, J=14.0, 7.1, 3.3 Hz, 1H), 1.53 (ddt, J=17.6, 14.3, 7.5 Hz, 1H), 0.93 (t, J=7.3 Hz, 3H).

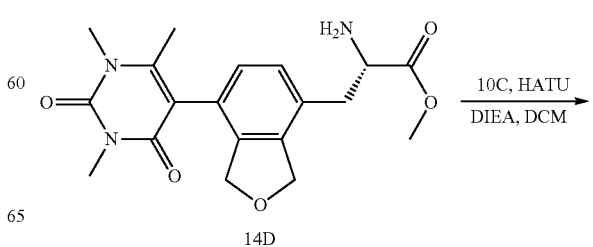

14D

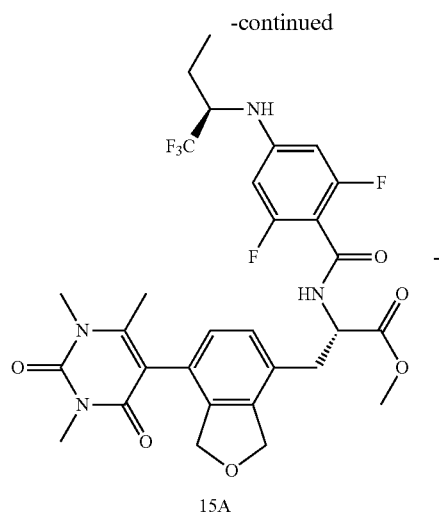

15A

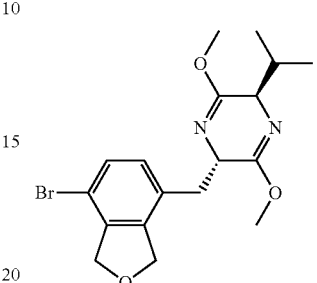

15

Example 16

Synthesis of (2S,5R)-2-((7-(2,6-dichloro-4-fluorophenyl)-1,3-dihydroisobenzofuran-4-yl)methyl)-5-isopropyl-3,6-dimethoxy-2,5-dihydropyrazine (16A): The title compound was prepared according to the method presented for the synthesis of compound 4B of Example 4 starting with (2,6-dichloro-4-fluorophenyl)boronic acid and 14A.

Synthesis of methyl (S)-2-amino-3-(7-(2,6-dichloro-4-fluorophenyl)-1,3-dihydroisobenzofuran-4-yl)propanoate (16B): The title compound was prepared according to the method presented for the synthesis of compound 4C of Example 4 starting with 16A.

Synthesis of methyl (S)-3-(7-(2,6-dichloro-4-fluorophenyl)-1,3-dihydroisobenzofuran-4-yl)-2-(2,6-difluorobenzamido)propanoate (16C): The title compound was prepared according to the method presented for the synthesis of compound 1F of Example 1 starting with 2,6-difluorobenzoyl chloride and 16B.

Synthesis of (S)-3-(7-(2,6-dichloro-4-fluorophenyl)-1,3-dihydroisobenzofuran-4-yl)-2-(2,6-difluorobenzamido)propanoic acid (16): The title compound was prepared according to the method presented for the synthesis of compound 1 of Example 1 starting with 16C. MS (m/z) 510.0 [M+H]⁺. 1H NMR (400 MHz, DMSO-d6) δ 12.94 (s, 1H), 9.18 (d, J=8.2 Hz, 1H), 7.70-7.61 (m, 2H), 7.49 (tt, J=8.4, 6.5 Hz, 1H), 7.31 (d, J=7.8 Hz, 1H), 7.17-7.08 (m, 2H), 7.06 (d, J=7.7 Hz, 1H), 5.22-5.09 (m, 2H), 4.79-4.69 (m, 3H), 3.16 (dd, J=14.6, 4.7 Hz, 1H), 2.93 (dd, J=14.6, 10.4 Hz, 1H).

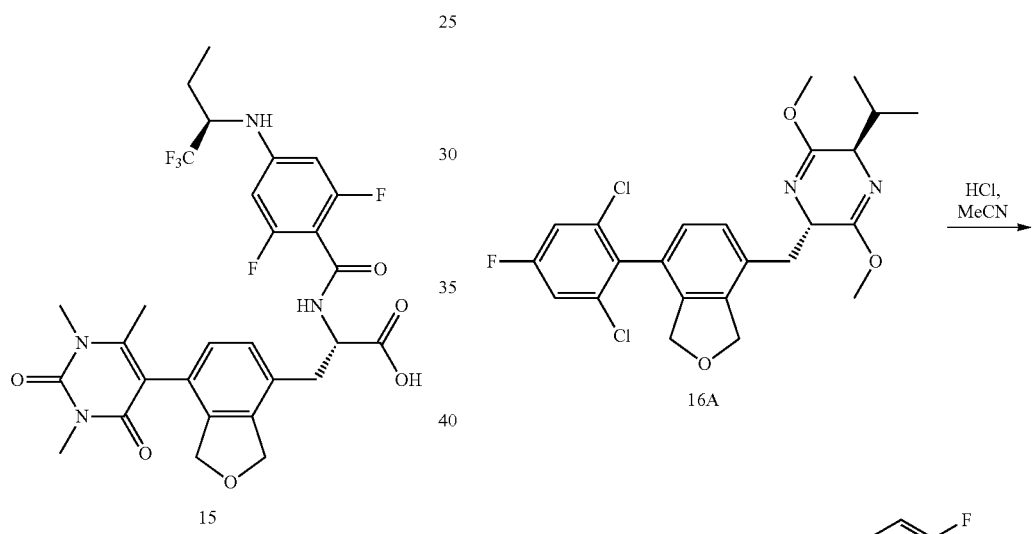

-continued

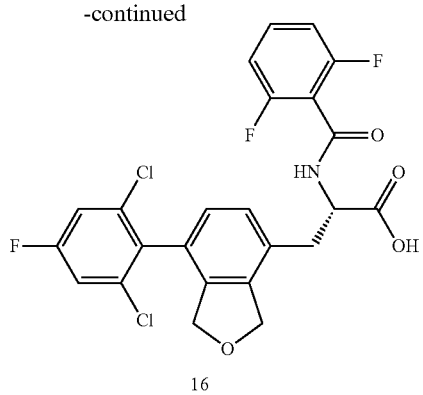

16

Example 17

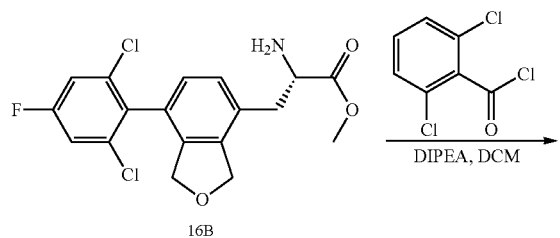

16B

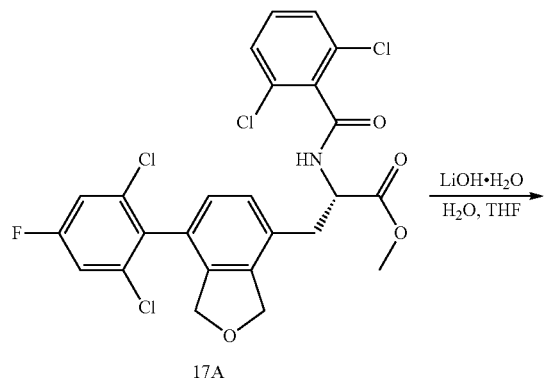

17A

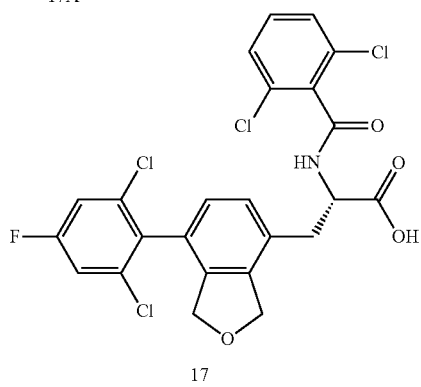

17

Synthesis of methyl (S)-3-(7-(2,6-dichloro-4-fluorophenyl)-1,3-dihydroisobenzofuran-4-yl)-2-(2,6-dichlorobenzamido)propanoate (17A): The title compound was prepared according to the method presented for the synthesis of compound 1F of Example 1 starting with 2,6-dichlorobenzoyl chloride and 16B.

(S)-3-(7-(2,6-dichloro-4-fluorophenyl)-1,3-dihydroisobenzofuran-4-yl)-2-(2,6-dichlorobenzamido)propanoic acid (17): The title compound was prepared according to the method presented for the synthesis of compound 1 of Example 1 starting with 17A. MS (m/z) 542.0 [M+H]$^+$. 1H NMR (400 MHz, DMSO-d6) δ 12.91 (s, 1H), 9.16 (d, J=8.7 Hz, 1H), 7.69-7.63 (m, 2H), 7.46-7.33 (m, 4H), 7.06 (d, J=7.7 Hz, 1H), 5.26-5.09 (m, 2H), 4.82 (ddd, J=11.1, 8.6, 4.0 Hz, 1H), 4.72 (q, J=1.8 Hz, 2H), 3.18 (dd, J=14.6, 4.0 Hz, 1H), 2.87 (dd, J=14.5, 11.2 Hz, 1H).

Example 18

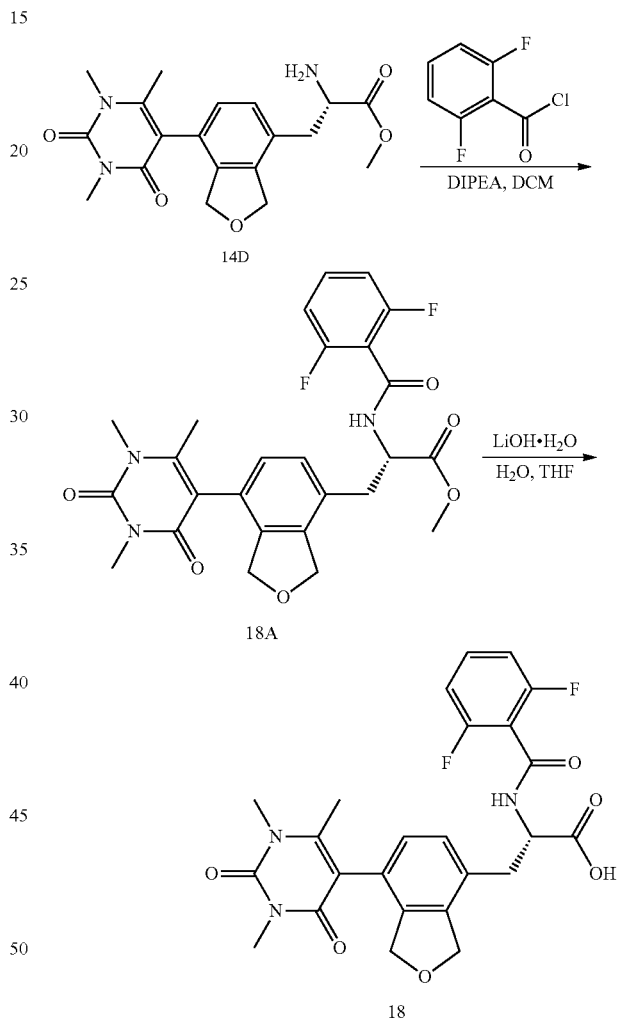

Synthesis of methyl (S)-2-(2,6-difluorobenzamido)-3-(7-(1,3,6-trimethyl-2,4-dioxo-1,2,3,4-tetrahydropyrimidin-5-yl)-1,3-dihydroisobenzofuran-4-yl)propanoate (18A): The title compound was prepared according to the method presented for the synthesis of compound 1F of Example 1 starting with 2,6-difluorobenzoyl chloride and 14D.

(S)-2-(2,6-difluorobenzamido)-3-(7-(1,3,6-trimethyl-2,4-dioxo-1,2,3,4-tetrahydropyrimidin-5-yl)-1,3-dihydroisobenzofuran-4-yl)propanoic acid (18): The title compound was prepared according to the method presented for the synthesis of compound 1 of Example 1 starting with 18A. MS (m/z) 500.2 [M+H]$^+$. 1H NMR (400 MHz, DMSO-d6) δ 12.91 (s, 1H), 9.16 (dd, J=11.5, 8.2 Hz, 1H), 7.49 (ttd, J=8.9, 6.6, 2.7

Hz, 1H), 7.20 (dd, J=15.5, 7.8 Hz, 1H), 7.12 (td, J=8.0, 3.2 Hz, 2H), 6.96 (dd, J=7.7, 5.9 Hz, 1H), 5.10 (d, J=14.7 Hz, 2H), 4.83-4.77 (m, 2H), 4.70 (dddd, J=22.6, 10.3, 8.2, 4.7 Hz, 1H), 3.40 (d, J=1.3 Hz, 3H), 3.21 (s, 3H), 3.11 (dd, J=14.5, 4.7 Hz, 1H), 2.89 (dt, J=14.5, 10.3 Hz, 1H), 2.06 (d, J=8.4 Hz, 3H).

Example 19

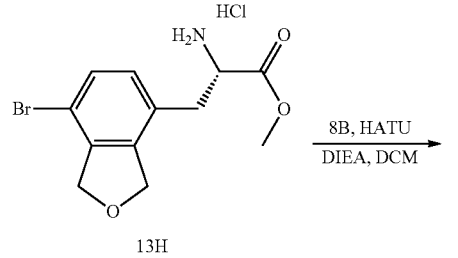

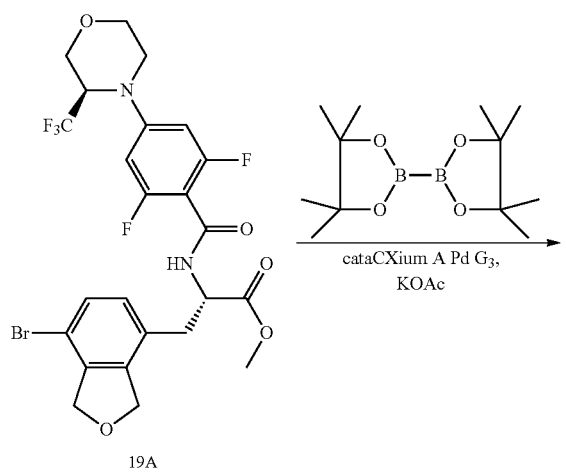

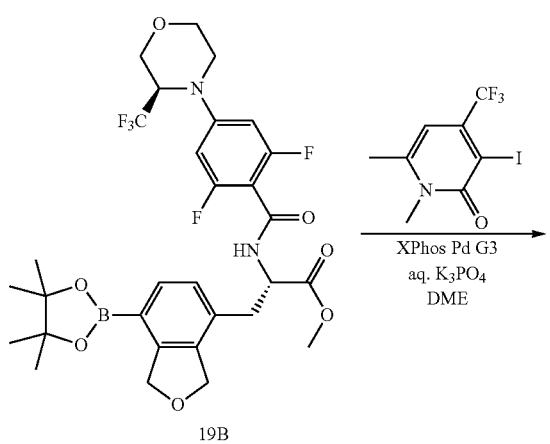

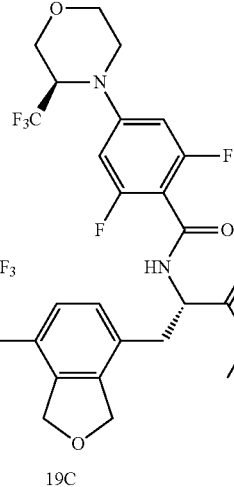

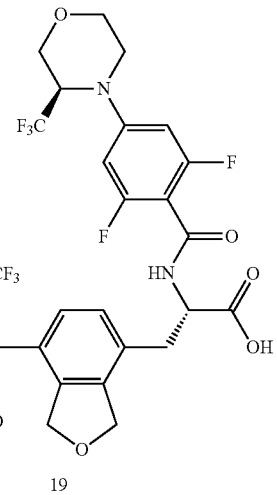

Synthesis of methyl (S)-3-(7-bromo-1,3-dihydroisobenzofuran-4-yl)-2-(2,6-difluoro-4-((R)-3-(trifluoromethyl)morpholino)benzamido)propanoate (19A): The title compound was prepared according to the method presented for the synthesis of compound 8F of Example 8 starting with 8B and 13H.

Synthesis of methyl (S)-2-(2,6-difluoro-4-((R)-3-(trifluoromethyl)morpholino) benzamido)-3-(7-(4,4,5,5-tetramethyl-1,3,2-dioxaborolan-2-yl)-1,3-dihydroisobenzofuran-4-yl)propanoate (19B): The title compound was prepared according to the method presented for the synthesis of compound 1G of Example 1 starting with 19A.

Synthesis of methyl (S)-2-(2,6-difluoro-4-((R)-3-(trifluoromethyl)morpholino) benzamido)-3-(7-(1,6-dimethyl-2-oxo-4-(trifluoromethyl)-1,2-dihydropyridin-3-yl)-1,3-dihydroisobenzofuran-4-yl)propanoate (19C): The title compound was prepared according to the method presented for the synthesis of compound 13K of Example 13 starting with 3-iodo-1,6-dimethyl-4-(trifluoromethyl)pyridin-2(1H)-one and 19B.

Synthesis of (S)-2-(2,6-difluoro-4-((R)-3-(trifluoromethyl)morpholino)benzamido)-3-(7-(1,6-dimethyl-2-oxo-4-(trifluoromethyl)-1,2-dihydropyridin-3-yl)-1,3-dihydroisobenzofuran-4-yl)propanoic acid (19): The title compound was prepared according to the method presented for the synthesis of compound 1 of Example 1 starting with 19B. MS (m/z) 690.2 [M+H]$^+$. 1H NMR (400 MHz, DMSOd6) δ 8.87 (d, J=8.0 Hz, 1H), 7.19 (t, J=8.5 Hz, 1H), 6.95-6.88 (m, 1H), 6.76 (dd, J=11.7, 2.7 Hz, 2H), 6.52 (t, J=0.9 Hz, 1H), 5.14 (d, J=13.3 Hz, 2H), 4.91 (d, J=9.8 Hz, 1H), 4.77 (d, J=12.3 Hz, 1H), 4.69-4.57 (m, 2H), 4.16 (d, J=12.7 Hz, 1H), 3.95 (dd, J=11.5, 3.8 Hz, 1H), 3.74 (d, J=12.8 Hz, 1H), 3.61-3.51 (m, 1H), 3.49 (d, J=1.4 Hz, 3H), 3.43 (d, J=12.7 Hz, 1H), 3.24 (t, J=12.3 Hz, 1H), 3.08 (dt, J=14.6, 5.2 Hz, 1H), 2.92 (dd, J=14.5, 9.9 Hz, 1H), 2.48 (s, 3H).

Example 20

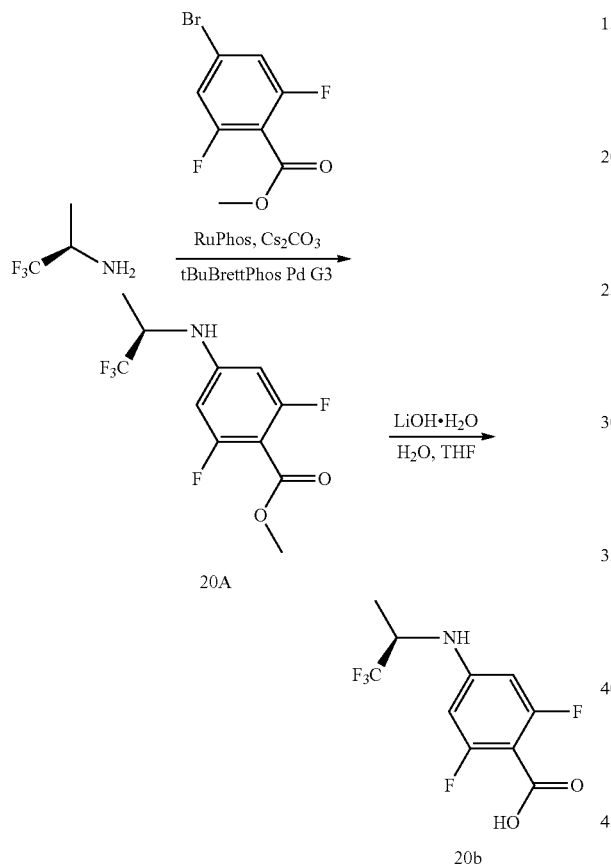

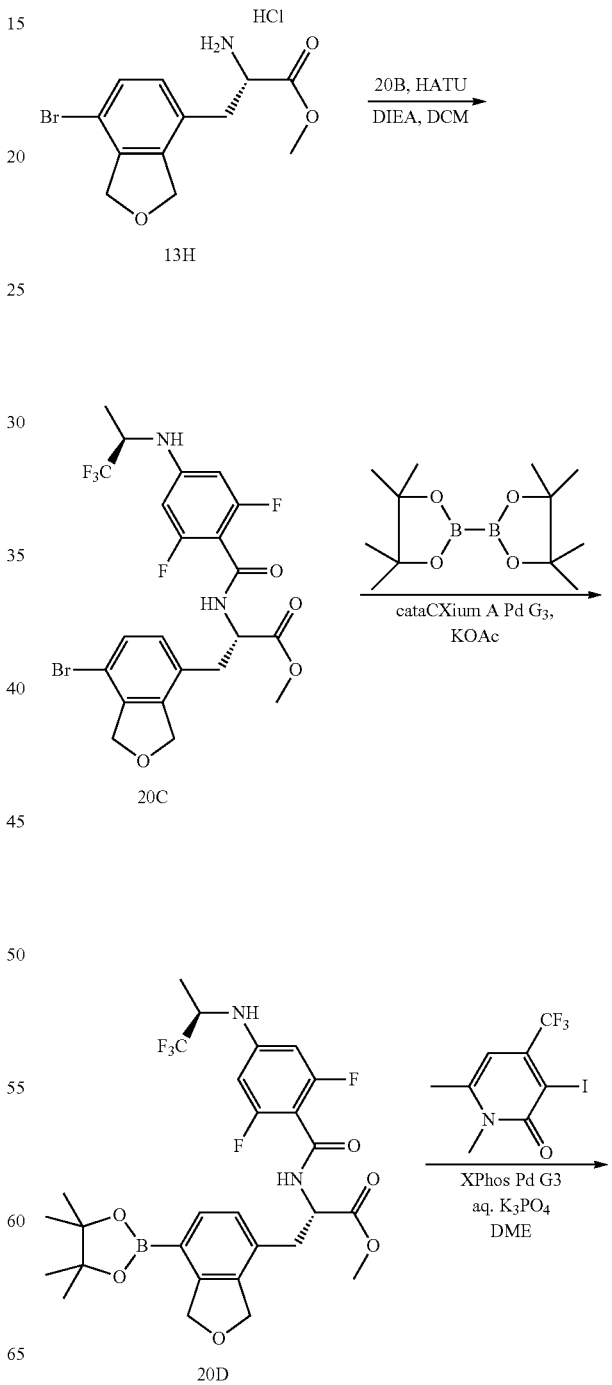

Synthesis of methyl (R)-2,6-difluoro-4-((1,1,1-trifluoropropan-2-yl)amino)benzoate (20A): The title compound was prepared according to the method presented for the synthesis of compound 8A of Example 8 starting with methyl 4-bromo-2,6-difluorobenzoate and (R)-1,1,1-trifluoropropan-2-amine.

Synthesis of (R)-2,6-difluoro-4-((1,1,1-trifluoropropan-2-yl)amino)benzoic acid (20B): The title compound was prepared according to the method presented for the synthesis of compound 8B of Example 8 starting with 20A.

Synthesis of methyl (S)-3-(7-bromo-1,3-dihydroisobenzofuran-4-yl)-2-(2,6-difluoro-4-(((R)-1,1,1-trifluoropropan-2-yl)amino)benzamido)propanoate (20C): The title compound was prepared according to the method presented for the synthesis of compound 6A of Example 6 starting with 13H and 20B.

Synthesis of methyl (S)-2-(2,6-difluoro-4-(((R)-1,1,1-trifluoropropan-2-yl)amino) benzamido)-3-(7-(4,4,5,5-tetramethyl-1,3,2-dioxaborolan-2-yl)-1,3-dihydroisobenzofuran-4-yl)propanoate (20D): The title compound was prepared according to the method presented for the synthesis of compound 1G of Example 1 starting with 20C.

Synthesis of methyl (S)-2-(2,6-difluoro-4-(((R)-1,1,1-trifluoropropan-2-yl)amino)benzamido)-3-(7-(1,6-dimethyl-2-oxo-4-(trifluoromethyl)-1,2-dihydropyridin-3-yl)-1,3-dihydroisobenzofuran-4-yl)propanoate (20E): The title compound was prepared according to the method presented for the synthesis of compound 13K of Example 13 starting with 3-iodo-1,6-dimethyl-4-(trifluoromethyl)pyridin-2(1H)-one and 20D.

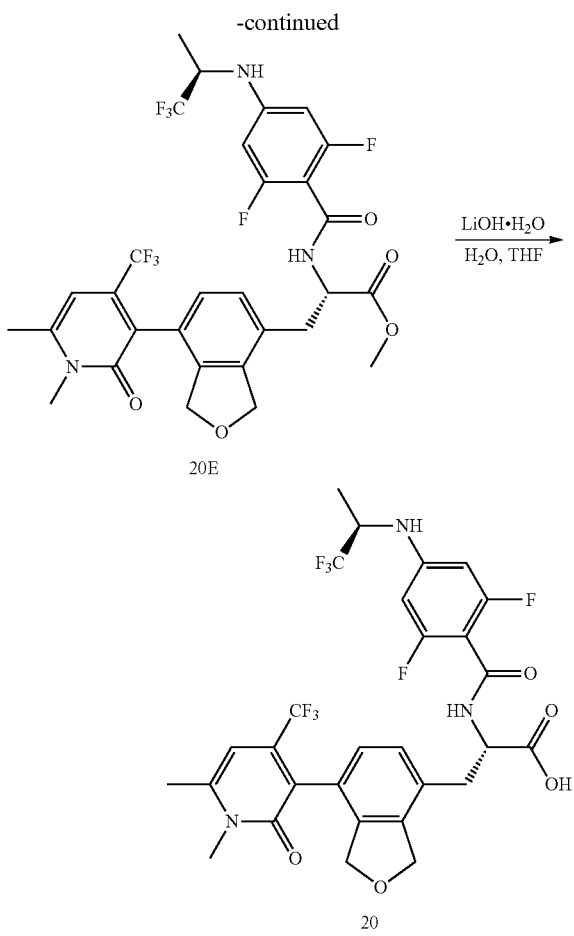

20E

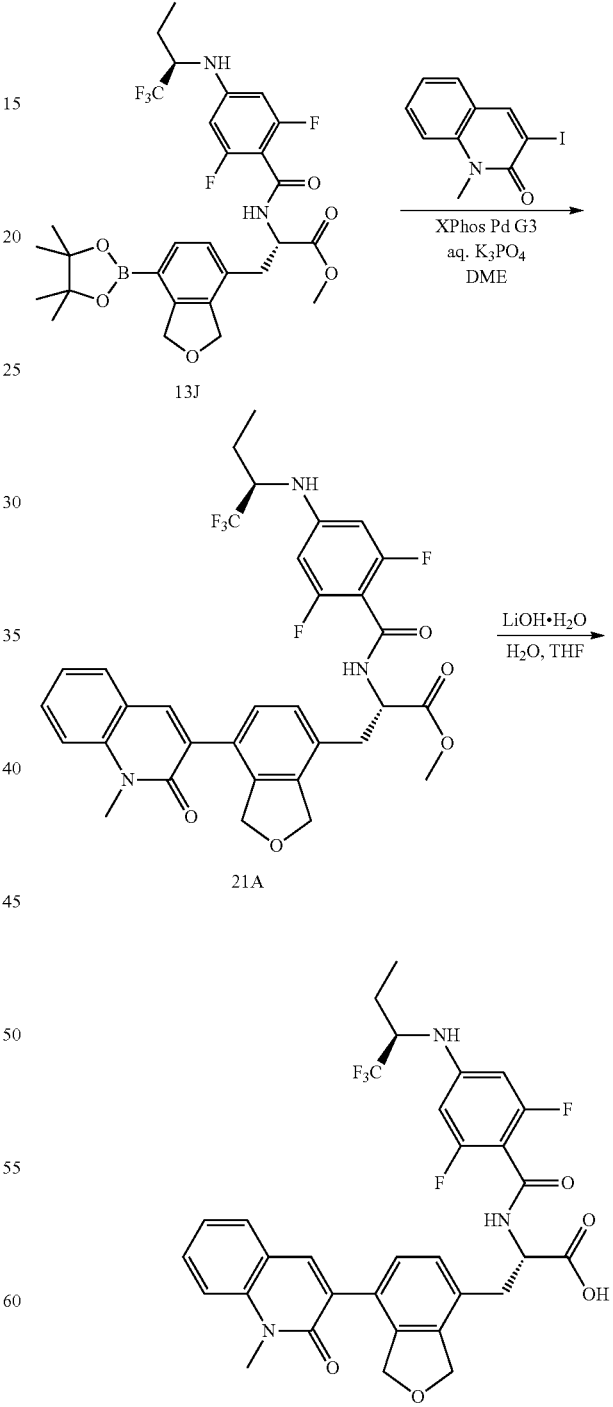

630.2 [M+H]⁺. 1H NMR (400 MHz, DMSO-d6) δ 12.79 (s, 1H), 8.72 (d, J=8.0 Hz, 1H), 7.96 (s, 1H), 7.79 (dd, J=7.9, 1.5 Hz, 1H), 7.65 (ddd, J=8.7, 7.1, 1.6 Hz, 1H), 7.56 (d, J=8.5 Hz, 1H), 7.34-7.21 (m, 3H), 6.78 (d, J=9.4 Hz, 1H), 6.47 (d, J=11.5 Hz, 2H), 5.11 (q, J=12.4 Hz, 2H), 4.99 (d, J=2.0 Hz, 2H), 4.59 (td, J=8.7, 4.9 Hz, 1H), 4.31 (d, J=8.6 Hz, 1H), 3.70 (s, 3H), 3.08 (dd, J=14.4, 5.0 Hz, 1H), 2.94 (dd, J=14.3, 9.5 Hz, 1H), 1.78 (ddd, J=13.7, 7.2, 3.3 Hz, 1H), 1.53 (ddd, J=13.8, 10.4, 7.2 Hz, 1H), 0.93 (t, J=7.3 Hz, 3H).

Synthesis of (S)-2-(2,6-difluoro-4-(((R)-1,1,1-trifluoropropan-2-yl)amino)benzamido)-3-(7-(1,6-dimethyl-2-oxo-4-(trifluoromethyl)-1,2-dihydropyridin-3-yl)-1,3-dihydroisobenzofuran-4-yl)propanoic acid (20): The title compound was prepared according to the method presented for the synthesis of compound 1 of Example 1 starting with 20D. MS (m/z) 648.2 [M+H]⁺. 1H NMR (400 MHz, DMSO-d6) δ 8.70 (d, J=8.1 Hz, 1H), 7.18 (t, J=8.2 Hz, 1H), 6.91 (d, J=7.7 Hz, 1H), 6.82 (dd, J=9.2, 2.2 Hz, 1H), 6.52 (d, J=0.9 Hz, 1H), 6.42 (dd, J=11.2, 2.4 Hz, 2H), 5.12 (t, J=10.1 Hz, 2H), 4.76 (d, J=12.4 Hz, 1H), 4.65 (d, J=12.6 Hz, 1H), 4.63-4.46 (m, 2H), 3.49 (d, J=1.2 Hz, 3H), 3.07 (dt, J=14.5, 5.6 Hz, 1H), 2.92 (dd, J=14.6, 9.8 Hz, 1H), 2.48 (s, 3H), 1.28 (d, J=6.6 Hz, 3H).

Example 21

Synthesis of methyl (S)-2-(2,6-difluoro-4-(((R)-1,1,1-trifluorobutan-2-yl)amino) benzamido)-3-(7-(1-methyl-2-oxo-1,2-dihydroquinolin-3-yl)-1,3-dihydroisobenzofuran-4-yl)propanoate (21A): The title compound was prepared according to the method presented for the synthesis of compound 13K of Example 13 starting with 3-iodo-1-methylquinolin-2(1H)-one and 13J.

Synthesis of (S)-2-(2,6-difluoro-4-(((R)-1,1,1-trifluorobutan-2-yl)amino)benzamido)-3-(7-(1-methyl-2-oxo-1,2-dihydroquinolin-3-yl)-1,3-dihydroisobenzofuran-4-yl)propanoic acid (21): The title compound was prepared according to the method presented for the synthesis of compound 1 of Example 1 starting with 21A. MS (m/z)

Example 22

Synthesis 3-chloro-1,4,6-trimethylpyridin-2(1H)-one (22A): To a stirred solution of 3-chloro-4,6-dimethylpyridin-2(1H)-one (486 mg, 3.1 mmol) in DME was added $K_2CO_3$ (426 mg, 3.1 mmol) and iodomethane (0.19 mL, 3.1 mmol). The reaction mixture was refluxed for 2 hr. EtOAc and water was added to the reaction mixture. The aqueous layer was separated and extracted with EtOAc (2×). The combined organics were dried over anhydrous $Na_2SO_4$, and concentrated under reduced pressure. The material was purified on silica gel eluting with MeOH in DCM (0-30%) to give the title compound.

Synthesis of methyl (S)-2-(2,6-difluoro-4-(((R)-1,1,1-trifluorobutan-2-yl)amino) benzamido)-3-(7-(1,4,6-trimethyl-2-oxo-1,2-dihydropyridin-3-yl)-1,3-dihydroisobenzofuran-4-yl)propanoate (22B): The title compound was prepared according to the method presented for the synthesis of compound 13K of Example 13 starting with 22A and 13J.

Synthesis of (S)-2-(2,6-difluoro-4-(((R)-1,1,1-trifluorobutan-2-yl)amino)benzamido)-3-(7-(1,4,6-trimethyl-2-oxo-1,2-dihydropyridin-3-yl)-1,3-dihydroisobenzofuran-4-yl)propanoic acid (22): The title compound was prepared according to the method presented for the synthesis of compound 1 of Example 1 starting with 22B. MS (m/z) 608.2 [M+H]$^+$. 1H NMR (400 MHz, DMSO-d6) δ 12.76 (s, 1H), 8.69 (t, J=7.7 Hz, 1H), 7.17 (t, J=8.1 Hz, 1H), 6.91 (dd, J=7.7, 4.4 Hz, 1H), 6.79-6.71 (m, 1H), 6.44 (dd, J=11.4, 3.1 Hz, 2H), 6.11 (s, 1H), 5.09 (d, J=12.5 Hz, 2H), 4.86-4.78 (m, 1H), 4.60 (dd, J=18.3, 8.4 Hz, 2H), 4.30 (d, J=9.6 Hz, 1H), 3.41 (s, 3H), 3.06 (dd, J=14.5, 4.9 Hz, 1H), 2.89 (ddd, J=14.7, 9.8, 5.4 Hz, 1H), 2.35 (s, 3H), 1.86 (d, J=7.4 Hz, 3H), 1.83-1.71 (m, 1H), 1.60-1.46 (m, 1H), 0.93 (t, J=7.3 Hz, 3H).

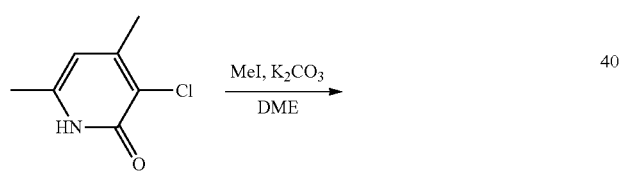

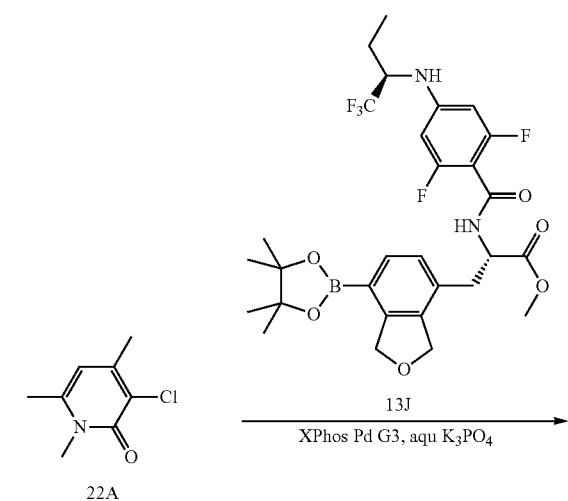

22A

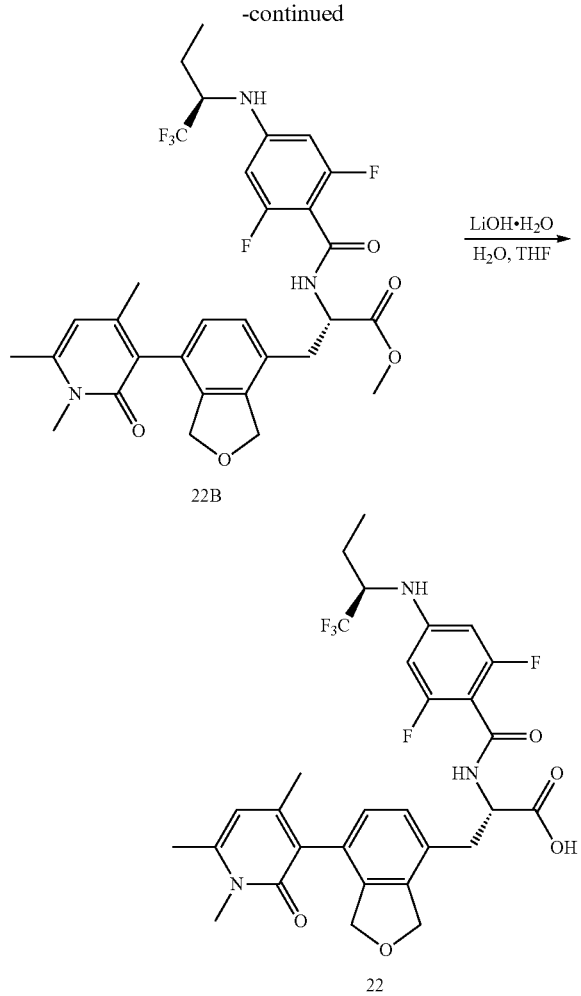

22B

22

Example 23

Synthesis 4-methoxy-1,6-dimethylpyridin-2(1H)-one (23A): To a stirred solution of 4-hydroxy-1,6-dimethylpyridin-2(1H)-one (250 mg, 1.8 mmol) in DMF (13.8 mL) was added $K_2CO_3$ (745 mg, 5.4 mmol) and iodomethane (0.34 mL, 5.4 mmol) at RT. The reaction mixture was stirred for 16 hrs. The mixture was concentrated and then DCM and water was added. The aqueous layer was separated and extracted with DCM (2×). The combined organics were washed with brine, dried over anhydrous $Na_2SO_4$, and concentrated under reduced pressure. The material was purified on silica gel eluting with MeOH in DCM (0-20%) to give the title compound.

Synthesis of 3-bromo-4-methoxy-1,6-dimethylpyridin-2 (1H)-one (23B): To a stirred solution of 23A (215 mg, 1.4 mmol) in DCM (28 mL) cooled −40° C. was added a solution of $Br_2$ (0.072 mL, 1.4 mmol) in DCM (7 mL) dropwise. After 5 min, added aq. 5% $NaHSO_3$ and the reaction mixture allowed to warm to RT for 15 min. Water was added to the reaction mixture. The aqueous layer was extracted with DCM (2×). The organic layer was washed with brine, dried over anhydrous $Na_2SO_4$, and concentrated under reduced pressure. The material was purified by silica gel chromatography using MeOH in DCM to afford the title compound.

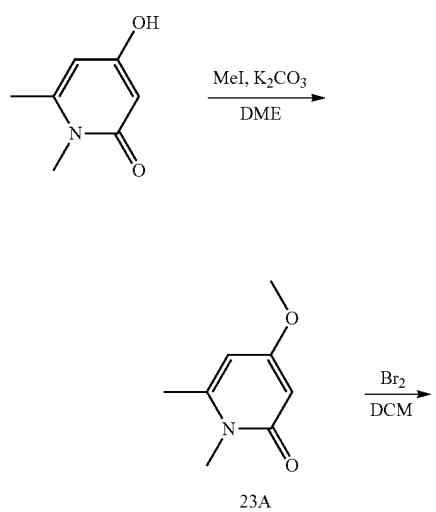

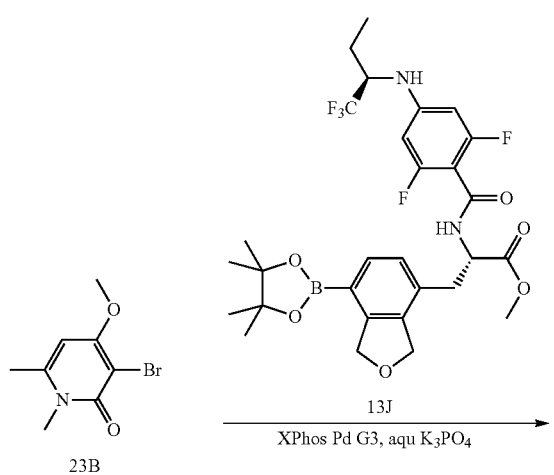

Synthesis of methyl (S)-2-(2,6-difluoro-4-(((R)-1,1,1-trifluorobutan-2-yl)amino) benzamido)-3-(7-(4-methoxy-1,6-dimethyl-2-oxo-1,2-dihydropyridin-3-yl)-1,3-dihydroisobenzofuran-4-yl)propanoate (23C): The title compound was prepared according to the method presented for the synthesis of compound 13K of Example 13 starting with 23B and 13J.

Synthesis of (S)-2-(2,6-difluoro-4-(((R)-1,1,1-trifluorobutan-2-yl)amino)benzamido)-3-(7-(4-methoxy-1,6-dimethyl-2-oxo-1,2-dihydropyridin-3-yl)-1,3-dihydroisobenzofuran-4-yl) propanoic acid (23): The title compound was prepared according to the method presented for the synthesis of compound 1 of Example 1 starting with 23C. MS (m/z) 624.3 [M+H]$^+$. 1H NMR (400 MHz, DMSO-d6) δ 8.71 (d, J=7.8 Hz, 1H), 7.11 (d, J=7.8 Hz, 1H), 7.00 (d, J=7.8 Hz, 1H), 6.77 (d, J=9.4 Hz, 1H), 6.46 (d, J=11.5 Hz, 2H), 6.31 (s, 1H), 5.13-5.00 (m, 2H), 4.79 (s, 1H), 4.69 (s, 1H), 4.60-4.49 (m, 1H), 4.31 (d, J=9.7 Hz, 1H), 3.72 (s, 3H), 3.41 (s, 3H), 3.02 (dd, J=14.5, 5.0 Hz, 1H), 2.89 (dd, J=14.4, 9.3 Hz, 1H), 2.41 (s, 3H), 1.78 (ddd, J=13.7, 7.2, 3.2 Hz, 1H), 1.53 (ddt, J=17.4, 14.1, 7.1 Hz, 1H), 0.93 (t, J=7.3 Hz, 3H).

Example 24

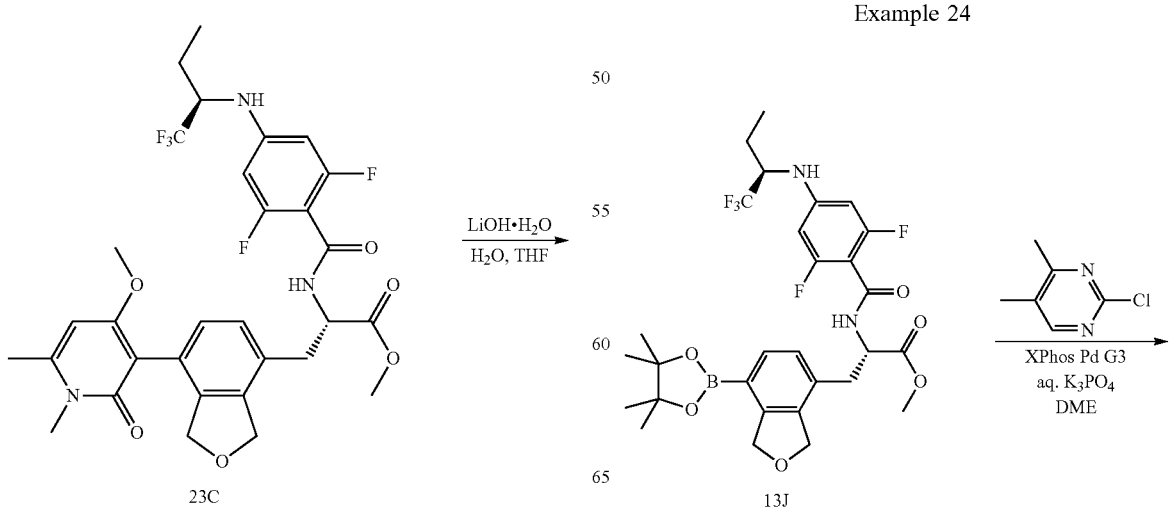

-continued

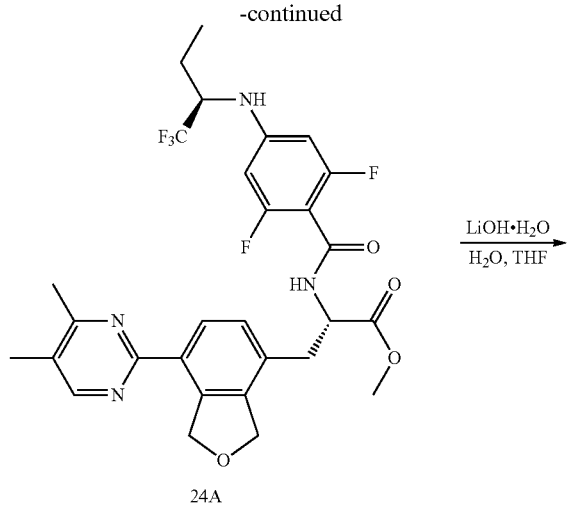

24A

LiOH·H₂O
H₂O, THF
→

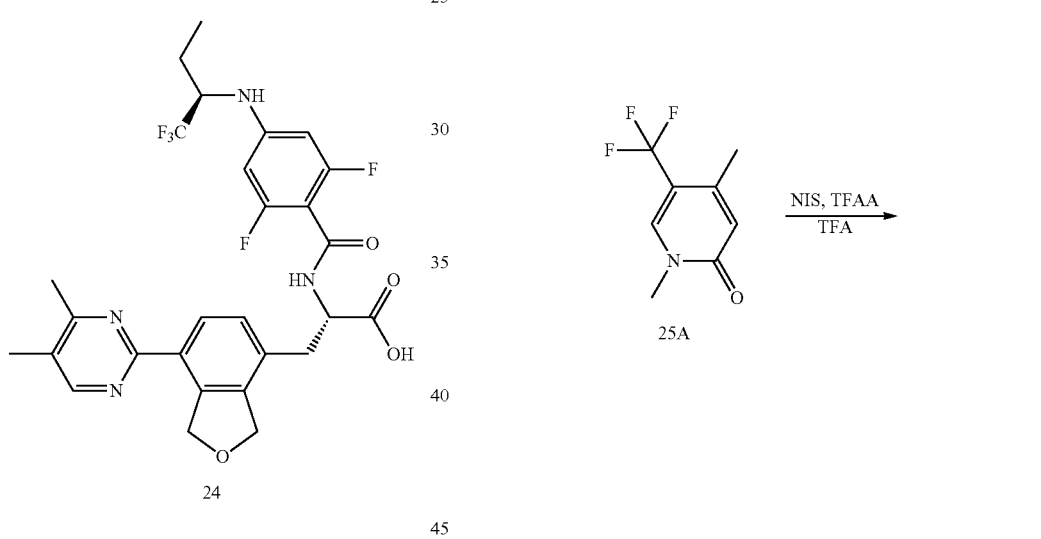

24

Synthesis of methyl (S)-2-(2,6-difluoro-4-(((R)-1,1,1-trifluorobutan-2-yl)amino) benzamido)-3-(7-(4,5-dimethylpyrimidin-2-yl)-1,3-dihydroisobenzofuran-4-yl)propanoate (24A): The title compound was prepared according to the method presented for the synthesis of compound 13K of Example 13 starting with 2-chloro-4,5-dimethylpyrimidine and 13J.

Synthesis of (S)-2-(2,6-difluoro-4-(((R)-1,1,1-trifluorobutan-2-yl)amino)benzamido)-3-(7-(4,5-dimethylpyrimidin-2-yl)-1,3-dihydroisobenzofuran-4-yl)propanoic acid (24): The title compound was prepared according to the method presented for the synthesis of compound 1 of Example 1 starting with 24A. MS (m/z) 579.2 [M+H]⁺. 1H NMR (400 MHz, DMSO-d6) δ 8.70 (d, J=8.1 Hz, 1H), 8.57 (d, J=0.9 Hz, 1H), 8.23 (d, J=8.0 Hz, 1H), 7.32 (d, J=8.1 Hz, 1H), 6.76 (d, J=9.4 Hz, 1H), 6.45 (d, J=11.6 Hz, 2H), 5.44 (d, J=2.2 Hz, 2H), 5.17-5.04 (m, 2H), 4.62 (ddd, J=10.1, 8.1, 4.8 Hz, 1H), 4.29 (d, J=8.3 Hz, 1H), 3.10 (dd, J=14.4, 4.7 Hz, 1H), 2.99-2.79 (m, 1H), 2.50 (s, 3H), 2.26 (s, 3H), 1.76 (dtd, J=14.3, 7.3, 3.2 Hz, 1H), 1.53 (ddd, J=13.8, 10.4, 7.2 Hz, 1H), 0.92 (t, J=7.3 Hz, 3H).

Example 25

Synthesis of 1,4-dimethyl-5-(trifluoromethyl)pyridin-2(1H)-one (25A): To a stirred solution of 4-methyl-5-(trifluoromethyl)pyridin-2(1H)-one (100 mg, 0.056 mmol) in DMF was added NaH (25 mg, 0.62 mmol). The reaction mixture was allowed to stir for 30 min at which time the bubbling ceased. The reaction mixture was cooled to 0° C. and methyl p-toluene sulfonate (116 mg, 0.062 mmol) was added dropwise. After 4 hrs the reaction mixture was allowed to warm to RT, concentrated under reduced pressure, and purified on silica gel chromatography eluting with Hex/EA 0-100% to afford the title compound.

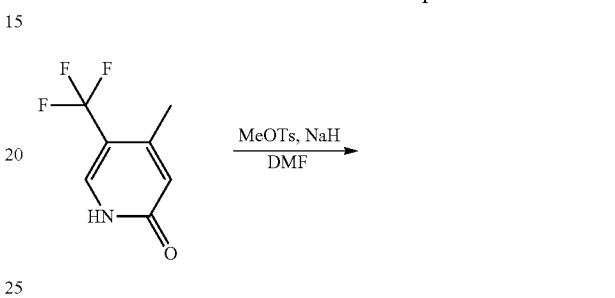

25A
NIS, TFAA
TFA
→

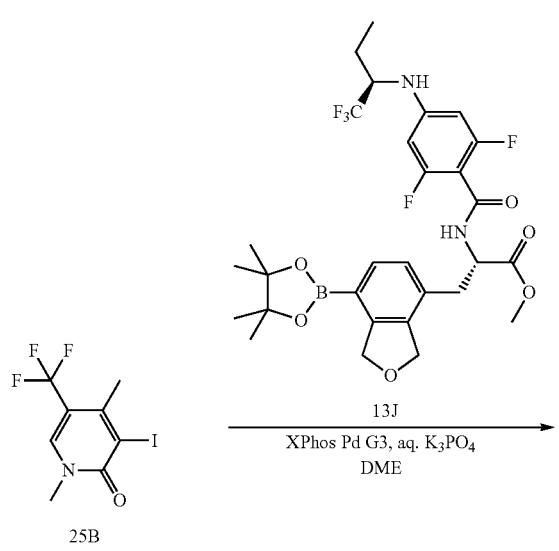

25B
XPhos Pd G3, aq. K₃PO₄
DME
→

-continued

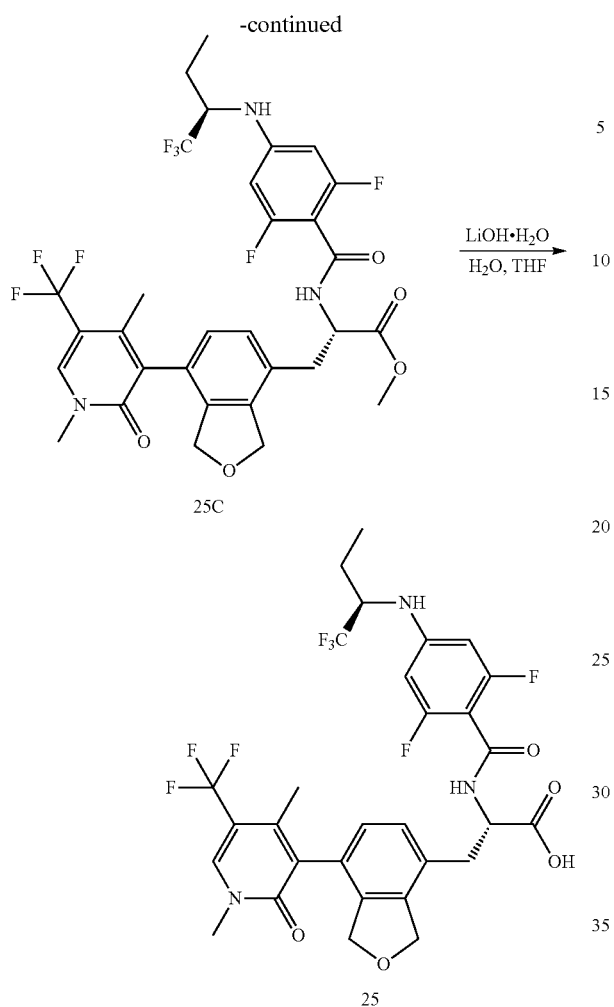

25C

25

Synthesis of 3-iodo-1,4-dimethyl-5-(trifluoromethyl) pyridin-2(1H)-one (25B): To a stirred solution of 25A (0.72 g, 4 mmol) in TFA (0.8 mL) was added TFAA (1.6 g, 8 mmol). The reaction mixture was heated to 100° C. for 5 min in a sealed vial, followed by the addition of NIS (1.08 g, 5 mmol) and further heating at 60° C. for 3 hrs. The reaction mixture was cooled and the TFA removed under reduced pressure. The residue was dissolved in EA and washed with sat. sodium bicarbonate then brine. The organic layer was filtered then concentrated to give the title compound without further purification.

Synthesis of methyl (S)-2-(2,6-difluoro-4-(((R)-1,1,1-trifluorobutan-2-yl)amino) benzamido)-3-(7-(1,4-dimethyl-2-oxo-5-(trifluoromethyl)-1,2-dihydropyridin-3-yl)-1,3-dihydroisobenzofuran-4-yl)propanoate (25C): The title compound was prepared according to the method presented for the synthesis of compound 13K of Example 13 starting with 25B and 13J.

Synthesis of (S)-2-(2,6-difluoro-4-(((R)-1,1,1-trifluorobutan-2-yl)amino)benzamido)-3-(7-(1,4-dimethyl-2-oxo-5-(trifluoromethyl)-1,2-dihydropyridin-3-yl)-1,3-dihydroisobenzofuran-4-yl)propanoic acid (25): The title compound was prepared according to the method presented for the synthesis of compound 1 of Example 1 starting with 25C. MS (m/z) 676.3 [M+H]$^+$. 1H NMR (400 MHz, DMSO-d6) δ 8.84 (t, J=7.7 Hz, 1H), 8.33 (s, 1H), 7.20 (t, J=7.0 Hz, 1H), 6.97 (dd, J=7.8, 4.1 Hz, 1H), 6.77 (d, J=9.3 Hz, 1H), 6.45 (dd, J=11.4, 3.1 Hz, 2H), 5.18-5.02 (m, 2H), 4.81-4.61 (m, 3H), 4.36-4.26 (m, 1H), 3.65 (s, 3H), 3.50 (s, 3H), 3.08 (dd, J=14.5, 5.3 Hz, 1H), 2.94 (dt, J=14.4, 9.2 Hz, 1H), 1.98 (d, J=6.9 Hz, 3H), 1.78 (ddd, J=13.9, 7.2, 3.1 Hz, 1H), 1.53 (ddt, J=17.5, 14.4, 7.5 Hz, 1H), 0.93 (t, J=7.3 Hz, 3H).

Example 26

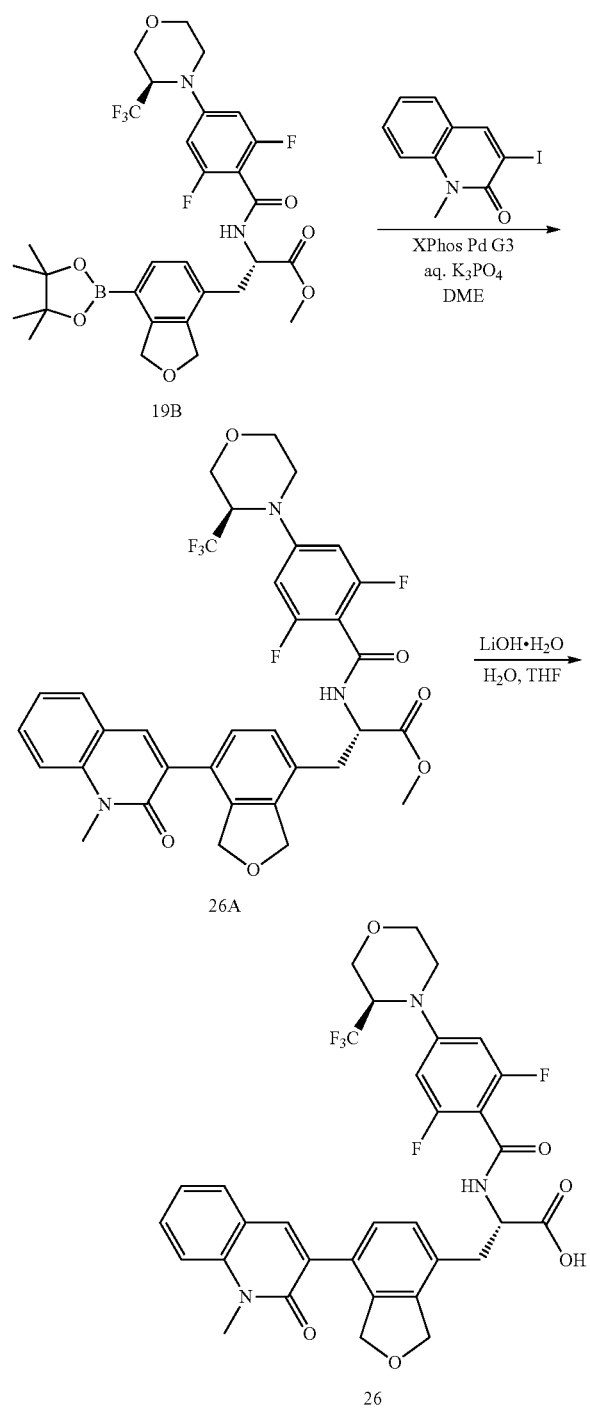

Synthesis of methyl (S)-2-(2,6-difluoro-4-((R)-3-(trifluoromethyl)morpholino) benzamido)-3-(7-(1-methyl-2-oxo-1,2-dihydroquinolin-3-yl)-1,3-dihydroisobenzofuran-4-yl)

propanoate (26A): The title compound was prepared according to the method presented for the synthesis of compound 19C of Example 19 starting with 3-iodo-1-methylquinolin-2(1H)-one and 19B.

Synthesis of (S)-2-(2,6-difluoro-4-((R)-3-(trifluoromethyl)morpholino)benzamido)-3-(7-(1-methyl-2-oxo-1,2-dihydroquinolin-3-yl)-1,3-dihydroisobenzofuran-4-yl)propanoic acid (26): The title compound was prepared according to the method presented for the synthesis of compound 1 of Example 1 starting with 26A. MS (m/z) 658.3 [M+H]⁺. 1H NMR (400 MHz, DMSO-d6) δ 12.85 (s, 1H), 8.88 (d, J=8.0 Hz, 1H), 7.96 (s, 1H), 7.79 (dd, J=7.9, 1.5 Hz, 1H), 7.65 (ddd, J=8.7, 7.1, 1.5 Hz, 1H), 7.56 (d, J=8.5 Hz, 1H), 7.34-7.22 (m, 3H), 6.78 (d, J=11.7 Hz, 2H), 5.19-5.04 (m, 2H), 4.99 (d, J=2.0 Hz, 2H), 4.91 (dt, J=11.8, 5.8 Hz, 1H), 4.62 (ddd, J=9.6, 7.9, 5.0 Hz, 1H), 4.16 (d, J=12.7 Hz, 1H), 3.96 (dd, J=11.6, 3.7 Hz, 1H), 3.79-3.71 (m, 1H), 3.70 (s, 3H), 3.61-3.51 (m, 1H), 3.30-3.19 (m, 2H), 3.10 (dd, J=14.3, 5.0 Hz, 1H), 2.95 (dd, J=14.3, 9.6 Hz, 1H).

Example 27

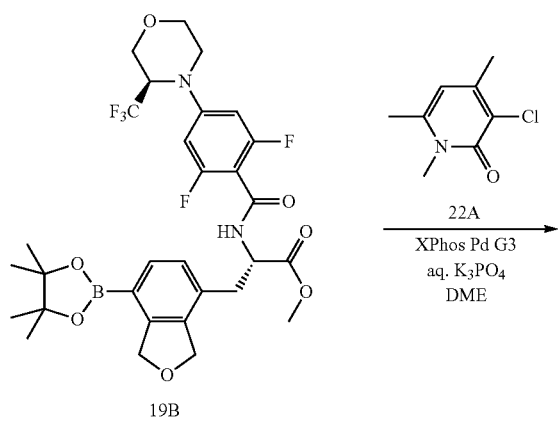

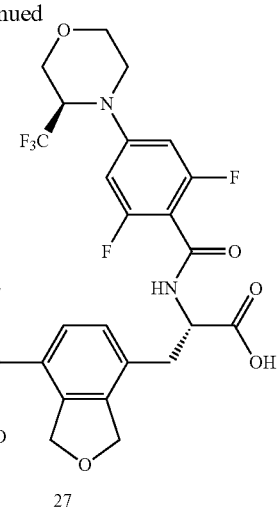

Synthesis of methyl (S)-2-(2,6-difluoro-4-((R)-3-(trifluoromethyl)morpholino) benzamido)-3-(7-(1,4,6-trimethyl-2-oxo-1,2-dihydropyridin-3-yl)-1,3-dihydroisobenzofuran-4-yl)propanoate (27A): The title compound was prepared according to the method presented for the synthesis of compound 19C of Example 19 starting with 22A and 19B.

Synthesis of (S)-2-(2,6-difluoro-4-((R)-3-(trifluoromethyl)morpholino)benzamido)-3-(7-(1,4,6-trimethyl-2-oxo-1,2-dihydropyridin-3-yl)-1,3-dihydroisobenzofuran-4-yl) propanoic acid (27): The title compound was prepared according to the method presented for the synthesis of compound 1 of Example 1 starting with 27A. MS (m/z) 636.3 [M+H]⁺. 1H NMR (400 MHz, DMSO-d6) δ 12.81 (s, 1H), 8.85 (t, J=8.1 Hz, 1H), 7.23-7.13 (m, 1H), 6.91 (dd, J=7.7, 5.4 Hz, 1H), 6.76 (dd, J=11.5, 3.4 Hz, 2H), 6.11 (s, 1H), 5.09 (d, J=12.9 Hz, 2H), 4.91 (d, J=9.1 Hz, 1H), 4.86-4.77 (m, 1H), 4.69-4.56 (m, 2H), 4.16 (d, J=12.7 Hz, 1H), 3.95 (dd, J=11.4, 3.7 Hz, 1H), 3.74 (d, J=12.7 Hz, 1H), 3.61-3.50 (m, 1H), 3.44 (s, 1H), 3.41 (s, 3H), 3.24 (t, J=12.4 Hz, 1H), 3.08 (dd, J=14.4, 4.9 Hz, 1H), 2.91 (ddd, J=14.8, 9.9, 5.5 Hz, 1H), 2.34 (s, 3H), 1.86 (d, J=7.7 Hz, 3H).

Example 28

Synthesis of methyl (S)-2-(2,6-difluoro-4-((R)-3-(trifluoromethyl)morpholino) benzamido)-3-(7-(4,5-dimethylpyrimidin-2-yl)-1,3-dihydroisobenzofuran-4-yl)propanoate (28A): The title compound was prepared according to the method presented for the synthesis of compound 19C of Example 19 starting with 2-chloro-4,5-dimethylpyrimidine and 19B.

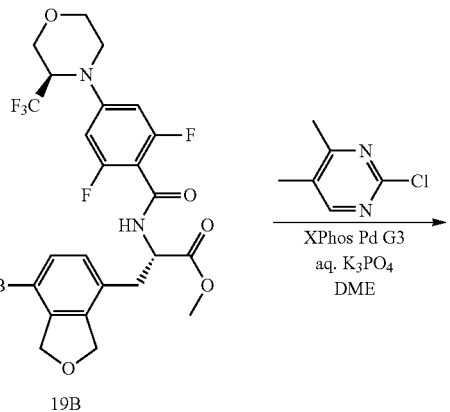

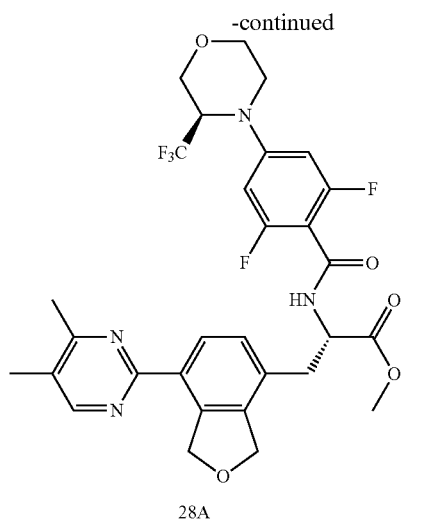

28A

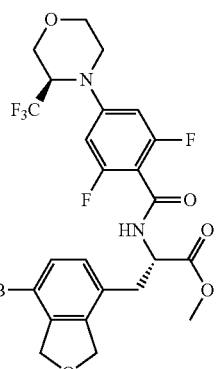

19B

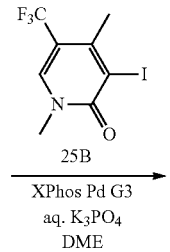

25B

XPhos Pd G3
aq. K₃PO₄
DME

LiOH·H₂O
H₂O, THF

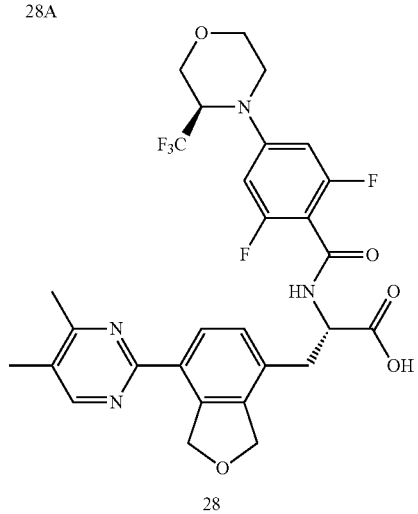

28

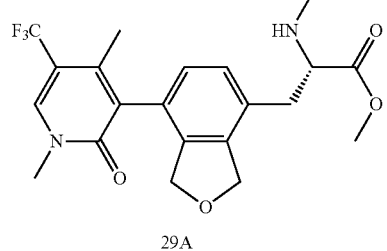

29A

LiOH·H₂O
H₂O, THF

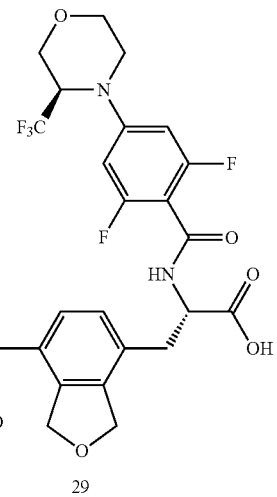

29

Synthesis of (S)-2-(2,6-difluoro-4-((R)-3-(trifluoromethyl)morpholino)benzamido)-3-(7-(4,5-dimethylpyrimidin-2-yl)-1,3-dihydroisobenzofuran-4-yl)propanoic acid (28): The title compound was prepared according to the method presented for the synthesis of compound 1 of Example 1 starting with 28A. MS (m/z) 607.2 [M+H]⁺. 1H NMR (400 MHz, DMSO-d6) δ 8.86 (d, J=8.1 Hz, 1H), 8.57 (d, J=0.9 Hz, 1H), 8.23 (d, J=8.0 Hz, 1H), 7.33 (d, J=8.1 Hz, 1H), 6.76 (d, J=11.7 Hz, 2H), 5.45 (d, J=2.2 Hz, 2H), 5.18-5.05 (m, 2H), 4.95-4.84 (m, 1H), 4.65 (ddd, J=10.1, 8.0, 4.7 Hz, 1H), 4.16 (dd, J=12.8, 5.1 Hz, 1H), 3.95 (dd, J=11.5, 4.0 Hz, 1H), 3.73 (ddd, J=12.9, 4.1, 2.2 Hz, 1H), 3.55 (td, J=11.9, 3.3 Hz, 1H), 3.48-3.37 (m, 1H), 3.24 (dt, J=14.2, 7.2 Hz, 1H), 3.12 (dd, J=14.3, 4.7 Hz, 1H), 2.99-2.80 (m, 1H), 2.50 (s, 2H), 2.26 (s, 3H).

Example 29

Synthesis of methyl (S)-2-(2,6-difluoro-4-((R)-3-(trifluoromethyl)morpholino) benzamido)-3-(7-(1,4-dimethyl-2-oxo-5-(trifluoromethyl)-1,2-dihydropyridin-3-yl)-1,3-dihydroisobenzofuran-4-yl)propanoate (29A): The title compound was prepared according to the method presented for the synthesis of compound 19C of Example 19 starting with 25B and 19B.

Synthesis of (S)-2-(2,6-difluoro-4-((R)-3-(trifluoromethyl)morpholino)benzamido)-3-(7-(1,4-dimethyl-2-oxo-5-(trifluoromethyl)-1,2-dihydropyridin-3-yl)-1,3-dihydroisobenzofuran-4-yl)propanoic acid (29): The title compound was prepared according to the method presented for the synthesis of compound 1 of Example 1 starting with 29A. MS (m/z) 690.3 [M+H]⁺. 1H NMR (400 MHz, DMSO-d6) δ 8.85 (t, J=7.8 Hz, 1H), 8.32 (s, 1H), 7.22 (dd, J=12.3, 7.7 Hz, 1H), 6.97 (t, J=7.2 Hz, 1H), 6.75 (dd, J=11.6, 3.6 Hz, 2H), 5.11 (d, J=14.8 Hz, 2H), 4.91 (q, J=9.6 Hz, 1H), 4.78 (d, J=12.4 Hz, 1H), 4.65 (ddd, J=22.4, 11.0, 4.7 Hz, 2H), 4.16 (d, J=12.7 Hz, 1H), 3.95 (dd, J=11.7, 3.6 Hz, 1H), 3.74

(d, J=13.4 Hz, 1H), 3.56 (m, 1H), 3.50 (s, 3H), 3.43 (d, J=15.1 Hz, 1H), 3.24 (t, J=12.6 Hz, 1H), 3.10 (dd, J=14.7, 4.7 Hz, 1H), 2.92 (dt, J=14.5, 10.3 Hz, 1H), 1.98 (d, J=8.6 Hz, 3H).

Example 30

Synthesis of methyl (S)-2-(2,6-difluoro-4-(((R)-1,1,1-trifluoropropan-2-yl)amino) benzamido)-3-(7-(1,4,6-trimethyl-2-oxo-1,2-dihydropyridin-3-yl)-1,3-dihydroisobenzofuran-4-yl)propanoate (30A): The title compound was prepared according to the method presented for the synthesis of compound 20E of Example 20 starting with 20D and 22A.

Synthesis of (S)-2-(2,6-difluoro-4-(((R)-1,1,1-trifluoropropan-2-yl)amino)benzamido)-3-(7-(1,4,6-trimethyl-2-oxo-1,2-dihydropyridin-3-yl)-1,3-dihydroisobenzofuran-4-yl)propanoic acid (30): The title compound was prepared according to the method presented for the synthesis of compound 1 of Example 1 starting with 29A. MS (m/z) 594.2 [M+H]$^+$. 1H NMR (400 MHz, DMSO-d6) δ 8.69 (dd, J=8.0, 6.4 Hz, 1H), 7.17 (t, J=8.3 Hz, 1H), 6.91 (dd, J=7.7, 4.8 Hz, 1H), 6.82 (d, J=9.1 Hz, 1H), 6.42 (dd, J=11.2, 2.9 Hz, 2H), 6.11 (s, 1H), 5.09 (q, J=13.0, 12.3 Hz, 2H), 4.82 (d, J=12.2 Hz, 1H), 4.71-4.43 (m, 3H), 3.41 (d, J=0.9 Hz, 3H), 3.06 (dd, J=14.5, 4.9 Hz, 1H), 2.90 (ddd, J=14.9, 10.0, 5.3 Hz, 1H), 2.42-2.30 (m, 3H), 1.86 (d, J=7.0 Hz, 3H), 1.35-1.20 (m, 3H).

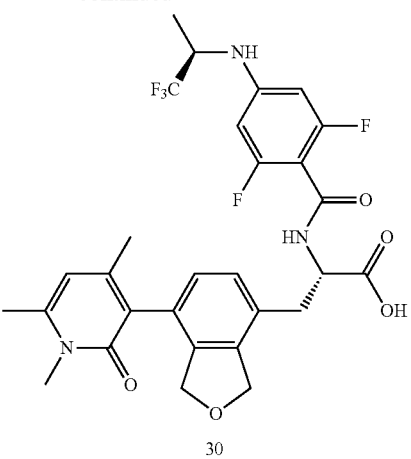 [SMILES: Cc1cc(C(F)(F)F)c(-c2ccc(C[C@H](NC(=O)c3c(F)cc(N[C@H](C)C(F)(F)F)cc3F)C(=O)O)c3c2COC3)c(=O)n1C]

30

Example 31

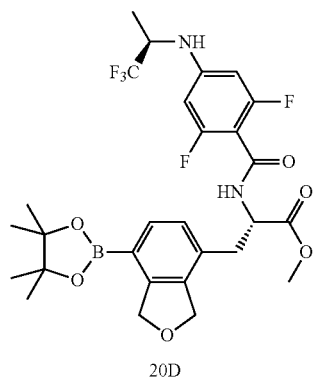

20D

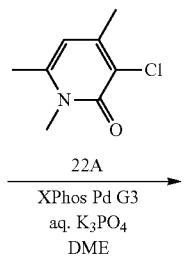

22A

XPhos Pd G3
aq. K$_3$PO$_4$
DME

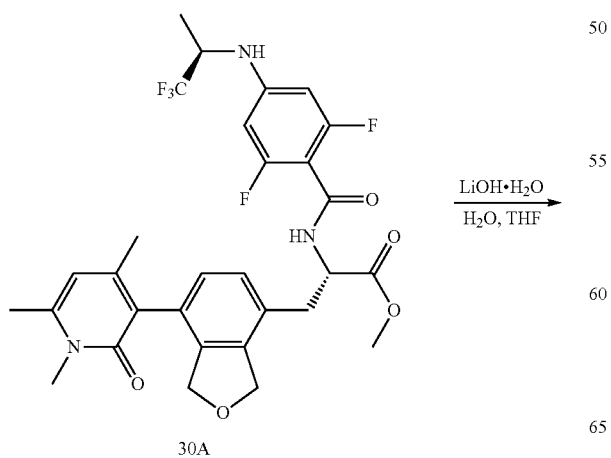

30A

LiOH·H$_2$O
H$_2$O, THF

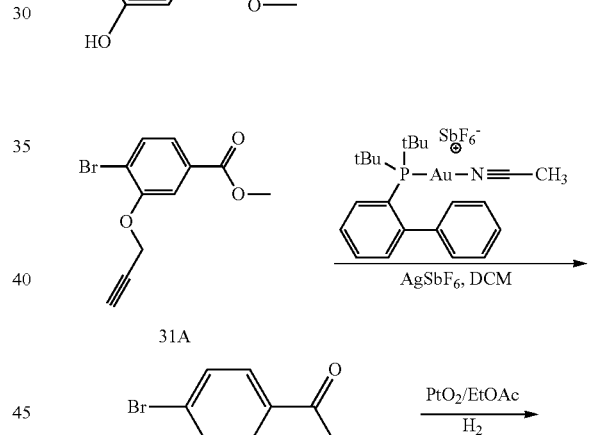

31A

PtO$_2$/EtOAc
H$_2$

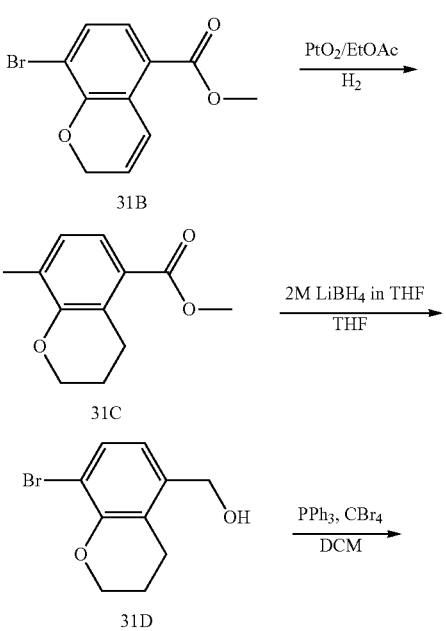

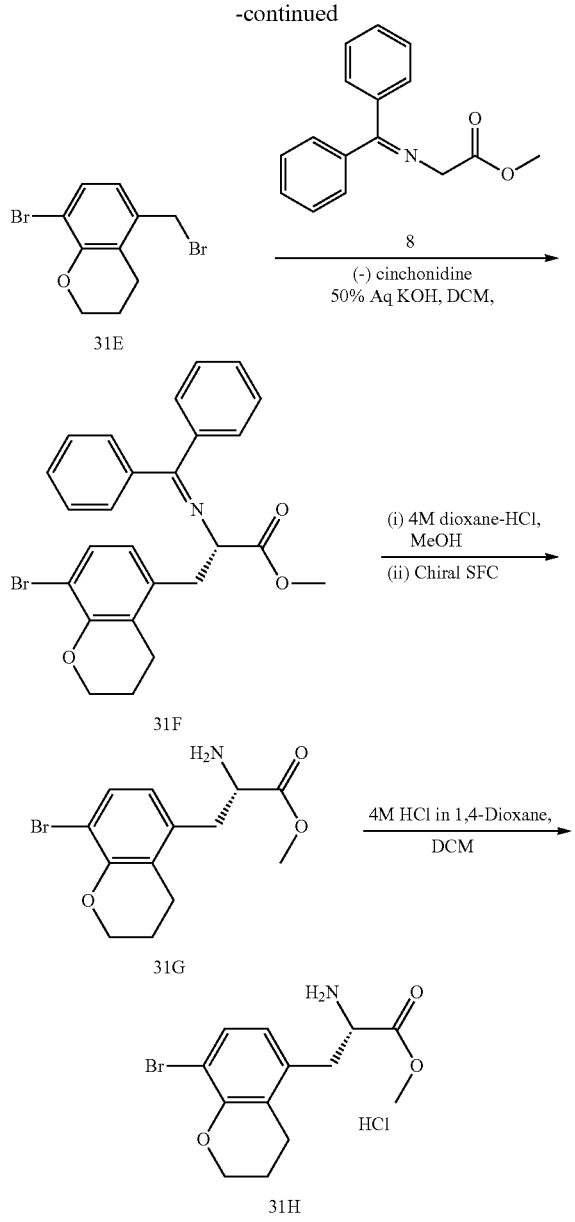

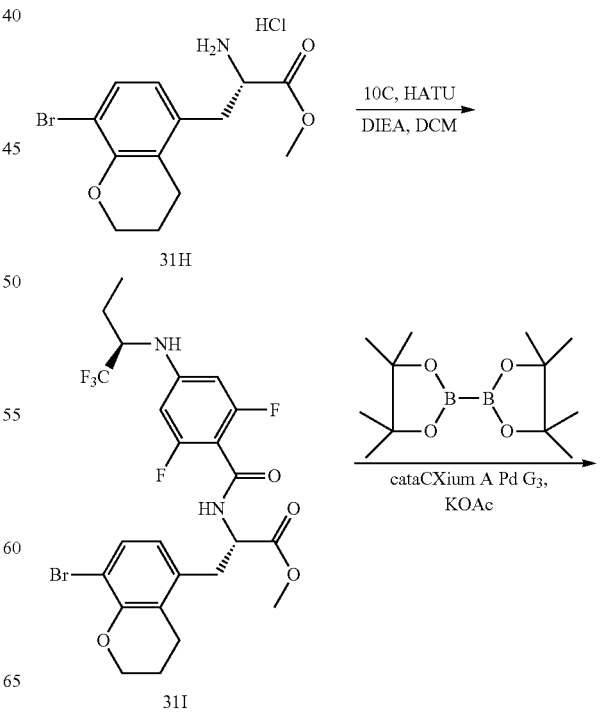

Synthesis of methyl 8-bromochromane-5-carboxylate (31C): To a stirred suspension of platinum oxide (1.25 g, 5 mol %) in EtOAc (500 mL) was added compound 31B (25 g, 93.3 mmol). The reaction mixture was hydrogenated under balloon pressure for 8 h at rt. After completion the reaction mixture was filtered through a pad of celite, the filtrate was concentrated under reduced pressure to afford crude material. This material was purified by 100-200 mesh silica gel column chromatography and eluted with 5% EtOAc in hexane to afford compound 31C.

Synthesis of (8-bromochroman-5-yl)methanol (31D): To a stirred solution of compound 31C in THF (200 mL) was slowly added 2M $LiBH_4$ in THF (111 mL, 222 mmol) at 0° C., the reaction mixture was heated to 40° C. for 4 h. After which time the reaction mixture was cooled to 0° C., quenched with ice water and stirred for 30 min. The mixture was adjusted to pH~4-5 using aq. 2N HCl and heated to 40° C. for 2 h. The reaction mixture was cooled to rt and adjusted to pH~8 using sat. $NaHCO_3$ and extracted with EtOAc. The organic layer was separated, dried over $Na_2SO_4$ and concentrated under reduced pressure to obtain crude material. This material was purified by 100-200 mesh silica gel column chromatography and eluted with 30% EtOAc in hexane to afford compound 31D.

Synthesis of 8-bromo-5-(bromomethyl)chromane (31E): To a stirred solution of compound 31D (25 g, 103.3 mmol) in DCM (350 mL) was added triphenylphosphine (40.59 g, 154.9 mmol) and carbon tetrabromide (51.38 g, 154.9 mmol) at 0° C. and the reaction mixture was allowed to stir at rt for 1 h. The reaction mixture was concentrated reduced pressure to obtain crude material. This material was purified by 100-200 mesh silica gel column chromatography and eluted with 4-10% EtOAc in hexane to afford compound 31E.

Synthesis of methyl 4-bromo-3-(prop-2-yn-1-yloxy)benzoate (31A): To a stirred suspension of methyl 4-bromo-3-hydroxybenzoate (200 g, 865.8 mmol), and $K_2CO_3$ (239 g, 1731.3 mmol) in acetone (1500 mL) was added propargyl bromide 80% in toluene (193 mL, 1298.1 mmol). After stirring for 8 hours at 50° C. the reaction mixture was cooled to room temperature, the mixture was filtered off and evaporated under reduced pressure. The resultant material was further washed with pentane to afford 31A.

Synthesis of methyl 8-bromo-2H-chromene-5-carboxylate (31B): To a stirred solution of (acetonitrile)[(2-biphenyl)di-tert-butylphosphine]gold(I) hexafluoroantimonate (1.8 g, 2.33 mmol) in DCM (750 mL) in an aluminum foil covered round bottom flask was added silver hexafluoro antimonite (0.64 g, 1.86 mmol). The resultant solution was stirred at rt for 30 min. To the reaction mixture was added compound 31A in one portion, the resultant was stirred for 16 h at rt. The reaction mixture was concentrated under reduced pressure to obtain crude compound. The crude compound was used for the next step without any purification.

-continued

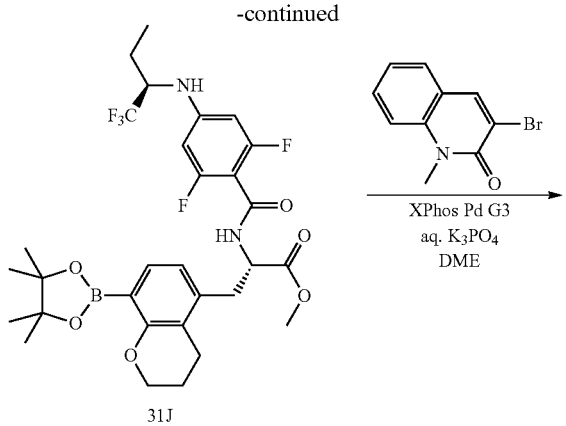

31J

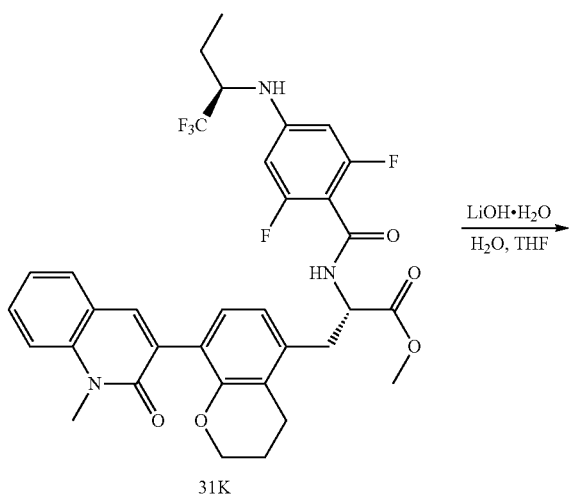

31K

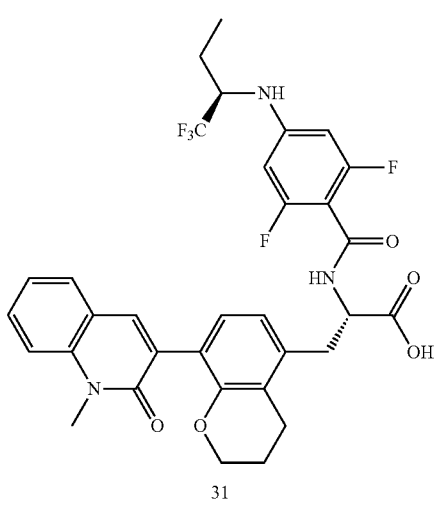 [SMILES: CC[C@@H](Nc1cc(F)c(C(=O)N[C@@H](Cc2ccc(-c3cc4ccccc4n(C)c3=O)c3c2CCCO3)C(=O)O)c(F)c1)C(F)(F)F]

31

Synthesis of methyl 3-(8-bromochroman-5-yl)-2-((diphenylmethylene) amino) propanoate (31F): To a stirred solution of methyl 2-((diphenylmethylene)amino)acetate (16 g, 63.16 mmol) in DCM (480 mL) was added (−)-cinchonidine (1.86 g, 6.31 mmol) at rt. To the reaction mixture were added 50% aq. KOH solution (128 mL) and compound 31E (24 g, 78.9 mmol) at 0° C. The resultant reaction mixture was allowed to stir at rt for 6 h. The reaction mixture was diluted with water and stirred for 15 mins. The combined organic layer was dried over $Na_2SO_4$ and concentrated under reduced pressure to afford compound 31F. The crude compound was used for the next step without any purification.

Synthesis of methyl (S)-2-amino-3-(8-bromochroman-5-yl)propanoate (31G): To a stirred suspension of 31F (70 g, 146.8 mmol) in MeOH (350 mL) was added 4M HCl in 1,4-dioxane (490 mL) at 0° C. The reaction mixture was allowed to stir at rt for 3 days. The reaction mixture was concentrated under reduced pressure, dissolved in water and washed with EtOAc. The aqueous layer was separated and adjusted to pH~8 using sat. $NaHCO_3$ and extracted with EtOAc. The organic layer was dried over $Na_2SO_4$ and concentrated under reduced pressure to obtain crude material. This material was purified by 230-400 mesh silica gel column chromatography and eluted with 4% MeOH in DCM. The resultant material was purified by chiral SFC using a 5µ Lux Cellulose-2 (30×250 mm) column and eluted with 30% (15 mM methanolic ammonia in MeOH) in $CO_2$, to obtain compound 31G (desired compound is peak-1 from SFC).

Synthesis of methyl (S)-2-amino-3-(8-bromochroman-5-yl)propanoate hydrochloride (31H): To a stirred solution of compound 31G (25 g, 79.9 mmol) in DCM (250 mL) was added 4M HCl in 1,4-dioxane (79 mL, 317.8 mmol) at 0° C. The reaction mixture was allowed to stir at rt for 1 h. The reaction mixture was concentrated under reduced pressure to afford compound 31H.

Synthesis of methyl (S)-3-(8-bromochroman-5-yl)-2-(2,6-difluoro-4-(((R)-1,1,1-trifluorobutan-2-yl)amino)benzamido)propanoate (31I): The title compound was prepared according to the method presented for the synthesis of compound 10D of Example 10 starting with 10C and 31H.

Synthesis of methyl (S)-2-(2,6-difluoro-4-(((R)-1,1,1-trifluorobutan-2-yl)amino) benzamido)-3-(8-(4,4,5,5-tetramethyl-1,3,2-dioxaborolan-2-yl)chroman-5-yl)propanoate (31J): The title compound was prepared according to the method presented for the synthesis of compound 1G of Example 1 starting with 31I.

Synthesis of methyl (S)-2-(2,6-difluoro-4-(((R)-1,1,1-trifluorobutan-2-yl)amino) benzamido)-3-(8-(1-methyl-2-oxo-1,2-dihydroquinolin-3-yl)chroman-5-yl)propanoate (31K): The title compound was prepared according to the method presented for the synthesis of compound 13K of Example 13 starting with 3-bromo-1-methylquinolin-2(1H)-one and 31J.

Synthesis of (S)-2-(2,6-difluoro-4-(((R)-1,1,1-trifluorobutan-2-yl)amino)benzamido)-3-(8-(1-methyl-2-oxo-1,2-dihydroquinolin-3-yl)chroman-5-yl)propanoic acid (31): The title compound was prepared according to the method presented for the synthesis of compound 1 of Example 1 starting with 31K. MS (m/z) 644.3 [M+H]$^+$. 1H NMR (400 MHz, DMSO-d6) δ 12.74 (s, 1H), 8.73 (d, J=7.9 Hz, 1H), 7.79 (s, 1H), 7.71 (dd, J=7.8, 1.5 Hz, 1H), 7.61 (ddd, J=8.6, 7.0, 1.5 Hz, 1H), 7.52 (d, J=8.5 Hz, 1H), 7.26 (t, J=7.4 Hz, 1H), 6.97 (d, J=7.7 Hz, 1H), 6.84 (d, J=7.8 Hz, 1H), 6.77 (d, J=9.4 Hz, 1H), 6.47 (d, J=11.6 Hz, 2H), 4.51 (td, J=9.1, 4.4 Hz, 1H), 4.32 (d, J=9.5 Hz, 1H), 4.01 (dq, J=7.5, 5.2, 3.7 Hz, 2H), 3.66 (s, 3H), 3.10 (dd, J=14.5, 4.5 Hz, 1H), 2.91 (dd, J=14.5, 9.7 Hz, 1H), 2.78 (q, J=6.8 Hz, 2H), 2.00-1.89 (m, 2H), 1.78 (ddd, J=13.7, 7.3, 3.2 Hz, 1H), 1.54 (ddd, J=13.7, 10.4, 7.1 Hz, 1H), 0.94 (t, J=7.3 Hz, 3H).

Example 32

Synthesis of methyl (S)-3-(8-bromochroman-5-yl)-2-(2,6-difluoro-4-((R)-3-(trifluoromethyl)morpholino)benzamido)propanoate (32A): The title compound was prepared according to the method presented for the synthesis of compound 8F of Example 8 starting with 8B and 31H.

Synthesis of methyl (S)-2-(2,6-difluoro-4-((R)-3-(trifluoromethyl)morpholino) benzamido)-3-(8-(4,4,5,5-tetramethyl-1,3,2-dioxaborolan-2-yl)chroman-5-yl)propanoate (32B): The title compound was prepared according to the method presented for the synthesis of compound 1G of Example 1 starting with 32A.

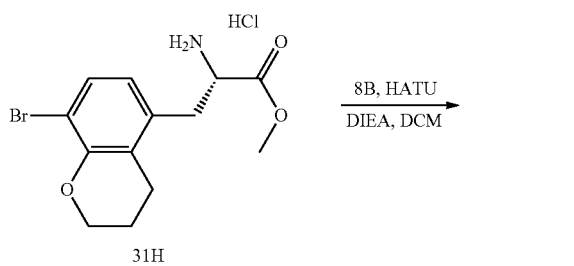

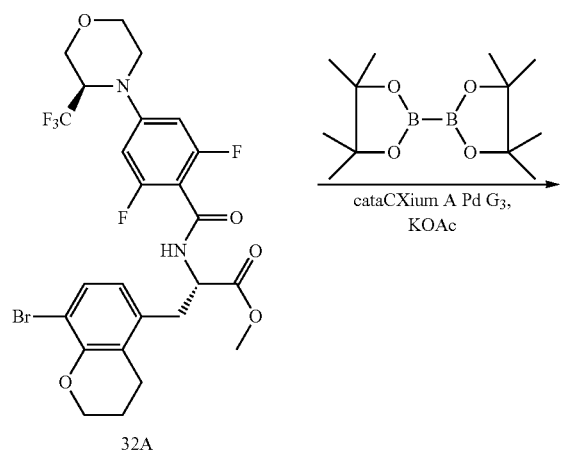

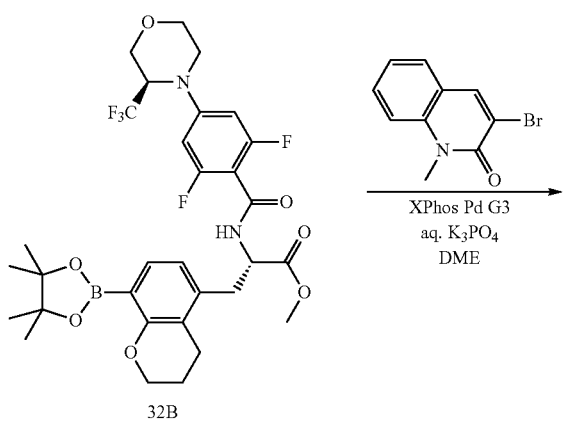

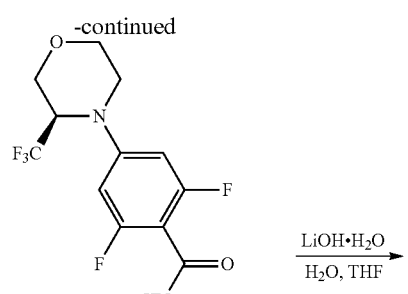

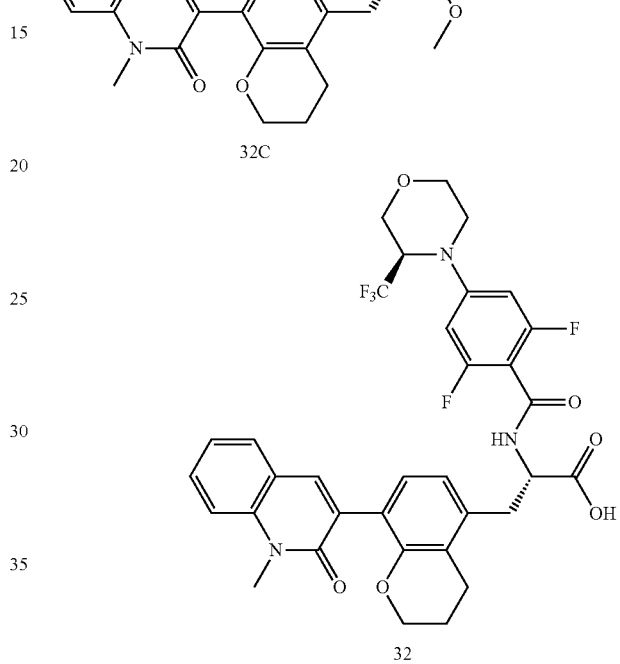

Synthesis of methyl (S)-2-(2,6-difluoro-4-((R)-3-(trifluoromethyl)morpholino) benzamido)-3-(8-(1-methyl-2-oxo-1,2-dihydroquinolin-3-yl)chroman-5-yl)propanoate (32C): The title compound was prepared according to the method presented for the synthesis of compound 13K of Example 13 starting with 3-bromo-1-methylquinolin-2(1H)-one and 32B.

Synthesis of (S)-2-(2,6-difluoro-4-((R)-3-(trifluoromethyl)morpholino)benzamido)-3-(8-(1-methyl-2-oxo-1,2-dihydroquinolin-3-yl)chroman-5-yl)propanoic acid (32): The title compound was prepared according to the method presented for the synthesis of compound 1 of Example 1 starting with 32C. MS (m/z) 672.3 [M+H]$^+$. 1H NMR (400 MHz, DMSO-d6) δ 12.76 (s, 1H), 8.89 (d, J=7.9 Hz, 1H), 7.79 (s, 1H), 7.71 (dd, J=7.9, 1.5 Hz, 1H), 7.62 (ddd, J=8.6, 7.1, 1.6 Hz, 1H), 7.52 (d, J=8.5 Hz, 1H), 7.30-7.23 (m, 1H), 6.97 (d, J=7.7 Hz, 1H), 6.84 (d, J=7.8 Hz, 1H), 6.79 (d, J=11.6 Hz, 2H), 4.97-4.86 (m, 1H), 4.54 (ddd, J=9.6, 7.8, 4.5 Hz, 1H), 4.17 (d, J=12.7 Hz, 1H), 4.02 (td, J=6.6, 6.0, 3.6 Hz, 2H), 3.96 (dd, J=11.6, 3.7 Hz, 1H), 3.79-3.71 (m, 1H), 3.66 (s, 3H), 3.62-3.51 (m, 1H), 3.43-3.39 (m, 1H), 3.25 (t, J=12.5 Hz, 1H), 3.12 (dd, J=14.5, 4.5 Hz, 1H), 2.92 (dd, J=14.5, 9.7 Hz, 1H), 2.79 (q, J=6.8 Hz, 2H), 1.99-1.89 (m, 2H).

Example 33

Synthesis of N-(4-fluorophenyl)-N-methyl-3-oxobutanamide (33A): To a solution of 4-fluoro-N-methylaniline (0.500 g, 4.00 mmol) in toluene (4.0 mL) at 110° C. in an open vial (to evaporate off acetone-byproduct) was added 2,2,6-trimethyl-4H-1,3-dioxin-4-one (0.568 g, 4.00 mmol) and the mixture was heated at 110° C. for 3 h. Upon completion, the solvent was evaporated off under reduced pressure. The material was purified by flash chromatography using EA in hexanes to afford the product (mixture of keto and enol form).

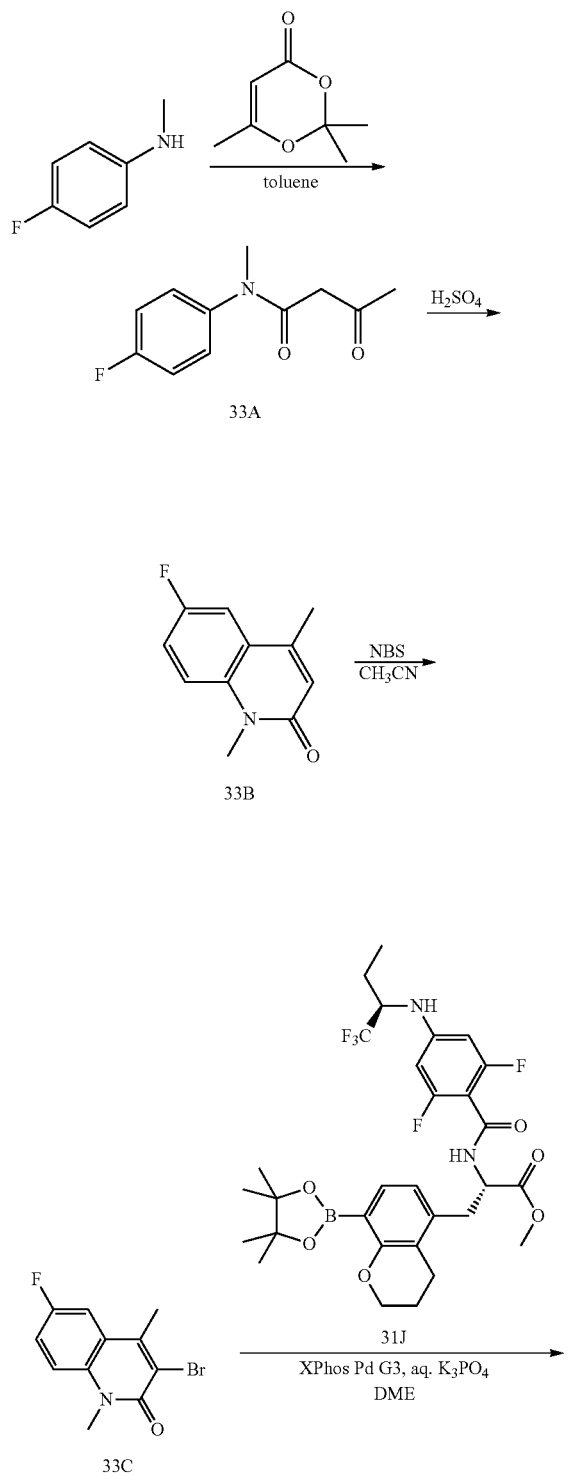

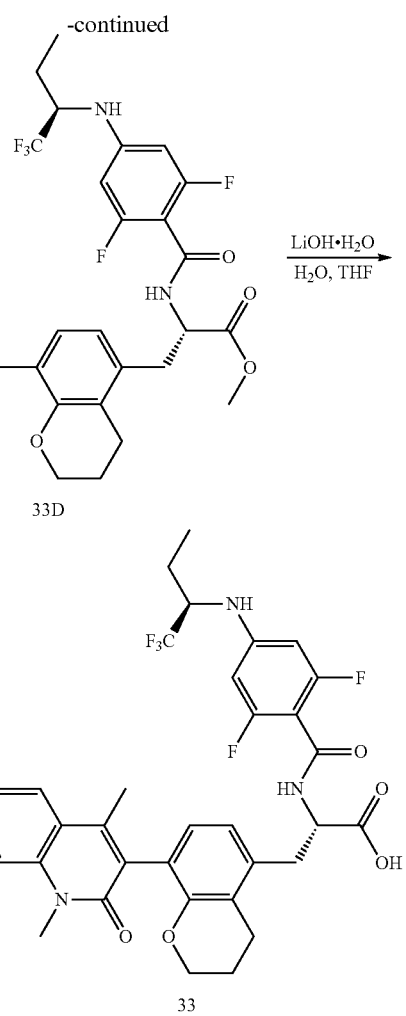

Synthesis of 6-fluoro-1,4-dimethylquinolin-2(1H)-one (33B): A mixture of 33A (0.250 g, 1.20 mmol) and concentrated $H_2SO_4$ (5.53 g, 56.4 mmol) was heated at 95° C. for 2 h. Upon completion, the reaction mixture was poured over ice. The mixture was filtered off to afford the product that was used without further purification.

Synthesis of 6-fluoro-1,4-dimethylquinolin-2(1H)-one (33C): To a microwave vial was added 33B (0.210 g, 1.10 mmol), NBS (0.489 g, 2.75 mmol) and $CH_3CN$ (11 mL), and the mixture was heated in the microwave at 100° C. for 1 h. The mixture was filtered off to afford the title compound and used without further purification.

Synthesis of methyl (S)-2-(2,6-difluoro-4-(((R)-1,1,1-trifluorobutan-2-yl)amino) benzamido)-3-(8-(6-fluoro-1,4-dimethyl-2-oxo-1,2-dihydroquinolin-3-yl)chroman-5-yl)propanoate (33D): The title compound was prepared according to the method presented for the synthesis of compound 13K of Example 13 starting with 33C and 31J.

Synthesis of (S)-2-(2,6-difluoro-4-(((R)-1,1,1-trifluorobutan-2-yl)amino)benzamido)-3-(8-(6-fluoro-1,4-dimethyl-2-oxo-1,2-dihydroquinolin-3-yl)chroman-5-yl)propanoic acid (33): The title compound was prepared according to the method presented for the synthesis of compound 1 of Example 1 starting with 33D. MS (m/z) 676.3 [M+H]$^+$. 1H NMR (400 MHz, DMSO-d6) δ 8.72 (dd, J=7.9, 4.0 Hz, 1H), 7.68-7.45 (m, 3H), 6.91-6.70 (m, 3H), 6.46 (dd, J=11.3, 4.1 Hz, 2H), 4.57 (dtd, J=13.7, 9.2, 8.5, 4.6

Hz, 1H), 4.31 (s, 1H), 3.97 (t, J=5.1 Hz, 2H), 3.63 (d, J=1.5 Hz, 3H), 3.11 (ddd, J=19.2, 14.5, 4.6 Hz, 1H), 2.91 (ddd, J=19.9, 14.5, 10.0 Hz, 1H), 2.82-2.62 (m, 2H), 2.14 (d, J=4.8 Hz, 3H), 1.93 (d, J=6.1 Hz, 2H), 1.77 (d, J=4.9 Hz, 1H), 1.60-1.44 (m, 1H), 0.93 (t, J=7.3 Hz, 3H).

Example 34

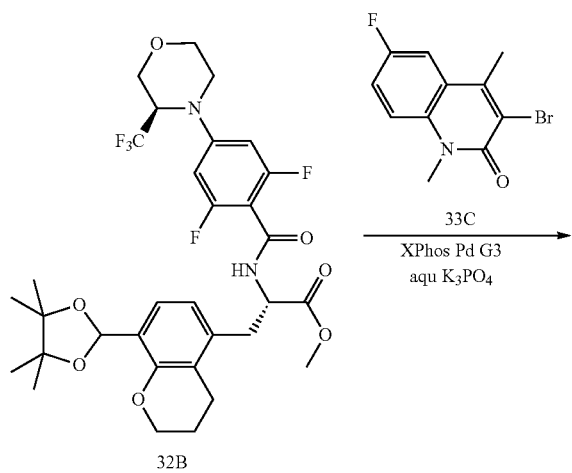

Synthesis of methyl (S)-2-(2,6-difluoro-4-((R)-3-(trifluoromethyl)morpholino) benzamido)-3-(8-(6-fluoro-1,4-dimethyl-2-oxo-1,2-dihydroquinolin-3-yl)chroman-5-yl)propanoate (34A): The title compound was prepared according to the method presented for the synthesis of compound 13K of Example 13 starting with 33C and 32B.

Synthesis of (S)-2-(2,6-difluoro-4-((R)-3-(trifluoromethyl)morpholino)benzamido)-3-(8-(6-fluoro-1,4-dimethyl-2-oxo-1,2-dihydroquinolin-3-yl)chroman-5-yl)propanoic acid (34): The title compound was prepared according to the method presented for the synthesis of compound 1 of Example 1 starting with 34A. MS (m/z) 704.3 [M+H]$^+$. 1H NMR (400 MHz, DMSO-d6) δ 8.87 (dd, J=8.0, 4.6 Hz, 1H), 7.64 (dt, J=10.1, 2.7 Hz, 1H), 7.60-7.47 (m, 2H), 6.90-6.71 (m, 4H), 4.91 (d, J=8.5 Hz, 1H), 4.68-4.51 (m, 1H), 4.16 (d, J=12.7 Hz, 1H), 3.97 (q, J=8.1, 6.6 Hz, 3H), 3.74 (d, J=12.6 Hz, 1H), 3.63 (d, J=1.2 Hz, 3H), 3.56 (t, J=12.3 Hz, 1H), 3.43 (d, J=12.9 Hz, 1H), 3.26 (d, J=12.0 Hz, 1H), 3.13 (ddd, J=19.5, 14.5, 4.5 Hz, 1H), 2.93 (ddd, J=23.7, 14.5, 10.0 Hz, 1H), 2.78 (q, J=8.0, 7.2 Hz, 2H), 2.14 (d, J=5.3 Hz, 3H), 1.93 (d, J=5.9 Hz, 2H).

Example 35

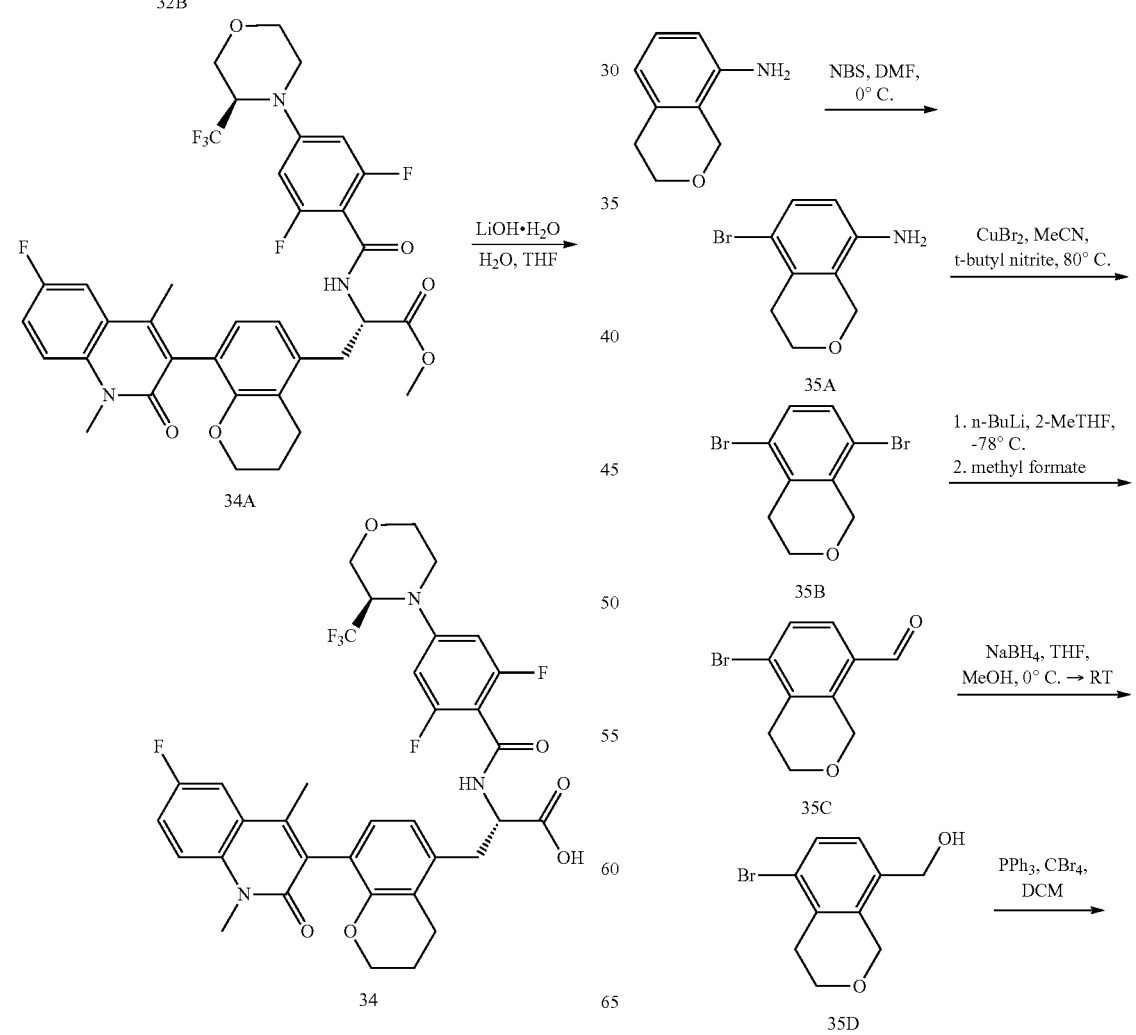

-continued

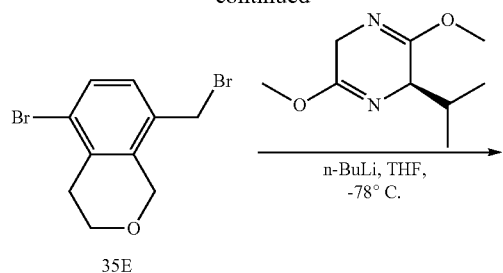

35E

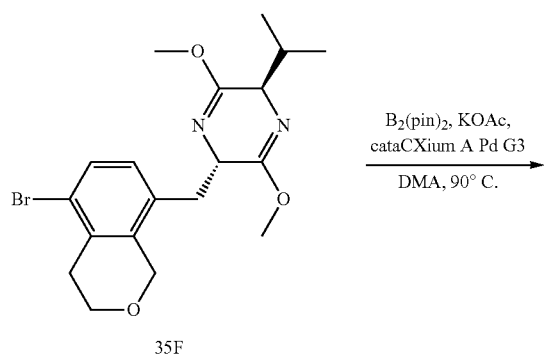

35F

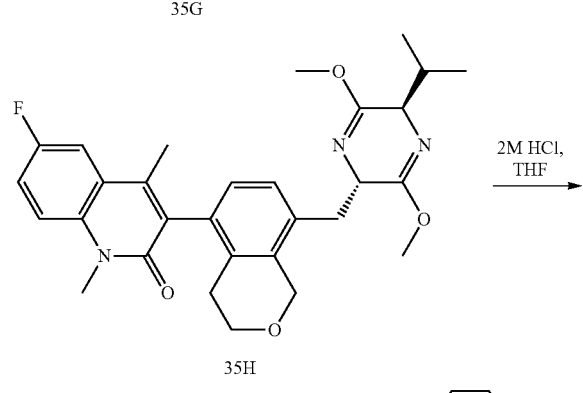

35G

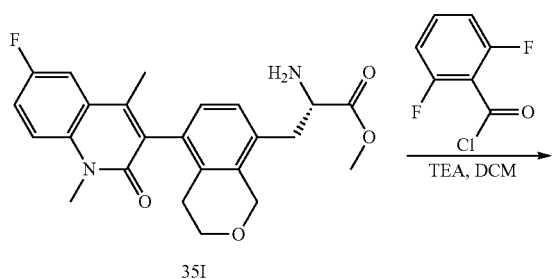

35H

-continued

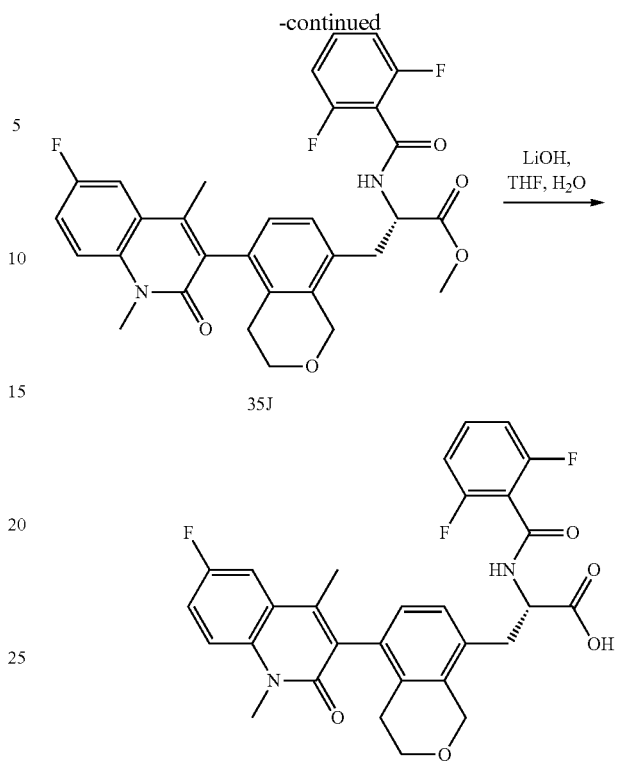

35J

Synthesis of 5-bromoisochroman-8-amine (35A): To a stirred solution of isochroman-8-amine (2.07 g, 11.15 mmol) in DMF (22.3 mL) at 0° C. was added N-bromosuccinimde (2.18 g, 12.16 mmol). After stirring for 5 min at 0° C., the reaction was diluted with water and EtOAc. Aqueous layer was extracted and the organic layer was dried over anhydrous MgSO$_4$ and concentrated under reduced pressure. The material was purified by silica gel chromatography using 0-50% EtOAc in hexanes to afford the title compound.

Synthesis of 5,8-dibromoisochromane (35B): To a stirred solution of copper(II) bromide (756.9 mg, 3.39 mmol) in ACN (15.58 mL) under N$_2$ was added tert-butyl nitrite (0.44 mL, 3.73 mmol) dropwise. To this was added a solution of 35A (772.9 mg, 3.39 mmol) in ACN (7.79 mL). The reaction was stirred at 80° C. under N$_2$ for 2 hours. After cooling to room temperature, the reaction was diluted with water and EtOAc. The aqueous layer was extracted and the organic layer was dried over anhydrous MgSO$_4$ and concentrated under reduced pressure. The material was purified by silica gel chromatography using 0-5% EtOAc in hexanes to afford the title compound.

Synthesis of 5-bromoisochromane-8-carbaldehyde (35C): To a stirred solution of 35B (1.29 g, 4.42 mmol) in 2-MeTHF (12.63 mL) under N$_2$ at −78° C. was added n-BuLi (1.65M in hexanes, 2.41 mL, 3.98 mmol) dropwise, and this was stirred at −78° C. for 2 hours. Methyl formate (0.55 mL, 8.84 mmol) was added dropwise, and the reaction was stirred at −78° C. for 45 min. The dry ice/acetone bath was removed and the reaction was stirred for 15 min. The reaction was quenched with water and diluted with EtOAc. The aqueous layer was extracted and the organic layer was dried over anhydrous MgSO$_4$ and concentrated under reduced pressure. The material was purified by silica gel chromatography using 0-20% EtOAc in hexanes to afford the title compound.

Synthesis of (5-bromoisochroman-8-yl)methanol (35D): To a stirred solution of 35C (232.4 mg, 0.96 mmol) in THF (6.43 mL) and MeOH (9.64 mL) at 0° C. was added sodium borohydride (36.5 mg, 0.96 mmol). The reaction was stirred at 0° C. for 5 min and then it was allowed to warm to room temperature while stirring for 45 min. The reaction was quenched with water and diluted with EtOAc. The aqueous layer was extracted and the organic layer was dried over anhydrous $MgSO_4$ and concentrated under reduced pressure. The material was purified by silica gel chromatography using 0-50% EtOAc in hexanes to afford the title compound.

Synthesis of 5-bromo-8-(bromomethyl)isochromane (35E): The title compound was prepared according to the method presented for the synthesis of compound 13E of Example 13 starting with 35D.

Synthesis of (2S,5R)-2-((5-bromoisochroman-8-yl)methyl)-5-isopropyl-3,6-dimethoxy-2,5-dihydropyrazine (35F): The title compound was prepared according to the method presented for the synthesis of compound 4A of Example 4 starting with 35E.

Synthesis of (2R,5S)-2-isopropyl-3,6-dimethoxy-5-((5-(4,4,5,5-tetramethyl-1,3,2-dioxaborolan-2-yl)isochroman-8-yl)methyl)-2,5-dihydropyrazine (35G): The title compound was prepared according to the method presented for the synthesis of compound 1G of Example 1 starting with 35F.

Synthesis of 6-fluoro-3-(8-(((2S,5R)-5-isopropyl-3,6-dimethoxy-2,5-dihydropyrazin-2-yl)methyl)isochroman-5-yl)-1,4-dimethylquinolin-2(1H)-one (35H): The title compound was prepared according to the method presented for the synthesis of compound 1G of Example 1 starting with 35G.

Synthesis of methyl (S)-2-amino-3-(5-(6-fluoro-1,4-dimethyl-2-oxo-1,2-dihydroquinolin-3-yl)isochroman-8-yl)propanoate (35I): The title compound was prepared according to the method presented for the synthesis of compound 4C of Example 4 starting with 35H.

Synthesis of methyl (S)-2-(2,6-difluorobenzamido)-3-(5-(6-fluoro-1,4-dimethyl-2-oxo-1,2-dihydroquinolin-3-yl)isochroman-8-yl)propanoate (35J): The title compound was prepared according to the method presented for the synthesis of compound 1F of Example 1 starting with 2,6-difluorobenzoyl chloride and 35I.

Synthesis of (S)-2-(2,6-difluorobenzamido)-3-(5-(6-fluoro-1,4-dimethyl-2-oxo-1,2-dihydroquinolin-3-yl)isochroman-8-yl)propanoic acid (35): The title compound was prepared according to the method presented for the synthesis of compound 1 of Example 1 starting with 35J. MS (m/z) 551.2 [M+H]$^+$. 1H NMR (400 MHz, DMSO-d6) δ 12.91 (s, 1H), 9.20 (dd, J=9.9, 8.1 Hz, 1H), 7.68 (dt, J=10.1, 3.3 Hz, 1H), 7.62 (dd, J=9.3, 4.8 Hz, 1H), 7.59-7.45 (m, 2H), 7.15 (dt, J=15.7, 7.9 Hz, 3H), 6.88 (t, J=7.4 Hz, 1H), 4.90-4.73 (m, 2H), 4.73-4.60 (m, 1H), 3.83-3.71 (m, J=5.6 Hz, 2H), 3.66 (d, J=1.7 Hz, 3H), 3.07 (td, J=15.7, 4.4 Hz, 1H), 2.92-2.78 (m, 1H), 2.48-2.27 (m, 2H), 2.12 (d, J=6.7 Hz, 3H).

Preparation of (S)-2-(2,6-difluorobenzamido)-3-((R)-8-(4-fluoro-2-methoxy-6-(trifluoromethyl)phenyl)quinolin-5-yl)propanoic acid (7): 6C was separated into its 2 diastereomeric atropisomers by supercritical fluid chromatography using 25% EtOH/TFA co-solvent, at a flow rate of 50 mL/min, using an AD-H 5 µm 21×250 mm column. The title compound was identified as the first eluting peak. MS (m/z) 549.1 [M+H]$^+$. 1H NMR (400 MHz, Methanol-d4) δ 9.36 (dd, J=8.7, 1.6 Hz, 1H), 8.95 (dd, J=5.0, 1.5 Hz, 1H), 8.00 (dd, J=8.7, 5.0 Hz, 1H), 7.89 (d, J=7.4 Hz, 1H), 7.78 (dd, J=7.4, 0.9 Hz, 1H), 7.45 (tt, J=8.4, 6.4 Hz, 1H), 7.32 (s, 1H), 7.30 (s, 1H), 7.02-6.95 (m, 2H), 5.12 (dd, J=9.8, 5.2 Hz, 1H), 4.03 (dd, J=14.4, 5.2 Hz, 1H), 3.71-3.63 (m, 4H).

Example 36

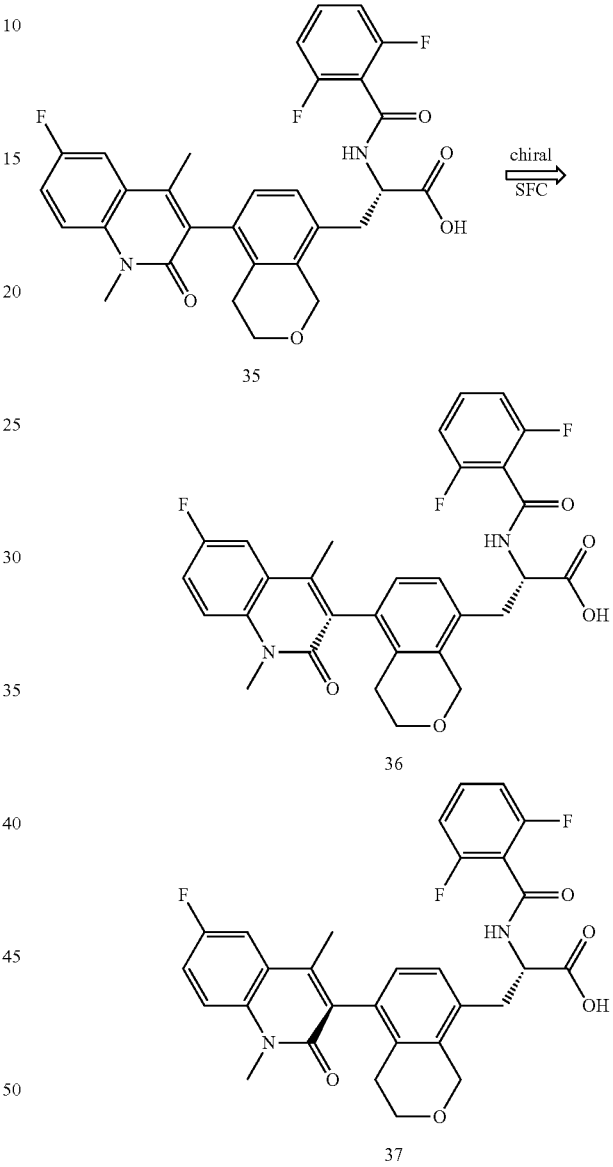

Preparation of (S)-2-(2,6-difluorobenzamido)-3-((R)-8-(4-fluoro-2-methoxy-6-(trifluoromethyl)phenyl)quinolin-5-yl)propanoic acid atropisomer 1 (36): 35 was separated into its 2 diastereomeric atropisomers by supercritical fluid chromatography using 30% MeOH co-solvent, at a flow rate of 3 mL/min, using an AD-H 4.6×100 mm column. The title compound was identified as corresponding to the first eluting peak. MS (m/z) 551.2 [M+H]$^+$. 1H NMR (400 MHz, DMSO-d6) δ 9.18 (d, J=8.2 Hz, 1H), 7.68 (dt, J=10.0, 3.3 Hz, 1H), 7.62 (dd, J=9.3, 4.9 Hz, 1H), 7.59-7.45 (m, 2H), 7.21-7.08 (m, 3H), 6.88 (d, J=7.7 Hz, 1H), 4.91-4.73 (m, 2H), 4.68 (ddd, J=10.1, 8.1, 4.4 Hz, 1H), 3.76 (t, J=5.8 Hz, 2H), 3.66 (s, 3H), 3.04 (dd, J=15.0, 4.5 Hz, 1H), 2.86 (dd, J=14.8, 10.3 Hz, 1H), 2.47-2.27 (m, 2H), 2.12 (d, J=6.7 Hz, 3H).

Example 37

Preparation of (S)-2-(2,6-difluorobenzamido)-3-((R)-8-(4-fluoro-2-methoxy-6-(trifluoromethyl)phenyl)quinolin-5-yl)propanoic acid atropisomer 2 (37): 35 was separated into its 2 diastereomeric atropisomers by supercritical fluid chromatography using 30% MeOH co-solvent, at a flow rate of 3 mL/min, using an AD-H 4.6×100 mm column. The title compound was identified as atropisomer 2 corresponding to the second eluting peak. MS (m/z) 551.2 [M+H]$^+$. 1H NMR (400 MHz, DMSO-d6) δ 12.90 (s, 1H), 9.21 (d, J=8.2 Hz, 1H), 7.68 (dd, J=10.1, 2.9 Hz, 1H), 7.62 (dd, J=9.4, 4.9 Hz, 1H), 7.59-7.45 (m, 2H), 7.13 (t, J=7.8 Hz, 3H), 6.87 (d, J=7.7 Hz, 1H), 4.82 (d, J=2.9 Hz, 2H), 4.65 (ddd, J=10.3, 8.0, 4.2 Hz, 1H), 3.78 (dp, J=12.0, 5.8 Hz, 2H), 3.66 (s, 3H), 3.09 (dd, J=14.9, 4.2 Hz, 1H), 2.83 (dd, J=14.8, 10.5 Hz, 1H), 2.48-2.27 (m, 2H), 2.13 (s, 3H).

Example 38

Synthesis of methyl 4-bromo-3-((2-methylallyl)oxy)benzoate (38A): To a stirred solution of methyl 4-bromo-3-hydroxybenzoate (50 g, 216 mmol) in DMF (350 mL) at 0° C. was added sodium hydride (60% in mineral oil, 9.52 g, 238 mmol), and the reaction was stirred at this temperature for 10 minutes. To this, 3-chloro-2-methylprop-1-ene (54.9 g, 606 mmol) was added, the reaction was warmed to room temperature, and it was stirred for 16 hours. It was poured onto 500 mL of ice water and extracted three times with 3:1 petroleum ether/EtOAc. The extracts were washed twice with saturated sodium chloride, dried over anhydrous sodium sulfate, filtered, and concentrated to give the title compound.

Synthesis of methyl 4-bromo-3-hydroxy-2-(2-methylallyl)benzoate (38B): A solution of 38A (31.5 g 111 mmol) in N,N-diethylaniline (157.5 mL) was heated to 200° C. in a microwave reactor for 3 hours. It was cooled to room temperature, and the solvent was removed by distillation. The residue was dissolved in EtOAc (100 mL) and was washed six times with 1 N hydrochloric acid and twice with brine. It was dried over anhydrous sodium sulfate, filtered, and concentrated. It was purified by column chromatography on silica gel (0-3% EtOAc/petroleum ether) to yield the title compound.

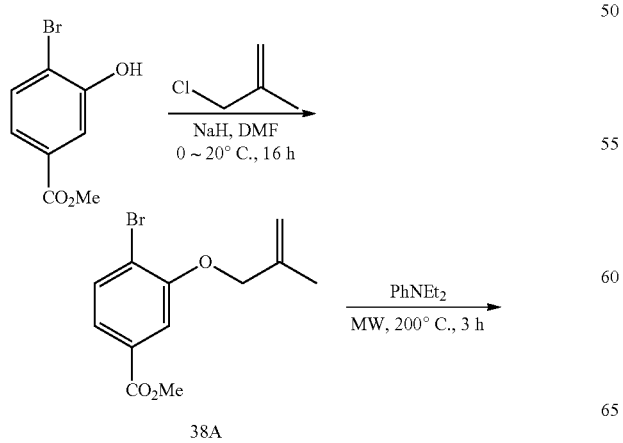

38A

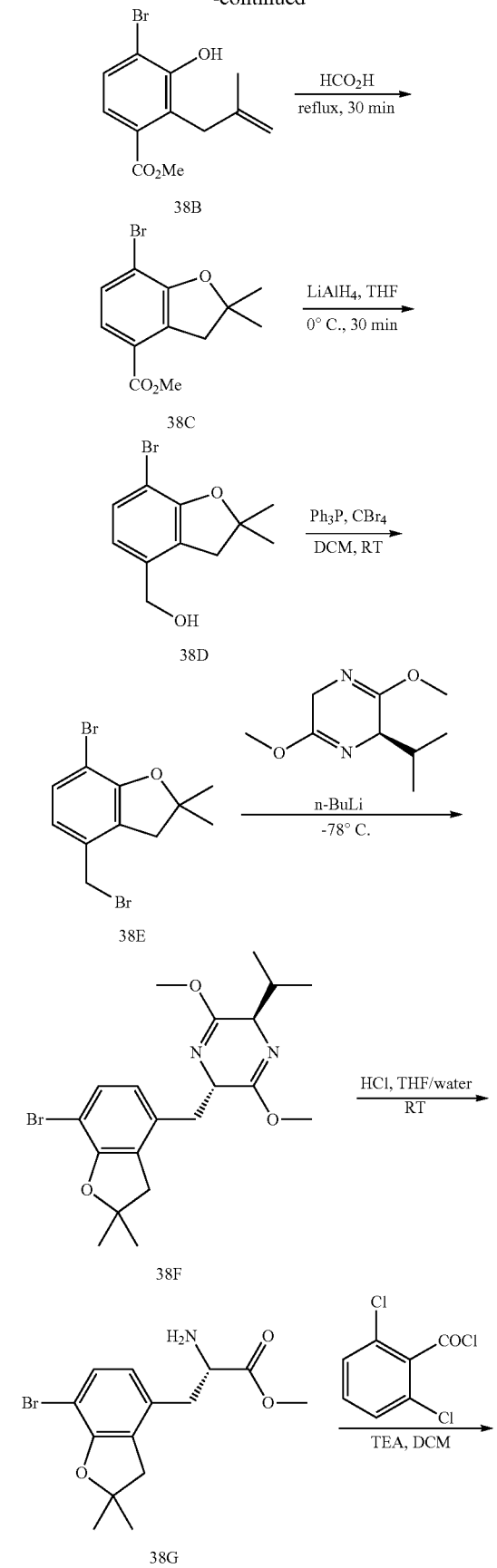

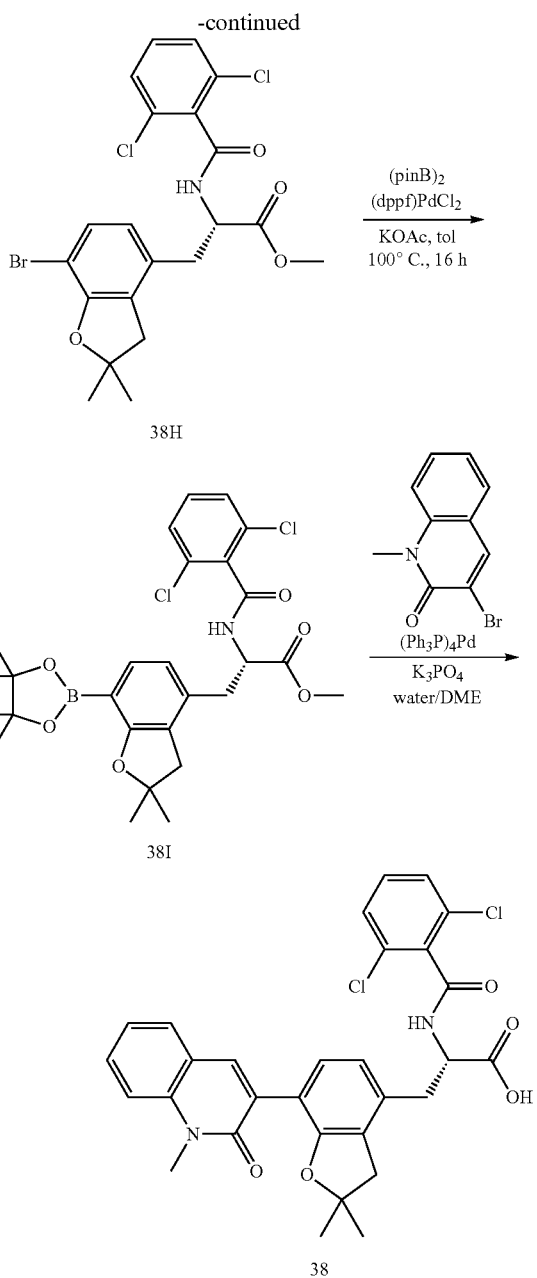

Synthesis of methyl 7-bromo-2,2-dimethyl-2,3-dihydrobenzofuran-4-carboxylate (38C): A stirred solution of 38B (18.0 g, 63.1 mmol) in formic acid (120 mL) was heated to 100° C. for 30 minutes. It was cooled to room temperature, and the resulting material was collected via filtration and washed twice with water to give the title compound.

Synthesis of (7-bromo-2,2-dimethyl-2,3-dihydrobenzofuran-4-yl)methanol (38D): To a stirred solution of 38C (7.6 g, 27 mmol) in THF (50 mL) at 0° C. was added lithium aluminum hydride (1.06 g, 28 mmol), and the reaction was stirred at this temperature for 30 minutes. It was quenched at 0° C. by the addition of saturated aq. ammonium chloride (20 mL). To this, EtOAc (50 mL) was added, and it warmed to room temperature and stirred for 30 min. The solids were removed by filtration, and the filter cake was washed 4 times with EtOAc. The filtrate and washings were combined and concentrated in vacuo. It was purified by flash chromatography on silica gel (eluent 5:1 petroleum ether/EtOAc) to yield the title compound.

Synthesis of 7-bromo-4-(bromomethyl)-2,2-dimethyl-2,3-dihydrobenzofuran (38E): The title compound was prepared according to the method presented for the synthesis of compound 13E of Example 13 starting with 38D.

Synthesis of (2S,5R)-2-((7-bromo-2,2-dimethyl-2,3-dihydrobenzofuran-4-yl)methyl)-5-isopropyl-3,6-dimethoxy-2,5-dihydropyrazine (38F): The title compound was prepared according to the method presented for the synthesis of compound 4A of Example 4 starting with 38E.

Synthesis of methyl (S)-2-amino-3-(7-bromo-2,2-dimethyl-2,3-dihydrobenzofuran-4-yl)propanoate (38G): The title compound was prepared according to the method presented for the synthesis of compound 4C of Example 4 starting with 38F.

Synthesis of methyl (S)-3-(7-bromo-2,2-dimethyl-2,3-dihydrobenzofuran-4-yl)-2-(2,6-dichlorobenzamido)propanoate (38H): The title compound was prepared according to the method presented for the synthesis of compound 1F of Example 1 starting with 2,6-dichlorobenzoyl chloride and 38G.

Synthesis of methyl (S)-2-(2,6-dichlorobenzamido)-3-(2,2-dimethyl-7-(4,4,5,5-tetramethyl-1,3,2-dioxaborolan-2-yl)-2,3-dihydrobenzofuran-4-yl)propanoate (38G): To a stirred solution of 38H (1.0 g, 2.0 mmol) in toluene was added bis(pinacolato)diboron (0.56 g, 1.1 mmol), followed by KOAc (0.59 g, 6.0 mmol), Pd(dppf)Cl$_2$ (0.081 g, 0.01 mmol). The reaction vessel was flushed with nitrogen then heated to 100° C. for 16 hrs. The reaction mixture was concentrated under reduced pressure and purified on silica gel eluting with EtOAc in Hex (5-100%) to give the title compound.

Synthesis of (S)-2-(2,6-dichlorobenzamido)-3-(2,2-dimethyl-7-(1-methyl-2-oxo-1,2-dihydroquinolin-3-yl)-2,3-dihydrobenzofuran-4-yl)propanoic acid (38): To a microwave vial was added 38G (150 mg, 0.27 mmol), 3-bromo-1-methylquinolin-2(1H)-one (78 mg, 0.33 mmol), Pd(PPh$_3$)$_4$ (16 mg, 0.014 mmol), and aq. K$_3$PO$_4$ (0.96 mL, 1M) in DME (2 mL). The reaction mixture was allowed to stir at 120° C. for 30 min. and concentrated under reduced pressure. The material was concentrated and then purified via reverse phase HPLC to afford the title compound. MS (m/z) 565.1 [M+H]$^+$. 1H NMR (400 MHz, DMSO-d6) δ 9.12 (d, J=8.3 Hz, 1H), 7.92 (d, J=0.6 Hz, 1H), 7.75-7.67 (m, 1H), 7.61 (ddd, J=8.7, 7.2, 1.6 Hz, 1H), 7.56-7.48 (m, 1H), 7.45-7.34 (m, 3H), 7.29-7.23 (m, 2H), 6.77 (d, J=8.0 Hz, 1H), 4.76 (td, J=8.8, 5.8 Hz, 1H), 3.66 (s, 3H), 3.15-2.98 (m, 3H), 2.88 (dd, J=14.2, 9.2 Hz, 1H), 1.41 (s, 3H), 1.40 (s, 3H).

Example 39

Synthesis of methyl (S)-2-(2,6-difluoro-4-((R)-3-(trifluoromethyl)morpholino) benzamido)-3-(8-(1,6-dimethyl-2-oxo-4-(trifluoromethyl)-1,2-dihydropyridin-3-yl)chroman-5-yl)propanoate (39A): The title compound was prepared according to the method presented for the synthesis of compound 13K of Example 13 starting with 25B and 32B.

Preparation of (S)-2-(2,6-difluoro-4-((R)-3-(trifluoromethyl)morpholino)benzamido)-3-(8-(1,6-dimethyl-2-oxo-4-(trifluoromethyl)-1,2-dihydropyridin-3-yl)chroman-5-yl) propanoate atropisomer 1 (39B) and (S)-2-(2,6-difluoro-4-((R)-3-(trifluoromethyl)morpholino)benzamido)-3-(8-(1,6-dimethyl-2-oxo-4-(trifluoromethyl)-1,2-dihydropyridin-3-yl)chroman-5-yl) propanoate atropisomer 2 (39C): 39A was separated into its 2 diastereomeric atropisomers by supercritical fluid chromatography using 30% MeOH co-solvent, at a flow rate of 60 mL/min, using an IC 21×250 mm column. The title compounds were identified as 39B and 39C corresponding to the first and second eluting peaks.

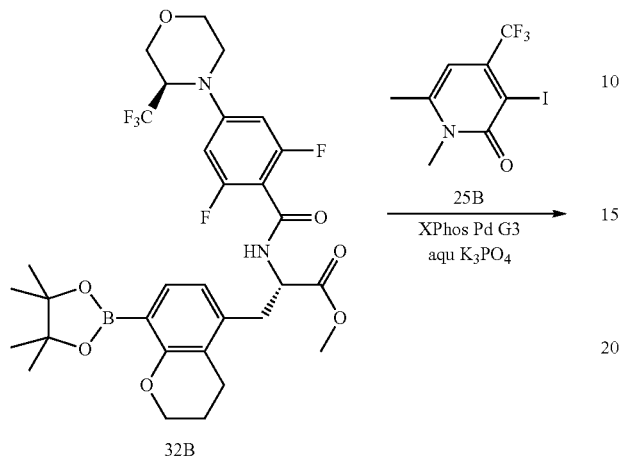

32B

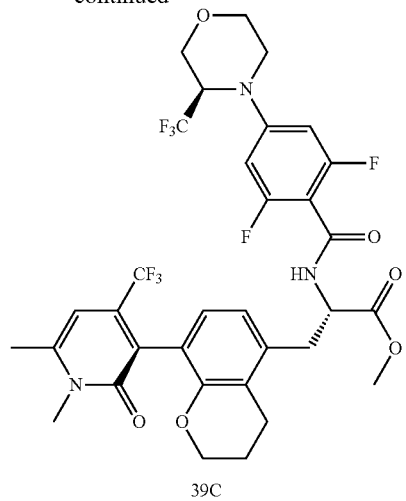

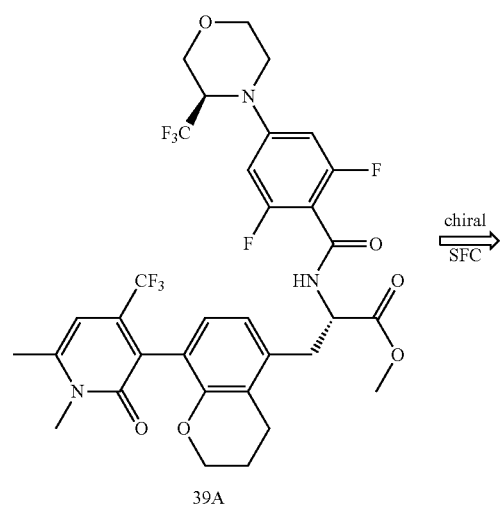

39A

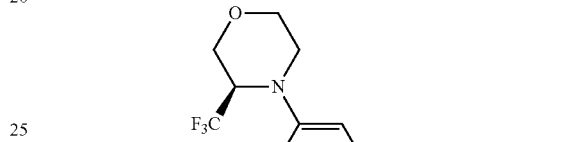

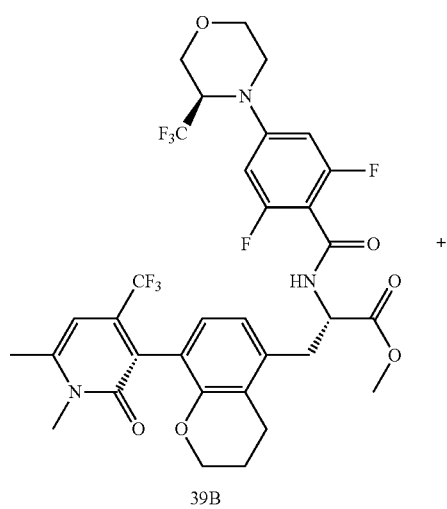

39B

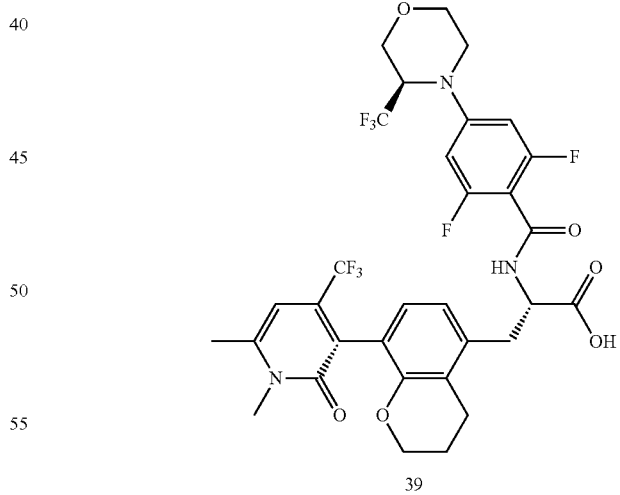

39B

39

Synthesis of (S)-2-(2,6-difluoro-4-((R)-3-(trifluoromethyl)morpholino)benzamido)-3-(8-(1,6-dimethyl-2-oxo-4-(trifluoromethyl)-1,2-dihydropyridin-3-yl)chroman-5-yl)propanoic acid atropisomer 1 (39): The title compound was prepared according to the method presented for the synthesis of compound 1 of Example 1 starting with 39B. MS (m/z) 704.3 [M+H]+. 1H NMR (400 MHz, DMSO-d6) δ 12.71 (br s, 1H), 8.86 (d, J=7.8 Hz, 1H), 6.83-6.72 (m, 3H), 6.70 (d, J=7.7 Hz, 1H), 6.42 (s, 1H), 4.91 (dd, J=8.8, 3.6 Hz, 1H), 4.57 (td, J=8.7, 4.6 Hz, 1H), 4.16 (d, J=12.6 Hz, 1H), 3.94 (ddt, J=21.0, 10.6, 5.4 Hz, 3H), 3.74 (d, J=12.7 Hz, 1H), 3.61-3.51 (m, 1H), 3.46 (s, 3H), 3.46-3.39 (m, 1H), 3.24 (t, J=12.3 Hz, 1H), 3.09 (dd, J=14.8, 4.6 Hz, 1H), 2.90 (dd, J=14.8, 9.8 Hz, 1H), 2.82-2.65 (m, 2H), 2.45 (s, 3H), 1.90 (p, J=6.1 Hz, 2H).

Example 40

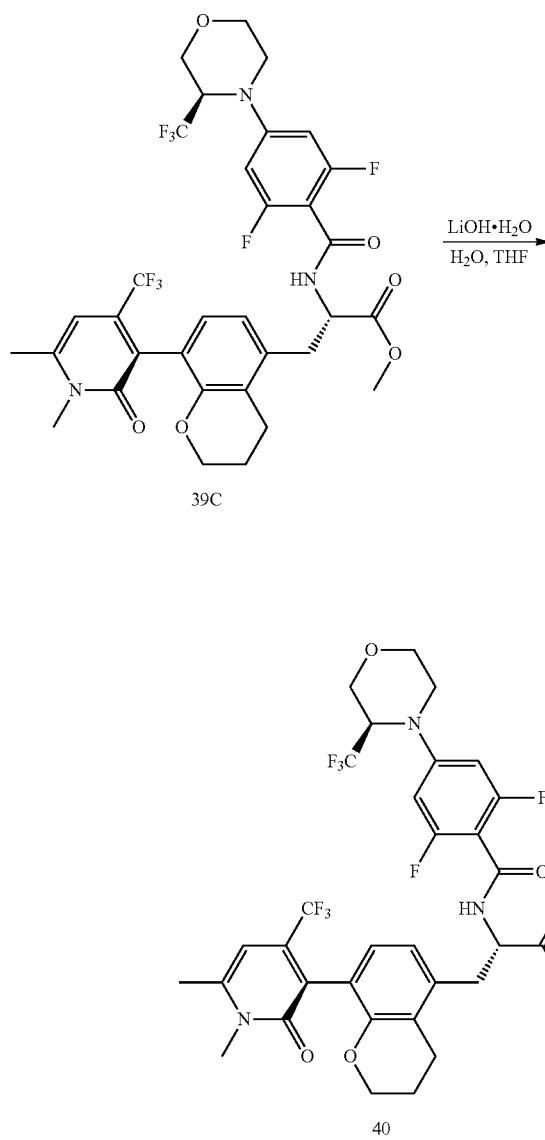

Synthesis of (S)-2-(2,6-difluoro-4-((R)-3-(trifluoromethyl)morpholino)benzamido)-3-(8-(1,6-dimethyl-2-oxo-4-(trifluoromethyl)-1,2-dihydropyridin-3-yl)chroman-5-yl)propanoic acid atropisomer 2 (40): The title compound was prepared according to the method presented for the synthesis of compound 1 of Example 1 starting with 39C. MS (m/z) 704.3 [M+H]+. 1H NMR (400 MHz, DMSO-d6) δ 12.74 (br s, 1H), 8.87 (d, J=7.8 Hz, 1H), 6.84-6.73 (m, 3H), 6.70 (d, J=7.8 Hz, 1H), 6.42 (s, 1H), 4.92 (dd, J=9.0, 3.6 Hz, 1H), 4.55 (td, J=8.9, 4.2 Hz, 1H), 4.16 (d, J=12.7 Hz, 1H), 3.95 (dddd, J=22.0, 17.3, 8.4, 5.2 Hz, 3H), 3.74 (d, J=12.7 Hz, 1H), 3.61-3.51 (m, 1H), 3.47 (s, 3H), 3.46-3.38 (m, 1H), 3.24 (t, J=12.3 Hz, 1H), 3.08 (dd, J=14.8, 4.3 Hz, 1H), 2.91 (dd, J=14.8, 9.9 Hz, 1H), 2.81-2.65 (m, 2H), 2.45 (s, 3H), 1.91 (d, J=9.6 Hz, 2H).

Example 41

Synthesis of methyl (S)-3-(8-bromochroman-5-yl)-2-(2,6-difluoro-4-(((R)-1,1,1-trifluoropropan-2-yl)amino)benzamido)propanoate (41A): The title compound was prepared according to the method presented for the synthesis of compound 6A of Example 6 starting with 31H and 20B.

Synthesis of methyl (S)-2-(2,6-difluoro-4-(((R)-1,1,1-trifluoropropan-2-yl)amino)benzamido)-3-(8-(4,4,5,5-tetramethyl-1,3,2-dioxaborolan-2-yl)chroman-5-yl)propanoate (41B): The title compound was prepared according to the method presented for the synthesis of compound 1G of Example 1 starting with 41A.

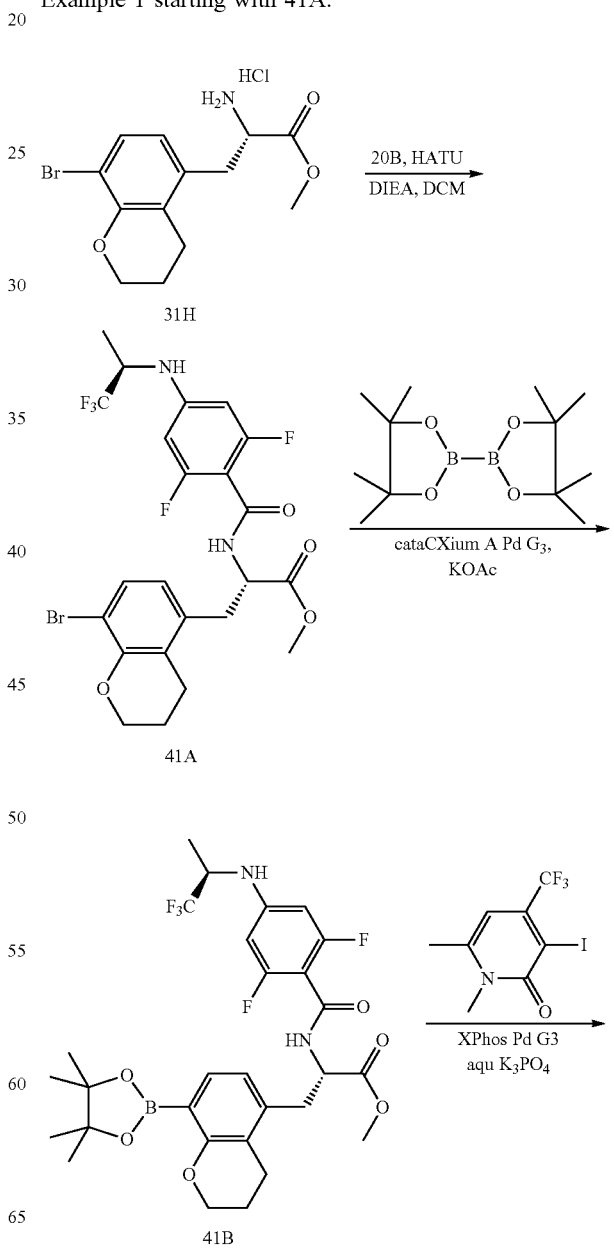

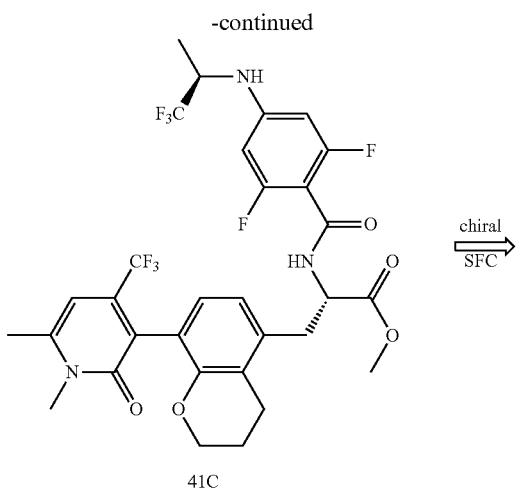

41C

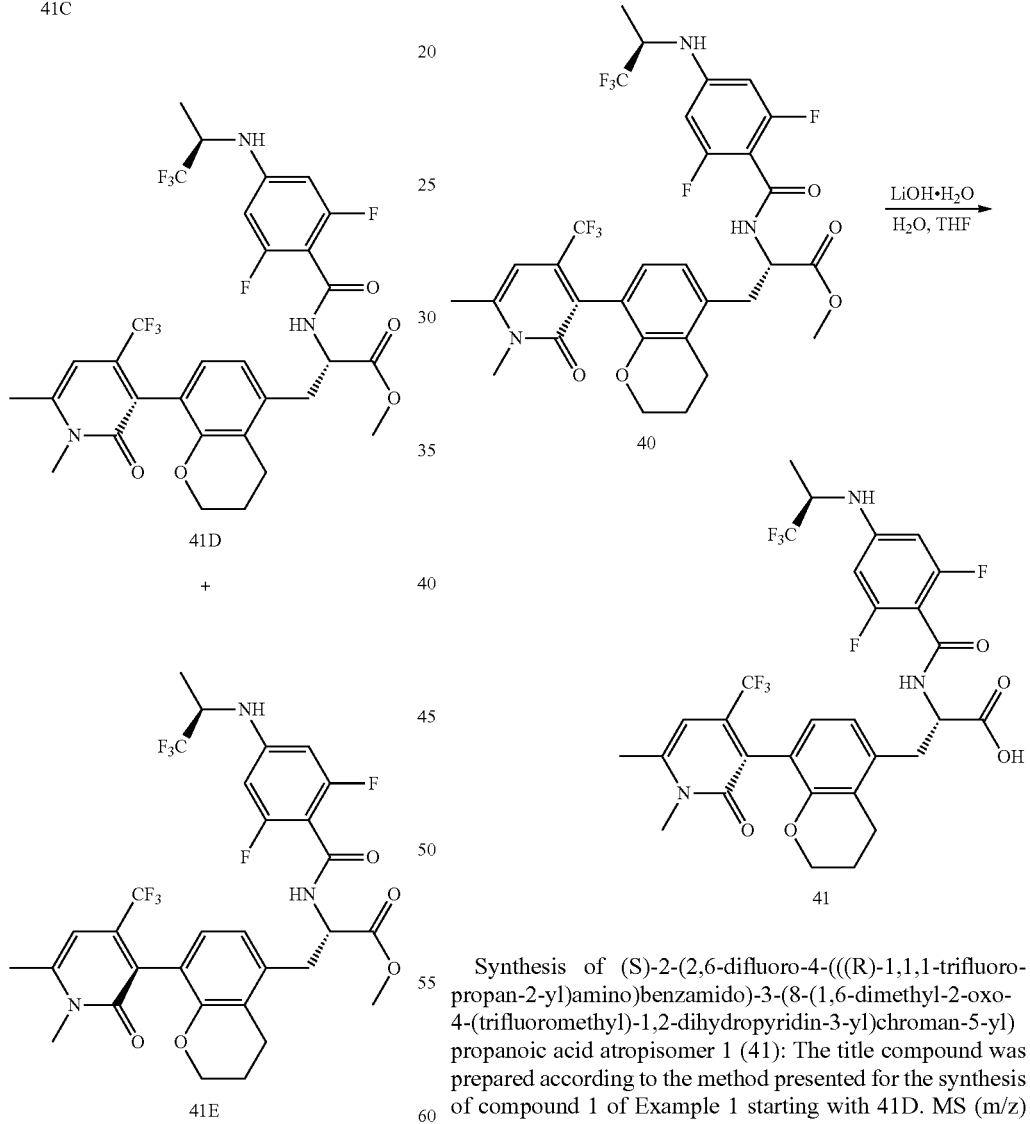

Synthesis of methyl (S)-2-(2,6-difluoro-4-(((R)-1,1,1-trifluoropropan-2-yl)amino) benzamido)-3-(8-(1,6-dimethyl-2-oxo-4-(trifluoromethyl)-1,2-dihydropyridin-3-yl)chroman-5-yl)propanoate (41C): The title compound was prepared according to the method presented for the synthesis of compound 13K of Example 13 starting with 3-iodo-1,6-dimethyl-4-(trifluoromethyl)pyridin-2(1H)-one and 41B.

Preparation of methyl (S)-2-(2,6-difluoro-4-(((R)-1,1,1-trifluoropropan-2-yl)amino) benzamido)-3-(8-(1,6-dimethyl-2-oxo-4-(trifluoromethyl)-1,2-dihydropyridin-3-yl) chroman-5-yl)propanoate atropisomer 1 (41D) and methyl (S)-2-(2,6-difluoro-4-(((R)-1,1,1-trifluoropropan-2-yl)amino)benzamido)-3-(8-(1,6-dimethyl-2-oxo-4-(trifluoromethyl)-1,2-dihydropyridin-3-yl)chroman-5-yl)propanoate atropisomer 2 (41E): 41C was separated into its 2 diastereomeric atropisomers by supercritical fluid chromatography using 30% MeOH co-solvent, at a flow rate of 60 mL/min, using an IC 21×250 mm column. The title compounds were identified as the atropisomer 1 and 2 corresponding to the first and second eluting peaks.

Synthesis of (S)-2-(2,6-difluoro-4-(((R)-1,1,1-trifluoropropan-2-yl)amino)benzamido)-3-(8-(1,6-dimethyl-2-oxo-4-(trifluoromethyl)-1,2-dihydropyridin-3-yl)chroman-5-yl) propanoic acid atropisomer 1 (41): The title compound was prepared according to the method presented for the synthesis of compound 1 of Example 1 starting with 41D. MS (m/z) 662.2 [M+H]$^+$. 1H NMR (400 MHz, DMSO-d6) δ 8.69 (d, J=7.7 Hz, 1H), 6.80 (dd, J=19.5, 8.6 Hz, 2H), 6.69 (d, J=7.8 Hz, 1H), 6.43 (d, J=10.3 Hz, 3H), 4.53 (td, J=14.4, 13.9, 7.0 Hz, 2H), 3.93 (dp, J=21.2, 5.4 Hz, 2H), 3.46 (s, 3H), 3.07 (dd, J=15.0, 4.7 Hz, 1H), 2.89 (dd, J=14.8, 9.7 Hz, 1H), 2.72 (d, J=7.6 Hz, 2H), 2.45 (s, 3H), 1.97-1.78 (m, 2H), 1.28 (d, J=6.6 Hz, 3H).

Example 42

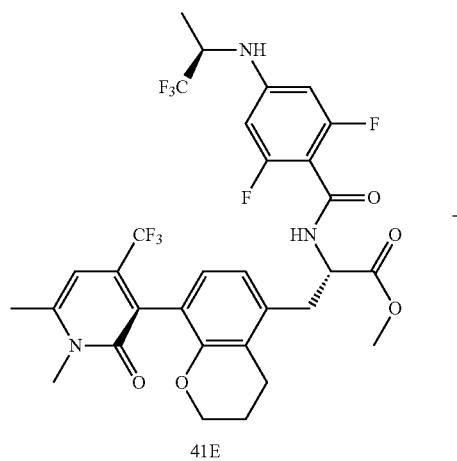

Synthesis of (S)-2-(2,6-difluoro-4-(((R)-1,1,1-trifluoropropan-2-yl)amino)benzamido)-3-(8-(1,6-dimethyl-2-oxo-4-(trifluoromethyl)-1,2-dihydropyridin-3-yl)chroman-5-yl)propanoic acid atropisomer 1 (41): The title compound was prepared according to the method presented for the synthesis of compound 1 of Example 1 starting with 41E. MS (m/z) 662.2 [M+H]$^+$. 1H NMR (400 MHz, DMSO-d6) δ 8.71 (d, J=7.7 Hz, 1H), 6.81 (dd, J=11.5, 8.5 Hz, 2H), 6.70 (d, J=7.7 Hz, 1H), 6.43 (d, J=11.6 Hz, 3H), 4.52 (t, J=11.1 Hz, 2H), 3.96-3.86 (m, 2H), 3.47 (s, 3H), 3.07 (dd, J=14.8, 4.3 Hz, 1H), 2.90 (dd, J=14.8, 9.9 Hz, 1H), 2.73 (t, J=6.3 Hz, 2H), 2.45 (s, 3H), 1.90 (s, 2H), 1.28 (d, J=6.6 Hz, 3H).

Example 43

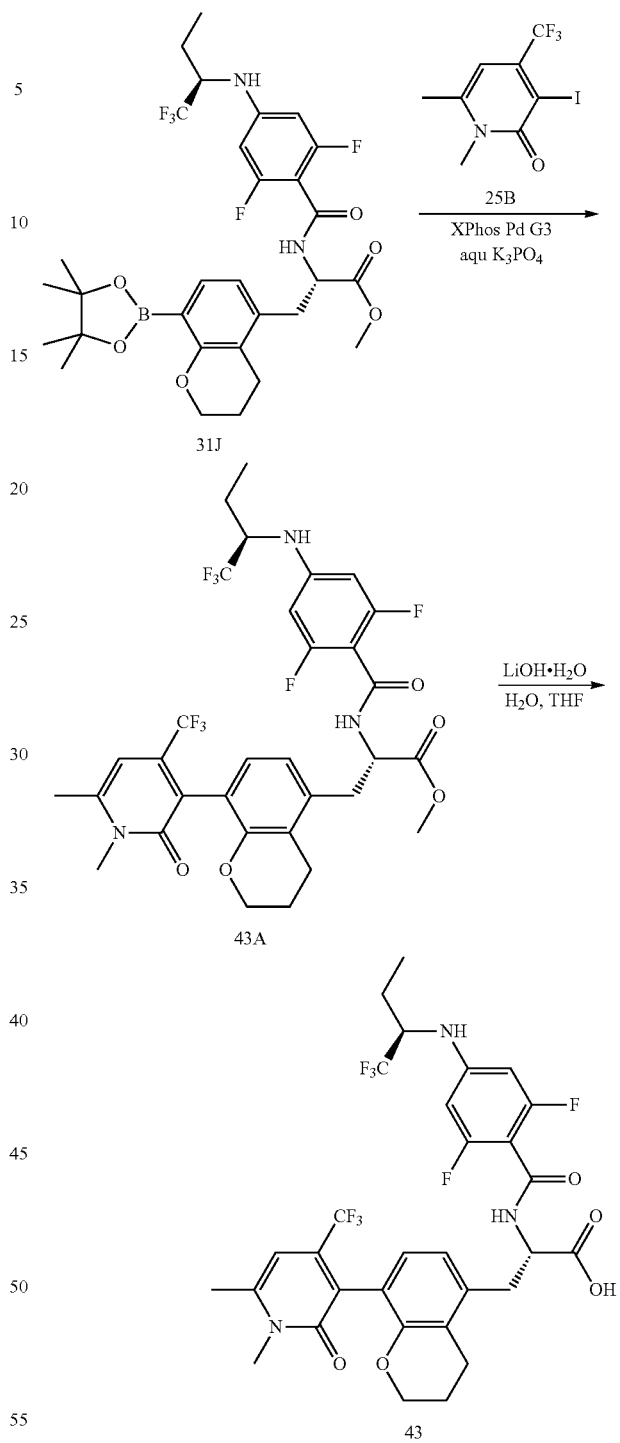

Synthesis of methyl (S)-2-(2,6-difluoro-4-(((R)-1,1,1-trifluorobutan-2-yl)amino) benzamido)-3-(8-(1,6-dimethyl-2-oxo-4-(trifluoromethyl)-1,2-dihydropyridin-3-yl)chroman-5-yl)propanoate (43A): The title compound was prepared according to the method presented for the synthesis of compound 13K of Example 13 starting with 25B and 31J.

Synthesis of (S)-2-(2,6-difluoro-4-(((R)-1,1,1-trifluorobutan-2-yl)amino)benzamido)-3-(8-(1,6-dimethyl-2-oxo-4-(trifluoromethyl)-1,2-dihydropyridin-3-yl)chroman-5-yl)propanoic acid (43): The title compound was prepared according to the method presented for the synthesis of compound 1 of Example 1 starting with 43A. MS (m/z) 676.2 [M+H]$^+$. 1H NMR (400 MHz, DMSO-d6) δ 8.70 (dd, J=7.9, 4.9 Hz, 1H), 6.84-6.72 (m, 2H), 6.70 (dd, J=7.8, 3.0 Hz, 1H), 6.50-6.40 (m, 3H), 4.53 (dtd, J=12.4, 8.3, 4.4 Hz, 1H), 4.37-4.25 (m, 1H), 3.94 (ddt, J=26.1, 10.6, 5.6 Hz, 2H), 3.46 (s, 3H), 3.07 (dd, J=14.9, 4.4 Hz, 1H), 2.89 (dd, J=14.9, 9.8 Hz, 1H), 2.72 (h, J=6.3 Hz, 2H), 2.45 (s, 3H), 1.90 (h, J=6.2 Hz, 2H), 1.77 (ddd, J=14.1, 7.3, 3.3 Hz, 1H), 1.53 (ddt, J=17.6, 14.5, 7.5 Hz, 1H), 0.93 (t, J=7.3 Hz, 3H).

Examples 44 and 45

Preparation of (S)-2-(2,6-difluoro-4-(((R)-1,1,1-trifluorobutan-2-yl)amino)benzamido)-3-(8-(1,6-dimethyl-2-oxo-4-(trifluoromethyl)-1,2-dihydropyridin-3-yl)chroman-5-yl)propanoic acid atropisomer 1 (44) and (S)-2-(2,6-difluoro-4-(((R)-1,1,1-trifluorobutan-2-yl)amino)benzamido)-3-(8-(1,6-dimethyl-2-oxo-4-(trifluoromethyl)-1,2-dihydropyridin-3-yl)chroman-5-yl)propanoic acid atropisomer 2 (45): 43 was separated into its 2 diastereomeric atropisomers by supercritical fluid chromatography using 20% MeOH co-solvent, at a flow rate of 60 mL/min, using an IC 21×250 mm column. The title compounds were identified as the atropisomers 1 (44) and 2 (45) corresponding to the first and second eluting peaks.

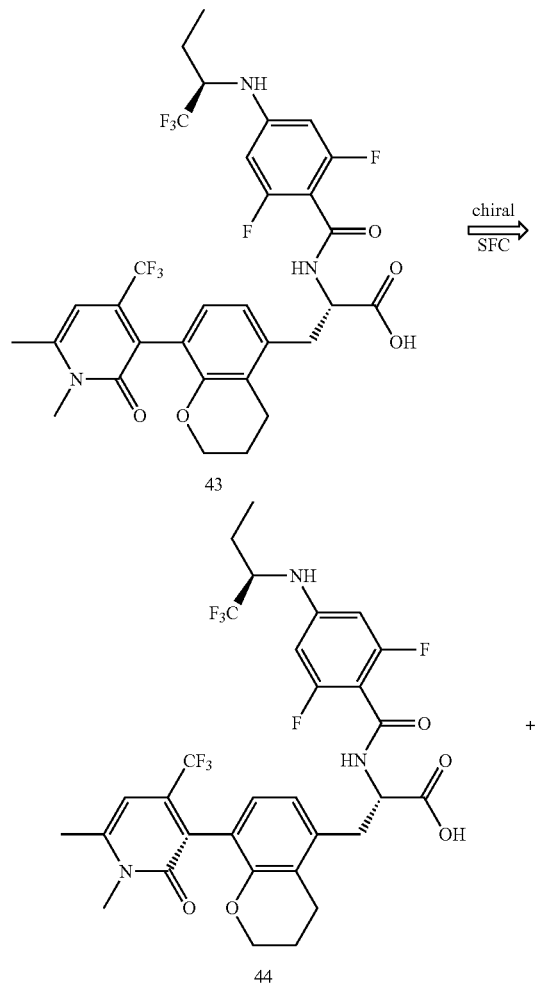

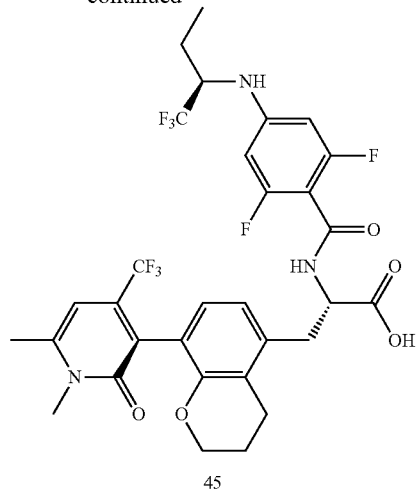

(S)-2-(2,6-difluoro-4-(((R)-1,1,1-trifluorobutan-2-yl)amino)benzamido)-3-(8-(1,6-dimethyl-2-oxo-4-(trifluoromethyl)-1,2-dihydropyridin-3-yl)chroman-5-yl)propanoic acid atropisomer 1 (44): MS (m/z) 676.3 [M+H]$^+$. 1H NMR (400 MHz, DMSO-d6) δ 8.71 (dd, J=7.8, 4.8 Hz, 1H), 6.84-6.72 (m, 2H), 6.72-6.65 (m, 1H), 6.50-6.40 (m, 3H), 4.55 (ddd, J=9.7, 7.8, 4.7 Hz, 1H), 4.31 (d, J=9.8 Hz, 1H), 3.93 (dp, J=21.2, 5.5 Hz, 2H), 3.47 (d, J=1.6 Hz, 3H), 3.07 (dd, J=14.8, 4.6 Hz, 1H), 2.89 (dd, J=14.8, 9.7 Hz, 1H), 2.73 (td, J=6.5, 2.9 Hz, 2H), 2.45 (s, 3H), 1.90 (p, J=6.2 Hz, 2H), 1.77 (ddt, J=15.0, 7.7, 3.9 Hz, 1H), 1.53 (ddq, J=14.4, 10.3, 7.3 Hz, 1H), 0.93 (t, J=7.3 Hz, 3H).

(S)-2-(2,6-difluoro-4-(((R)-1,1,1-trifluorobutan-2-yl)amino)benzamido)-3-(8-(1,6-dimethyl-2-oxo-4-(trifluoromethyl)-1,2-dihydropyridin-3-yl)chroman-5-yl)propanoic acid atropisomer 2 (45): MS (m/z) 676.3 [M+H]$^+$. 1H NMR (400 MHz, DMSO-d6) δ 8.71 (dd, J=7.9, 4.8 Hz, 1H), 6.83-6.73 (m, 2H), 6.73-6.66 (m, 1H), 6.50-6.40 (m, 3H), 4.52 (ddd, J=9.9, 7.8, 4.3 Hz, 1H), 4.31 (d, J=8.5 Hz, 1H), 3.98 (td, J=6.9, 3.3 Hz, 1H), 3.90 (ddt, J=10.5, 6.9, 4.1 Hz, 1H), 3.47 (s, 3H), 3.07 (dd, J=14.9, 4.3 Hz, 1H), 2.89 (dd, J=14.8, 9.9 Hz, 1H), 2.82-2.66 (m, 2H), 2.45 (s, 3H), 1.90 (ddt, J=11.4, 6.4, 3.5 Hz, 2H), 1.78 (ddd, J=13.8, 7.3, 3.3 Hz, 1H), 1.53 (ddq, J=14.3, 10.2, 7.2 Hz, 1H), 0.93 (t, J=7.3 Hz, 3H).

Example 46

Synthesis of methyl (S)-2-(2,6-difluoro-4-((R)-3-(trifluoromethyl)morpholino) benzamido)-3-(8-(4-methoxy-1,6-dimethyl-2-oxo-1,2-dihydropyridin-3-yl)chroman-5-yl) propanoate (46A): The title compound was prepared according to the method presented for the synthesis of compound 13K of Example 13 starting with 23B and 32B.

Synthesis of (S)-2-(2,6-difluoro-4-((R)-3-(trifluoromethyl)morpholino)benzamido)-3-(8-(4-methoxy-1,6-dimethyl-2-oxo-1,2-dihydropyridin-3-yl)chroman-5-yl)propanoic acid (46): The title compound was prepared according to the method presented for the synthesis of compound 1 of Example 1 starting with 46A. MS (m/z) 666.2 [M+H]$^+$. 1H NMR (400 MHz, DMSO-d6) δ 8.88 (t, J=7.6 Hz, 1H), 6.83-6.66 (m, 4H), 6.23 (s, 1H), 4.92 (d, J=9.9 Hz, 1H), 4.55-4.44 (m, 1H), 4.16 (d, J=12.7 Hz, 1H), 4.01-3.89 (m, 3H), 3.75 (d, J=12.6 Hz, 1H), 3.66 (d, J=3.4 Hz, 3H), 3.63-3.51 (m, 1H), 3.48-3.34 (m, 4H), 3.32-3.17

(m, 1H), 3.06 (dd, J=14.9, 4.6 Hz, 1H), 2.88 (dd, J=14.7, 9.6 Hz, 1H), 2.80-2.64 (m, 2H), 2.39 (s, 3H), 1.90 (s, 2H).

Example 47

Synthesis of methyl (S)-2-(2,6-difluoro-4-(((R)-1,1,1-trifluorobutan-2-yl)amino) benzamido)-3-(8-(4-methoxy-1,6-dimethyl-2-oxo-1,2-dihydropyridin-3-yl)chroman-5-yl)propanoate (47A): The title compound was prepared according to the method presented for the synthesis of compound 13K of Example 13 starting with 23B and 31J.

Synthesis of (S)-2-(2,6-difluoro-4-(((R)-1,1,1-trifluorobutan-2-yl)amino)benzamido)-3-(8-(4-methoxy-1,6-dimethyl-2-oxo-1,2-dihydropyridin-3-yl)chroman-5-yl)propanoic acid (47): The title compound was prepared according to the method presented for the synthesis of compound 1 of Example 1 starting with 47A. MS (m/z) 638.2 [M+H]+. 1H NMR (400 MHz, DMSO-d6) δ 8.72 (t, J=7.8 Hz, 1H), 6.81-6.65 (m, 3H), 6.47 (d, J=11.5 Hz, 2H), 6.23 (s, 1H), 4.48 (td, J=8.6, 4.5 Hz, 1H), 4.35-4.25 (m, 1H), 3.99-3.89 (m, 2H), 3.69-3.63 (m, 3H), 3.41-3.32 (m, 3H), 3.04 (dd, J=14.7, 4.6 Hz, 1H), 2.86 (dd, J=14.7, 9.5 Hz, 1H), 2.79-2.64 (m, 2H), 2.39 (s, 3H), 1.95-1.84 (m, 2H), 1.77 (ddq, J=11.5, 7.4, 4.3, 3.7 Hz, 1H), 1.54 (ddt, J=17.5, 14.3, 7.2 Hz, 1H), 0.93 (t, J=7.3 Hz, 3H).

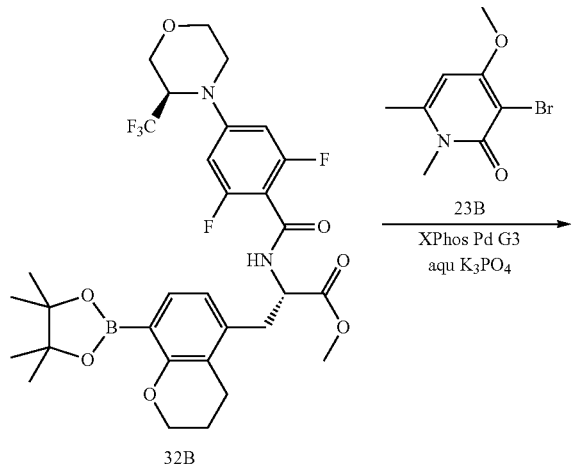

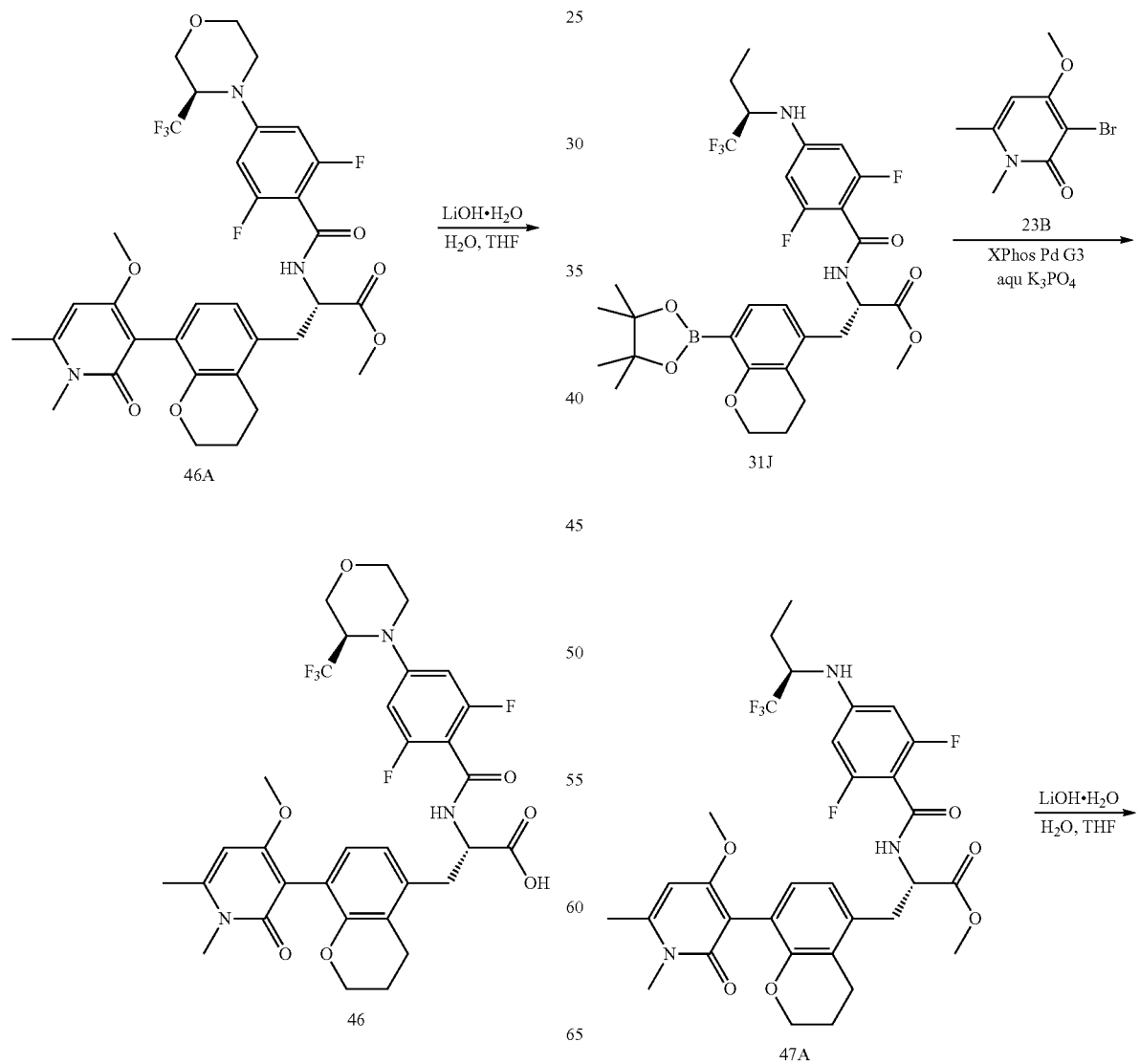

Example 48

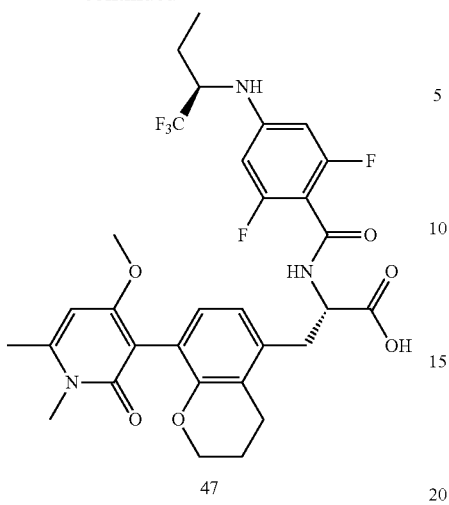

47

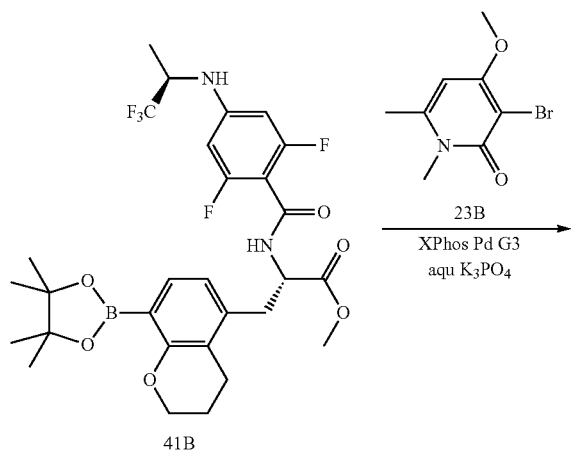

Example 49

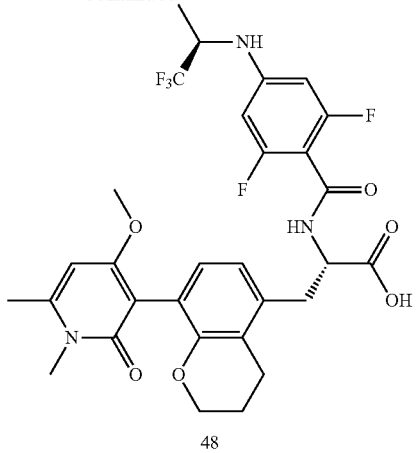

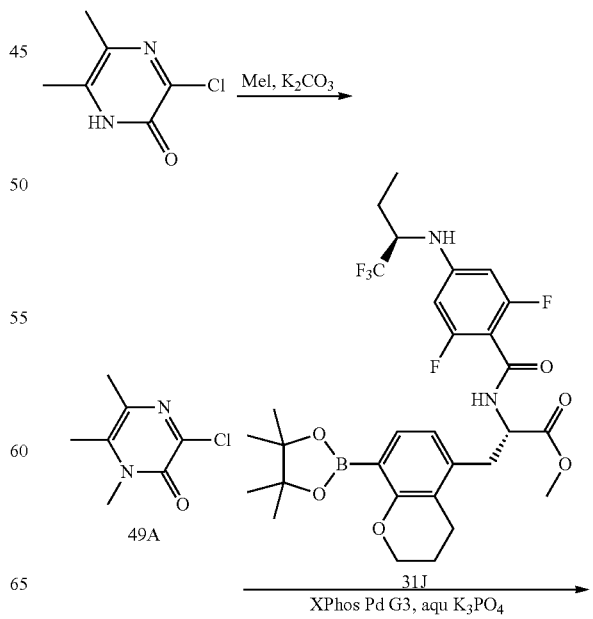

-continued

48

Synthesis of methyl (S)-2-(2,6-difluoro-4-(((R)-1,1,1-trifluoropropan-2-yl)amino) benzamido)-3-(8-(4-methoxy-1,6-dimethyl-2-oxo-1,2-dihydropyridin-3-yl)chroman-5-yl) propanoate (48A): The title compound was prepared according to the method presented for the synthesis of compound 13K of Example 13 starting with 23B and 41B.

Synthesis of (S)-2-(2,6-difluoro-4-(((R)-1,1,1-trifluoropropan-2-yl)amino)benzamido)-3-(8-(4-methoxy-1,6-dimethyl-2-oxo-1,2-dihydropyridin-3-yl)chroman-5-yl)propanoic acid (48): The title compound was prepared according to the method presented for the synthesis of compound 1 of Example 1 starting with 48A. MS (m/z) 624.2 [M+H]+. 1H NMR (400 MHz, DMSO-d6) δ 8.71 (t, J=7.7 Hz, 1H), 6.84 (d, J=9.2 Hz, 1H), 6.78-6.63 (m, 2H), 6.44 (d, J=11.3 Hz, 2H), 6.23 (s, 1H), 4.49 (dt, J=13.6, 7.9 Hz, 2H), 3.95 (dd, J=6.3, 3.7 Hz, 2H), 3.66 (d, J=3.2 Hz, 3H), 3.38 (d, J=1.3 Hz, 3H), 3.04 (dd, J=14.7, 4.6 Hz, 1H), 2.87 (dd, J=14.7, 9.5 Hz, 1H), 2.72 (d, J=5.8 Hz, 2H), 2.39 (s, 3H), 1.90 (t, J=5.7 Hz, 3H), 1.28 (d, J=6.7 Hz, 3H).

Example 49

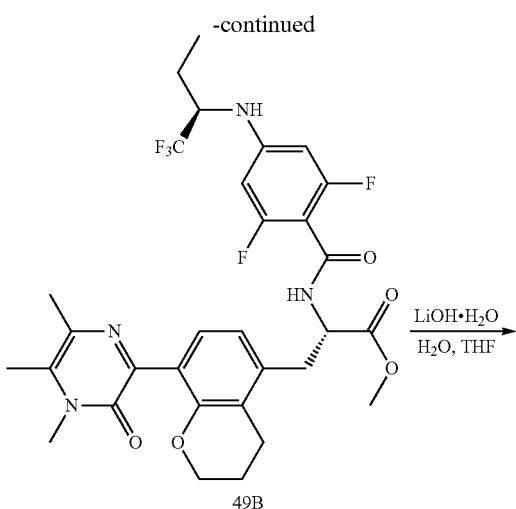

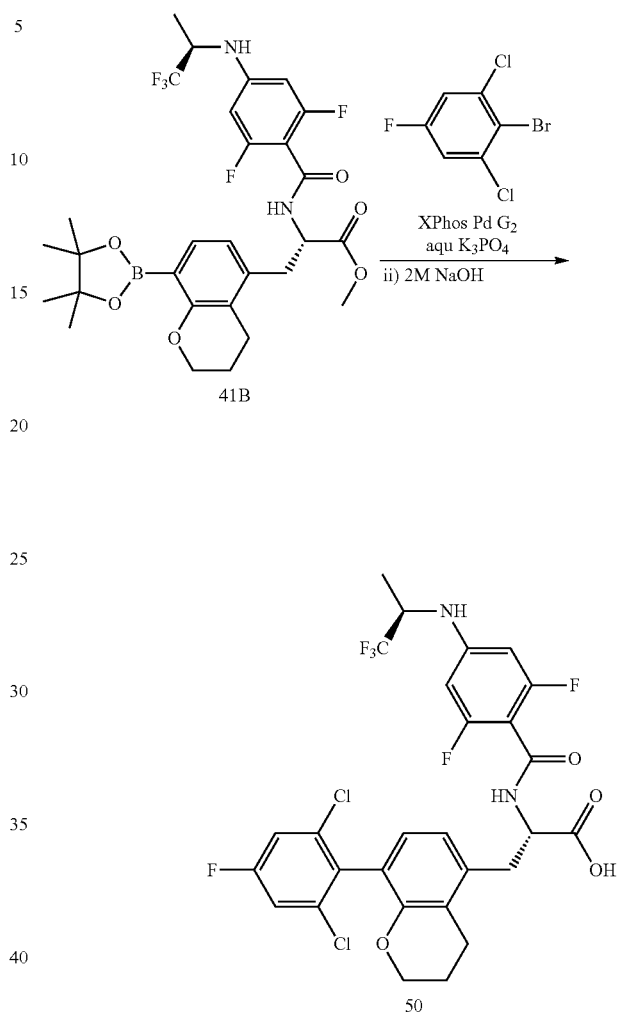

Example 50

Synthesis of 3-chloro-1,5,6-trimethylpyrazin-2(1H)-one (49A): The title compound was prepared according to the method presented for the synthesis of compound 22A of Example 22 starting with 3-chloro-5,6-dimethylpyrazin-2 (1H)-one.

Synthesis of methyl (S)-2-(2,6-difluoro-4-(((R)-1,1,1-trifluorobutan-2-yl)amino) benzamido)-3-(8-(4,5,6-trimethyl-3-oxo-3,4-dihydropyrazin-2-yl)chroman-5-yl)propanoate (49B): The title compound was prepared according to the method presented for the synthesis of compound 13K of Example 13 starting with 49A and 31J.

Synthesis of (S)-2-(2,6-difluoro-4-(((R)-1,1,1-trifluorobutan-2-yl)amino)benzamido)-3-(8-(4,5,6-trimethyl-3-oxo-3,4-dihydropyrazin-2-yl)chroman-5-yl)propanoic acid (49): The title compound was prepared according to the method presented for the synthesis of compound 1 of Example 1 starting with 49B. MS (m/z) 618.2 [M+H]$^+$. 1H NMR (400 MHz, DMSO-d6) δ 8.91 (d, J=4.4 Hz, 1H), 8.80 (d, J=7.9 Hz, 2H), 7.84-7.69 (m, 2H), 7.64 (d, J=7.4 Hz, 1H), 6.78 (d, J=9.4 Hz, 1H), 6.45 (d, J=11.6 Hz, 2H), 4.68 (dt, J=8.6, 4.1 Hz, 1H), 4.36-4.29 (m, 1H), 3.73 (dd, J=14.4, 4.6 Hz, 1H), 3.53 (s, 3H), 3.45 (dd, J=14.4, 9.7 Hz, 1H), 2.42 (s, 3H), 2.34 (s, 3H), 1.77 (ddd, J=13.8, 7.2, 3.3 Hz, 1H), 1.57-1.47 (m, 1H), 0.93 (t, J=7.3 Hz, 3H).

Synthesis of (S)-3-(8-(2,6-dichloro-4-fluorophenyl)chroman-5-yl)-2-(2,6-difluoro-4-(((R)-1,1,1-trifluoropropan-2-yl)amino)benzamido)propanoic acid (50): To a microwave vial was added 41B (150 mg, 0.29 mmol), 2-bromo-1,3-dichloro-5-fluorobenzene (209 mg, 0.21 mmol), XPhos Pd G2 (22 mg, 0.029 mmol), and aq. K$_3$PO$_4$ (01 mL, 1M) in DME (1.3 mL). The reaction mixture was heated in a microwave at 130° C. for 30 min. The mixture was allowed to cool to RT and 2 M aq. NaOH (1 mL) was added. After 30 min, the pH was adjusted to ~3 with 1M HCl. EtOAc was added to the reaction mixture. The aqueous layer was separated and extracted with EtOAc (2×). The combined organics were washed dried over anhydrous Na$_2$SO$_4$, and concentrated under reduced pressure. The material was purified via reverse phase HPLC to afford the title compound. MS (m/z) 635.1 [M+H]$^+$. 1H NMR (400 MHz, DMSO-d6) δ 8.71 (d, J=7.9 Hz, 1H), 7.63-7.48 (m, 2H), 6.95-6.74 (m, 3H), 6.41 (d, J=11.3 Hz, 2H), 4.66-4.37 (m, 2H), 3.99 (t, J=5.3 Hz, 2H), 3.10 (dd, J=14.8, 4.4 Hz, 1H), 2.90 (dd, J=14.7, 10.1 Hz, 1H), 2.76 (q, J=6.3 Hz, 2H), 2.00-1.83 (m, 2H), 1.26 (d, J=6.7 Hz, 3H).

Example 51
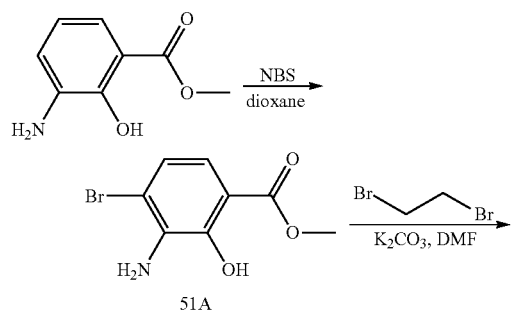
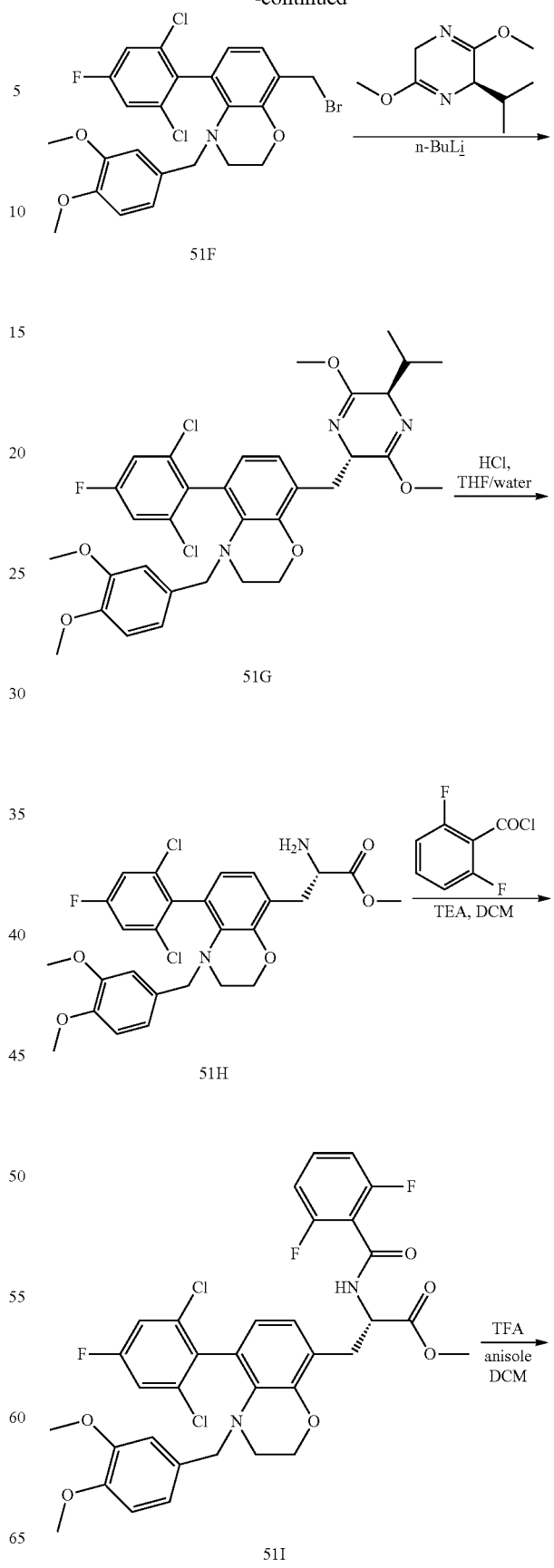

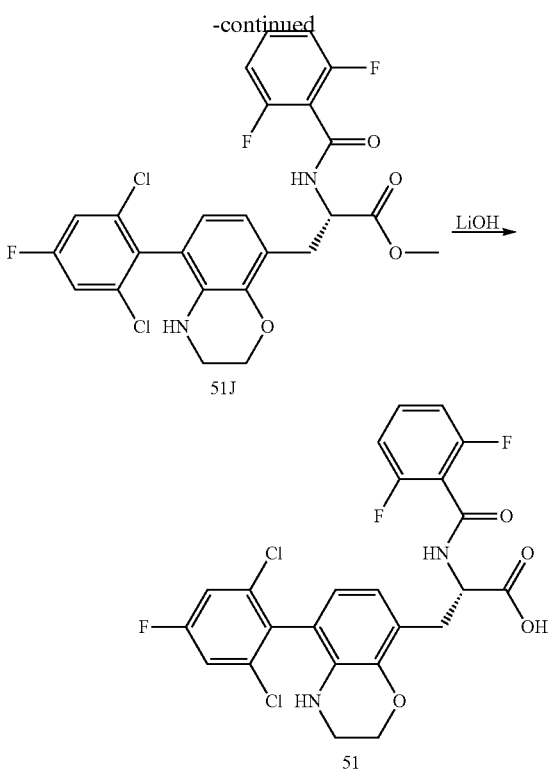

Synthesis of methyl 3-amino-4-bromo-2-hydroxybenzoate (51A): To a stirred solution of methyl 3-amino-2-hydroxybenzoate (3 g, 18 mmol) in dioxane (22.4 mL) at 75° C. was added a solution of NBS (3.5 g, 19.7 mmol) in dioxane (22.4 mL) dropwise. The reaction mixture was stirred for 10 min. EtOAc and sat. aq. NaHCO$_3$ was added to the reaction mixture. The aqueous layer was separated and extracted with EtOAc (2×). The combined organics were washed with brine, dried over anhydrous Na$_2$SO$_4$, and concentrated under reduced pressure. The material was purified on silica gel eluting with EtOAc in Hex (0-10%) to give the title compound.

Synthesis of methyl 5-bromo-3,4-dihydro-2H-benzo[b][1,4]oxazine-8-carboxylate (51B): To a stirred solution of 51A (980 mg, 4.0 mmol) and K$_2$CO$_3$ (2.75 g, 138 mmol) in DMF (10 mL) was added 1,2-dibromoethane (0.52 mL, 6.0 mmol) at RT. The reaction mixture was heated to 125° C. and stirred for 16 hrs. The reaction mixture was cooled to RT and EtOAc and water was added. The aqueous layer was separated and extracted with EtOAc (2×). The combined organics were washed with brine, dried over anhydrous Na$_2$SO$_4$, and concentrated under reduced pressure. The material was purified on silica gel eluting with EtOAc in Hex (0-50%) to give the title compound.

Synthesis of methyl 5-(2,6-dichloro-4-fluorophenyl)-3,4-dihydro-2H-benzo[b][1,4]oxazine-8-carboxylate (51C): The title compound was prepared according to the method presented for the synthesis of compound 4B of Example 4 starting with (2,6-dichloro-4-fluorophenyl)boronic acid and 51B.

Synthesis of methyl 5-(2,6-dichloro-4-fluorophenyl)-4-(3,4-dimethoxybenzyl)-3,4-dihydro-2H-benzo[b][1,4]oxazine-8-carboxylate (51D): To a stirred solution of 51C (207 mg, 0.58 mmol), KI (289 mg, 1.74 mmol) and K$_2$CO$_3$ (402 mg, 2.9 mmol) in ACN (2.9 mL) was added 4-(chloromethyl)-1,2-dimethoxybenzene (0.30 mL, 1.74 mmol) at RT. The reaction mixture was heated to 100° C. and stirred for 45 min. The reaction mixture was cooled to RT and EtOAc and water was added. The aqueous layer was separated and extracted with EtOAc (2×). The combined organics were washed with brine, dried over anhydrous Na$_2$SO$_4$, and concentrated under reduced pressure. The material was purified on silica gel eluting with EtOAc in Hex (0-30%) to give the title compound.

Synthesis of methyl (5-(2,6-dichloro-4-fluorophenyl)-4-(3,4-dimethoxybenzyl)-3,4-dihydro-2H-benzo[b][1,4]oxazin-8-yl)methanol (51E): The title compound was prepared according to the method presented for the synthesis of compound 1B of Example 1 starting with 51D.

Synthesis of 8-(bromomethyl)-5-(2,6-dichloro-4-fluorophenyl)-4-(3,4-dimethoxybenzyl)-3,4-dihydro-2H-benzo[b][1,4]oxazine (51F): The title compound was prepared according to the method presented for the synthesis of compound 13E of Example 13 starting with 51E.

Synthesis of 5-(2,6-dichloro-4-fluorophenyl)-4-(3,4-dimethoxybenzyl)-8-(((2S,5R)-5-isopropyl-3,6-dimethoxy-2,5-dihydropyrazin-2-yl) methyl)-3,4-dihydro-2H-benzo[b][1,4]oxazine (51G): The title compound was prepared according to the method presented for the synthesis of compound 4A of Example 4 starting with 51F.

Synthesis of methyl (S)-2-amino-3-(5-(2,6-dichloro-4-fluorophenyl)-4-(3,4-dimethoxybenzyl)-3,4-dihydro-2H-benzo[b][1,4]oxazin-8-yl)propanoate (51H): The title compound was prepared according to the method presented for the synthesis of compound 4C of Example 4 starting with 51G.

Synthesis of methyl (S)-3-(5-(2,6-dichloro-4-fluorophenyl)-4-(3,4-dimethoxybenzyl)-3,4-dihydro-2H-benzo[b][1,4]oxazin-8-yl)-2-(2,6-difluorobenzamido)propanoate (51I): The title compound was prepared according to the method presented for the synthesis of compound 1F of Example 1 starting with 2,6-difluorobenzoyl chloride and 51H.

Synthesis of methyl (S)-3-(5-(2,6-dichloro-4-fluorophenyl)-3,4-dihydro-2H-benzo[b][1,4]oxazin-8-yl)-2-(2,6-difluorobenzamido)propanoate (51J): To a stirred solution of 51I (45 mg, 0.065 mmol) in DCM (1.3 mL) and TFA (1.3 mL) was added anisole (0.71 mL, 6.5 mmol) at RT. The reaction mixture was heated to 40° C. and stirred for 4 hrs. DCM and water was added. The aqueous layer was separated and extracted with DCM (2×). The combined organics were washed with brine, dried over anhydrous Na$_2$SO$_4$, and concentrated under reduced pressure to give the title compound.

Synthesis of (S)-3-(5-(2,6-dichloro-4-fluorophenyl)-3,4-dihydro-2H-benzo[b][1,4]oxazin-8-yl)-2-(2,6-difluorobenzamido)propanoic acid (51): The title compound was prepared according to the method presented for the synthesis of compound 1 of Example 1 starting with 51J. MS (m/z) 525.1 [M+H]$^+$. 1H NMR (400 MHz, DMSO-d6) δ 9.02 (d, J=7.9 Hz, 1H), 7.59 (d, J=8.7 Hz, 2H), 7.54-7.43 (m, 1H), 7.12 (dd, J=8.4, 7.4 Hz, 2H), 6.51 (d, J=7.8 Hz, 1H), 6.34 (d, J=7.8 Hz, 1H), 4.67 (ddd, J=9.9, 7.9, 5.1 Hz, 1H), 4.13 (s, 1H), 3.29-3.19 (m, 2H), 3.13 (dd, J=14.0, 5.1 Hz, 1H), 2.80 (dd, J=14.0, 9.9 Hz, 1H).

Example 52

Synthesis of methyl (S)-2-(2,6-difluoro-4-(((R)-1,1,1-trifluorobutan-2-yl)amino) benzamido)-3-(8-(1,4,6-trimethyl-2-oxo-1,2-dihydropyridin-3-yl)chroman-5-yl)propanoate (52A): The title compound was prepared according to the method presented for the synthesis of compound 13K of Example 13 starting with 22A and 31J.

Synthesis of (S)-2-(2,6-difluoro-4-(((R)-1,1,1-trifluorobutan-2-yl)amino)benzamido)-3-(8-(1,4,6-trimethyl-2-oxo-1,2-dihydropyridin-3-yl)chroman-5-yl)propanoic acid (52): The title compound was prepared according to the method presented for the synthesis of compound 1 of Example 1 starting with 52A. MS (m/z) 622.2 [M+H]⁺. 1H NMR (400 MHz, DMSO-d6) δ 8.74-8.66 (m, 1H), 6.77 (q, J=8.2 Hz, 2H), 6.69 (t, J=7.8 Hz, 1H), 6.52-6.42 (m, 2H), 6.04 (s, 1H), 4.60-4.46 (m, 1H), 4.40-4.25 (m, 1H), 4.04-3.90 (m, 2H), 3.38 (s, 3H), 3.14-3.00 (m, 1H), 2.96-2.82 (m, 1H), 2.82-2.65 (m, 2H), 2.32 (s, 3H), 2.00-1.83 (m, 2H), 1.83-1.72 (m, 4H), 1.60-1.45 (m, 1H), 0.93 (t, J=7.4 Hz, 3H).
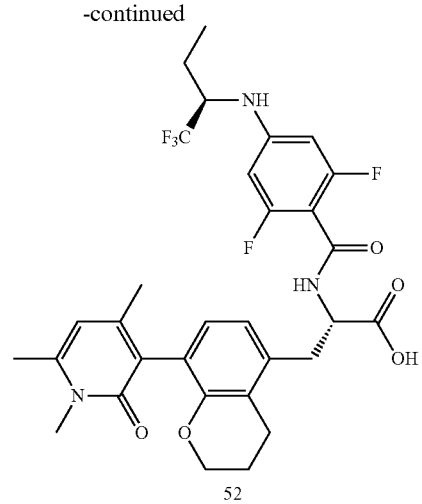
52
Example 53
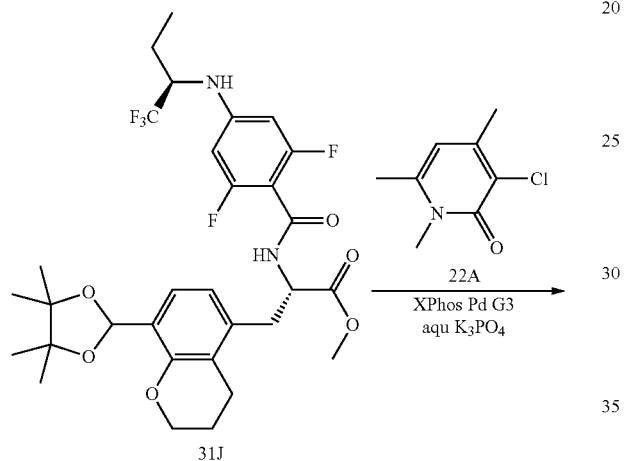
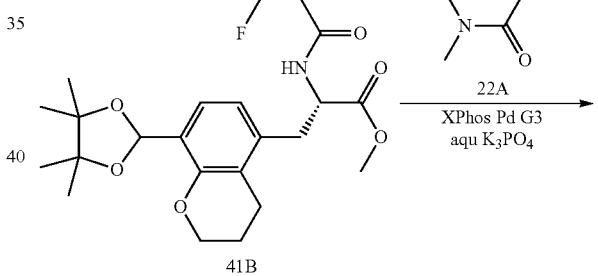
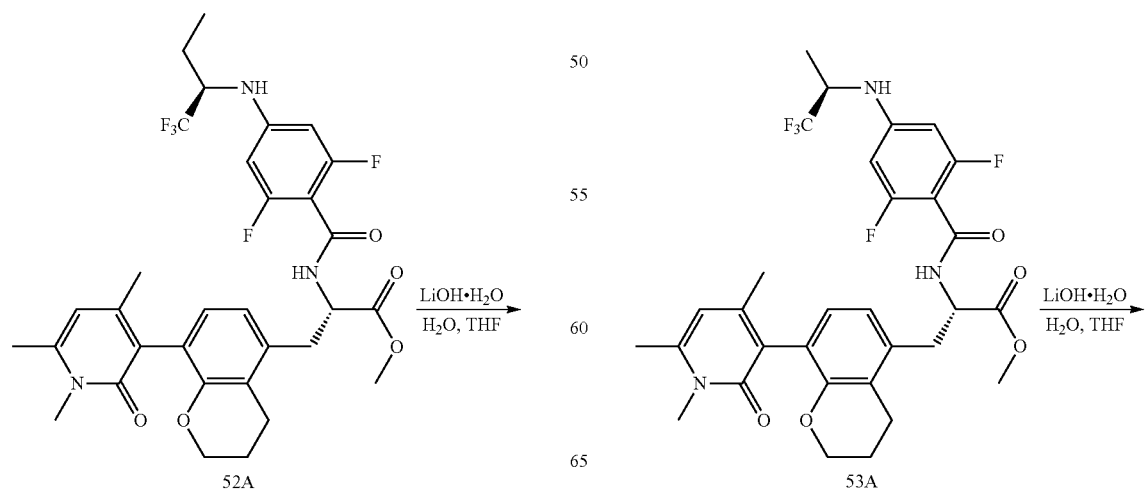

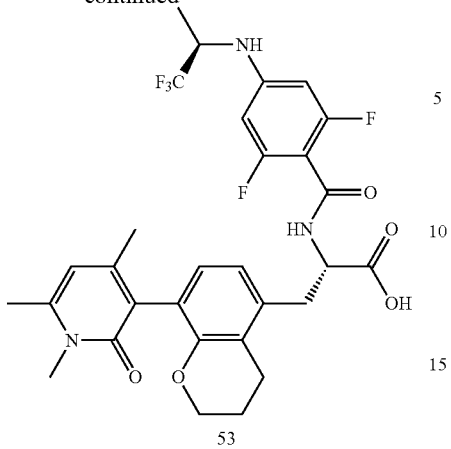

53

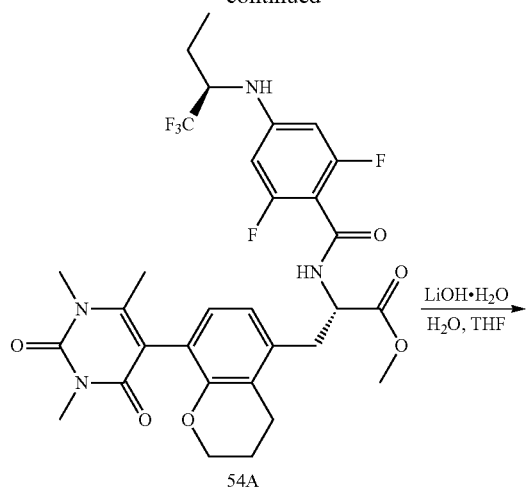

54A

Synthesis of methyl (S)-2-(2,6-difluoro-4-(((R)-1,1,1-trifluoropropan-2-yl)amino) benzamido)-3-(8-(1,4,6-trimethyl-2-oxo-1,2-dihydropyridin-3-yl)chroman-5-yl)propanoate (53A): The title compound was prepared according to the method presented for the synthesis of compound 13K of Example 13 starting with 22A and 53A.

Synthesis of (S)-2-(2,6-difluoro-4-(((R)-1,1,1-trifluoropropan-2-yl)amino)benzamido)-3-(8-(1,4,6-trimethyl-2-oxo-1,2-dihydropyridin-3-yl)chroman-5-yl)propanoic acid (53): The title compound was prepared according to the method presented for the synthesis of compound 1 of Example 1 starting with 53A. MS (m/z) 608.2 [M+H]⁺. 1H NMR (400 MHz, DMSO-d6) δ 8.69 (dd, J=7.9, 3.7 Hz, 1H), 6.86-6.75 (m, 2H), 6.69 (t, J=7.9 Hz, 1H), 6.43 (dd, J=11.2, 3.7 Hz, 2H), 6.10-5.96 (m, 1H), 4.53 (td, J=14.2, 8.4 Hz, 2H), 3.97 (m, 1H), 3.38 (d, J=1.2 Hz, 3H), 3.07 (ddd, J=15.1, 10.6, 4.7 Hz, 1H), 2.89 (dt, J=14.6, 10.4 Hz, 1H), 2.79-2.67 (m, 2H), 2.38-2.29 (m, 3H), 1.97-1.85 (m, 4H), 1.78 (d, J=4.2 Hz, 3H), 1.28 (d, J=6.6 Hz, 3H).

Example 54

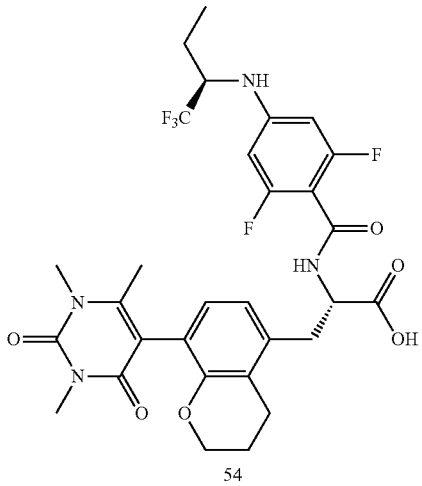

54

Synthesis of methyl (S)-2-(2,6-difluoro-4-(((R)-1,1,1-trifluorobutan-2-yl)amino) benzamido)-3-(8-(1,3,6-trimethyl-2,4-dioxo-1,2,3,4-tetrahydropyrimidin-5-yl)chroman-5-yl)propanoate (54A): The title compound was prepared according to the method presented for the synthesis of compound 13K of Example 13 starting with 5-bromo-1,3,6-trimethylpyrimidine-2,4(1H,3H)-dione and 31J.

Synthesis of (S)-2-(2,6-difluoro-4-(((R)-1,1,1-trifluorobutan-2-yl)amino)benzamido)-3-(8-(1,3,6-trimethyl-2,4-dioxo-1,2,3,4-tetrahydropyrimidin-5-yl)chroman-5-yl)propanoic acid (54): The title compound was prepared according to the method presented for the synthesis of compound 1 of Example 1 starting with 54A. MS (m/z) 639.2 1H NMR (400 MHz, DMSO-d6) δ 12.67 (s, 1H), 8.71 (dd, J=7.9, 2.5 Hz, 1H), 6.78 (p, J=8.0 Hz, 3H), 6.45 (dd, J=11.3, 3.7 Hz, 2H), 4.60-4.48 (m, 1H), 4.36-4.26 (m, 1H), 4.01 (t, J=5.2 Hz, 2H), 3.39 (s, 3H), 3.19 (d, J=1.3 Hz, 3H), 3.16-3.02 (m, 1H), 2.87 (ddd, J=21.4, 17.3, 8.4 Hz, 1H), 2.80-2.65 (m, 2H), 2.00 (d, J=5.7 Hz, 3H), 1.97-1.86 (m, 2H), 1.77 (dq, J=10.5, 3.6, 3.2 Hz, 1H), 1.53 (ddt, J=17.6, 14.2, 7.3 Hz, 1H), 0.93 (t, J=7.3 Hz, 3H).

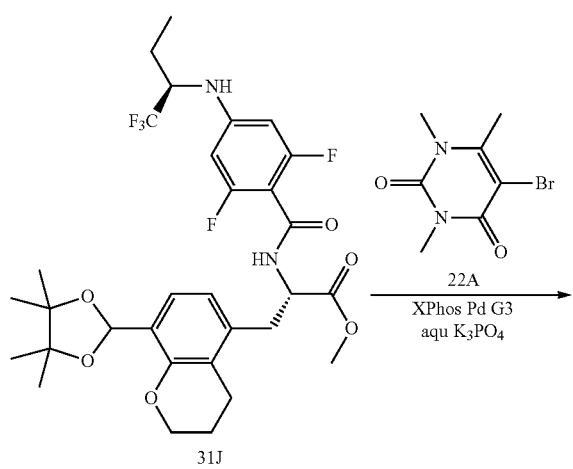

31J

Examples 55 and 56

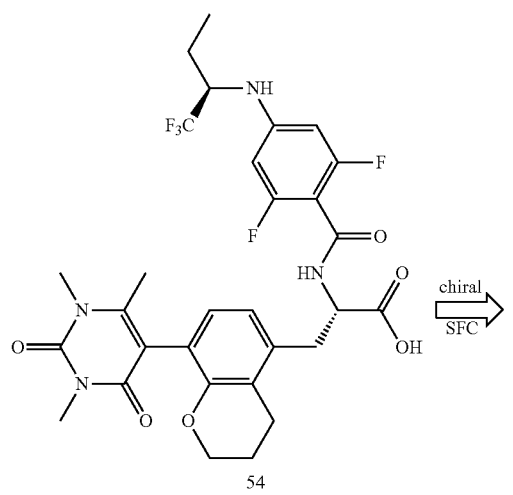

Preparation of (S)-2-(2,6-difluoro-4-(((R)-1,1,1-trifluorobutan-2-yl)amino)benzamido)-3-(8-(1,3,6-trimethyl-2,4-dioxo-1,2,3,4-tetrahydropyrimidin-5-yl)chroman-5-yl)propanoic acid atropisomer 1 (55) and (S)-2-(2,6-difluoro-4-(((R)-1,1,1-trifluorobutan-2-yl)amino)benzamido)-3-(8-(1,3,6-trimethyl-2,4-dioxo-1,2,3,4-tetrahydropyrimidin-5-yl)chroman-5-yl)propanoic acid atropisomer 2 (56): 54 was separated into its 2 diastereomeric atropisomers by supercritical fluid chromatography using 35% MeOH co-solvent, at a flow rate of 60 mL/min, using an IC 21×250 mm column. The title compounds were identified as the atropisomer 1 and 2 corresponding to the first and second eluting peaks.

(S)-2-(2,6-difluoro-4-(((R)-1,1,1-trifluorobutan-2-yl)amino)benzamido)-3-(8-(1,3,6-trimethyl-2,4-dioxo-1,2,3,4-tetrahydropyrimidin-5-yl)chroman-5-yl)propanoic acid atropisomer 1 (55): MS (m/z) 639.2 [M+H]$^+$. 1H NMR (400 MHz, DMSO-d6) δ 12.77 (s, 1H), 8.71 (d, J=8.0 Hz, 1H), 6.83-6.70 (m, 3H), 6.50-6.39 (m, 2H), 4.55 (ddd, J=9.9, 7.9, 4.4 Hz, 1H), 4.31 (d, J=9.6 Hz, 1H), 4.01 (t, J=5.2 Hz, 2H), 3.39 (s, 3H), 3.19 (s, 3H), 3.10 (dd, J=14.6, 4.4 Hz, 1H), 2.85 (dd, J=14.6, 10.2 Hz, 1H), 2.74 (d, J=7.8 Hz, 2H), 2.00 (d, J=5.7 Hz, 3H), 1.92 (d, J=5.3 Hz, 2H), 1.77 (dq, J=10.6, 4.4, 3.2 Hz, 1H), 1.53 (ddd, J=13.8, 10.4, 7.1 Hz, 1H), 0.93 (t, J=7.3 Hz, 3H).

(S)-2-(2,6-difluoro-4-(((R)-1,1,1-trifluorobutan-2-yl)amino)benzamido)-3-(8-(1,3,6-trimethyl-2,4-dioxo-1,2,3,4-tetrahydropyrimidin-5-yl)chroman-5-yl)propanoic acid atropisomer 2 (56): MS (m/z) 639.2 [M+H]$^+$. 1H NMR (400 MHz, DMSO-d6) δ 12.73 (s, 1H), 8.71 (d, J=7.9 Hz, 1H), 6.78 (p, J=7.8 Hz, 3H), 6.45 (dd, J=11.1, 3.6 Hz, 2H), 4.58-4.48 (m, 1H), 4.31 (d, J=8.2 Hz, 1H), 4.01 (q, J=5.5, 4.1 Hz, 2H), 3.39 (s, 3H), 3.19 (s, 3H), 3.06 (dd, J=14.6, 4.6 Hz, 1H), 2.90 (dd, J=14.7, 9.8 Hz, 1H), 2.84-2.64 (m, 2H), 2.00 (d, J=5.7 Hz, 3H), 1.91 (d, J=5.8 Hz, 2H), 1.84-1.71 (m, 1H), 1.53 (ddd, J=13.7, 10.3, 6.9 Hz, 1H), 0.93 (t, J=7.3 Hz, 3H).

Example 57

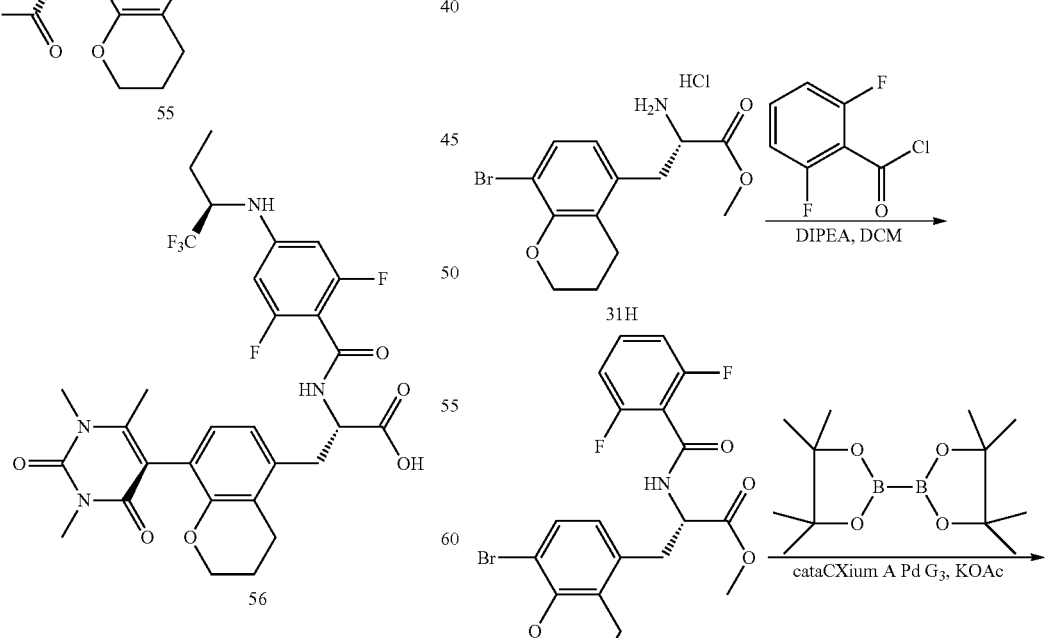

Hz, 1H), 7.83 (ddd, J=8.1, 2.4, 1.4 Hz, 1H), 7.61 (ddd, J=8.5, 7.1, 1.5 Hz, 1H), 7.57-7.40 (m, 2H), 7.28 (ddd, J=8.1, 7.1, 1.2 Hz, 1H), 7.12 (ddd, J=8.4, 7.5, 3.7 Hz, 2H), 6.93-6.70 (m, 2H), 4.71-4.54 (m, 1H), 3.96 (t, J=5.2 Hz, 2H), 3.62 (d, J=1.6 Hz, 3H), 3.14 (ddd, J=19.8, 14.7, 4.5 Hz, 1H), 2.91 (ddd, J=24.4, 14.6, 10.0 Hz, 1H), 2.77 (q, J=7.7, 6.8 Hz, 2H), 2.15 (d, J=6.4 Hz, 3H), 1.98-1.79 (m, 2H).

Examples 58 and 59

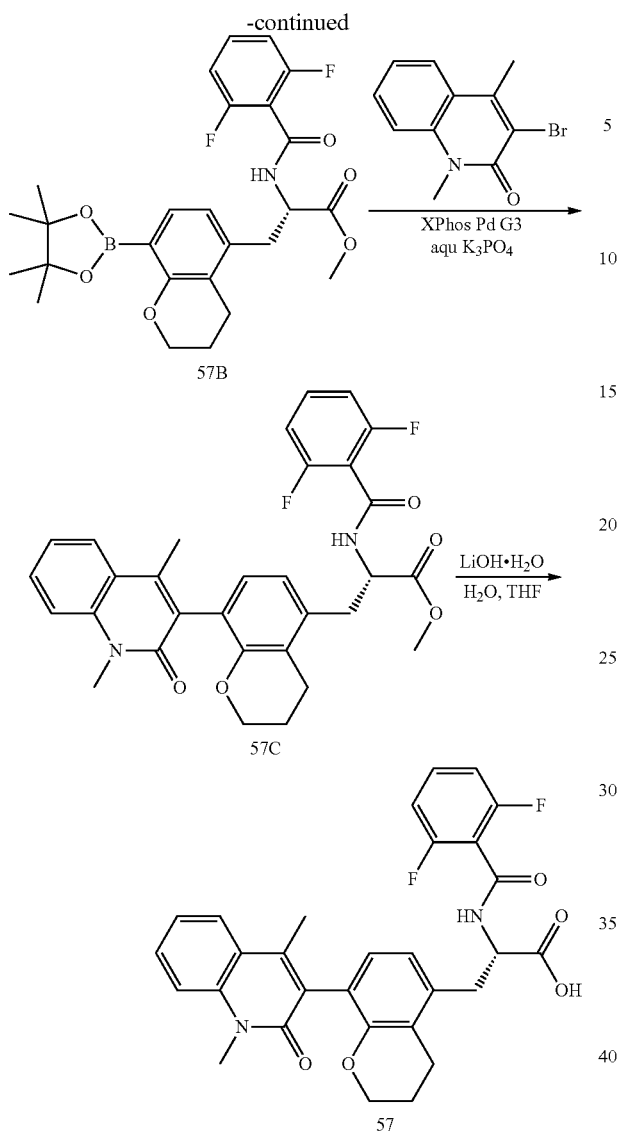

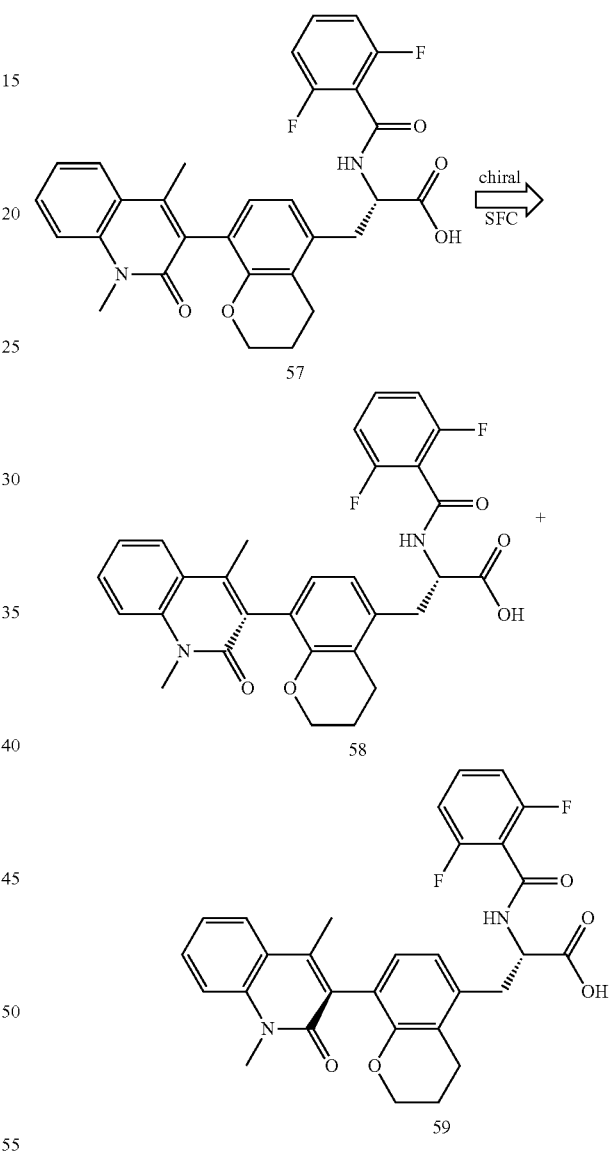

Synthesis of methyl (S)-3-(8-bromochroman-5-yl)-2-(2,6-difluorobenzamido) propanoate (57A): The title compound was prepared according to the method presented for the synthesis of compound 1F of Example 1 starting with 2,6-difluorobenzoyl chloride and 31H.

Synthesis of methyl (S)-2-(2,6-difluorobenzamido)-3-(8-(4,4,5,5-tetramethyl-1,3,2-dioxaborolan-2-yl)chroman-5-yl) propanoate (57B): The title compound was prepared according to the method presented for the synthesis of compound 1G of Example 1 starting with 57A.

Synthesis of methyl (S)-2-(2,6-difluorobenzamido)-3-(8-(1,4-dimethyl-2-oxo-1,2-dihydroquinolin-3-yl)chroman-5-yl)propanoate (57C): The title compound was prepared according to the method presented for the synthesis of compound 13K of Example 13 starting with 3-bromo-1,4-dimethylquinolin-2(1H)-one and 57C.

Synthesis of (S)-2-(2,6-difluorobenzamido)-3-(8-(1,4-dimethyl-2-oxo-1,2-dihydroquinolin-3-yl)chroman-5-yl)propanoic acid (57): The title compound was prepared according to the method presented for the synthesis of compound 1 of Example 1 starting with 57C. MS (m/z) 533.2. 1H NMR (400 MHz, DMSO-d6) δ 12.84 (s, 1H), 9.18 (dd, J=8.0, 2.8

Preparation of (S)-2-(2,6-difluorobenzamido)-3-(8-(1,4-dimethyl-2-oxo-1,2-dihydroquinolin-3-yl)chroman-5-yl) propanoic acid atropisomer 1 (58) and (S)-2-(2,6-difluorobenzamido)-3-(8-(1,4-dimethyl-2-oxo-1,2-dihydroquinolin-3-yl)chroman-5-yl)propanoic acid atropisomer 2 (59): 57 was separated into its 2 diastereomeric atropisomers by supercritical fluid chromatography using 35% MeOH co-solvent, at a flow rate of 60 mL/min, using an IC 21×250 mm column. The title compounds were identified as the atropisomer 1 and 2 corresponding to the first and second eluting peaks.

(S)-2-(2,6-difluorobenzamido)-3-(8-(1,4-dimethyl-2-oxo-1,2-dihydroquinolin-3-yl)chroman-5-yl)propanoic acid atropisomer 1 (58): MS (m/z) 533.2 [M+H]⁺. 1H NMR (400 MHz, DMSO-d6) δ 12.85 (s, 1H), 9.18 (dd, J=8.0, 2.8 Hz, 1H), 7.83 (ddd, J=8.1, 2.5, 1.5 Hz, 1H), 7.61 (ddd, J=8.5, 7.0, 1.5 Hz, 1H), 7.56-7.41 (m, 2H), 7.28 (ddd, J=8.2, 7.1, 1.1 Hz, 1H), 7.12 (ddd, J=8.5, 7.5, 3.8 Hz, 2H), 6.88-6.72 (m, 2H), 4.63 (td, J=12.6, 7.4 Hz, 1H), 4.03-3.87 (m, 2H), 3.62 (d, J=1.6 Hz, 3H), 3.13 (ddd, J=19.7, 14.6, 4.5 Hz, 1H), 2.91 (ddd, J=24.3, 14.7, 10.1 Hz, 1H), 2.76 (q, J=7.5, 6.5 Hz, 2H), 2.15 (d, J=6.4 Hz, 3H), 1.91 (q, J=5.9 Hz, 2H).

(S)-2-(2,6-difluorobenzamido)-3-(8-(1,4-dimethyl-2-oxo-1,2-dihydroquinolin-3-yl)chroman-5-yl)propanoic acid atropisomer 2 (59): MS (m/z) 533.2 [M+H]⁺. 1H NMR (400 MHz, DMSO-d6) δ 12.86 (s, 1H), 9.18 (d, J=8.1 Hz, 1H), 7.83 (dd, J=8.1, 1.6 Hz, 1H), 7.62 (ddd, J=8.6, 7.1, 1.5 Hz, 1H), 7.55-7.41 (m, 2H), 7.28 (ddd, J=8.2, 7.1, 1.2 Hz, 1H), 7.12 (ddd, J=8.5, 7.6, 3.8 Hz, 2H), 6.89-6.70 (m, 2H), 4.72-4.53 (m, 1H), 3.96 (t, J=5.2 Hz, 2H), 3.62 (d, J=1.7 Hz, 3H), 3.16 (dd, J=14.7, 4.5 Hz, 1H), 2.88 (dd, J=14.5, 10.1 Hz, 1H), 2.78 (t, J=6.5 Hz, 2H), 2.15 (d, J=6.4 Hz, 3H), 1.91 (q, J=5.9 Hz, 2H).

Example 60

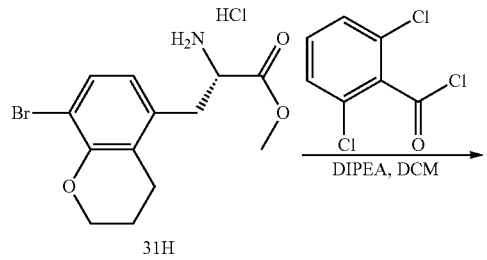

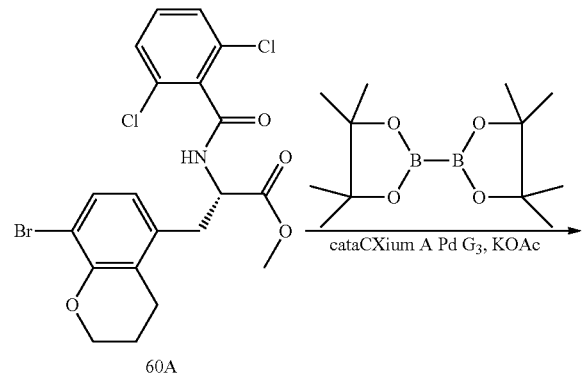

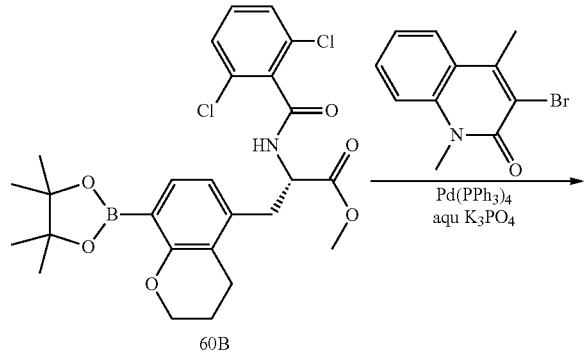

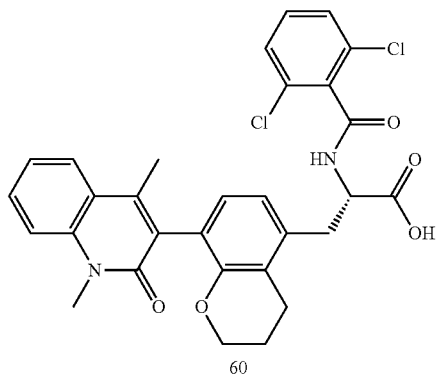

Synthesis of methyl (S)-3-(8-bromochroman-5-yl)-2-(2,6-dichlorobenzamido) propanoate (60A): The title compound was prepared according to the method presented for the synthesis of compound 1F of Example 1 starting with 2,6-difluorobenzoyl chloride and 31H.

Synthesis of methyl (S)-2-(2,6-dichlorobenzamido)-3-(8-(4,4,5,5-tetramethyl-1,3,2-dioxaborolan-2-yl)chroman-5-yl) propanoate (60B): The title compound was prepared according to the method presented for the synthesis of compound 1G of Example 1 starting with 60A.

Synthesis of (S)-2-(2,6-dichlorobenzamido)-3-(8-(1,4-dimethyl-2-oxo-1,2-dihydroquinolin-3-yl)chroman-5-yl)propanoic acid (60): The title compound was prepared according to the method presented for the synthesis of compound 38 of Example 38 starting with 3-bromo-1,4-dimethylquinolin-2(1H)-one and 60B. MS (m/z) 565.1. 1H NMR (400 MHz, DMSO-d6) δ 12.81 (s, 1H), 9.17 (dd, J=10.8, 8.3 Hz, 1H), 7.83 (dt, J=8.0, 1.7 Hz, 1H), 7.62 (ddd, J=8.5, 7.1, 1.5 Hz, 1H), 7.52 (dd, J=8.7, 1.1 Hz, 1H), 7.47-7.42 (m, 2H), 7.41-7.35 (m, 1H), 7.28 (ddd, J=8.1, 7.1, 1.1 Hz, 1H), 6.88 (dd, J=7.8, 4.5 Hz, 1H), 6.78 (dd, J=11.1, 7.6 Hz, 1H), 4.84-4.61 (m, 1H), 3.96 (q, J=5.6, 5.2 Hz, 2H), 3.62 (d, J=1.6 Hz, 3H), 3.19-3.03 (m, 1H), 2.91 (ddd, J=24.7, 14.8, 10.1 Hz, 1H), 2.83-2.68 (m, 1H), 2.15 (d, J=0.7 Hz, 3H), 1.90 (d, J=9.0 Hz, 2H).

Examples 61 and 62

Preparation of (S)-2-(2,6-dichlorobenzamido)-3-(8-(1,4-dimethyl-2-oxo-1,2-dihydroquinolin-3-yl)chroman-5-yl) propanoic acid atropisomer 1 (61) and (S)-2-(2,6-dichlorobenzamido)-3-(8-(1,4-dimethyl-2-oxo-1,2-dihydroquinolin-3-yl)chroman-5-yl)propanoic acid atropisomer 2 (62): 60 was separated into its 2 diastereomeric atropisomers by supercritical fluid chromatography using 30% MeOH co-solvent, at a flow rate of 60 mL/min, using an AD-H 21×250 mm column. The title compounds were identified as the atropisomer 1 and 2 corresponding to the first and second eluting peaks.

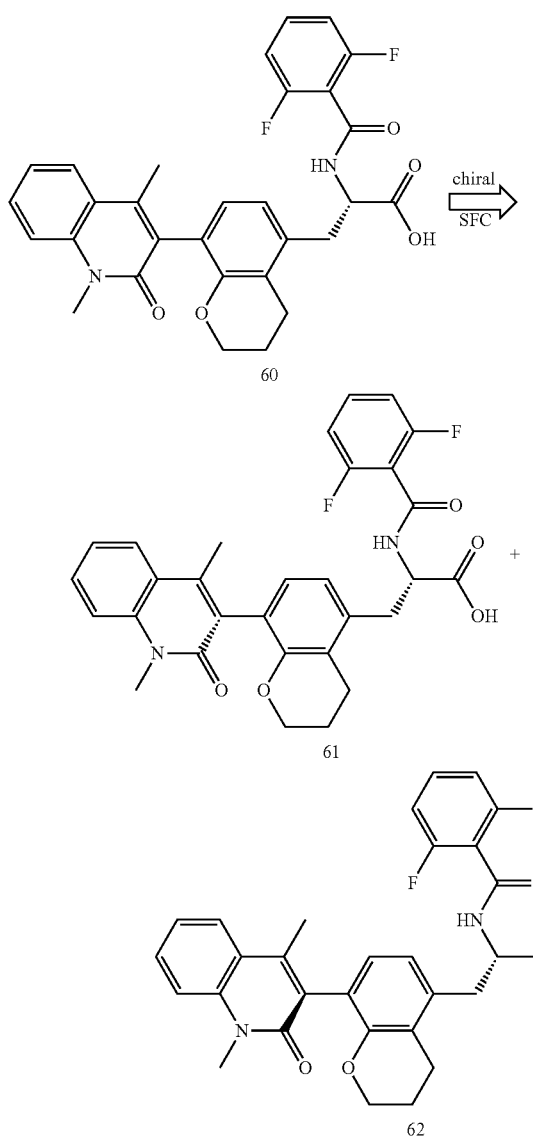

3H), 3.08 (dd, J=14.8, 4.8 Hz, 1H), 2.94 (dd, J=14.6, 9.8 Hz, 1H), 2.88-2.67 (m, 2H), 2.15 (d, J=0.7 Hz, 3H), 1.91 (s, 2H).

Example 63

Synthesis of (S)-3-(8-(4-bromoisoquinolin-3-yl)chroman-5-yl)-2-(2,6-dichlorobenzamido) propanoic acid (63): To a microwave vial was added 60B (100 mg, 0.19 mmol), 3,4-dibromoisoquinoline (70 mg, 0.24 mmol), Pd(PPh$_3$)$_4$ (11 mg, 0.009 mmol), and aq. K$_3$PO$_4$ (0.37 mL, 1M) in DME (2 mL). The reaction mixture was heated in microwave at 120° C. for 20 min. The mixture was allowed to cool to RT and 2 M aq. NaOH (1 mL) was added. After 30 min, the pH was adjusted to ~3 with 1M HCl. EtOAc was added to the reaction mixture. The aqueous layer was separated and extracted with EtOAc (2×). The combined organics were washed dried over anhydrous Na$_2$SO$_4$, and concentrated under reduced pressure. The material was purified via reverse phase HPLC to afford the title compound. MS (m/z) 599.0. 1H NMR (400 MHz, DMSO-d6) δ 9.33 (d, J=2.9 Hz, 1H), 9.19 (d, J=8.7 Hz, 1H), 8.20 (dd, J=16.5, 8.4 Hz, 2H), 7.97 (ddd, J=8.5, 7.0, 1.3 Hz, 1H), 7.80 (ddd, J=8.0, 6.9, 1.1 Hz, 1H), 7.53-7.30 (m, 3H), 7.09-6.87 (m, 2H), 4.71 (t, J=11.9 Hz, 1H), 4.03 (d, J=19.2 Hz, 2H), 3.15 (dd, J=14.6, 4.7 Hz, 1H), 2.94 (t, J=12.3 Hz, 1H), 2.81 (d, J=8.8 Hz, 2H), 1.94 (s, 2H).

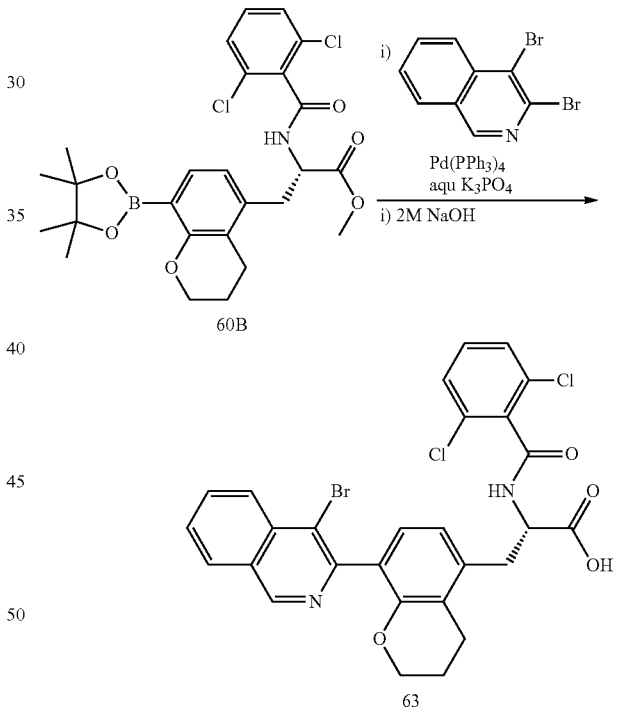

(S)-2-(2,6-dichlorobenzamido)-3-(8-(1,4-dimethyl-2-oxo-1,2-dihydroquinolin-3-yl)chroman-5-yl)propanoic acid atropisomer 1 (61): MS (m/z) 565.1 [M+H]$^+$. 1H NMR (400 MHz, DMSO-d6) δ 9.20-9.15 (m, 1H), 7.83 (dd, J=8.1, 1.6 Hz, 1H), 7.62 (ddd, J=8.5, 7.0, 1.5 Hz, 1H), 7.52 (dd, J=8.6, 1.2 Hz, 1H), 7.45 (dd, J=2.3, 0.8 Hz, 1H), 7.43 (d, J=0.8 Hz, 1H), 7.41-7.35 (m, 1H), 7.28 (ddd, J=8.1, 7.1, 1.2 Hz, 1H), 6.87 (dd, J=7.8, 4.5 Hz, 1H), 6.77 (dd, J=11.1, 7.7 Hz, 1H), 4.68 (td, J=9.4, 9.0, 4.5 Hz, 1H), 3.97 (t, J=5.0 Hz, 2H), 3.62 (d, J=1.6 Hz, 3H), 3.14 (dd, J=14.6, 4.5 Hz, 1H), 2.88 (dd, J=14.6, 10.1 Hz, 1H), 2.79 (d, J=4.6 Hz, 2H), 2.15 (d, J=0.7 Hz, 3H), 1.93 (d, J=11.3 Hz, 2H).

(S)-2-(2,6-dichlorobenzamido)-3-(8-(1,4-dimethyl-2-oxo-1,2-dihydroquinolin-3-yl)chroman-5-yl)propanoic acid atropisomer 2 (62): MS (m/z) 565.1 [M+H]$^+$. 1H NMR (400 MHz, DMSO-d6) δ 9.16 (dd, J=10.8, 8.3 Hz, 1H), 7.83 (dd, J=8.1, 1.5 Hz, 1H), 7.61 (ddd, J=8.6, 7.1, 1.5 Hz, 1H), 7.52 (dd, J=8.4, 1.1 Hz, 1H), 7.47-7.42 (m, 2H), 7.41-7.35 (m, 1H), 7.28 (ddd, J=8.1, 7.1, 1.1 Hz, 1H), 6.87 (dd, J=7.8, 4.5 Hz, 1H), 6.77 (dd, J=11.0, 7.7 Hz, 1H), 4.75 (td, J=9.0, 4.7 Hz, 1H), 3.95 (dd, J=6.0, 4.4 Hz, 2H), 3.62 (d, J=1.6 Hz, Example 64

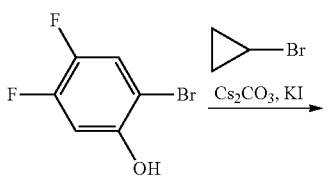

211
-continued

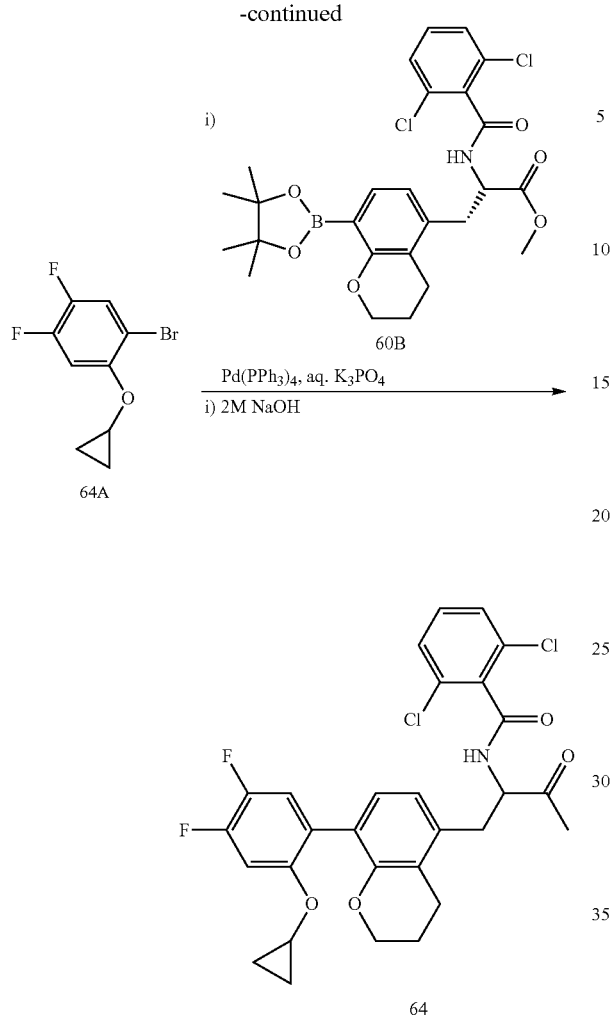

Synthesis of 1-bromo-2-cyclopropoxy-4,5-difluorobenzene (64A): To a microwave vial with a solution of 2-bromo-4,5-difluorophenol (500 mg, 2.4 mmol) in DMF was added KI (397 mg, 2.4 mmol), $Cs_2CO_3$ (426 mg, 7.2 mmol) and bromocyclopropane (0.58 mL, 7.2 mmol). The reaction mixture was heated in the microwave for 2 hr at 180° C. After cooling to RT, EtOAc and water was added to the reaction mixture. The aqueous layer was separated and extracted with EtOAc (2×). The combined organics were dried over anhydrous $Na_2SO_4$, and concentrated under reduced pressure. The material was purified on silica gel eluting with EtOAc in hexanes (0-10%) to give the title compound.

Synthesis of (S)-3-(8-(2-cyclopropoxy-4,5-difluorophenyl)chroman-5-yl)-2-(2,6-dichlorobenzamido)propanoic acid (64): The title compound was prepared according to the method presented for the synthesis of compound 63 of Example 63 starting with 64A and 60A. MS (m/z) 562.1 [M+H]⁺. 1H NMR (400 MHz, DMSO-d6) δ 9.12 (d, J=8.3 Hz, 1H), 7.46-7.31 (m, 4H), 7.09 (dd, J=11.2, 9.3 Hz, 1H), 6.82 (d, J=1.4 Hz, 2H), 4.68 (td, J=9.4, 4.8 Hz, 1H), 3.96 (t, J=5.2 Hz, 2H), 3.82 (tt, J=6.1, 2.9 Hz, 1H), 3.07 (dd, J=14.7, 4.8 Hz, 1H), 2.86 (dd, J=14.7, 9.8 Hz, 1H), 2.75 (q, J=7.0 Hz, 2H), 1.90 (q, J=5.9 Hz, 2H), 0.72 (td, J=5.7, 1.8 Hz, 2H), 0.56 (dt, J=4.3, 2.8 Hz, 2H).

212

Example 65

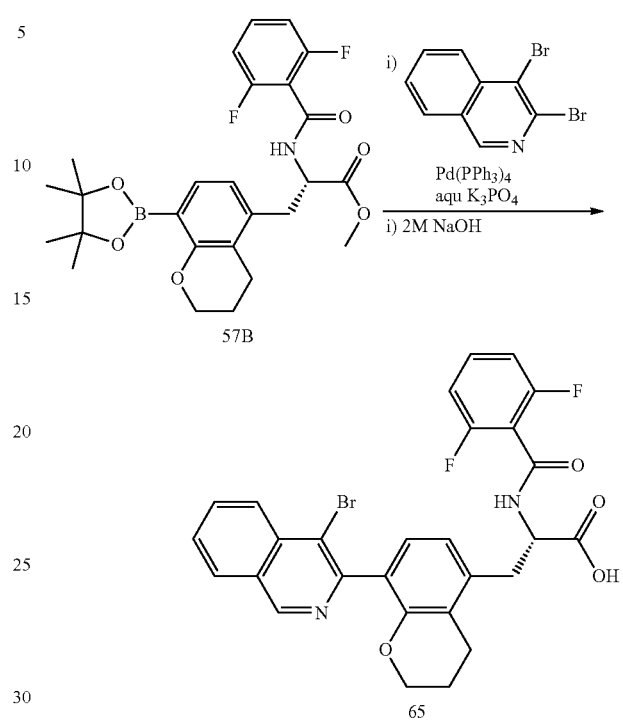

Synthesis of (S)-3-(8-(4-bromoisoquinolin-3-yl)chroman-5-yl)-2-(2,6-difluorobenzamido)propanoic acid (65): The title compound was prepared according to the method presented for the synthesis of compound 63 of Example 63 starting with 3,4-dibromoisoquinoline and 57B. MS (m/z) 567.1. 1H NMR (400 MHz, DMSO-d6) δ 12.48-13.35 (s, 1H), 9.37-9.30 (m, 1H), 9.21 (t, J=7.3 Hz, 1H), 8.21 (dd, J=17.2, 8.3 Hz, 2H), 7.96 (ddd, J=8.4, 6.9, 1.3 Hz, 1H), 7.80 (ddd, J=8.1, 6.9, 1.1 Hz, 1H), 7.50 (p, J=7.7, 7.0 Hz, 1H), 7.13 (td, J=7.9, 3.5 Hz, 3H), 7.01 (d, J=7.8 Hz, 1H), 6.91 (dd, J=11.4, 7.7 Hz, 1H), 4.74-4.46 (m, 1H), 4.01 (t, J=5.3 Hz, 2H), 3.17 (ddd, J=25.6, 14.6, 4.4 Hz, 1H), 2.94 (ddd, J=24.9, 14.5, 10.0 Hz, 1H), 2.82 (d, J=7.5 Hz, 1H), 2.03-1.82 (m, 3H).

Example 66

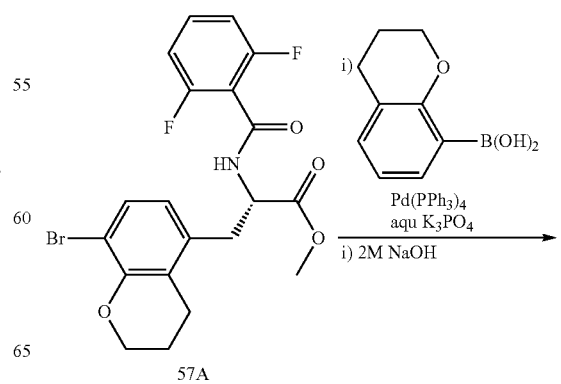

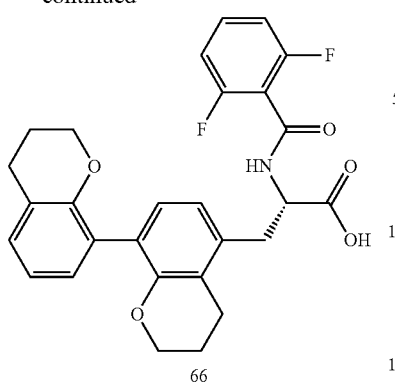

66

Synthesis of (S)-3-([8,8'-bichroman]-5-yl)-2-(2,6-difluorobenzamido)propanoic acid (66): The title compound was prepared according to the method presented for the synthesis of compound 63 of Example 63 starting with chroman-8-ylboronic acid and 57A. MS (m/z) 494.1. 1H NMR (400 MHz, DMSO-d6) δ 12.84 (s, 1H), 9.17 (d, J=7.9 Hz, 1H), 7.49 (tt, J=8.4, 6.5 Hz, 1H), 7.19-7.07 (m, 2H), 7.01-6.91 (m, 1H), 6.90-6.80 (m, 2H), 6.80-6.70 (m, 2H), 4.56 (ddd, J=9.8, 7.9, 4.5 Hz, 1H), 4.06-3.90 (m, 4H), 3.09 (dd, J=14.6, 4.5 Hz, 1H), 2.86 (dd, J=14.6, 9.8 Hz, 1H), 2.75 (q, J=6.3 Hz, 4H), 1.99-1.78 (m, 3H).

Example 67

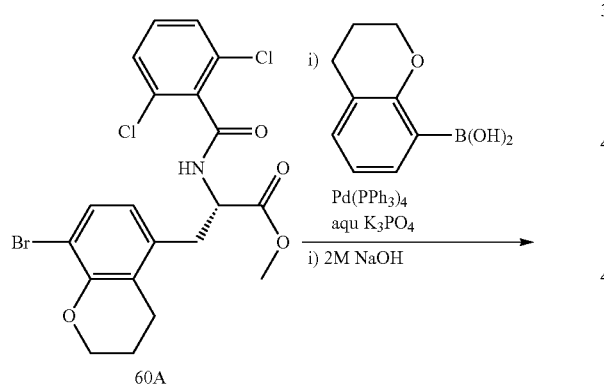

Synthesis of (S)-3-([8,8'-bichroman]-5-yl)-2-(2,6-dichlorobenzamido)propanoic acid (67): The title compound was prepared according to the method presented for the synthesis of compound 63 of Example 63 starting with chroman-8-ylboronic acid and 60A. MS (m/z) 526.1. 1H NMR (400 MHz, DMSO-d6) δ 12.93-12.60 (s, 1H), 9.13 (d, J=8.3 Hz, 1H), 7.47-7.31 (m, 3H), 7.02-6.87 (m, 1H), 6.87-6.70 (m, 4H), 4.68 (td, J=9.0, 5.0 Hz, 1H), 4.00 (dt, J=15.8, 5.1 Hz, 4H), 3.07 (dd, J=14.6, 5.0 Hz, 1H), 2.86 (dd, J=14.6, 9.7 Hz, 1H), 2.76 (t, J=5.1 Hz, 3H), 1.88 (dq, J=17.3, 6.4, 5.5 Hz, 3H).

Example 68

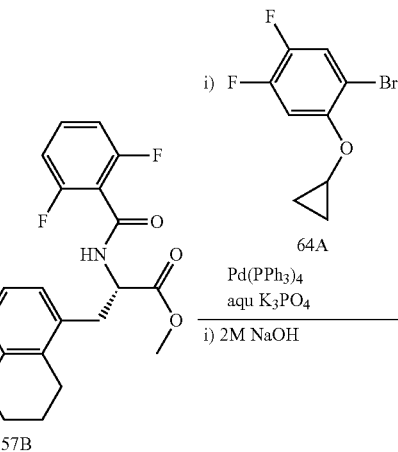

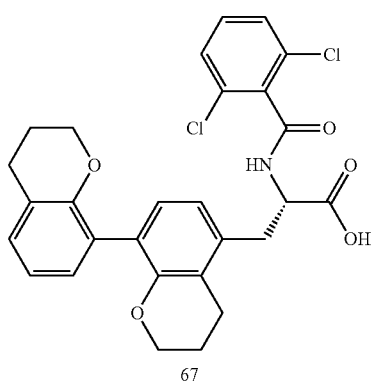

68

Synthesis of (S)-3-(8-(2-cyclopropoxy-4,5-difluorophenyl)chroman-5-yl)-2-(2,6-difluorobenzamido)propanoic acid (68): The title compound was prepared according to the method presented for the synthesis of compound 63 of Example 63 starting with 64A and 57B. MS (m/z) 530.1. 1H NMR (400 MHz, DMSO-d6) δ 12.86 (s, 1H), 9.16 (d, J=8.0 Hz, 1H), 7.49 (tt, J=8.4, 6.5 Hz, 1H), 7.35 (dd, J=12.9, 7.2 Hz, 1H), 7.19-7.02 (m, 3H), 6.87-6.70 (m, 2H), 4.56 (ddd, J=10.0, 8.0, 4.3 Hz, 1H), 4.03-3.91 (m, 2H), 3.82 (tt, J=6.0, 3.0 Hz, 1H), 3.10 (dd, J=14.7, 4.3 Hz, 1H), 2.86 (dd, J=14.7, 10.1 Hz, 1H), 2.78-2.69 (m, 2H), 1.91 (s, 2H), 0.79-0.67 (m, 2H), 0.55 (dqt, J=3.9, 3.0, 1.5 Hz, 2H).

Example 69

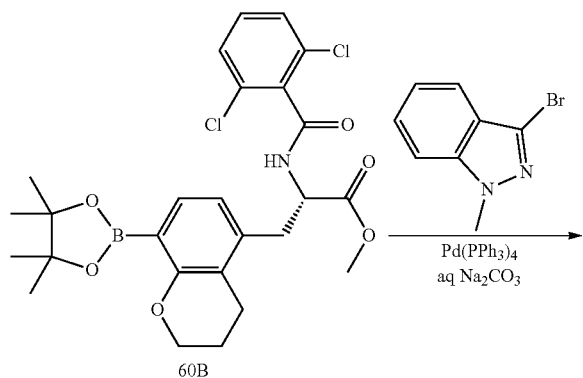

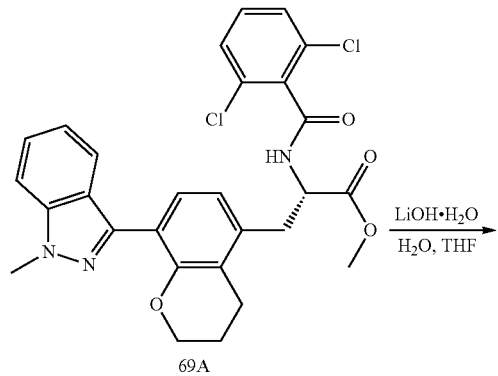

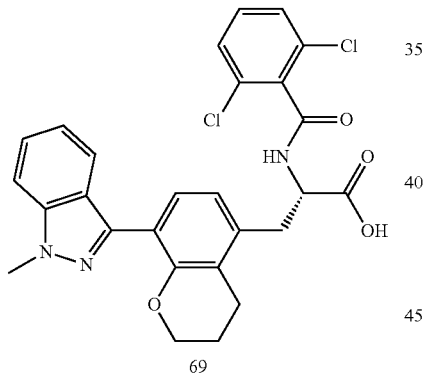

Synthesis of methyl (S)-2-(2,6-dichlorobenzamido)-3-(8-(1-methyl-1H-indazol-3-yl) chroman-5-yl)propanoate (69A): The title compound was prepared according to the method presented for the synthesis of compound 1H of Example 1 starting with 3-bromo-1-methyl-1H-indazole and 60B.

Synthesis of (S)-2-(2,6-dichlorobenzamido)-3-(8-(1-methyl-1H-indazol-3-yl)chroman-5-yl)propanoic acid (69): The title compound was prepared according to the method presented for the synthesis of compound 1 of Example 1 starting with 69A. MS (m/z) 524.1 [M+H]$^+$. 1H NMR (400 MHz, Chloroform-d) δ 7.74 (d, J=8.3 Hz, 1H), 7.54-7.38 (m, 2H), 7.35-7.31 (m, 1H), 7.31-7.27 (m, 2H), 7.24 (d, J=5.9 Hz, 0H), 7.22-7.14 (m, 1H), 6.90 (d, J=7.9 Hz, 1H), 6.44 (d, J=7.6 Hz, 1H), 5.18 (q, J=7.2 Hz, 1H), 4.19-4.15 (m, 2H), 4.14 (s, 3H), 3.33 (d, J=7.1 Hz, 2H), 3.05-2.87 (m, 2H), 2.09 (q, J=5.8 Hz, 2H).

Example 70

Synthesis of (2S,5R)-2-((8-bromochroman-5-yl)methyl)-5-isopropyl-3,6-dimethoxy-2,5-dihydropyrazine (70A): The title compound was prepared according to the method presented for the synthesis of compound 4A of Example 4 starting with 31E.

Synthesis of (2S,5R)-2-((8-(4,5-difluoro-2-methoxyphenyl)chroman-5-yl)methyl)-5-isopropyl-3,6-dimethoxy-2,5-dihydropyrazine (70B): The title compound was prepared according to the method presented for the synthesis of compound 1H of Example 1 starting with 70A.

Synthesis of methyl (S)-2-amino-3-(8-(4,5-difluoro-2-methoxyphenyl)chroman-5-yl)propanoate (70C): The title compound was prepared according to the method presented for the synthesis of compound 4C of Example 4 starting with 70B.

Synthesis of methyl (S)-2-(2,6-dichlorobenzamido)-3-(8-(4,5-difluoro-2-methoxyphenyl)chroman-5-yl)propanoate (70D): The title compound was prepared according to the method presented for the synthesis of compound 1F of Example 1 starting with 2,6-dichlorobenzoyl chloride and 70C.

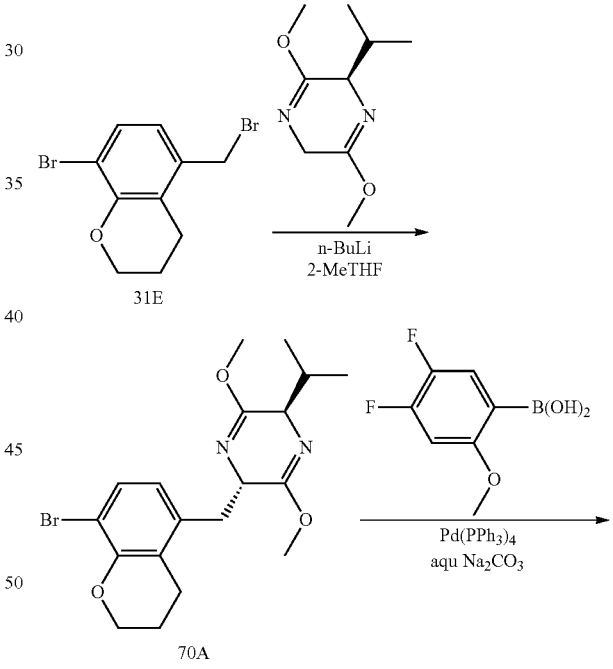

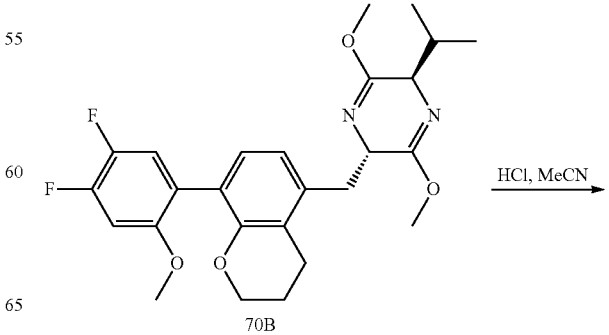

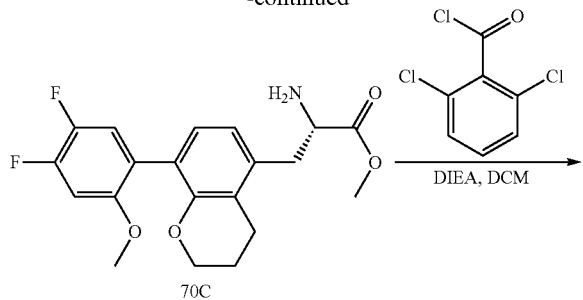

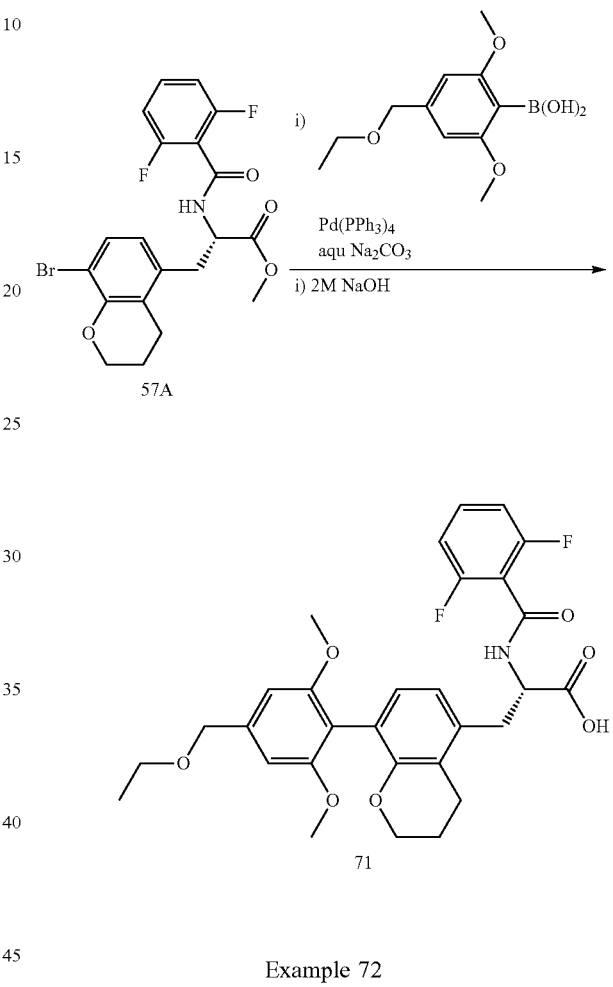

DMSO-d6) δ 9.19 (d, J=7.8 Hz, 1H), 7.49 (t, J=8.5 Hz, 1H), 7.13 (dd, J=8.4, 7.5 Hz, 2H), 6.83-6.64 (m, 2H), 6.60 (q, J=1.3 Hz, 2H), 4.64-4.50 (m, 1H), 4.43 (s, 2H), 3.93 (dt, J=7.5, 4.2 Hz, 2H), 3.61 (d, J=4.7 Hz, 6H), 3.51 (q, J=7.0 Hz, 2H), 3.08 (dd, J=14.9, 4.5 Hz, 1H), 2.87 (dd, J=14.9, 9.7 Hz, 1H), 2.72 (d, J=7.1 Hz, 2H), 1.89 (d, J=6.6 Hz, 2H), 1.17 (t, J=7.0 Hz, 3H).

Example 72

Synthesis of (S)-2-(2,6-dichlorobenzamido)-3-(8-(4,5-difluoro-2-methoxyphenyl) chroman-5-yl)propanoic acid (70): The title compound was prepared according to the method presented for the synthesis of compound 1 of Example 1 starting with 70D. MS (m/z) 535.9 [M+H]$^+$. 1H NMR (400 MHz, DMSO-d6) δ 12.81 (s, 1H), 9.13 (d, J=8.3 Hz, 1H), 7.46-7.35 (m, 3H), 7.13 (ddd, J=24.2, 12.1, 8.2 Hz, 2H), 6.88-6.77 (m, 2H), 5.74 (s, 0H), 4.69 (ddd, J=9.8, 8.3, 4.9 Hz, 1H), 3.99 (t, J=5.2 Hz, 2H), 3.68 (s, 3H), 3.09 (dd, J=14.6, 4.9 Hz, 1H), 2.93-2.68 (m, 3H), 2.05 (s, 1H), 1.92 (q, J=6.5, 6.0 Hz, 2H).

Example 71

Synthesis of (S)-2-(2,6-difluorobenzamido)-3-(8-(4-(ethoxymethyl)-2,6-dimethoxyphenyl)chroman-5-yl)propanoic acid (71): The title compound was prepared according to the method presented for the synthesis of compound 63 starting with (4-(ethoxymethyl)-2,6-dimethoxyphenyl) boronic acid and 57A. MS (m/z) 556.2. 1H NMR (400 MHz,

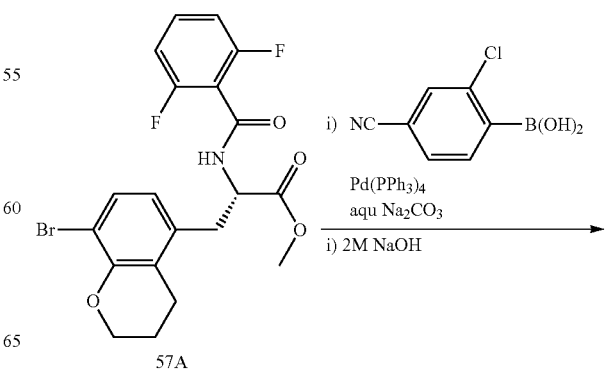

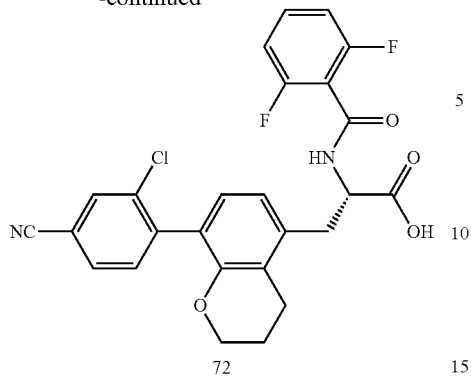

72

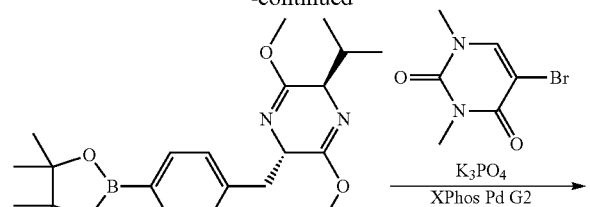

73A

Synthesis of (S)-3-(8-(2-chloro-4-cyanophenyl)chroman-5-yl)-2-(2,6-difluorobenzamido)propanoic acid (72): The title compound was prepared according to the method presented for the synthesis of compound 63 starting with (2-chloro-4-cyanophenyl)boronic acid and 57A. MS (m/z) 497.1 [M+H]$^+$. 1H NMR (400 MHz, DMSO-d6) δ 9.18 (d, J=8.1 Hz, 1H), 8.07 (d, J=1.6 Hz, 1H), 7.82 (dd, J=7.9, 1.7 Hz, 1H), 7.53-7.40 (m, 2H), 7.12 (dd, J=8.4, 7.5 Hz, 2H), 6.93-6.84 (m, 2H), 4.61 (s, 1H), 4.03 (d, J=5.9 Hz, 2H), 3.15 (dd, J=14.6, 4.3 Hz, 1H), 2.96-2.83 (m, 1H), 2.78 (q, J=6.4 Hz, 2H), 1.93 (d, J=5.5 Hz, 2H).

Example 73

Synthesis of (2R,5S)-2-isopropyl-3,6-dimethoxy-5-((8-(4,4,5,5-tetramethyl-1,3,2-dioxaborolan-2-yl)chroman-5-yl)methyl)-2,5-dihydropyrazine (73A): The title compound was prepared according to the method presented for the synthesis of compound 1G of Example 1 starting with 70A.

Synthesis of 5-(5-(((2S,5S)-5-isopropyl-3,6-dimethoxy-2,5-dihydropyrazin-2-yl) methyl)chroman-8-yl)-1,3-dimethylpyrimidine-2,4(1H,3H)-dione (73B): To a vial was added rac-(5S)-3,6-dimethoxy-2-(1-methylethyl)-5-[[8-(4,4,5,5-tetramethyl-1,3,2-dioxaborolan-2-yl) chroman-5-yl]methyl]-2,5-dihydropyrazine 73A (0.1 g, 0.2 mmol), 5-bromo-1,3-dimethyl-pyrimidine-2,4-dione (0.24 g, 1.1 mmol), potassium phosphate (0.23 g, 1.1 mmol), XPhos Pd G2 (0.01 g, 0.01 mmol) followed by DME (2 mL). System was purged and flushed with nitrogen three times, sealed and stirred at 85° C. for 4h, then diluted with 5 mL EtOAc and 5 mL water. The mixtures were separated and washed the aqueous layer with EtOAc (2×5 mL). The organic layers were combined and purified on silica gel (DCM:MeOH, 0 to 50%) to afford the title compound.

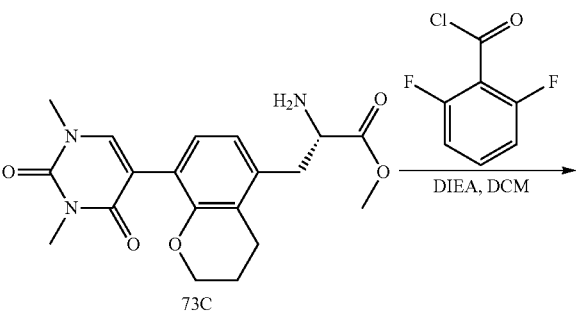

73B

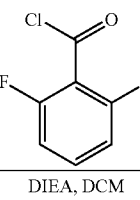

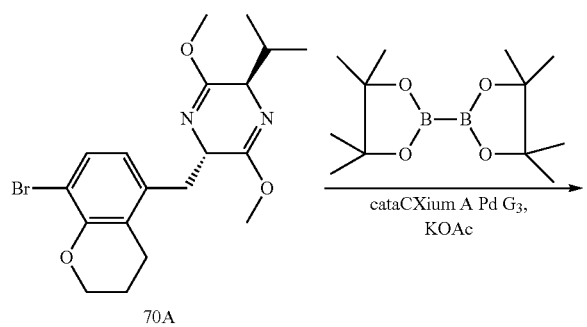

70A

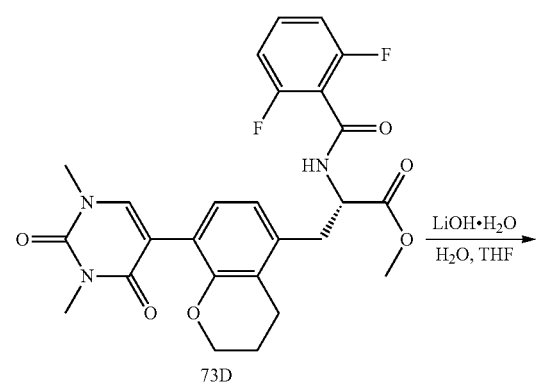

73C

73D

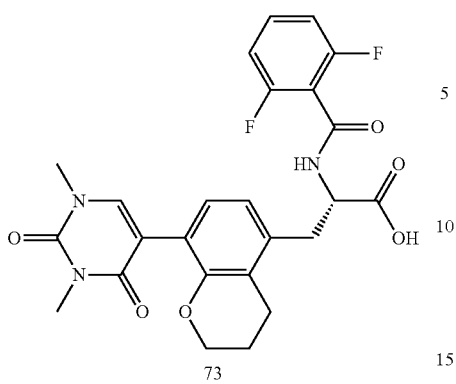

Synthesis of methyl (S)-2-amino-3-(8-(1,3-dimethyl-2,4-dioxo-1,2,3,4-tetrahydropyrimidin-5-yl)chroman-5-yl)propanoate (73C): To a solution of 1,3-dimethyl-5-[5-[[rac-(2S)-3,6-dimethoxy-5-(1-methylethyl)-2,5-dihydropyrazin-2-yl]methyl]chroman-8-yl]pyrimidine-2,4-dione (0.1 g, 0 mol) in THF was added 2 N HCl in dioxane (0.58 mL). The reaction mixture was stirred at RT for 30 min, and concentrated to afford the title compound.

Synthesis of methyl (S)-2-(2,6-difluorobenzamido)-3-(8-(1,3-dimethyl-2,4-dioxo-1,2,3,4-tetrahydropyrimidin-5-yl)chroman-5-yl)propanoate (73D): The title compound was prepared according to the method presented for the synthesis of compound 1F of Example 1 starting with 2,6-difluorobenzoyl chloride and 73C.

Synthesis of (S)-2-(2,6-difluorobenzamido)-3-(8-(1,3-dimethyl-2,4-dioxo-1,2,3,4-tetrahydropyrimidin-5-yl)chroman-5-yl)propanoic acid (73): The title compound was prepared according to the method presented for the synthesis of compound 1 starting with 73D. MS (m/z) 500.1 [M+H]$^+$. 1H NMR (400 MHz, DMSO-d6) δ 9.17 (d, J=7.9 Hz, 1H), 7.65 (s, 1H), 7.49 (tt, J=8.4, 6.5 Hz, 1H), 7.12 (dd, J=8.5, 7.5 Hz, 2H), 6.90 (d, J=7.8 Hz, 1H), 6.78 (d, J=7.8 Hz, 1H), 4.60-4.45 (m, 1H), 4.02 (dt, J=6.9, 3.7 Hz, 2H), 3.32 (s, 3H), 3.18 (s, 3H), 3.09 (dd, J=14.6, 4.4 Hz, 1H), 2.86 (dd, J=14.6, 9.8 Hz, 1H), 2.74 (q, J=6.3 Hz, 2H), 1.92 (dd, J=7.0, 4.1 Hz, 2H).

Example 74

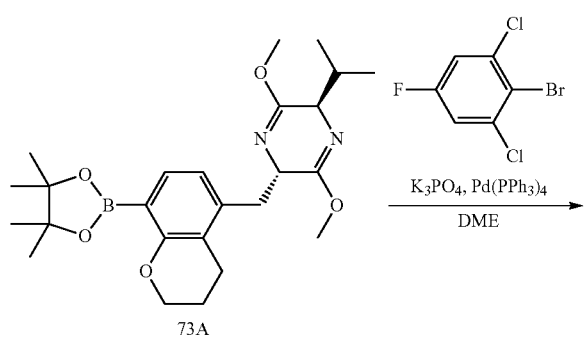

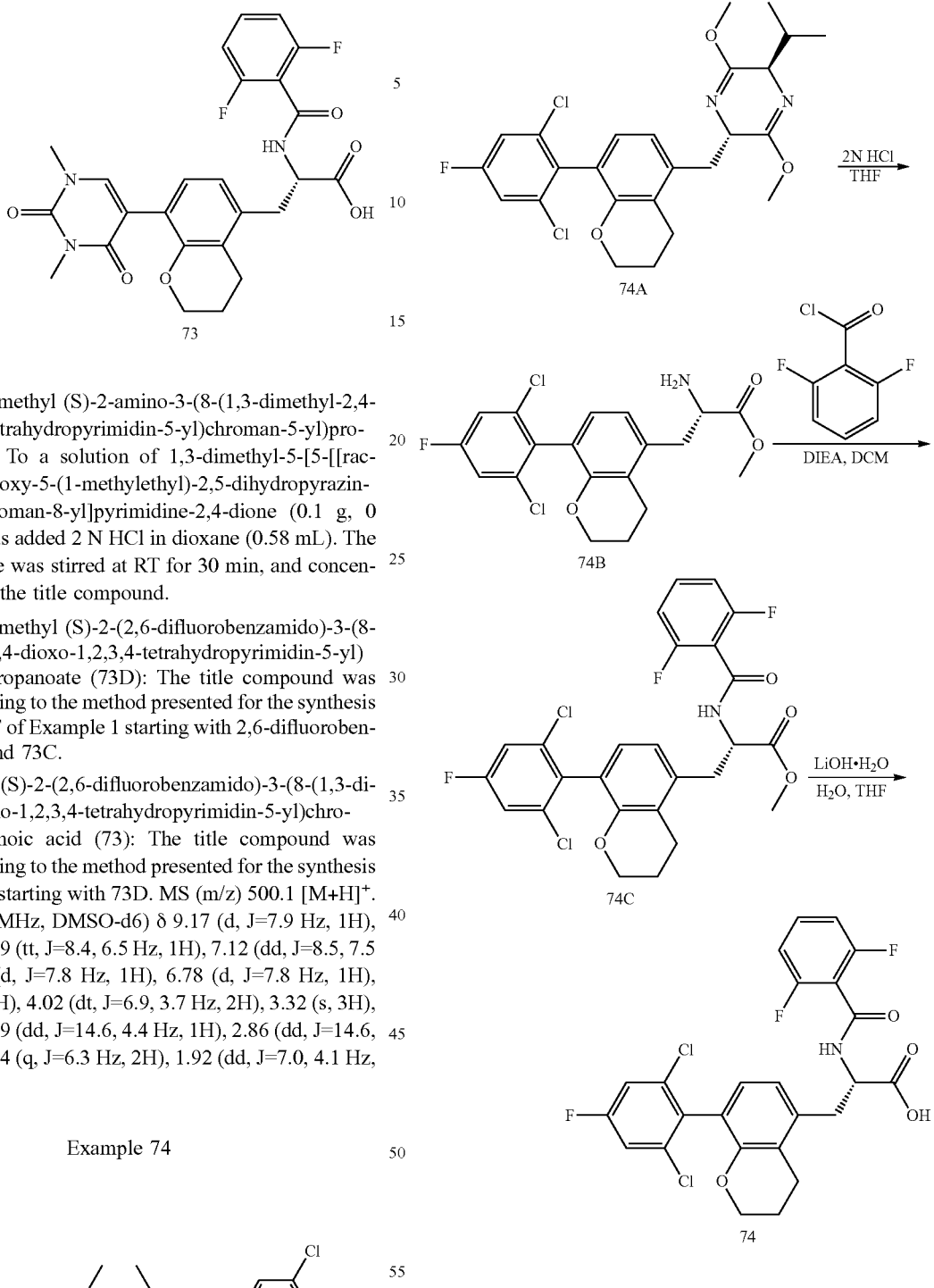

Synthesis of (2S,5S)-2-((8-(2,6-dichloro-4-fluorophenyl)chroman-5-yl)methyl)-5-isopropyl-3,6-dimethoxy-2,5-dihydropyrazine (74A): The title compound was prepared according to the method presented for the synthesis of compound 38 of Example 38 starting with 2-bromo-1,3-dichloro-5-fluorobenzene and 73A.

Synthesis of methyl (S)-2-amino-3-(8-(2,6-dichloro-4-fluorophenyl)chroman-5-yl)propanoate (74A): The title compound was prepared according to the method presented for the synthesis of compound 38 starting with 2-bromo-1,3-dichloro-5-fluorobenzene and 73A.

Synthesis of methyl (S)-2-amino-3-(8-(2,6-dichloro-4-fluorophenyl)chroman-5-yl)propanoate (74B): The title compound was prepared according to the method presented for the synthesis of compound 4C of Example 4 starting with 74A.

Synthesis of methyl (S)-3-(8-(2,6-dichloro-4-fluorophenyl)chroman-5-yl)-2-(2,6-difluorobenzamido)propanoate (74C): The title compound was prepared according to the method presented for the synthesis of compound 1F of Example 1 starting with 2,6-difluorobenzoyl chloride and 74B.

Synthesis of (S)-3-(8-(2,6-dichloro-4-fluorophenyl)chroman-5-yl)-2-(2,6-difluorobenzamido)propanoic acid (74): The title compound was prepared according to the method presented for the synthesis of compound 1 of Example 1 starting with 73D. MS (m/z) 524.1 [M+H]$^+$. 1H NMR (400 MHz, DMSO-d6) δ 12.87 (s, 1H), 9.17 (d, J=8.0 Hz, 1H), 7.56 (d, J=0.6 Hz, 1H), 7.53 (d, J=0.6 Hz, 1H), 7.48 (tt, J=8.5, 6.6 Hz, 1H), 7.11 (dd, J=8.5, 7.5 Hz, 2H), 6.91-6.80 (m, 2H), 4.64 (ddd, J=10.2, 8.0, 4.4 Hz, 1H), 4.00 (t, J=5.3 Hz, 2H), 3.14 (dd, J=14.8, 4.4 Hz, 1H), 2.90 (dd, J=14.8, 10.2 Hz, 1H), 2.77 (q, J=6.1 Hz, 2H), 1.92 (q, J=5.6 Hz, 2H).

Example 75

Synthesis of methyl (S)-3-(8-(2,6-dichloro-4-fluorophenyl)chroman-5-yl)-2-(2,6-dichlorobenzamido)propanoate (75A): The title compound was prepared according to the method presented for the synthesis of compound 1F of Example 1 starting with 2,6-dichlorobenzoyl chloride and 74B.

Synthesis of (S)-3-(8-(2,6-dichloro-4-fluorophenyl)chroman-5-yl)-2-(2,6-dichloro benzamido)propanoic acid (74): The title compound was prepared according to the method presented for the synthesis of compound 1 of Example 1 starting with 75A. MS (m/z) 558.0 [M+H]$^+$. 1H NMR (400 MHz, DMSO-d6) δ 12.83 (s, 1H), 9.15 (d, J=8.4 Hz, 1H), 7.56 (d, J=0.6 Hz, 1H), 7.54 (d, J=0.7 Hz, 1H), 7.45-7.35 (m, 3H), 6.94 (d, J=7.8 Hz, 1H), 6.80 (d, J=7.7 Hz, 1H), 4.71 (ddd, J=10.6, 8.4, 4.0 Hz, 1H), 4.00 (t, J=5.2 Hz, 2H), 3.12 (dd, J=14.7, 4.0 Hz, 1H), 2.98-2.84 (m, 1H), 2.84-2.64 (m, 1H), 2.01-1.74 (m, 2H).

Example 76

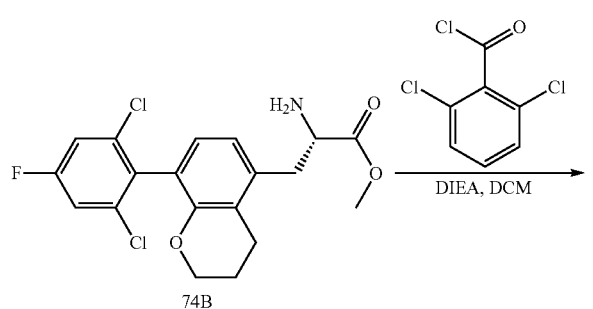

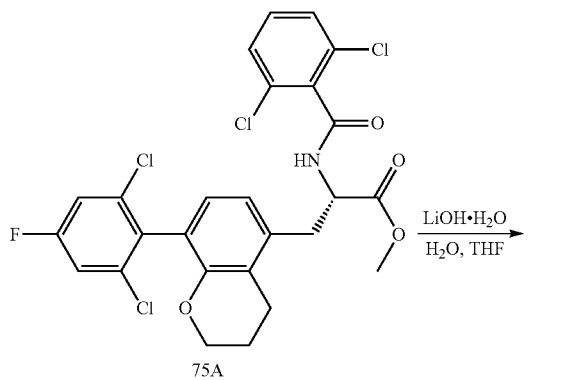

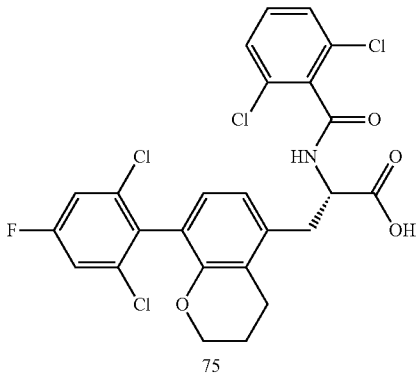 [SMILES: COc1cc(F)c(F)cc1-c1ccc(C[C@H](NC(=O)c2c(Cl)cccc2Cl)C(=O)O)c2c1OCCC2]

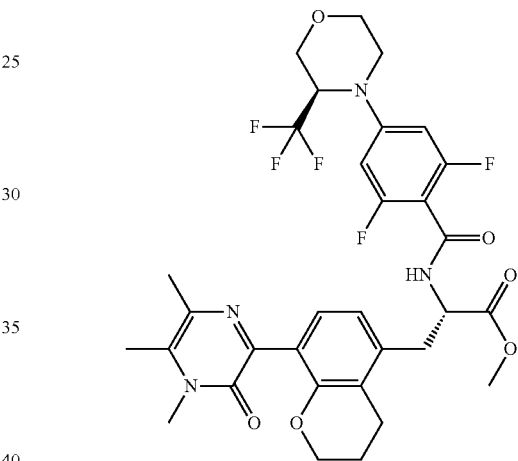

Synthesis of methyl (S)-2-(2,6-difluoro-4-((R)-3-(trifluoromethyl)morpholino) benzamido)-3-(8-(4,5,6-trimethyl-3-oxo-3,4-dihydropyrazin-2-yl)chroman-5-yl)propanoate (76): The title compound was prepared according to the method presented for the synthesis of compound 13K of Example 13 starting with 49A and 32B. MS (m/z) 665.2 [M+H]$^+$. 1H NMR (400 MHz, DMSO-d6) δ 9.01 (d, J=7.6 Hz, 1H), 6.88 (d, J=7.6 Hz, 1H), 6.83-6.65 (m, 3H), 5.01-4.84 (m, 1H), 4.58 (q, J=7.5 Hz, 1H), 4.17 (d, J=12.7 Hz, 1H), 4.06-3.89 (m, 3H), 3.75 (d, J=12.7 Hz, 1H), 3.67 (d, J=1.3 Hz, 3H), 3.56 (t, J=11.4 Hz, 1H), 3.47 (d, J=1.3 Hz, 4H), 3.25 (t, J=12.5 Hz, 1H), 3.09 (dd, J=14.5, 5.1 Hz, 1H), 3.01-2.85 (m, 1H), 2.75 (d, J=7.6 Hz, 1H), 2.32 (s, 3H), 2.26 (s, 3H), 1.93 (t, J=5.8 Hz, 2H).

Example 77

Synthesis of (methyl 4-bromo-3-(prop-2-yn-1-yloxy)benzoate (77A): To a stirred solution of methyl 4-bromo-3-hydroxybenzoate (1.17 g, 5.08 mmol) in acetone (17 mL) was added potassium carbonate (1.40 g, 10.15 mmol), followed by propargyl bromide (0.56 mL, 7.36 mmol). The reaction vessel was sealed and heated to 65° C. for 4 hours. After cooling to room temperature, the reaction was diluted with water and EtOAc. The aqueous layer was extracted and the organic layer was dried over anhydrous MgSO$_4$ and concentrated under reduced pressure. The material was purified by silica gel chromatography using 0-20% EtOAc in hexanes to afford the title compound.

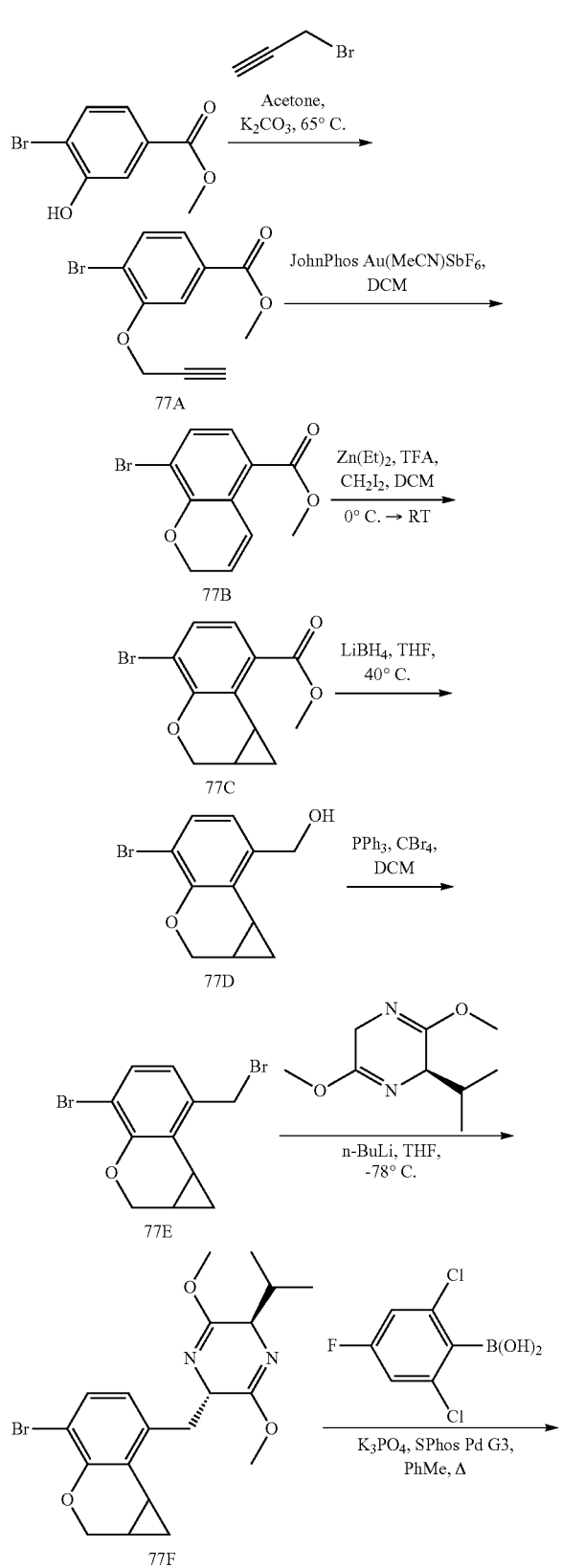

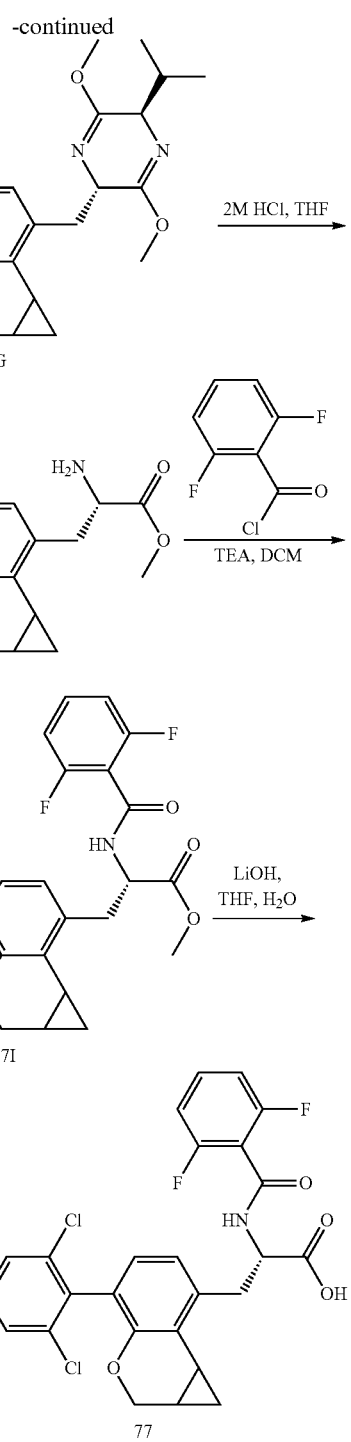

Synthesis of methyl 8-bromo-2H-chromene-5-carboxylate (77B): A reaction vessel containing a solution of 77A (209 mg, 0.778 mmol) in dichloromethane (7.78 mL) was wrapped in aluminum foil to avoid decomposition from light. To this solution was added (acetonitrile)[(2-biphenyl)di-tert-butylphosphine]gold(I) hexafluoroantimonate (30 mg, 0.039 mmol) and the reaction was stirred at room temperature for 16 hours. The reaction was filtered through celite, rinsing with DCM, and the filtrate was concentrated under reduced pressure. The material was purified by silica gel chromatography using 0-30% EtOAc in hexanes to afford the title compound.

Synthesis of methyl 4-bromo-1,1a,2,7b-tetrahydrocyclopropa[c]chromene-7-carboxylate (77C): A solution of diethylzinc (1.0 M in hexanes, 0.61 mL, 0.61 mmol) in dichloromethane (0.61 mL) was flushed with nitrogen and cooled to 0° C. To this solution was added a solution of trifluoroacetic acid (0.05 mL, 0.61 mmol) in dichloromethane (0.30 mL) and this was stirred at 0° C. for 1 hour. To this was added a solution of diiodomethane (0.05 mL, 0.61 mmol) in dichloromethane (0.30 mL) and this was stirred at 0° C. for 1 hour. To this was added a solution of 77B (82 mg, 0.30 mmol) in dichloromethane (0.30 mL) and the reaction was allowed to warm to room temperature and it was stirred for 3 hours. The reaction was quenched with saturated ammonium chloride and diluted with DCM. The aqueous layer was extracted and the organic layer was dried over anhydrous MgSO$_4$ and concentrated under reduced pressure. The material was purified by silica gel chromatography using 0-20% EtOAc in hexanes to afford the title compound.

Synthesis of (4-bromo-1,1a,2,7b-tetrahydrocyclopropa[c]chromen-7-yl)methanol (77D): To a stirred solution of 77C (2.81 g, 9.91 mmol) in THF (50 mL) under N$_2$ was added lithium borohydride in one portion (2.16 g, 99.1 mmol). The reaction was stirred at 40° C. for 2 hours. 1M HCl was added dropwise and the reaction was diluted with EtOAc. The aqueous layer was extracted and the organic layer was dried over anhydrous MgSO$_4$ and concentrated under reduced pressure. The material was purified by silica gel chromatography using 0-50% EtOAc in hexanes to afford the title compound.

Synthesis of 4-bromo-7-(bromomethyl)-1,1a,2,7b-tetrahydrocyclopropa[c]chromene (77E): The title compound was prepared according to the method presented for the synthesis of compound 13E of Example 13 starting with 77D.

Synthesis of (2S,5R)-2-((4-bromo-1,1a,2,7b-tetrahydrocyclopropa[c]chromen-7-yl)methyl)-5-isopropyl-3,6-dimethoxy-2,5-dihydropyrazine (77F): The title compound was prepared according to the method presented for the synthesis of compound 4A of Example 4 starting with 77E.

Synthesis of (2S,5R)-2-((4-(2,6-dichloro-4-fluorophenyl)-1,1a,2,7b-tetrahydrocyclopropa[c]chromen-7-yl)methyl)-5-isopropyl-3,6-dimethoxy-2,5-dihydropyrazine (77G): The title compound was prepared according to the method presented for the synthesis of compound 4B of Example 4 starting with (2,6-dichloro-4-fluorophenyl)boronic acid and 77F.

Synthesis of methyl (2S)-2-amino-3-(4-(2,6-dichloro-4-fluorophenyl)-1,1a,2,7b-tetrahydrocyclopropa[c]chromen-7-yl)propanoate (77H): The title compound was prepared according to the method presented for the synthesis of compound 4C of Example 4 starting with 77G.

Synthesis of methyl (2S)-3-(4-(2,6-dichloro-4-fluorophenyl)-1,1a,2,7b-tetrahydrocyclopropa[c]chromen-7-yl)-2-(2,6-difluorobenzamido)propanoate (77I): The title compound was prepared according to the method presented for the synthesis of compound 1F of Example 1 starting with 2,6-difluorobenzoyl chloride and 77H.

Synthesis of (2S)-3-(4-(2,6-dichloro-4-fluorophenyl)-1,1a,2,7b-tetrahydrocyclopropa[c]chromen-7-yl)-2-(2,6-difluorobenzamido)propanoic acid (77): The title compound was prepared according to the method presented for the synthesis of compound 1 of Example 1 starting with 77I. MS (m/z) 536.1 [M+H]$^+$. 1H NMR (400 MHz, DMSO-d6) δ 12.86 (s, 2H), 9.21 (d, J=8.0 Hz, 1H), 9.12 (d, J=8.2 Hz, 1H), 7.60-7.53 (m, 3H), 7.53-7.42 (m, 2H), 7.12 (td, J=8.8, 7.5 Hz, 4H), 6.95 (dd, J=7.9, 6.3 Hz, 2H), 6.80 (dd, J=7.8 Hz, 2H), 4.82-4.73 (m, 1H), 4.69 (td, J=8.8, 4.9 Hz, 1H), 4.10 (ddd, J=10.7, 3.3, 1.8 Hz, 2H), 3.87 (ddd, J=10.7, 6.3, 2.5 Hz, 2H), 3.36 (ddd, J=18.9, 14.4, 4.6 Hz, 2H), 3.07 (dt, J=14.5, 9.6 Hz, 2H), 2.19 (ddd, J=13.7, 8.6, 5.1 Hz, 2H), 1.89-1.76 (m, 2H), 1.15 (qd, J=7.9, 4.2 Hz, 2H).

Examples 78 and 79

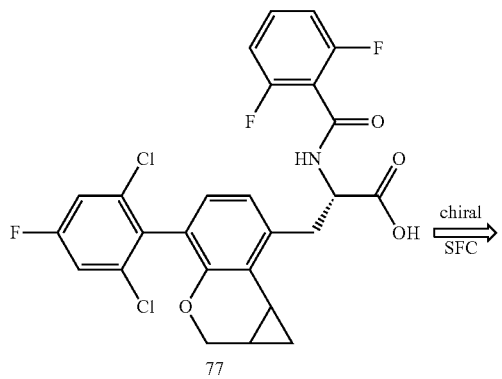

Preparation of (S)-3-((1aR,7bS)-4-(2,6-dichloro-4-fluorophenyl)-1,1a,2,7b-tetrahydrocyclopropa[c]chromen-7-yl)-2-(2,6-difluorobenzamido)propanoic acid (78): 77 was separated into its 2 diastereomers by supercritical fluid chromatography using 15% IPA co-solvent, at a flow rate of 3 mL/min, using an IE 4.6×150 mm column. The title compound was identified as the first eluting peak. MS (m/z) 536.1 [M+H]$^+$. 1H NMR (400 MHz, DMSO-d6) δ 12.89 (s, 1H), 9.23 (d, J=8.0 Hz, 1H), 7.57 (dtd, J=8.9, 5.8, 3.2 Hz, 2H), 7.54-7.44 (m, 1H), 7.18-7.08 (m, 2H), 6.95 (d, J=7.9 Hz, 1H), 6.80 (d, J=7.8 Hz, 1H), 4.69 (ddd, J=9.6, 7.9, 4.8 Hz, 1H), 4.10 (dd, J=10.8, 1.7 Hz, 1H), 3.86 (dd, J=10.7, 2.4 Hz, 1H), 3.34 (dd, J=14.4, 4.8 Hz, 1H), 3.08 (dd, J=14.4, 9.6 Hz, 1H), 2.18 (td, J=8.5, 4.5 Hz, 1H), 1.85 (td, J=8.1, 5.7 Hz, 1H), 1.14 (td, J=8.2, 4.2 Hz, 1H), 0.79 (q, J=4.7 Hz, 1H).

Preparation of (S)-3-((1aS,7bR)-4-(2,6-dichloro-4-fluorophenyl)-1,1a,2,7b-tetrahydrocyclopropa[c]chromen-7-yl)-2-(2,6-difluorobenzamido)propanoic acid (79): 77 was separated into its 2 diastereomers by supercritical fluid chromatography using 15% IPA co-solvent, at a flow rate of 3 mL/min, using an IE 4.6×100 mm column. The title compound was identified as the second eluting peak. MS (m/z) 536.1 [M+H]$^+$. 1H NMR (400 MHz, DMSO-d6) δ 12.89 (s, 1H), 9.14 (d, J=8.1 Hz, 1H), 7.57 (dq, J=8.7, 2.6 Hz, 2H), 7.49 (tt, J=8.5, 6.5 Hz, 1H), 7.15-7.07 (m, 2H), 6.94 (d, J=7.9 Hz, 1H), 6.80 (d, J=7.8 Hz, 1H), 4.78 (ddd, J=10.4, 8.1, 4.2 Hz, 1H), 4.09 (dd, J=10.7, 1.8 Hz, 1H), 3.87 (dd, J=10.7, 2.5 Hz, 1H), 3.38 (dd, J=14.4, 4.3 Hz, 1H), 3.05 (dd, J=14.5, 10.4 Hz, 1H), 2.20 (td, J=8.5, 4.5 Hz, 1H), 1.81 (dtt, J=8.2, 5.8, 2.6 Hz, 1H), 1.16 (td, J=8.2, 4.2 Hz, 1H), 0.79 (q, J=4.7 Hz, 1H).

Example 80 the synthesis of compound 1F of Example 1 starting with 2,6-dichlorobenzoyl chloride and 80A.

Synthesis of (2S)-3-(4-(2,6-dichloro-4-fluorophenyl)-1,1a,2,7b-tetrahydrocyclopropa[c]chromen-7-yl)-2-(2,6-dichlorobenzamido)propanoic acid (80): The title compound was prepared according to the method presented for synthesis of compound 1 of Example 1 starting with 80A. MS (m/z) 568.0 [M+H]$^+$. 1H NMR (400 MHz, DMSO-d6) δ 12.81 (s, 2H), 9.17 (d, J=8.2 Hz, 1H), 9.09 (d, J=8.4 Hz, 1H), 7.59-7.50 (m, 3H), 7.47-7.33 (m, 6H), 6.98 (dd, J=9.2, 7.9 Hz, 2H), 6.76 (dd, J=7.8, 1.7 Hz, 2H), 4.94-4.81 (m, 1H), 4.73 (td, J=9.4, 4.6 Hz, 1H), 4.07 (td, J=11.2, 1.8 Hz, 2H), 3.86 (ddd, J=13.4, 10.7, 2.6 Hz, 2H), 3.34 (td, J=15.2, 4.3 Hz, 2H), 3.03 (ddd, J=14.4, 10.4, 7.0 Hz, 2H), 2.19 (dtd, J=13.0, 8.5, 4.6 Hz, 2H), 1.84 (dt, J=26.1, 8.3 Hz, 2H), 1.15 (qd, J=8.1, 4.4 Hz, 2H), 0.77 (dq, J=9.2, 4.7 Hz, 2H).

Examples 81 and 82

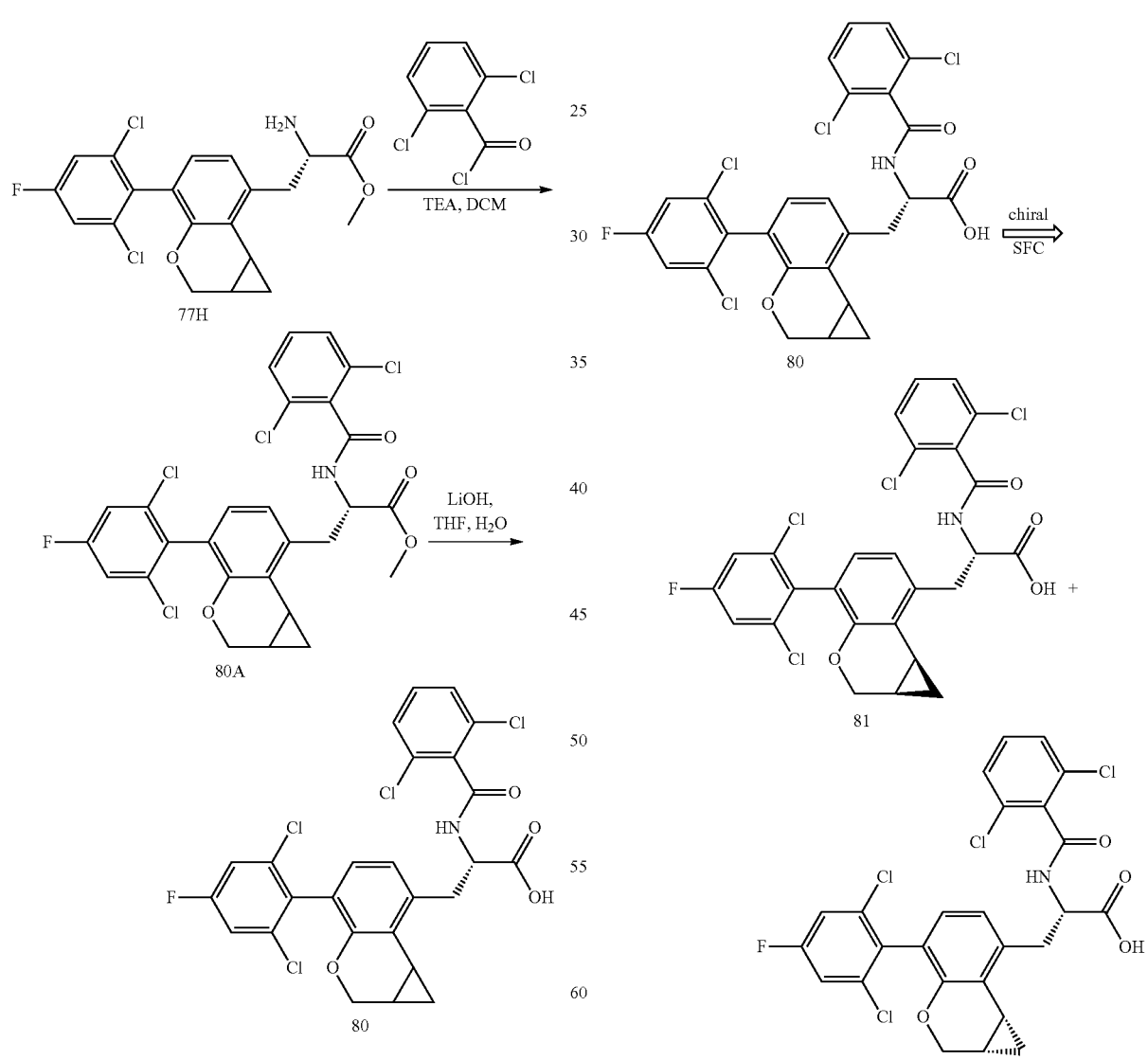

Synthesis of methyl (2S)-3-(4-(2,6-dichloro-4-fluorophenyl)-1,1a,2,7b-tetrahydrocyclopropa[c]chromen-7-yl)-2-(2,6-dichlorobenzamido)propanoate (80A): The title compound was prepared according to the method presented for Preparation of (S)-3-((1aR,7bS)-4-(2,6-dichloro-4-fluorophenyl)-1,1a,2,7b-tetrahydrocyclopropa[c]chromen-7-yl)-

2-(2,6-dichlorobenzamido)propanoic acid (81): 80 was separated into its 2 diastereomers by supercritical fluid chromatography using 20% EtOH co-solvent, at a flow rate of 60 mL/min, using an IC 21×250 mm column. The title compound was identified as the first eluting peak. MS (m/z) 568.0 [M+H]$^+$. 1H NMR (400 MHz, DMSO-d6) δ 12.85 (s, 1H), 9.20 (d, J=8.2 Hz, 1H), 7.57 (dt, J=8.4, 2.8 Hz, 2H), 7.50-7.36 (m, 3H), 7.01 (d, J=7.9 Hz, 1H), 6.78 (d, J=7.8 Hz, 1H), 4.80-4.68 (m, 1H), 4.11 (dd, J=10.8, 1.7 Hz, 1H), 3.86 (dd, J=10.7, 2.4 Hz, 1H), 3.33 (dd, J=14.4, 4.5 Hz, 1H), 3.05 (dd, J=14.4, 10.1 Hz, 1H), 2.19 (td, J=8.5, 4.5 Hz, 1H), 1.88 (q, J=8.0, 7.4 Hz, 1H), 1.16 (td, J=8.2, 4.2 Hz, 1H), 0.80 (q, J=4.6 Hz, 1H).

Preparation of (S)-3-((1aS,7bR)-4-(2,6-dichloro-4-fluorophenyl)-1,1a,2,7b-tetrahydrocyclopropa[c]chromen-7-yl)-2-(2,6-dichlorobenzamido)propanoic acid (82): 80 was separated into its 2 diastereomers by supercritical fluid chromatography using 20% EtOH co-solvent, at a flow rate of 60 mL/min, using an IC 21×250 mm column. The title compound was identified as the second eluting peak. MS (m/z) 568.0 [M+H]$^+$. 1H NMR (400 MHz, DMSO-d6) δ 12.83 (s, 1H), 9.12 (d, J=8.4 Hz, 1H), 7.57 (dq, J=8.7, 2.6 Hz, 2H), 7.47-7.33 (m, 3H), 6.98 (d, J=7.9 Hz, 1H), 6.78 (d, J=7.8 Hz, 1H), 4.89 (ddd, J=10.6, 8.3, 3.9 Hz, 1H), 4.08 (dd, J=10.9, 2.0 Hz, 1H), 3.89 (dd, J=10.8, 2.7 Hz, 1H), 3.39 (m, J=8.3 Hz, 1H), 3.04 (dd, J=14.4, 10.8 Hz, 1H), 2.22 (td, J=8.5, 4.6 Hz, 1H), 1.81 (td, J=8.2, 5.5 Hz, 1H), 1.18 (td, J=8.2, 4.3 Hz, 1H), 0.78 (q, J=4.7 Hz, 1H).

Example 83

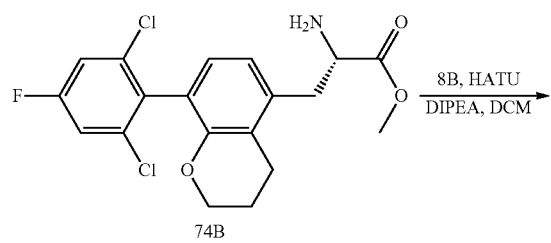

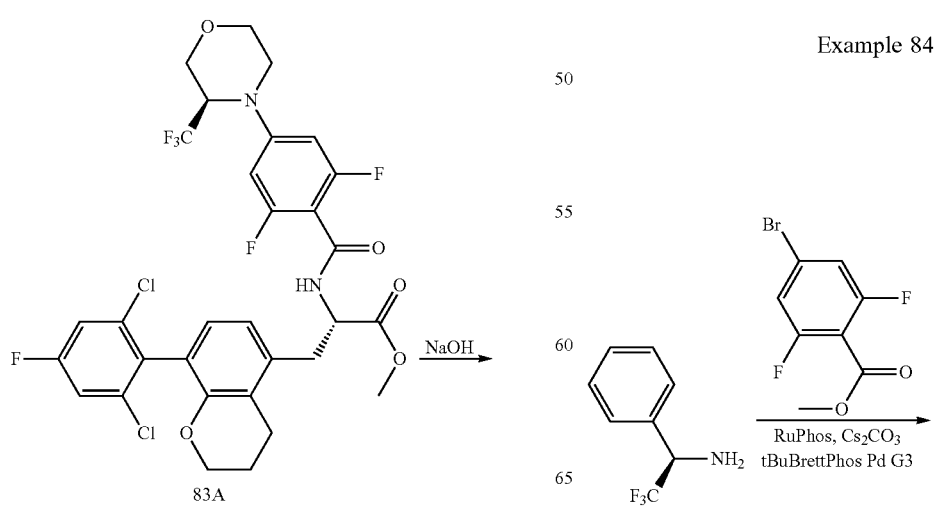

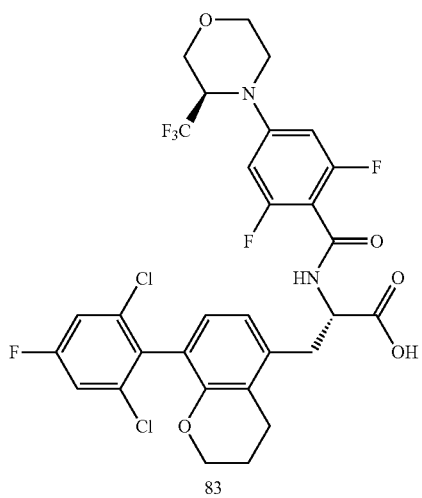

Synthesis of methyl (S)-3-(8-(2,6-dichloro-4-fluorophenyl)chroman-5-yl)-2-(2,6-difluoro-4-((R)-3-(trifluoromethyl) morpholino)benzamido)propanoate (83A): The title compound was prepared according to the method presented for the synthesis of compound 8F of Example 8 starting with 8B and 83A.

Synthesis of (S)-3-(8-(2,6-dichloro-4-fluorophenyl)chroman-5-yl)-2-(2,6-difluoro-4-((R)-3-(trifluoromethyl)morpholino)benzamido)propanoic acid (83): To a stirred solution of 83A (45 mg, 0.07 mmol) in THF (0.5 mL) was added a solution of NaOH (0.7 mL, 2M in water). The reaction mixture was allowed to stir for 30 min then concentrated under reduced pressure. The material was purified via reverse phase HPLC to afford the title compound. MS (m/z) 677.1 [M+H]$^+$. 1H NMR (400 MHz, DMSO-d6) δ 12.76 (s, 1H), 8.86 (d, J=8.0 Hz, 1H), 7.54 (dd, J=8.6, 0.5 Hz, 2H), 6.88 (d, J=7.9 Hz, 1H), 6.80 (d, J=7.8 Hz, 1H), 6.75 (d, J=11.6 Hz, 2H), 4.89 (dd, J=8.6, 3.6 Hz, 1H), 4.65-4.53 (m, 1H), 4.14 (d, J=12.7 Hz, 1H), 4.00 (t, J=5.3 Hz, 2H), 3.94 (dd, J=11.4, 3.8 Hz, 1H), 3.78-3.67 (m, 1H), 3.60-3.48 (m, 1H), 3.22 (t, J=12.1 Hz, 1H), 3.11 (dd, J=14.8, 4.4 Hz, 1H), 2.91 (dd, J=14.7, 10.2 Hz, 1H), 2.77 (q, J=6.4 Hz, 2H), 1.92 (q, J=5.3 Hz, 2H).

Example 84

233

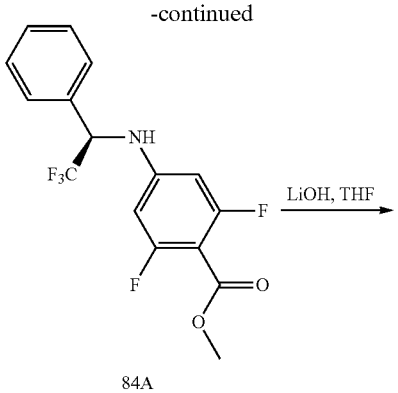

84A

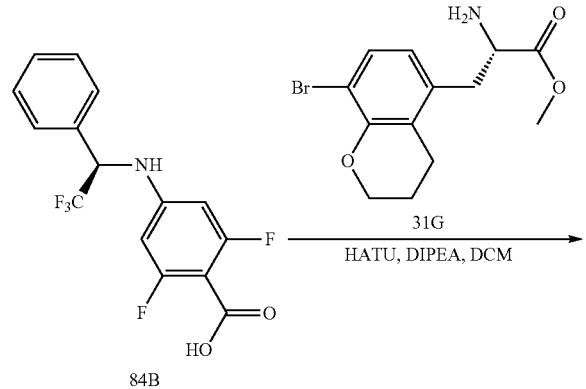

84B

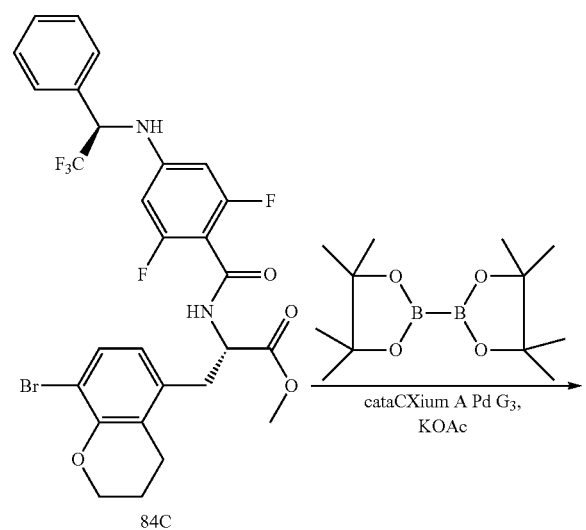

84C

234

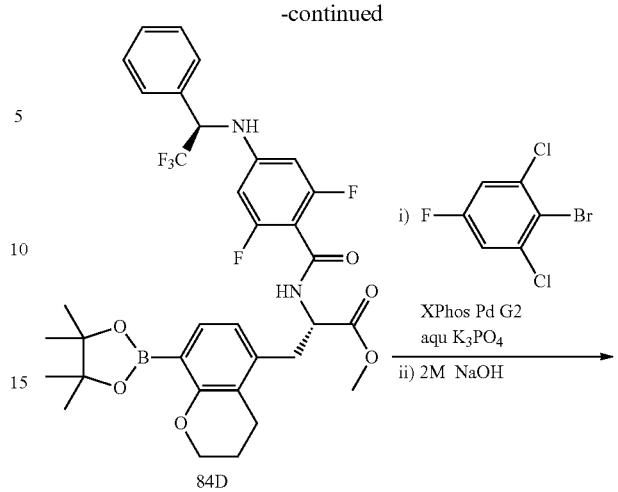

84D

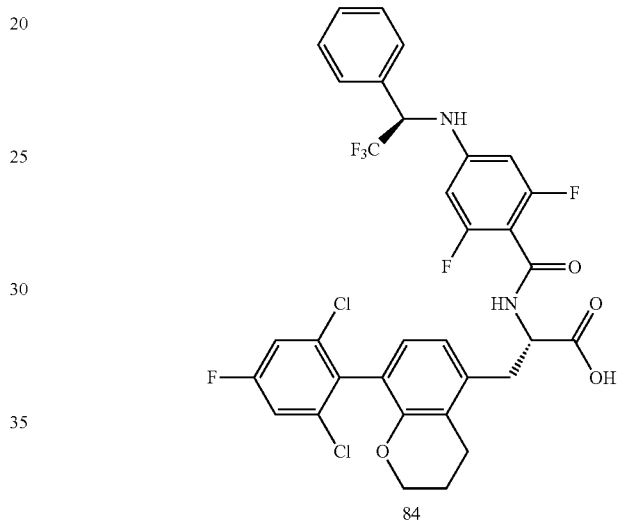

84

Synthesis of methyl (R)-2,6-difluoro-4-((2,2,2-trifluoro-1-phenylethyl)amino)benzoate (84A): The title compound was prepared according to the method presented for the synthesis of compound 8A in Example 8 starting with (R)-2,2,2-trifluoro-1-phenylethan-1-amine and methyl 4-bromo-2,6-difluorobenzoate.

Synthesis of (R)-2,6-difluoro-4-((2,2,2-trifluoro-1-phenylethyl)amino)benzoic acid (84B): The title compound was prepared according to the method presented for the synthesis of compound 8B in Example 8 starting with 84A.

Synthesis of methyl (S)-3-(8-bromochroman-5-yl)-2-(2,6-difluoro-4-(((R)-2,2,2-trifluoro-1-phenylethyl)amino)benzamido)propanoate (84C): The title compound was prepared according to the method presented for the synthesis of compound 8F in Example 8 starting with 31G and 84B.

Synthesis of methyl (S)-2-(2,6-difluoro-4-(((R)-2,2,2-trifluoro-1-phenylethyl)amino) benzamido)-3-(8-(4,4,5,5-tetramethyl-1,3,2-dioxaborolan-2-yl)chroman-5-yl)propanoate (84D): The title compound was prepared according to the method presented for the synthesis of compound 1G in Example 1 starting with 84C.

Synthesis of (S)-3-(8-(2,6-dichloro-4-fluorophenyl)chroman-5-yl)-2-(2,6-difluoro-4-(((R)-2,2,2-trifluoro-1-phenylethyl)amino)benzamido)propanoic acid (84): To a microwave vial was added 84D (150 mg, 0.26 mmol), 2-bromo-1,3-dichloro-5-fluorobenzene (125 mg, 0.51 mmol), XPhos Pd G2 (20 mg, 0.026 mmol), and aq. $K_3PO_4$ (0.89 mL, 1M)

in DME (1.3 mL). The reaction mixture was heated in a microwave at 130° C. for 30 min. The mixture was allowed to cool to RT and 2 M aq. NaOH (1 mL) was added. After 30 min, the pH was adjusted to ~3 with 1M HCl. EtOAc was added to the reaction mixture. The aqueous layer was separated and extracted with EtOAc (2×). The combined organics were washed dried over anhydrous Na$_2$SO$_4$, and concentrated under reduced pressure. The material was purified via reverse phase HPLC to afford the title compound. MS (m/z) 697.1 [M+H]$^+$. 1H NMR (400 MHz, DMSO-d6) δ 8.72 (d, J=7.9 Hz, 1H), 7.62-7.45 (m, 5H), 7.45-7.30 (m, 3H), 6.85 (d, J=7.9 Hz, 1H), 6.79 (d, J=7.8 Hz, 1H), 6.54 (d, J=11.2 Hz, 2H), 5.75-5.63 (m, 1H), 4.59-4.47 (m, 1H), 3.99 (t, J=5.3 Hz, 2H), 3.08 (dd, J=14.6, 4.3 Hz, 1H), 2.87 (dd, J=14.7, 10.2 Hz, 1H), 2.74 (q, J=6.0 Hz, 2H), 1.90 (q, J=5.6 Hz, 2H).

Example 85

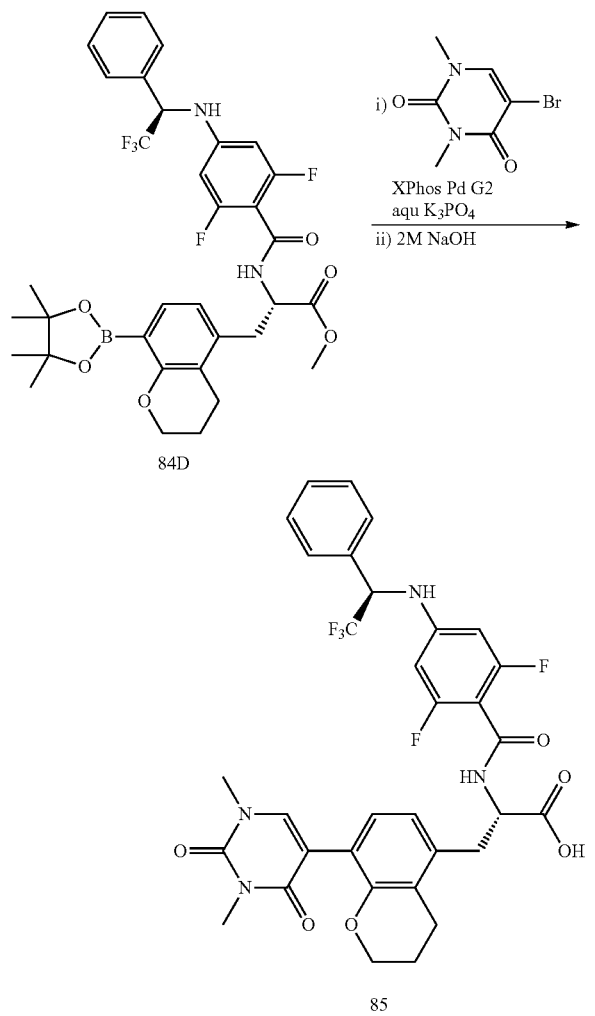

85

Synthesis of (S)-2-(2,6-difluoro-4-(((R)-2,2,2-trifluoro-1-phenylethyl)amino) benzamido)-3-(8-(1,3-dimethyl-2,4-dioxo-1,2,3,4-tetrahydropyrimidin-5-yl)chroman-5-yl) propanoic acid (85): The title compound was prepared according to the method presented for the synthesis of compound 84 of Example 84 starting with 5-bromo-1,3-dimethylpyrimidine-2,4(1H,3H)-dione and 84D. MS (m/z) 673.2 [M+H]$^+$. 1H NMR (400 MHz, DMSO-d6) δ 8.71 (d, J=7.9 Hz, 1H), 7.65 (s, 1H), 7.55 (dd, J=17.6, 8.7 Hz, 3H), 7.49-7.33 (m, 3H), 6.87 (d, J=7.8 Hz, 1H), 6.75 (d, J=7.9 Hz, 1H), 6.55 (d, J=11.4 Hz, 2H), 5.78-5.62 (m, 1H), 4.51-4.38 (m, 1H), 4.01 (t, J=5.2 Hz, 2H), 3.31 (s, 3H), 3.19 (s, 3H), 3.04 (dd, J=14.5, 4.4 Hz, 1H), 2.82 (dd, J=14.5, 9.9 Hz, 1H), 2.76-2.64 (m, 1H), 1.90 (d, J=2.6 Hz, 2H).

Example 86

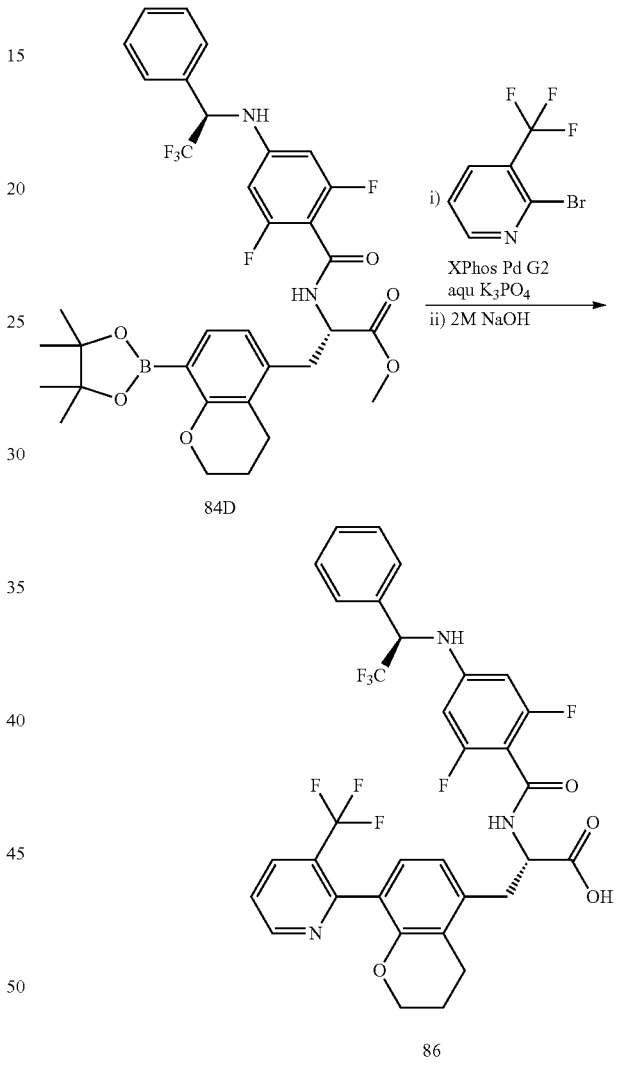

86

Synthesis of (S)-2-(2,6-difluoro-4-(((R)-2,2,2-trifluoro-1-phenylethyl)amino) benzamido)-3-(8-(3-(trifluoromethyl)pyridin-2-yl)chroman-5-yl)propanoic acid (86): The title compound was prepared according to the method presented for the synthesis of compound 84 of Example 84 starting with 2-bromo-3-(trifluoromethyl)pyridine and 84D. MS (m/z) 680.2 [M+H]$^+$. 1H NMR (400 MHz, DMSO-d6) δ 8.88-8.78 (m, 1H), 8.78-8.66 (m, 1H), 8.26-8.14 (m, 1H), 7.64-7.55 (m, 3H), 7.51 (d, J=9.9 Hz, 1H), 7.47-7.30 (m, 3H), 6.92-6.73 (m, 2H), 6.55 (d, J=11.6 Hz, 2H), 5.69 (dd, J=9.9, 7.6 Hz, 1H), 4.46 (d, J=11.4 Hz, 1H), 3.89 (d, J=3.9 Hz, 0H), 3.20-3.00 (m, 1H), 2.98-2.80 (m, 1H), 2.75 (s, 2H), 1.89 (s, 2H).

Example 87

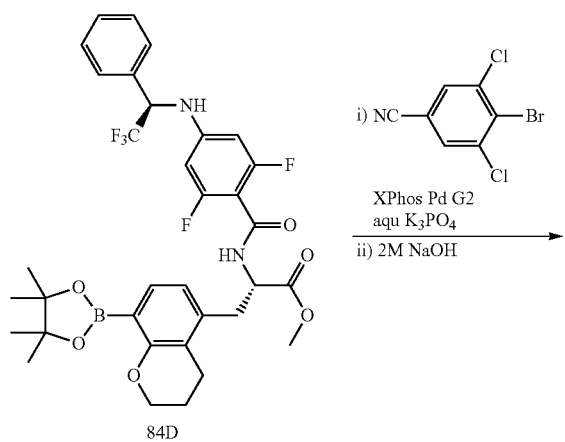

Example 88

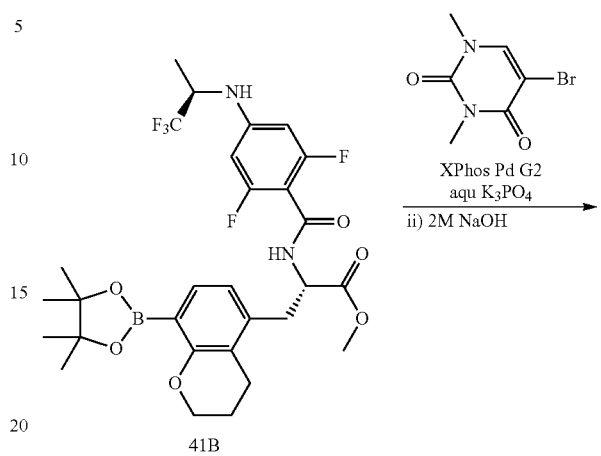

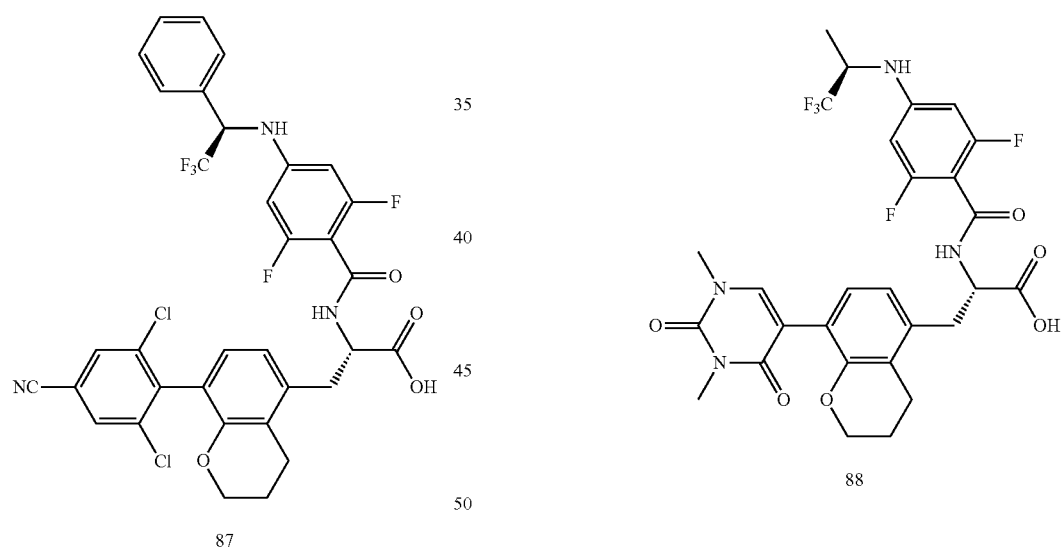

Synthesis of (S)-3-(8-(2,6-dichloro-4-cyanophenyl)chroman-5-yl)-2-(2,6-difluoro-4-(((R)-2,2,2-trifluoro-1-phenylethyl)amino)benzamido)propanoic acid (87): The title compound was prepared according to the method presented for the synthesis of compound 84 of Example 84 starting with 4-bromo-3,5-dichlorobenzonitrile and 84D. MS (m/z) 704.2 [M+H]$^+$. 1H NMR (400 MHz, DMSO-d6) δ 8.72 (d, J=8.0 Hz, 1H), 8.17-8.07 (m, 1H), 7.56 (d, J=7.2 Hz, 2H), 7.50 (d, J=10.2 Hz, 1H), 7.46-7.30 (m, 3H), 6.88 (d, J=7.9 Hz, 1H), 6.83 (d, J=7.8 Hz, 1H), 6.54 (d, J=11.2 Hz, 2H), 5.76-5.59 (m, 1H), 4.61-4.46 (m, 1H), 3.99 (t, J=5.2 Hz, 2H), 3.09 (dd, J=14.7, 4.3 Hz, 1H), 2.87 (dd, J=14.7, 10.2 Hz, 1H), 2.75 (q, J=6.2 Hz, 2H), 1.98-1.81 (m, 2H).

Synthesis of (S)-2-(2,6-difluoro-4-(((R)-1,1,1-trifluoropropan-2-yl)amino)benzamido)-3-(8-(1,3-dimethyl-2,4-dioxo-1,2,3,4-tetrahydropyrimidin-5-yl)chroman-5-yl)propanoic acid (88): The title compound was prepared according to the method presented for the synthesis of compound 84 of Example 84 starting with 5-bromo-1,3-dimethylpyrimidine-2,4(1H,3H)-dione and 41B. MS (m/z) 611.2 [M+H]$^+$. 1H NMR (400 MHz, DMSO-d6) δ 8.70 (d, J=7.9 Hz, 1H), 7.65 (s, 1H), 6.86 (dd, J=17.9, 8.5 Hz, 2H), 6.78 (d, J=7.9 Hz, 1H), 6.43 (d, J=11.4 Hz, 2H), 4.59-4.37 (m, 2H), 4.09-3.96 (m, 1H), 3.31 (s, 3H), 3.19 (s, 3H), 3.06 (dd, J=14.6, 4.4 Hz, 1H), 2.86 (dd, J=14.5, 9.7 Hz, 1H), 2.74 (q, J=6.8 Hz, 2H), 1.97-1.84 (m, 2H), 1.71 (s, 0H), 1.27 (d, J=6.7 Hz, 3H).

Example 89

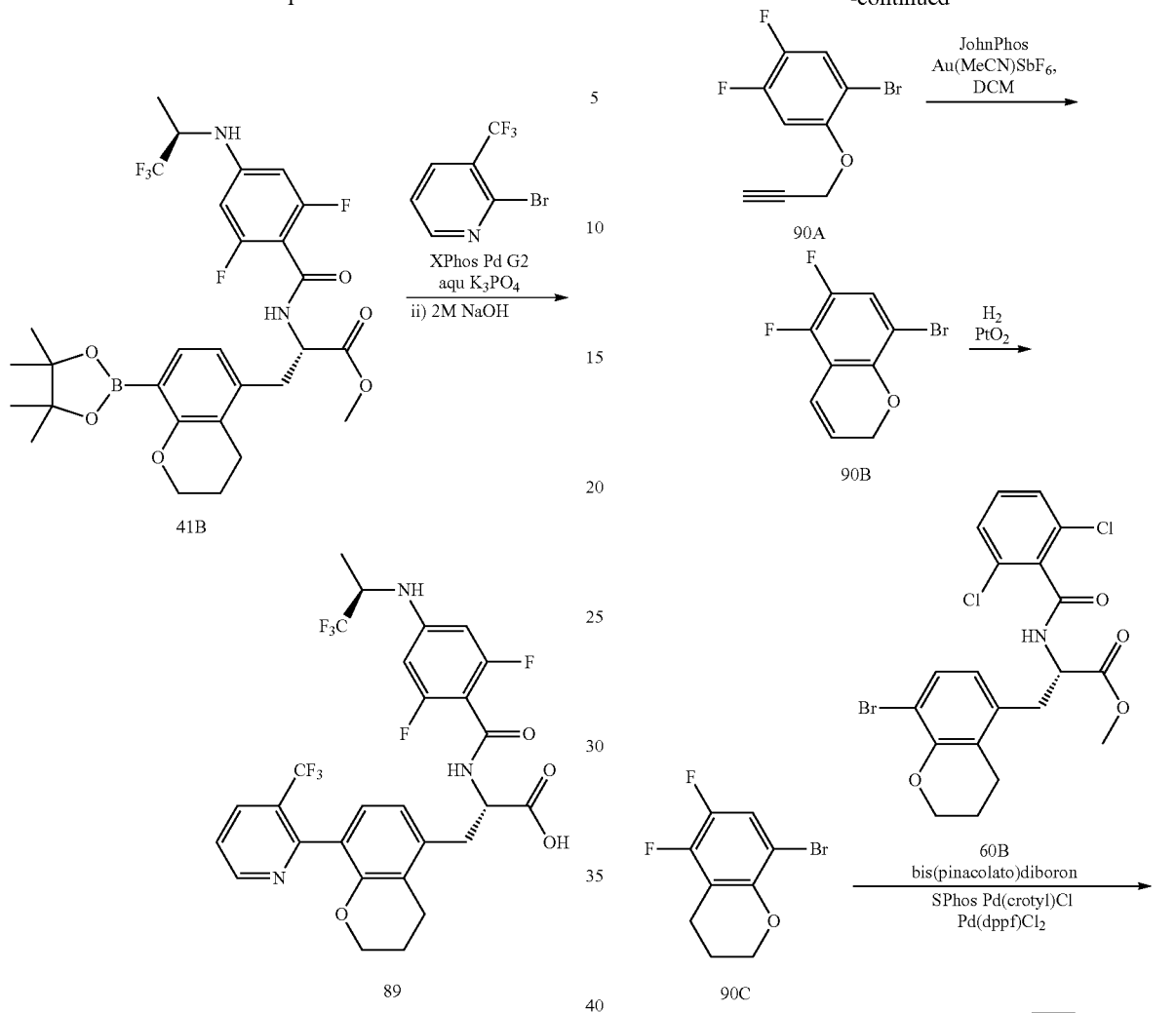

Synthesis of (S)-2-(2,6-difluoro-4-(((R)-1,1,1-trifluoropropan-2-yl)amino)benzamido)-3-(8-(3-(trifluoromethyl)pyridin-2-yl)chroman-5-yl)propanoic acid (89): The title compound was prepared according to the method presented for the synthesis of compound 84 of Example 84 starting with 2-bromo-3-(trifluoromethyl)pyridine and 41B. MS (m/z) 618.2 [M+H]$^+$. 1H NMR (400 MHz, DMSO-d6) δ 8.82 (d, J=4.9 Hz, 1H), 8.80-8.62 (m, 1H), 8.20 (dd, J=8.1, 1.7 Hz, 1H), 7.66-7.51 (m, 1H), 6.94-6.79 (m, 4H), 6.42 (dd, J=11.0, 2.8 Hz, 3H), 4.51 (d, J=7.5 Hz, 3H), 4.13-3.94 (m, 1H), 3.23-2.99 (m, 1H), 2.99-2.82 (m, 1H), 2.82-2.60 (m, 2H), 1.90 (s, 3H), 1.26 (d, J=6.7 Hz, 4H).

Example 90

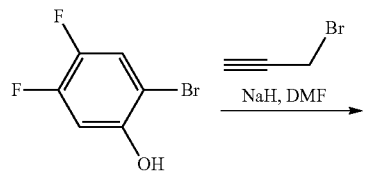

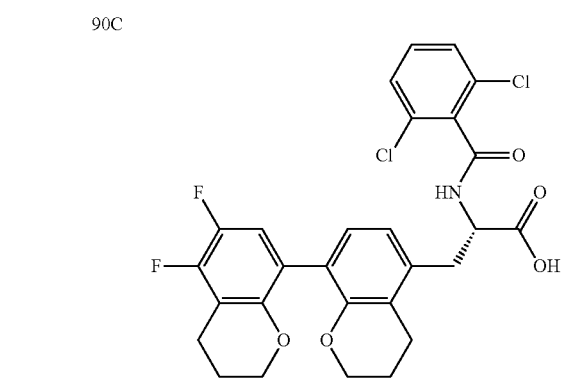

Synthesis of 1-bromo-2-(ethynyloxy)-4,5-difluorobenzene (90A): To a solution of 2-bromo-4,5-difluorophenol (1 g, 4.8 mmol) in DMF (5 mL) was added 60% NaH in mineral oil (230 mg, 4.8 mmol) at RT. After stirring for 10 min, added 1-bromoprop-1-yne (0.5 mL, 5.7 mmol) and stirring continued for 10 min. EtOAc and water was added to the reaction mixture. The aqueous layer was separated and extracted with EtOAc (2×). The combined organics were dried over anhydrous Na$_2$SO$_4$, and concentrated under reduced pressure. The material was purified on silica gel eluting with EtOAc in hexanes to give the title compound.

Synthesis of 8-bromo-5,6-difluoro-2H-chromene (90B): The title compound was prepared according to the method presented for the synthesis of compound 77B in Example 77 starting with 90A.

Synthesis of 8-bromo-5,6-difluoro-2H-chromene (90C): To a solution of 90B (242 mg, 0.98 mmol) in EtOAc (5 mL) in a flask that was fitted with a balloon under $H_2$ was added $PtO_2$ (22 mg, 0.098 mmol). The reaction was stirred for 4 hrs. The reaction mixture was filtered through Celite and concentrated to give the title compound.

Synthesis of (S)-2-(2,6-dichlorobenzamido)-3-(5',6'-difluoro-[8,8'-bichroman]-5-yl)propanoic acid (90): Combined 90C (100 mg, 0.40 mmol), 60B (235 mg, 0.48 mmol), bis(pinacolato)diboron (102 mg, 0.40 mmol), SPhos Pd(crotyl)Cl (49 mg, 0.08 mmol) in dioxane (4 mL). Purged solution with $N_2$ for 10 min and then added dichloro[1,1'-bis(dialkyl/diaryl phosphino)ferrocene]palladium(II) (49 mg, 0.060 mmol) and water (1 mL). The reaction mixture was heated to 105° C. for 3 hrs. The material was purified via reverse phase HPLC to afford the title compound. MS (m/z) 562.1. [M+H]$^+$. 1H NMR (400 MHz, DMSO-d6) δ 9.13 (d, J=8.4 Hz, 1H), 7.49-7.32 (m, 3H), 6.92 (dd, J=11.1, 9.3 Hz, 1H), 6.83 (q, J=7.8 Hz, 2H), 4.68 (td, J=9.0, 4.9 Hz, 1H), 4.01 (dt, J=7.5, 4.9 Hz, 4H), 3.08 (dd, J=14.6, 5.0 Hz, 1H), 2.97-2.59 (m, 6H), 1.99-1.74 (m, 2H).

Example 91

Synthesis of (S)-3-(8-(2,6-dichloro-4-cyanophenyl)chroman-5-yl)-2-(2,6-difluoro-4-(((R)-1,1,1-trifluoropropan-2-yl)amino)benzamido)propanoic acid (91): The title compound was prepared according to the method presented for the synthesis of compound 84 of Example 84 starting with 4-bromo-3,5-dichlorobenzonitrile and 41B. MS (m/z) 642.1 [M+H]$^+$. 1H NMR (400 MHz, DMSO-d6) δ 8.72 (d, J=8.0 Hz, 1H), 8.21-8.03 (m, 2H), 6.91 (d, J=7.9 Hz, 1H), 6.87-6.77 (m, 2H), 6.41 (d, J=11.3 Hz, 2H), 4.64-4.41 (m, 2H), 4.00 (t, J=5.3 Hz, 2H), 3.11 (dd, J=14.8, 4.4 Hz, 1H), 2.91 (dd, J=14.7, 10.1 Hz, 1H), 2.77 (q, J=6.5 Hz, 2H), 1.92 (q, J=5.7 Hz, 2H), 1.26 (d, J=6.7 Hz, 3H).

Example 92

Synthesis of methyl 2,6-difluoro-4-(methylsulfonamido)benzoate (92A): To a stirred solution of methyl 4-amino-2,6-difluorobenzoate (500 mg, 0.3 mmol) in DCM was added methyl sulfonyl chloride (0.31 ml, 0.4 mmol), and pyridine (1.08 mL, 1.3 mmol). The reaction was stirred for at RT overnight. The reaction mixture was diluted with EA, washed with 1 M HCl, sodium bicarbonate, brine, and dried, filtered, and concentrated to afford the title compound.

Synthesis of 2,6-difluoro-4-(methylsulfonamido)benzoic acid (92B): To a stirred solution of 92A (534 mg, 0.2 mmol) in THF was added aqueous LiOH (5 mL, 2 M). The mixture was allowed to stir at RT for 2 days, diluted with water and acidified with 1 M HCl. The material was extracted with DCM, dried, filtered, and concentrated under reduced pressure. The material was purified by silica gel chromatography using EA/hexanes as eluent to afford the title compound.

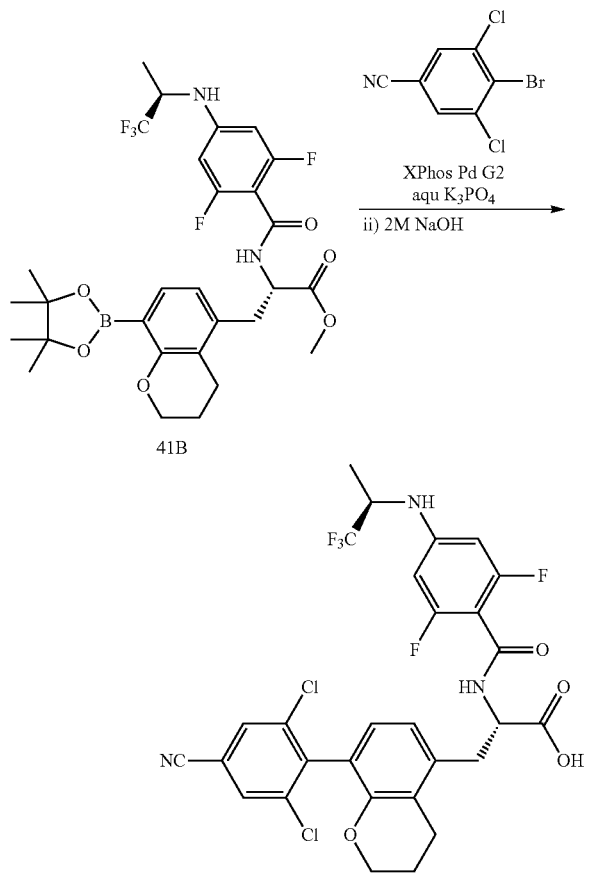

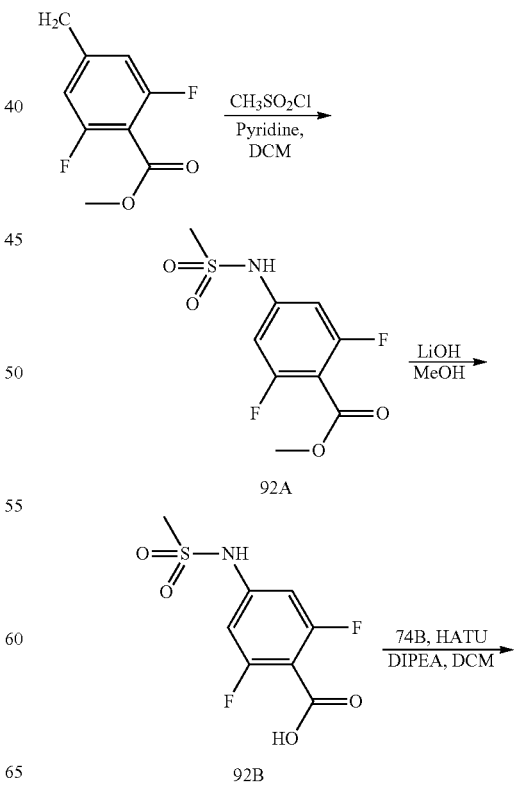

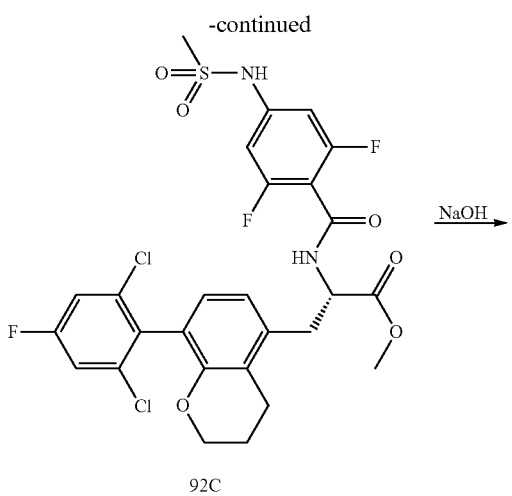

92C

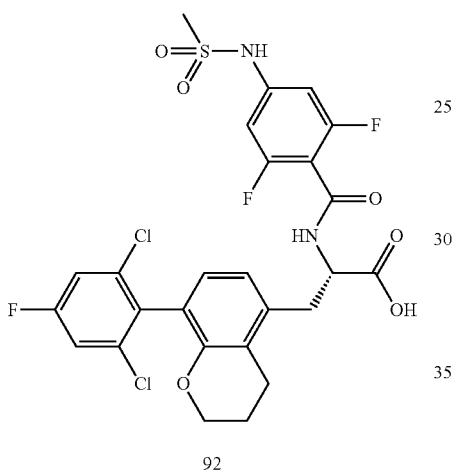

92

Synthesis of methyl (S)-3-(8-(2,6-dichloro-4-fluorophenyl)chroman-5-yl)-2-(2,6-difluoro-4-(methylsulfonamido)benzamido)propanoate (92C): The title compound was prepared according to the method presented for the synthesis of compound 8F in Example 8 starting with 74B and 92B.

Synthesis of (S)-3-(8-(2,6-dichloro-4-fluorophenyl)chroman-5-yl)-2-(2,6-difluoro-4-(methylsulfonamido)benzamido)propanoic acid (92): To a stirred solution of 92C (23 mg, 0.04 mmol) in THF (0.5 mL) was added a solution of aq. NaOH (0.4 mL, 2M). The reaction mixture was allowed to stir for 30 min then concentrated under reduced pressure. The material was purified via reverse phase HPLC to afford the title compound. MS (m/z) 617.0 [M+H]$^+$. 1H NMR (400 MHz, DMSO-d6) δ 10.43 (s, 1H), 9.05 (d, J=8.0 Hz, 1H), 7.54 (d, J=8.6 Hz, 2H), 6.93-6.73 (m, 4H), 4.61 (ddd, J=10.2, 8.0, 4.4 Hz, 1H), 3.99 (t, J=5.3 Hz, 2H), 3.12 (m, 4H), 2.90 (dd, J=14.8, 10.2 Hz, 1H), 2.76 (d, J=5.8 Hz, 1H), 1.92 (q, J=5.7 Hz, 2H).

Example 93

Synthesis of 2-bromo-1,3-dimethoxy-5-((4-(trifluoromethoxy)phenyl)ethynyl) benzene (93A): To a solution of 2-bromo-5-iodo-1,3-dimethoxybenzene (155 mg, 0.45 mmol), CuI (9 mg, 0.045 mmol), bis(triphenylphosphine)palladium(II) dichloride (16 mg, 0.023 mmol) in THF (1 mL) was added 1-ethynyl-4-(trifluoromethoxy)benzene (84 mg, 0.45 mmol) followed by DIPEA (0.24 mL, 1.4 mmol). The reaction vessel was sealed and heated to 40° C. for 16 hrs. The reaction was concentrated under reduced pressure. The material was purified by silica gel chromatography using 0-50% EtOAc in hexanes to afford the title compound.

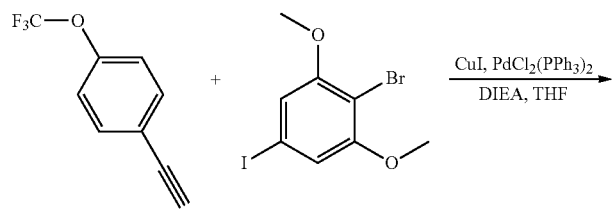

-continued
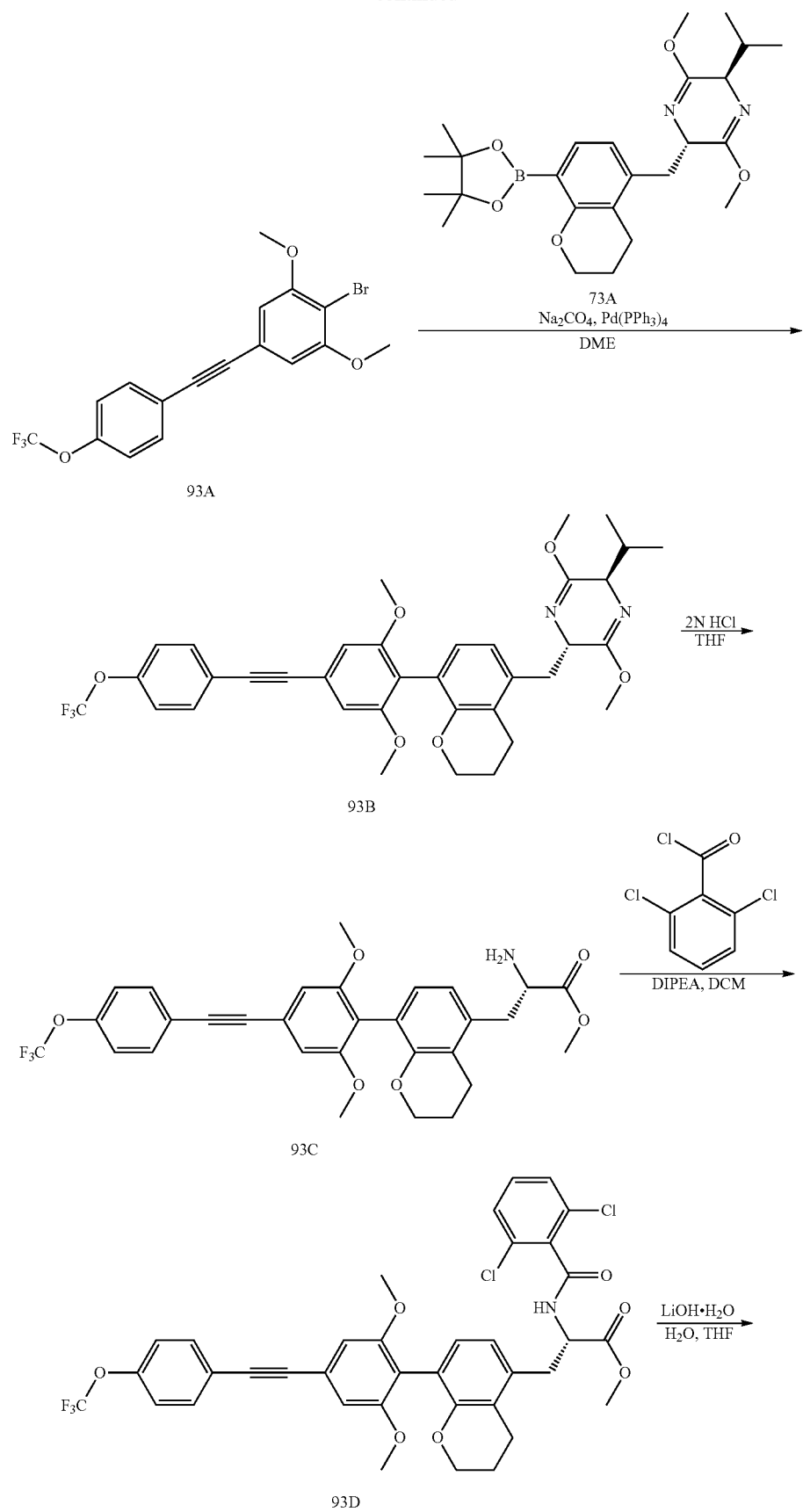

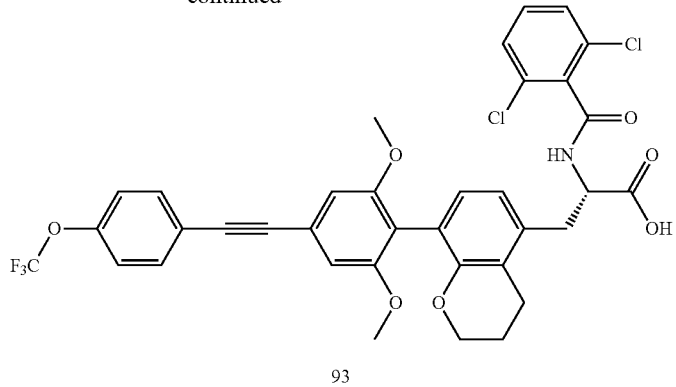

93

Synthesis of (2S,5S)-2-((8-(2,6-dichloro-4-fluorophenyl)chroman-5-yl)methyl)-5-isopropyl-3,6-dimethoxy-2,5-dihydropyrazine (93B): The title compound was prepared according to the method presented for the synthesis of compound 1H of Example 1 starting with 78A and 93B.

Synthesis of methyl (S)-2-amino-3-(8-(2,6-dimethoxy-4-((4-(trifluoromethoxy) phenyl)ethynyl)phenyl)chroman-5-yl)propanoate (93C): The title compound was prepared according to the method presented for the synthesis of compound 4C of Example 4 starting with 93B.

Synthesis of methyl (S)-2-(2,6-dichlorobenzamido)-3-(8-(2,6-dimethoxy-4-((4-(trifluoromethoxy)phenyl)ethynyl)phenyl)chroman-5-yl)propanoate (93D): The title compound was prepared according to the method presented for the synthesis of compound 1F of Example 1 starting with 2,6-dichlorobenzoyl chloride and 93D.

Synthesis of (S)-2-(2,6-dichlorobenzamido)-3-(8-(2,6-dimethoxy-4-((4-(trifluoromethoxy)phenyl)ethynyl)phenyl)chroman-5-yl)propanoic acid (93): The title compound was prepared according to the method presented for the synthesis of compound 1 of Example 1 starting with 93D. MS (m/z) 714.3 [M+H]$^+$. $^1$H NMR (400 MHz, DMSO-d6) δ 12.79 (s, 1H), 9.13 (d, J=8.5 Hz, 1H), 7.70 (d, J=8.7 Hz, 1H), 7.50-7.32 (m, 3H), 6.86 (d, J=1.2 Hz, 2H), 6.76 (dd, J=36.4, 7.8 Hz, 2H), 4.69 (s, 2H), 3.93 (d, J=5.1 Hz, 2H), 3.67 (d, J=2.6 Hz, 6H), 3.07 (s, 1H), 2.89 (s, 1H), 2.77 (s, 1H), 1.89 (s, 2H).

Example 94

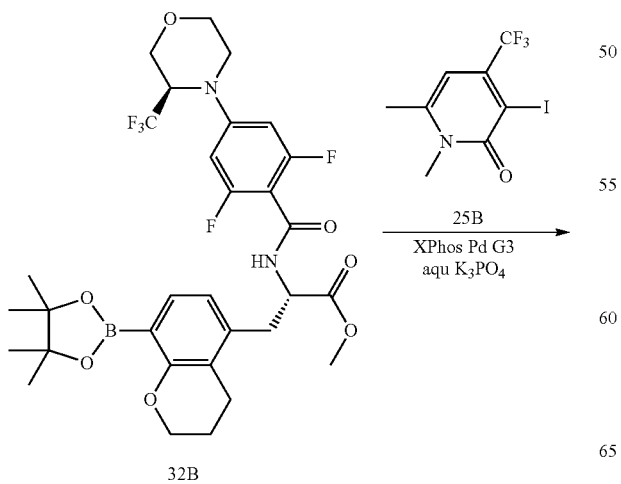

32B

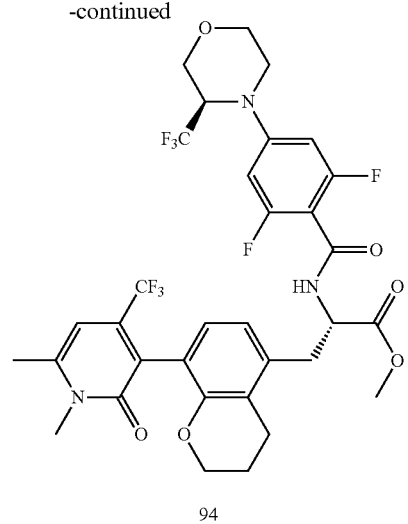

94

Synthesis of methyl (S)-2-(2,6-difluoro-4-((R)-3-(trifluoromethyl)morpholino) benzamido)-3-(8-(1,6-dimethyl-2-oxo-4-(trifluoromethyl)-1,2-dihydropyridin-3-yl)chroman-5-yl)propanoate (94): The title compound was prepared according to the method presented for the synthesis of compound 13K of Example 13 starting with 25B and 32B. MS (m/z) 718.3, [M+H]$^+$. $^1$H NMR (400 MHz, DMSO-d6) δ 9.02 (dd, J=7.5, 3.7 Hz, 1H), 6.83-6.68 (m, 4H), 6.43 (d, J=0.9 Hz, 1H), 4.92 (dd, J=8.7, 3.6 Hz, 1H), 4.61 (dq, J=8.4, 6.2 Hz, 1H), 4.17 (d, J=12.7 Hz, 1H), 4.00-3.87 (m, 2H), 3.75 (d, J=13.0 Hz, 1H), 3.61 (d, J=7.1 Hz, 3H), 3.60-3.51 (m, 2H), 3.47 (s, 3H), 3.42 (d, J=3.2 Hz, 1H), 3.30-3.20 (m, 1H), 3.11-2.90 (m, 2H), 2.80-2.66 (m, 2H), 2.46 (s, 3H), 1.95-1.84 (m, 2H).

Example 95

Synthesis of methyl 4-bromo-3-((2-methylbut-3-yn-2-yl)oxy)benzoate (95A): To a flame dried flask containing methyl 4-bromo-3-hydroxybenzoate (2.3 g, 10 mmol) and ACN (100 mL) at 0° C. was added 1,8-diazabicyclo[5.4.0]undec-7-ene (1.94 mL, 13 mmol) and copper(II) chloride (13 mg, 0.1 mmol). 3-Chloro-3-methylbut-1-yne (1.33 g, 13 mmol) was then added and the mixture was stirred for 16h, concentrated and chromatographed on silica gel eluting with EtOAc in hexanes to afford the title compound.

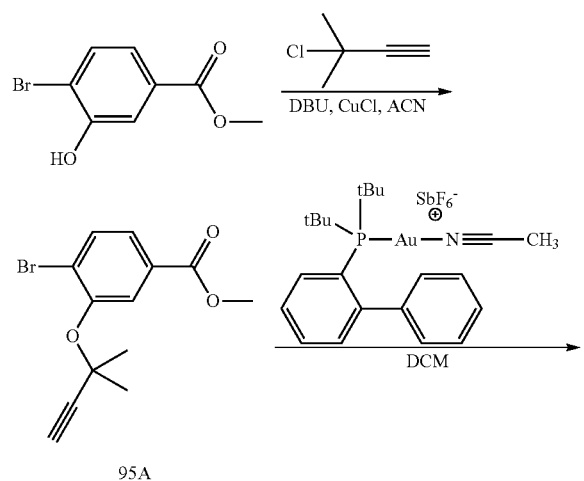
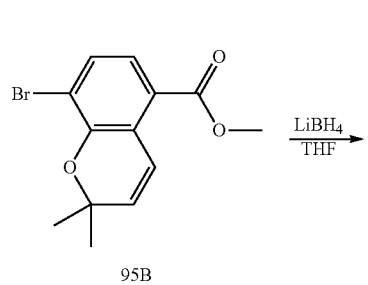
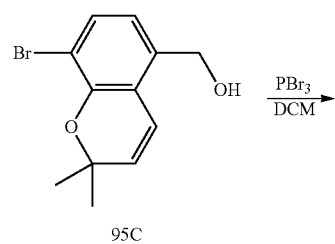
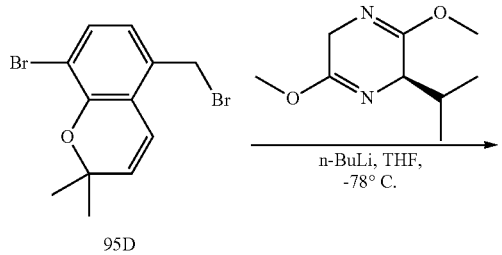
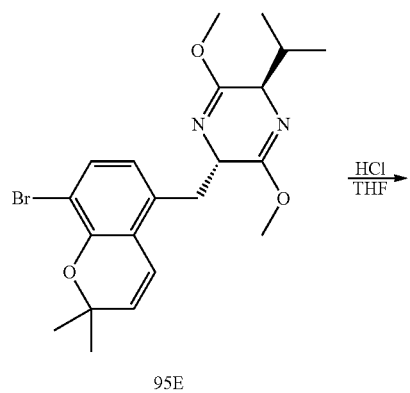
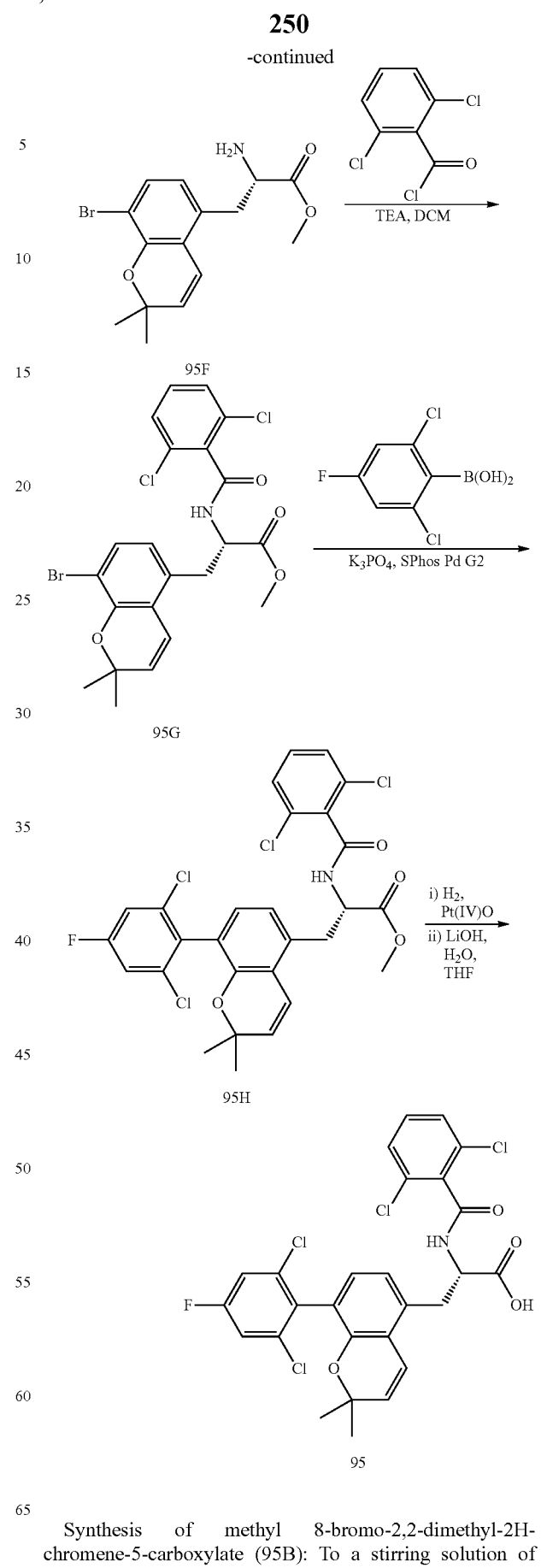
Synthesis of methyl 8-bromo-2,2-dimethyl-2H-chromene-5-carboxylate (95B): To a stirring solution of methyl 4-bromo-3-((2-methylbut-3-yn-2-yl)oxy)benzoate (3 g, 10.1 mmol) in DCM (50 mL) was added (acetonitrile)[(2-biphenyl)di-tert-butylphosphine]gold(I) hexafluoro antimonate (0.39 g, 0.5 mmol). After 2 hours the mixture was concentrated and chromatographed on silica gel eluting with EtOAc in hexanes (0-40%) to afford the title compound.

Synthesis of (8-bromo-2,2-dimethyl-2H-chromen-5-yl)methanol (95C): To a stirring solution of methyl 8-bromo-2,2-dimethyl-2H-chromene-5-carboxylate (600 mg, 2 mmol) and THF (5 mL) at 0° C. was added lithium borohydride (5 mL, 5 mmol, 1 N) and the mixture was stirred overnight. 1 mL of a concentrated Rochelle's salt solution was added and the mixture was stirred for an additional 1 h. The mixture was filtered washed with EtOAc and the eluent was concentrated and the residue was chromatographed on silica gel eluting with EtOAc in hexanes (0-60%) to afford the title compound.

Synthesis of 8-bromo-5-(bromomethyl)-2,2-dimethyl-2H-chromene (95D): To a stirring solution of (8-bromo-2,2-dimethyl-2H-chromen-5-yl)methanol (527 mg, 1.96 mmol) in DCM (3 mL) was added phosphorous tribromide (1N in DCM, 1.96 mL, 1.96 mmol) and the mixture was stirred ON, loaded directly onto silica gel and chromatographed eluting with EtOAc in hexanes (0-20%) to afford the title compound.

Synthesis of (2S,5R)-2-((8-bromo-2,2-dimethyl-2H-chromen-5-yl)methyl)-5-isopropyl-3,6-dimethoxy-2,5-dihydropyrazine (95E): To a flame dried vial containing (R)-2,5-dihydro-3,6-dimethoxy-2-isopropylpyrazine (1.01 ml, 5.66 mmol) and THF (28 mL) at −78° C. was added n-butyllithium 2.5 M in hexanes (2.26 ml, 5.66 mmol) dropwise. The reaction was stirred for 20 minutes when 8-bromo-5-(bromomethyl)-2,2-dimethyl-2H-chromene was added (1.044 g, 3.1 mmol) and the mixture was stirred for 1h at −78° C. and ammonium chloride (sat) was added and the mixture was extracted with EtOAc, concentrated, and the residue was chromatographed on silica gel eluting with EtOAc in hexanes (0-10%) to afford the title compound.

Synthesis of methyl (S)-2-amino-3-(8-bromo-2,2-dimethyl-2H-chromen-5-yl)propanoate (95F)

To a stirred solution of (2S,5R)-2-((8-bromo-2,2-dimethyl-2H-chromen-5-yl)methyl)-5-isopropyl-3,6-dimethoxy-2,5-dihydropyrazine and THF (20 mL) was added 2 N HCl (11.5 mL, 23 mmol) and the mixture was stirred for 2h, diluted with EtOAc and treated with sodium bicarbonate (sat) until basic. The organic layer was concentrated and chromatographed on silica gel eluting with MeOH in dichloromethane (0-30%) to afford the title compound.

Synthesis of methyl (S)-3-(8-bromo-2,2-dimethyl-2H-chromen-5-yl)-2-(2,6-dichlorobenzamido)propanoate (95G): To a stirred solution methyl (S)-2-amino-3-(8-bromo-2,2-dimethyl-2H-chromen-5-yl)propanoate (360 mg, 1.06 mmol) and DCM (5 mL) at 0° C. was added N-ethyl-N-isopropylpropan-2-amine (0.37 mL, 2.12 mmol), and 2,6-dichlorobenzoyl chloride (0.15 ml, 1.06 mmol) dropwise. The mixture was stirred for 4h and sodium bicarbonate (sat, 1 mL) was added and the organic layer was concentrated and chromatographed on silica gel eluting with EtOAc in hexanes (0-100%) to afford the title compound.

Synthesis of (S)-3-(8-(2,6-dichloro-4-fluorophenyl)-2,2-dimethylchroman-5-yl)-2-(2,6-dichlorobenzamido)propanoic acid (95): A vial containing THF (5 mL) and methyl (S)-3-(8-(2,6-dichloro-4-fluorophenyl)-2,2-dimethyl-2H-chromen-5-yl)-2-(2,6-dichlorobenzamido) propanoate (129 mg, 0.216 mmol) was purged with nitrogen and added platinum (IV) oxide (10 mg, 0.044 mmol). The mixture was then sparged with hydrogen gas and placed under a balloon of hydrogen for 4 h. Lithium hydroxide (1N, 0.5 mL, 0.5 mmol) was then added and the mixture stirred an additional 2h. The mixture was concentrated, TFA was added and the mixture was again concentrated under reduced pressure and chromatographed on reversed phase eluting with ACN and water containing 0.4% TFA to afford the title compound. MS (m/z) 586.0 [M+H]⁺. 1H NMR (400 MHz, DMSO-d6) δ 12.79 (s, 1H), 9.14 (d, J=8.4 Hz, 1H), 8.81 (d, J=8.4 Hz, 0H), 7.59-7.48 (m, 2H), 7.48-7.32 (m, 3H), 6.89 (d, J=7.8 Hz, 1H), 6.78 (d, J=7.7 Hz, 1H), 4.76 (ddd, J=10.6, 8.4, 4.2 Hz, 1H), 3.16 (dd, J=14.7, 4.2 Hz, 1H), 2.92 (dd, J=14.7, 10.6 Hz, 1H), 2.85-2.74 (m, 2H), 1.78 (dq, J=13.5, 6.9 Hz, 2H), 1.13 (d, J=2.0 Hz, 6H).

Example 96

Synthesis of ethyl 9-bromo-3,4-dihydro-2H-benzo[b][1,4]dioxepine-6-carboxylate (96A): To a stirred solution of ethyl 4-bromo-2,3-dihydroxybenzoate (1.10 g, 4.21 mmol) and potassium carbonate (2.91 g, 21.1 mmol) in DMF (10.5 mL) was added 1,3-dibromopropane (1.28 g, 6.23 mmol) at room temperature. The reaction mixture was allowed to stir at 125° C. for 16 hrs then quenched by the addition of water (30.0 mL) and EA (30.0 mL). The aqueous layer was extracted with EA (30.0 mL, 3×), combined organics washed with brine, and concentrated under reduced pressure. The crude product was purified via silica gel chromatography eluting hexane/EA 0-50% to afford the title compound.

Synthesis of (9-bromo-3,4-dihydro-2H-benzo[b][1,4]dioxepin-6-yl)methanol (96B): To a stirred solution of 96A (1.24 g, 4.32 mmol) in THF (28.8 mL) at 0° C. was added lithium aluminum hydride (4.76 mL, 4.76 mmol). The reaction mixture was allowed to stir at 0° C. for 10 min. The reaction mixture was quenched at 0° C. by the dropwise addition of water (0.90 mL), followed by 1M NaOH (0.90 mL), and a second aliquot of water (2.70 mL). Anhydrous sodium sulfate was added and the reaction mixture was allowed to stir for 45 min while warming to room temperature. The reaction was filtered and concentrated under reduced pressure to afford the title compound without further purification.

Synthesis of 6-bromo-9-(bromomethyl)-3,4-dihydro-2H-benzo[b][1,4]dioxepine (96C): The title compound was prepared according to the method presented for the synthesis of compound 13E of Example 13 starting with 96B.

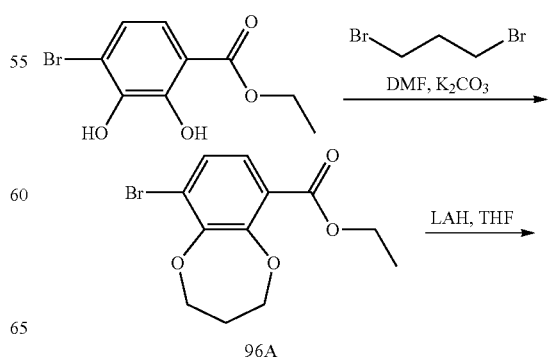

96A

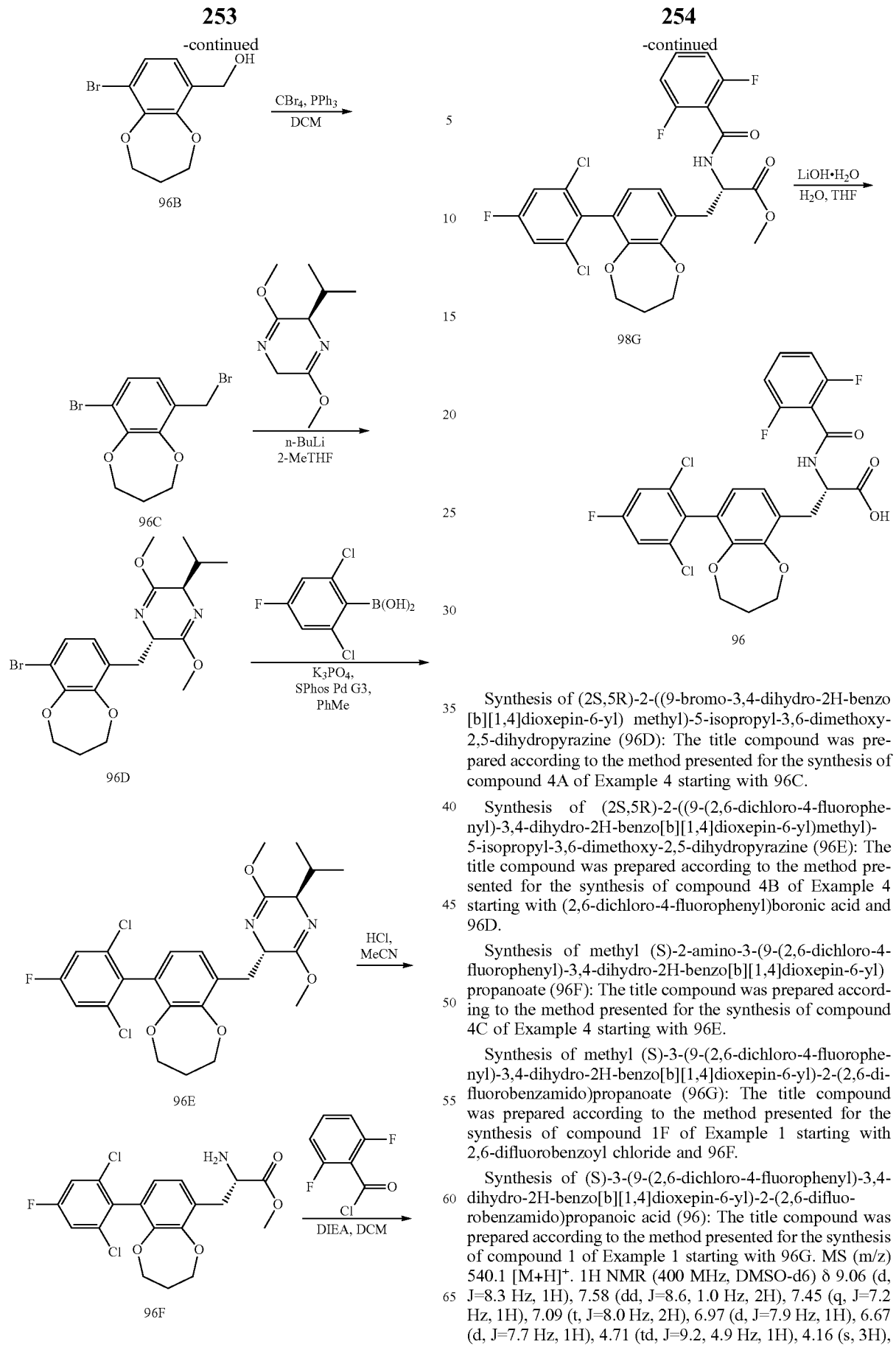

Synthesis of (2S,5R)-2-((9-bromo-3,4-dihydro-2H-benzo[b][1,4]dioxepin-6-yl) methyl)-5-isopropyl-3,6-dimethoxy-2,5-dihydropyrazine (96D): The title compound was prepared according to the method presented for the synthesis of compound 4A of Example 4 starting with 96C.

Synthesis of (2S,5R)-2-((9-(2,6-dichloro-4-fluorophenyl)-3,4-dihydro-2H-benzo[b][1,4]dioxepin-6-yl)methyl)-5-isopropyl-3,6-dimethoxy-2,5-dihydropyrazine (96E): The title compound was prepared according to the method presented for the synthesis of compound 4B of Example 4 starting with (2,6-dichloro-4-fluorophenyl)boronic acid and 96D.

Synthesis of methyl (S)-2-amino-3-(9-(2,6-dichloro-4-fluorophenyl)-3,4-dihydro-2H-benzo[b][1,4]dioxepin-6-yl)propanoate (96F): The title compound was prepared according to the method presented for the synthesis of compound 4C of Example 4 starting with 96E.

Synthesis of methyl (S)-3-(9-(2,6-dichloro-4-fluorophenyl)-3,4-dihydro-2H-benzo[b][1,4]dioxepin-6-yl)-2-(2,6-difluorobenzamido)propanoate (96G): The title compound was prepared according to the method presented for the synthesis of compound 1F of Example 1 starting with 2,6-difluorobenzoyl chloride and 96F.

Synthesis of (S)-3-(9-(2,6-dichloro-4-fluorophenyl)-3,4-dihydro-2H-benzo[b][1,4]dioxepin-6-yl)-2-(2,6-difluorobenzamido)propanoic acid (96): The title compound was prepared according to the method presented for the synthesis of compound 1 of Example 1 starting with 96G. MS (m/z) 540.1 [M+H]$^+$. 1H NMR (400 MHz, DMSO-d6) δ 9.06 (d, J=8.3 Hz, 1H), 7.58 (dd, J=8.6, 1.0 Hz, 2H), 7.45 (q, J=7.2 Hz, 1H), 7.09 (t, J=8.0 Hz, 2H), 6.97 (d, J=7.9 Hz, 1H), 6.67 (d, J=7.7 Hz, 1H), 4.71 (td, J=9.2, 4.9 Hz, 1H), 4.16 (s, 3H), 4.00 (p, J=5.9, 5.2 Hz, 2H), 3.25 (dd, J=13.6, 5.0 Hz, 1H), 2.85 (dd, J=13.7, 10.3 Hz, 1H), 2.05 (d, J=6.3 Hz, 3H).

Example 97

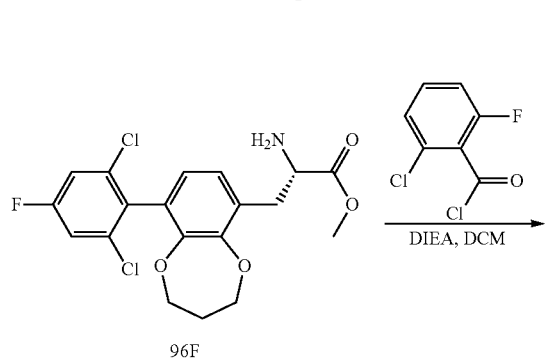

96F

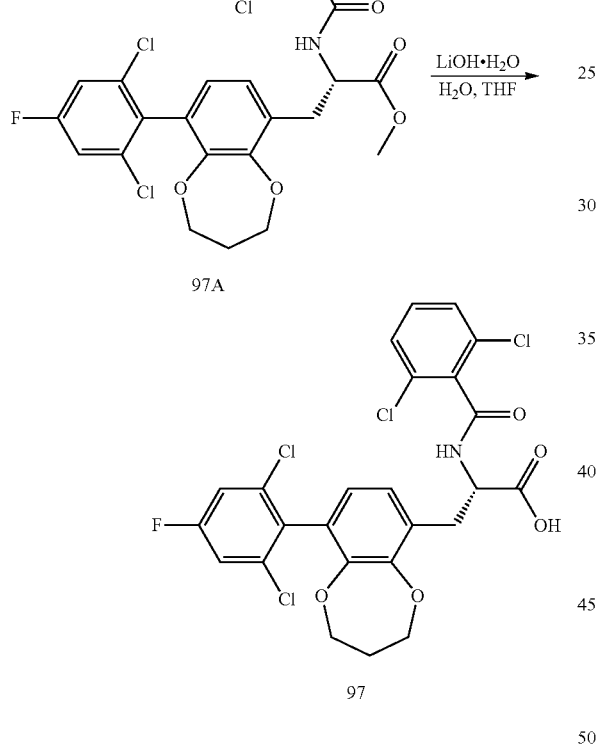

97A

97

Synthesis of methyl (S)-3-(9-(2,6-dichloro-4-fluorophenyl)-3,4-dihydro-2H-benzo[b][1,4]dioxepin-6-yl)-2-(2,6-dichlorobenzamido)propanoate (97A): The title compound was prepared according to the method presented for the synthesis of compound 1F of Example 1 starting with 2,6-dichlorobenzoyl chloride and 96F.

Synthesis of (S)-3-(9-(2,6-dichloro-4-fluorophenyl)-3,4-dihydro-2H-benzo[b][1,4]dioxepin-6-yl)-2-(2,6-dichlorobenzamido)propanoic acid (97): The title compound was prepared according to the method presented for the synthesis of compound 1 of Example 1 starting with 96G. MS (m/z) 572.0 [M+H]$^+$. 1H NMR (400 MHz, DMSO-d6) δ 9.06 (d, J=8.6 Hz, 1H), 7.61-7.57 (m, 2H), 7.43-7.34 (m, 3H), 7.02 (d, J=7.8 Hz, 1H), 6.66 (d, J=7.8 Hz, 1H), 4.81 (ddd, J=11.0, 8.6, 4.3 Hz, 1H), 4.27-4.08 (m, 2H), 4.06-3.88 (m, 2H), 3.25 (dd, J=13.7, 4.3 Hz, 1H), 2.82 (dd, J=13.8, 11.0 Hz, 1H), 2.06 (t, J=5.4 Hz, 2H).

Example 98

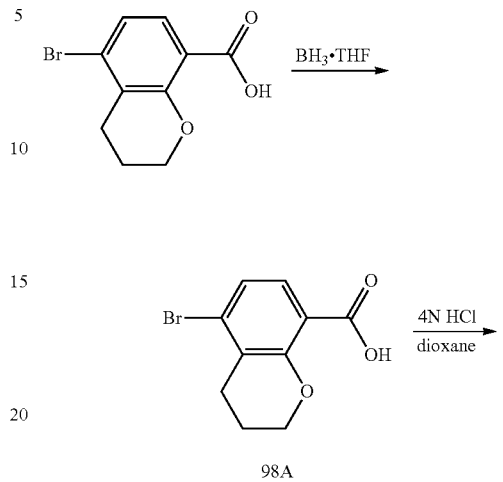

98A

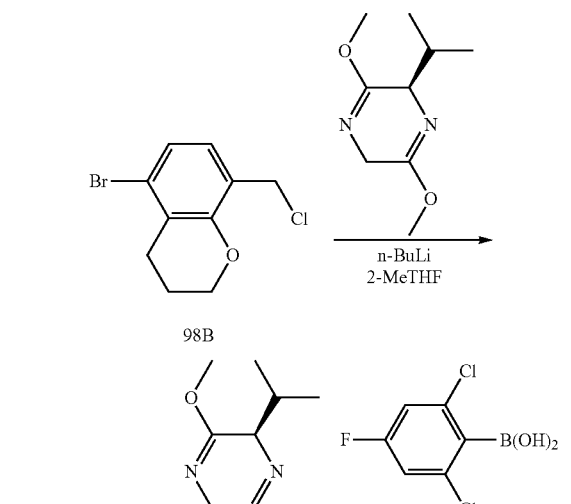

98B

98C

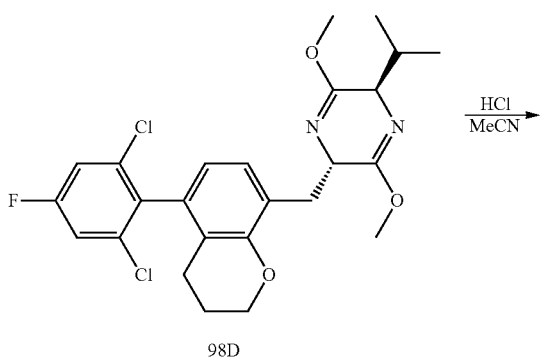

98D

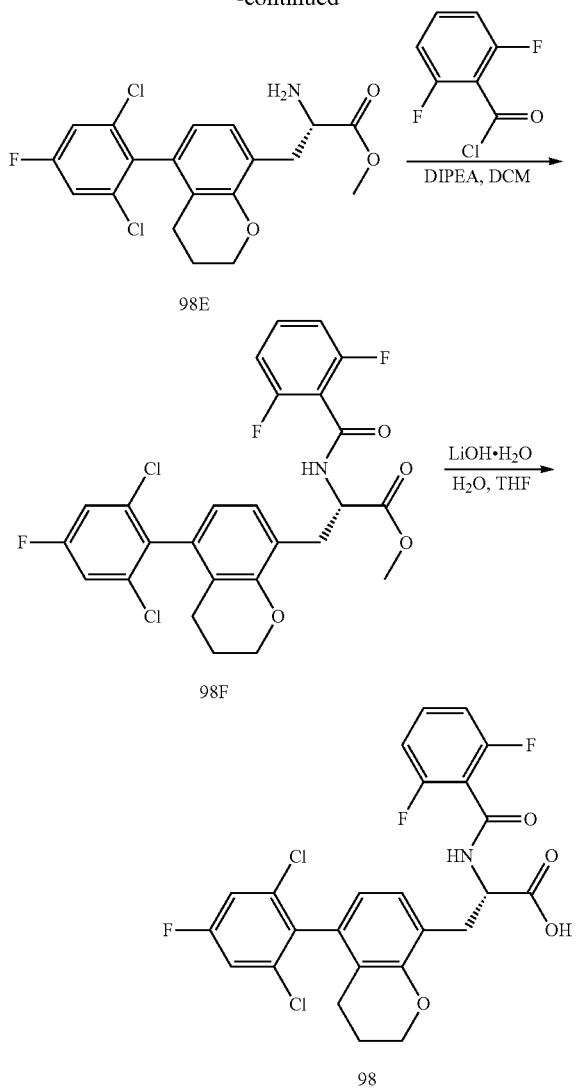

Synthesis of (5-bromochroman-8-yl)methanol (98A): To a stirred suspension of 5-bromochromane-8-carboxylic acid (1.5 g, 5.8 mol) in THF (4 mL) was slowly added a solution of 1 M BH$_3$ in THF (17.5 mL, 17.5 mmol) at 0° C. The reaction mixture was heated to reflux and stirred for 1 h. Upon completion, the mixture was cooled to RT, quenched with 6 M HCl (10 mL) and stirred for 1 hr. The pH of the mixture was adjusted to ~13 with KOH. The mixture was extracted with DCM. The organic layer was dried over Na$_2$SO$_4$ and concentrated under vacuum to afford the crude material. The material was purified by 230-400 mesh silica gel column chromatography and eluted with EtOAc in hexane (10-100%) to afford the title compound.

Synthesis of 5-bromo-8-(chloromethyl)chromane (98B): To compound 98A (597 mg, 2 mmol) was added a solution of 4 N HCl in dioxane (2.5 mL). The reaction mixture was allowed to stir at room temperature for 16 hrs. The reaction mixture was concentrated under reduced pressure to afford the title compound.

Synthesis of (2S,5R)-2-((5-bromochroman-8-yl)methyl)-5-isopropyl-3,6-dimethoxy-2,5-dihydropyrazine (98C): The title compound was prepared according to the method presented for the synthesis of compound 4A of Example 4 starting with (R)-2-isopropyl-3,6-dimethoxy-2,5-dihydropyrazine and 98B.

Synthesis of (2S,5R)-2-((5-(2,6-dichloro-4-fluorophenyl)chroman-8-yl)methyl)-5-isopropyl-3,6-dimethoxy-2,5-dihydropyrazine (98D): The title compound was prepared according to the method presented for the synthesis of compound 4B of Example 4 starting with (2,6-dichloro-4-fluorophenyl)boronic acid and 98C.

Synthesis of methyl (S)-2-amino-3-(5-(2,6-dichloro-4-fluorophenyl)chroman-8-yl)propanoate (98E): The title compound was prepared according to the method presented for the synthesis of compound 4C of Example 4 starting with 98D.

Synthesis of methyl (S)-3-(5-(2,6-dichloro-4-fluorophenyl)chroman-8-yl)-2-(2,6-difluorobenzamido)propanoate (98F): The title compound was prepared according to the method presented for the synthesis of compound 1F of Example 1 starting with 2,6-difluorobenzoyl chloride and 98E.

Synthesis of (S)-3-(5-(2,6-dichloro-4-fluorophenyl)chroman-8-yl)-2-(2,6-difluorobenzamido)propanoic acid (98): The title compound was prepared according to the method presented for the synthesis of compound 1 of Example 1 starting with 98F. MS (m/z) 568.8 [M+H]$^+$. 1H NMR (400 MHz, DMSO-d6) δ 12.71 (s, 1H), 9.02 (d, J=8.1 Hz, 1H), 7.63 (d, J=8.6 Hz, 2H), 7.46 (tt, J=8.4, 6.5 Hz, 1H), 7.15-7.04 (m, 3H), 6.52 (d, J=7.7 Hz, 1H), 4.69 (ddd, J=10.1, 8.1, 4.8 Hz, 1H), 4.16 (t, J=5.2 Hz, 2H), 3.16 (dd, J=14.1, 4.9 Hz, 1H), 2.81 (dd, J=14.1, 10.2 Hz, 1H), 2.21 (t, J=6.5 Hz, 2H), 1.85 (dd, J=6.5, 3.8 Hz, 1H).

Example 99

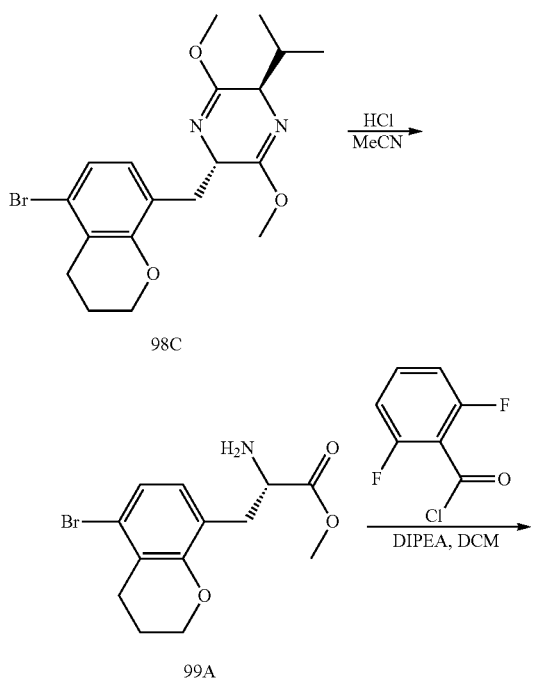

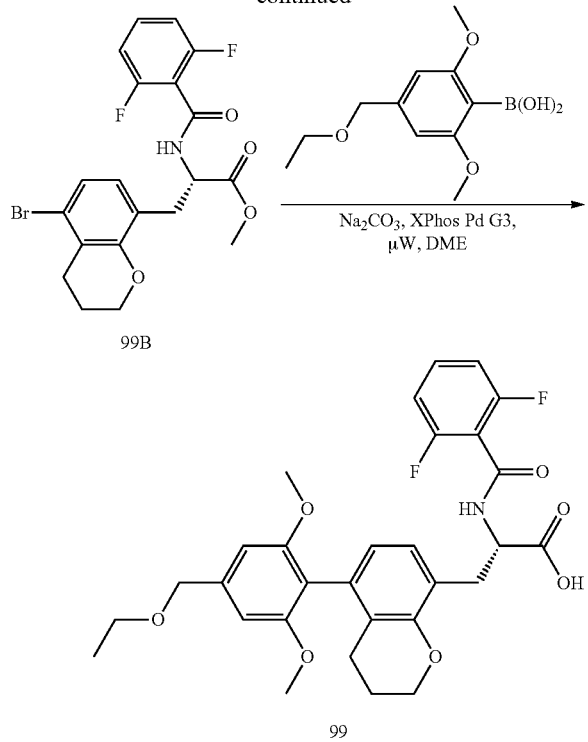

Synthesis of methyl (S)-2-amino-3-(5-bromochroman-8-yl)propanoate (99A): The title compound was prepared according to the method presented for the synthesis of compound 4C of Example 4 starting with 98C.

Synthesis of methyl (S)-3-(5-bromochroman-8-yl)-2-(2,6-difluorobenzamido) propanoate (99B): The title compound was prepared according to the method presented for the synthesis of compound 1F of Example 1 starting with 2,6-difluorobenzoyl chloride and 99A.

Synthesis of (S)-2-(2,6-difluorobenzamido)-3-(5-(4-(ethoxymethyl)-2,6-dimethoxyphenyl)chroman-8-yl)propanoic acid (99): To a solution 99B (103 mg, 0.23 mmol) in DME (1.5 mL) in a microwave tube was added (4-(ethoxymethyl)-2,6-dimethoxyphenyl)boronic acid (60 mg, 0.25 mmol), XPhos Pd G3 (10 mg, 0.011 mmol) and aq. Na$_2$CO$_3$ (0.4 mL, 2 M). The reaction was degassed with nitrogen and heated in a microwave at 130° C. for 30 min. The material was filtered and then was purified via reverse phase HPLC to afford the title compound. MS (m/z) 556.2 [M+H]$^+$. 1H NMR (400 MHz, DMSO-d6) δ 7.45 (ddd, J=15.0, 8.3, 6.5 Hz, 1H), 7.14-6.99 (m, 3H), 6.64 (s, 2H), 6.40 (d, J=7.7 Hz, 1H), 4.46 (s, 2H), 4.17-4.00 (m, 2H), 3.62 (d, J=1.9 Hz, 6H), 3.52 (q, J=7.0 Hz, 2H), 3.23-3.13 (m, 1H), 2.76 (dd, J=14.9, 8.9 Hz, 1H), 2.69-2.57 (m, 1H), 2.22 (t, J=6.6 Hz, 2H), 1.76 (s, 2H), 1.17 (t, J=7.0 Hz, 3H).

Example 100

Synthesis of methyl (S)-3-(5-bromochroman-8-yl)-2-(2,6-difluoro-4-((4-(2-fluoro pyridin-4-yl)phenyl)sulfonamido)benzamido)propanoate (100A): The title compound was prepared according to the method presented for the synthesis of compound 8F of Example 8 starting with 2,6-difluoro-4-((4-(2-fluoropyridin-4-yl)phenyl)sulfonamido)benzoic acid and 99A.

Synthesis of (S)-2-(2,6-difluoro-4-((4-(2-fluoropyridin-4-yl)phenyl)sulfonamido) benzamido)-3-(5-(4-(ethoxymethyl)-2,6-dimethoxyphenyl)chroman-8-yl)propanoic acid (100): The title compound was prepared according to the method presented for the synthesis of compound 99 of Example 99 starting with (4-(ethoxymethyl)-2,6-dimethoxyphenyl)boronic acid and 100A. MS (m/z) 806.2 [M+H]$^+$. 1H NMR (400 MHz, DMSO-d6) δ 8.41 (s, 1H), 8.33-8.23 (m, 1H), 7.92 (d, J=8.4 Hz, 2H), 7.84 (d, J=8.4 Hz, 2H), 7.69 (dt, J=5.4, 1.8 Hz, 1H), 7.54 (s, 1H), 6.92 (d, J=7.7 Hz, 1H), 6.63 (s, 2H), 6.50 (d, J=11.6 Hz, 2H), 6.40 (d, J=7.6 Hz, 1H), 4.45 (s, 3H), 4.06 (t, J=5.4 Hz, 2H), 3.59 (d, J=1.0 Hz, 6H), 3.52 (q, J=7.0 Hz, 2H), 3.06 (dd, J=14.3, 4.7 Hz, 1H), 2.76 (dd, J=14.2, 9.6 Hz, 1H), 2.20 (t, J=6.5 Hz, 2H), 1.74 (d, J=6.1 Hz, 2H), 1.17 (t, J=7.0 Hz, 3H).

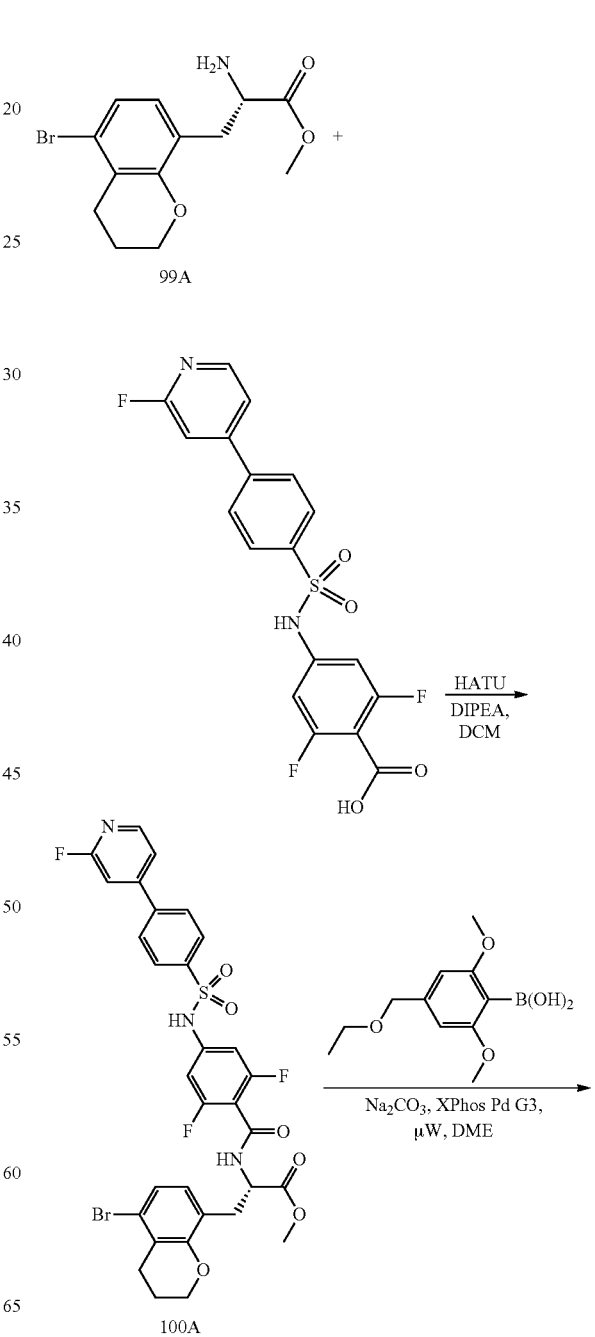

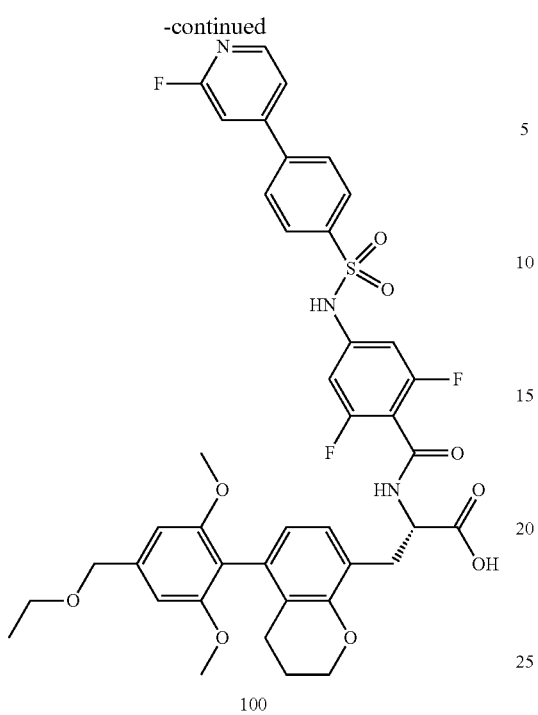

100

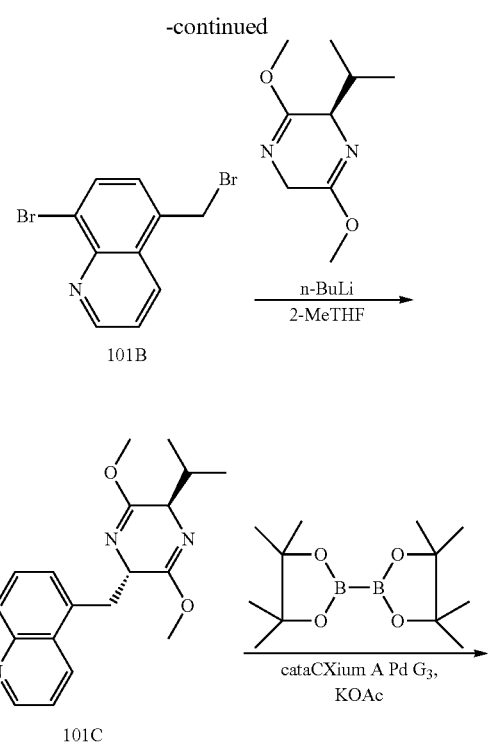

Example 101

Synthesis of 8-bromo-5-methylquinoline (101A): To a stirred solution of 2-bromo-5-methyl aniline (1200 g, 6.45 mol) in nitrobenzene (660 mL) and 75% H₂SO₄ (3.6 L) was added glycerol (1180 g, 6.45 mol) at RT and then slowly heated to 150° C. for 3 h. Caution: highly exothermic reaction. The mixture was cooled to RT and poured into ice-water while maintaining the temperature below 10° C. The pH was adjusted ~10 with aq. 10N NaOH and the product was extracted with EtOAc. The combined organic layer was washed with brine, dried over anhydrous Na₂SO₄ and concentrated under vacuum to afford crude material. This material was dissolved in DCM/hexanes (5:1) and stirred for 30 minutes. The solid was filtered off and the filtrate was evaporated under reduced pressure to afford 101A.

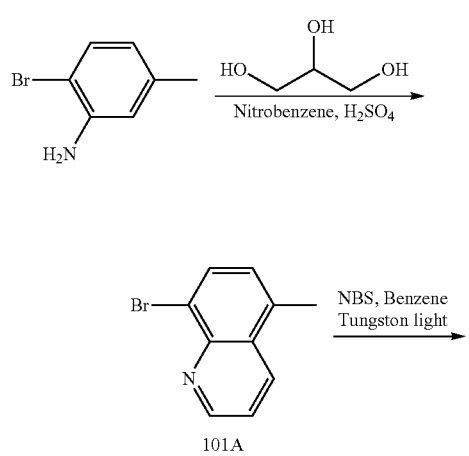

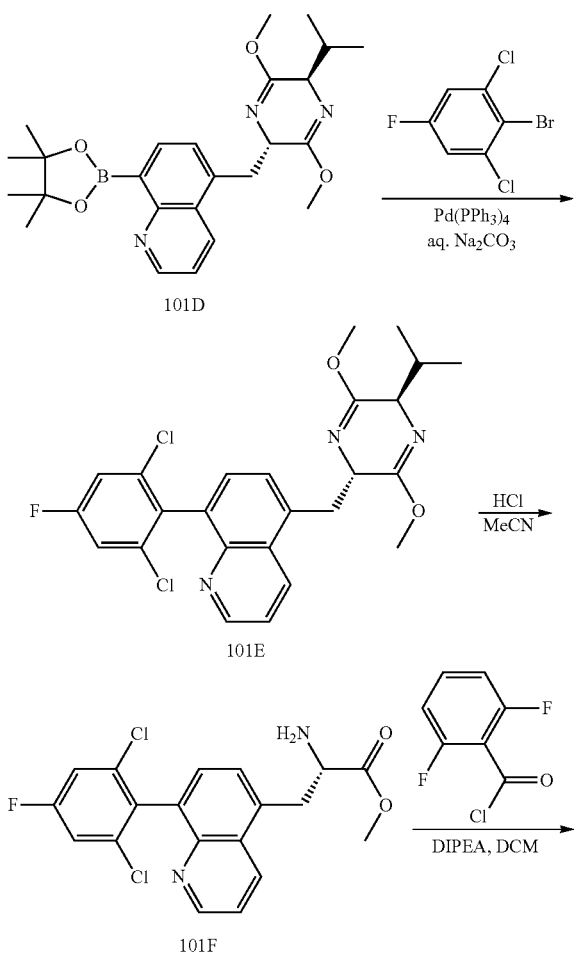

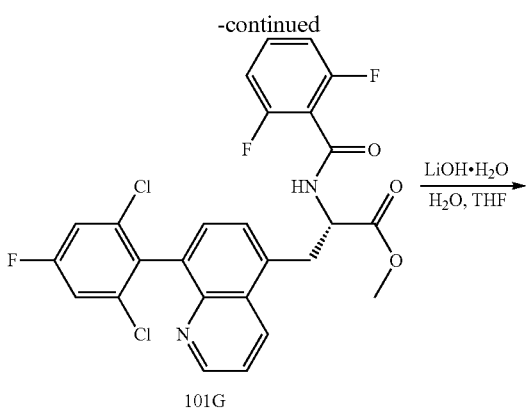

Synthesis of 8-bromo-5-(bromomethyl)quinoline (101B): To a stirred solution of compound 101A (500 g, 2.25 mol) in benzene (7.5 L) was added NBS (481 g, 2.7 mol) at RT. The reaction mixture was heated to 80° C. under tungsten light for 12 h. The reaction was cooled to RT, water added and extracted with EtOAc. The organic layer was separated, washed with water, brine, and dried over anhydrous $Na_2SO_4$ and concentrated under reduced pressure to afford crude material. This material was triturated with 20% EtOAc in hexane at RT, washed with hexane and dried under reduced pressure to afford 101B.

Synthesis of 8-bromo-5-(((2S,5R)-5-isopropyl-3,6-dimethoxy-2,5-dihydropyrazin-2-yl)methyl)quinoline (101C): The title compound was prepared according to the method presented for the synthesis of compound 4A of Example 4 starting with (R)-2-isopropyl-3,6-dimethoxy-2,5-dihydropyrazine and 101B.

Synthesis of 5-(((2S,5R)-5-isopropyl-3,6-dimethoxy-2,5-dihydropyrazin-2-yl)methyl)-8-(4,4,5,5-tetramethyl-1,3,2-dioxaborolan-2-yl)quinoline (101D): The title compound was prepared according to the method presented for the synthesis of compound 1G in Example 1 starting with 101C.

Synthesis of 8-(2,6-dichloro-4-fluorophenyl)-5-(((2S,5R)-5-isopropyl-3,6-dimethoxy-2,5-dihydropyrazin-2-yl)methyl)quinoline (101E): The title compound was prepared according to the method presented for the synthesis of compound 1G in Example 1 starting with 2-bromo-1,3-dichloro-5-fluorobenzene and 101D.

Synthesis of methyl (S)-2-amino-3-(8-(2,6-dichloro-4-fluorophenyl)quinolin-5-yl) propanoate (101F): The title compound was prepared according to the method presented for the synthesis of compound 4C of Example 4 starting with 101E.

Synthesis of methyl (S)-3-(8-(2,6-dichloro-4-fluorophenyl)quinolin-5-yl)-2-(2,6-difluorobenzamido)propanoate (101G): The title compound was prepared according to the method presented for the synthesis of compound 1F of Example 1 starting with 2,6-difluorobenzoyl chloride and 101F.

Synthesis of (S)-3-(8-(2,6-dichloro-4-fluorophenyl)quinolin-5-yl)-2-(2,6-difluorobenzamido)propanoic acid (101H): The title compound was prepared according to the method presented for the synthesis of compound 1 of Example 1 starting with 101G.

Synthesis of (S)-3-(8-(2,6-dichloro-4-fluorophenyl)-1,2,3,4-tetrahydroquinolin-5-yl)-2-(2,6-difluorobenzamido)propanoic acid (101): Compound 101H (61 mg, 0.18 mmol) was added to a Parr shaker bottle, followed by EtOAc (15 mL) and MeOH (10 mL). $PtO_2$ (12 mg, 0.06 mmol) and AcOH (several drops) were added and the bottle was put on the shaker under 60 psi hydrogen gas, shake at RT ON. The reaction mixture was filtered through Celite, concentrated and purified with prep HPLC to give the title compound. MS (m/z) 524.7 [M+H]$^+$. 1H NMR (400 MHz, DMSO-d6) δ 9.12 (d, J=7.9 Hz, 1H), 7.58-7.51 (m, 2H), 7.48 (tt, J=8.4, 6.5 Hz, 1H), 7.11 (dd, J=8.5, 7.5 Hz, 2H), 6.57-6.44 (m, 2H), 4.58 (ddd, J=9.8, 7.9, 4.5 Hz, 1H), 3.12-3.02 (m, 3H), 2.83 (dd, J=14.7, 9.9 Hz, 1H), 2.77-2.63 (m, 2H), 1.80 (q, J=5.9 Hz, 2H).

Example 102

Synthesis of (S)-3-(8-(2,6-dichloro-4-fluorophenyl)-1-methyl-1,2,3,4-tetrahydroquinolin-5-yl)-2-(2,6-difluorobenzamido)propanoic acid (102): To a solution of 101 (70 mg, 0.134 mmol) in MeOH (5 mL) was added $CH_2O$ (37% aq. solution, 0.02 mL, 0.67 mmol) and HOAc (0.01 mL, 0.134 mmol). The mixture was stirred at room temperature for 10 min then was cooled to 0° C. before $NaBH_3CN$ (25 mg, 0.4 mmol) was added. After 1 h, the solvent was removed under reduced pressure. The reaction was quenched with saturated aq. $NaHCO_3$ then extracted with $CH_2Cl_2$. The combined organic layers were dried over $Na_2SO_4$ then concentrated and purified with prep HPLC to give the desired product. MS (m/z) 538.4 [M+H]$^+$. 1H NMR (400 MHz, DMSO-d6) δ 9.15 (d, J=8.0 Hz, 1H), 7.62-7.53 (m, 2H), 7.48 (tt, J=8.4, 6.5 Hz, 1H), 7.20-7.04 (m, 2H), 6.88 (d, J=7.9 Hz, 1H), 6.74 (d, J=7.8 Hz, 1H), 4.62 (ddd, J=9.9, 8.0, 4.4 Hz, 1H), 3.12 (dd, J=14.8, 4.4 Hz, 1H), 2.99 (t, J=5.5 Hz, 2H), 2.89 (dd, J=14.9, 10.0 Hz, 1H), 2.72 (q, J=6.1, 5.0 Hz, 2H), 2.28 (s, 3H), 1.83 (q, J=6.1 Hz, 2H).

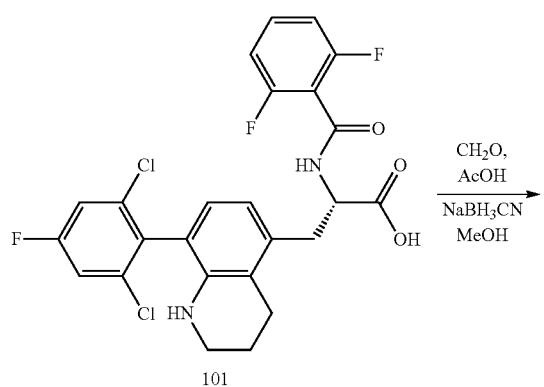

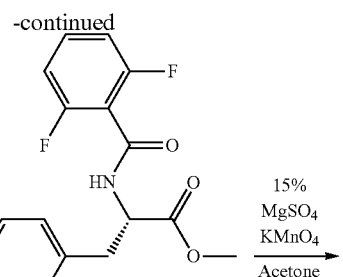

Example 103

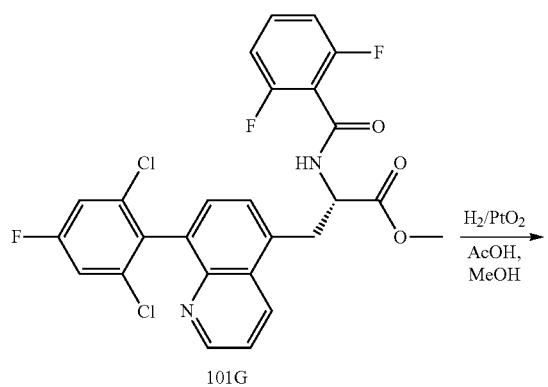

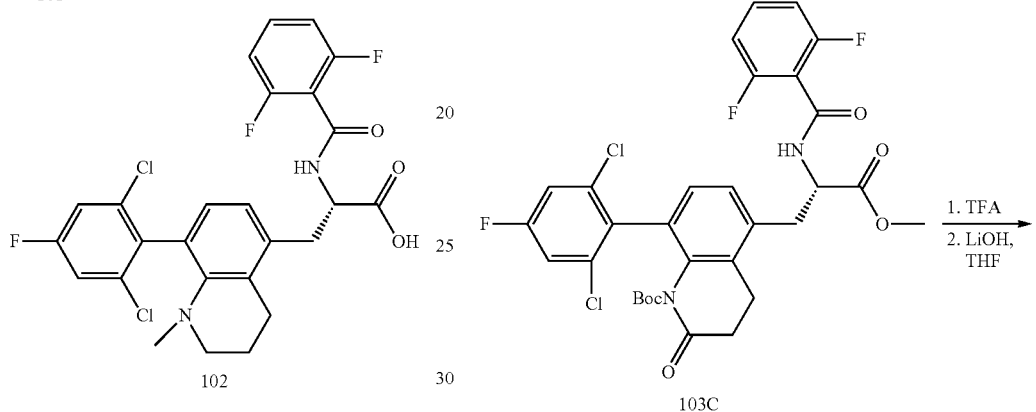

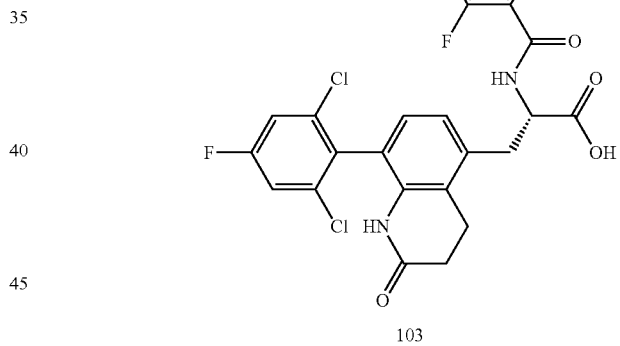

Synthesis of methyl (S)-3-(8-(2,6-dichloro-4-fluorophenyl)-1,2,3,4-tetrahydroquinolin-5-yl)-2-(2,6-difluorobenzamido)propanoate (103A): The title compound was prepared according to the method presented for the synthesis of 101 starting with 101G.

Synthesis of tert-butyl (S)-8-(2,6-dichloro-4-fluorophenyl)-5-(2-(2,6-difluorobenzamido)-3-methoxy-3-oxopropyl)-3,4-dihydroquinoline-1(2H)-carboxylate (103B): To a stirred solution of 103A (188 mg, 0.35 mmol) in DCM, di-tert-butyl dicarbonate (115 mg, 0.53 mmol), TEA (0.15 mL, 1.05 mmol) and DMAP (5 mg, 0.04 mmol) were added and reaction mixture was stirred at rt for 2 hours. The solvent was evaporated and the crude was purified by silica gel chromatography using 0-30% EtOAc in Hexanes to afford the title compound.

Synthesis of tert-butyl (S)-8-(2,6-dichloro-4-fluorophenyl)-5-(2-(2,6-difluorobenzamido)-3-methoxy-3-oxopropyl)-2-oxo-3,4-dihydroquinoline-1(2H)-carboxylate (103C): To a stirred solution of 103B (154 mg, 0.24 mmol) in acetone, 15% MgSO$_4$ (0.24 mL, 1.95 mmol), KMnO$_4$ (191 mg, 1.2 mmol) were added and reaction mixture was stirred at rt for 2 hours. Evaporate solvent and the crude was purified by silica gel chromatography using 0-50% EtOAc in Hexanes to afford the title compound.

Synthesis of (S)-3-(8-(2,6-dichloro-4-fluorophenyl)-2-oxo-1,2,3,4-tetrahydroquinolin-5-yl)-2-(2,6-difluorobenzamido)propanoic acid (103): To a stirred solution of 4 (115 mg, 0.18 mmol) in DCM, TFA (0.41 mL, 5.3 mmol) was added and the reaction mixture was stirred at rt for 2 h. Solvent was removed and the crude was re-dissolved in THF, LiOH (0.65 mL, 1M) was added and stir for 1 h. Evaporate solvent and the crude was purified with prep HPLC to give the desired product. MS (m/z) 537.0 [M+H]$^+$. 1H NMR (400 MHz, DMSO-d6) δ 12.90 (s, 1H), 9.25 (s, 1H), 9.16 (d, J=8.2 Hz, 1H), 7.57 (d, J=8.7 Hz, 2H), 7.47 (tt, J=8.4, 6.5 Hz, 1H), 7.18-7.03 (m, 2H), 6.98 (d, J=8.0 Hz, 1H), 6.84 (d, J=7.9 Hz, 1H), 4.62 (ddd, J=10.0, 8.1, 4.6 Hz, 1H), 3.24 (dd, J=14.4, 4.7 Hz, 1H), 3.02-2.87 (m, 3H), 2.45-2.37 (m, 2H).

Example 104

Synthesis of 7-bromo-2,3-dihydro-1H-indene-4-carbaldehyde (104A): The title compound was prepared according to the method presented for the synthesis of 13C of Example 13 starting with 4,7-dibromo-2,3-dihydro-1H-indene.

Synthesis of (7-bromo-2,3-dihydro-1H-inden-4-yl)methanol (104B): The title compound was prepared according to the method presented for the synthesis of 13D of Example 13 starting with 104A.

Synthesis of 4-bromo-7-(bromomethyl)-2,3-dihydro-1H-indene (104C): The title compound was prepared according to the method presented for the synthesis of 13E of Example 13 starting with 104B.

Synthesis of (2S,5R)-2-((7-bromo-2,3-dihydro-1H-inden-4-yl)methyl)-5-isopropyl-3,6-dimethoxy-2,5-dihydropyrazine (104D): The title compound was prepared according to the method presented for the synthesis of compound 4A of Example 4 starting with (R)-2-isopropyl-3,6-dimethoxy-2,5-dihydropyrazine and 104C.

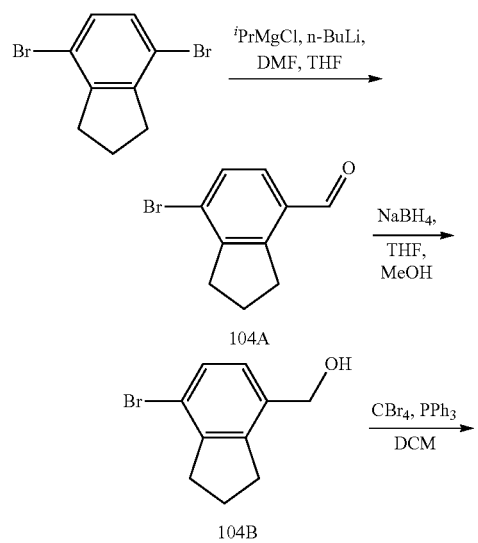

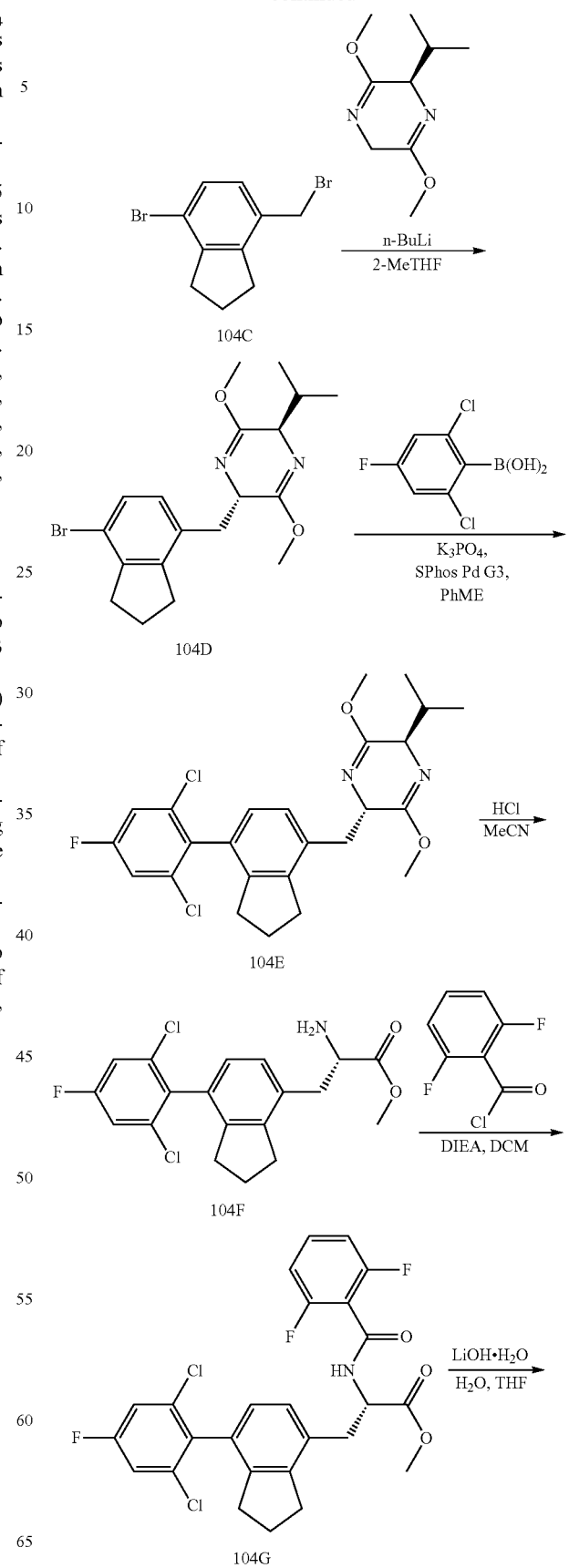

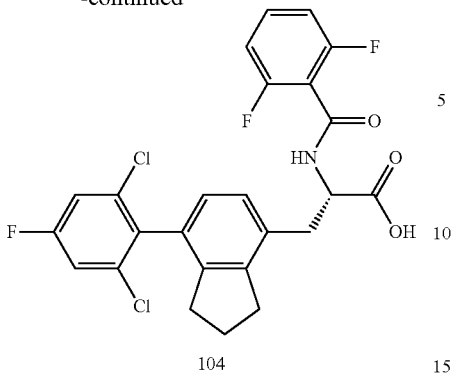

104

Synthesis of methyl (S)-2-amino-3-(7-(2,6-dichloro-4-fluorophenyl)-2,3-dihydro-1H-inden-4-yl)propanoate (104F): The title compound was prepared according to the method presented for the synthesis of compound 4C of Example 4 starting with 104E.

Synthesis of methyl (S)-3-(7-(2,6-dichloro-4-fluorophenyl)-2,3-dihydro-1H-inden-4-yl)-2-(2,6-difluorobenzamido)propanoate (104G): The title compound was prepared according to the method presented for the synthesis of compound 1F of Example 1 starting with 2,6-difluorobenzoyl chloride and 104F.

Synthesis of (S)-3-(7-(2,6-dichloro-4-fluorophenyl)-2,3-dihydro-1H-inden-4-yl)-2-(2,6-difluorobenzamido)propanoic acid (104): The title compound was prepared according to the method presented for the synthesis of compound 1 of Example 1 starting with 104G. MS (m/z) 508.0 [M+H]⁺. 1H NMR (400 MHz, DMSO-d6) δ 12.87 (s, 1H), 9.18 (d, J=8.1 Hz, 1H), 7.64 (d, J=8.6 Hz, 2H), 7.49 (ddd, J=14.9, 8.5, 6.5 Hz, 1H), 7.22-7.05 (m, 3H), 6.88 (d, J=7.7 Hz, 1H), 4.68 (td, J=9.5, 8.7, 4.6 Hz, 1H), 3.18 (dd, J=14.5, 4.7 Hz, 1H), 3.03-2.90 (m, 3H), 2.55-2. (d, J=7.5 Hz, 2H), 2.00 (q, J=7.2, 6.8 Hz, 2H).

Example 105

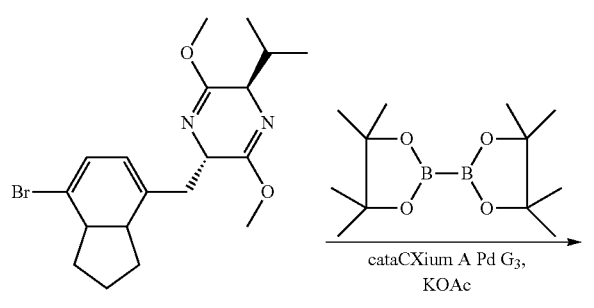

104D

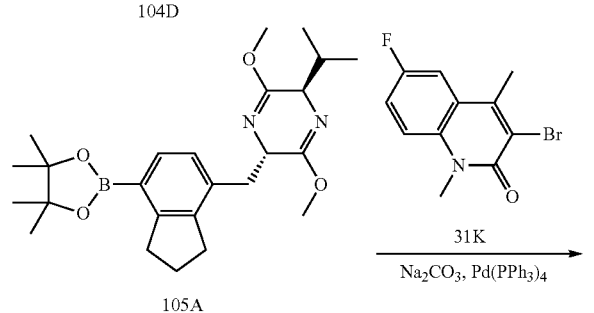

105A

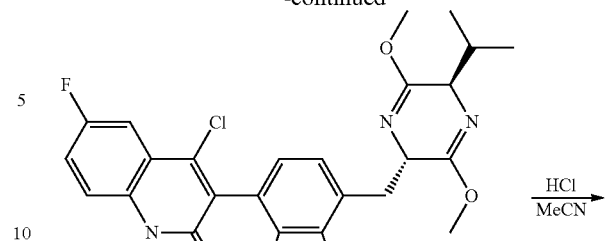

105B

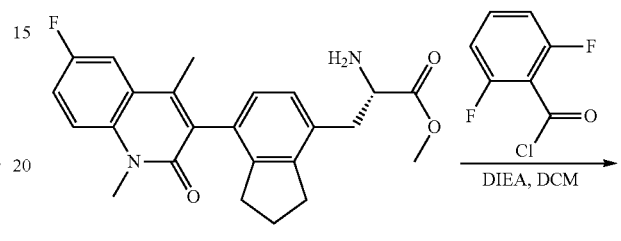

105C

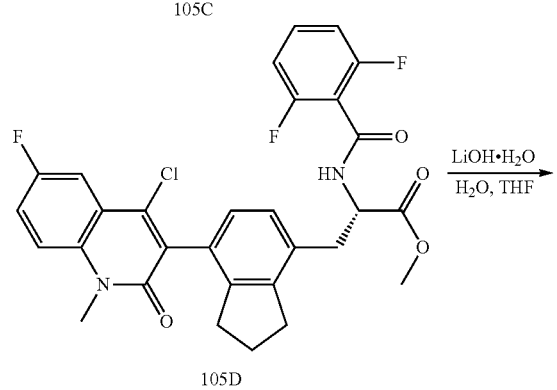

105D

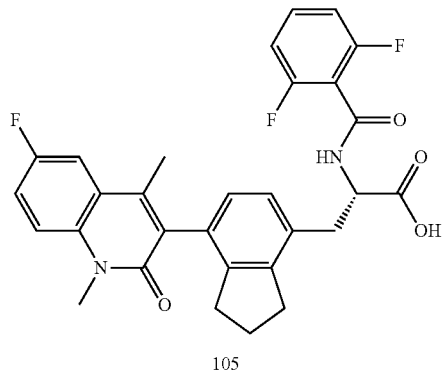 [SMILES: Cc1c(-c2ccc(C[C@H](NC(=O)c3c(F)cccc3F)C(=O)O)c3c2CCC3)c(=O)n(C)c2ccc(F)cc12]

105

Synthesis of (2R,5S)-2-isopropyl-3,6-dimethoxy-5-((7-(4,4,5,5-tetramethyl-1,3,2-dioxaborolan-2-yl)-2,3-dihydro-1H-inden-4-yl)methyl)-2,5-dihydropyrazine (105A): The title compound was prepared according to the method presented for the synthesis of compound 1G of Example 1 starting with 104D.

Synthesis of 6-fluoro-3-(7-(((2S,5R)-5-isopropyl-3,6-dimethoxy-2,5-dihydropyrazin-2-yl)methyl)-2,3-dihydro-1H-inden-4-yl)-1,4-dimethylquinolin-2(1H)-one (105B): The title compound was prepared according to the method presented for the synthesis of compound 1H of Example 1 starting with 31K and 105A.

Synthesis of methyl (S)-2-amino-3-(7-(6-fluoro-1,4-dimethyl-2-oxo-1,2-dihydroquinolin-3-yl)-2,3-dihydro-1H-inden-4-yl)propanoate (105C): The title compound was prepared according to the method presented for the synthesis of compound 4C of Example 4 starting with 105B.

Synthesis of methyl (S)-2-(2,6-difluorobenzamido)-3-(7-(6-fluoro-1,4-dimethyl-2-oxo-1,2-dihydroquinolin-3-yl)-2,3-dihydro-1H-inden-4-yl)propanoate (105D): The title compound was prepared according to the method presented for the synthesis of compound 1F of Example 1 starting with 105C.

Synthesis of (S)-2-(2,6-difluorobenzamido)-3-(7-(6-fluoro-1,4-dimethyl-2-oxo-1,2-dihydroquinolin-3-yl)-2,3-dihydro-1H-inden-4-yl)propanoic acid (105): The title compound was prepared according to the method presented for the synthesis of compound 1 of Example 1 starting with 105D. MS (m/z) 535.3 [M+H]⁺. 1H NMR (400 MHz, DMSO-d6) δ 9.19 (d, J=8.1 Hz, 1H), 7.73-7.43 (m, 4H), 7.19-7.04 (m, 3H), 6.84 (t, J=7.6 Hz, 1H), 4.68 (dt, J=9.1, 4.2 Hz, 1H), 3.66 (d, J=1.0 Hz, 3H), 3.17 (td, J=14.4, 4.8 Hz, 1H), 3.06-2.87 (m, 3H), 2.71-2.53 (m, 2H), 2.16 (d, J=6.8 Hz, 3H), 1.98 (q, J=6.7 Hz, 2H).

Example 106

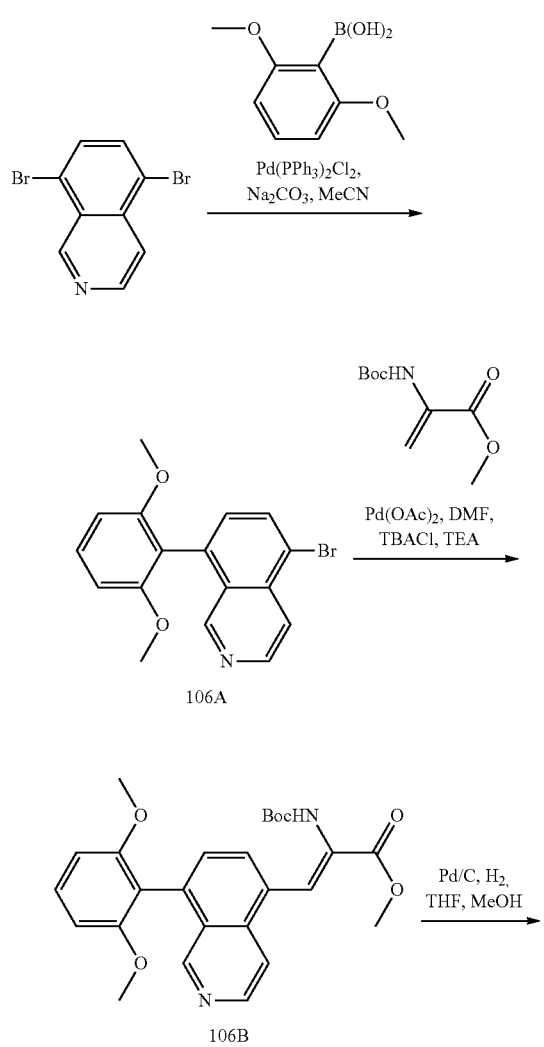

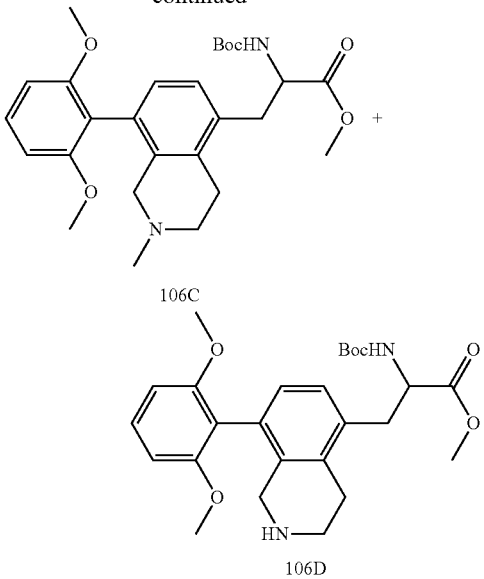

Synthesis of 5-bromo-8-(2,6-dimethoxyphenyl)isoquinoline (106A): To a stirred solution of 5,8-dibromoisoquinoline (1.58 g, 5.50 mmol) and (2,6-dimethoxyphenyl)boronic acid (1.00 g, 5.50 mmol) in ACN (20 mL) was added bis(triphenylphosphine)palladium(II) dichloride (193 mg, 0.275 mmol). A 2.0 M aq. solution of sodium carbonate (5.77 mL, 11.54 mmol) was added and the reaction was subjected to microwave irradiation at 120° C. for 30 minutes. From the reaction mixture, the organic layer was decanted and concentrated under reduced pressure. The resulting material was purified by silica gel chromatography using 10-100% EtOAc in hexanes to afford the title compound.

Synthesis of methyl (Z)-2-((tert-butoxycarbonyl)amino)-3-(8-(2,6-dimethoxyphenyl)isoquinolin-5-yl)acrylate (106B): To a stirred solution of 106A (250.0 mg, 0.726 mmol) in DMF (2.70 mL) was added palladium(II) acetate (24.5 mg, 0.109 mmol). This was degassed with N₂ for 30 minutes. In a separate vessel, methyl 2-((tert-butoxycarbonyl)amino)acrylate (292.3 mg, 1.45 mmol) and tetrabutylammonium chloride (242.2 mg, 0.872 mmol) were stirred in DMF (2 mL). The bromide solution was added to the acrylate solution and triethylamine was added (0.12 mL, 0.843 mmol). The reaction vessel was sealed and heated to 90° C. for 16 hours. The material was loaded directly onto silica and was purified by silica gel chromatography using 10-100% EtOAc in hexanes to afford the title compound.

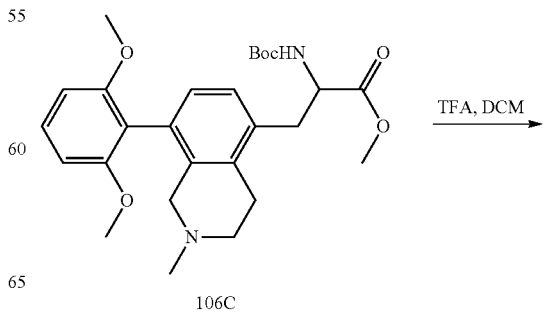

-continued

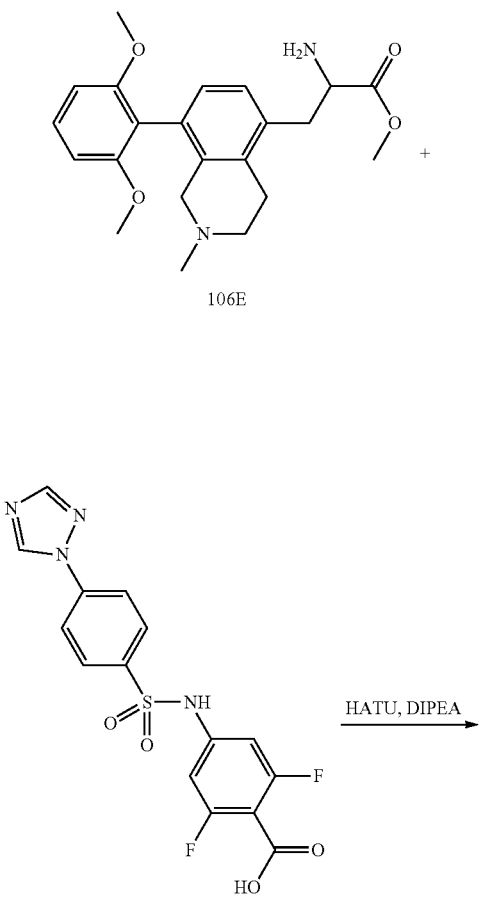

106E

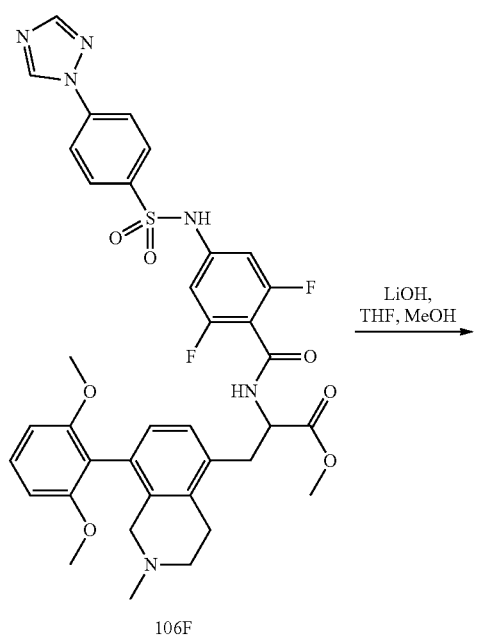

106F

-continued

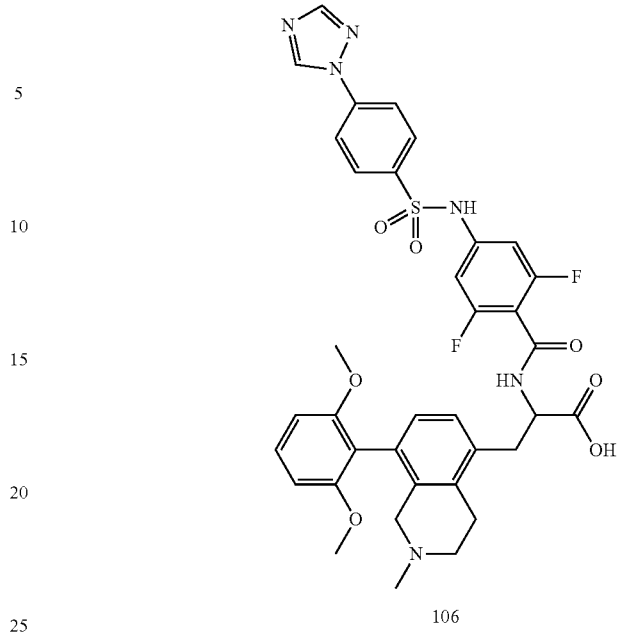

106

Synthesis of methyl 2-((tert-butoxycarbonyl)amino)-3-(8-(2,6-dimethoxyphenyl)-2-methyl-1,2,3,4-tetrahydroisoquinolin-5-yl)propanoate (106C) and methyl 2-((tert-butoxycarbonyl) amino)-3-(8-(2,6-dimethoxyphenyl)-1,2,3,4-tetrahydroisoquinolin-5-yl)propanoate (106D): To a stirred solution of 106B (200.0 mg, 0.431 mmol) in THF (2.70 mL) and MeOH was added palladium over carbon (25.5 mg, 0.022 mmol). The reaction vessel was shaken in a Parr hydrogenator at 65 psi for 3 hours at room temperature. The reaction mixture was filtered through Celite and concentrated. The crude material was purified by silica gel chromatography using 10-100% EtOAc in hexanes, followed by 0-20% MeOH in DCM to afford the two compounds.

Synthesis of methyl 2-amino-3-(8-(2,6-dimethoxyphenyl)-2-methyl-1,2,3,4-tetrahydroisoquinolin-5-yl)propanoate (106E): The title compound was prepared according to the method presented for the synthesis of compound 3D in Example 3 starting with 106C.

Synthesis of methyl 2-(4-((4-(1H-1,2,4-triazol-1-yl)phenyl)sulfonamido)-2,6-difluorobenzamido)-3-(8-(2,6-dimethoxyphenyl)-2-methyl-1,2,3,4-tetrahydroisoquinolin-5-yl) propanoate (106F): The title compound was prepared according to the method presented for the synthesis of compound 8F in Example 8 starting with 4-((4-(1H-1,2,4-triazol-1-yl)phenyl)sulfonamido)-2,6-difluorobenzoic acid and 106E.

Synthesis of 2-(4-((4-(1H-1,2,4-triazol-1-yl)phenyl)sulfonamido)-2,6-difluorobenzamido)-3-(8-(2,6-dimethoxyphenyl)-2-methyl-1,2,3,4-tetrahydroisoquinolin-5-yl)propanoic acid (106): The title compound was prepared according to the method presented for the synthesis of compound 1 of Example 1 starting with 106F. MS (m/z) 733.2 [M+H]$^+$. 1H NMR (400 MHz, DMSO-d6) δ 12.96 (s, 1H), 11.18 (d, J=3.7 Hz, 1H), 9.89 (s, 1H), 9.40 (d, J=0.8 Hz, 1H), 9.11 (dd, J=8.1, 5.1 Hz, 1H), 8.29 (d, J=0.5 Hz, 1H), 8.14-7.99 (m, 5H), 7.36 (t, J=8.4 Hz, 1H), 7.20 (dd, J=14.6, 7.8 Hz, 1H), 6.89 (dd, J=7.8, 3.5 Hz, 1H), 6.86-6.66 (m, 4H), 4.60-4.45 (m, 1H), 3.86 (s, 2H), 3.65-3.54 (m, 6H), 3.19 (d, J=15.2 Hz, 1H), 3.10 (s, 2H), 2.83 (d, J=4.4 Hz, 4H).

Example 107

Synthesis of methyl 3-(2-acetyl-8-(2,6-dimethoxyphenyl)-1,2,3,4-tetrahydroisoquinolin-5-yl)-2-((tert-butoxycarbonyl)amino)propanoate (107A): To a stirred solution of 106D (95 mg, 0.20 mmol) in DCM (6 mL) was added acetic anhydride (0.03 mL, 0.3 mmol). The reaction mixture was allowed to stir for 1 h, then EtOAc and sat. aq. NH$_4$OH were added to the reaction mixture. The aqueous layer was separated and extracted with EtOAc (2×). The organic layer was dried over anhydrous Na$_2$SO$_4$, and concentrated under reduced pressure to give the title compound without further purification.

Synthesis of methyl 3-(2-acetyl-8-(2,6-dimethoxyphenyl)-1,2,3,4-tetrahydroisoquinolin-5-yl)-2-aminopropanoate (107B): The title compound was prepared according to the method presented for the synthesis of compound 4C in Example 4 starting with 107A.

Synthesis of methyl 2-(4-((4-(1H-1,2,4-triazol-1-yl)phenyl)sulfonamido)-2,6-difluorobenzamido)-3-(2-acetyl-8-(2,6-dimethoxyphenyl)-1,2,3,4-tetrahydroisoquinolin-5-yl)propanoate (107C): The title compound was prepared according to the method presented for the synthesis of compound 8F in Example 8 starting with 4-((4-(1H-1,2,4-triazol-1-yl)phenyl)sulfonamido)-2,6-difluorobenzoic acid and 107B.

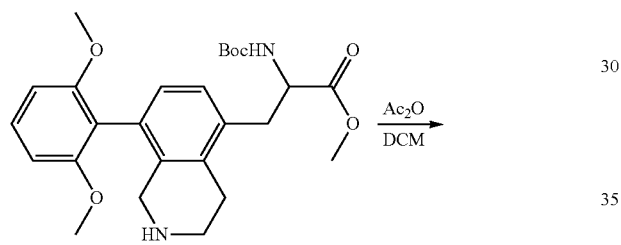

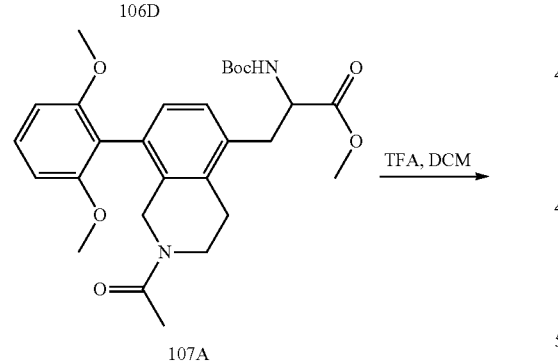

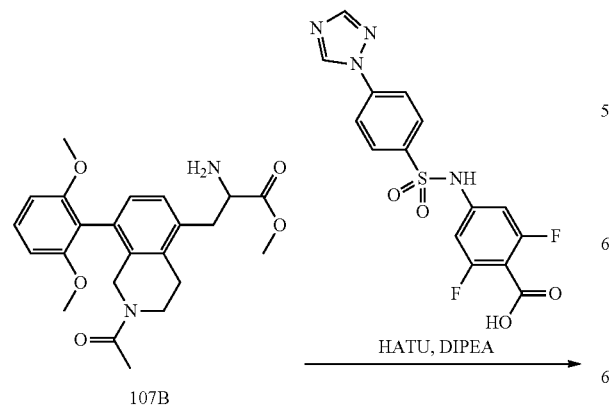

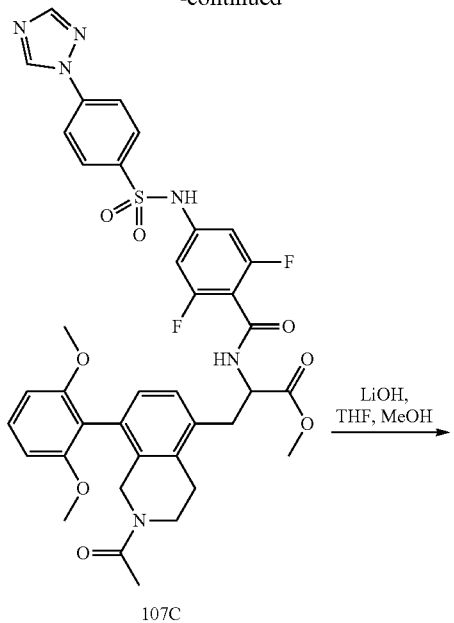

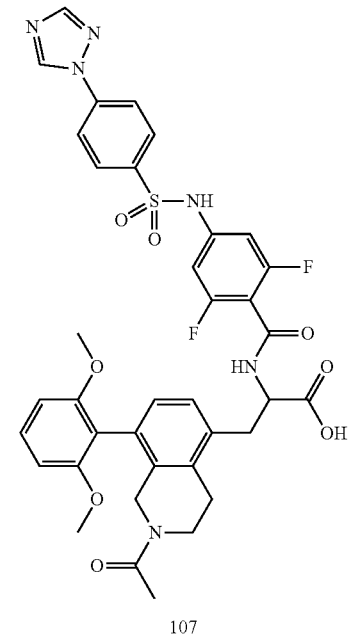 [SMILES: COc1cccc(OC)c1-c1ccc(CC(NC(=O)c2c(F)cc(NS(=O)(=O)c3ccc(-n4cncn4)cc3)cc2F)C(=O)O)c2c1CN(C(C)=O)CC2]

Synthesis of 2-(4-((4-(1H-1,2,4-triazol-1-yl)phenyl)sulfonamido)-2,6-difluorobenzamido)-3-(8-(2,6-dimethoxyphenyl)-2-methyl-1,2,3,4-tetrahydroisoquinolin-5-yl) propanoic acid (107): The title compound was prepared according to the method presented for the synthesis of compound 1 of Example 1 starting with 107. MS (m/z) 761.3. [M+H]$^+$. 1H NMR (400 MHz, DMSO-d6) δ 11.15 (s, 1H), 9.40 (d, J=4.0 Hz, 1H), 9.03 (d, J=7.9 Hz, 1H), 8.29 (d, J=3.1 Hz, 1H), 8.14-7.98 (m, 4H), 7.32 (q, J=8.4 Hz, 1H), 7.11-7.01 (m, 1H), 6.83-6.69 (m, 4H), 4.57-4.46 (m, 1H), 4.19-4.04 (m, 2H), 3.68-3.53 (m, 4H), 3.12 (dd, J=14.7, 4.6 Hz, 1H), 2.95-2.78 (m, 3H), 1.98 (s, 2H), 1.76 (s, 1H).

Example 108

Synthesis of methyl (S)-2-(2,6-difluoro-4-((R)-3-(trifluoromethyl)morpholino) benzamido)-3-(8-(4,5,6-trimethyl-3- oxo-3,4-dihydropyrazin-2-yl)chroman-5-yl)propanoate (108A): The title compound was prepared according to the method presented for the synthesis of compound 13K of Example 13 starting with 49A and 32B.

Synthesis of (S)-2-(2,6-difluoro-4-((R)-3-(trifluoromethyl)morpholino)benzamido)-3-(8-(4,5,6-trimethyl-3-oxo-3,4-dihydropyrazin-2-yl)chroman-5-yl)propanoic acid (108): The title compound was prepared according to the method presented for the synthesis of compound 1 of Example 1 starting with 108A. MS (m/z) 651.2 [M+H]⁺. 1H NMR (400 MHz, DMSO-d6) δ 8.87 (d, J=7.8 Hz, 1H), 6.87 (d, J=7.7 Hz, 1H), 6.84-6.72 (m, 3H), 4.96-4.87 (m, 1H), 4.57-4.47 (m, 1H), 4.15 (s, 1H), 4.01-3.96 (m, 3H), 3.75 (d, J=12.8 Hz, 1H), 3.60-3.54 (m, 1H), 3.47 (d, J=1.3 Hz, 4H), 3.26 (d, J=12.6 Hz, 1H), 3.10 (dd, J=14.6, 4.6 Hz, 1H), 2.95-2.85 (m, 1H), 2.77 (q, J=6.8 Hz, 2H), 2.32 (s, 3H), 2.26 (s, 3H), 1.96-1.86 (m, 2H).

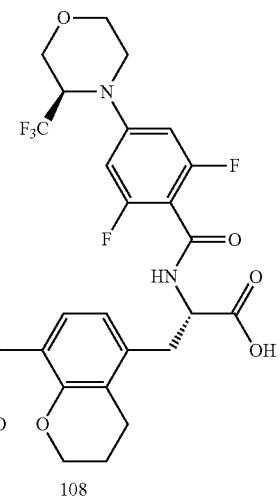

108

Example 114

Synthesis of methyl (S)-3-(8-((diphenylmethylene)amino)chroman-5-yl)-2-(tritylamino)propanoate (114B): A solution of 114A (6.30 g, 11.3 mmol), benzophenone imine (4.10 g, 22.6 mmol), cesium carbonate (11.1 g, 34.0 mmol), and Pd-176 (456 mg, 0.566 mmol) in dioxane (80 mL) was heated to 95° C. for 22 hours. The reaction mixture was diluted with water and EtOAc and the aqueous layer was extracted from EtOAc three times. The combined organic layers were dried and concentrated. The crude product was purified by silica gel chromatography using EtOAc in hexanes as eluent to afford the title compound.

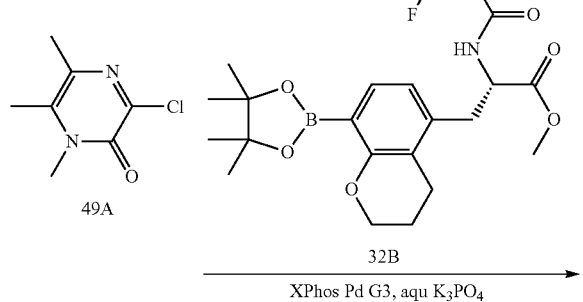

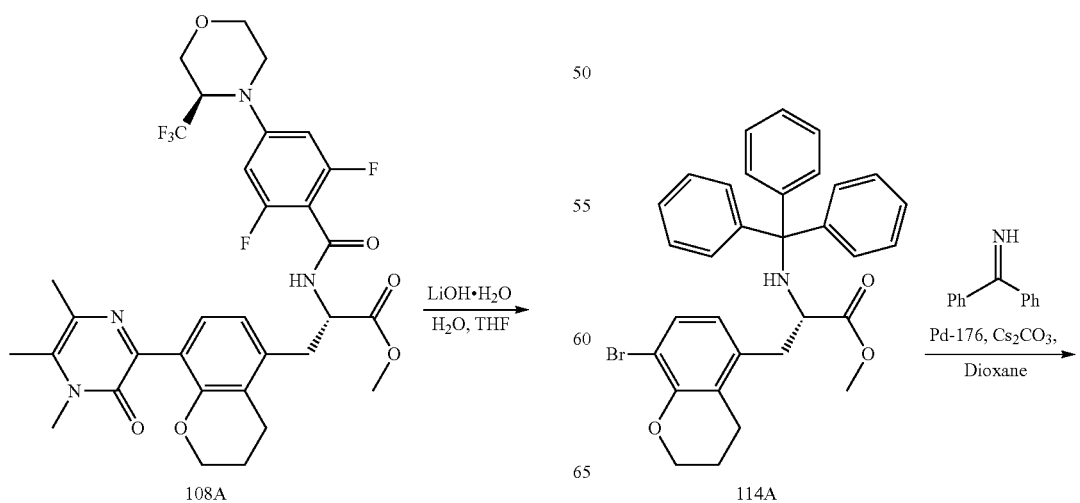

279
-continued

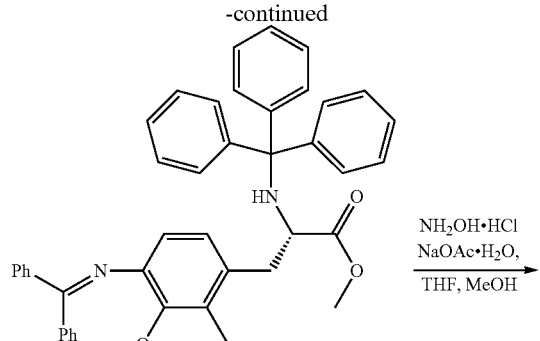

114B

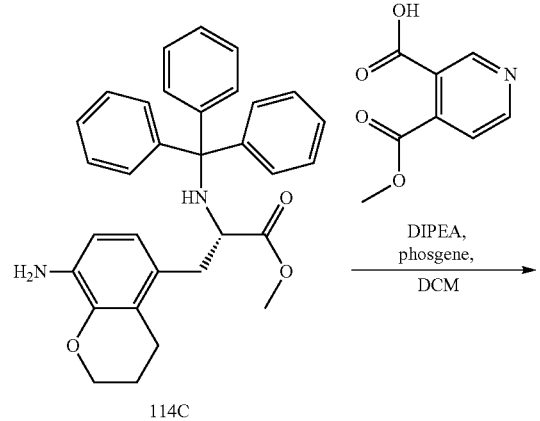

114C

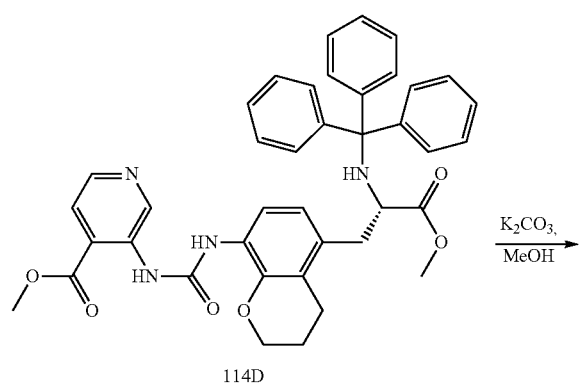

114D

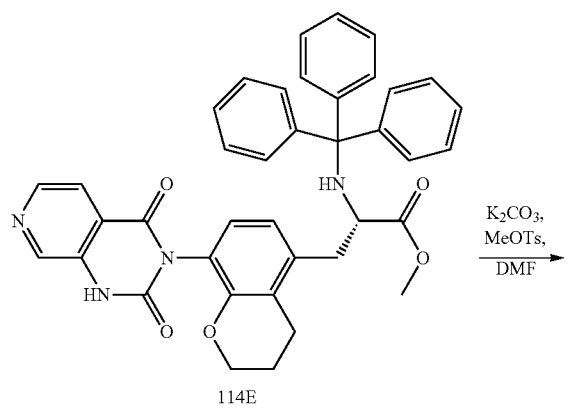

114E

280
-continued

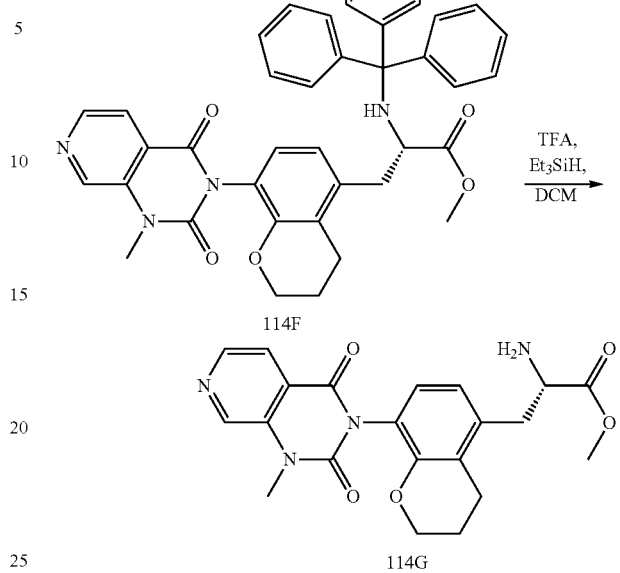

Synthesis of methyl (S)-3-(8-aminochroman-5-yl)-2-(tritylamino)propanoate (114C): To a solution of 114B (7.44 g, 11.3 mmol) in THF (50 mL) was added hydroxylamine hydrochloride (1.57 g, 22.6 mmol), followed by sodium acetate trihydrate (4.62 g, 34.0 mmol) and methanol (20 mL). The reaction was stirred at RT for 1 hour and then concentrated. The crude product was purified by silica gel chromatography using EtOAc in hexanes as eluent to afford the title compound.

Synthesis of methyl (S)-3-(3-(5-(3-methoxy-3-oxo-2-(tritylamino)propyl)chroman-8-yl)ureido)isonicotinate (114D): Under anhydrous conditions, diisopropylethylamine (1.06 mL, 6.09 mmol) was added to a solution of 4-(methoxycarbonyl)nicotinic acid (618 mg, 4.06 mmol) in DCM (2.00 mL), followed by the addition of phosgene (2.90 mL, 4.06 mmol). This was stirred at RT for 1 hour and then 114C (1.00 g, 2.03 mmol) was added. The reaction was stirred at RT for 1 hour and then purified by silica gel chromatography using MeOH in DCM as eluent to afford the title compound.

Synthesis of methyl (S)-3-(8-(2,4-dioxo-1,4-dihydropyrido[3,4-d]pyrimidin-3(2H)-yl)chroman-5-yl)-2-(tritylamino)propanoate (114E): Potassium carbonate (773 mg, 5.59 mmol) was added to a solution of 114D (750 mg, 1.12 mmol) in methanol (25.0 mL) and this was stirred at RT for 1 hour. The reaction was concentrated and the crude product was purified by silica gel chromatography using MeOH in DCM as eluent to afford the title compound.

Synthesis of methyl (S)-3-(8-(1-methyl-2,4-dioxo-1,4-dihydropyrido[3,4-d]pyrimidin-3(2H)-yl)chroman-5-yl)-2-(tritylamino)propanoate (114F): To a solution of 114E (696 mg, 1.09 mmol) in DMF (1.50 mL) was added potassium carbonate (753 mg, 5.45 mmol) and methyl tosylate (0.16 mL, 1.09 mmol). This was stirred at RT for 16 hours. The crude product was purified by silica gel chromatography using MeOH in DCM as eluent to afford the title compound.

Synthesis of methyl (S)-2-amino-3-(8-(1-methyl-2,4-dioxo-1,4-dihydropyrido[3,4-d]pyrimidin-3(2H)-yl)chroman-5-yl)propanoate (114G): To a solution of 114F (110 mg, 0.169 mmol) in DCM (5.00 mL) was added TFA (0.13 mL, 1.69 mmol) and triethylsilane (2 drops). The reaction was stirred at RT for 10 minutes and then concentrated. The product was used in the next reaction without further purification.

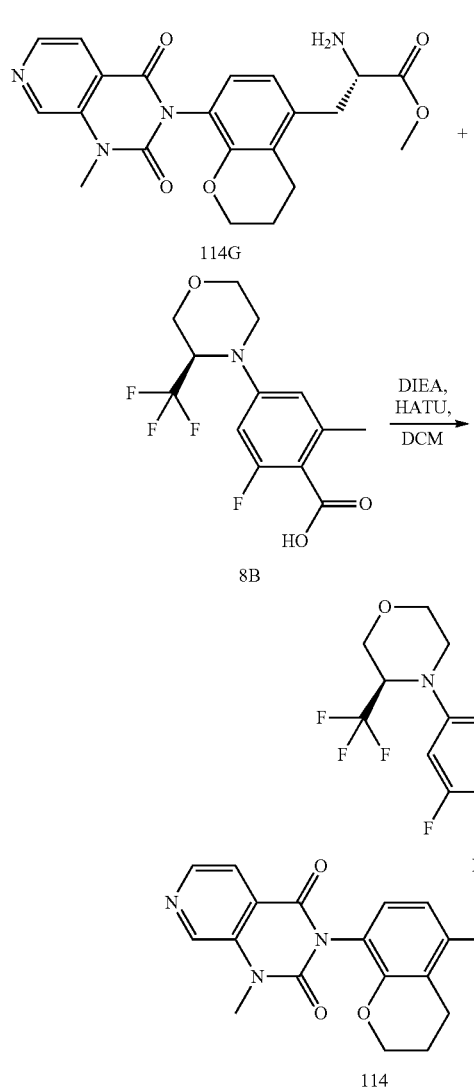

Synthesis of methyl (S)-2-(2-fluoro-6-methyl-4-((R)-3-(trifluoromethyl)morpholino) benzamido)-3-(8-(1-methyl-2,4-dioxo-1,4-dihydropyrido[3,4-d]pyrimidin-3(2H)-yl)chroman-5-yl)propanoate (114): To a solution of 7 (692 mg, 1.69 mmol) in DCM (15.0 mL) was added 8B (630 mg, 2.02 mmol), HATU (769 mg, 2.02 mmol) and diisopropylethylamine (1.76 mL, 10.1 mmol). The reaction was stirred at RT for 1 hour and then concentrated. The crude product was purified by reverse phase prep-HPLC using MeCN in water as eluent to afford the title compound. MS (m/z) 701.3 [M+H]$^+$. 1H NMR (400 MHz, Chloroform-d) δ 8.89 (d, J=2.1 Hz, 1H), 8.79-8.47 (m, 1H), 8.22 (d, J=5.2 Hz, 1H), 7.26 (t, J=1.6 Hz, 1H), 6.96 (dd, J=8.0, 2.1 Hz, 1H), 6.83 (dd, J=8.0, 2.1 Hz, 1H), 6.66-6.24 (m, 6H), 5.07 (q, J=6.7 Hz, 1H), 4.30 (d, J=12.5 Hz, 1H), 4.21-3.97 (m, 5H), 3.88-3.79 (m, 1H), 3.73 (dd, J=10.7, 2.2 Hz, 6H), 3.65 (t, J=11.8 Hz, 1H), 3.51 (t, J=12.2 Hz, 1H), 3.27 (d, J=13.1 Hz, 1H), 3.19 (dt, J=7.8, 3.9 Hz, 2H), 2.98-2.57 (m, 2H), 2.35 (d, J=2.2 Hz, 3H), 2.05 (q, J=6.0 Hz, 2H).

Example 115

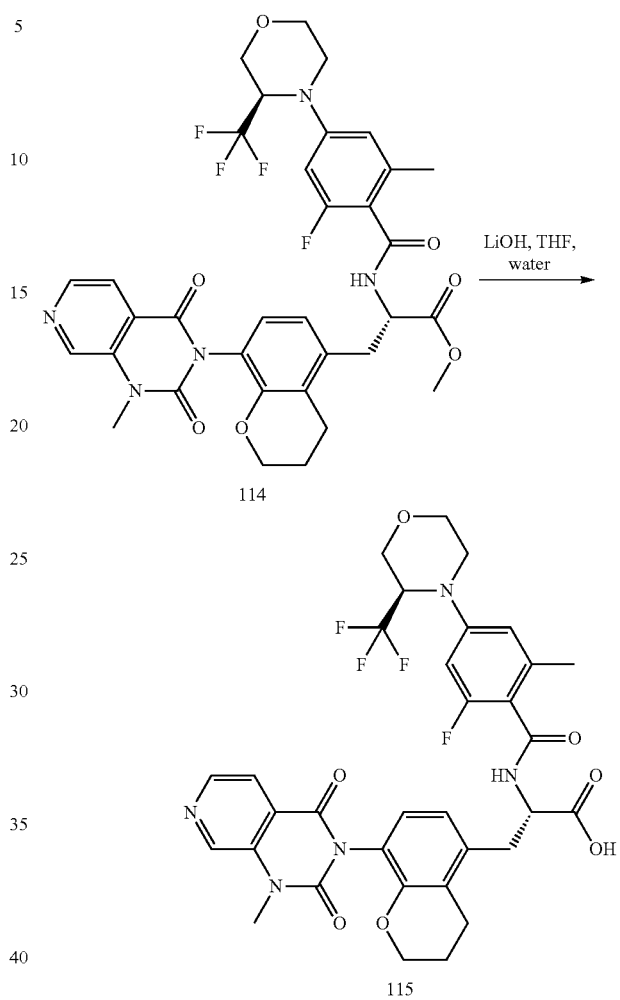

Synthesis of (S)-2-(2-fluoro-6-methyl-4-((R)-3-(trifluoromethyl)morpholino) benzamido)-3-(8-(1-methyl-2,4-dioxo-1,4-dihydropyrido[3,4-d]pyrimidin-3(2H)-yl)chroman-5-yl)propanoic acid (115): To a solution of 114 (293 mg, 0.416 mmol) in THF (2.00 mL) was added 1.5 M aq. LiOH solution (0.56 mL, 0.833 mmol). The reaction was stirred at RT for 1 hour. Then 4N HCl in dioxane (0.21 mL, 4.16 mmol) was added and the reaction was stirred at RT for 20 min. Then more 4N HCl in dioxane (0.42 mL, 8.33 mmol) was added and the reaction was stirred at RT for 90 min. The reaction was concentrated and the crude product was purified by silica gel chromatography using MeOH in DCM as eluent to afford the title compound. MS (m/z) 686.6 [M+H]$^+$. 1H NMR (400 MHz, DMSO-d6) δ 8.97 (d, J=2.1 Hz, 1H), 8.76 (d, J=8.0 Hz, 1H), 8.56 (d, J=5.1 Hz, 1H), 7.88 (d, J=5.1 Hz, 1H), 7.00 (d, J=8.0 Hz, 1H), 6.91 (d, J=8.1 Hz, 1H), 6.69 (d, J=15.4 Hz, 2H), 4.84 (d, J=9.5 Hz, 1H), 4.64 (s, 1H), 4.15 (d, J=12.8 Hz, 2H), 3.98 (d, 2H), 3.74 (d, J=12.8 Hz, 1H), 3.61 (s, 3H), 3.55 (t, J=11.8 Hz, 1H), 3.36 (d, J=12.4 Hz, 1H), 3.27 (d, J=12.2 Hz, 1H), 3.14 (d, J=15.5 Hz, 1H), 3.02-2.88 (m, 2H), 2.78 (d, J=7.5 Hz, 2H), 2.20-2.06 (m, 3H), 1.93 (s, 3H).

The compounds in table 1 below were prepared by processes described herein.

TABLE 1

| Example | Structure | 1H-NMR | M/Z [M + H]+ |
|---|---|---|---|
| 109 | 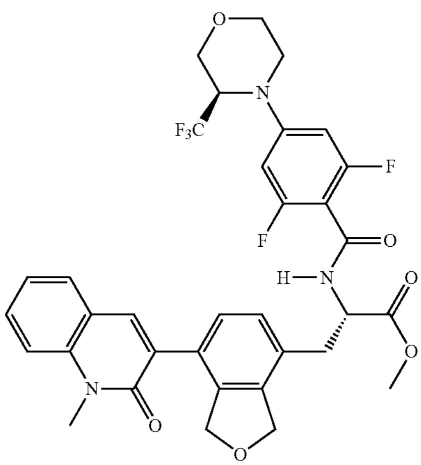 [SMILES: COC(=O)[C@H](Cc1ccc(-c2cc3ccccc3n(C)c2=O)c2c1COC2)NC(=O)c1c(F)cc(N2CCOC[C@@H]2C(F)(F)F)cc1F] | 1H NMR (400 MHz, DMSO-d6) δ 9.02 (d, J = 7.8 Hz, 1H), 7.96 (s, 1H), 7.79 (dd, J = 7.9, 1.5 Hz, 1H), 7.66 (ddd, J = 8.6, 7.1, 1.5 Hz, 1H), 7.57 (d, J = 8.5 Hz, 1H), 7.34-7.27 (m, 2H), 7.24 (d, J = 7.8 Hz, 1H), 6.79 (d, J = 11.7 Hz, 2H), 5.18-5.03 (m, 2H), 4.99 (d, J = 1.9 Hz, 2H), 4.97-4.86 (m, 1H), 4.68 (ddd, J = 9.6, 7.7, 5.2 Hz, 1H), 4.17 (d, J = 12.7 Hz, 1H), 3.96 (dd, J = 11.5, 3.8 Hz, 1H), 3.70 (s, 3H), 3.68 (s, 3H), 3.56 (td, J = 11.8, 3.2 Hz, 2H), 3.44 (d, J = 12.8 Hz, 1H), 3.25 (t, J = 12.3 Hz, 1H), 3.10 (dd, J = 14.3, 5.2 Hz, 1H), 2.98 (dd, J = 14.4, 9.6 Hz, 1H). | 672.3 |
| 110 | 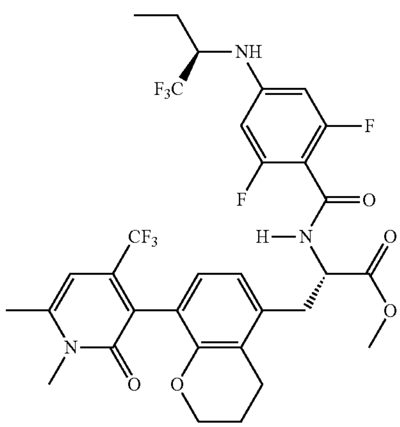 [SMILES: CC[C@@H](Nc1cc(F)c(C(=O)N[C@@H](Cc2ccc(-c3c(C(F)(F)F)cc(C)n(C)c3=O)c3c2CCCO3)C(=O)OC)c(F)c1)C(F)(F)F] | 1H NMR (400 MHz, DMSO-d6) δ 8.87 (dd, J = 7.7, 2.9 Hz, 1H), 6.82-6.67 (m, 3H), 6.47 (d, J = 11.8 Hz, 2H), 6.43 (s, 1H), 4.58 (p, J = 8.0 Hz, 1H), 4.32 (d, J = 9.9 Hz, 1H), 3.96 (dtt, J = 33.5, 10.5, 6.2 Hz, 2H), 3.60 (d, J = 7.2 Hz, 3H), 3.47 (s, 3H), 3.10-2.86 (m, 2H), 2.80-2.64 (m, 2H), 2.46 (s, 3H), 1.90 (q, J = 5.7 Hz, 2H), 1.84-1.71 (m, 1H), 1.54 (tt, J = 14.3, 7.4 Hz, 1H), 0.93 (t, J = 7.3 Hz, 3H). | 690.9 |
| 111 | 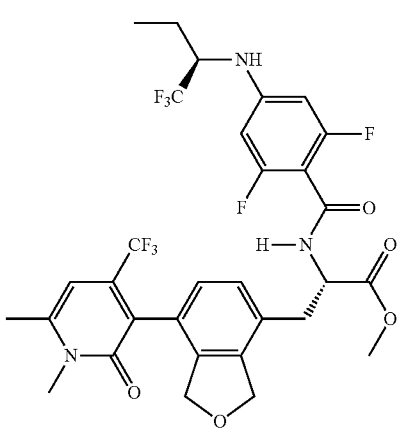 [SMILES: CC[C@@H](Nc1cc(F)c(C(=O)N[C@@H](Cc2ccc(-c3c(C(F)(F)F)cc(C)n(C)c3=O)c3c2COC3)C(=O)OC)c(F)c1)C(F)(F)F] | 1H NMR (400 MHz, DMSO-d6) δ 8.86 (dd, J = 7.6, 2.8 Hz, 1H), 7.16 (dd, J = 7.8, 3.6 Hz, 1H), 6.92 (d, J = 7.7 Hz, 1H), 6.81-6.74 (m, 1H), 6.53 (s, 1H), 6.46 (dd, J = 11.3, 2.3 Hz, 2H), 5.11 (t, J = 10.0 Hz, 2H), 4.76 (d, J = 12.4 Hz, 1H), 4.71-4.60 (m, 2H), 4.32 (d, J = 9.5 Hz, 1H), 3.61 (d, J = 1.9 Hz, 3H), 3.49 (s, 3H), 3.05 (dt, J = 14.5, 5.0 Hz, 1H), 2.95 (dd, J = 14.5, 9.6 Hz, 1H), 2.48 (s, 3H), 1.78 (ddd, J = 14.0, 7.6, 3.4 Hz, 1H), 1.53 (ddt, J = 17.7, 14.4, 7.5 Hz, 1H), 0.93 (t, J = 7.3 Hz, 3H). | 676.3 |

TABLE 1-continued

| Example | Structure | 1H-NMR | M/Z [M + H]+ |
|---|---|---|---|
| 112 | 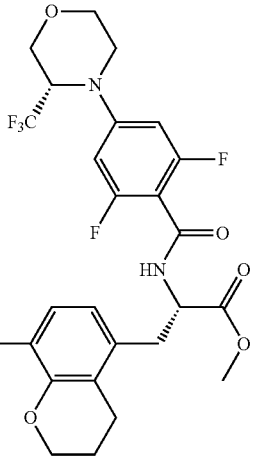 | 1H NMR (400 MHz, DMSO-d6) δ 9.00 (d, J = 7.6 Hz, 1H), 6.78 (qd, J = 5.6, 2.8 Hz, 4H), 4.92 (d, J = 9.4 Hz, 1H), 4.68-4.54 (m, 1H), 4.17 (d, J = 12.7 Hz, 1H), 4.08-3.99 (m, 2H), 3.96 (dd, J = 11.5, 3.7 Hz, 1H), 3.74 (d, J = 12.7 Hz, 1H), 3.65 (d, J = 6.9 Hz, 3H), 3.62-3.50 (m, 1H), 3.43 (d, J = 14.2 Hz, 1H), 3.39 (s, 3H), 3.30-3.21 (m, 1H), 3.19 (d, J = 0.9 Hz, 3H), 3.08 (td, J = 16.8, 15.8, 5.2 Hz, 1H), 3.02-2.88 (m, 1H), 2.81-2.65 (m, 2H), 2.01 (d, J = 4.2 Hz, 3H), 1.92 (s, 2H). | 681.3 |
| 113 | 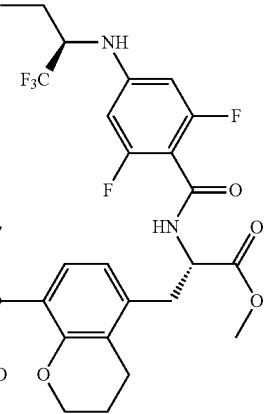 | 1H NMR (400 MHz, DMSO-d6) δ 8.86 (dd, J = 7.6, 1.8 Hz, 1H), 6.84-6.72 (m, 3H), 6.46 (dd, J = 11.4, 3.5 Hz, 2H), 4.59 (ddd, J = 13.5, 10.8, 6.4 Hz, 1H), 4.32 (d, J = 10.1 Hz, 1H), 4.07-3.96 (m, 2H), 3.63 (d, J = 7.7 Hz, 3H), 3.39 (s, 3H), 3.19 (d, J = 1.1 Hz, 3H), 3.14-2.99 (m, 1H), 2.92 (ddd, J = 19.9, 14.3, 9.6 Hz, 1H), 2.71 (dd, J = 18.1, 11.7 Hz, 2H), 2.03-1.97 (m, 3H), 1.97-1.86 (m, 2H), 1.78 (ddd, J = 13.8, 7.3, 3.2 Hz, 1H), 1.53 (ddt, J = 17.7, 14.4, 7.5 Hz, 1H), 0.93 (t, J = 7.3 Hz, 3H). | 653.2 |
| 114 | 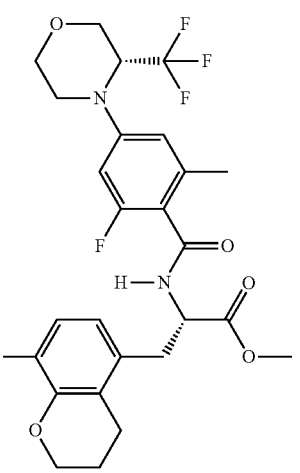 | 1H NMR (400 MHz, Chloroform-d) δ 8.89 (d, J = 2.1 Hz, 1H), 8.79-8.47 (m, 1H), 8.22 (d, J = 5.2 Hz, 1H), 7.26 (t, J = 1.6 Hz, 1H), 6.96 (dd, J = 8.0, 2.1 Hz, 1H), 6.83 (dd, J = 8.0, 2.1 Hz, 1H), 6.66-6.24 (m, 6H), 5.07 (q, J = 6.7 Hz, 1H), 4.30 (d, J = 12.5 Hz, 1H), 4.21-3.97 (m, 5H), 3.88-3.79 (m, 1H), 3.73 (dd, J = 10.7, 2.2 Hz, 6H), 3.65 (t, J = 11.8 Hz, 1H), 3.51 (t, J = 12.2 Hz, 1H), 3.27 (d, J = 13.1 Hz, 1H), 3.19 (dt, J = 7.8, 3.9 Hz, 2H), 2.98-2.57 (m, 2H), 2.35 (d, J = 2.2 Hz, 3H), 2.05 (q, J = 6.0 Hz, 2H). | 701.3 |

TABLE 1-continued

| Example | Structure | 1H-NMR | M/Z [M + H]+ |
|---|---|---|---|
| 115 | 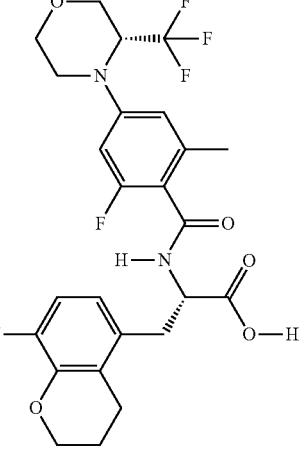 | 1H NMR (400 MHz, DMSO-d6) δ 8.97 (d, J = 2.1 Hz, 1H), 8.76 (d, J = 8.0 Hz, 1H), 8.56 (d, J = 5.1 Hz, 1H), 7.88 (d, J = 5.1 Hz, 1H), 7.00 (d, J = 8.0 Hz, 1H), 6.91 (d, J = 8.1 Hz, 1H), 6.69 (d, J = 15.4 Hz, 2H), 4.84 (d, J = 9.5 Hz, 1H), 4.64 (s, 1H), 4.15 (d, J = 12.8 Hz, 2H), 3.98 (d, 2H), 3.74 (d, J = 12.8 Hz, 1H), 3.61 (s, 3H), 3.55 (t, J = 11.8 Hz, 1H), 3.36 (d, J = 12.4 Hz, 1H), 3.27 (d, J = 12.2 Hz, 1H), 3.14 (d, J = 15.5 Hz, 1H), 3.02-2.88 (m, 1H), 2.78 (d, J = 7.5 Hz, 2H), 2.20-2.06 (m, 3H), 1.93 (s, 3H). | 686.6 |
| 116 | 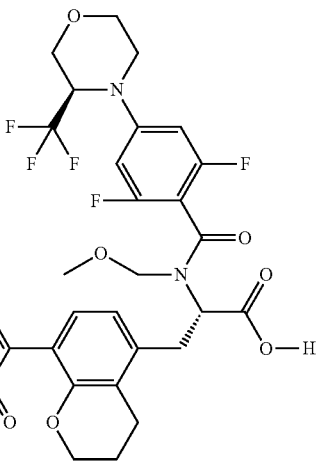 | 1H NMR (400 MHz, DMSO-d6) δ 6.93-6.73 (m, 4H), 4.91 (dt, J = 9.1, 3.8 Hz, 1H), 4.53 (dd, J = 9.8, 4.9 Hz, 1H), 4.44 (dd, J = 11.2, 4.7 Hz, 1H), 4.15 (t, J = 12.0 Hz, 2H), 4.05-3.89 (m, 3H), 3.74 (d, J = 12.6 Hz, 1H), 3.56 (t, J = 11.0 Hz, 1H), 3.46 (s, 4H), 3.41-3.31 (m, 1H), 3.22 (dd, J = 14.5, 10.1 Hz, 1H), 2.91 (s, 3H), 2.76 (t, J = 6.5 Hz, 2H), 2.38-2.29 (m, 3H), 2.29-2.21 (m, 3H), 1.92 (d, J = 6.7 Hz, 2H). | 695.2 |
| 117 | 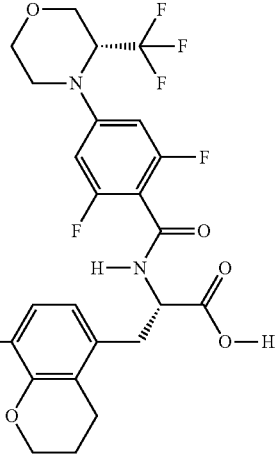 | 1H NMR (400 MHz, DMSO-d6) δ 12.75 (s, 1H), 8.86 (dd, J = 8.0, 4.3 Hz, 1H), 6.87-6.72 (m, 4H), 4.91 (d, J = 9.4 Hz, 1H), 4.57 (dtd, J = 13.5, 9.4, 8.9, 4.5 Hz, 1H), 4.16 (d, J = 12.7 Hz, 1H), 4.01 (t, J = 5.2 Hz, 2H), 3.96 (dd, J = 11.5, 3.8 Hz, 1H), 3.74 (d, J = 12.7 Hz, 1H), 3.56 (t, J = 11.4 Hz, 1H), 3.44 (s, 3H), 3.41 (s, 1H), 3.24 (t, J = 12.2 Hz, 1H), 3.16-3.05 (m, 1H), 2.91 (td, J = 14.1, 10.0 Hz, 1H), 2.77 (t, J = 6.7 Hz, 2H), 2.55 (s, 3H), 1.96 (d, J = 6.3 Hz, 3H), 1.93 (s, 2H). | 651.2 |

TABLE 1-continued

| Example | Structure | 1H-NMR | M/Z [M + H]+ |
|---|---|---|---|
| 118 | 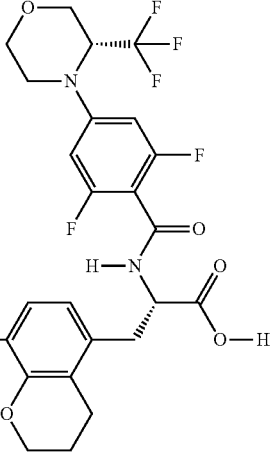 | 1H NMR (400 MHz, DMSO-d6) δ 12.92-12.53 (s, 1H), 8.86 (dd, J = 8.0, 4.3 Hz, 1H), 6.86-6.72 (m, 4H), 4.91 (d, J = 9.9 Hz, 1H), 4.64-4.50 (m, 1H), 4.16 (d, J = 12.7 Hz, 1H), 4.01 (t, J = 5.2 Hz, 2H), 3.99-3.93 (m, 1H), 3.74 (d, J = 12.9 Hz, 1H), 3.56 (t, J = 11.6 Hz, 1H), 3.44 (s, 3H), 3.41 (s, 1H), 3.24 (t, J = 12.4 Hz, 1H), 3.16-3.06 (m, 1H), 2.97-2.85 (m, 1H), 2.77 (t, J = 6.7 Hz, 2H), 2.53 (s, 3H), 1.94 (d, J = 6.3 Hz, 4H), 1.93-1.88 (m, 1H). | 650.9 |
| 119 | 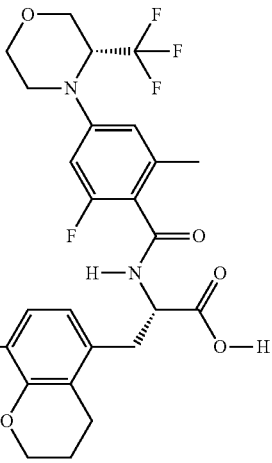 | 1H NMR (400 MHz, DMSO-d6) δ 12.95-12.37 (s, 1H), 8.71 (dd, J = 8.1, 2.5 Hz, 1H), 6.85 (dd, J = 9.6, 7.8 Hz, 1H), 6.79 (t, J = 7.9 Hz, 1H), 6.72-6.63 (m, 2H), 4.83 (d, J = 9.5 Hz, 1H), 4.65 (td, J = 9.5, 7.9, 4.0 Hz, 1H), 4.14 (d, J = 12.6 Hz, 1H), 4.01 (q, J = 4.4 Hz, 2H), 3.95 (dd, J = 11.4, 3.6 Hz, 1H), 3.73 (d, J = 12.6 Hz, 1H), 3.54 (t, J = 10.4 Hz, 1H), 3.44 (d, J = 2.2 Hz, 3H), 3.35 (d, J = 12.4 Hz, 1H), 3.27 (d, J = 11.9 Hz, 1H), 3.11 (s, 1H), 2.90 (ddd, J = 19.4, 14.8, 10.8 Hz, 1H), 2.81-2.73 (m, 2H), 2.54 (s, 3H), 2.08 (d, J = 10.8 Hz, 3H), 1.95 (d, J = 5.7 Hz, 4H), 1.93-1.88 (m, 1H). | 647.3 |
| 120 | 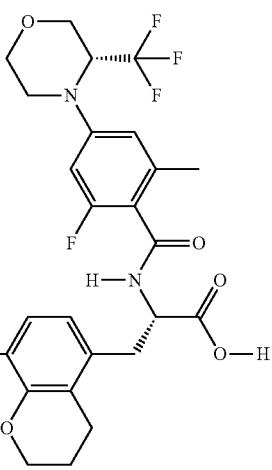 | 1H NMR (400 MHz, DMSO-d6) δ 12.92-12.52 (s, 1H), 8.71 (dd, J = 8.1, 2.4 Hz, 1H), 6.88-6.82 (m, 1H), 6.78 (t, J = 7.9 Hz, 1H), 6.72-6.61 (m, 2H), 4.83 (d, J = 9.7 Hz, 1H), 4.69-4.59 (m, 1H), 4.15 (d, J = 12.6 Hz, 1H), 4.00 (d, J = 2.2 Hz, 2H), 3.95 (d, J = 10.3 Hz, 1H), 3.73 (d, J = 12.6 Hz, 1H), 3.54 (t, J = 11.8 Hz, 1H), 3.44 (d, J = 2.2 Hz, 3H), 3.35 (d, J = 12.5 Hz, 1H), 3.25 (t, J = 11.9 Hz, 1H), 3.18-3.05 (m, 1H), 2.90 (ddd, J = 19.7, 14.7, 10.6 Hz, 1H), 2.78 (d, J = 5.8 Hz, 2H), 2.55-2.53 (m, 3H), 2.08 (d, J = 10.9 Hz, 3H), 1.95 (d, J = 5.7 Hz, 4H), 1.93-1.87 (m, 1H). | 647.3 |

TABLE 1-continued
| Example | Structure | 1H-NMR | M/Z [M + H]+ |
|---|---|---|---|
| 121 | 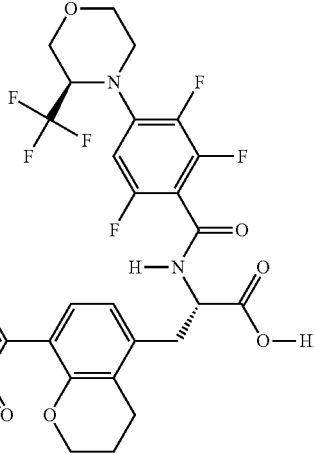 | 1H NMR (400 MHz, DMSO-d6) δ 9.13 (d, J = 7.9 Hz, 1H), 7.02 (t, J = 9.3 Hz, 1H), 6.88 (d, J = 7.6 Hz, 1H), 6.80 (d, J = 7.8 Hz, 1H), 4.60-4.49 (m, 1H), 4.49-4.38 (m, 1H), 4.12 (d, J = 12.9 Hz, 1H), 4.02-3.83 (m, 4H), 3.65-3.50 (m, 2H), 3.47 (s, 3H), 3.13 (d, J = 13.1 Hz, 2H), 2.96-2.86 (m, 1H), 2.81-2.71 (m, 2H), 2.32 (s, 3H), 2.26 (s, 3H), 1.97-1.88 (m, 2H). | 669.2 |
| 122 | 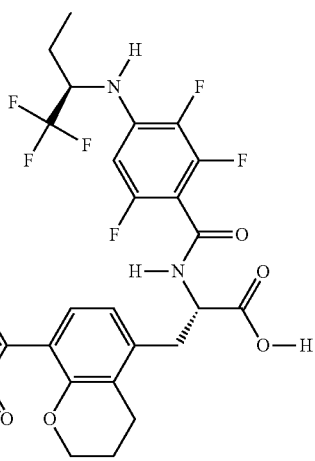 | 1H NMR (400 MHz, DMSO-d6) δ 8.89 (d, J = 7.8 Hz, 1H), 6.95-6.75 (m, 3H), 6.70 (d, J = 9.3 Hz, 1H), 4.55-4.46 (m, 1H), 4.44-4.30 (m, 1H), 4.03-3.94 (m, 1H), 3.47 (s, 3H), 3.15-3.04 (m, 1H), 2.95-2.82 (m, 2H), 2.82-2.70 (m, 2H), 2.32 (s, 3H), 2.26 (s, 3H), 1.98-1.84 (m, 2H), 1.84-1.69 (m, 2H), 10.93 (t, J = 7.3 Hz, 3H). | 641.2 |
| 123 | 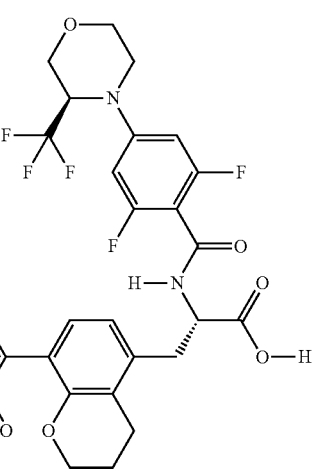 | 1H NMR (400 MHz, DMSO-d6) δ 12.74 (s, 1H), 8.88 (d, J = 7.8 Hz, 1H), 8.42 (s, 1H), 6.97 (d, J = 7.7 Hz, 1H), 6.87 (d, J = 7.8 Hz, 1H), 6.78 (d, J = 11.9 Hz, 2H), 4.97-4.85 (m, 1H), 4.58-4.47 (m, 1H), 4.16 (d, J = 12.7 Hz, 1H), 4.07-3.99 (m, 2H), 3.96 (d, J = 11.7 Hz, 1H), 3.74 (d, J = 12.8 Hz, 1H), 3.62-3.48 (m, 4H), 3.43 (d, J = 12.6 Hz, 1H), 3.24 (t, J = 12.4 Hz, 1H), 3.19-3.07 (m, 1H), 3.00-2.87 (m, 1H), 2.83-2.72 (m, 2H), 2.02-1.86 (m, 2H). | 691.2 |

TABLE 1-continued

| Example | Structure | 1H-NMR | M/Z [M + H]+ |
|---|---|---|---|
| 124 | 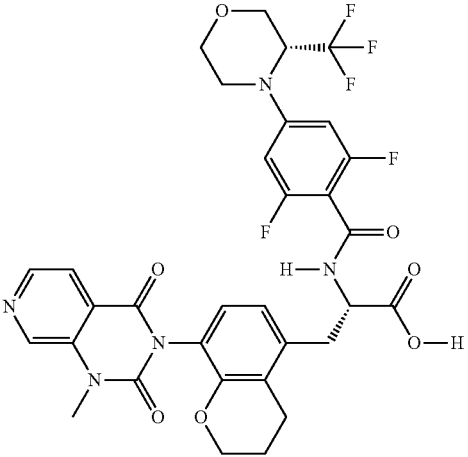 [SMILES: Cc1cc(N2CCOC[C@@H]2C(F)(F)F)cc(F)c1C(=O)N[C@@H](Cc1ccc(-n2c(=O)c3ccncc3n(C)c2=O)c2c1CCCO2)C(=O)O] | 1H NMR (400 MHz, DMSOd6) δ 8.97 (s, 1H), 8.92 (d, J = 7.7 Hz, 1H), 8.56 (d, J = 5.1 Hz, 1H), 7.88 (dd, J = 5.0, 2.5 Hz, 1H), 7.00 (d, J = 7.9 Hz, 1H), 6.90 (d, J = 8.1 Hz, 1H), 6.79 (d, J = 11.8 Hz, 2H), 4.92 (d, J = 9.5 Hz, 1H), 4.56 (s, 1H), 4.17 (d, J = 12.7 Hz, 1H), 4.05-3.93 (m, 5H), 3.75 (d, 2H), 3.61 (s, 3H), 3.55 (d, J = 12.1 Hz, 1H), 3.44 (d, J = 12.8 Hz, 1H), 3.25 (t, J = 12.4 Hz, 1H), 3.19-3.09 (m, 1H), 2.95 (dd, J = 14.9, 10.0 Hz, 1H), 2.78 (d, J = 6.0 Hz, 2H), 1.93 (s, 3H). | 690.6 |
| 125 | 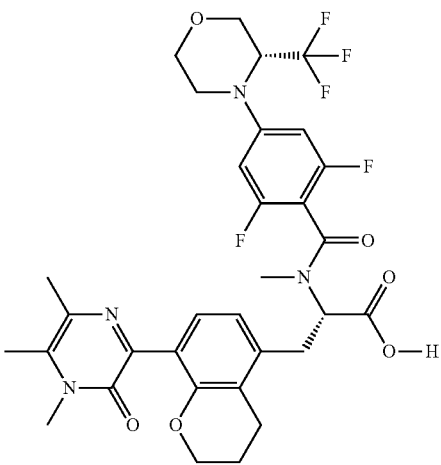 [SMILES: Cc1nc(-c2ccc(C[C@@H](C(=O)O)N(C)C(=O)c3c(F)cc(N4CCOC[C@@H]4C(F)(F)F)cc3F)c3c2OCCC3)c(=O)n(C)c1C] | 1H NMR (400 MHz, DMSO-d6) δ 6.97-6.69 (m, 5H), 5.11-4.77 (m, 3H), 4.17 (d, J = 12.8 Hz, 2H), 3.97 (dt, J = 11.7, 4.8 Hz, 3H), 3.79-3.63 (m, 6H), 3.63-3.39 (m, 6H), 3.33-2.93 (m, 5H), 2.82-2.62 (m, 5H), 2.33 (s, 3H), 2.26 (s, 3H), 1.99-1.71 (m, 4H).; 1H NMR (400 MHz, DMSO-d6) δ 6.94-6.72 (m, 4H), 4.97 (d, J = 54.8 Hz, 2H), 4.16 (d, J = 12.6 Hz, 1H), 4.06-3.88 (m, 3H), 3.74 (d, J = 12.4 Hz, 1H), 3.63-3.38 (m, 5H), 3.35-2.88 (m, 5H), 2.84-2.61 (m, 4H), 2.33 (s, 3H), 2.26 (s, 3H), 1.84 (m, 3H). | 665.3 |
| 126 | 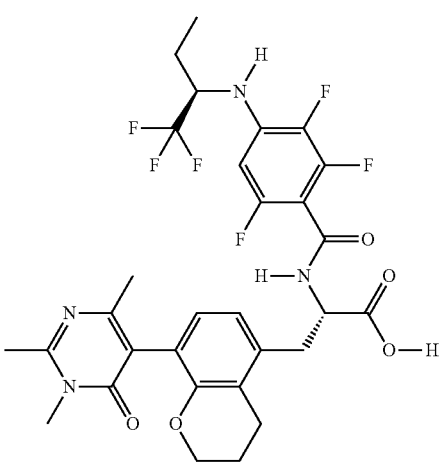 [SMILES: CC[C@@H](Nc1cc(F)c(C(=O)N[C@@H](Cc2ccc(-c3c(C)nc(C)n(C)c3=O)c3c2CCCO3)C(=O)O)c(F)c1F)C(F)(F)F] | 1H NMR (400 MHz, DMSO-d6) δ 8.87 (dd, J = 8.1, 3.3 Hz, 1H), 6.89-6.76 (m, 3H), 6.69 (d, J = 9.4 Hz, 1H), 4.57 (s, 1H), 4.37 (s, 1H), 4.01 (d, J = 5.4 Hz, 2H), 3.45 (s, 3H), 3.12 (t, J = 13.4 Hz, 1H), 2.89 (q, J = 13.2 Hz, 1H), 2.76 (q, J = 8.7, 7.5 Hz, 2H), 2.57 (s, 3H), 1.95 (dd, J = 15.5, 5.9 Hz, 5H), 1.78 (dt, J = 14.1, 7.1 Hz, 2H), 0.93 (t, J = 7.3 Hz, 3H). | 641.5 |

TABLE 1-continued

| Example | Structure | 1H-NMR | M/Z [M + H]+ |
|---|---|---|---|
| 127 | 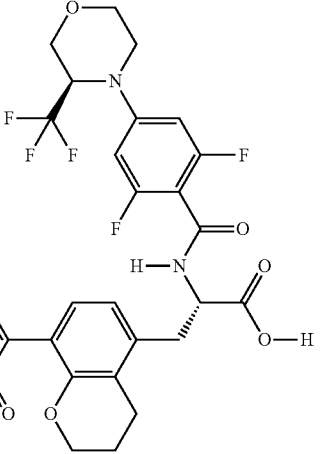 | 1H NMR (400 MHz, DMSO-d6) δ 8.87 (d, J = 7.9 Hz, 1H), 6.88 (d, J = 7.5 Hz, 1H), 6.84-6.73 (m, 3H), 4.91 (d, J = 16.0 Hz, 1H), 4.51 (t, J = 8.4 Hz, 1H), 4.16 (d, J = 12.7 Hz, 1H), 3.97 (m, 4H), 3.75 (d, J = 12.1 Hz, 1H), 3.58 (d, J = 13.4 Hz, 1H), 3.45 (s, 1H), 3.40 (s, 3H), 3.28-3.21 (m, 1H), 3.10 (dd, J = 14.4, 4.3 Hz, 1H), 2.94-2.87 (m, 1H), 2.81-2.68 (m, 4H), 2.60 (m, 2H), 1.98-1.89 (m, 2H), 1.82-1.65 (m, 4H). | 677.2 |
| 128 | 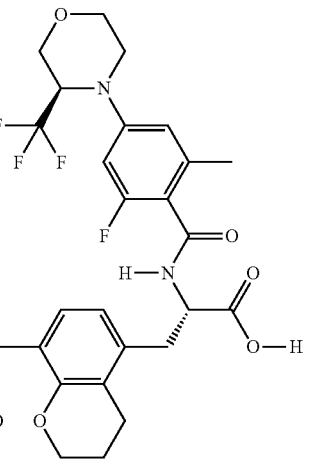 | 1H NMR (400 MHz, DMSO-d6) δ 8.71 (d, J = 8.0 Hz, 1H), 7.78 (s, 1H), 6.95 (d, J = 7.7 Hz, 1H), 6.83 (d, J = 7.8 Hz, 1H), 6.68 (d, J = 15.1 Hz, 2H), 4.84 (dd, J = 9.0, 3.3 Hz, 1H), 4.60 (td, J = 9.2, 8.4, 4.1 Hz, 1H), 4.15 (d, J = 12.6 Hz, 1H), 4.08-3.87 (m, 3H), 3.74 (d, J = 12.2 Hz, 1H), 3.61-3.40 (m, 4H), 3.31 (dd, J = 32.8, 12.4 Hz, 2H), 3.11 (dd, J = 14.5, 4.3 Hz, 1H), 2.96-2.82 (m, 1H), 2.77 (q, J = 7.0 Hz, 2H), 2.56 (s, 3H), 2.11 (s, 3H), 1.95 (p, J = 6.0 Hz, 2H). | 633.6 |
| 129 | 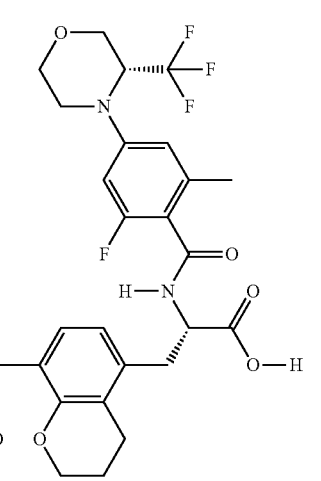 | 1H NMR (400 MHz, DMSO-d6) δ 13.09-12.5 (s, 1H), 8.71 (dd, J = 8.2, 2.4 Hz, 1H), 6.82 (dt, J = 23.5, 8.0 Hz, 2H), 6.73-6.62 (m, 2H), 4.84 (d, J = 9.3 Hz, 1H), 4.65 (td, J = 9.6, 8.2, 4.0 Hz, 1H), 4.15 (d, J = 12.6 Hz, 1H), 4.00 (d, J = 5.5 Hz, 2H), 3.95 (dd, J = 11.6, 3.5 Hz, 1H), 3.73 (d, J = 12.7 Hz, 1H), 3.54 (t, J = 11.4 Hz, 1H), 3.44 (d, J = 2.1 Hz, 3H), 3.35 (d, J = 12.3 Hz, 1H), 3.27 (d, J = 11.9 Hz, 1H), 3.17-3.06 (m, 1H), 2.98-2.86 (m, 1H), 2.76 (dd, J = 16.5, 6.2 Hz, 2H), 2.55 (s, 3H), 2.08 (d, J = 10.5 Hz, 3H), 1.96 (d, J = 5.8 Hz, 3H), 1.95-1.80 (m, 2H). | 647.2 |

TABLE 1-continued

| Example | Structure | 1H-NMR | M/Z [M + H]+ |
|---|---|---|---|
| 130 | 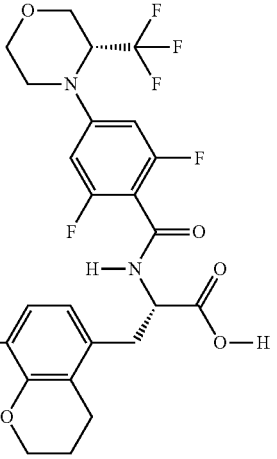 | 1H NMR (400 MHz, DMSO-d6) δ 13.02-12.48 (s, 1H), 8.86 (dd, J = 8.0, 4.3 Hz, 1H), 6.87-6.74 (m, 4H), 4.91 (d, J = 9.6 Hz, 1H), 4.57 (q, J = 13.9, 13.3 Hz, 1H), 4.16 (d, J = 12.7 Hz, 1H), 4.01 (t, J = 5.2 Hz, 2H), 3.96 (dd, J = 11.7, 3.8 Hz, 1H), 3.74 (d, J = 13.2 Hz, 1H), 3.61-3.50 (m, 1H), 3.44 (s, 3H), 3.40 (d, J = 10.0 Hz, 1H), 3.24 (t, J = 12.2 Hz, 1H), 3.16-3.05 (m, 1H), 2.91 (td, J = 14.0, 9.9 Hz, 1H), 2.76 (q, J = 7.5, 6.9 Hz, 2H), 2.56 (s, 3H), 2.01-1.85 (m, 5H). | 651.2 |
| 131 | 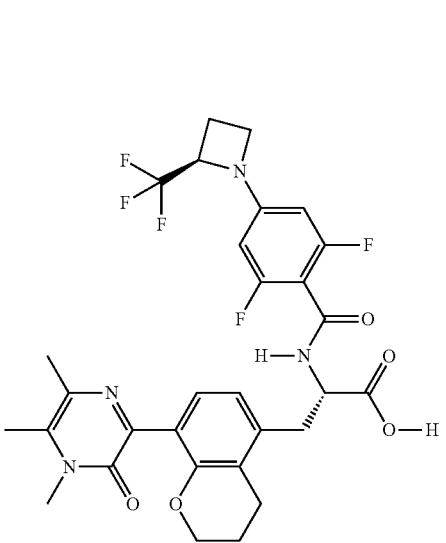 [SMILES: Cc1nc(-c2ccc(C[C@H](NC(=O)c3c(F)cc(N4CC[C@@H]4C(F)(F)F)cc3F)C(=O)O)c3c2OCCC3)c(=O)n(C)c1C] | 1H NMR (400 MHz, DMSO-d6) δ 8.84 (d, J = 7.9 Hz, 1H), 6.87 (d, J = 7.7 Hz, 1H), 6.80 (d, J = 7.8 Hz, 1H), 6.33-6.24 (m, 2H), 4.99-4.88 (m, 1H), 4.57-4.47 (m, 1H), 4.13-4.05 (m, 1H), 4.03-3.94 (m, 2H), 3.76 (q, J = 9.7, 7.2 Hz, 1H), 3.47 (s, 3H), 3.10 (dd, J = 14.5, 4.7 Hz, 1H), 2.91 (dd, J = 14.4, 9.5 Hz, 1H), 2.83-2.69 (m, 2H), 2.69-2.56 (m, 1H), 2.45-2.35 (m, 1H), 2.32 (s, 3H), 2.26 (s, 3H), 1.98-1.87 (m, 2H). | 621.1 |
| 132 | 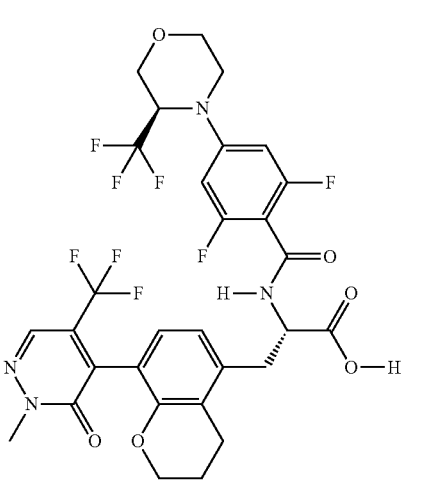 [SMILES: Cn1ncc(C(F)(F)F)c(-c2ccc(C[C@H](NC(=O)c3c(F)cc(N4CCOC[C@@H]4C(F)(F)F)cc3F)C(=O)O)c3c2OCCC3)c1=O] | 1H NMR (400 MHz, DMSO-d6) δ 8.87 (dd, J = 7.9, 6.1 Hz, 1H), 8.22 (s, 1H), 6.86 (d, J = 8.6 Hz, 2H), 6.77 (dd, J = 11.7, 2.4 Hz, 2H), 4.91 (d, J = 9.8 Hz, 1H), 4.58 (dt, J = 12.5, 8.5 Hz, 1H), 4.16 (d, J = 12.7 Hz, 1H), 3.98 (ddd, J = 21.3, 10.7, 4.7 Hz, 4H), 3.73 (d, J = 1.2 Hz, 3H), 3.58-3.51 (m, 1H), 3.43 (d, J = 12.9 Hz, 1H), 3.24 (t, J = 12.2 Hz, 1H), 3.11 (dt, J = 14.7, 4.9 Hz, 1H), 2.98-2.87 (m, 1H), 2.76 (d, J = 6.3 Hz, 2H), 1.97-1.86 (m, 2H). | 690.9 |

TABLE 1-continued

| Example | Structure | 1H-NMR | M/Z [M + H]+ |
|---|---|---|---|
| 133 | 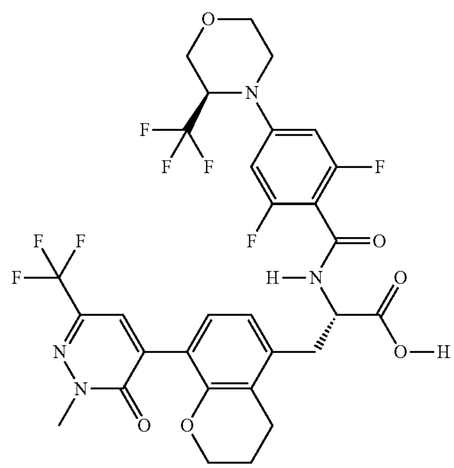 [SMILES: Cn1nc(C(F)(F)F)cc(-c2ccc(C[C@H](NC(=O)c3c(F)cc(N4CCOC[C@@H]4C(F)(F)F)cc3F)C(=O)O)c3c2OCCC3)c1=O] | 1H NMR (400 MHz, DMSO-d6) δ 8.88 (d, J = 7.9 Hz, 1H), 7.77 (s, 1H), 7.17 (d, J = 7.9 Hz, 1H), 6.88 (d, J = 7.9 Hz, 1H), 6.78 (d, J = 11.7 Hz, 2H), 4.91 (dd, J = 8.7, 3.6 Hz, 1H), 4.62-4.45 (m, 1H), 4.17 (d, J = 12.7 Hz, 1H), 4.11-4.03 (m, 2H), 3.96 (dd, J = 11.5, 3.8 Hz, 1H), 3.77 (s, 4H), 3.61-3.49 (m, 1H), 3.43 (d, J = 12.7 Hz, 1H), 3.26 (d, J = 12.2 Hz, 1H), 3.13 (dd, J = 14.5, 4.4 Hz, 1H), 2.92 (dd, J = 14.6, 9.8 Hz, 1H), 2.79 (q, J = 7.1 Hz, 2H), 2.02-1.88 (m, 2H). | 691 |
| 134 | 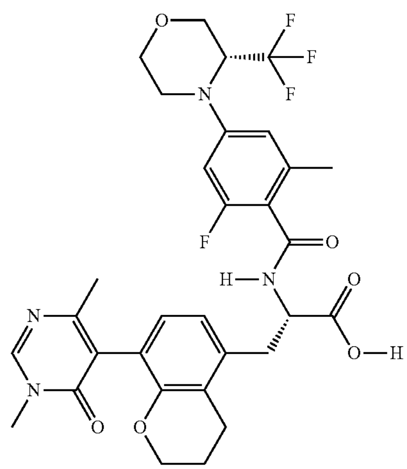 [SMILES: Cc1cc(N2CCOC[C@@H]2C(F)(F)F)cc(F)c1C(=O)N[C@@H](Cc1ccc(-c2c(C)ncn(C)c2=O)c2c1CCCO2)C(=O)O] | 1H NMR (400 MHz, DMSO-d6) δ 8.71 (d, J = 8.1 Hz, 1H), 8.41 (s, 1H), 6.82 (dt, J = 19.9, 8.1 Hz, 2H), 6.75-6.54 (m, 2H), 4.83 (d, J = 9.4 Hz, 1H), 4.75-4.54 (m, 1H), 4.14 (d, J = 12.7 Hz, 1H), 3.97 (d, J = 30.0 Hz, 3H), 3.73 (d, J = 12.6 Hz, 1H), 3.54 (t, J = 11.5 Hz, 1H), 3.46-3.31 (m, 4H), 3.25 (t, J = 12.3 Hz, 1H), 3.19-3.02 (m, 1H), 3.02-2.66 (m, 4H), 2.09 (d, J = 12.1 Hz, 3H), 1.96 (d, J = 5.3 Hz, 3H). | 633.2 |
| 135 | 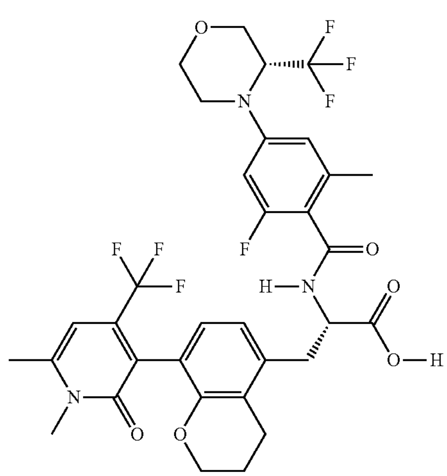 [SMILES: Cc1cc(N2CCOC[C@@H]2C(F)(F)F)cc(F)c1C(=O)N[C@@H](Cc1ccc(-c2c(C(F)(F)F)cc(C)n(C)c2=O)c2c1CCCO2)C(=O)O] | 1H NMR (400 MHz, DMSO-d6) δ 8.72 (t, J = 7.2 Hz, 1H), 6.81 (t, J = 7.2 Hz, 1H), 6.69 (dd, J = 19.5, 6.8 Hz, 3H), 6.42 (s, 1H), 4.84 (d, J = 9.0 Hz, 1H), 4.64 (dt, J = 21.9, 9.3 Hz, 1H), 4.14 (d, J = 12.7 Hz, 1H), 3.95 (qd, J = 11.7, 6.5 Hz, 3H), 3.73 (d, J = 12.6 Hz, 1H), 3.54 (t, J = 11.5 Hz, 1H), 3.47 (d, J = 2.7 Hz, 3H), 3.42-3.16 (m, 2H), 3.09 (t, J = 12.3 Hz, 1H), 3.01-2.84 (m, 1H), 2.83-2.64 (m, 2H), 2.46 (s, 3H), 2.09 (d, J = 11.9 Hz, 3H), 1.91 (s, 2H). | 700.2 |

TABLE 1-continued

| Example | Structure | 1H-NMR | M/Z [M + H]+ |
|---|---|---|---|
| 136 | 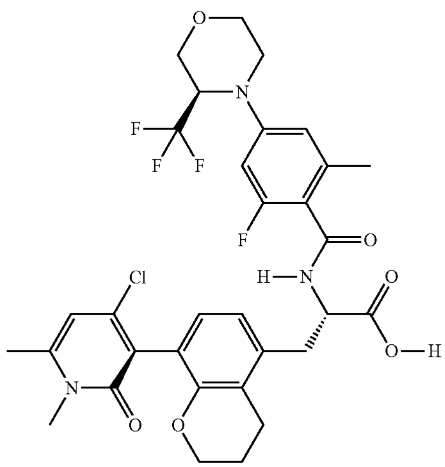 | 1H NMR (400 MHz, DMSO-d6) δ 8.62 (td, J = 10.7, 7.9 Hz, 1H), 6.63 (qd, J = 17.7, 15.3, 6.2 Hz, 4H), 5.96 (d, J = 2.4 Hz, 1H), 4.82 (td, J = 9.0, 4.6 Hz, 1H), 4.56 (d, J = 51.9 Hz, 1H), 4.14 (d, J = 12.6 Hz, 1H), 3.93 (t, J = 13.0 Hz, 2H), 3.73 (d, J = 12.6 Hz, 1H), 3.44 (s, 3H), 3.41 (s, 1H), 3.33 (s, 1H), 3.25 (t, J = 12.5 Hz, 1H), 3.03-2.88 (m, 1H), 2.84-2.72 (m, 1H), 2.70-2.53 (m, 1H), 2.50 (s, 3H), 2.37 (d, J = 7.3 Hz, 2H), 2.08 (dd, J = 16.7, 11.9 Hz, 3H), 1.94-1.67 (m, 2H). | 660.1 |
| 137 | 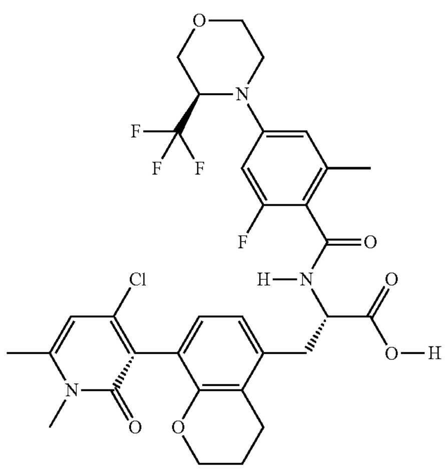 | 1H NMR (400 MHz, DMSO-d6) δ 8.72 (dd, J = 8.1, 3.8 Hz, 1H), 6.82 (t, J = 7.2 Hz, 1H), 6.75 (t, J = 6.8 Hz, 1H), 6.72-6.61 (m, 2H), 6.35 (s, 1H), 4.83 (tt, J = 8.5, 5.1 Hz, 1H), 4.62 (ddd, J = 11.7, 7.3, 3.6 Hz, 1H), 4.14 (d, J = 12.6 Hz, 1H), 3.97 (qd, J = 12.0, 11.4, 4.7 Hz, 3H), 3.73 (d, J = 13.1 Hz, 2H), 3.41 (d, J = 2.4 Hz, 3H), 3.35 (d, J = 12.56 Hz, 1H), 3.25 (t, J = 12.3 Hz, 1H), 3.09 (ddd, J = 14.1, 9.2, 4.1 Hz, 1H), 2.90 (dt, J = 14.7, 10.6 Hz, 1H), 2.80-2.67 (m, 2H), 2.38 (s, 3H), 2.10 (d, J = 13.6 Hz, 3H), 1.91 (h, J = 5.6 Hz, 2H). | 666.1 |
| 138 | 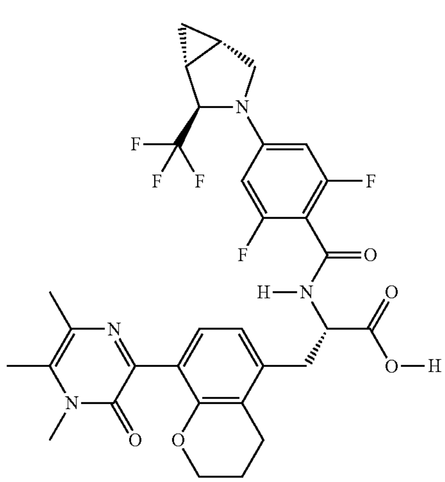 [SMILES: Cc1nc(-c2ccc(C[C@H](NC(=O)c3c(F)cc(N4C[C@H]5C[C@H]5[C@@H]4C(F)(F)F)cc3F)C(=O)O)c3c2OCCC3)c(=O)n(C)c1C] | 1H NMR (400 MHz, DMSO-d6) δ 8.86 (d, J = 7.9 Hz, 1H), 6.88 (d, J = 7.7 Hz, 1H), 6.80 (d, J = 7.8 Hz, 1H), 6.56 (d, J = 11.0 Hz, 2H), 5.02 (p, J = 5.7 Hz, 1H), 4.52 (td, J = 8.7, 4.6 Hz, 1H), 4.00-3.95 (m, 2H), 3.77 (d, J = 9.7 Hz, 1H), 3.47 (s, 3H), 3.40 (dd, J = 9.8, 5.9 Hz, 1H), 3.09 (dd, J = 14.5, 4.7 Hz, 1H), 2.90 (dd, J = 14.5, 9.6 Hz, 1H), 2.76 (q, J = 6.6 Hz, 2H), 2.32 (s, 3H), 2.26 (s, 3H), 2.08-1.98 (m, 1H), 1.91 (tq, J = 12.6, 6.7 Hz, 3H), 0.89 (td, J = 8.1, 5.2 Hz, 1H), 0.80 (d, J = 4.8 Hz, 1H). | 647.2 |

TABLE 1-continued

| Example | Structure | 1H-NMR | M/Z [M + H]+ |
|---|---|---|---|
| 139 | 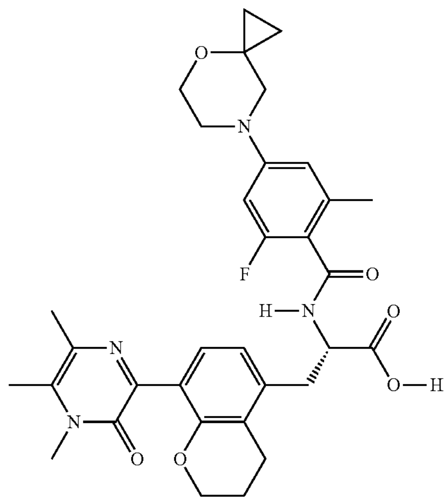 [SMILES: Cc1cc(N2CCOC3(CC3)C2)cc(F)c1C(=O)N[C@@H](Cc1ccc(-c2nc(C)c(C)n(C)c2=O)c2c1CCCO2)C(=O)O] | 1H NMR (400 MHz, DMSO-d6) δ 8.65 (d, J = 7.9 Hz, 1H), 6.87 (d, J = 7.7 Hz, 1H), 6.81 (d, J = 7.8 Hz, 1H), 6.56 (d, J = 11.3 Hz, 2H), 4.57 (td, J = 9.0, 4.4 Hz, 1H), 3.98 (t, J = 5.2 Hz, 2H), 3.77-3.74 (m, 2H), 3.47 (s, 3H), 3.20 (t, J = 5.0 Hz, 2H), 3.11 (d, J = 20.0 Hz, 3H), 2.90 (dd, J = 14.6, 10.0 Hz, 1H), 2.77 (q, J = 6.8 Hz, 2H), 2.32 (s, 3H), 2.26 (s, 3H), 2.14 (s, 3H), 1.93 (dd, J = 8.2, 4.6 Hz, 2H), 0.71 (d, J = 5.0 Hz, 2H), 0.65-0.58 (m, 2H). | 605.3 |
| 140 | 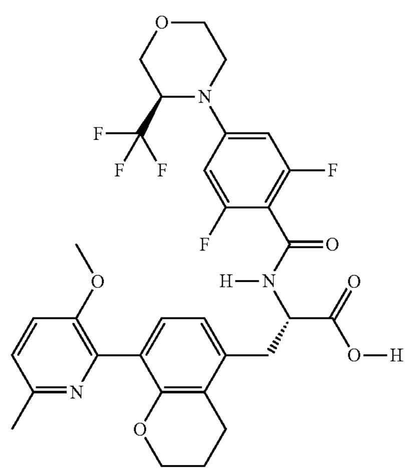 [SMILES: COc1ccc(C)nc1-c1ccc(C[C@H](NC(=O)c2c(F)cc(N3CCOC[C@@H]3C(F)(F)F)cc2F)C(=O)O)c2c1OCCC2] | 1H NMR (400 MHz, DMSO-d6) δ 8.94 (d, J = 8.1 Hz, 1H), 8.09 (s, 1H), 7.74 (s, 1H), 7.13 (s, 1H), 6.98 (d, J = 7.9 Hz, 1H), 6.78 (d, J = 11.7 Hz, 2H), 4.92 (dd, J = 8.7, 3.6 Hz, 1H), 4.56 (td, J = 9.0, 4.2 Hz, 1H), 4.17 (d, J = 12.7 Hz, 1H), 4.08 (q, J = 5.3, 4.3 Hz, 2H), 3.97 (dd, J = 11.4, 3.7 Hz, 1H), 3.75 (d, J = 12.7 Hz, 1H), 3.60-3.53 (m, 1H), 3.43 (d, J = 12.6 Hz, 1H), 3.30-3.14 (m, 2H), 3.01-2.88 (m, 1H), 2.83 (dq, J = 16.8, 9.9, 8.2 Hz, 2H), 2.58 (s, 3H), 2.05-1.88 (m, 2H). | 636.2 |
| 141 | 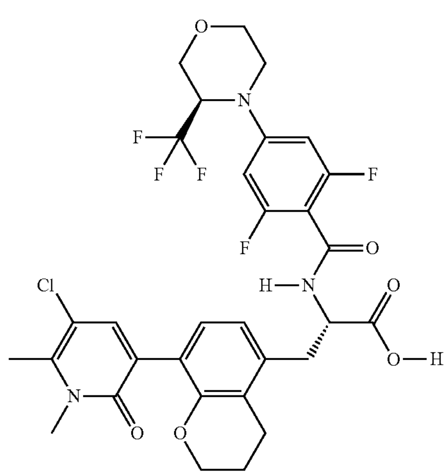 | 1H NMR (400 MHz, DMSO-d6) δ 8.87 (d, J = 7.9 Hz, 1H), 7.32 (s, 1H), 6.95 (d, J = 7.8 Hz, 1H), 6.80 (d, J = 7.0 Hz, 2H), 6.76 (s, 1H), 4.97-4.86 (m, 1H), 4.56-4.47 (m, 1H), 4.16 (d, J = 12.7 Hz, 1H), 4.04-4.00 (m, 2H), 3.96 (dd, J = 11.5, 3.6 Hz, 1H), 3.74 (d, J = 12.9 Hz, 1H), 3.61-3.53 (m, 1H), 3.51 (s, 3H), 3.43 (d, J = 12.1 Hz, 1H), 3.30-3.19 (m, 1H), 3.09 (dd, J = 14.5, 4.5 Hz, 1H), 2.89 (dd, J = 14.5, 9.7 Hz, 1H), 2.84-2.69 (m, 2H), 2.48 (s, 3H), 1.99-1.88 (m, 2H). | 670.2 |

TABLE 1-continued

| Example | Structure | 1H-NMR | M/Z [M + H]+ |
|---|---|---|---|
| 142 | 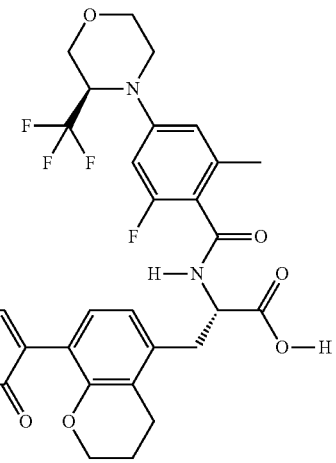 | 1H NMR (400 MHz, DMSO-d6) δ 8.71 (d, J = 8.0 Hz, 1H), 7.30 (s, 1H), 6.94 (d, J = 7.8 Hz, 1H), 6.80 (d, J = 7.8 Hz, 1H), 6.68 (d, J = 13.7 Hz, 2H), 4.89-4.78 (m, 1H), 4.63-4.55 (m, 1H), 4.14 (d, J = 12.6 Hz, 1H), 4.01 (t, J = 5.2 Hz, 2H), 3.95 (dd, J = 11.4, 3.7 Hz, 1H), 3.74 (d, 1H), 3.56 (dd, J = 11.7, 3.4 Hz, 1H), 3.51 (s, 3H), 3.35 (d, J = 12.3, 2.8 Hz, 1H), 3.31-3.20 (m, 1H), 3.09 (dd, J = 14.6, 4.3 Hz, 1H), 2.89 (dd, J = 14.6, 10.2 Hz, 1H), 2.84-2.69 (m, 2H), 2.48 (s, 4H), 2.11 (s, 3H), 2.00-1.87 (m, 2H). | 666.2 |
| 143 | 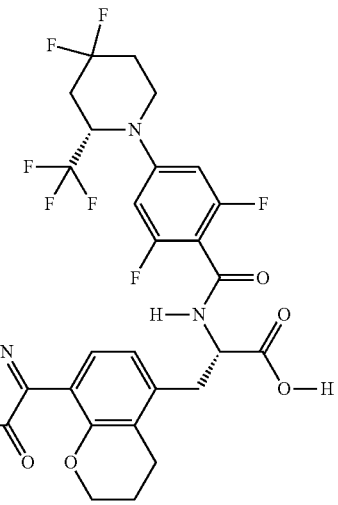 | 1H NMR (400 MHz, DMSO-d6) δ 8.89 (d, J = 7.9 Hz, 1H), 6.91-6.78 (m, 4H), 5.24 (d, J = 11.6 Hz, 1H), 4.51 (td, J = 8.9, 8.4, 4.5 Hz, 1H), 3.98 (t, J = 5.3 Hz, 1H), 3.89 (s, 2H), 3.47 (s, 3H), 3.35 (dt, J = 15.0, 7.6 Hz, 1H), 3.10 (dd, J = 14.6, 4.6 Hz, 1H), 2.91 (dd, J = 14.4, 9.7 Hz, 1H), 2.77 (q, J = 7.1 Hz, 2H), 2.56-2.38 (m, 2H), 2.32 (s, 3H), 2.26 (s, 3H), 2.21-2.04 (m, 2H), 1.94 (dd, J = 11.0, 5.9 Hz, 2H). | 685.2 |
| 144 | 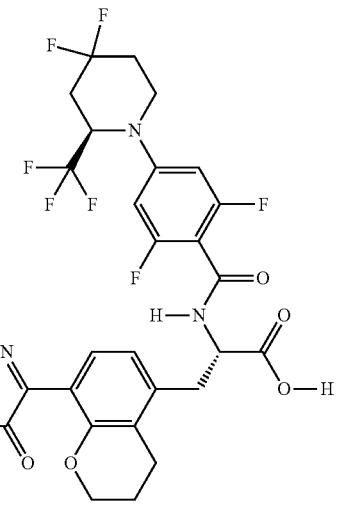 | 1H NMR (400 MHz, DMSO-d6) δ 8.89 (d, J = 7.9 Hz, 1H), 6.91-6.78 (m, 4H), 5.21 (d, J = 12.0 Hz, 1H), 4.52 (td, J = 8.7, 4.5 Hz, 1H), 4.02-3.86 (m, 3H), 3.47 (s, 3H), 3.42-3.28 (m, 1H), 3.10 (dd, J = 14.5, 4.6 Hz, 1H), 2.91 (dd, J = 14.5, 9.7 Hz, 1H), 2.77 (q, J = 7.0 Hz, 2H), 2.56-2.38 (m, 2H), 2.33 (s, 3H), 2.26 (s, 3H), 2.20-2.04 (m, 2H), 1.94 (q, J = 6.1 Hz, 2H). | 685.2 |

TABLE 1-continued

| Example | Structure | 1H-NMR | M/Z [M + H]+ |
|---|---|---|---|
| 145 | 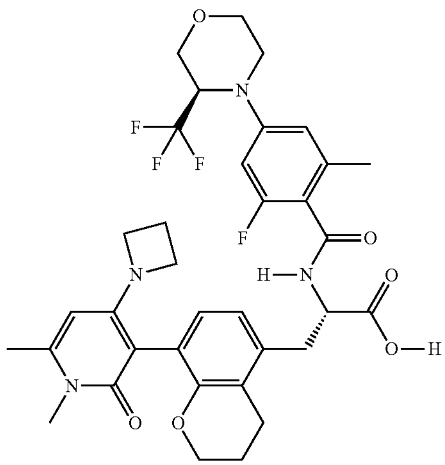 [SMILES: Cc1cc(N2CCOC[C@@H]2C(F)(F)F)cc(F)c1C(=O)N[C@@H](Cc1ccc(-c2c(N3CCC3)cc(C)n(C)c2=O)c2c1CCCO2)C(=O)O] | 1H NMR (400 MHz, DMSO-d6) δ 8.74-8.62 (m, 1H), 6.80-6.59 (m, 4H), 5.57 (d, J = 2.6 Hz, 1H), 4.84 (d, J = 9.6 Hz, 1H), 4.67-4.48 (m, 1H), 4.15 (d, J = 12.6 Hz, 1H), 4.06-3.91 (m, 3H), 3.74 (d, J = 12.7 Hz, 1H), 3.54 (dd, J = 17.6, 9.0 Hz, 3H), 3.39 (d, J = 17.2 Hz, 3H), 3.31 (d, J = 3.0 Hz, 3H), 3.15-3.06 (m, 0H), 3.06-2.64 (m, 3H), 2.29 (s, 3H), 2.16 (s, 3H), 1.93 (q, J = 8.4, 7.9 Hz, 5H). | 687.3 |
| 146 | 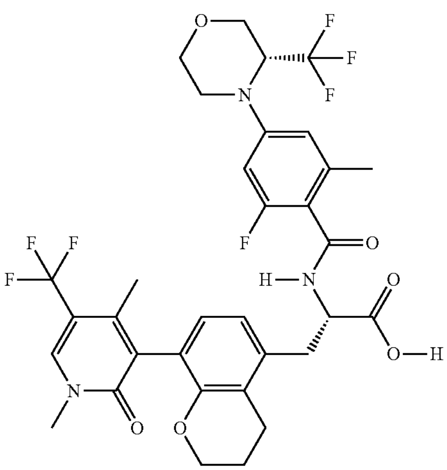 [SMILES: Cc1cc(N2CCOC[C@@H]2C(F)(F)F)cc(F)c1C(=O)N[C@@H](Cc1ccc(-c2c(C)c(C(F)(F)F)cn(C)c2=O)c2c1CCCO2)C(=O)O] | 1H NMR (400 MHz, DMSO-d6) δ 13.0-12.42 (s, 1H), 8.71 (dd, J = 8.1, 2.9 Hz, 1H), 8.25 (s, 1H), 6.85 (t, J = 8.5 Hz, 1H), 6.75 (dd, J = 10.4, 7.7 Hz, 1H), 6.71-6.62 (m, 2H), 4.83 (d, J = 9.5 Hz, 1H), 4.65 (ddd, J = 12.1, 8.8, 3.8 Hz, 1H), 4.14 (d, J = 12.6 Hz, 1H), 3.99 (t, J = 5.1 Hz, 2H), 3.95 (dd, J = 11.5, 3.4 Hz, 1H), 3.73 (d, J = 12.5 Hz, 1H), 3.54 (t, J = 12.1 Hz, 1H), 3.48 (d, J = 2.2 Hz, 3H), 3.35 (d, J = 12.2 Hz, 1H), 3.25 (t, J = 12.2 Hz, 1H), 3.12 (ddd, J = 23.0, 14.5, 4.1 Hz, 1H), 2.99-2.82 (m, 1H), 2.78 (s, 2H), 2.75-2.65 (m, 1H), 2.08 (d, J = 16.4 Hz, 3H), 1.92 (d, J = 5.8 Hz, 4H). | 700.2 |
| 147 | 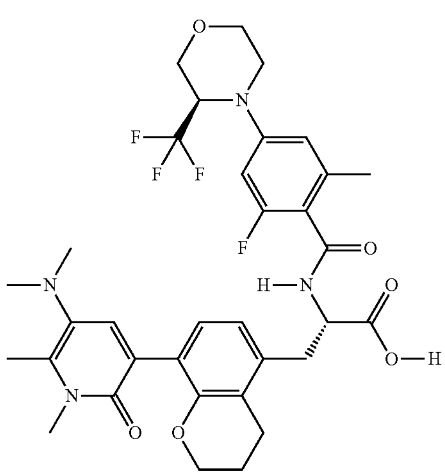 [SMILES: Cc1cc(N2CCOC[C@@H]2C(F)(F)F)cc(F)c1C(=O)N[C@@H](Cc1ccc(-c2cc(N(C)C)c(C)n(C)c2=O)c2c1CCCO2)C(=O)O] | 1H NMR (400 MHz, DMSO-d6) δ 8.72 (d, J = 8.0 Hz, 1H), 7.48 (s, 1H), 6.95 (d, J = 7.7 Hz, 1H), 6.80 (d, J = 7.8 Hz, 1H), 6.69 (d, J = 13.0 Hz, 2H), 4.84 (dd, J = 9.0, 3.6 Hz, 1H), 4.57 (ddd, J = 10.0, 8.1, 4.4 Hz, 1H), 4.15 (d, J = 12.6 Hz, 1H), 4.01 (t, J = 5.4 Hz, 2H), 3.95 (dd, J = 11.4, 3.6 Hz, 1H), 3.75 (s, 1H), 3.57-3.50 (m, 1H), 3.47 (s, 3H), 3.35 (d, J = 12.2 Hz, 1H), 3.26 (t, J = 12.0 Hz, 1H), 3.09 (dd, J = 14.4, 4.4 Hz, 1H), 2.89 (dd, J = 14.5, 10.1 Hz, 1H), 2.77 (q, J = 6.7 Hz, 2H), 2.65 (d, J = 12.6 Hz, 6H), 2.44 (s, 3H), 2.14 (s, 3H), 1.99-1.88 (m, 2H). | 675.3 |

TABLE 1-continued
| Example | Structure | 1H-NMR | M/Z [M + H]+ |
|---|---|---|---|
| 148 | 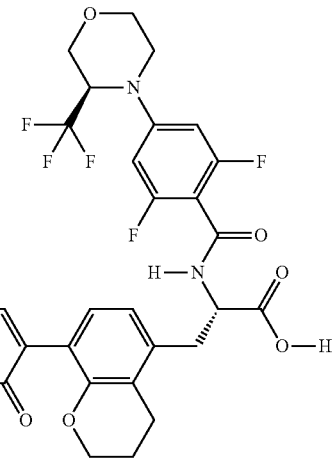 | 1H NMR (400 MHz, DMSO-d6) δ 8.87 (d, J = 7.9 Hz, 1H), 7.25 (s, 1H), 7.03 (d, J = 7.8 Hz, 1H), 6.84 (d, J = 7.8 Hz, 1H), 6.78 (d, J = 11.7 Hz, 2H), 4.91 (qd, J = 8.7, 3.4 Hz, 1H), 4.53 (td, J = 8.9, 4.5 Hz, 1H), 4.17 (d, J = 12.7 Hz, 1H), 4.04 (dq, J = 7.4, 5.2, 3.6 Hz, 2H), 3.96 (dd, J = 11.6, 3.8 Hz, 1H), 3.80-3.71 (m, 1H), 3.63 (s, 3H), 3.43 (d, J = 13.9 Hz, 2H), 3.31-3.18 (m, 1H), 3.11 (dd, J = 14.5, 4.5 Hz, 1H), 2.91 (dd, J = 14.6, 9.9 Hz, 1H), 2.77 (q, J = 6.9 Hz, 2H), 2.26 (s, 3H), 2.02-1.87 (m, 2H). | 637.3 |
| 149 | 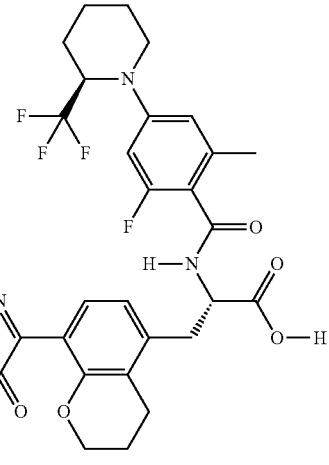 | 1H NMR (400 MHz, DMSO-d6) δ 8.69 (d, J = 7.9 Hz, 1H), 6.90-6.78 (m, 2H), 6.70-6.62 (m, 2H), 4.91-4.77 (m, 1H), 4.62-4.50 (m, 1H), 3.98 (t, J = 5.3 Hz, 1H), 3.62-3.48 (m, 2H), 3.47 (s, 3H), 3.15-2.99 (m, 2H), 2.91 (dd, J = 14.5, 10.1 Hz, 1H), 2.76 (q, J = 6.6 Hz, 2H), 2.32 (s, 3H), 2.26 (s, 3H), 2.14 (s, 3H), 2.02-1.87 (m, 3H), 1.87-1.67 (m, 1H), 1.67-1.43 (m, 4H). | 645.2 |
| 150 | 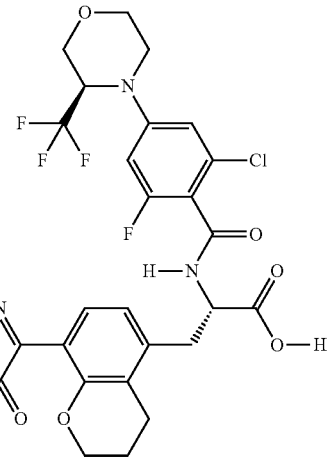 | 1H NMR (400 MHz, DMSO-d6) δ 8.99 (d, J = 8.0 Hz, 1H), 6.96-6.78 (m, 4H), 4.99-4.86 (m, 1H), 4.62-4.52 (m, 1H), 4.16 (d, J = 12.7 Hz, 1H), 4.00-3.91 (m, 3H), 3.79-3.67 (m, 1H), 3.62-3.50 (m, 1H), 3.47 (s, 3H), 3.45-3.38 (m, 1H), 3.32-3.20 (m, 1H), 3.09 (dd, J = 14.6, 5.0 Hz, 1H), 2.90 (dd, J = 14.6, 9.4 Hz, 1H), 2.76 (q, J = 6.2 Hz, 2H), 2.32 (s, 3H), 2.26 (s, 3H), 1.99-1.88 (m, 2H). | 667.2 |

| Example | Structure | 1H-NMR | M/Z [M + H]+ |
|---|---|---|---|
| 151 | 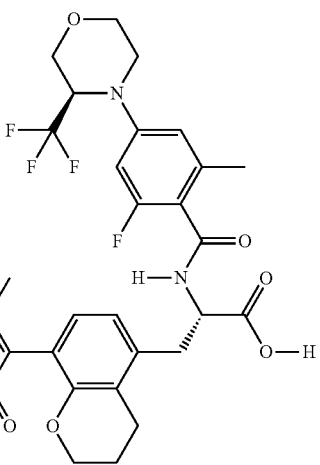 | 1H NMR (400 MHz, DMSO-d6) δ 8.70 (dd, J = 8.0, 2.6 Hz, 1H), 6.83-6.77 (m, 1H), 6.71-6.63 (m, 3H), 4.83 (d, J = 8.4 Hz, 1H), 4.67-4.59 (m, 1H), 4.14 (d, J = 12.6 Hz, 1H), 3.96 (d, J = 20.5 Hz, 3H), 3.73 (d, J = 12.7 Hz, 1H), 3.55 (t, J = 11.0 Hz, 1H), 3.45 (d, J = 2.1 Hz, 3H), 3.35 (d, J = 12.0 Hz, 1H), 3.27 (d, J = 13.1 Hz, 1H), 3.16-3.02 (m, 1H), 2.91 (dd, J = 26.7, 15.1 Hz, 1H), 2.74 (d, J = 24.6 Hz, 2H), 2.34 (s, 3H), 2.10 (d, J = 19.1 Hz, 3H), 2.02 (s, 3H), 1.92 (t, J = 14.4 Hz, 2H), 1.80 (d, J = 4.6 Hz, 3H). | 660.3 |
| 152 | 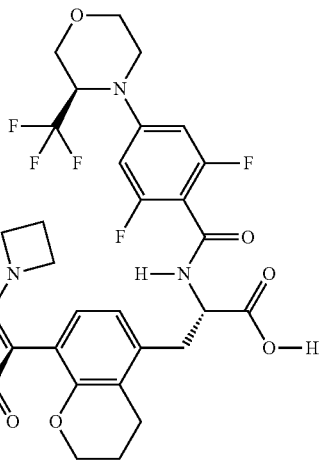 | 1H NMR (400 MHz, DMSO-d6) δ 8.78 (dd, J = 12.0, 8.0 Hz, 1H), 6.91-6.54 (m, 4H), 5.56 (d, J = 6.6 Hz, 2H), 4.91 (d, J = 8.0 Hz, 2H), 4.62-4.50 (m, 1H), 4.16 (d, J = 12.7 Hz, 1H), 4.06-3.90 (m, 4H), 3.74 (d, J = 12.8 Hz, 1H), 3.62-3.35 (m, 6H), 3.31 (d, J = 2.5 Hz, 3H), 3.26 (d, J = 13.9 Hz, 2H), 3.13 (dd, J = 14.5, 4.5 Hz, 1H), 3.06-2.91 (m, 1H), 2.91-2.63 (m, 3H), 2.28 (s, 3H), 1.91 (d, J = 9.1 Hz, 7H). | 691.3 |
| 153 | 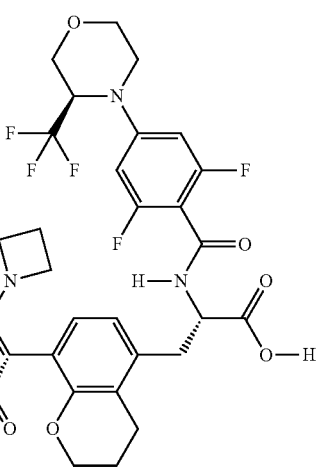 | 1H NMR (400 MHz, DMSO-d6) δ 8.78 (dd, J = 11.9, 8.0 Hz, 1H), 6.88-6.59 (m, 4H), 5.55 (s, 1H), 4.98-4.83 (m, 1H), 4.56 (d, J = 6.7 Hz, 1H), 4.16 (d, J = 12.7 Hz, 1H), 4.08-3.88 (m, 3H), 3.74 (d, J = 12.9 Hz, 1H), 3.47 (dq, J = 38.6, 14.0, 11.8 Hz, 5H), 3.31 (d, J = 2.0 Hz, 3H), 3.26 (d, J = 12.8 Hz, 1H), 3.13 (dd, J = 14.4, 4.4 Hz, 1H), 3.05-2.87 (m, 1H), 2.76 (ddd, J = 30.5, 23.8, 14.2 Hz, 2H), 2.28 (s, 3H), 1.97-1.82 (m, 5H). | 691.3 |

TABLE 1-continued

| Example | Structure | 1H-NMR | M/Z [M + H]+ |
|---|---|---|---|
| 154 | 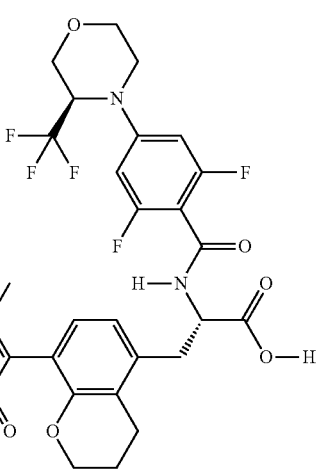 | 1H NMR (400 MHz, DMSO-d6) δ 8.85 (dd, J = 7.8, 4.4 Hz, 1H), 6.82-6.73 (m, 3H), 6.67 (dd, J = 10.2, 7.8 Hz, 1H), 4.97-4.85 (m, 1H), 4.62-4.49 (m, 1H), 4.16 (d, J = 12.6 Hz, 1H), 3.99-3.91 (m, 3H), 3.74 (d, J = 12.5 Hz, 1H), 3.56 (t, J = 11.5 Hz, 1H), 3.45 (s, 3H), 3.41 (s, 1H), 3.24 (t, J = 12.4 Hz, 1H), 3.09 (td, J = 15.4, 4.6 Hz, 1H), 2.97-2.84 (m, 1H), 2.83-2.70 (m, 2H), 2.34 (s, 3H), 2.02 (s, 3H), 1.88 (d, J = 15.1 Hz, 2H), 1.80 (d, J = 4.7 Hz, 3H). | 664.2 |
| 155 | 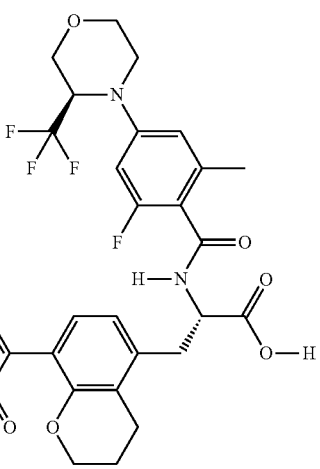 | 1H NMR (400 MHz, DMSO-d6) δ 8.70 (d, J = 8.0 Hz, 1H), 7.10 (s, 1H), 6.88 (d, J = 7.7 Hz, 1H), 6.77 (d, J = 7.8 Hz, 1H), 6.69 (d, J = 14.2 Hz, 2H), 4.83 (d, J = 3.3 Hz, 1H), 4.59-4.56 (m, 1H), 4.15 (d, J = 12.6 Hz, 1H), 4.00-3.95 (m, 2H), 3.74 (d, J = 12.5 Hz, 1H), 3.57-3.51 (m, 1H), 3.47 (s, 3H), 3.27 (d, J = 12.5 Hz, 1H), 3.08 (dd, J = 14.6, 4.4 Hz, 1H), 2.88 (dd, J = 14.6, 10.2 Hz, 2H), 2.75 (t, J = 6.6 Hz, 2H), 2.30 (s, 3H), 2.12 (s, 3H), 2.06 (s, 3H), 1.95-1.89 (m, 2H). | 646.3 |
| 156 | 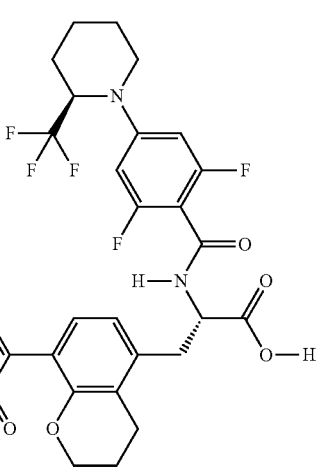 | 1H NMR (400 MHz, DMSO-d6) δ 8.82 (d, J = 7.9 Hz, 1H), 6.92-6.71 (m, 4H), 5.01-4.88 (m, 1H), 4.51 (td, J = 8.7, 4.6 Hz, 1H), 3.98 (dt, J = 6.2, 3.1 Hz, 2H), 3.63 (d, J = 13.3 Hz, 1H), 3.47 (s, 3H), 3.14-2.96 (m, 2H), 2.91 (dd, J = 14.5, 9.6 Hz, 1H), 2.76 (q, J = 6.8 Hz, 2H), 2.32 (s, 3H), 2.26 (s, 3H), 2.02-1.88 (m, 3H), 1.88-1.69 (m, 2H), 1.57 (dd, J = 23.5, 11.3 Hz, 3H). | 649.2 |

TABLE 1-continued

| Example | Structure | 1H-NMR | M/Z [M + H]+ |
|---|---|---|---|
| 157 | 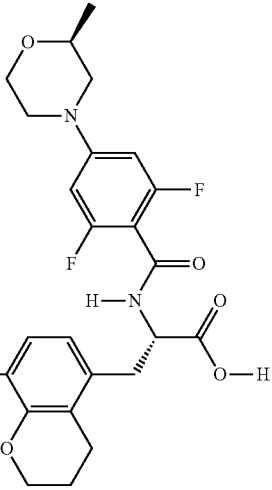 | 1H NMR (400 MHz, DMSO-d6) δ 8.77 (d, J = 7.8 Hz, 1H), 6.87 (d, J = 7.7 Hz, 1H), 6.81 (d, J = 7.8 Hz, 1H), 6.65 (d, J = 11.8 Hz, 2H), 4.51 (td, J = 8.8, 8.3, 4.5 Hz, 1H), 4.02-3.95 (m, 2H), 3.92-3.84 (m, 1H), 3.72 (d, J = 12.3 Hz, 1H), 3.65-3.50 (m, 2H), 3.47 (s, 3H), 3.10 (dd, J = 14.4, 4.7 Hz, 1H), 2.91 (dd, J = 14.4, 9.6 Hz, 1H), 2.84-2.64 (m, 3H), 2.39 (dd, J = 12.4, 10.3 Hz, 2H), 2.32 (s, 3H), 2.26 (s, 3H), 1.98-1.87 (m, 2H), 1.13 (d, J = 6.2 Hz, 3H). | 597.2 |
| 158 | 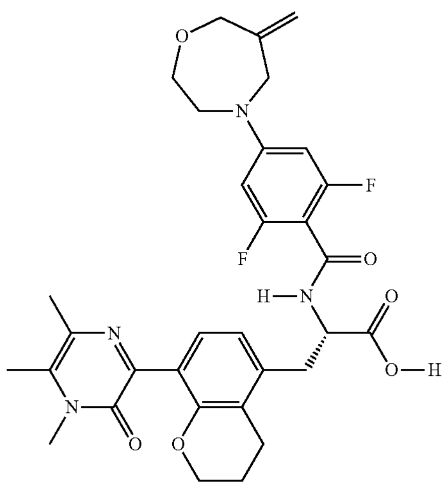 [SMILES: C=C1COCCN(c2cc(F)c(C(=O)N[C@@H](Cc3ccc(-c4nc(C)c(C)n(C)c4=O)c4c3CCCO4)C(=O)O)c(F)c2)C1] | 1H NMR (400 MHz, DMSO-d6) δ 8.71 (d, J = 7.8 Hz, 1H), 6.90-6.78 (m, 2H), 6.45 (d, J = 12.0 Hz, 2H), 5.16 (s, 1H), 5.04 (s, 1H), 4.53-4.46 (m, 1H), 4.23 (s, 2H), 3.98 (dt, J = 6.1, 2.8 Hz, 2H), 3.94 (s, 2H), 3.69 (s, 4H), 3.47 (s, 3H), 3.09 (dd, J = 14.4, 4.5 Hz, 1H), 2.90 (dd, J = 14.5, 9.7 Hz, 1H), 2.76 (q, J = 6.8 Hz, 2H), 2.32 (s, 3H), 2.26 (s, 3H), 1.93 (d, J = 7.8 Hz, 2H). | 609.2 |
| 159 | 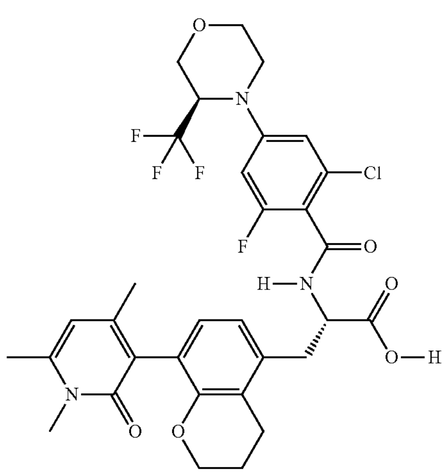 [SMILES: Cc1cc(C)n(C)c(=O)c1-c1ccc(C[C@H](NC(=O)c2c(F)cc(N3CCOC[C@@H]3C(F)(F)F)cc2Cl)C(=O)O)c2c1OCCC2] | 1H NMR (400 MHz, DMSO-d6) δ 8.97 (dd, J = 8.0, 4.3 Hz, 1H), 6.94-6.87 (m, 2H), 6.80 (t, J = 7.2 Hz, 1H), 6.69 (dd, J = 10.8, 7.7 Hz, 1H), 6.04 (s, 1H), 4.98-4.87 (m, 1H), 4.66-4.56 (m, 1H), 4.15 (d, J = 12.7 Hz, 1H), 4.00-3.90 (m, 3H), 3.74 (d, J = 13.3 Hz, 1H), 3.55 (t, J = 11.8 Hz, 1H), 3.42 (s, 1H), 3.38 (s, 3H), 3.24 (t, J = 13.8 Hz, 1H), 3.13-3.02 (m, 1H), 2.90 (s, 1H), 2.83-2.65 (m, 2H), 2.32 (s, 3H), 1.91 (p, J = 6.5, 5.9 Hz, 2H), 1.78 (d, J = 3.1 Hz, 3H). | 666.2 |

TABLE 1-continued
| Example | Structure | 1H-NMR | M/Z [M + H]+ |
|---|---|---|---|
| 160 | 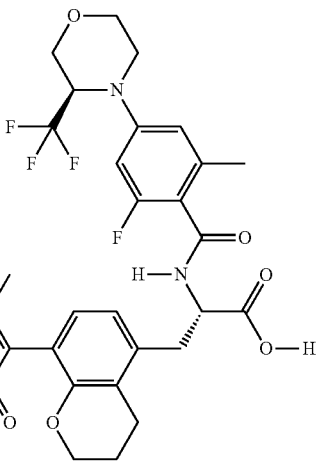 | 1H NMR (400 MHz, DMSO-d6) δ 8.85 (dd, J = 7.8, 3.6 Hz, 1H), 6.82-6.66 (m, 4H), 6.04 (s, 1H), 4.96-4.85 (m, 1H), 4.61-4.50 (m, 1H), 4.16 (d, J = 12.7 Hz, 1H), 4.00-3.91 (m, 4H), 3.74 (d, J = 16.1 Hz, 1H), 3.59-3.50 (m, 1H), 3.43 (d, J = 13.8 Hz, 1H), 3.38 (s, 3H), 3.30-3.19 (m, 1H), 3.14-3.03 (m, 1H), 2.95-2.84 (m, 1H), 2.78-2.71 (m, 2H), 2.32 (s, 3H), 1.94-1.87 (m, 2H), 1.78 (d, J = 4.7 Hz, 3H). | 645.21 |
| 161 | 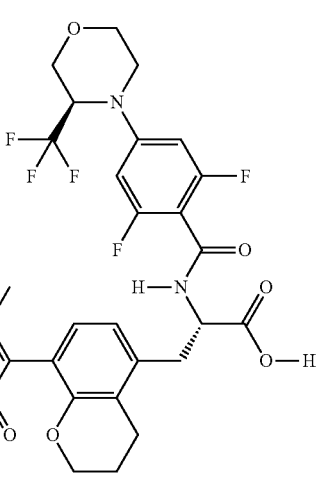 | 1H NMR (400 MHz, DMSO-d6) δ 8.85 (dd, J = 7.8, 3.6 Hz, 1H), 6.82-6.66 (m, 4H), 6.04 (s, 1H), 4.96-4.85 (m, 1H), 4.61-4.50 (m, 1H), 4.16 (d, J = 12.7 Hz, 1H), 4.00-3.91 (m, 3H), 3.74 (d, J = 16.1 Hz, 1H), 3.59-3.50 (m, 1H), 3.43 (d, J = 13.8 Hz, 1H), 3.38 (s, 3H), 3.30-3.19 (m, 1H), 3.14-3.03 (m, 1H), 2.95-2.84 (m, 1H), 2.78-2.71 (m, 2H), 2.32 (s, 3H), 1.94-1.87 (m, 2H), 1.78 (d, J = 4.7 Hz, 3H). | 650.20 |
| 162 | 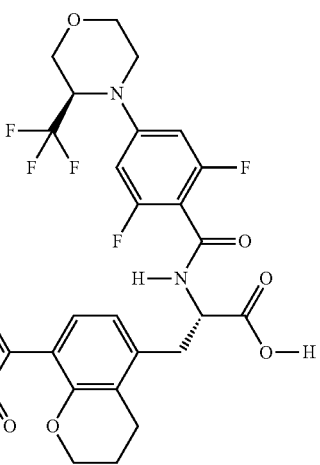 | 1H NMR (400 MHz, DMSO-d6) δ 8.86 (d, J = 7.9 Hz, 1H), 7.12 (s, 1H), 6.88 (d, J = 7.7 Hz, 1H), 6.77 (dd, J = 9.7, 3.3 Hz, 3H), 4.91 (dd, J = 8.8, 3.6 Hz, 1H), 4.51 (td, J = 9.0, 4.6 Hz, 1H), 4.16 (d, J = 12.7 Hz, 2H), 3.99 (t, J = 4.9 Hz, 2H), 3.74 (d, J = 12.7 Hz, 1H), 3.63-3.49 (m, 2H), 3.43 (d, J = 13.2 Hz, 4H), 3.24 (t, J = 12.1 Hz, 1H), 3.08 (dd, J = 14.5, 4.6 Hz, 1H), 2.75 (q, J = 6.6 Hz, 2H), 2.30 (s, 3H), 2.06 (s, 3H), 1.99-1.88 (m, 2H). | 650.2 |

TABLE 1-continued
| Example | Structure | 1H-NMR | M/Z [M + H]+ |
|---|---|---|---|
| 163 | 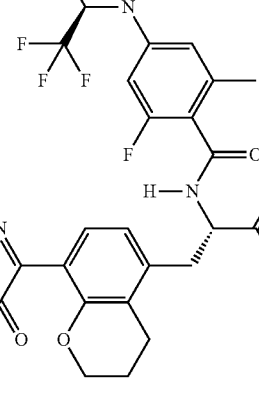 | 1H NMR (400 MHz, DMSO-d6) δ 8.72 (d, J = 8.0 Hz, 1H), 7.46 (s, 1H), 6.90 (d, J = 7.7 Hz, 1H), 6.83 (d, J = 7.8 Hz, 1H), 6.72-6.63 (m, 2H), 4.90-4.77 (m, 1H), 4.61-4.53 (m, 1H), 4.15 (d, J = 12.6 Hz, 1H), 3.99 (t, J = 5.3 Hz, 2H), 3.98-3.93 (m, 1H), 3.79-3.69 (m, 1H), 3.59-3.50 (m, 1H), 3.41 (s, 3H), 3.38-3.31 (m, 1H), 3.30-3.20 (m, 1H), 3.10 (dd, J = 14.6, 4.4 Hz, 1H), 2.91 (dd, J = 14.6, 10.1 Hz, 1H), 2.84-2.70 (m, 2H), 2.18 (s, 3H), 2.15 (s, 3H), 1.99-1.86 (m, 2H). | 633.2 |
| 164 | 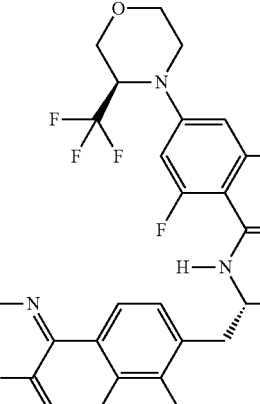 | 1H NMR (400 MHz, DMSO-d6) δ 8.88 (d, J = 7.9 Hz, 1H), 6.91 (d, J = 7.7 Hz, 1H), 6.84-6.73 (m, 3H), 4.98-4.84 (m, 1H), 4.58-4.45 (m, 1H), 4.16 (d, J = 12.7 Hz, 1H), 4.04-3.90 (m, 3H), 3.78-3.69 (m, 2H), 3.60-3.52 (m, 1H), 3.49 (s, 3H), 3.30-3.18 (m, 1H), 3.10 (dd, J = 14.5, 4.7 Hz, 1H), 2.92 (dd, J = 14.5, 9.6 Hz, 1H), 2.84-2.63 (m, 4H), 2.61-2.52 (m, 2H), 1.99-1.86 (m, 2H), 1.19 (t, J = 7.5 Hz, 3H), 1.14 (t, J = 7.5 Hz, 3H). | 679.2 |
| 165 | 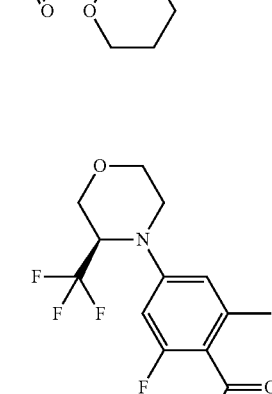 | 1H NMR (400 MHz, DMSO-d6) δ 8.72 (d, J = 7.9 Hz, 1H), 6.88 (d, J = 7.7 Hz, 1H), 6.82 (d, J = 7.8 Hz, 1H), 6.74-6.62 (m, 2H), 4.90-4.77 (m, 1H), 4.62-4.51 (m, 1H), 4.15 (d, J = 12.6 Hz, 1H), 4.02-3.91 (m, 3H), 3.77-3.70 (m, 1H), 3.59-3.49 (m, 1H), 3.47 (s, 3H), 3.38-3.33 (m, 1H), 3.30-3.18 (m, 1H), 3.10 (dd, J = 14.6, 4.5 Hz, 1H), 2.91 (dd, J = 14.6, 10.0 Hz, 1H), 2.82-2.72 (m, 2H), 2.32 (s, 3H), 2.26 (s, 3H), 2.15 (s, 3H), 2.00-1.86 (m, 2H). | 647.3 |

| Example | Structure | 1H-NMR | M/Z [M + H]+ |
|---|---|---|---|
| 166 | 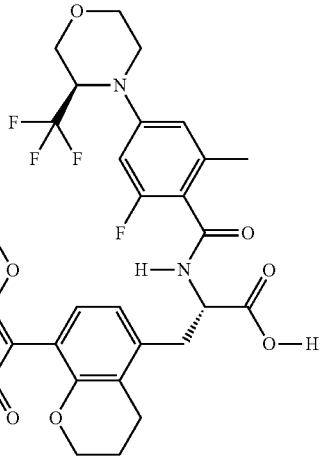 | 1H NMR (400 MHz, DMSO-d6) δ 8.72 (t, J = 7.2 Hz, 1H), 6.87-6.54 (m, 4H), 6.23 (d, J = 2.1 Hz, 1H), 4.84 (dd, J = 8.8, 3.7 Hz, 1H), 4.65-4.50 (m, 1H), 4.15 (d, J = 12.6 Hz, 1H), 3.96-3.93 (m, 3H), 3.79-3.70 (m, 1H), 3.66 (d, J = 5.2 Hz, 3H), 3.55 (td, J = 11.7, 3.4 Hz, 1H), 3.38 (d, J = 2.3 Hz, 4H), 3.33-3.18 (m, 1H), 3.06 (ddd, J = 14.9, 7.4, 4.3 Hz, 1H), 2.88 (ddd, J = 14.7, 10.4, 8.3 Hz, 1H), 2.78-2.62 (m, 2H), 2.39 (s, 3H), 2.14 (d, J = 9.9 Hz, 3H), 1.90 (q, J = 6.1 Hz, 2H). | 662.3 |
| 167 | 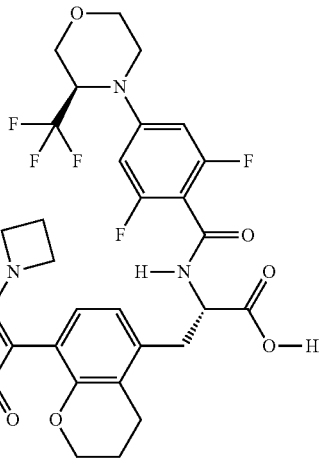 | 1H NMR (400 MHz, DMSO-d6) δ 8.78 (dd, J = 11.8, 8.1 Hz, 1H), 6.86-6.60 (m, 4H), 5.61 (d, J = 3.6 Hz, 1H), 4.90 (dt, J = 10.7, 5.4 Hz, 1H), 4.66-4.49 (m, 1H), 4.16 (d, J = 12.7 Hz, 1H), 4.06-4.01 (m, 6H), 3.74 (d, J = 12.9 Hz, 2H), 3.62-3.47 (m, 2H), 3.46-3.37 (m, 2H), 3.33 (d, J = 2.3 Hz, 3H), 3.30-3.19 (m, 1H), 3.14 (dd, J = 14.2, 4.4 Hz, 1H), 3.06-2.88 (m, 1H), 2.86-2.62 (m, 2H), 2.30 (s, 3H), 1.92 (q, J = 7.9, 7.2 Hz, 4H). | 691.3 |
| 168 | 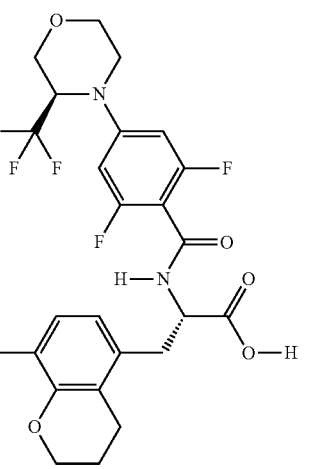 | 1H NMR (400 MHz, DMSO-d6) δ 8.87 (d, J = 7.9 Hz, 1H), 7.46 (s, 1H), 6.90 (d, J = 7.7 Hz, 1H), 6.86-6.73 (m, 3H), 4.97-4.86 (m, 1H), 4.57-4.47 (m, 1H), 4.16 (d, J = 12.7 Hz, 1H), 4.04-3.91 (m, 3H), 3.74 (d, J = 12.9 Hz, 1H), 3.56 (t, J = 10.5 Hz, 1H), 3.48-3.35 (m, 4H), 3.24 (t, J = 12.7 Hz, 1H), 3.11 (dd, J = 14.4, 4.3 Hz, 1H), 2.91 (dd, J = 14.4, 9.9 Hz, 1H), 2.84-2.69 (m, 2H), 2.18 (s, 3H), 2.01-1.86 (m, 2H). | 637.2 |

TABLE 1-continued

| Example | Structure | 1H-NMR | M/Z [M + H]+ |
|---|---|---|---|
| 169 | 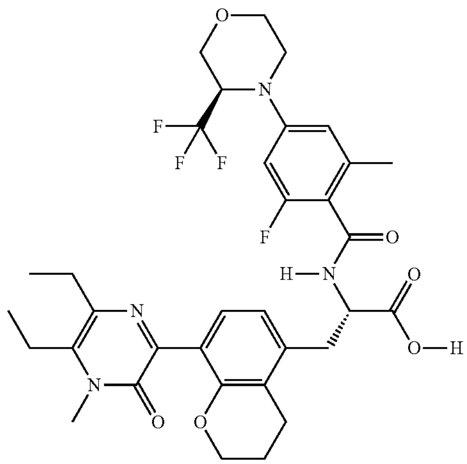 [SMILES: CCc1nc(-c2ccc(C[C@H](NC(=O)c3c(C)cc(N4CCOC[C@@H]4C(F)(F)F)cc3F)C(=O)O)c3c2OCCC3)c(=O)n(C)c1CC] | 1H NMR (400 MHz, DMSO-d6) δ 12.95-12.468 (s, 1H), 8.73 (d, J = 7.9 Hz, 1H), 6.91 (d, J = 7.7 Hz, 1H), 6.82 (d, J = 7.8 Hz, 1H), 6.69 (d, J = 15.1 Hz, 2H), 4.84 (d, J = 9.8 Hz, 1H), 4.56 (d, J = 11.3 Hz, 1H), 4.15 (d, J = 12.6 Hz, 1H), 4.00 (t, J = 5.2 Hz, 1H), 3.97-3.91 (m, 1H), 3.74 (d, J = 12.6 Hz, 1H), 3.60-3.51 (m, 1H), 3.49 (d, J = 1.4 Hz, 3H), 3.35 (d, J = 12.4 Hz, 1H), 3.27 (d, J = 12.4 Hz, 1H), 3.10 (dd, J = 14.8, 4.5 Hz, 1H), 2.91 (dd, J = 14.5, 10.0 Hz, 1H), 2.74 (dp, J = 23.2, 8.0, 7.4 Hz, 4H), 2.56 (q, J = 7.8 Hz, 3H), 2.14 (s, 3H), 1.94 (s, 2H), 1.19 (t, J = 7.5 Hz, 3H), 1.14 (td, J = 7.5, 1.4 Hz, 3H). | 675.3 |
| 170 | 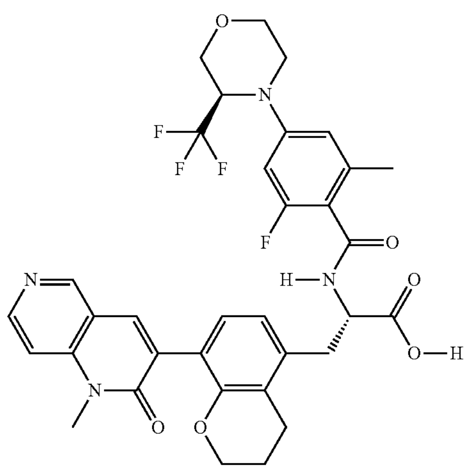 [SMILES: Cc1cc(N2CCOC[C@@H]2C(F)(F)F)cc(F)c1C(=O)N[C@@H](Cc1ccc(-c2cc3cnccc3n(C)c2=O)c2c1CCCO2)C(=O)O] | 1H NMR (400 MHz, DMSO-d6) δ 12.77 (s, 1H), 9.09 (s, 1H), 8.73 (t, J = 7.7 Hz, 2H), 8.01 (s, 1H), 7.76 (s, 1H), 7.00 (d, J = 7.8 Hz, 1H), 6.88 (d, J = 7.8 Hz, 1H), 6.69 (d, J = 14.9 Hz, 2H), 4.90-4.78 (m, 1H), 4.68-4.58 (m, 1H), 4.15 (d, J = 12.6 Hz, 1H), 4.03 (t, J = 5.4 Hz, 2H), 3.95 (d, J = 11.4 Hz, 1H), 3.74 (d, J = 12.9 Hz, 1H), 3.68 (d, J = 1.8 Hz, 3H), 3.60-3.48 (m, 1H), 3.35 (d, J= 12.3 Hz, 1H), 3.26 (t, J = 12.2 Hz, 1H), 3.18-3.08 (m, 1H), 2.93 (dd, J = 14.5, 10.4 Hz, 1H), 2.80 (q, J = 7.2 Hz, 2H), 2.13 (s, 3H), 2.01-1.90 (m, 2H). | 669.2 |
| 171 | 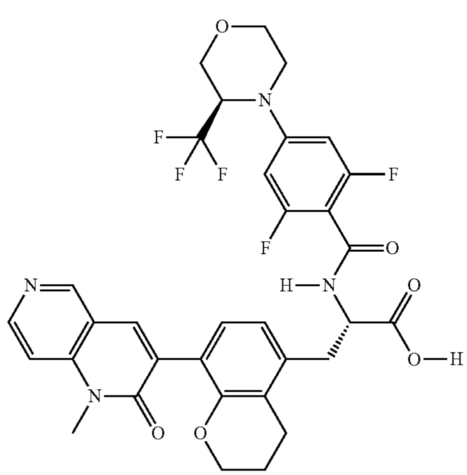 | 1H NMR (400 MHz, DMSO-d6) δ 12.79 (br s, 1H) 9.03 (s, 1H) 8.89 (d, J = 7.8 Hz, 1H), 8.68 (d, J = 6.4 Hz, 1H), 8.00 (s, 1H), 7.70 (s, 1H), 7.00 (d, J = 7.7 Hz, 1H), 6.87 (d, J = 7.8 Hz, 1H), 6.78 (d, J = 11.9 Hz, 2H), 4.91 (d, J = 9.5 Hz, 1H), 4.54 (d, J = 11.3 Hz, 1H), 4.17 (d, J = 12.7 Hz, 1H), 4.04 (d, J = 5.3 Hz, 2H), 4.00-3.92 (m, 1H), 3.75 (d, J = 12.7 Hz, 2H), 3.67 (s, 3H), 3.56 (s, 2H), 3.25 (d, J = 3.2 Hz, 1H), 3.13 (dd, J = 14.8, 4.4 Hz, 1H), 2.93 (dd, J = 14.5, 9.9 Hz, 1H), 2.80 (d, J = 7.1 Hz, 1H), 1.96 (s, 2H). | 673.2 |

TABLE 1-continued

| Example | Structure | 1H-NMR | M/Z [M + H]+ |
|---|---|---|---|
| 172 | 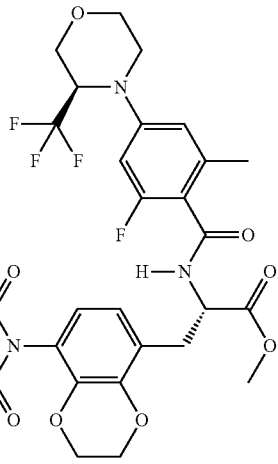 | 1H NMR (400 MHz, DMSO-d6) δ 8.98 (s, 1H), 8.81 (d, J = 7.6 Hz, 1H), 8.56 (d, J = 5.0 Hz, 1H), 7.90 (d, J = 5.0 Hz, 1H), 6.85 (d, J = 8.1 Hz, 1H), 6.77 (d, J = 8.1 Hz, 1H), 6.74-6.65 (m, 2H), 4.91-4.80 (m, 1H), 4.77-4.67 (m, 1H), 4.33-4.24 (m, 2H), 4.21-4.11 (m, 3H), 3.95 (d, 1H), 3.74 (d, J = 12.6 Hz, 1H), 3.65 (s, 3H), 3.62 (s, 3H), 3.55 (t, 1H), 3.36 (d, J = 12.4 Hz, 1H), 3.32-3.21 (m, 1H), 3.17 (dd, J = 14.0, 5.5 Hz, 1H), 2.94 (dd, J = 13.9, 9.9 Hz, 1H), 2.12 (s, 3H). | 702.022 |
| 173 | 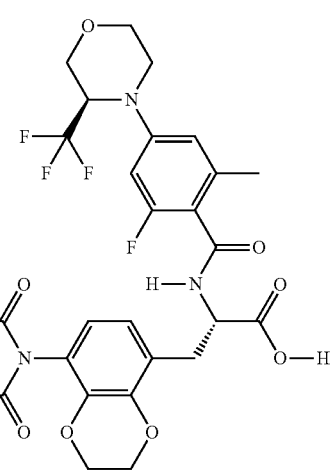 | 1H NMR (400 MHz, DMSO-d6) δ 8.97 (s, 1H), 8.65 (d, J = 8.0 Hz, 1H), 8.56 (d, J = 5.1 Hz, 1H), 7.90 (d, J = 5.0 Hz, 1H), 6.87 (d, J = 8.1 Hz, 1H), 6.75 (d, 1H), 6.73-6.63 (m, 2H), 4.91-4.78 (m, 1H), 4.74-4.63 (m, 1H), 4.28 (s, 2H), 4.22-4.11 (m, 3H), 4.00-3.91 (m, 1H), 3.74 (d, J = 12.6 Hz, 1H), 3.62 (s, 3H), 3.55 (t, 1H), 3.36 (d, J = 12.5 Hz, 1H), 3.32-3.16 (m, 2H), 2.96-2.84 (m, 1H), 2.10 (s, 3H). | 687.916 |
| 174 | 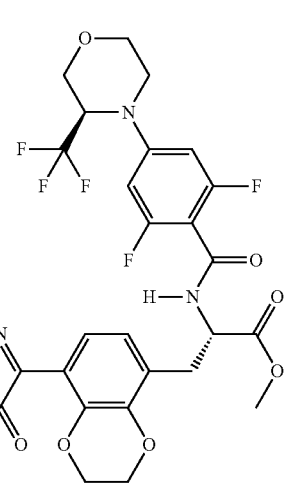 | 1H NMR (400 MHz, DMSO-d6) δ 8.88 (d, J = 7.5 Hz, 1H), 6.83-6.71 (m, 3H), 6.65 (d, J = 7.7 Hz, 1H), 4.92 (dd, J = 8.8, 3.6 Hz, 1H), 4.72-4.53 (m, 1H), 4.27 (dd, J = 5.1, 2.5 Hz, 2H), 4.21-4.07 (m, 3H), 3.96 (dd, J = 11.5, 3.8 Hz, 1H), 3.75 (d, J = 12.5 Hz, 1H), 3.64 (s, 3H), 3.59-3.53 (m, 1H), 3.44 (d, J = 12.3 Hz, 4H), 3.25 (t, J = 12.2 Hz, 1H), 3.13 (dd, J = 13.7, 5.8 Hz, 1H), 2.91 (dd, J = 13.7, 8.9 Hz, 1H), 2.39-2.29 (m, 3H), 2.27 (d, J = 0.8 Hz, 3H). | 667.2 |

TABLE 1-continued

| Example | Structure | 1H-NMR | M/Z [M + H]+ |
|---|---|---|---|
| 175 | 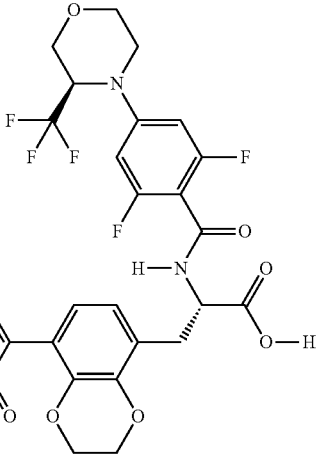 | 1H NMR (400 MHz, DMSO-d6) δ 8.72 (d, J = 7.8 Hz, 1H), 6.90-6.69 (m, 3H), 6.64 (d, J = 7.7 Hz, 1H), 4.91 (dd, J = 8.9, 3.7 Hz, 1H), 4.62-4.45 (m, 1H), 4.26 (dd, J = 5.5, 3.0 Hz, 2H), 4.19-4.07 (m, 3H), 3.96 (dd, J = 11.5, 3.8 Hz, 1H), 3.74 (d, J = 11.7 Hz, 1H), 3.63-3.52 (m, 1H), 3.42 (s, 4H), 3.24 (t, J = 12.6 Hz, 1H), 3.15 (dd, J = 13.8, 5.2 Hz, 1H), 2.87 (dd, J = 13.9, 9.4 Hz, 1H), 2.35-2.31 (m, 3H), 2.30-2.25 (m, 3H). | 653.2 |
| 176 | 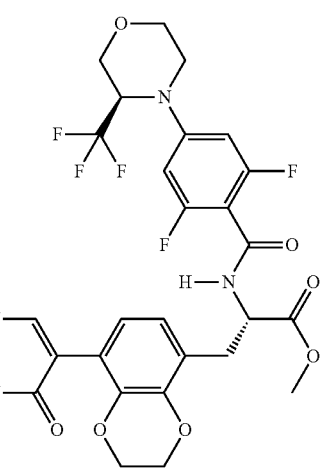 | 1H NMR (400 MHz, DMSO-d6) δ 8.88 (d, J = 7.6 Hz, 1H), 7.82 (d, J = 5.0 Hz, 1H), 6.87-6.65 (m, 4H), 4.92 (dd, J = 8.6, 3.7 Hz, 1H), 4.68-4.55 (m, 1H), 4.27 (t, J = 2.9 Hz, 2H), 4.17 (d, J = 12.2 Hz, 3H), 3.96 (dd, J = 11.4, 3.8 Hz, 1H), 3.74 (d, J = 11.7 Hz, 1H), 3.64 (s, 3H), 3.60-3.51 (m, 1H), 3.49 (s, 3H), 3.44 (d, J = 12.8 Hz, 1H), 3.24 (t, J = 12.1 Hz, 1H), 3.13 (dd, J = 13.7, 5.7 Hz, 1H), 2.89 (dd, J = 13.8, 9.1 Hz, 1H), 2.55 (d, J = 2.3 Hz, 3H). | 653.2 |
| 177 | 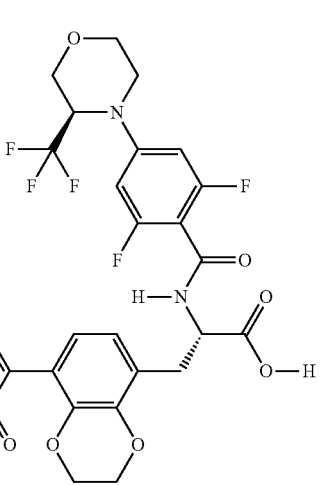 | 1H NMR (400 MHz, DMSO-d6) δ 8.72 (d, J = 7.9 Hz, 1H), 7.83 (d, J = 4.8 Hz, 0H), 6.85-6.66 (m, 4H), 4.91 (dd, J = 8.7, 3.7 Hz, 1H), 4.57 (td, J = 8.8, 5.1 Hz, 1H), 4.27 (d, J = 4.6 Hz, 2H), 4.22-4.11 (m, 3H), 3.96 (dd, J = 11.4, 3.8 Hz, 1H), 3.74 (d, J = 13.0 Hz, 1H), 3.60-3.52 (m, 1H), 3.49 (s, 3H), 3.43 (d, J = 12.7 Hz, 1H), 3.24 (t, J = 12.4 Hz, 1H), 3.16 (dd, J = 13.8, 5.2 Hz, 1H), 2.85 (dd, J = 13.9, 9.6 Hz, 1H) 2.60-2.54 (m, 3H). | 639.2 |

TABLE 1-continued

| Example | Structure | 1H-NMR | M/Z [M + H]+ |
|---|---|---|---|
| 178 | 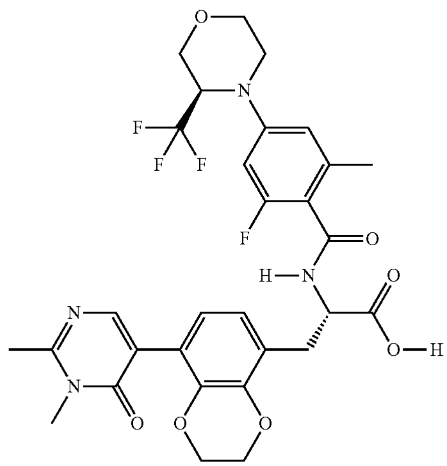 [SMILES: Cc1cc(N2CCOC[C@@H]2C(F)(F)F)cc(F)c1C(=O)N[C@@H](Cc1ccc(-c2cnc(C)n(C)c2=O)c2c1OCCO2)C(=O)O] | 1H NMR (400 MHz, DMSO-d6) δ 8.57 (d, J = 8.1 Hz, 1H), 7.80 (d, J = 3.7 Hz, 1H), 6.78 (dd, J = 8.6, 2.3 Hz, 1H), 6.73-6.68 (m, 1H), 6.66 (d, J = 6.5 Hz, 1H), 4.83 (d, J = 9.4 Hz, 1H), 4.67 (s, 1H), 4.28 (d, J = 5.0 Hz, 2H), 4.22-4.10 (m, 3H), 3.95 (d, J = 11.4 Hz, 1H), 3.73 (d, J = 12.7 Hz, 1H), 3.56 (d, J = 11.4 Hz, 1H), 3.49 (s, 3H), 3.35 (d, J = 12.3 Hz, 1H), 3.30-3.12 (m, 2H), 2.83 (t, J = 12.1 Hz, 1H), 2.54 (d, J = 6.7 Hz, 4H), 2.06 (s, 3H). | 635.1 |
| 179 | 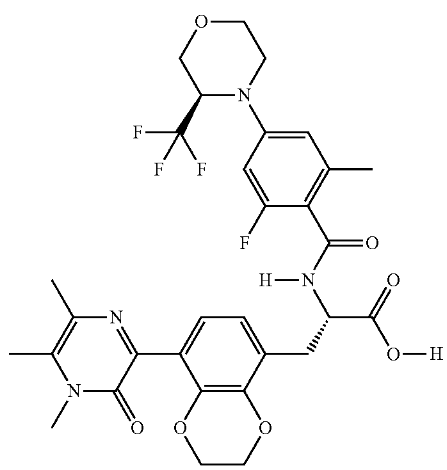 [SMILES: Cc1cc(N2CCOC[C@@H]2C(F)(F)F)cc(F)c1C(=O)N[C@@H](Cc1ccc(-c2nc(C)c(C)n(C)c2=O)c2c1OCCO2)C(=O)O] | 1H NMR (400 MHz, DMSO-d6) δ 8.59 (d, J = 7.9 Hz, 1H), 6.77 (d, J = 7.8 Hz, 1H), 6.73-6.62 (m, 3H), 4.84 (dd, J = 8.9, 3.6 Hz, 1H), 4.65-4.57 (m, 1H), 4.27 (dd, J = 5.4, 2.9 Hz, 2H), 4.17-4.12 (m, 2H), 3.98-3.93 (m, 1H), 3.74 (d, J = 12.8 Hz, 1H), 3.14 (d, J = 5.0 Hz, 2H), 2.86 (dd, J = 13.9, 9.9 Hz, 2H), 2.33 (s, 3H), 2.27 (s, 3H), 2.12 (s, 3H). | 649.2 |
| 180 | 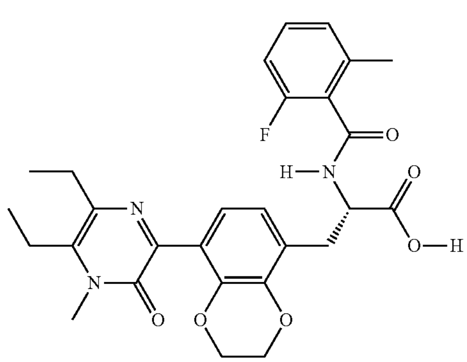 [SMILES: CCc1nc(-c2ccc(C[C@H](NC(=O)c3c(C)cccc3F)C(=O)O)c3c2OCCO3)c(=O)n(C)c1CC] | 1H NMR (400 MHz, DMSO-d6) δ 8.83 (d, J = 8.0 Hz, 1H), 7.29 (td, J = 8.0, 6.0 Hz, 1H), 7.06-6.98 (m, 2H), 6.78 (d, J = 7.8 Hz, 1H), 6.68 (d, J = 7.7 Hz, 1H), 4.69 (ddd, J = 9.9, 7.9, 5.0 Hz, 1H), 4.28 (d, J = 2.5 Hz, 1H), 4.15 (d, J = 3.1 Hz, 1H), 3.51 (s, 3H), 3.18 (dd, J = 13.9, 5.0 Hz, 2H), 2.86 (dd, J = 14.0, 10.0 Hz, 2H), 2.73 (q, J = 7.5 Hz, 2H), 2.56 (t, J = 7.4 Hz, 2H), 2.14 (s, 3H), 1.17 (dt, J = 17.0, 7.5 Hz, 6H). | 524.2 |

TABLE 1-continued

| Example | Structure | 1H-NMR | M/Z [M + H]+ |
|---|---|---|---|
| 181 | 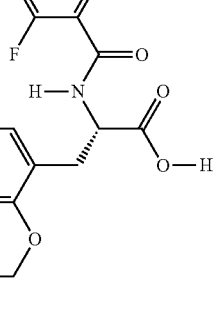 | 1H NMR (400 MHz, DMSO-d6) δ 8.84 (d, J = 8.0 Hz, 1H), 7.31-7.25 (m, 1H), 7.02 (t, J = 8.5 Hz, 2H), 6.77 (d, J = 7.8 Hz, 1H), 6.65 (d, J = 7.7 Hz, 1H), 4.73-4.63 (m, 1H), 4.27 (dd, J = 5.4, 2.8 Hz, 1H), 4.15 (d, J = 2.5 Hz, 1H), 3.48 (s, 3H), 3.18 (dd, J = 14.0, 5.0 Hz, 2H), 2.86 (dd, J = 13.9, 9.9 Hz, 2H), 2.33 (s, 3H), 2.27 (s, 3H), 2.15 (s, 3H). | 496.2 |
| 182 | 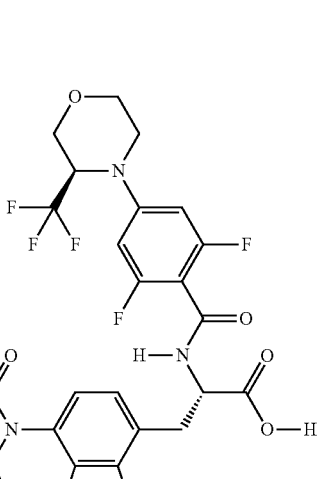 | 1H NMR (400 MHz, DMSO-d6) δ 12.85 (s, 1H), 8.98 (s, 1H), 8.92 (d, J = 7.9 Hz, 1H), 8.56 (d, J = 5.0 Hz, 1H), 7.93-7.86 (m, 1H), 7.29 (d, J = 8.2 Hz, 1H), 7.16 (d, J = 8.0 Hz, 1H), 6.78 (d, J = 11.8 Hz, 2H), 5.12 (t, J = 9.4 Hz, 2H), 4.97-4.75 (m, 3H), 4.62 (s, 1H), 4.16 (d, J = 12.8 Hz, 1H), 3.96 (d, J = 11.0 Hz, 1H), 3.75 (d, J = 13.3 Hz, 2H), 3.60 (s, 3H), 3.42 (s, 1H), 3.25 (t, J = 12.3 Hz, 1H), 3.15-3.05 (m, 1H), 2.97 (dd, J = 14.5, 9.9 Hz, 1H). | 676.3 |
| 183 | 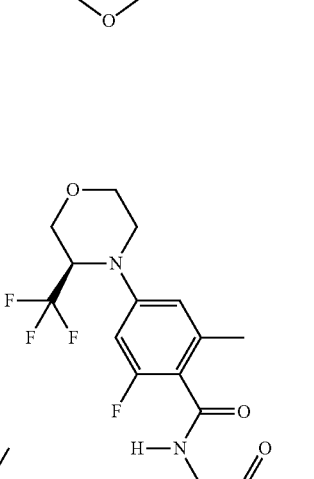 | 1H NMR (400 MHz, DMSO-d6) δ 12.81 (s, 1H), 8.71 (t, J = 10.2 Hz, 1H), 7.24 (t, J = 9.3 Hz, 1H), 7.02 (d, J = 6.6 Hz, 1H), 6.73-6.59 (m, 2H), 5.11 (q, J = 13.3, 12.9 Hz, 2H), 4.89-4.64 (m, 4H), 4.14 (d, J = 12.6 Hz, 1H), 3.94 (d, J = 11.4 Hz, 1H), 3.73 (d, J = 12.6 Hz, 1H), 3.54 (t, J = 11.8 Hz, 1H), 3.46 (d, J = 2.3 Hz, 3H), 3.34 (d, J = 12.6 Hz, 1H), 3.26 (d, J = 12.3 Hz, 1H), 3.12 (d, J = 14.4 Hz, 1H), 2.97-2.79 (m, 1H), 2.56 (s, 3H), 2.01 (d, J = 8.9 Hz, 6H). | 633.3 |

TABLE 1-continued

| Example | Structure | 1H-NMR | M/Z [M + H]+ |
|---|---|---|---|
| 184 | 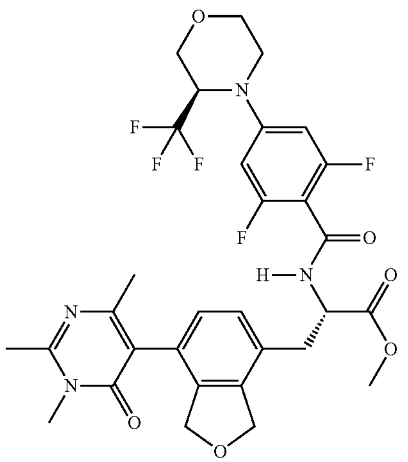 [SMILES: COC(=O)[C@H](Cc1ccc(-c2c(C)nc(C)n(C)c2=O)c2c1COC2)NC(=O)c1c(F)cc(N2CCOC[C@@H]2C(F)(F)F)cc1F] | 1H NMR (400 MHz, DMSO-d6) δ 8.99 (t, J = 7.9 Hz, 1H), 7.21 (d, J = 6.8 Hz, 1H), 7.00 (d, J = 7.7 Hz, 1H), 6.77 (d, J = 12.2 Hz, 2H), 5.10 (d, J = 9.1 Hz, 2H), 4.97-4.86 (m, 1H), 4.81 (d, J = 12.6 Hz, 1H), 4.71 (d, J = 12.8 Hz, 2H), 4.16 (d, J = 12.7 Hz, 1H), 3.96 (d, J = 11.9 Hz, 1H), 3.74 (d, J = 12.9 Hz, 1H), 3.65 (d, J = 1.7 Hz, 3H), 3.55 (t, J = 11.8 Hz, 1H), 3.45 (s, 4H), 3.24 (t, J = 12.7 Hz, 1H), 3.14-3.04 (m, 1H), 2.95 (t, J = 12.4 Hz, 1H), 2.55 (d, J = 2.5 Hz, 3H), 2.00 (dd, J = 7.4, 2.3 Hz, 3H). | 651.3 |
| 185 | 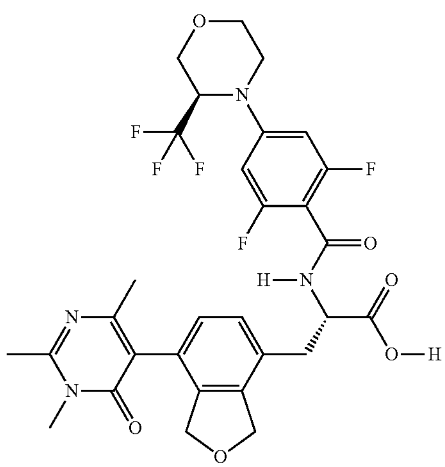 [SMILES: Cc1nc(C)n(C)c(=O)c1-c1ccc(C[C@H](NC(=O)c2c(F)cc(N3CCOC[C@@H]3C(F)(F)F)cc2F)C(=O)O)c2c1COC2] | 1H NMR (400 MHz, DMSO-d6) δ 12.82 (s, 1H), 8.85 (t, J = 7.2 Hz, 1H), 7.21 (t, J = 8.8 Hz, 1H), 6.99 (dd, J = 8.0, 4.0 Hz, 1H), 6.75 (d, J = 12.1 Hz, 2H), 5.10 (d, J = 12.8 Hz, 2H), 4.91 (d, J = 9.3 Hz, 1H), 4.81 (d, J = 12.6 Hz, 1H), 4.66 (dd, J = 28.0, 13.7 Hz, 2H), 4.16 (d, J = 12.8 Hz, 1H), 3.99-3.92 (m, 1H), 3.78-3.70 (m, 1H), 3.55 (t, J = 11.6 Hz, 1H), 3.45 (s, 4H), 3.25 (d, J = 12.6 Hz, 1H), 3.09 (dd, J = 14.8, 4.6 Hz, 1H), 2.92 (s, 1H), 2.56-2.52 (m, 3H), 1.99 (d, J = 8.5 Hz, 3H). | 637.3 |
| 186 | 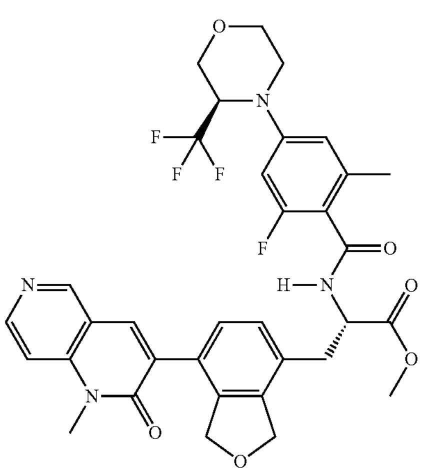 [SMILES: COC(=O)[C@H](Cc1ccc(-c2cc3cnccc3n(C)c2=O)c2c1COC2)NC(=O)c1c(C)cc(N2CCOC[C@@H]2C(F)(F)F)cc1F] | 1H NMR (400 MHz, DMSO-d6) δ 9.15 (s, 1H), 8.86 (d, J = 8.0 Hz, 1H), 8.76 (d, J = 6.5 Hz, 1H), 8.15 (s, 1H), 7.83 (d, J = 5.8 Hz, 1H), 7.31 (q, J = 8.0 Hz, 2H), 6.75-6.60 (m, 2H), 5.13 (q, J = 12.6 Hz, 2H), 4.99 (s, 2H), 4.90-4.72 (m, 2H), 4.15 (d, J = 12.7 Hz, 1H), 3.95 (d, J = 11.4 Hz, 1H), 3.70 (dd, J = 9.0, 2.0 Hz, 7H), 3.54 (t, J = 11.8 Hz, 1H), 3.35 (d, J = 12.4 Hz, 1H), 3.25 (t, J = 12.2 Hz, 1H), 3.15 (dd, J = 14.5, 4.6 Hz, 1H), 2.96 (t, J = 12.5 Hz, 1H), 2.05 (s, 3H). | 669.4 |

TABLE 1-continued

| Example | Structure | 1H-NMR | M/Z [M + H]+ |
|---|---|---|---|
| 187 | 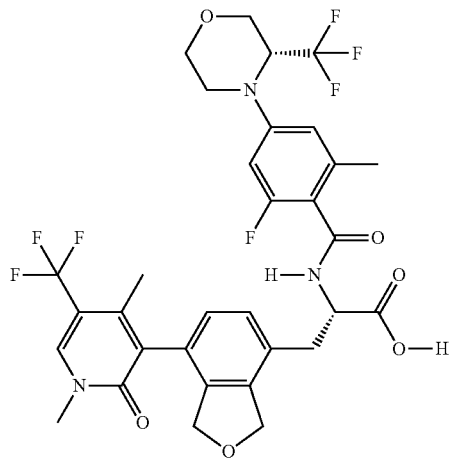 [SMILES: Cc1cc(N2CCOC[C@@H]2C(F)(F)F)cc(F)c1C(=O)N[C@@H](Cc1ccc(-c2c(C)c(C(F)(F)F)cn(C)c2=O)c2c1COC2)C(=O)O] | 1H NMR (400 MHz, DMSO-d6) δ 13.02-12.56 (s, 1H), 8.71 (dd, J = 13.4, 8.3 Hz, 1H), 8.33 (s, 1H), 7.24 (dd, J = 12.9, 7.7 Hz, 1H), 6.98 (t, J = 7.9 Hz, 1H), 6.71-6.60 (m, 2H), 5.19-5.04 (m, 2H), 4.83 (d, J = 6.7 Hz, 1H), 4.77 (d, J = 12.4 Hz, 1H), 4.68 (t, J = 10.9 Hz, 2H), 4.14 (d, J = 12.6 Hz, 1H), 3.94 (d, J = 11.2 Hz, 1H), 3.73 (d, J = 12.7 Hz, 1H), 3.55 (d, J = 12.4 Hz, 1H), 3.50 (s, 3H), 3.34 (d, J = 12.7 Hz, 1H), 3.26 (d, J = 12.6 Hz, 1H), 3.13 (d, J = 14.6 Hz, 1H), 2.89 (q, J = 12.4 Hz, 1H), 2.01 (d, J = 8.7 Hz, 3H), 1.98 (d, J = 7.1 Hz, 3H). | 686.1 |
| 188 | 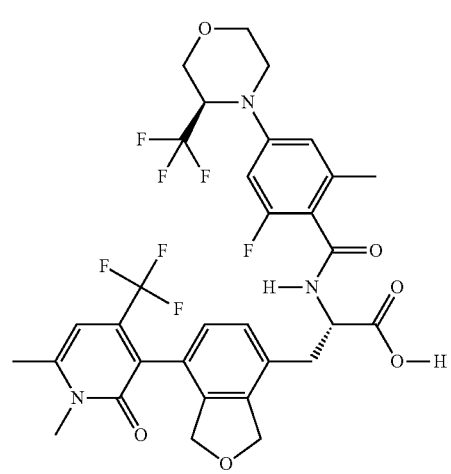 [SMILES: Cc1cc(N2CCOC[C@@H]2C(F)(F)F)cc(F)c1C(=O)N[C@@H](Cc1ccc(-c2c(C(F)(F)F)cc(C)n(C)c2=O)c2c1COC2)C(=O)O] | 1H NMR (400 MHz, DMSO-d6) δ 8.72 (dd, J = 10.2, 8.3 Hz, 1H), 7.28-7.18 (m, 1H), 6.92 (t, J = 6.9 Hz, 1H), 6.72-6.61 (m, 2H), 6.51 (d, J = 7.3 Hz, 1H), 5.11 (q, J = 12.3 Hz, 2H), 4.83 (d, J = 8.8 Hz, 1H), 4.80-4.71 (m, 1H), 4.71-4.61 (m, 1H), 4.14 (d, J = 12.6 Hz, 1H), 3.94 (d, J = 11.2 Hz, 1H), 3.73 (d, J = 12.7 Hz, 1H), 3.59-3.45 (m, 5H), 3.35 (d, J = 12.5 Hz, 1H), 3.25 (t, J = 12.5 Hz, 1H), 3.11 (dd, J = 14.7, 4.3 Hz, 1H), 2.98-2.82 (m, 1H), 2.48 (s, 3H), 2.02 (d, J = 5.7 Hz, 3H). | 686.2 |
| 189 | 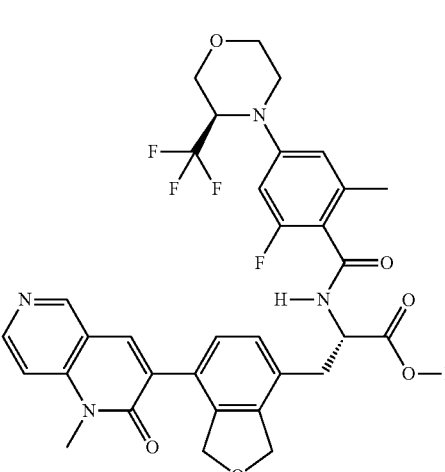 | 1H NMR (400 MHz, DMSO-d6) δ 9.05 (s, 1H), 8.73 (d, J = 8.3 Hz, 1H), 8.71-8.65 (m, 1H), 8.10 (s, 1H), 7.68 (s, 1H), 7.34-7.26 (m, 2H), 6.73-6.61 (m, 2H), 5.13 (q, J = 12.3 Hz, 2H), 4.99 (s, 2H), 4.83 (d, J = 9.5 Hz, 1H), 4.76-4.66 (m, 1H), 4.15 (d, J = 12.7 Hz, 1H), 3.95 (d, J = 11.7 Hz, 1H), 3.73 (d, J = 14.1 Hz, 2H), 3.69 (s, 3H), 3.55 (d, J = 12.1 Hz, 1H), 3.30-2.30 (m, 1H), 3.14 (dd, J = 14.5, 4.5 Hz, 1H), 2.92 (dd, J = 14.4, 10.6 Hz, 1H), 2.04 (s, 3H). | 655.2 |

TABLE 1-continued

| Example | Structure | 1H-NMR | M/Z [M + H]+ |
|---|---|---|---|
| 190 | 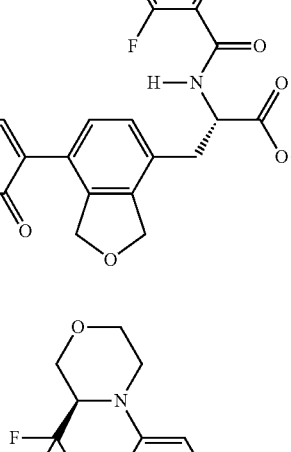 | 1H NMR (400 MHz, DMSO-d6) δ 12.86 (br s, 1H) 9.03 (s, 1H), 8.89 (d, J = 8.0 Hz, 1H), 8.68 (d, J = 6.2 Hz, 1H), 8.11 (s, 1H), 7.67 (d, J = 6.4 Hz, 1H), 7.30 (q, J = 7.9 Hz, 2H), 6.78 (d, J = 11.8 Hz, 2H), 5.12 (q, J = 12.4 Hz, 2H), 4.99 (s, 2H), 4.97-4.85 (m, 1H), 4.63 (q, J = 8.4 Hz, 1H), 4.17 (d, J = 12.7 Hz, 1H), 3.96 (dd, J = 11.4, 3.7 Hz, 1H), 3.74 (d, J = 12.7 Hz, 1H), 3.68 (s, 3H), 3.57 (d, J = 11.4 Hz, 2H), 3.25 (s, 1H), 3.11 (dd, J = 14.4, 5.0 Hz, 1H), 2.96 (dd, J = 14.3, 9.7 Hz, 1H). | 659.2 |
| 191 | 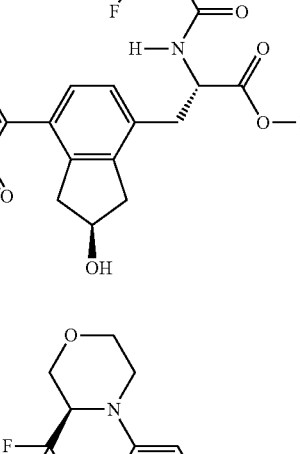 | 1H NMR (400 MHz, DMSO-d6) δ 8.85 (d, J = 7.9 Hz, 1H), 7.47 (d, J = 7.9 Hz, 1H), 7.09 (d, J = 7.9 Hz, 1H), 6.77 (d, J = 11.8 Hz, 2H), 4.96-4.86 (m, 1H), 4.57-4.42 (m, 2H), 4.16 (d, J = 12.7 Hz, 1H), 3.96 (dd, J = 11.7, 3.7 Hz, 1H), 3.74 (d, J = 12.7 Hz, 1H), 3.52 (s, 4H), 3.43 (d, J = 12.7 Hz, 1H), 3.24 (t, J = 12.4 Hz, 1H), 3.12 (td, J = 17.2, 6.0 Hz, 3H), 2.94 (dd, J = 14.0, 9.1 Hz, 1H), 2.84-2.74 (m, 2H), 2.36 (s, 3H), 2.30 (s, 4H). | 651.2 |
| 192 | 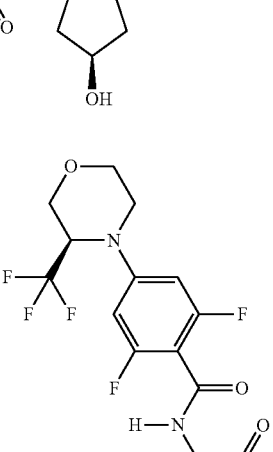 | 1H NMR (400 MHz, DMSO-d6) δ 8.85 (d, J = 7.9 Hz, 1H), 7.47 (d, J = 7.9 Hz, 1H), 7.10 (d, J = 7.9 Hz, 1H), 6.78 (d, J = 11.8 Hz, 2H), 4.97-4.83 (m, 1H), 4.50 (ddt, J = 27.6, 10.9, 5.0 Hz, 2H), 4.16 (d, J = 12.7 Hz, 1H), 3.96 (dd, J = 11.9, 3.7 Hz, 1H), 3.74 (d, J = 12.7 Hz, 1H), 3.52 (s, 4H), 3.43 (d, J = 12.0 Hz, 1H), 3.24 (t, J = 12.2 Hz, 1H), 3.12 (ddd, J = 17.3, 13.8, 5.7 Hz, 3H), 2.93 (dd, J = 14.1, 9.5 Hz, 1H), 2.78 (dd, J = 16.5, 3.9 Hz, 2H), 2.36 (s, 3H), 2.31 (s, 3H). | 651.2 |

TABLE 1-continued

| Example | Structure | 1H-NMR | M/Z [M + H]+ |
|---|---|---|---|
| 193 | 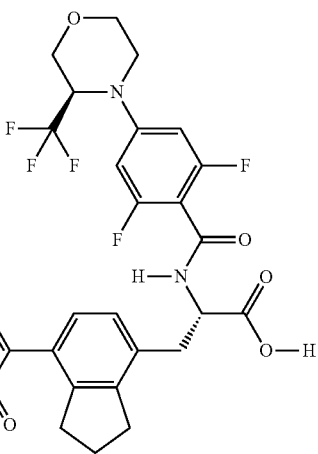 | 1H NMR (400 MHz, DMSO-d6) δ 8.84 (d, J = 7.9 Hz, 1H), 7.41 (d, J = 7.8 Hz, 1H), 7.08 (d, J = 7.9 Hz, 1H), 6.77 (d, J = 11.8 Hz, 2H), 4.90 (d, J = 7.9 Hz, 1H), 4.59-4.51 (m, 1H), 4.16 (d, J = 12.7 Hz, 1H), 3.96 (dd, J = 11.4, 3.6 Hz, 1H), 3.77-3.70 (m, 1H), 3.60-3.55 (m, 1H), 3.51 (s, 3H), 3.43 (d, J = 13.4 Hz, 1H), 3.30-3.18 (m, 1H), 3.12 (dd, J = 14.1, 5.0 Hz, 1H), 2.94 (dt, J = 25.6, 8.5 Hz, 5H), 2.35 (s, 3H), 2.30 (s, 3H), 1.97 (q, J = 7.9 Hz, 2H). | 635.3 |
| 194 | 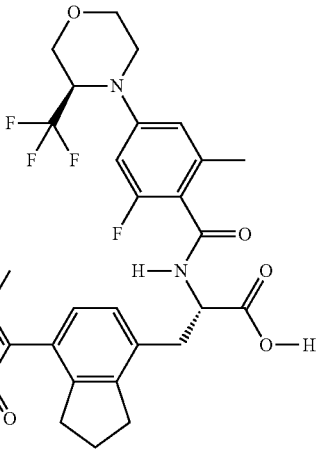 | 1H NMR (400 MHz, DMSO-d6) δ 12.94-12.04 (s, 1H), 8.70 (t, J = 7.8 Hz, 1H), 7.09 (t, J = 8.4 Hz, 1H), 6.82 (t, J = 7.5 Hz, 1H), 6.67 (d, J = 13.4 Hz, 1H), 6.64 (s, 1H), 4.83 (d, J = 10.0 Hz, 1H), 4.74-4.61 (m, 1H), 4.14 (d, J = 12.5 Hz, 1H), 3.94 (d, J = 11.8 Hz, 1H), 3.73 (d, J = 12.7 Hz, 1H), 3.60-3.49 (m, 1H), 3.45 (d, J = 1.5 Hz, 3H), 3.34 (d, J = 12.2 Hz, 1H), 3.26 (d, J = 12.1 Hz, 1H), 3.13 (t, J = 10.0 Hz, 1H), 3.00-2.87 (m, 3H), 2.62 (s, 1H), 2.54 (s, 4H), 2.04 (d, J = 2.4 Hz, 3H), 1.99 (d, J = 6.9 Hz, 1H), 1.96 (s, 2H), 1.95 (s, 2H). | 631.3 |
| 195 | 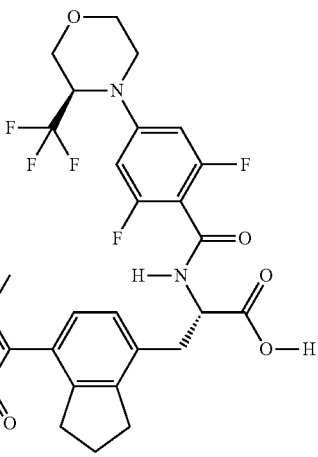 | 1H NMR (400 MHz, DMSO-d6) δ 8.83 (d, J = 7.7 Hz, 1H), 7.04 (t, J = 8.0 Hz, 1H), 6.79-6.71 (m, 3H), 6.09 (s, 1H), 4.96-4.85 (m, 1H), 4.63-4.53 (m, 1H), 4.16 (d, J = 12.6 Hz, 1H), 3.95 (d, J = 14.7 Hz, 1H), 3.74 (d, J = 12.3 Hz, 1H), 3.48 (m, 1H), 3.45 (m, 1H), 3.41 (s, 3H), 3.24 (t, J = 11.6 Hz, 1H), 3.11 (m, 1H), 3.00-2.85 (m, 3H), 2.69-2.58 (m, 1H), 2.49-2.39 (m, 1H), 2.34 (s, 3H), 1.99-1.89 (m, 2H), 1.81 (d, J = 6.1 Hz, 3H). | 634.2 |

TABLE 1-continued

| Example | Structure | 1H-NMR | M/Z [M + H]+ |
|---|---|---|---|
| 196 | 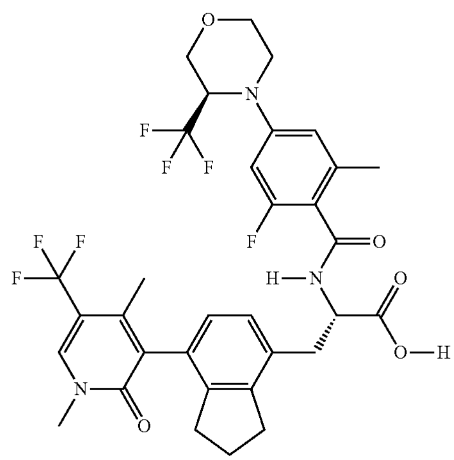 [SMILES: Cc1cc(N2CCOC[C@@H]2C(F)(F)F)cc(F)c1C(=O)N[C@@H](Cc1ccc(-c2c(C)c(C(F)(F)F)cn(C)c2=O)c2c1CCC2)C(=O)O] | 1H NMR (400 MHz, DMSO-d6) δ 8.70 (t, J = 7.7 Hz, 1H), 8.30 (s, 1H), 7.13-7.08 (m, 1H), 6.83-6.76 (m, 1H), 6.67 (d, J = 14.4 Hz, 1H), 6.64 (s, 1H), 4.88-4.79 (m, 1H), 4.67 (t, J = 10.7 Hz, 1H), 4.14 (d, J = 12.9 Hz, 1H), 3.97-3.92 (m, 1H), 3.73 (d, J = 14.1 Hz, 1H), 3.55 (d, J = 8.6 Hz, 1H), 3.50 (s, 3H), 3.34 (d, J = 11.1 Hz, 1H), 3.26 (d, J = 14.4 Hz, 1H), 3.19-3.09 (m, 1H), 3.01-2.86 (m, 3H), 2.57 (s, 2H), 2.03 (d, J = 7.9 Hz, 3H), 1.96 (s, 2H), 1.94 (d, J = 6.0 Hz, 3H). | 684.2 |
| 197 | 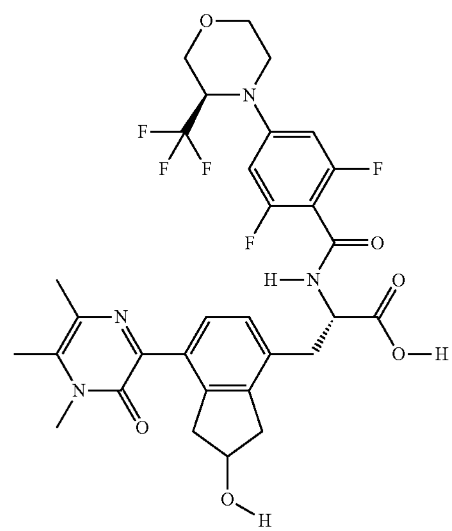 [SMILES: Cc1nc(-c2ccc(C[C@H](NC(=O)c3c(F)cc(N4CCOC[C@@H]4C(F)(F)F)cc3F)C(=O)O)c3c2CC(O)C3)c(=O)n(C)c1C] | 1H NMR (400 MHz, DMSO-d6) δ 8.85 (d, J = 7.9 Hz, 1H), 7.47 (d, J = 7.9 Hz, 1H), 7.09 (dd, J = 8.0, 5.3 Hz, 1H), 6.78 (d, J = 11.9 Hz, 2H), 4.91 (d, J = 9.2 Hz, 1H), 4.57-4.41 (m, 2H), 4.16 (d, J = 12.7 Hz, 1H), 3.96 (dd, J = 11.6, 3.7 Hz, 1H), 3.74 (d, J = 12.7 Hz, 1H), 3.56 (d, J = 3.4 Hz, 1H), 3.52 (s, 3H), 3.43 (d, J = 12.8 Hz, 1H), 3.26 (d, J = 12.4 Hz, 1H), 3.12 (td, J = 17.0, 6.1 Hz, 3H), 3.00-2.89 (m, 1H), 2.78 (dd, J = 16.9, 3.9 Hz, 2H), 2.36 (s, 3H), 2.30 (s, 3H). | 651.2 |
| 198 | 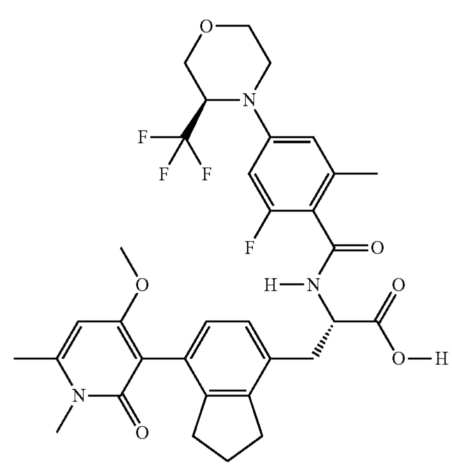 [SMILES: COc1cc(C)n(C)c(=O)c1-c1ccc(C[C@H](NC(=O)c2c(C)cc(N3CCOC[C@@H]3C(F)(F)F)cc2F)C(=O)O)c2c1CCC2] | 1H NMR (400 MHz, DMSO-d6) δ 8.72-8.67 (m, 1H), 6.99 (dd, J = 7.4, 3.1 Hz, 1H), 6.81 (dd, J = 7.6, 4.0 Hz, 1H), 6.71-6.64 (m, 2H), 6.29 (s, 1H), 4.89-4.78 (m, 1H), 4.59 (d, J = 16.7 Hz, 1H), 4.15 (d, J = 12.5 Hz, 1H), 3.95 (dd, J = 11.4, 3.4 Hz, 1H), 3.75 (s, 1H), 3.70 (d, J = 4.5 Hz, 3H), 3.55 (t, J = 13.6 Hz, 1H), 3.41 (s, 3H), 3.35 (d, J = 12.9 Hz, 1H), 3.27 (d, J = 15.7 Hz, 1H), 3.12-3.04 (m, 1H), 2.88 (d, J = 10.8 Hz, 2H), 2.67-2.59 (m, 2H), 2.41 (s, 3H), 2.09 (d, J = 9.0 Hz, 3H), 1.98-1.88 (m, 2H). | 646.3 |

TABLE 1-continued
| Example | Structure | 1H-NMR | M/Z [M + H]+ |
|---|---|---|---|
| 199 | 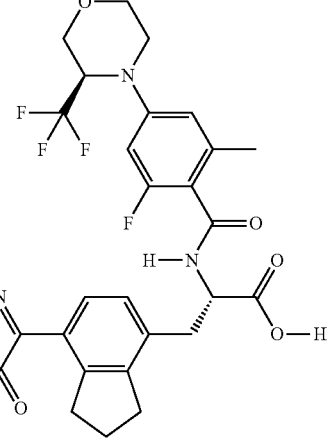 | 1H NMR (400 MHz, DMSO-d6) δ 8.70 (d, J = 8.0 Hz, 1H), 7.41 (d, J = 7.8 Hz, 1H), 7.10-7.06 (m, 1H), 6.71-6.63 (m, 2H), 4.89-4.78 (m, 1H), 4.65-4.55 (m, 1H), 4.13 (d, J = 12.6 Hz, 1H), 3.94 (dd, J = 11.5, 3.4 Hz, 1H), 3.75 (dd, J = 11.5, 3.4 Hz, 1H), 3.56 (d, J = 11.5 Hz, 1H), 3.52 (s, 3H), 3.35 (d, J = 15.7 Hz, 1H), 3.27 (d, J = 10.6 Hz, 1H), 3.13 (dd, J = 14.3, 4.9 Hz, 1H), 2.92 (q, J = 7.8, 7.0 Hz, 5H), 2.67 (s, 1H), 2.35 (s, 3H), 2.30 (s, 3H), 2.09 (s, 3H), 2.00-1.93 (m, 2H). | 631.3 |
| 200 | 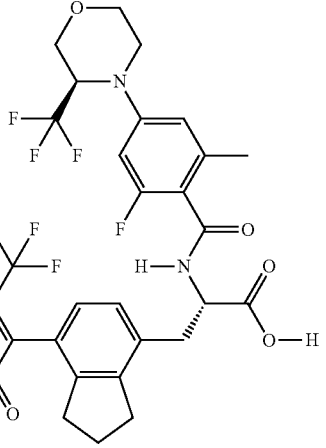 | 1H NMR (400 MHz, DMSO-d6) δ 8.74-8.69 (m, 1H), 7.07 (t, J = 7.7 Hz, 1H), 6.75 (t, J = 7.7 Hz, 1H), 6.72-6.62 (m, 2H), 6.49 (s, 1H), 4.89-4.77 (m, 1H), 4.72-4.60 (m, 1H), 4.14 (d, J = 12.8 Hz, 1H), 3.94 (d, J = 13.7 Hz, 1H), 3.73 (d, J = 13.1 Hz, 1H), 3.57 (s, 1H), 3.49 (s, 3H), 3.40-3.30 (m, 1H), 3.24 (d, J = 10.1 Hz, 1H), 3.12 (d, J = 25.0 Hz, 1H), 3.01-2.86 (m, 3H), 2.64-2.53 (m, 1H), 2.48 (s, 3H), 2.05 (s, 3H), 2.03-1.88 (m, 2H). | 684.20 |
| 201 | 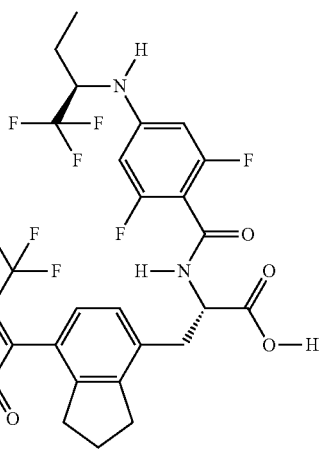 | 1H NMR (400 MHz, DMSO-d6) δ 8.71-8.65 (m, 1H), 7.08-7.02 (m, 1H), 6.74 (d, J = 8.6 Hz, 2H), 6.49 (s, 1H), 6.48-6.42 (m, 2H), 4.61-4.50 (m, 1H), 4.38-4.24 (m, 1H), 3.49 (s, 3H), 3.10 (s, 1H), 2.89 (s, 3H), 2.48 (s, 3H), 2.01-1.90 (m, 2H), 1.82-1.71 (m, 1H), 1.61-1.47 (m, 1H), 0.93 (t, J = 7.3 Hz, 3H). | 660.2 |

TABLE 1-continued

| Example | Structure | 1H-NMR | M/Z [M + H]+ |
|---|---|---|---|
| 202 | 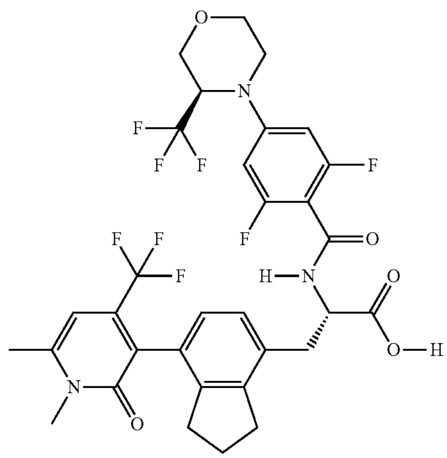 [SMILES: Cc1cc(N2CCOC[C@@H]2C(F)(F)F)cc(F)c1C(=O)N[C@@H](Cc1ccc(-c2c(C(F)(F)F)cc(C)n(C)c2=O)c2c1CCC2)C(=O)O] | 1H NMR (400 MHz, DMSO-d6) δ 8.87-8.82 (m, 1H), 7.08-7.02 (m, 1H), 6.76 (d, J = 11.7 Hz, 3H), 6.49 (s, 1H), 4.96-4.85 (m, 1H), 4.59 (t, J = 10.8 Hz, 1H), 4.16 (d, J = 12.7 Hz, 1H), 3.96 (d, J = 8.9 Hz, 1H), 3.76-3.66 (m, 1H), 3.56-3.53 (m, 1H), 3.49 (s, 3H), 3.43 (d, J = 12.5 Hz, 2H), 3.26 (d, J = 11.4 Hz, 1H), 3.12 (d, J = 18.3 Hz, 1H), 2.94 (d, J = 20.7 Hz, 3H), 2.66-2.53 (m, 2H), 2.48 (s, 3H), 2.02-1.89 (m, 2H). | 688.2 |
| 203 | 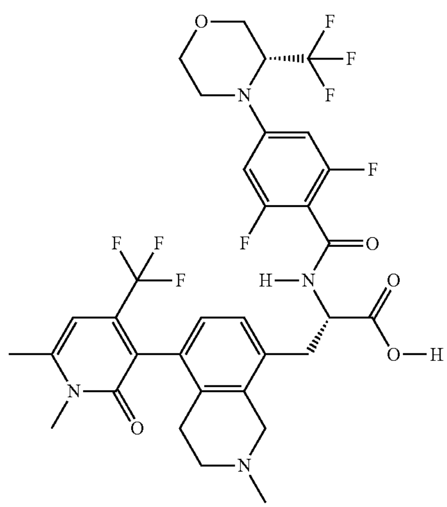 [SMILES: Cc1cc(C(F)(F)F)c(-c2ccc(C[C@H](NC(=O)c3c(F)cc(N4CCOC[C@@H]4C(F)(F)F)cc3F)C(=O)O)c3c2CCN(C)C3)c(=O)n1C] | 1H NMR (400 MHz, DMSO-d6) δ 12.92 (s, 1H), 9.95 (s, 1H), 9.22-8.77 (m, 1H), 8.77-8.49 (m, 1H), 7.71 (d, J = 28.7 Hz, 1H), 7.25 (dt, J = 11.8, 5.8 Hz, 1H), 7.07-6.88 (m, 1H), 6.77 (dd, J = 12.0, 3.8 Hz, 2H), 6.58 (s, 1H), 4.92 (d, J = 9.6 Hz, 1H), 4.71 (d, J = 17.6 Hz, 1H), 4.45-4.24 (m, 1H), 4.17 (d, J = 12.7 Hz, 1H), 3.96 (dd, J = 11.3, 3.7 Hz, 1H), 3.63-3.47 (m, 4H), 3.42 (d, J = 12.9 Hz, 1H), 3.24 (t, J = 2.7 Hz, 1H), 2.96 (q, J = 4.2 Hz, 3H). | 717.2 |
| 204 | 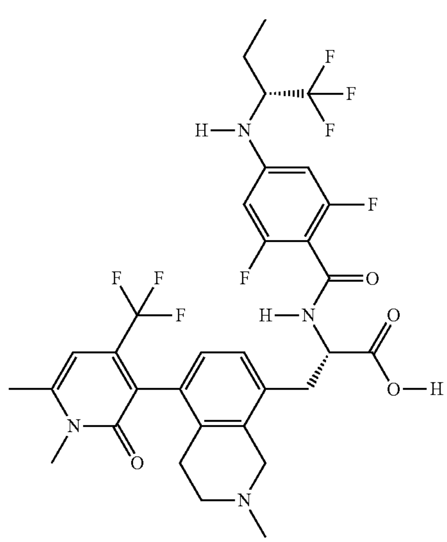 [SMILES: CC[C@@H](Nc1cc(F)c(C(=O)N[C@@H](Cc2ccc(-c3c(C(F)(F)F)cc(C)n(C)c3=O)c3c2CN(C)CC3)C(=O)O)c(F)c1)C(F)(F)F] | 1H NMR (400 MHz, DMSO-d6) δ 9.94 (s, 1H), 8.93-8.60 (m, 1H), 7.25 (q, J = 8.0 Hz, 1H), 7.10-6.82 (m, 1H), 6.77 (d, J = 9.4 Hz, 1H), 6.58 (s, 1H), 6.46 (d, J = 11.9 Hz, 2H), 4.86-4.62 (m, 1H), 4.33 (s, 2H), 3.52 (d, J = 4.6 Hz, 3H), 2.96 (t, J = 5.8 Hz, 4H), 1.76 (d, J = 11.1 Hz, 1H), 1.55 (dd, J = 10.3, 7.0 Hz, 1H), 0.93 (t, J = 7.4 Hz, 3H). | 689.2 |

TABLE 1-continued

| Example | Structure | 1H-NMR | M/Z [M + H]+ |
|---|---|---|---|
| 205 | 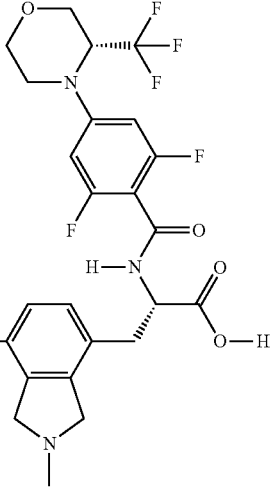 | 1H NMR (400 MHz, DMSO-d6) δ 12.96 (s, 1H), 10.39 (s, 1H), 8.91 (d, J = 8.1 Hz, 1H), 8.22 (d, J = 8.1 Hz, 1H), 7.37 (t, J = 10.3 Hz, 1H), 6.86-6.71 (m, 2H), 4.93 (d, J = 15.7 Hz, 3H), 4.76-4.47 (m, 3H), 4.17 (d, J = 12.7 Hz, 1H), 3.96 (d, J = 11.6 Hz, 1H), 3.74 (d, J = 12.5 Hz, 1H), 3.56 (d, J = 2.5 Hz, 3H), 3.52 (s, 1H), 3.42 (d, J = 11.6 Hz, 1H), 3.24 (t, J = 12.2 Hz, 1H), 3.19-3.09 (m, 1H), 3.03 (d, J = 6.9 Hz, 4H), 2.40 (s, 3H), 2.36 (s, 3H). | 650.0 |

Integrin Cell Capture Assay

The potency of inhibitors in preventing α4β7 integrin interaction with MadCAM-1 was measured by monitoring the capture of α4β7 integrin expressing cells on a recombinant MadCAM-1 extracellular domain-coated plate.

384-well plates (Corning 3702) were coated with MadCAM-1 extracellular domain by dispensing 20 µL of MadCAM-1 at 1.0 µg/mL per well and incubating overnight at 4° C. The plates were then washed with PBS and blocked with 3% BSA for 2 hours before being washed again.

RPMI8866 cells were spun down and re-suspended in assay medium (DMEM+0.5% FBS+0.5 mM $MnCl_2$) at a density of $0.5 \times 10^6$ cells/mL. The cells were then dispensed (60 µL/well) to a 384-well plate (Greiner 781280) that was previously spotted with 60 nL of test compound per well. The plates were incubated at 37° C. for 1 hour. 50 µL of cells were transferred to the blocked, MadCAM-1-coated plates and incubated for 30 minutes at 37° C. 10 µL of 12% glutaraldehyde containing Hoechst 33342 (0.06 mg/mL) was added to the cells (2% glutaraldehyde and 0.01 mg/mL final concentrations). The plates were incubated for 90 minutes at room temperature. The plates were then washed 3 times with 70 µL of PBS per well and imaged on a Cellomics ArrayScan instrument. The cells that were bound to the plate were counted and plotted against the compound concentration to determine the $EC_{50}$ of the test compounds. Results are presented in Table 2.

TABLE 2

α4β7 Integrin Cell Capture Assay Results

| Example # | α4β7 $EC_{50}$ (nM) | Example # | α4β7 $EC_{50}$ (nM) | Example # | α4β7 $EC_{50}$ (nM) | Example # | α4β7 $EC_{50}$ (nM) |
|---|---|---|---|---|---|---|---|
| 1 | 11.036 | 53 | 3.283 | 105 | 2.436 | 157 | 1.824 |
| 2 | 3.756 | 54 | 0.607 | 106 | 0.587 | 158 | 0.502 |
| 3 | 6.486 | 55 | 0.152 | 107 | 0.812 | 159 | 0.226 |
| 4 | 26.308 | 56 | 0.961 | 108 | 0.26 | 160 | 0.189 |
| 5 | 55.415 | 57 | 4.193 | 109 | NA | 161 | 0.364 |
| 6 | 444.38 | 58 | 2.56 | 110 | NA | 162 | 0.78 |
| 7 | 37.768 | 59 | 1.505 | 111 | NA | 163 | 0.731 |
| 8 | 0.301 | 60 | 4.119 | 112 | NA | 164 | 0.482 |
| 9 | 0.431 | 61 | 2.294 | 113 | NA | 165 | 0.25 |
| 10 | 0.864 | 62 | 3.302 | 114 | NA | 166 | 0.195 |
| 11 | 29.308 | 63 | 7.985 | 115 | 0.027 | 167 | 0.521 |
| 12 | 13.917 | 64 | 110.24 | 116 | 19.009 | 168 | 0.946 |
| 13 | 0.388 | 65 | 19.572 | 117 | 0.203 | 169 | 0.356 |
| 14 | 0.38 | 66 | 119.66 | 118 | 0.142 | 170 | 0.14 |
| 15 | 0.939 | 67 | 40.917 | 119 | 0.089 | 171 | 0.201 |
| 16 | 31.135 | 68 | 56.518 | 120 | 0.089 | 172 | NA |
| 17 | 126.7 | 69 | 157.8 | 121 | 0.758 | 173 | 0.056 |
| 18 | 5.222 | 70 | 30.524 | 122 | 0.271 | 174 | NA |
| 19 | 0.193 | 71 | 9.184 | 123 | 0.978 | 175 | 0.205 |
| 20 | 0.242 | 72 | 53.32 | 124 | 0.065 | 176 | NA |
| 21 | 5.997 | 73 | 17.254 | 125 | 94.934 | 177 | 0.593 |
| 22 | 1.349 | 74 | 79.673 | 126 | 0.379 | 178 | 0.348 |
| 23 | 0.692 | 75 | 67.735 | 127 | 0.455 | 179 | 0.267 |
| 24 | 100 | 76 | N/A | 128 | 0.446 | 180 | 5.038 |
| 25 | 2.846 | 77 | 70.28 | 129 | 0.189 | 181 | 4.338 |
| 26 | 1.045 | 78 | 120.14 | 130 | 0.341 | 182 | 0.277 |
| 27 | 0.822 | 79 | 33.119 | 131 | 1.565 | 183 | 0.106 |
| 28 | 94.932 | 80 | 67.67 | 132 | 0.193 | 184 | NA |
| 29 | 0.817 | 81 | 109.2 | 133 | 1.416 | 185 | 0.282 |
| 30 | 1.738 | 82 | 41.979 | 134 | 0.374 | 186 | NA |
| 31 | 8.814 | 83 | 35.508 | 135 | 0.094 | 187 | 0.41 |
| 32 | 1.776 | 84 | 64.049 | 136 | 0.337 | 188 | 0.227 |
| 33 | 2.724 | 85 | 0.53 | 137 | 0.089 | 189 | 0.242 |
| 34 | 0.236 | 86 | 3.338 | 138 | 0.964 | 190 | 0.338 |
| 35 | 1.964 | 87 | 12.823 | 139 | 1.997 | 191 | 0.371 |
| 36 | 24.751 | 88 | 2.419 | 140 | 0.55 | 192 | 0.228 |
| 37 | 1.603 | 89 | 8.468 | 141 | 0.529 | 193 | 0.264 |
| 38 | 20.572 | 90 | 16.036 | 142 | 0.25 | 194 | 0.099 |
| 39 | 0.126 | 91 | 11.016 | 143 | 4.723 | 195 | 0.198 |
| 40 | 0.889 | 92 | 9.192 | 144 | 0.552 | 196 | 0.264 |
| 41 | 0.594 | 93 | 491.4 | 145 | 0.714 | 197 | 0.308 |
| 42 | 1.415 | 94 | N/A | 146 | 0.416 | 198 | 0.081 |
| 43 | 0.633 | 95 | 624.72 | 147 | 2.421 | 199 | 0.19 |
| 44 | 0.29 | 96 | 42.327 | 148 | 0.76 | 200 | 0.083 |
| 45 | 0.964 | 97 | 62.025 | 149 | 0.715 | 201 | 0.63 |
| 46 | 0.25 | 98 | 97.797 | 150 | 0.14 | 202 | 0.144 |
| 47 | 0.58 | 99 | 9.331 | 151 | 0.144 | 203 | 0.36 |
| 48 | 1.23 | 100 | 1.668 | 152 | 0.791 | 204 | 1.34 |
| 49 | 0.83 | 101 | 26.925 | 153 | 0.551 | 205 | 1.27 |

TABLE 2-continued

α4β7 Integrin Cell Capture Assay Results

| Example # | α4β7 EC$_{50}$ (nM) | Example # | α4β7 EC$_{50}$ (nM) | Example # | α4β7 EC$_{50}$ (nM) | Example # | α4β7 EC$_{50}$ (nM) |
|---|---|---|---|---|---|---|---|
| 50 | 43.425 | 102 | 266.93 | 154 | 0.358 | | |
| 51 | 34.049 | 103 | 96.001 | 155 | 0.358 | | |
| 52 | 1.631 | 104 | 88.702 | 156 | 0.84 | | |

What is claimed is:

1. A compound of Formula (I):

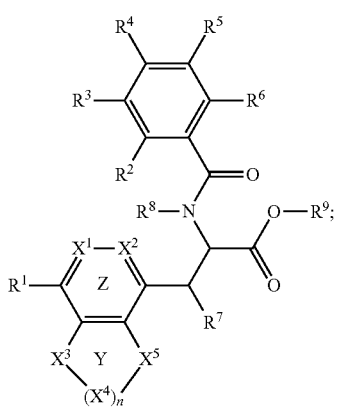

or a pharmaceutically acceptable salt thereof, wherein:
$X^1$ and $X^2$ are each independently selected from $CR^{10}$ and N;
$X^3$ and $X^5$ are each independently selected from $NR^{11}$, O, S, C(O), and $C(R^{10})_2$;
each $X^4$ is independently selected from $NR^{11}$, O, S, C(O), and $C(R^{10})_2$;
$R^1$ is selected from -L-$A^1$, -L-$A^2$, -L-$A^3$, and -L-$A^4$;
L is selected from a bond, —O—, —O—C(O)—*, —NH—, —C(O)—N(H)—*, and —N(H)—C(O)—*; wherein * indicates a point of attachment of L to $A^1$, $A^2$, $A^3$, or $A^4$;
$A^1$ is $C_{6-10}$aryl optionally substituted with one to six $R^a$;
$A^2$ is 5-10 membered heteroaryl containing one to five heteroatoms independently selected from S, N, and O, and optionally one or two C(O); wherein $A^2$ is optionally substituted with one to six $R^a$;
$A^3$ is 5-10 membered cycloalkyl or 5-14 membered heterocyclyl; wherein $A^3$ is optionally substituted with one to six $R^a$; and
$A^4$ is —$NR^{a1}R^{a2}$;
wherein each $R^a$ is independently selected from halo, cyano, hydroxyl, —$NR^{a1}R^{a2}$, $C_{1-6}$alkyl, $C_{2-6}$alkenyl, $C_{2-6}$alkynyl, $C_{1-6}$alkoxyl, $C_{1-6}$haloalkyl, $C_{1-6}$haloalkoxyl, —S(O)$_m$—$C_{1-6}$alkyl, $C_{3-8}$cycloalkyl, 3-6 membered heterocyclyl, $C_{6-10}$aryl, 5-6 membered heteroaryl, —O-(3-6 membered heterocyclyl), —O—$C_{1-4}$alkylene-$C_{3-8}$cycloalkyl, —O-phenyl, and —O—$C_{3-8}$cycloalkyl;
each $C_{1-6}$alkyl, $C_{2-6}$alkenyl, $C_{2-6}$alkynyl, $C_{1-6}$alkoxyl, $C_{1-6}$haloalkyl, $C_{1-6}$haloalkoxyl, and —S(O)$_m$—$C_{1-6}$-alkyl of $R^a$ are optionally substituted with one to three $R^{a3}$; wherein each $R^a3$ is independently selected from hydroxyl, cyano,
—$NR^{a1}R^{a2}$, $C_{1-6}$ alkoxyl, $C_{3-8}$cycloalkyl, phenyl, and 3-6 membered heterocyclyl; wherein each $C_{3-8}$cycloalkyl, phenyl, and 3-6 membered heterocyclyl of $R^{a3}$ is independently optionally substituted with one to three $R^{a4}$; wherein each $R^{a4}$ is independently selected from halo, cyano, hydroxyl, —$NR^{a1}R^{a2}$, $C_{1-6}$alkyl, $C_{1-6}$haloalkyl, $C_{1-6}$alkoxyl, $C_{1-6}$haloalkoxyl, $C_{3-8}$cycloalkyl, and 3-6 membered heterocyclyl; and
each $C_{3-8}$cycloalkyl, 3-6 membered heterocyclyl, $C_{6-10}$aryl, 5-6 membered heteroaryl, —O-(3-6 membered heterocyclyl), —O—$C_{1-4}$alkylene-$C_{3-8}$cycloalkyl, —O-phenyl, and —O—$C_{3-8}$cycloalkyl of $R^a$ is independently optionally substituted with one to three groups independently selected from halo, cyano, hydroxyl, —$NR^{a1}R^{a2}$, $C_{1-6}$ alkyl, $C_{1-6}$haloalkyl, $C_{1-6}$alkoxyl, and $C_{1-6}$haloalkoxyl;
each $R^2$, $R^3$, $R^4$, $R^5$, and $R^6$ is independently selected from H, halo, cyano, hydroxyl, $C_{1-6}$alkyl, $C_{2-6}$alkenyl, $C_{2-6}$alkynyl, $C_{1-6}$alkoxyl, $C_{1-8}$haloalkyl, $C_{1-8}$haloalkoxyl, —$NR^{b1}R^{b2}$, —$R^{b3}S(O)_mR^{b4}$, —$S(O)_mR^{b4}$, —$NR^{b1}S(O)_vR^{b4}$, —$COOR^{b1}$, —$CONR^{b1}R^{b2}$, —$NR^{b1}COOR^{b2}$, —$NR^{b1}COR^{b4}$, —$R^{b3}NR^{b1}R^{b2}$, —$S(O)_vNR^{b1}R^{b2}$, $C_{3-12}$cycloalkyl, $C_{6-10}$aryl, 5-6 membered heteroaryl, and 3-12 membered heterocyclyl;
each $C_{2-6}$alkyl, $C_{2-6}$alkenyl, $C_{2-6}$alkynyl, $C_{1-6}$alkoxyl, $C_{1-8}$haloalkyl, and $C_{1-8}$haloalkoxyl of $R^2$, $R^3$, $R^4$, $R^5$, and $R^6$ is independently optionally substituted with one to two $R^c$; wherein each $R^c$ is independently selected from azido, oxo, cyano, halo, hydroxyl, —$NR^{a1}R^{a2}$, $C_{1-4}$ alkoxyl, $C_{3-8}$cycloalkyl, $C_{6-10}$aryl, 5-6 membered heteroaryl, and 4-6 membered heterocyclyl; wherein each $C_{3-8}$cycloalkyl, $C_{6-10}$aryl, 5-6 membered heteroaryl, and 4-6 membered heterocyclyl of $R^c$ is independently optionally substituted with one to three groups independently selected from halo, hydroxyl, cyano, —$NR^{a1}R^{a2}$, $C_{1-4}$alkyl, $C_{1-6}$haloalkyl, $C_{1-4}$alkoxyl, and $C_{3-6}$cycloalkyl;
each $C_{6-10}$aryl and 5-6 membered heteroaryl of $R^2$, $R^3$, $R^4$, $R^5$, and $R^6$ is independently optionally substituted with one to five $R^b$; and
each $C_{3-12}$cycloalkyl and 3-12 membered heterocyclyl of $R^2$, $R^3$, $R^4$, $R^5$, and $R^6$ is independently optionally substituted with one to six groups independently selected from =$CR^{b1}R^{b2}$, and $R^b$;
wherein each $R^b$ is independently selected from azido, cyano, halo, hydroxyl, —$NR^{a1}R^{a2}$, $C_{1-6}$alkyl, $C_{1-8}$haloalkyl, $C_{1-6}$alkoxyl, $C_{3-6}$cycloalkyl, $C_{3-6}$aryl, 5-6 membered heteroaryl, and 4-6 membered heterocycly; wherein each $C_{3-6}$cycloalkyl, $C_{3-6}$aryl, 5-6 membered heteroaryl, and 4-6 membered heterocyclyl of $R^b$ is independently optionally substituted with one to three groups independently selected from halo, hydroxyl, cyano, —$NR^{a1}R^{a2}$, $C_{1-4}$alkyl, $C_{1-4}$haloalkyl, and $C_{1-4}$alkoxyl;
each $R^{b1}$ and $R^{b2}$ is independently selected from H, $C_{1-8}$alkyl, $C_{1-8}$haloalkyl, $C_{3-8}$cycloalkyl, $C_{6-10}$aryl, 5-6 membered heteroaryl, and 3-8 membered heterocyclyl;
each $C_{1-8}$alkyl and $C_{1-6}$haloalkyl of $R^{b1}$ and $R^{b2}$ is optionally substituted with one to two $R^{b5}$; and
each $C_{3-8}$cycloalkyl, $C_{6-10}$aryl, 5-6 membered heteroaryl, and 3-8 membered heterocyclyl of $R^{b1}$ and $R^{b2}$ is independently optionally substituted with one to three groups independently selected from halo, cyano, hydroxyl, —NR$^{a1}$R$^{a2}$, C$_{1-8}$alkyl, C$_{1-8}$haloalkyl, C$_{1-6}$alkoxyl, C$_{3-6}$cycloalkyl, C$_{6-10}$aryl, 5-6 membered heteroaryl, and 4-6 membered heterocyclyl;

R$^{b3}$ is C$_{1-4}$alkylene;

R$^{b4}$ is selected from C$_{1-4}$alkyl, C$_{1-4}$haloalkyl, C$_{3-6}$cycloalkyl, C$_{6-10}$aryl, 5-6 membered heteroaryl, and 4-6 membered heterocyclyl; wherein each C$_{1-4}$alkyl, C$_{1-4}$haloalkyl, C$_{3-8}$cycloalkyl, C$_{6-10}$aryl, 5-6 membered heteroaryl, and the 4-6 membered heterocyclyl of R$^{b4}$ is optionally substituted with one to three R$^{b6}$;

each R$^{b5}$ is independently selected from cyano, hydroxyl, C$_{1-4}$alkoxyl, C$_{3-8}$cycloalkyl, C$_{6-10}$aryl, 5-6 membered heteroaryl, and 4-6 membered heterocyclyl; wherein each C$_{3-8}$cycloalkyl, C$_{6-10}$aryl, 5-6 membered heteroaryl, and 4-6 membered heterocyclyl of R$^{b5}$ is optionally substituted with one to three groups independently selected from halo, cyano, hydroxyl, —NR$^{a1}$R$^{a2}$, C$_{1-4}$alkyl, C$_{1-4}$haloalkyl, C$_{1-4}$alkoxyl, and phenyl; and each R$^{b6}$ is independently selected from halo, cyano, C$_{1-4}$alkyl, C$_{1-4}$haloalkyl, C$_{1-4}$alkoxyl, C$_{3-6}$cycloalkyl, phenyl, 4-6 membered heterocyclyl, and 5-6 membered heteroaryl; wherein each C$_{3-6}$cycloalkyl, 4-6 membered heterocyclyl, and 5-6 membered heteroaryl of R$^{b6}$ is independently optionally substituted with one to three groups independently selected from halo, cyano, —NR$^{a1}$R$^{a2}$, C$_{1-4}$alkyl, C$_{1-4}$haloalkyl, and C$_{1-4}$alkoxyl; or R$^2$ and R$^3$, R$^3$ and R$^4$, or R$^5$ and R$^6$ together with the atoms to which they are attached may form a C$_{1-6}$aryl, 5-6 membered heteroaryl, C$_{3-6}$cycloalkyl, or 5-6 membered heterocyclyl;

wherein each C$_{6-10}$aryl, 5-6 membered heteroaryl, C$_{3-6}$cycloalkyl, or 5-6 membered heterocyclyl is optionally substituted with one to three groups independently selected from halo, cyano, —NR$^{a1}$R$^{a2}$, C$_{1-6}$alkyl, C$_{1-6}$alkoxyl, C$_{1-6}$haloalkyl, C$_{3-8}$cycloalkyl, 3-6 membered heterocyclyl, C$_{6-10}$-aryl, 5-6 membered heteroaryl, C$_{1-4}$alkylene-C$_{3-8}$cycloalkyl, C$_{1-4}$alkylene-C$_{6-10}$aryl, and C$_{1-4}$alkylene-(5-6 membered heteroaryl);

R$^7$ is selected from H, C$_{1-4}$alkyl, and C$_{1-4}$haloalkyl;

R$^8$ is selected from H, C$_{1-4}$alkyl, and C$_{1-4}$haloalkyl;

R$^9$ is selected from H, C$_{1-6}$alkyl, —C$_{1-4}$alkylene-NR$^{a1}$R$^{a2}$, —C$_{1-4}$alkylene-C(O)NR$^{a1}$R$^{a2}$, —C$_{1-4}$alkylene-O—C(O)—C$_{1-4}$alkyl, —C$_{1-4}$alkylene-O—C(O)—O—C$_{1-4}$alkyl, —C$_{1-4}$alkylene-O—C(O)—C$_{1-4}$alkylene-NR$^{a1}$R$^{a2}$, —C$_{1-4}$alkylene-O—C$_{1-4}$alkyl, C$_{3-8}$cycloalkyl, —C$_{1-4}$alkylene-C$_{3-8}$cycloalkyl, 4-6 membered heterocyclyl, and —C$_{1-4}$alkylene-(4-6 membered heterocyclyl);

wherein each C$_{3-8}$cycloalkyl, —C$_{1-4}$alkylene-C$_{3-8}$cycloalkyl, 4-6 membered heterocyclyl and —C$_{1-4}$alkylene-(4-6 membered heterocyclyl) of R$^9$ is optionally substituted with one to three groups independently selected from halo, C$_{1-4}$alkyl, C$_{1-4}$alkoxyl, and C$_{1-4}$haloalkyl; or R$^9$ together with the N that attaches to R$^8$ forms a 5 membered heterocyclyl; wherein the 5 membered heterocyclyl is optionally substituted with one to two groups independently selected from halo, C$_{1-6}$alkyl, C$_{1-6}$alkoxyl, C$_{1-6}$haloalkyl, and C$_{6-10}$aryl; wherein C$_{6-10}$aryl is optionally substituted with one to three groups independently selected from halo, C$_{1-6}$alkyl, C$_{1-6}$alkoxyl, and C$_{1-6}$haloalkyl;

each R$^{10}$ is independently selected from H, halo, cyano, hydroxyl, —C(O)R$^{b1}$, —NR$^{a1}$R$^{a2}$, C$_{1-4}$ alkyl, C$_{1-4}$alkoxyl, C$_{1-4}$haloalkyl, C$_{1-4}$haloalkoxyl, C$_{3-10}$cycloalkyl, 3-8 membered heterocyclyl, C$_{6-10}$aryl, and 5-6 membered heteroaryl; wherein each C$_{1-4}$alkyl, C$_{1-4}$alkoxyl, C$_{1-4}$haloalkyl, C$_{1-4}$haloalkoxyl, C$_{3-10}$cycloalkyl, 3-8-membered heterocyclyl, C$_{6-10}$aryl, and 5-6 membered heteroaryl is independently optionally substituted with one to three groups independently selected from halo, hydroxyl, cyano, —NR$^{a1}$R$^{a2}$, C$_{1-4}$alkyl, C$_{1-4}$haloalkyl, C$_{1-4}$alkoxyl, and C$_{3-6}$cycloalkyl;

or two R$^{10}$ either attached to the same or adjacent atoms form C$_{3-12}$cycloalkyl or 3-10 membered heterocyclyl; wherein each C$_{3-12}$cycloalkyl and 3-10 membered heterocyclyl is optionally substituted with one to three groups independently selected from H, halo, C$_{1-4}$alkyl, C$_{1-4}$alkoxyl, C$_{1-4}$haloalkyl, and C$_{1-4}$haloalkoxyl;

each R$^{11}$ is independently selected from H, C$_{1-4}$alkyl, and C$_{1-4}$haloalkyl; wherein each C$_{1-4}$alkyl, —C(O)R$^{b1}$, and C$_{1-4}$haloalkyl of R$^{11}$ is independently optionally substituted with one to three groups independently selected from halo, hydroxyl, cyano, —NR$^{a1}$R$^{a2}$, C$_{1-4}$alkyl, C$_{1-4}$haloalkyl, C$_{1-4}$alkoxyl, and C$_{3-6}$cycloalkyl;

or R$^{10}$ and R$^{11}$, or two R$^{11}$ together with the atoms to which they are attached to form 3-12 membered heterocyclyl; wherein 3-12 membered heterocyclyl is optionally substituted with one to three groups independently selected from H, halo, C$_{1-4}$alkyl, C$_{1-4}$alkoxyl, C$_{1-4}$haloalkyl, and C$_{1-4}$haloalkoxyl;

each R$^{a1}$ and R$^{a2}$ is independently selected from H, C$_{1-6}$alkyl, and C$_{1-6}$haloalkyl;

n is selected from 1, 2, and 3;

m is selected from 0, 1, and 2; and v is selected from 1 and 2.

2. The compound of claim 1, wherein the ring formed by Y and Z is selected from:

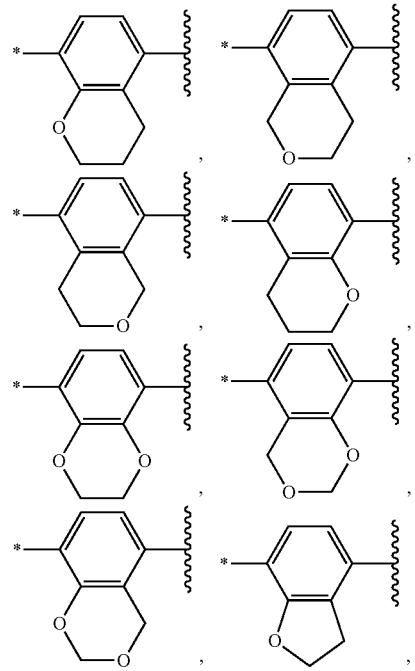

-continued

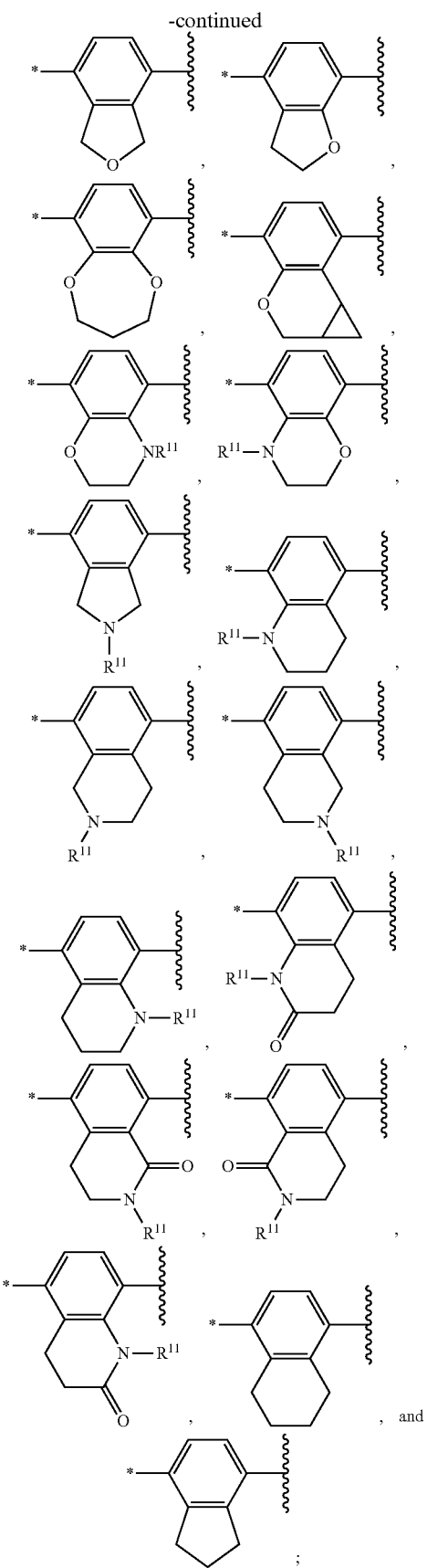

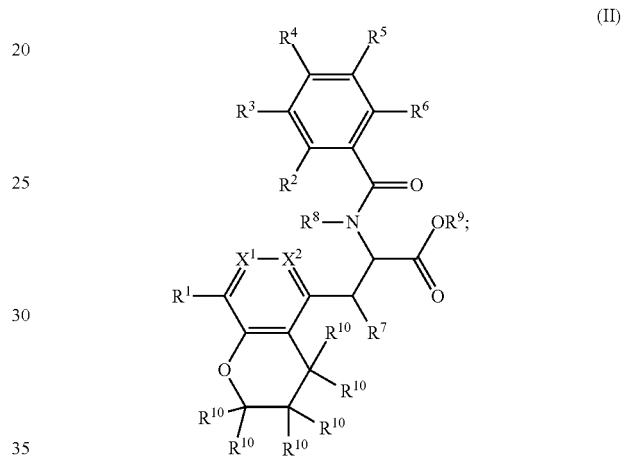

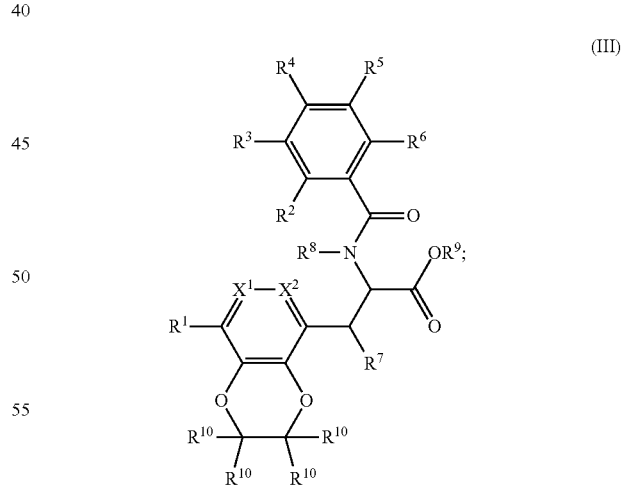

wherein * indicates a point of attachment to $R^1$;
wherein each group is optionally substituted with 1 to 7 $R^{10}$; and
wherein each $R^{10}$ is independently selected from halo, cyano, hydroxyl, $C_{1-4}$alkyl, $C_{1-4}$alkoxyl, $C_{1-4}$haloalkyl, $C_{1-4}$haloalkoxyl, $C_{3-10}$cycloalkyl, 3-8 membered heterocyclyl, $C_{6-10}$aryl, 5-6 membered heteroaryl, and —$NR^{a1}R^{a2}$; wherein each $C_{1-4}$alkyl, $C_{1-4}$alkoxyl, $C_{1-4}$haloalkyl, $C_{1-4}$haloalkoxyl, $C_{3-10}$cycloalkyl, 3-8 membered heterocyclyl, $C_{6-10}$aryl, and 5-6 membered heteroaryl of $R^{10}$ is independently optionally substituted with one to three groups independently selected from halo, hydroxyl, cyano, —$NR^{a1}R^{a2}$, $C_{1-4}$alkyl, $C_{1-4}$haloalkyl, $C_{1-4}$alkoxyl, and $C_{3-6}$cycloalkyl.

3. The compound of claim 1, of Formula (II)

or a pharmaceutically acceptable salt thereof.

4. The compound of claim 1, of Formula (III)

or a pharmaceutically acceptable salt thereof.

5. The compound of claim 1, or a pharmaceutically acceptable salt thereof, wherein $R^1$ is selected from phenyl, naphthyl, pyridinyl, pyridazinyl, pyrazinyl, pyrimidinyl, quinolinyl, isoquinolinyl, isoxazolyl, triazolyl, pyrazolyl, benzothiazolyl, pyridinonyl, quinolinonyl, isoquinolinonyl, quinazolindionyl, pyrazinonyl, pyrimidinonyl, pyrimidinedionyl, pyridazinonyl, quinazolinonyl, benzofuranyl, tetrahydrocyclopenta[b]pyridinonyl, naphthyridinonyl, chromanyl, isochromanyl, and chromenonyl, and wherein each $R^1$ is independently optionally substituted with one to four $R^a$.

6. The compound of claim 1, or a pharmaceutically acceptable salt thereof, wherein $R^1$ is selected from:

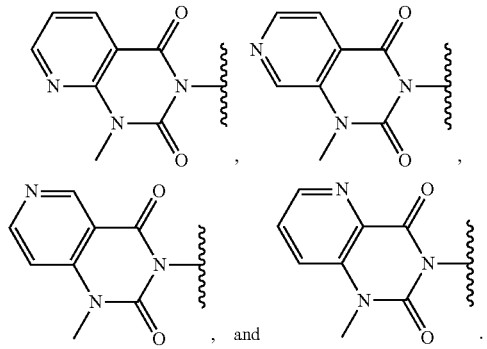

7. The compound of claim 1, or a pharmaceutically acceptable salt thereof, wherein $R^4$ is selected from

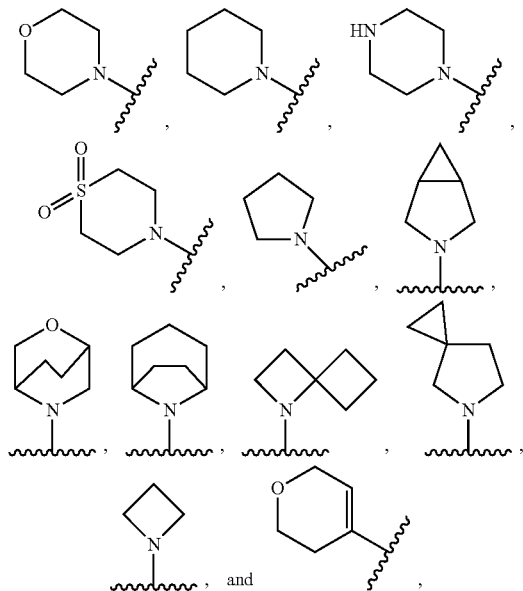

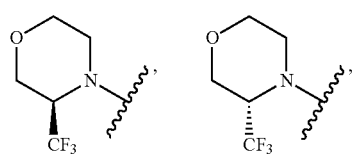

wherein each $R^4$ is optionally substituted with one to two groups independently selected from F, Cl, cyano, hydroxyl, $NH_2$, —$CH_3$, —$CH(CH_3)_2$, —$CH_2F$, —$CHF_2$, —$CF_3$, —$CH_2CH_2F$, —$CH_2CHF_2$, —$CH_2CF_3$, $C_{3-6}$cycloalkyl, and —$CH_2C_{3-6}$cycloalkyl.

8. The compound of claim 1, or a pharmaceutically acceptable salt thereof, wherein $R^4$ is selected from -continued

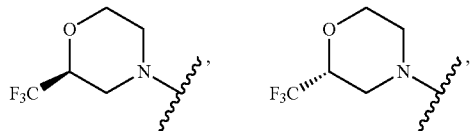

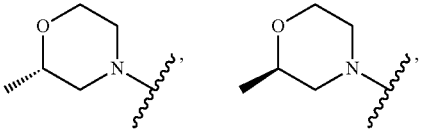

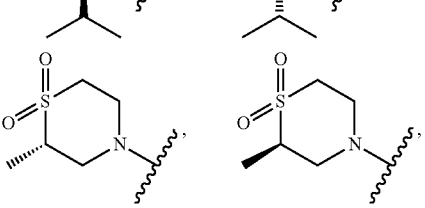

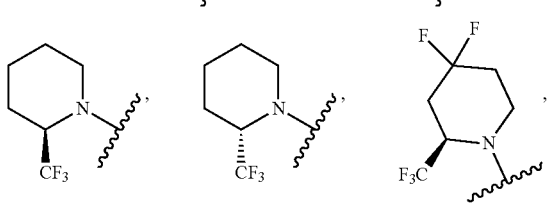

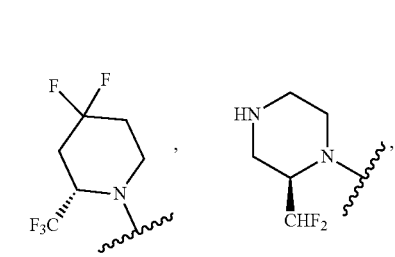

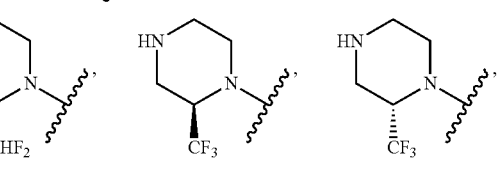

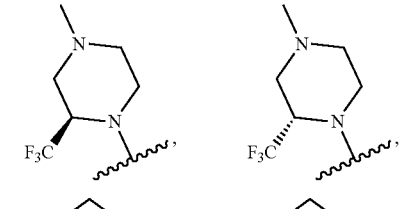

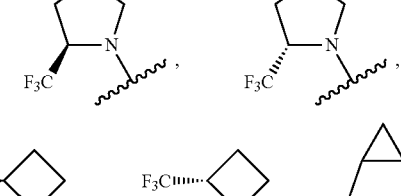

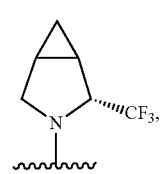

-continued

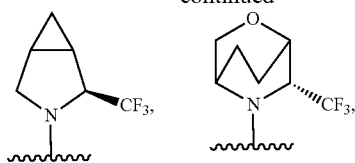

9. The compound of claim 1, or a pharmaceutically acceptable salt thereof, wherein $R^4$ is

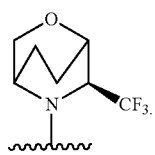

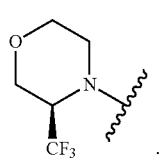

10. The compound of claim 1, or a pharmaceutically acceptable salt thereof, wherein $R^9$ is selected from H, methyl, ethyl, propyl, butyl, —CH$_2$C(O)N(CH$_3$)$_2$, —(CH$_2$)$_2$N(CH$_2$CH$_3$)$_2$, —CH$_2$—O—C(O)CH$_3$, —(CH$_2$)$_2$—O—C(O)CH$_3$, —CH$_2$—O—C(O)C(CH$_3$)$_3$, —(CH$_2$)$_2$—O—C(O)C(CH$_3$)$_3$, —CH$_2$—O—C(O)—O—CH$_3$, —CH$_2$—O—C(O)—O—CH$_2$CH$_3$, —CH$_2$—O—C(O)—O—CH(CH$_3$)$_2$, —CH$_2$—O—C(O)—O—C(CH$_3$)$_3$, —(CH$_2$)$_2$C(O)CH$_3$

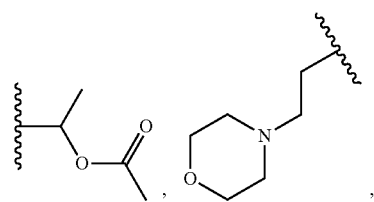

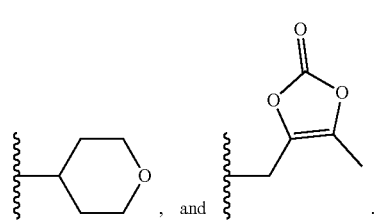

11. The compound of claim 1, or a pharmaceutically acceptable salt thereof, wherein $R^9$ is selected from H, methyl, and ethyl.

12. The compound of claim 1, having the structure of Formula (IIb):

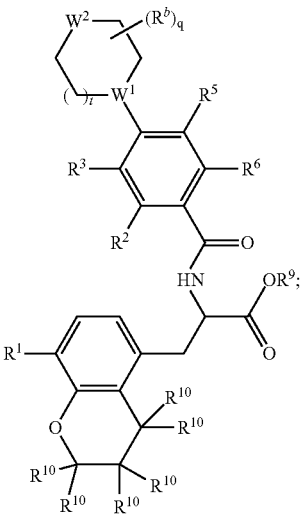

(IIb)

or a pharmaceutically acceptable salt thereof, wherein:
  $W^1$ is selected from CR$^{31}$ and N;
  $W^2$ is selected from CR$^{31}$R$^{31}$, NR$^{32}$, O, and S(O)$_2$;
  each R$^{31}$ is independently selected from H and R$^b$;
  R$^{32}$ is selected from H, C$_{1-4}$alkyl, and C$_{1-4}$haloalkyl;
  q is selected from 0, 1, 2, and 3; and
  t is 0 or 1.

13. The compound of claim 1, having the structure of Formula (IIIa):

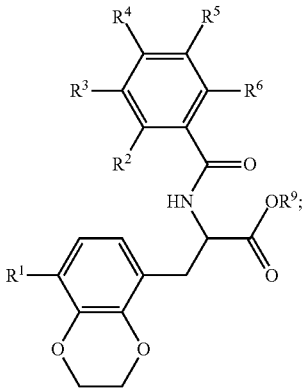

(IIIa)

or a pharmaceutically acceptable salt thereof.

14. A compound or a pharmaceutically acceptable salt thereof, selected from:
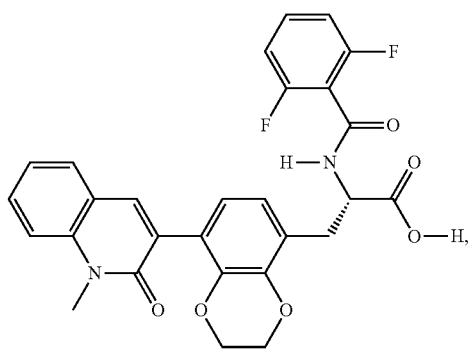
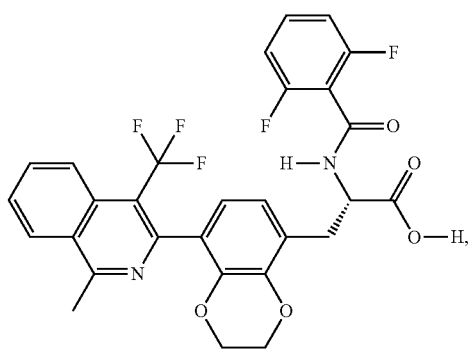
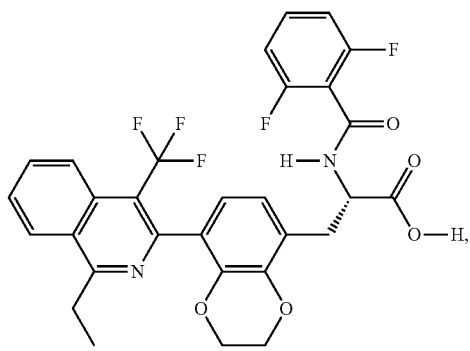
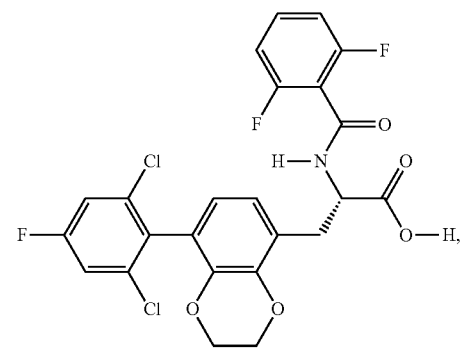
-continued
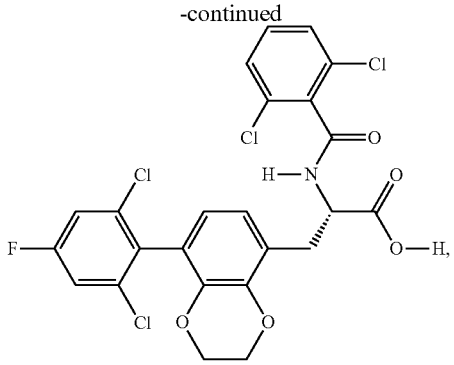
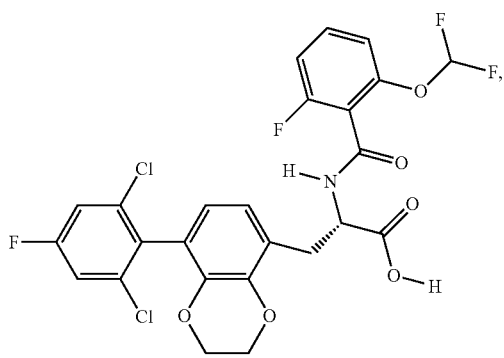
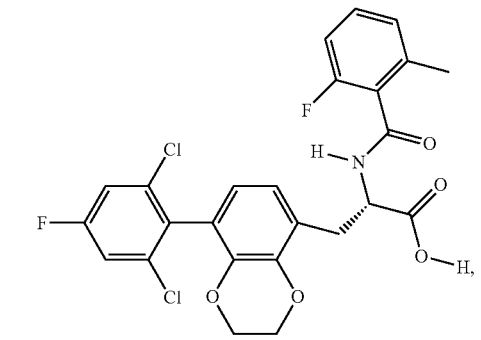
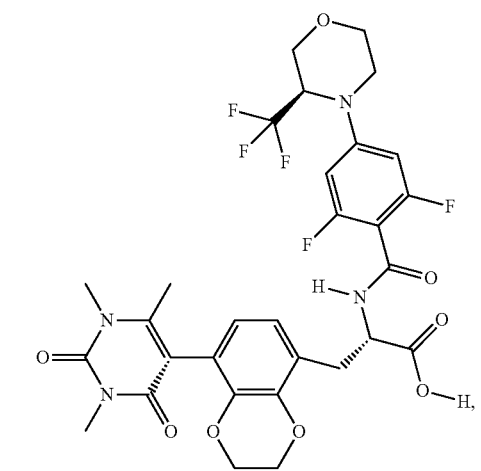

361
-continued
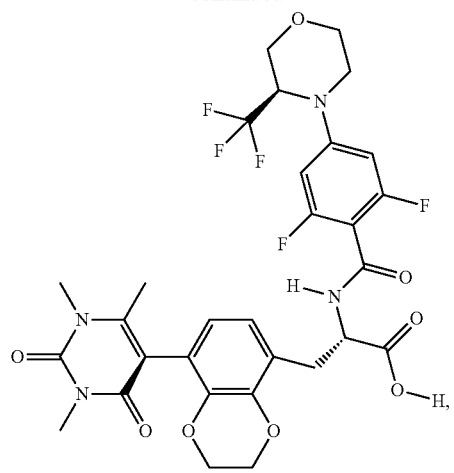
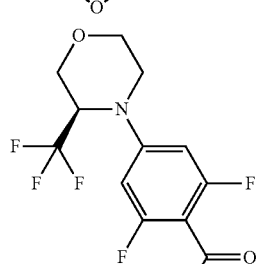
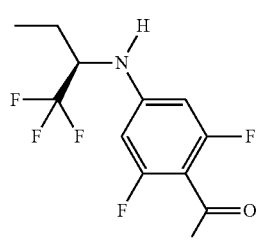
362
-continued
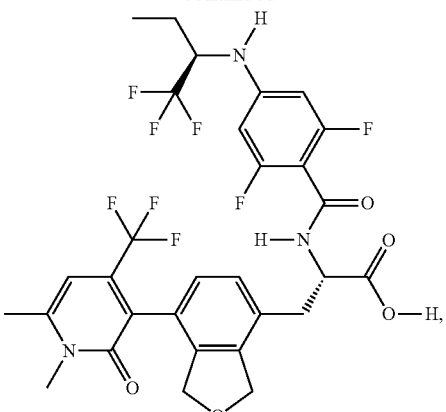
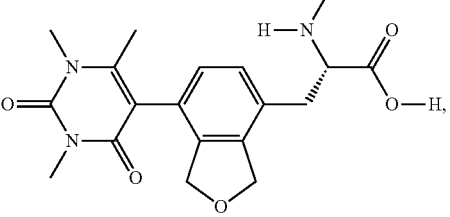
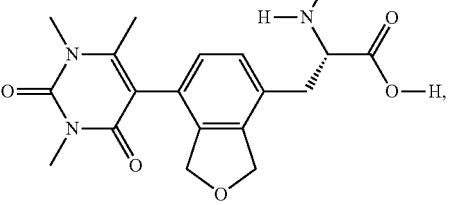
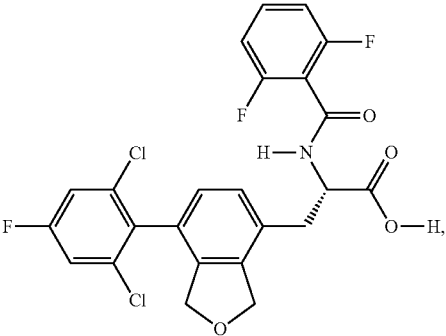

363
-continued
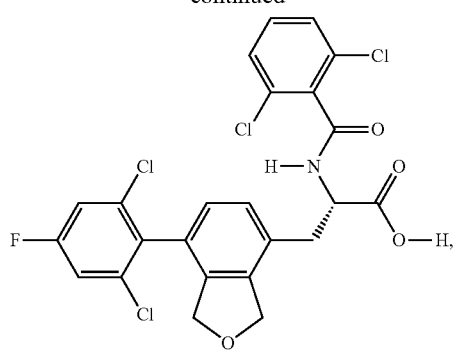
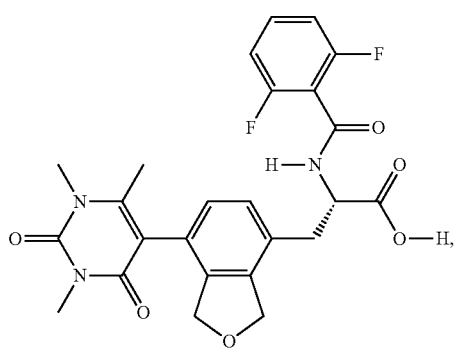
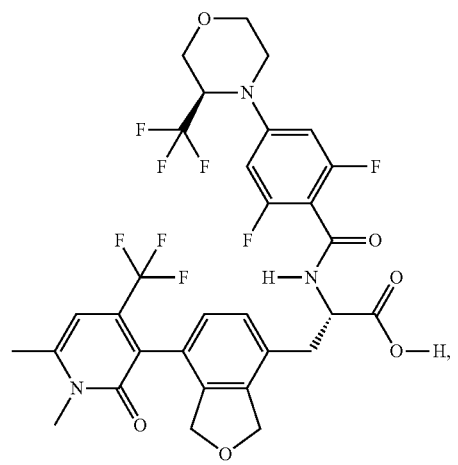
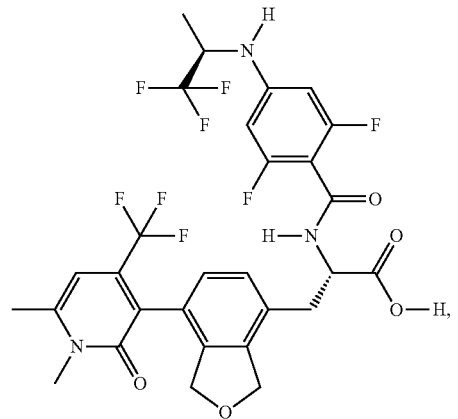
364
-continued
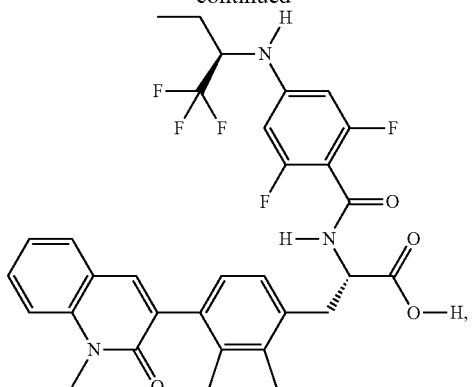
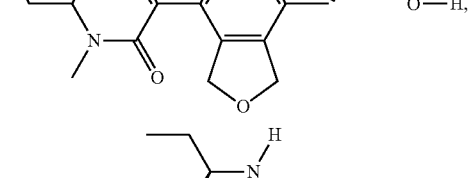
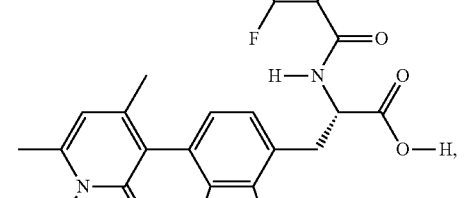
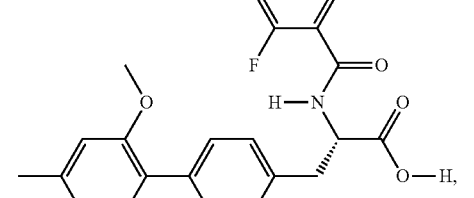
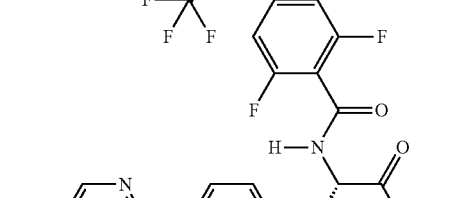

365
-continued
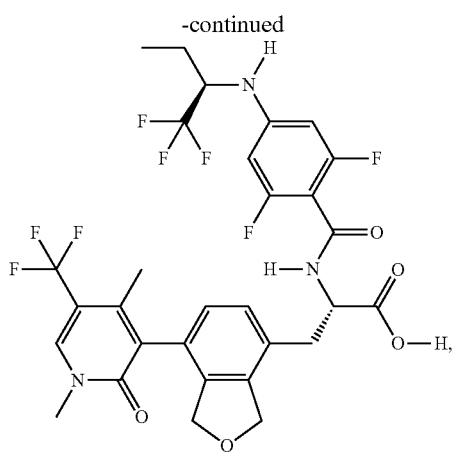
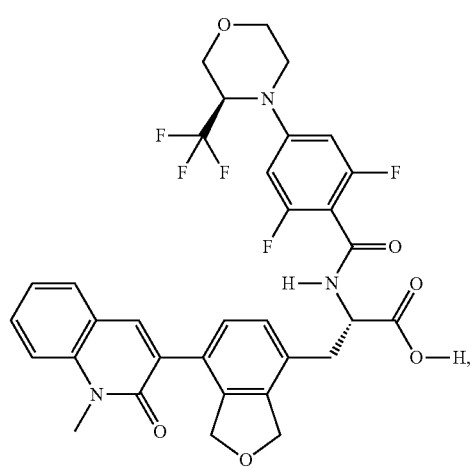
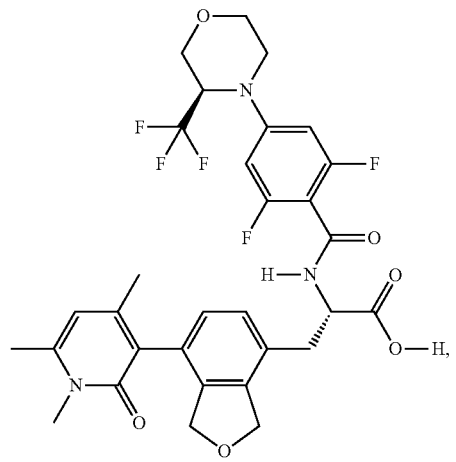
366
-continued
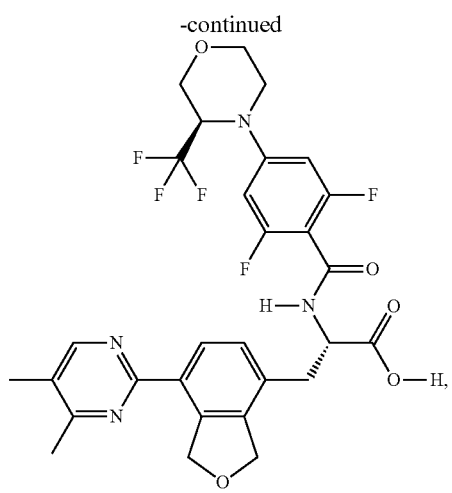
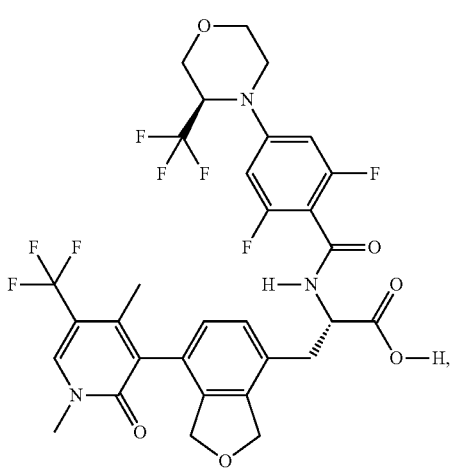
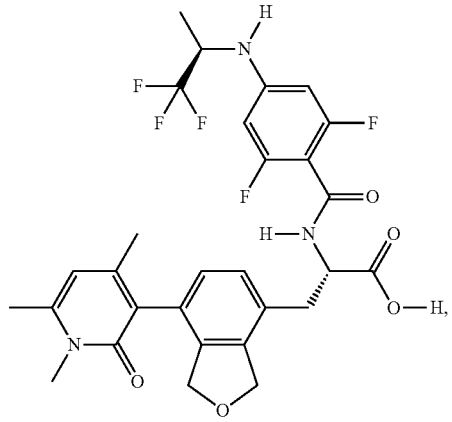

367
-continued
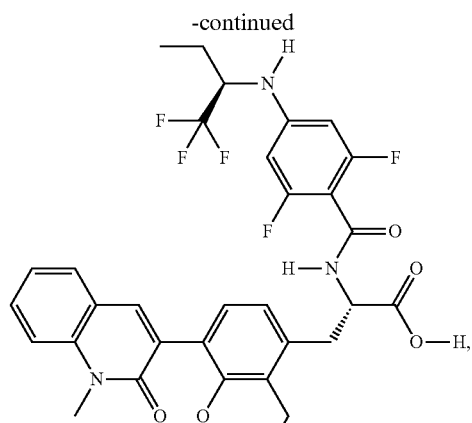
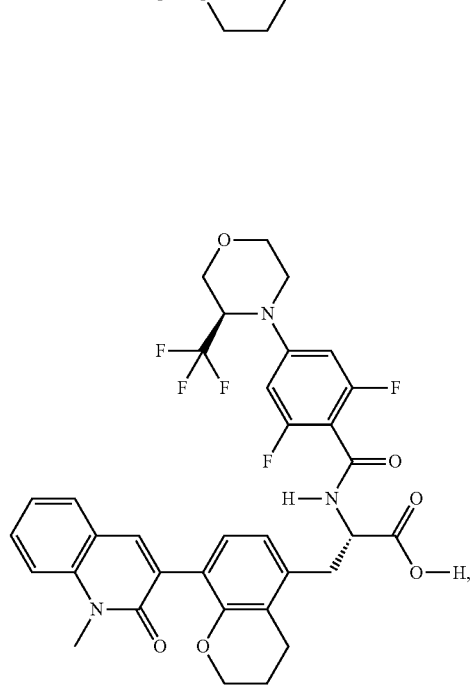
368
-continued
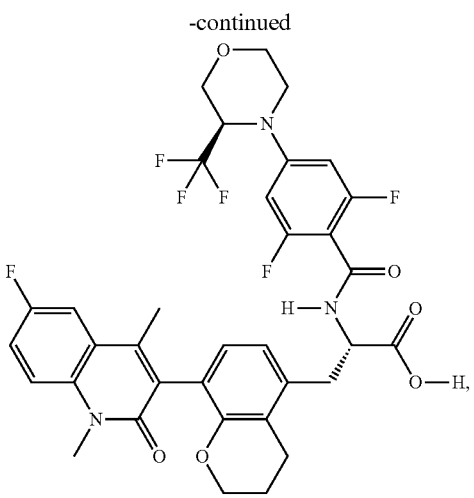
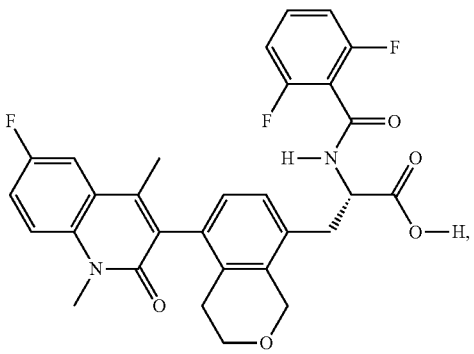
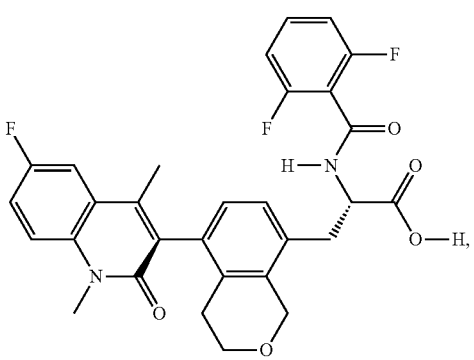
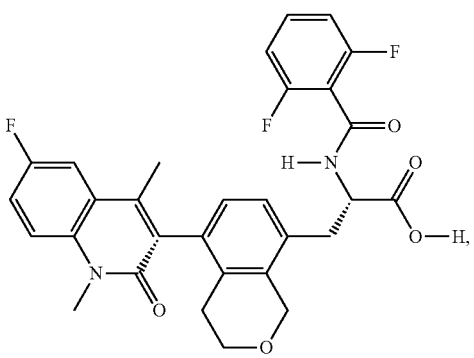

369
-continued
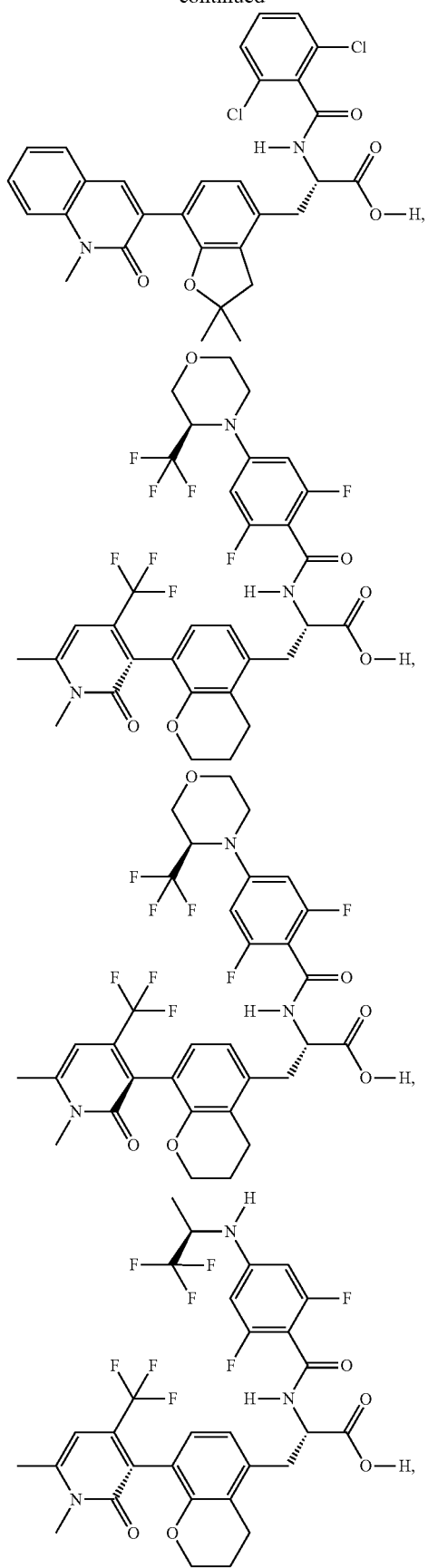
370
-continued
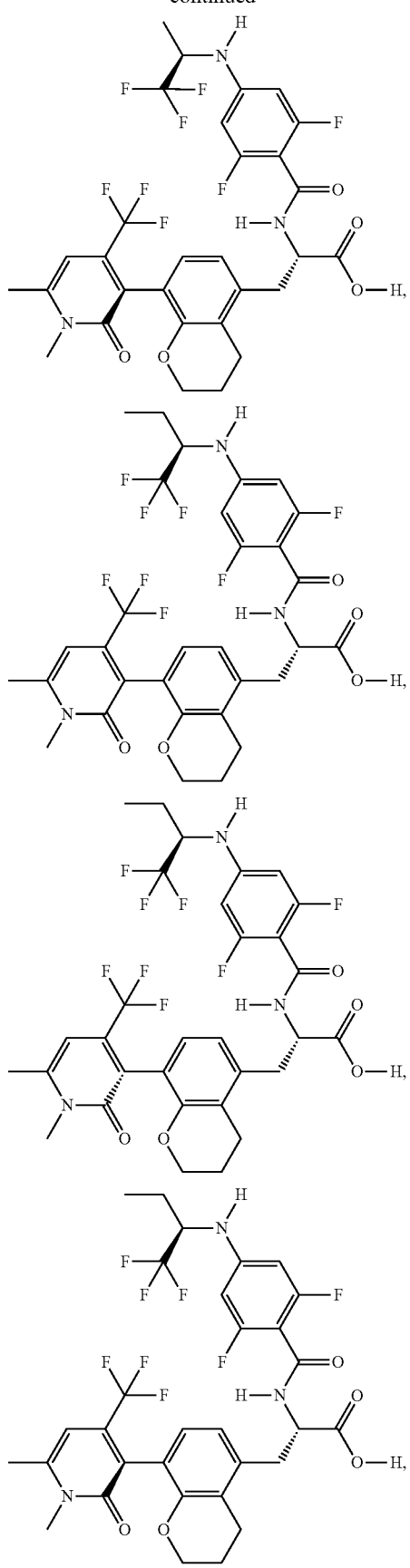

371
-continued
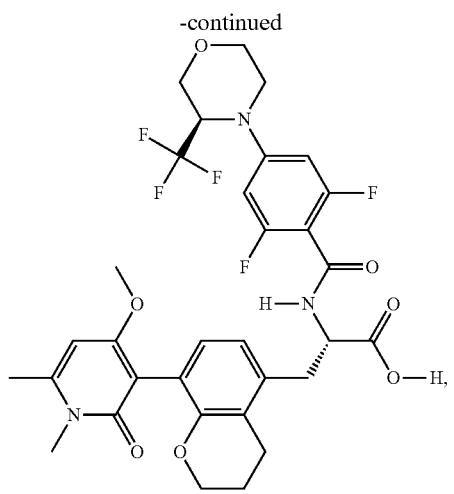
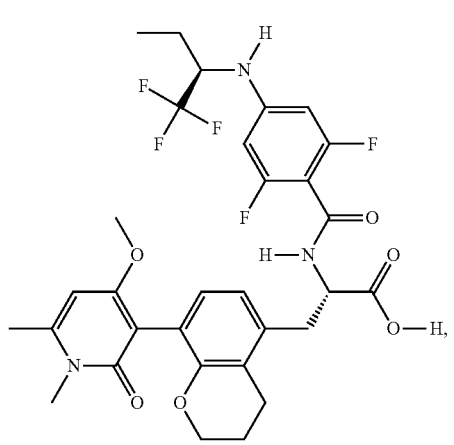
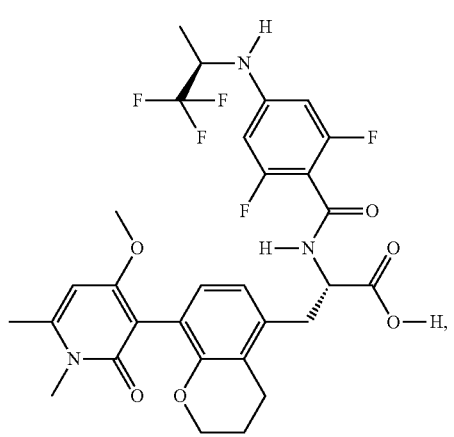
372
-continued
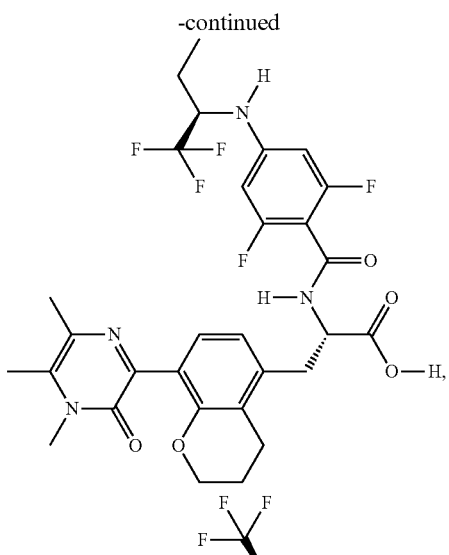
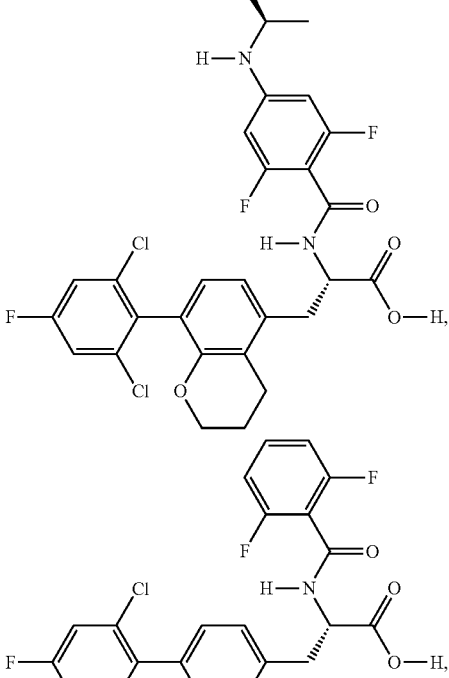
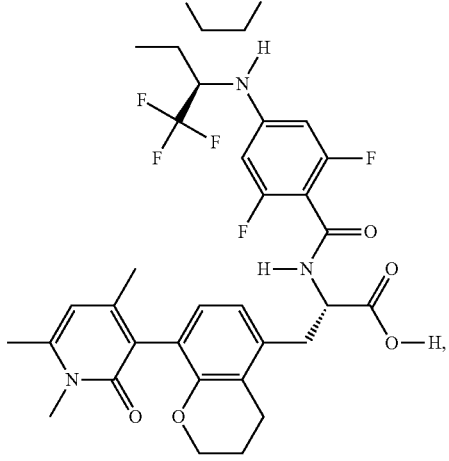

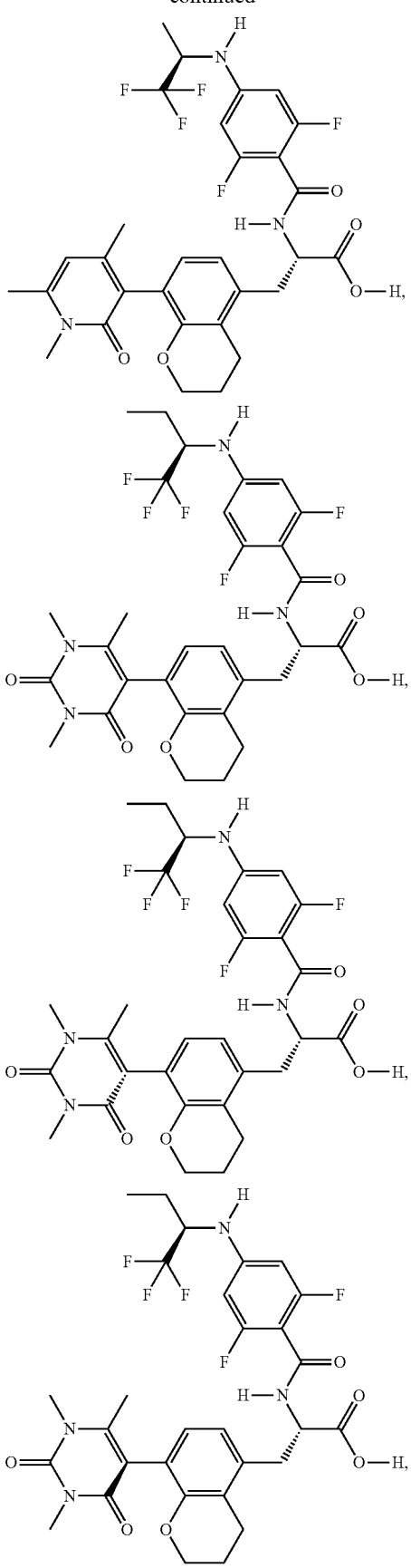
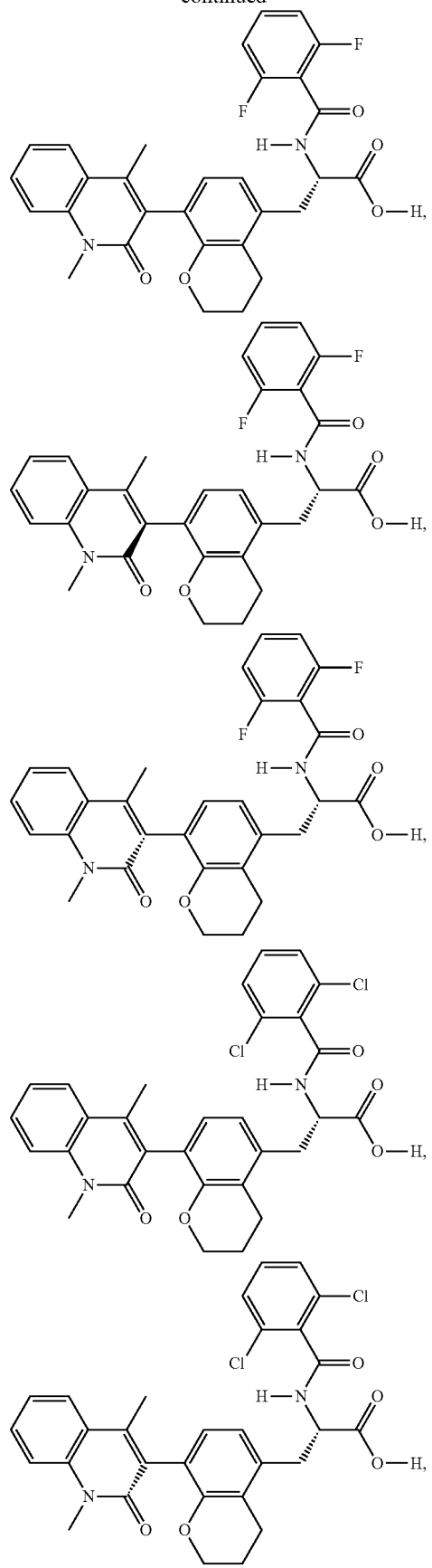

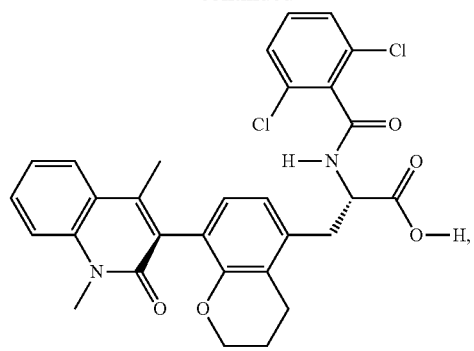
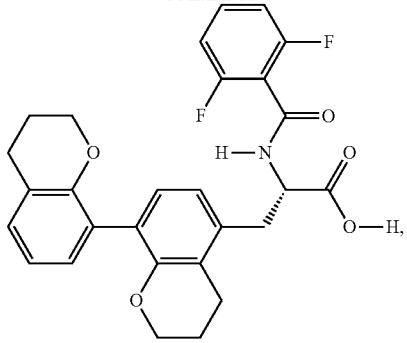
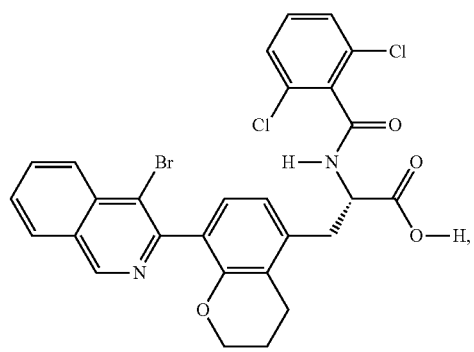
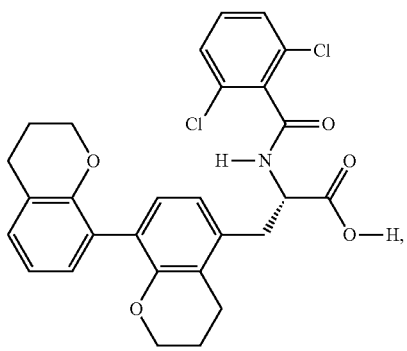
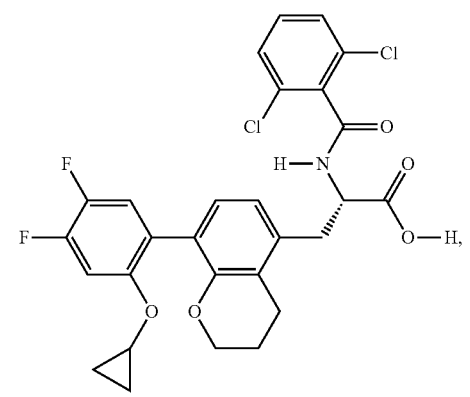
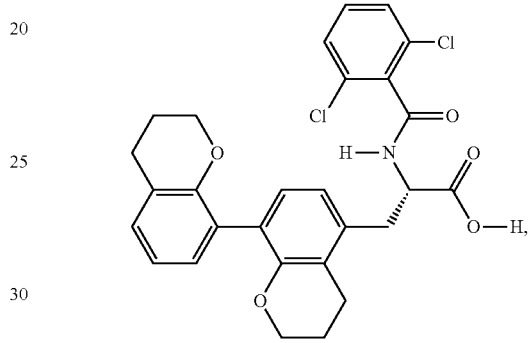
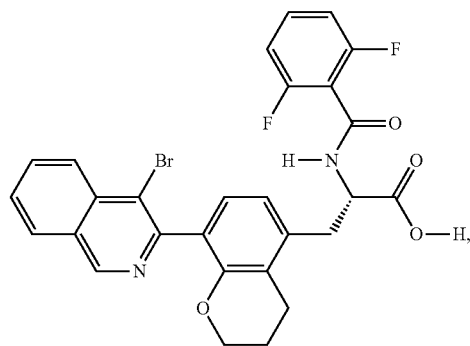
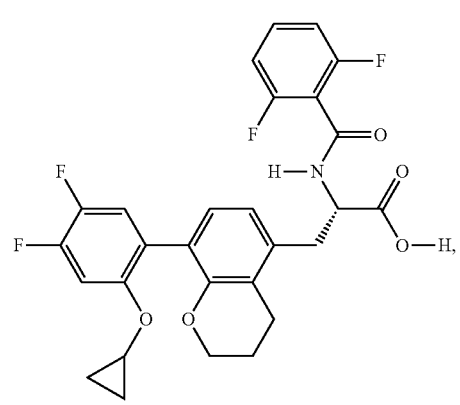
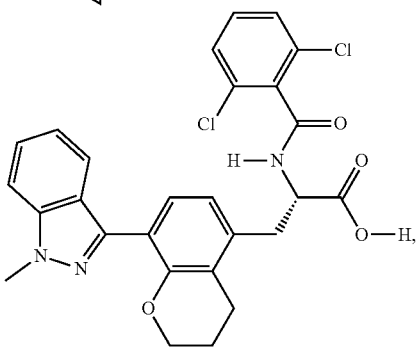

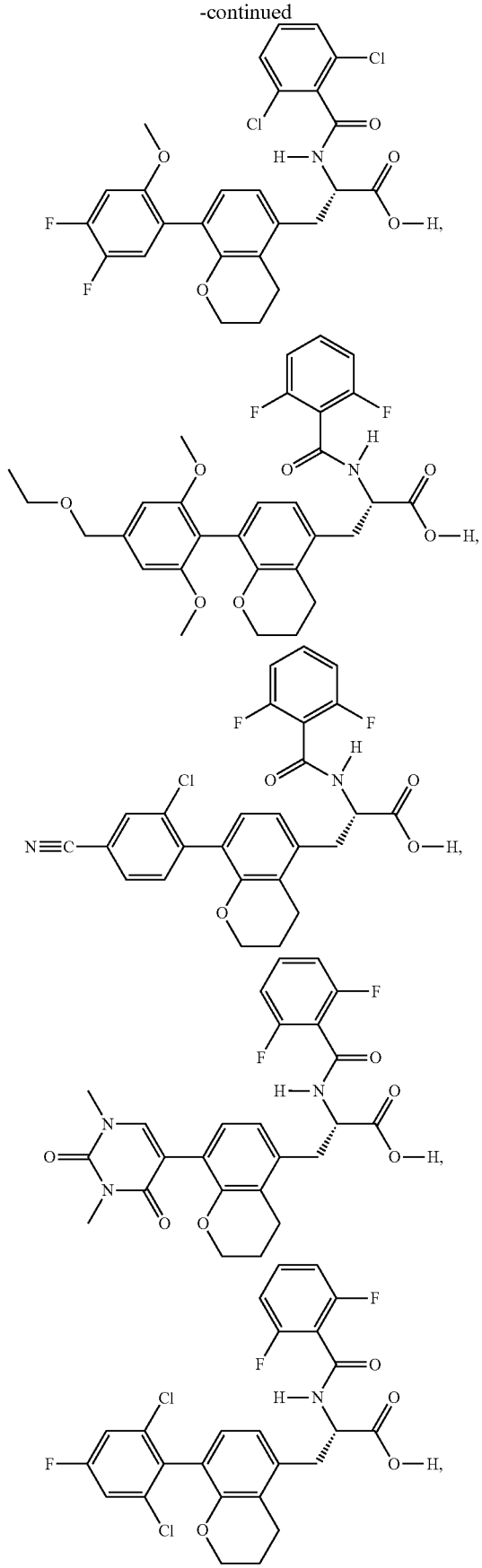
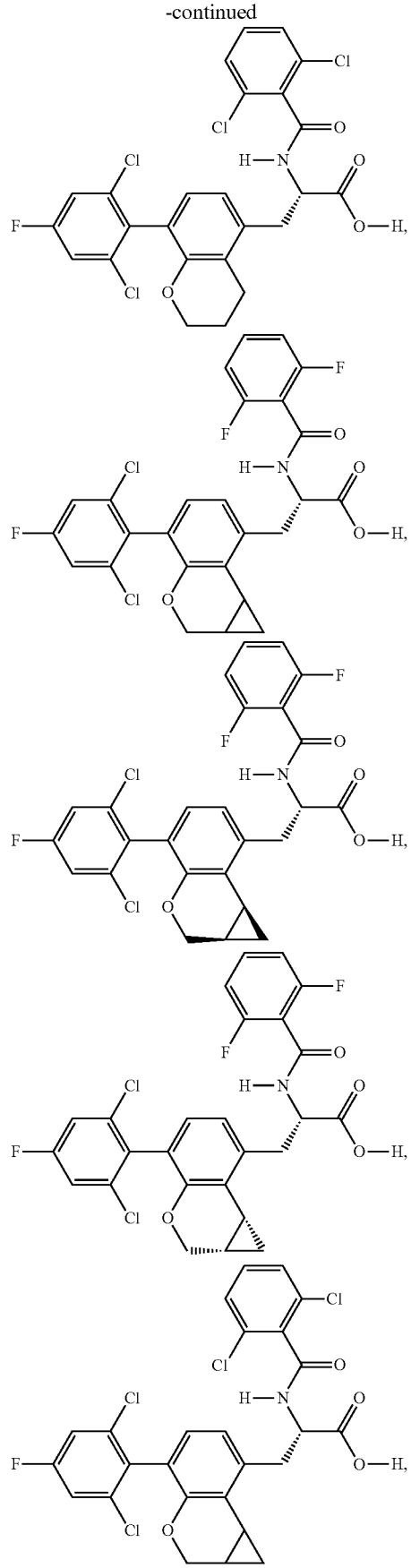

-continued
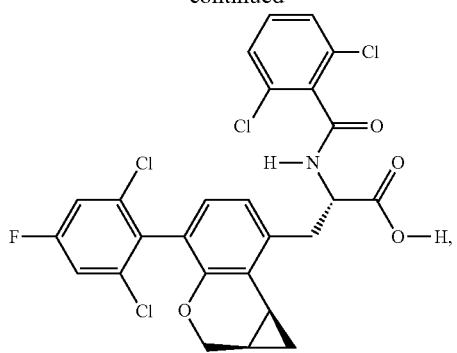
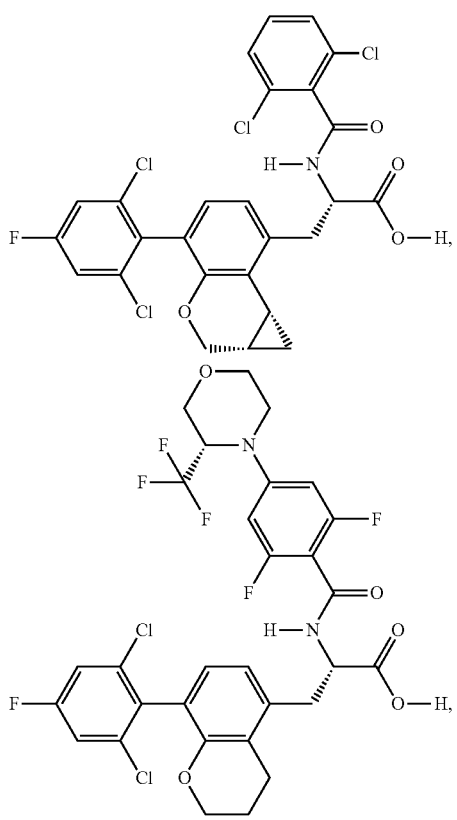
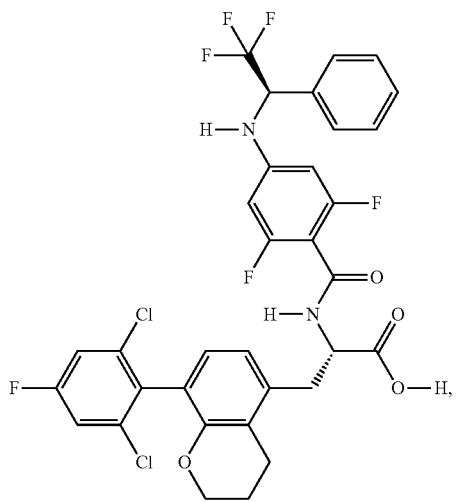
-continued
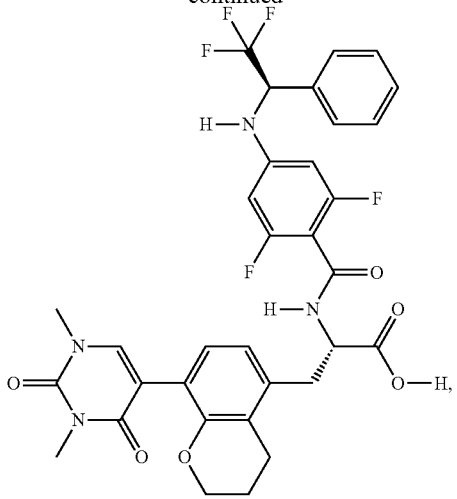
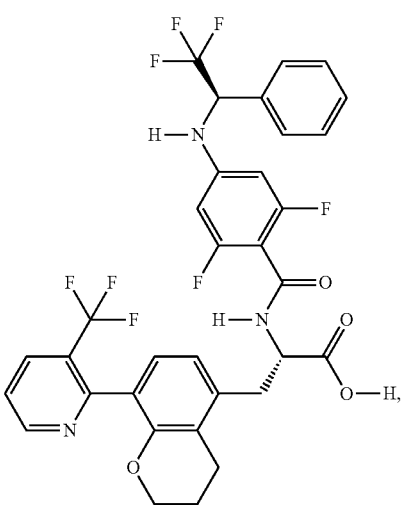
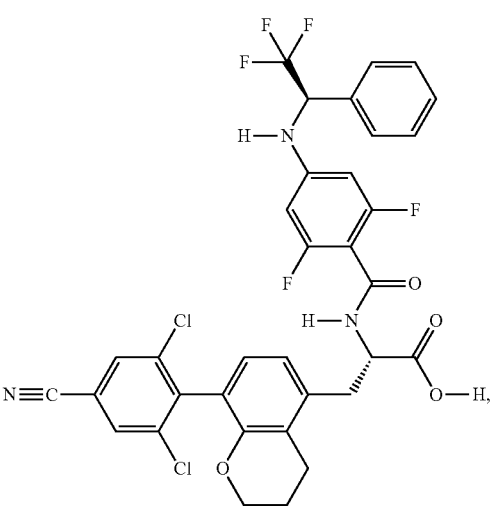

-continued
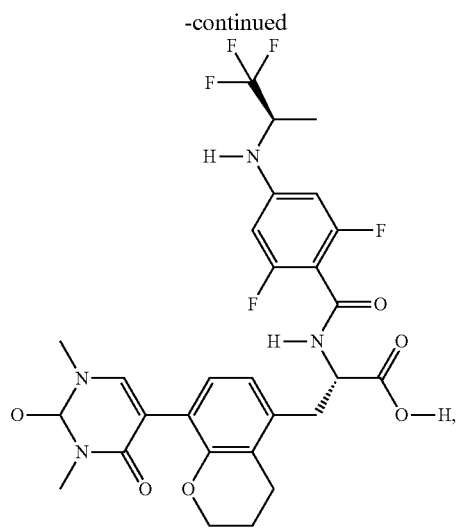
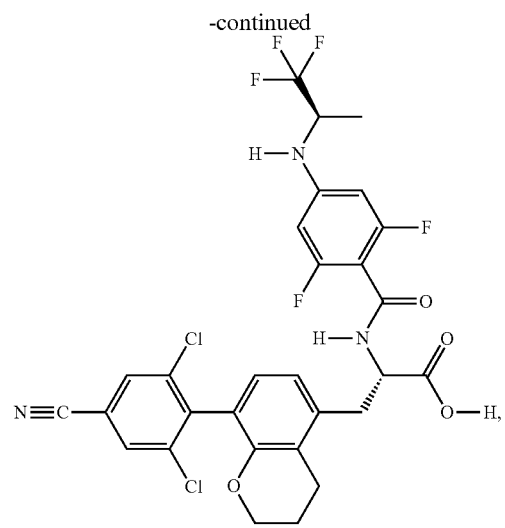
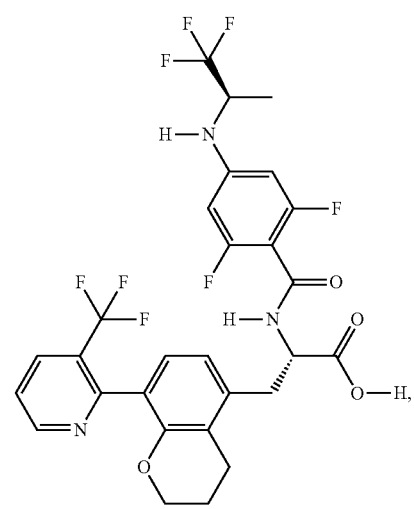
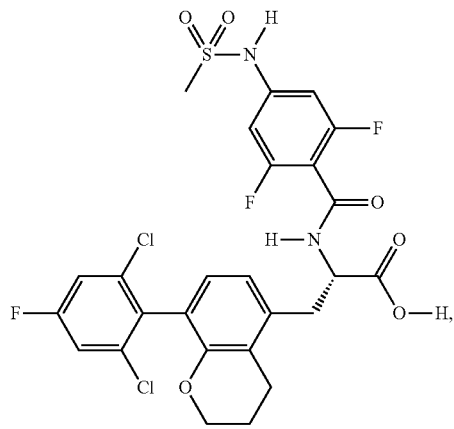
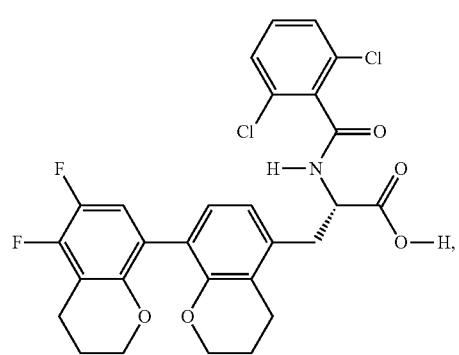
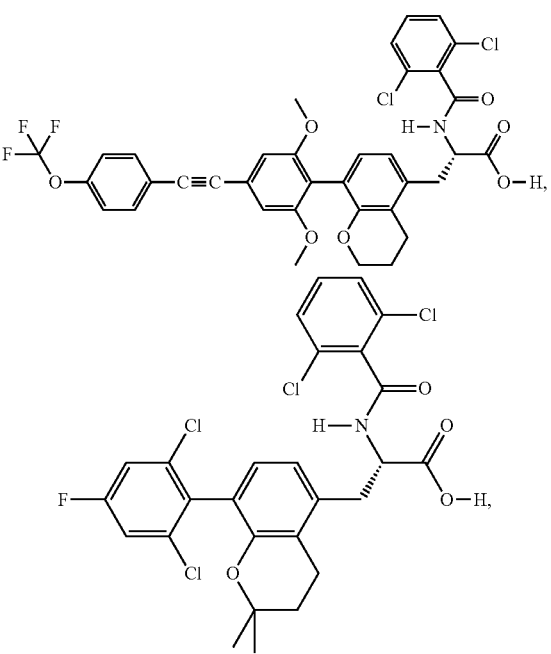

-continued
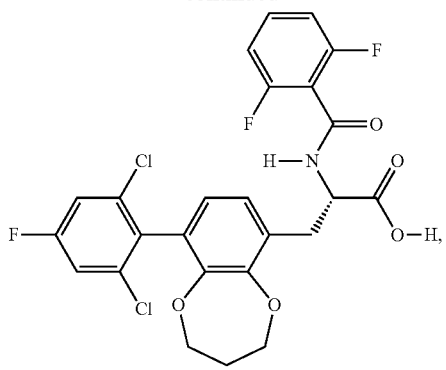
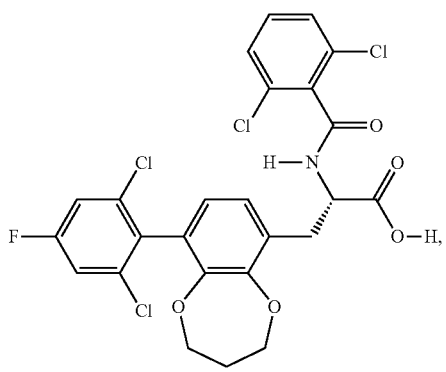
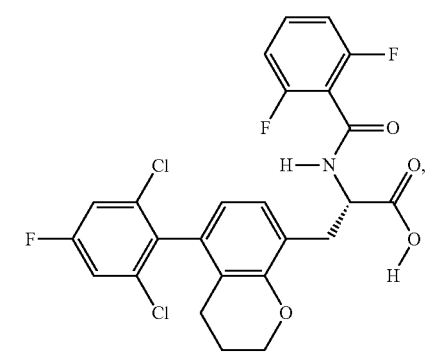
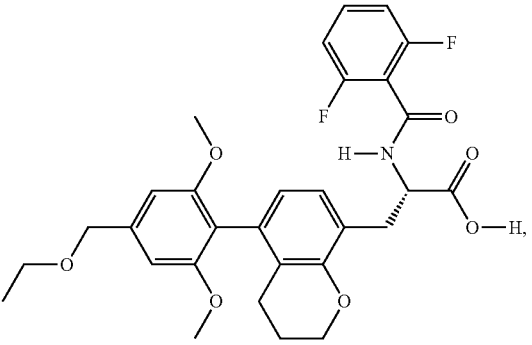
-continued
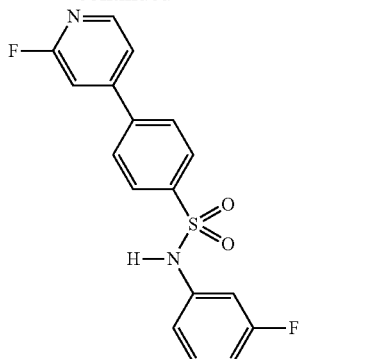
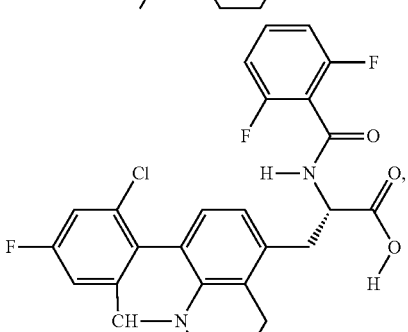
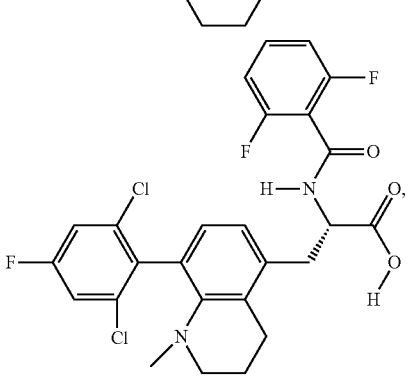
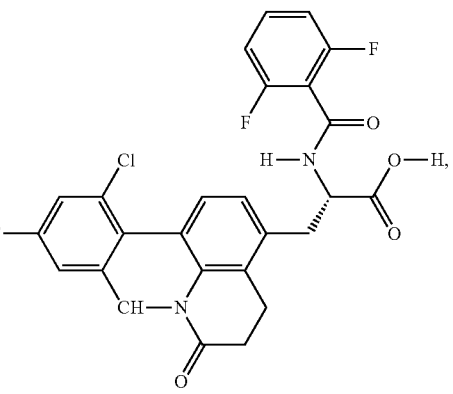

-continued
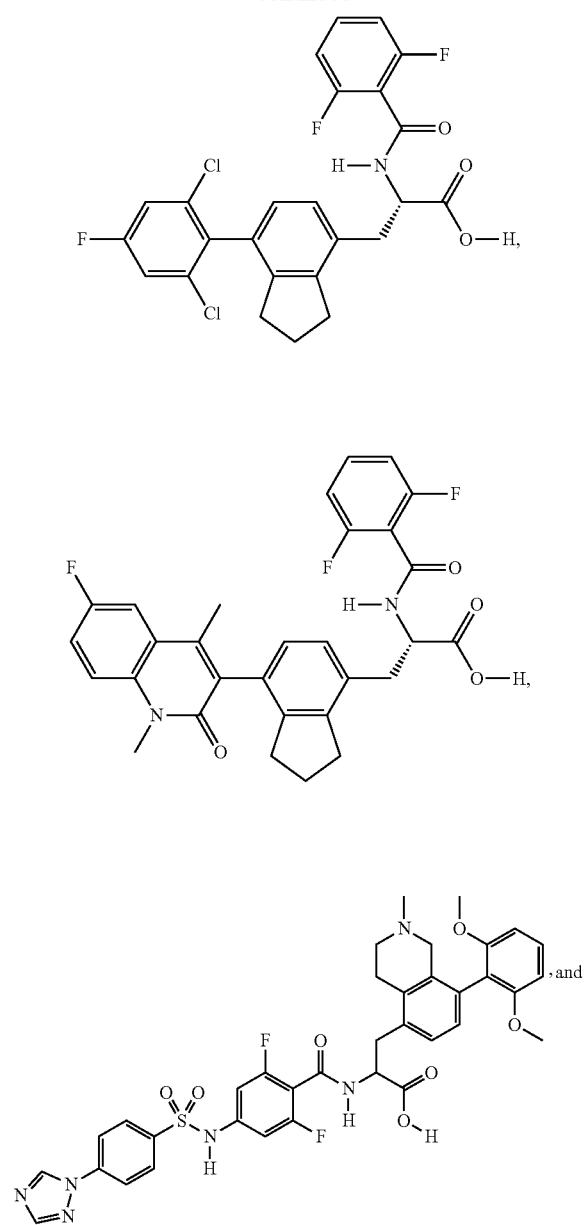
15. The compound of claim 1, or a pharmaceutically acceptable salt thereof, selected from:
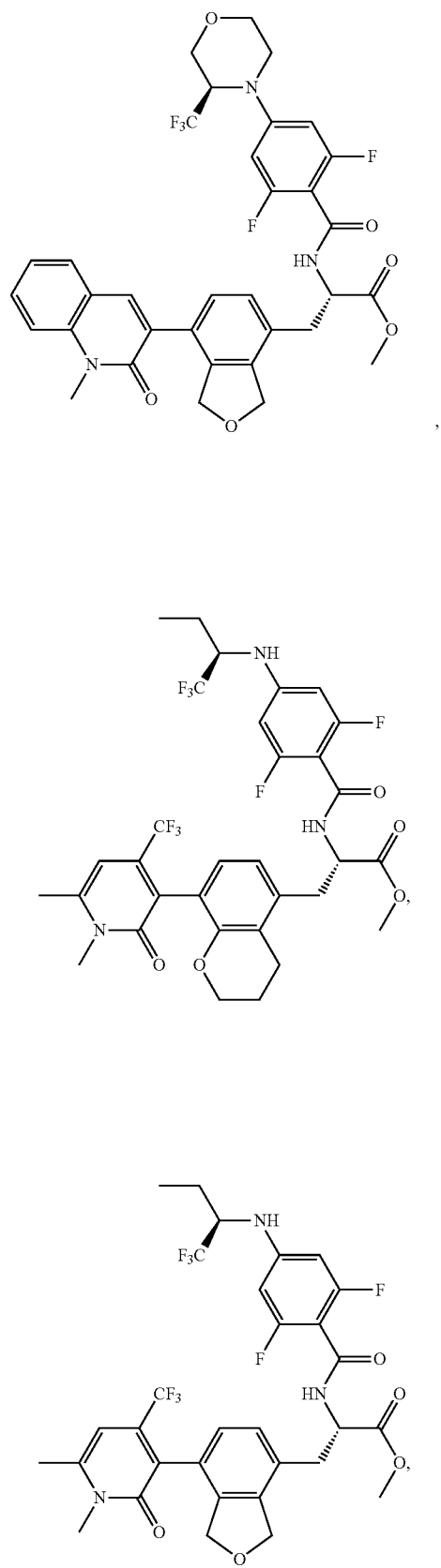

387
-continued
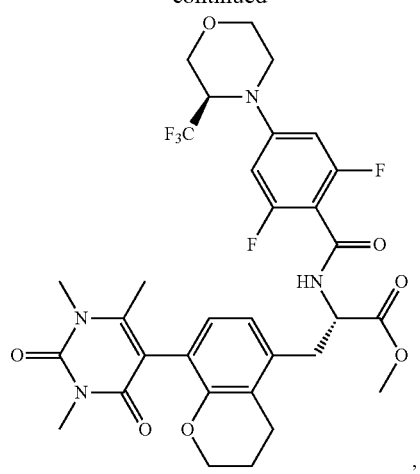
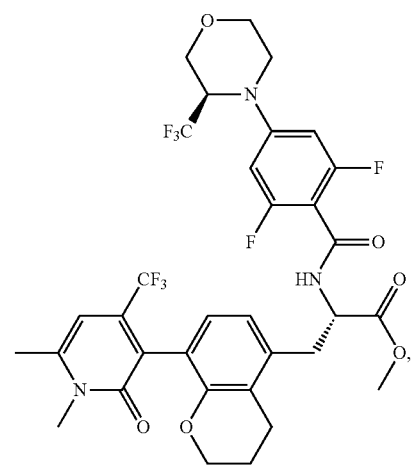
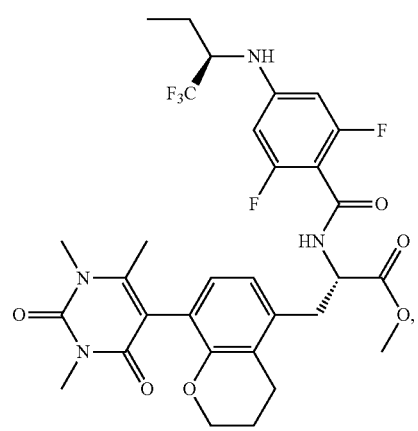
388
-continued
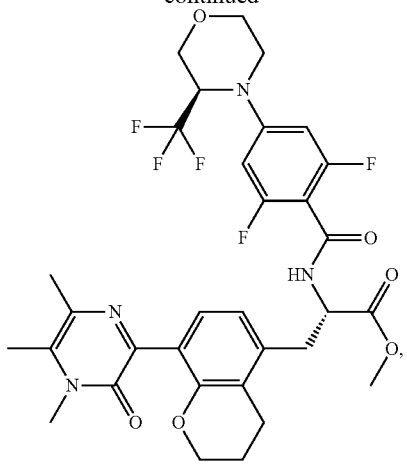
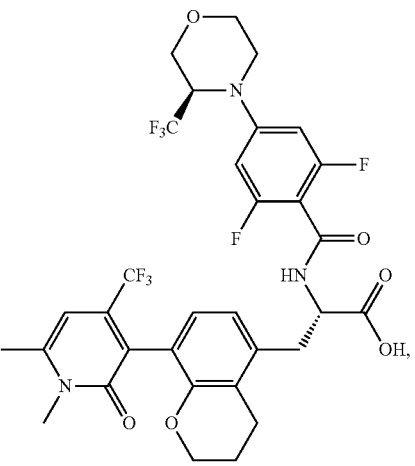
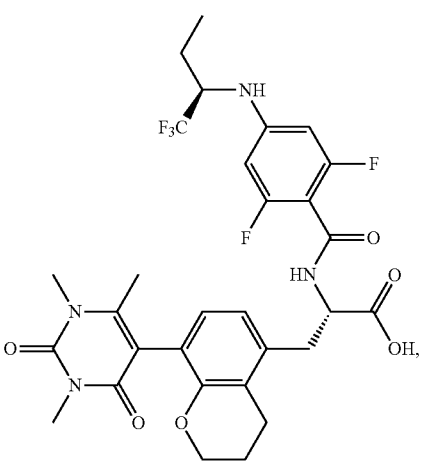

389
-continued
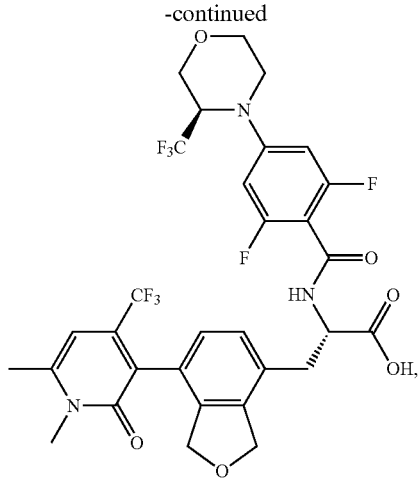
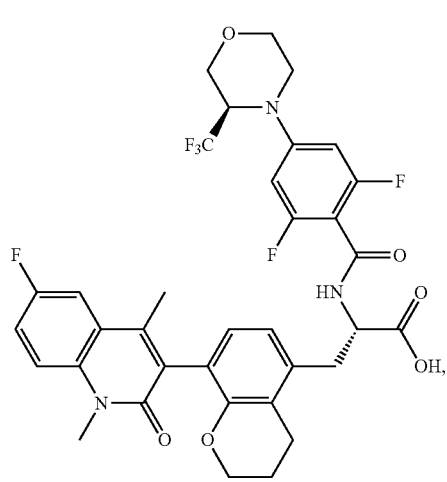
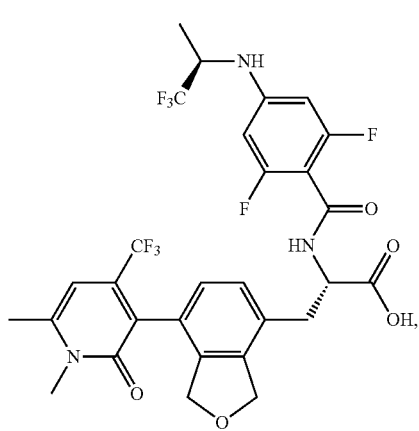
390
-continued
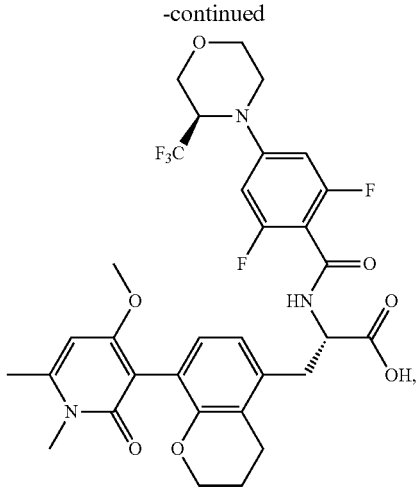
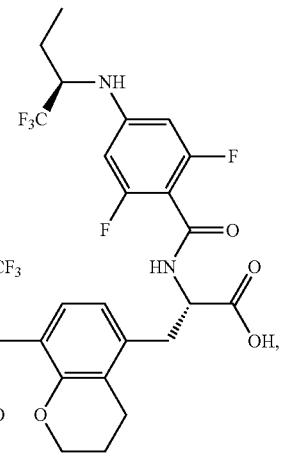
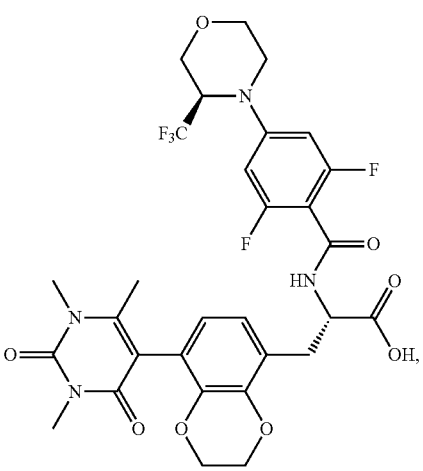

391
-continued
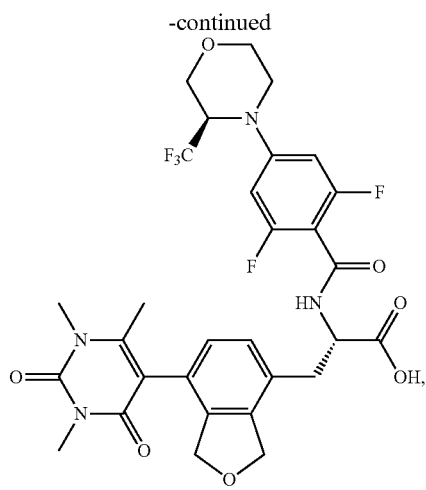
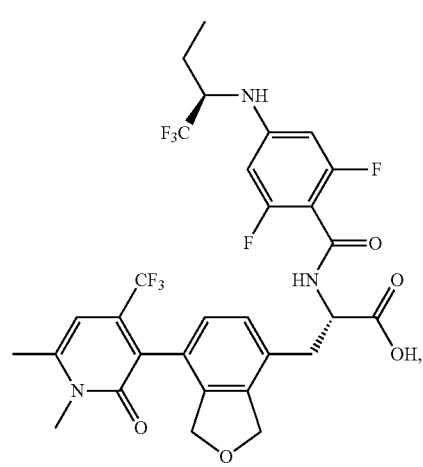
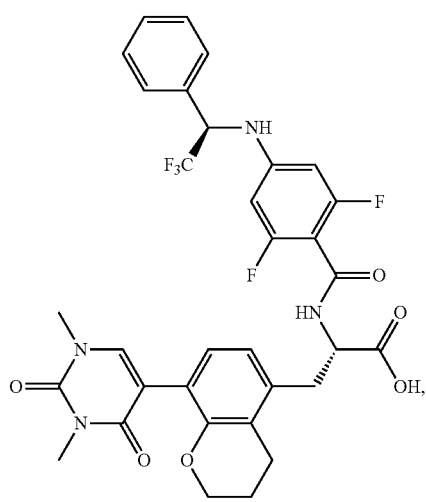
392
-continued
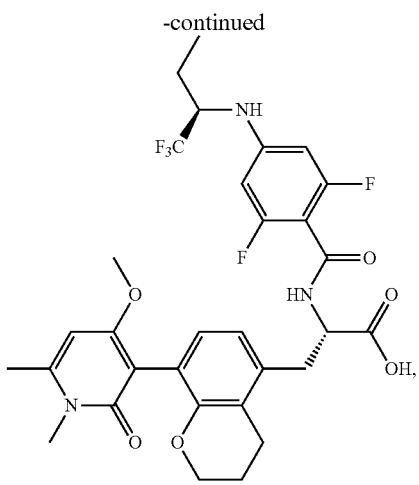
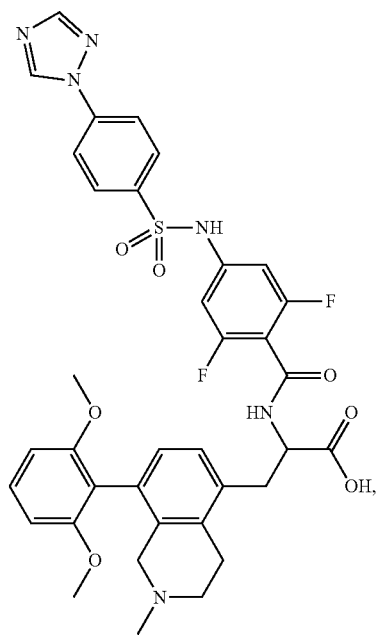
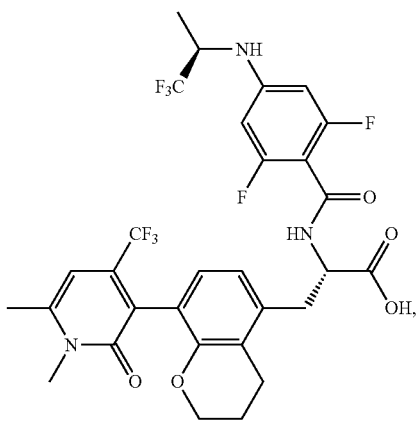

393
-continued
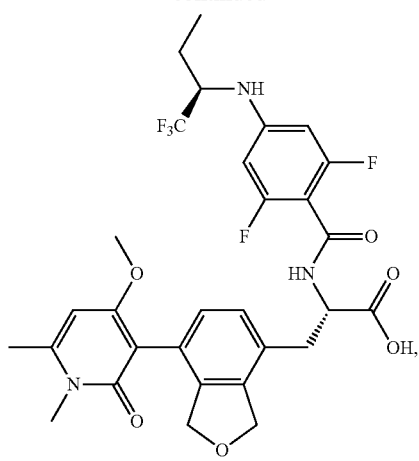
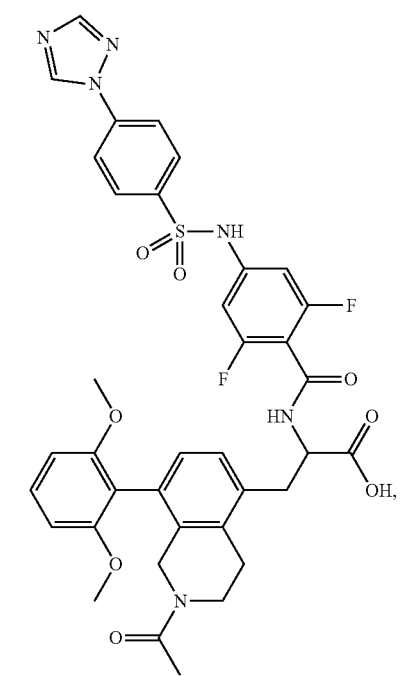
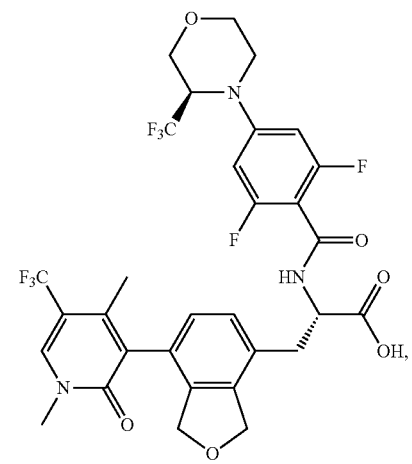
394
-continued
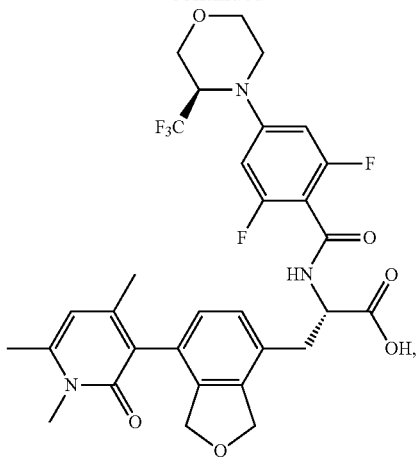
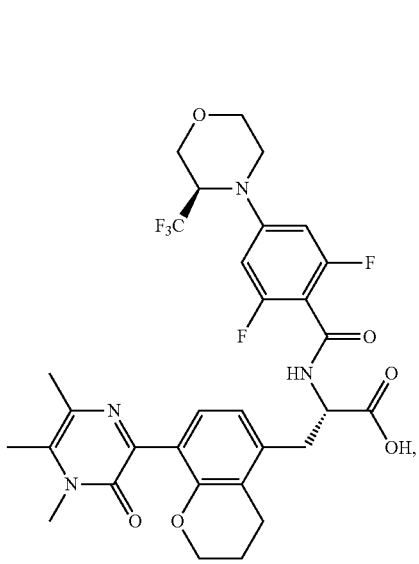
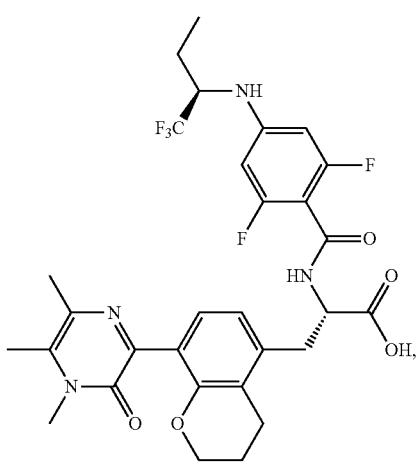

-continued
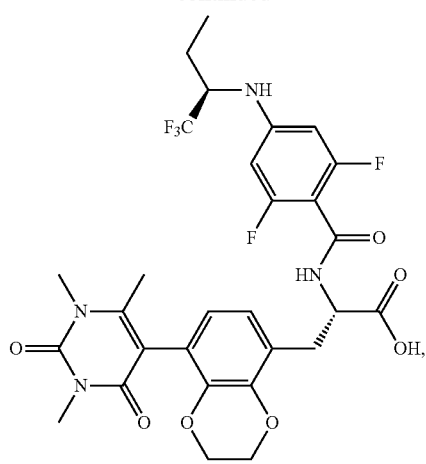
-continued
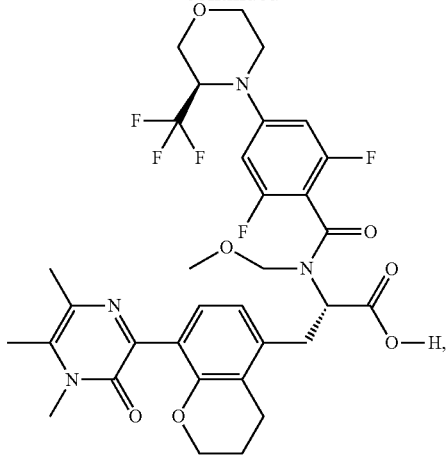
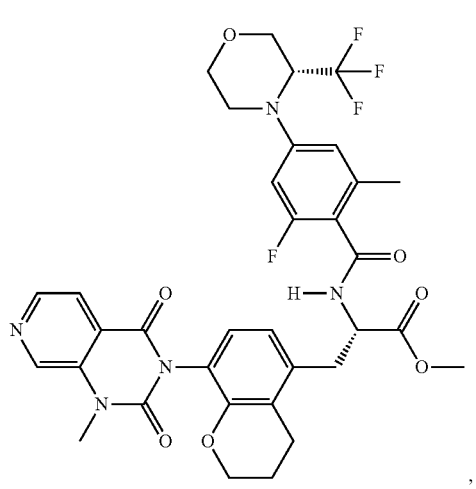
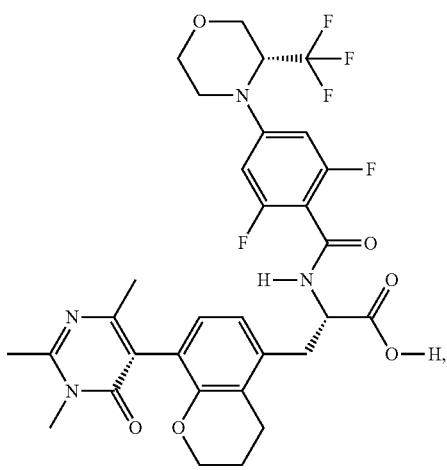
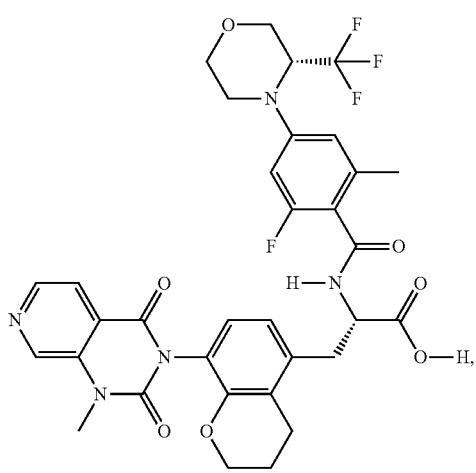
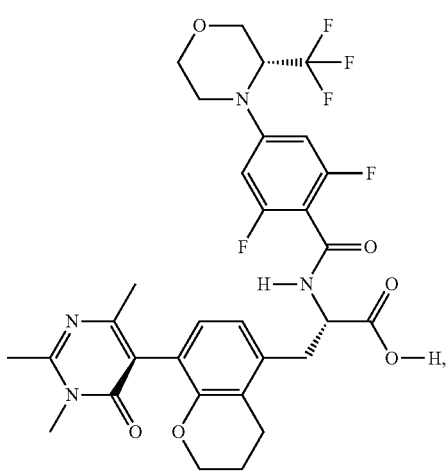

397
-continued
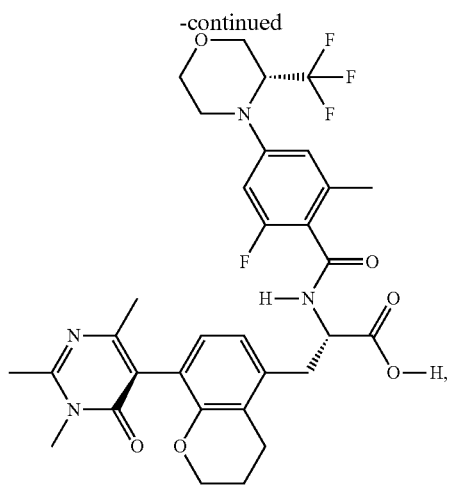
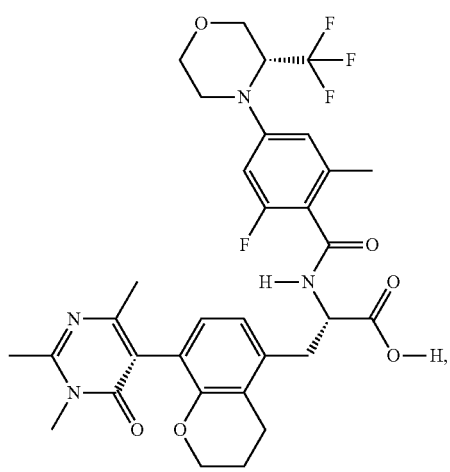
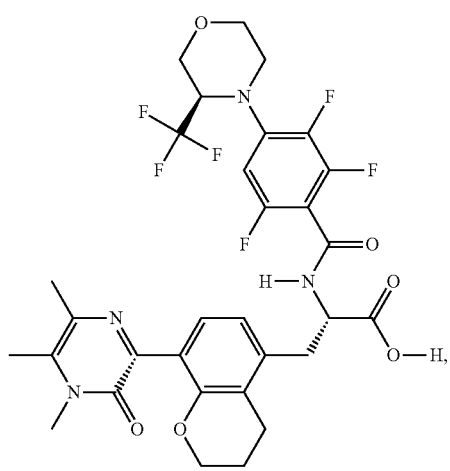
398
-continued
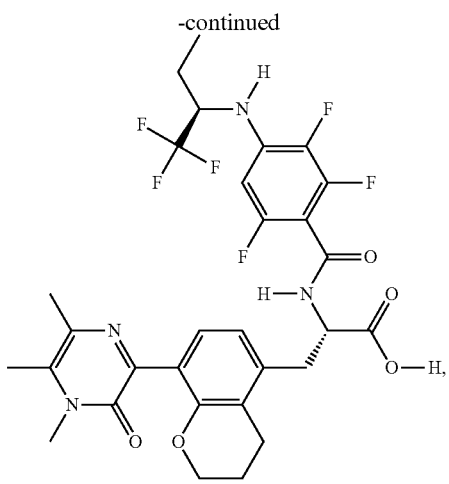
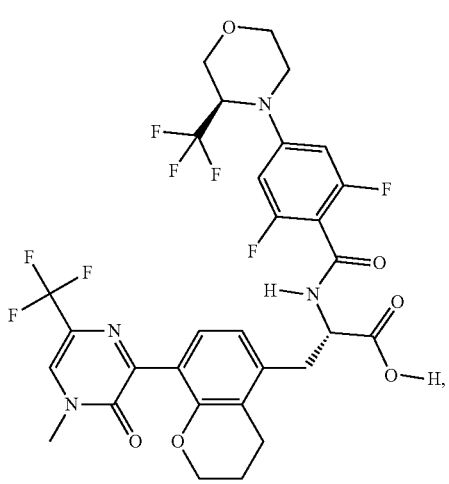
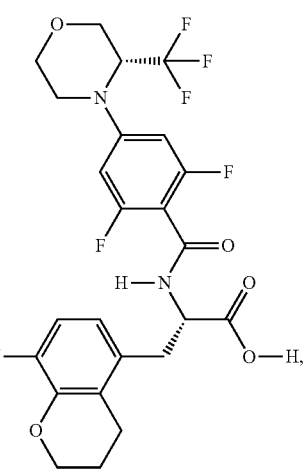

-continued
399
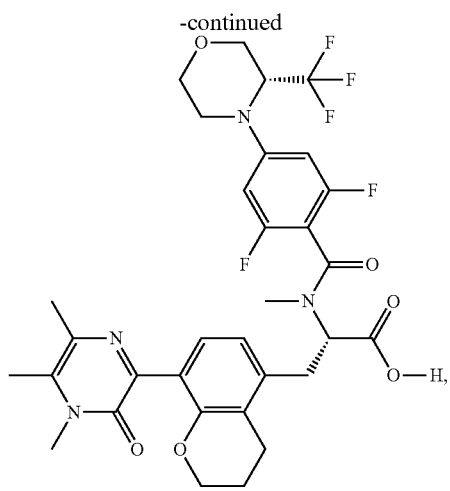
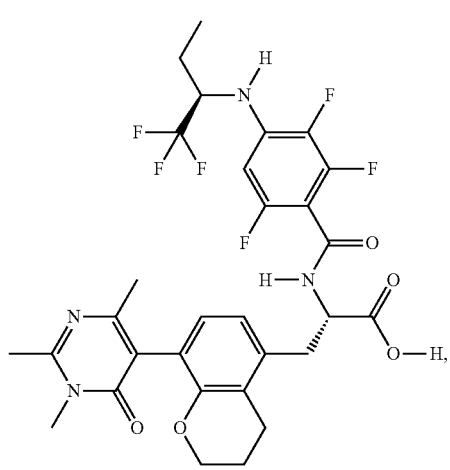
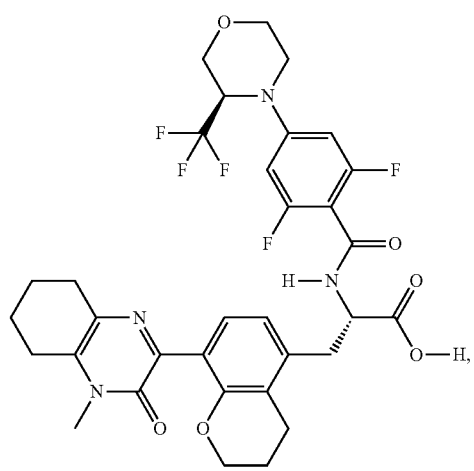
400
-continued
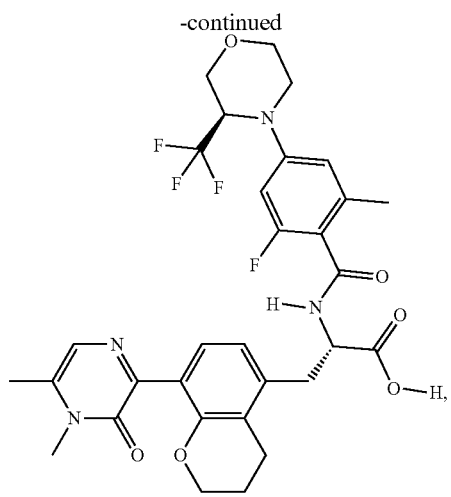
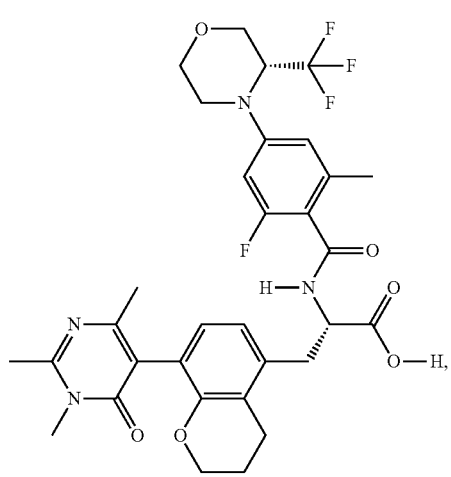
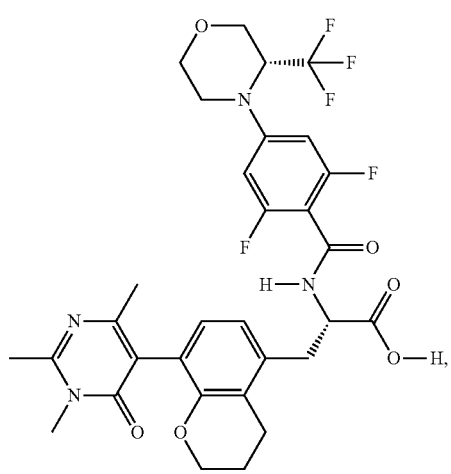

US 11,224,600 B2
401
-continued
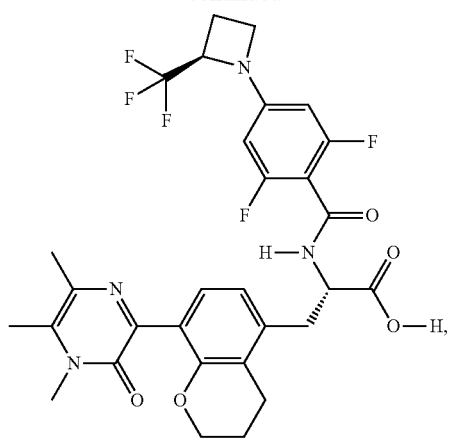
402
-continued
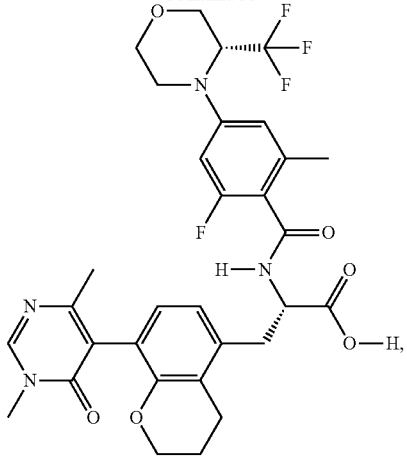
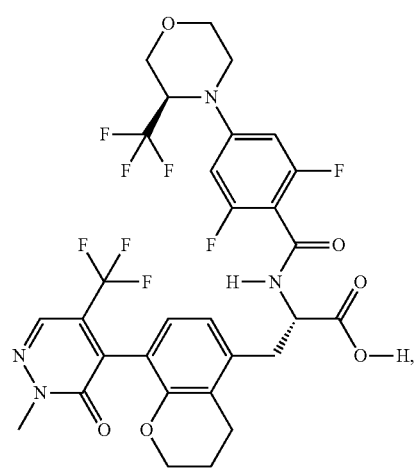
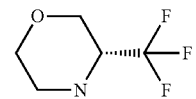
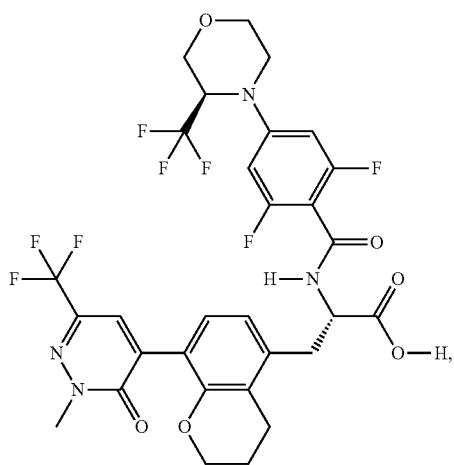
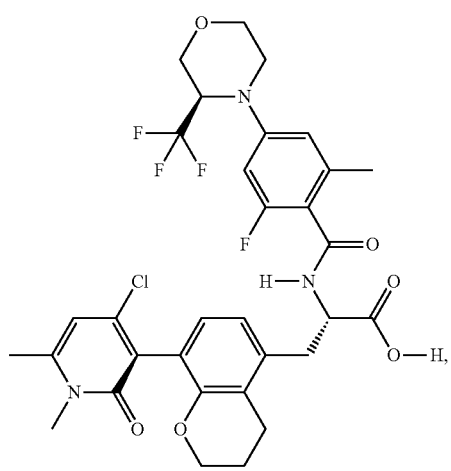

403
-continued
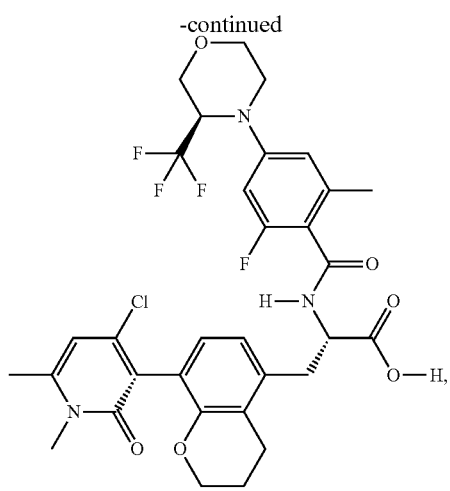
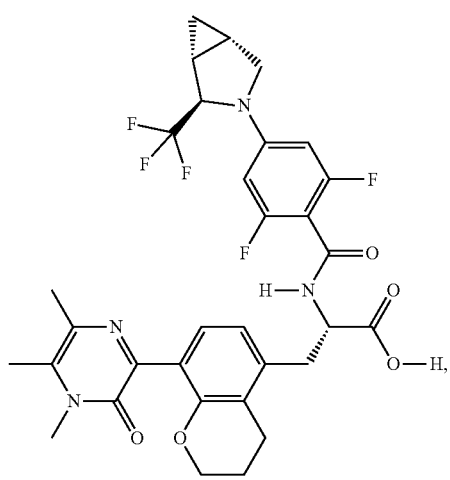
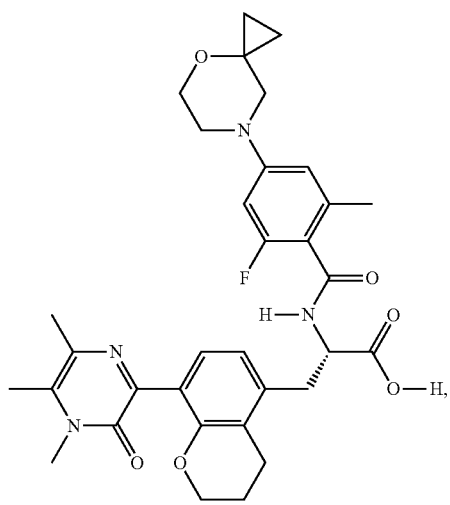
404
-continued
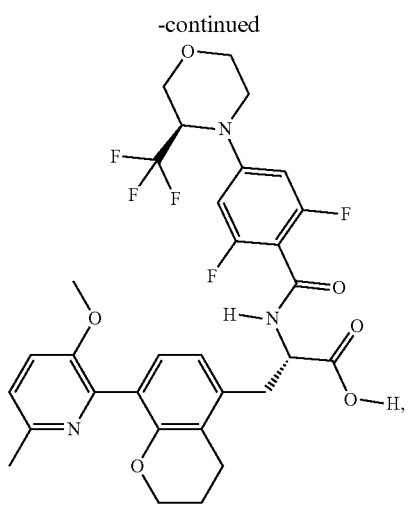
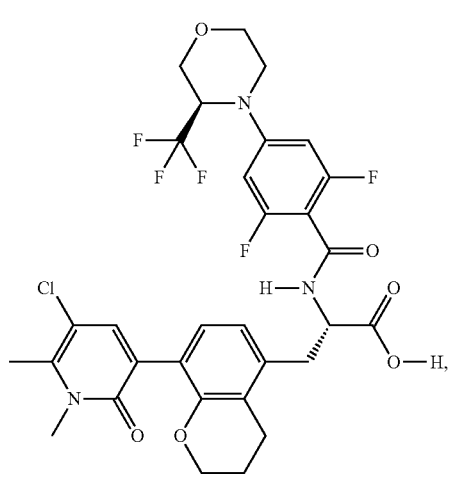
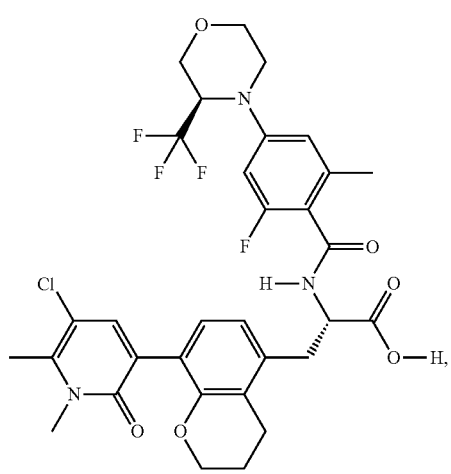

405
-continued
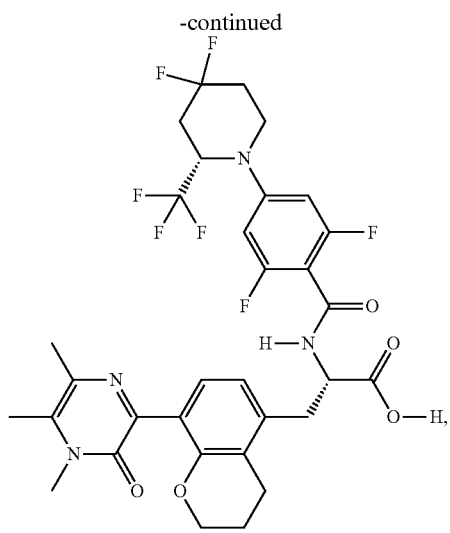
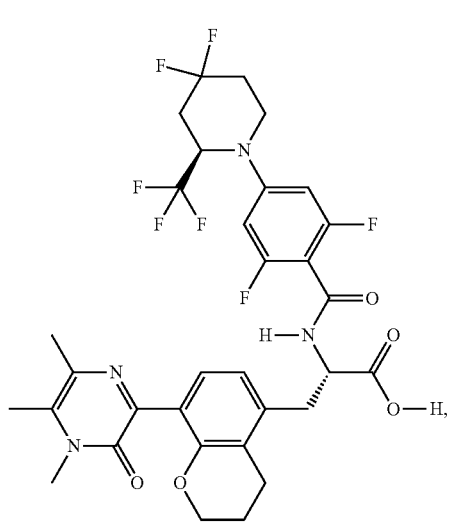
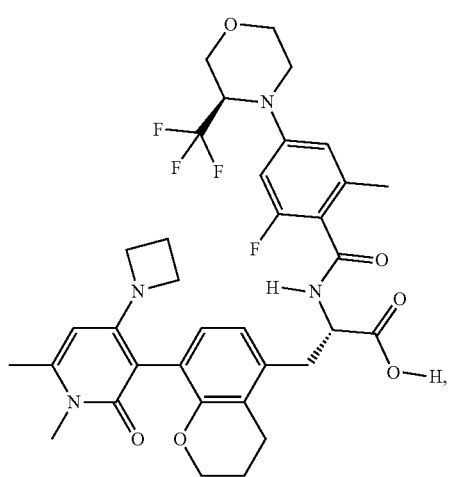
406
-continued
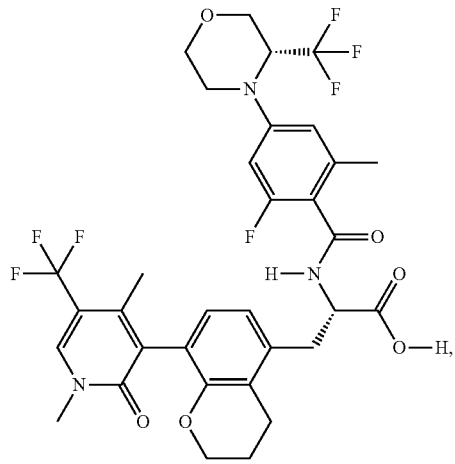
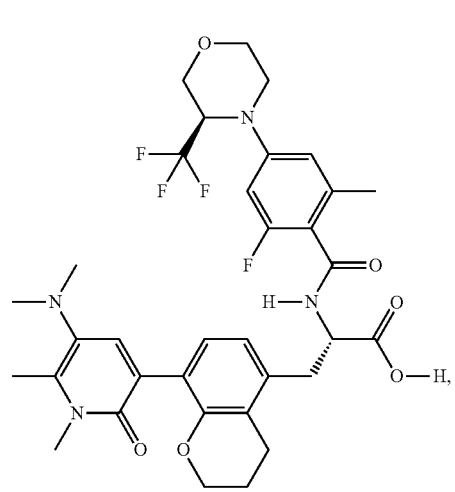
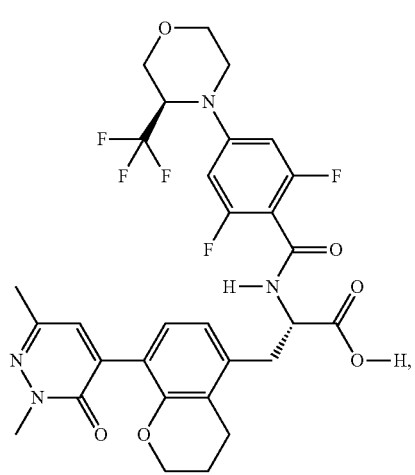

407
-continued
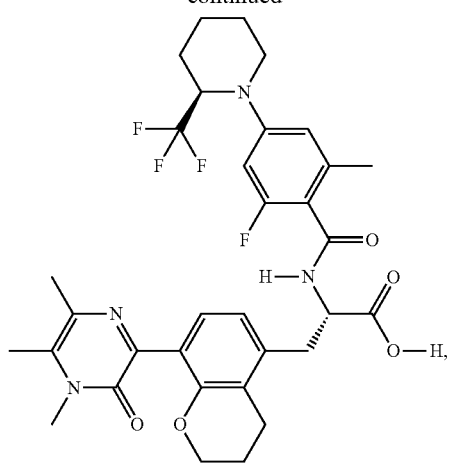
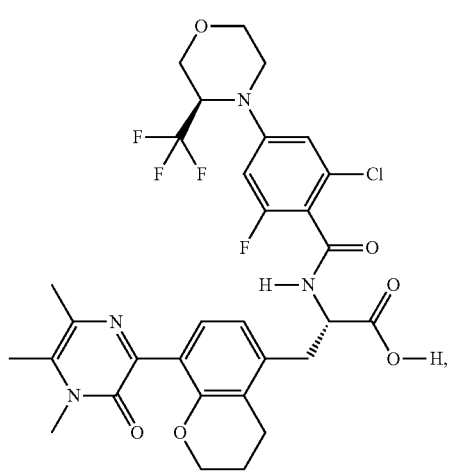
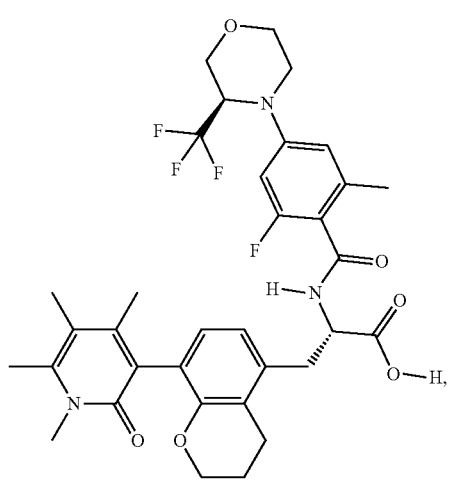
408
-continued
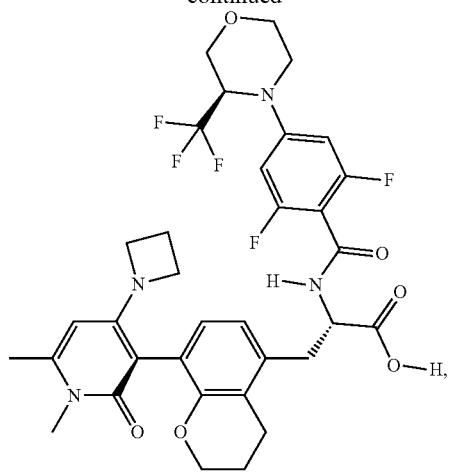
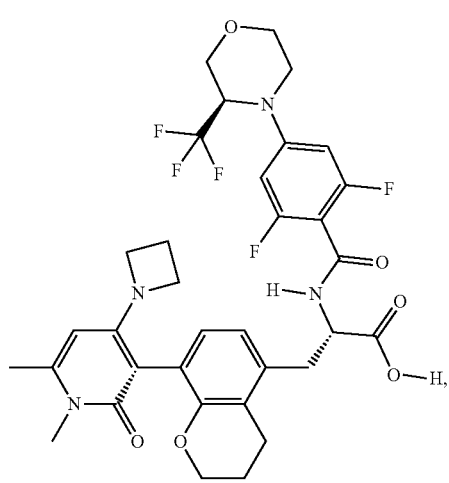
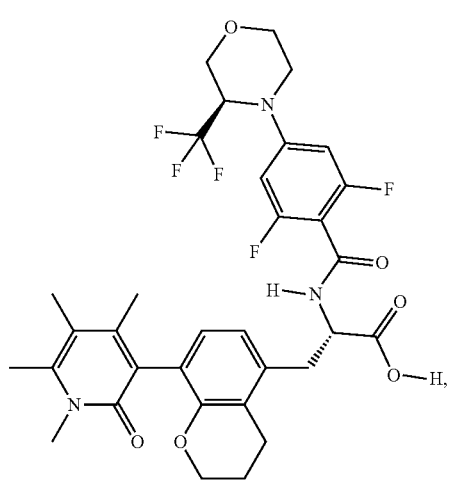

409
-continued
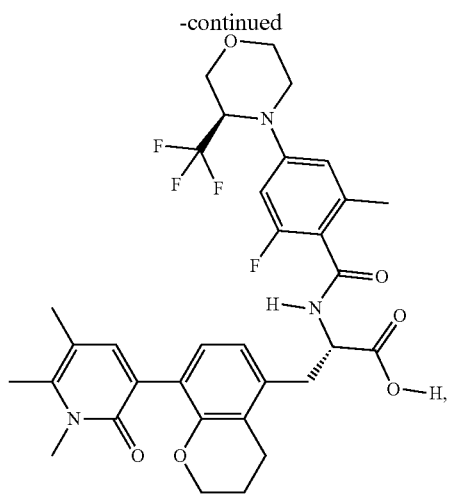
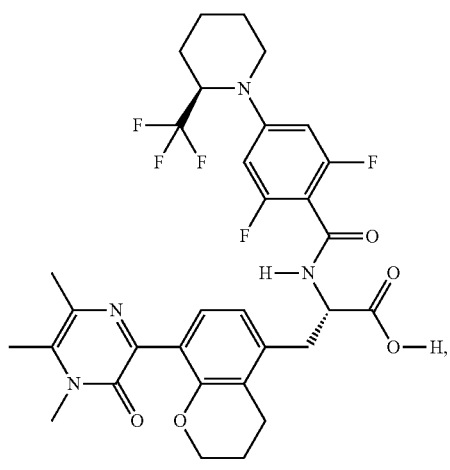
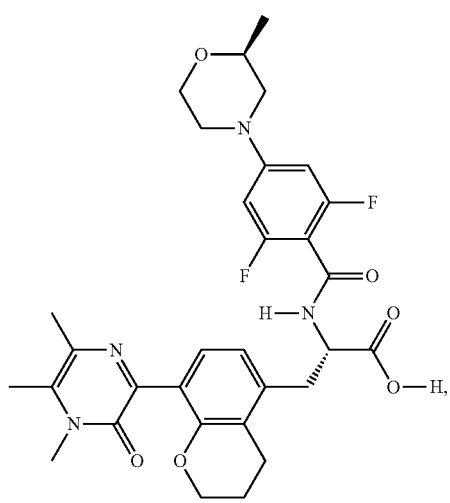
410
-continued
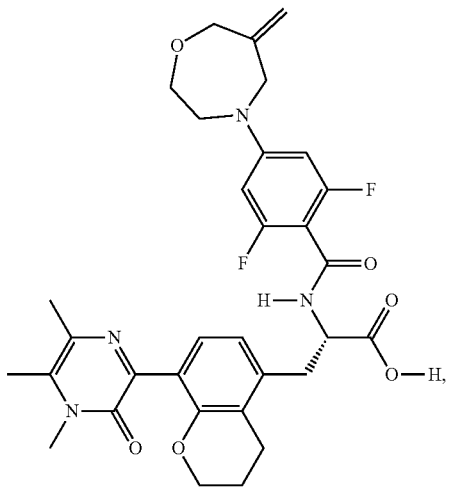
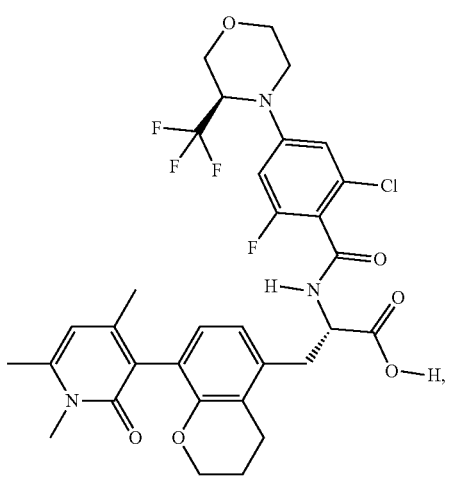
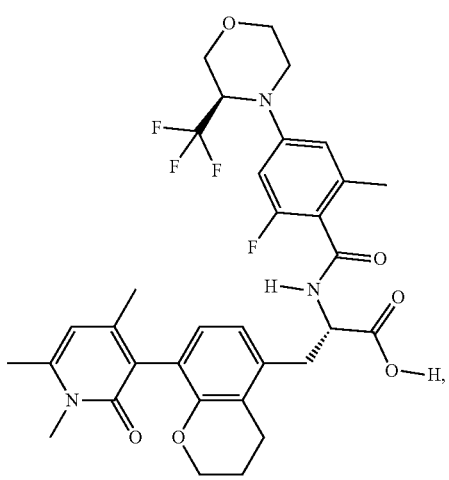

411
-continued
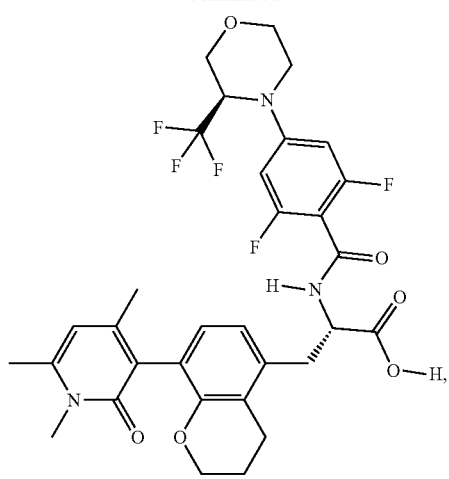
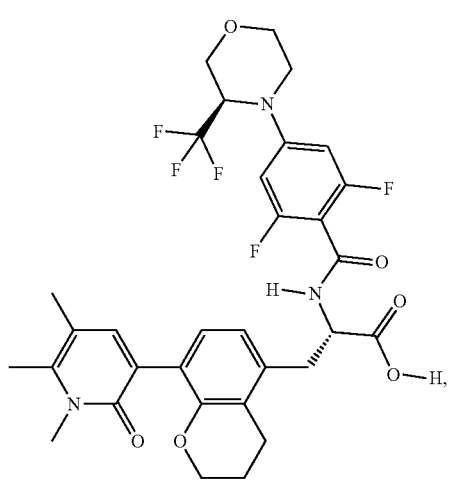
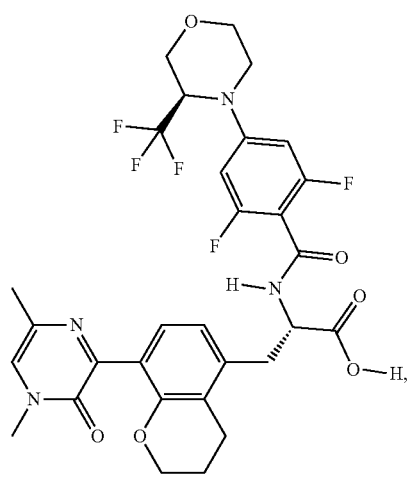
412
-continued
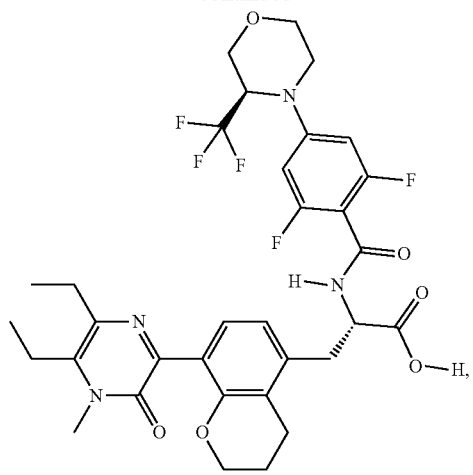
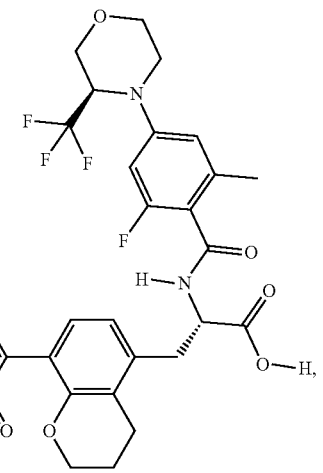
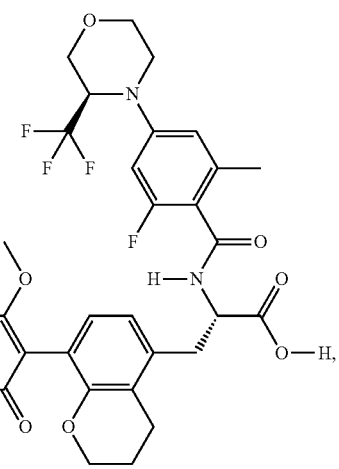

413
-continued
414
-continued
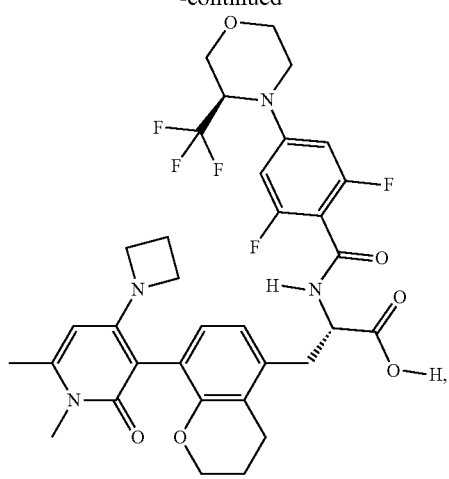
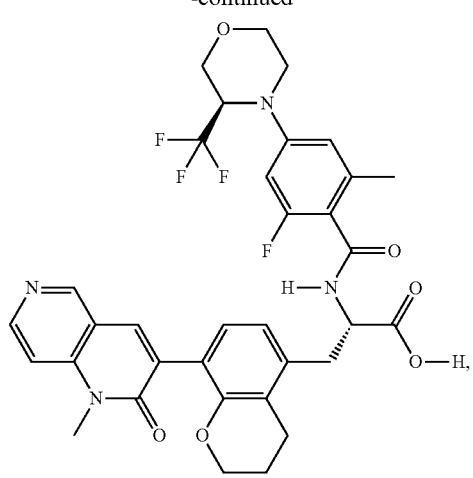
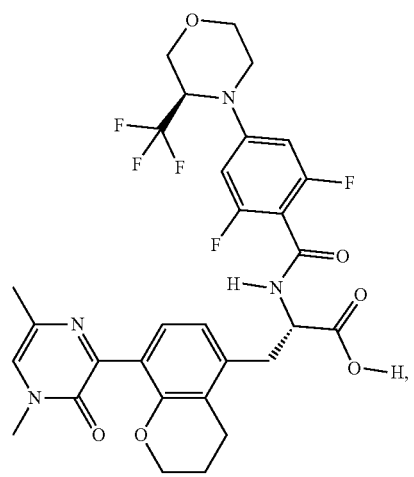
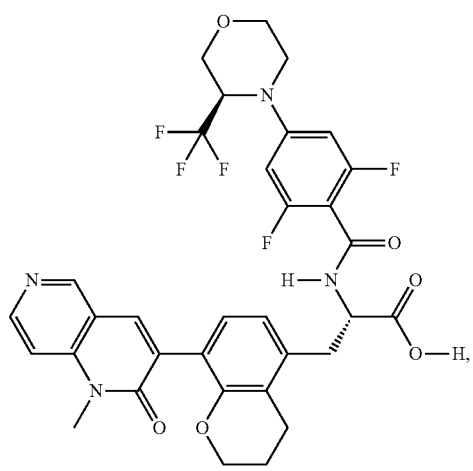
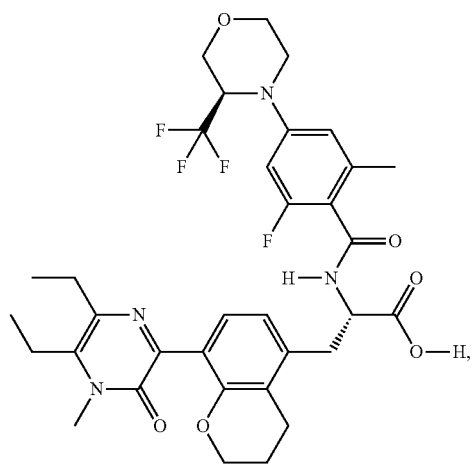
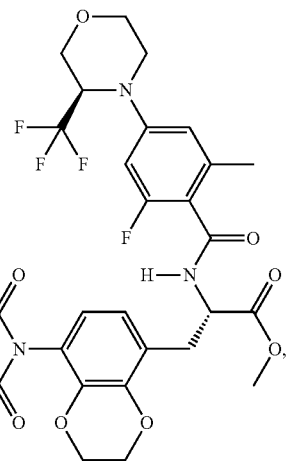

415
-continued
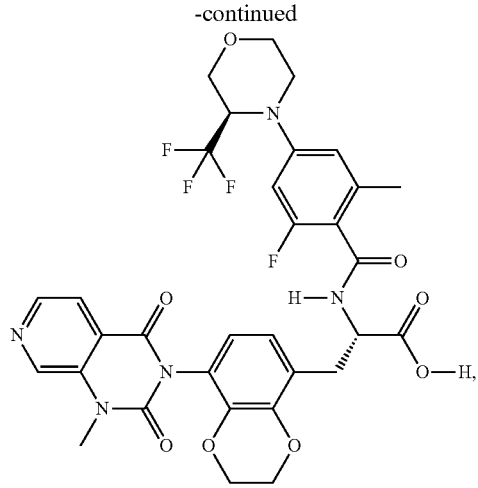
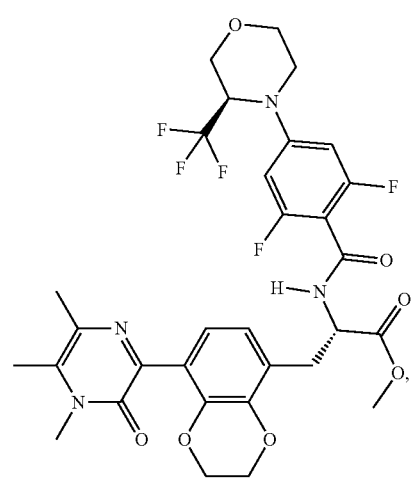
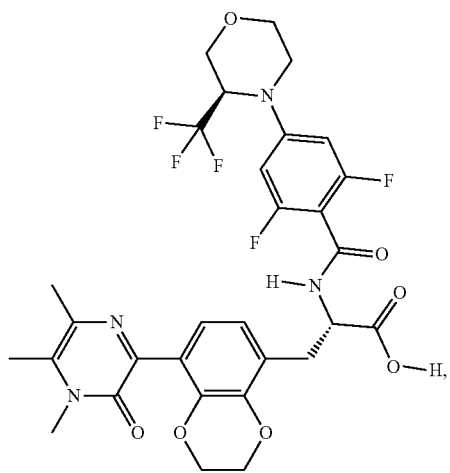
416
-continued
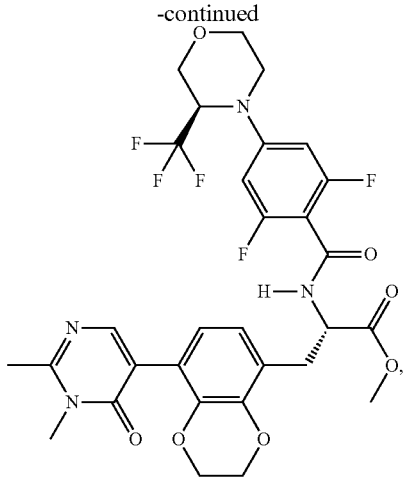
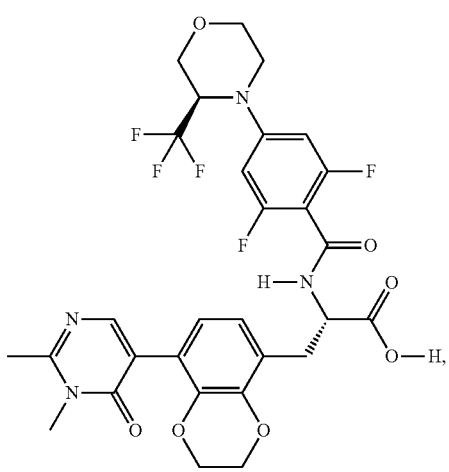
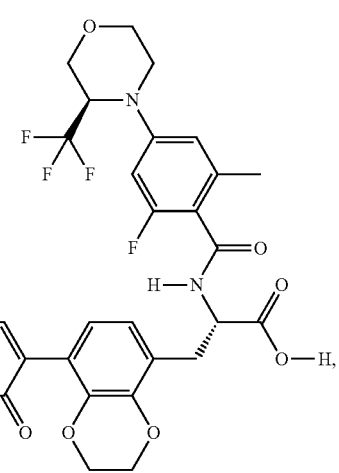

417
-continued
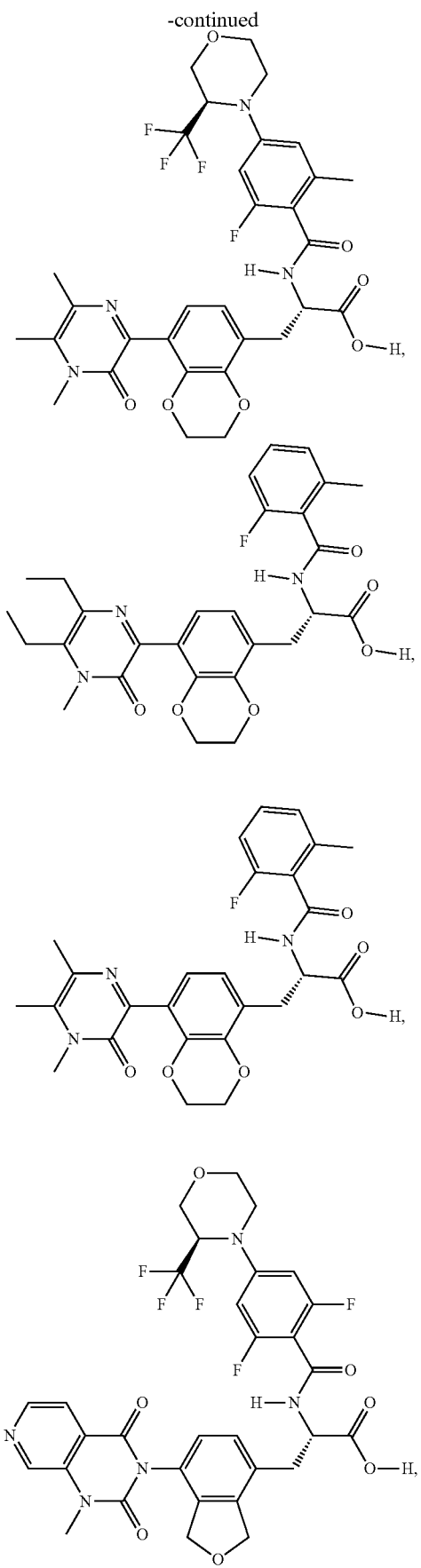
418
-continued
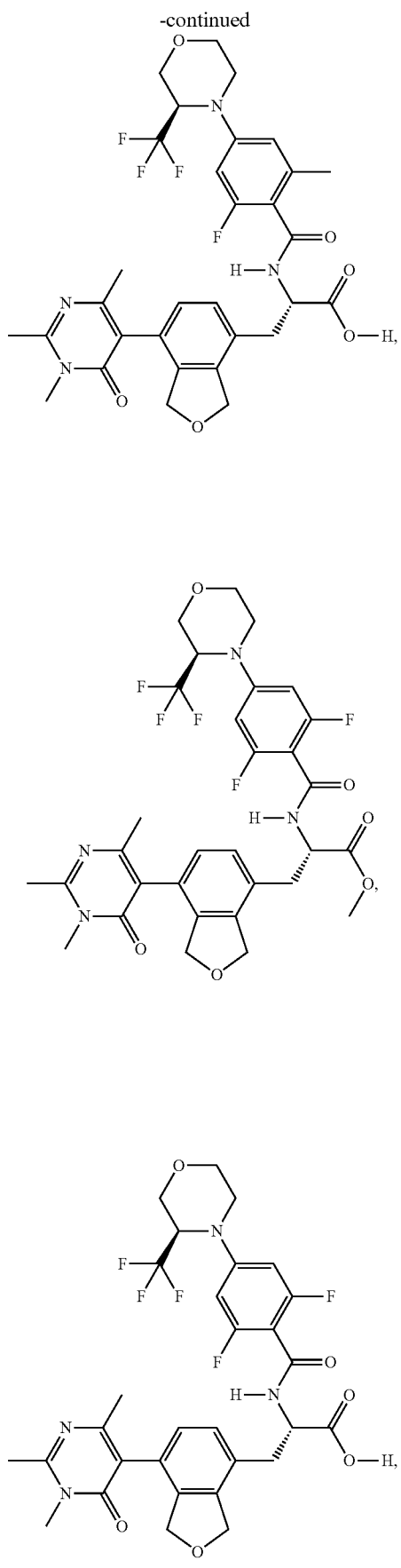

419
-continued
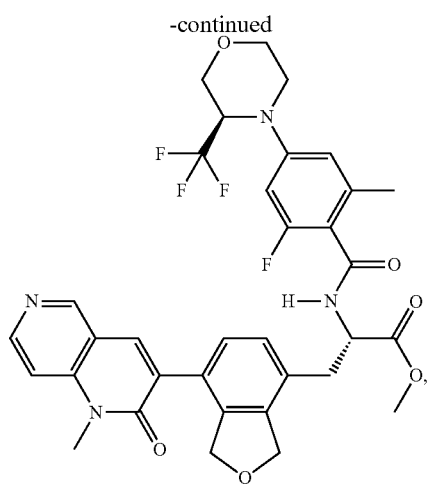
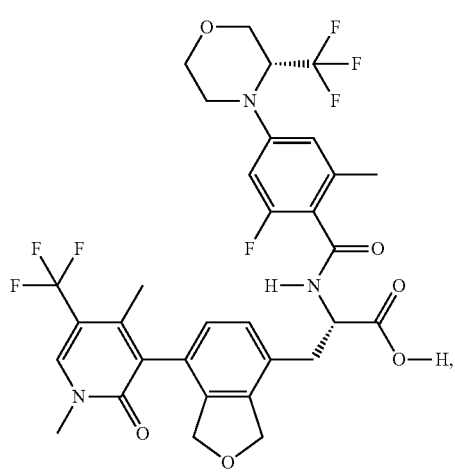
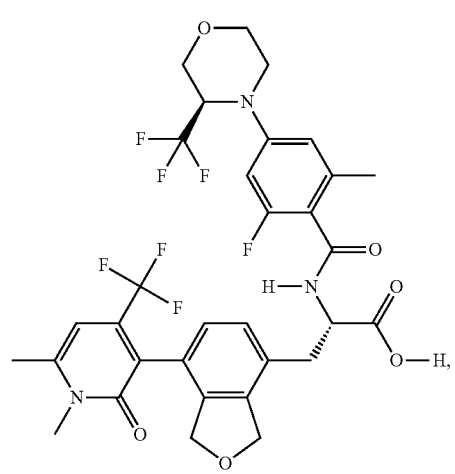
420
-continued
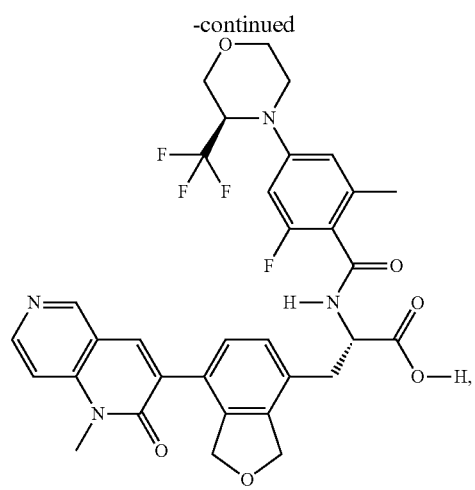
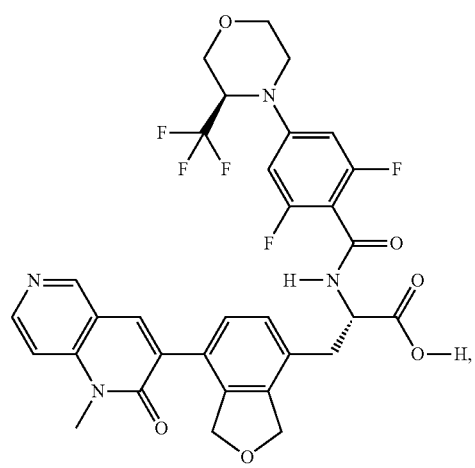
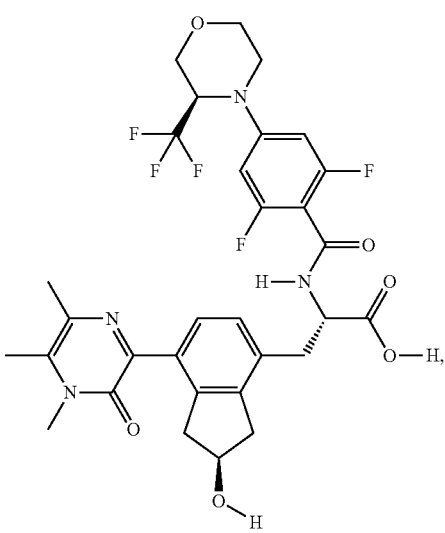

421
-continued
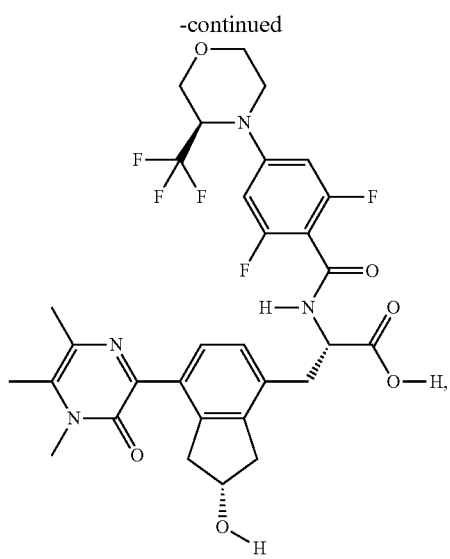
422
-continued
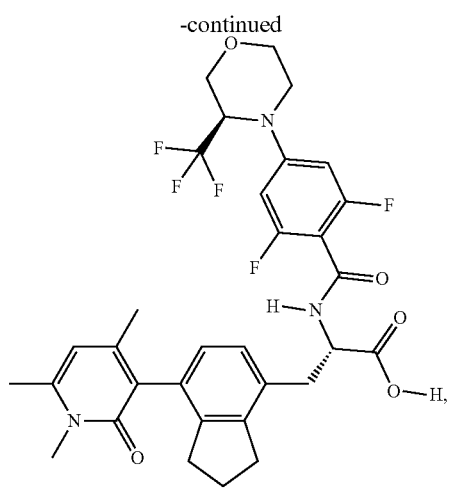
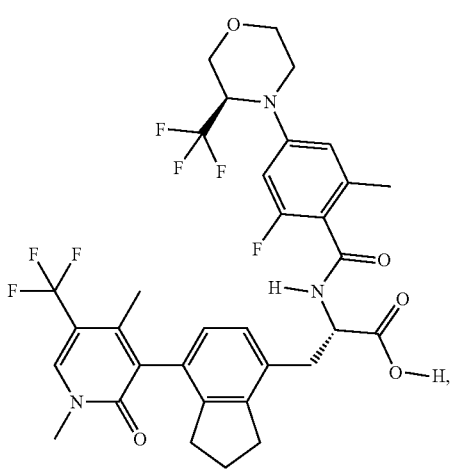
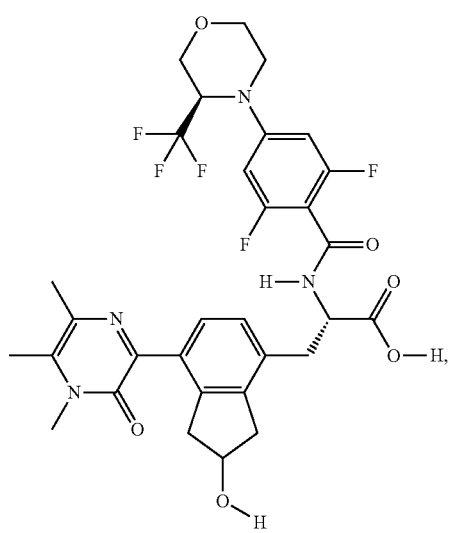

423
-continued
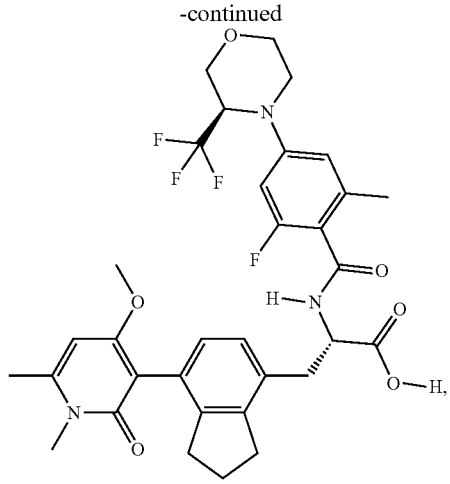
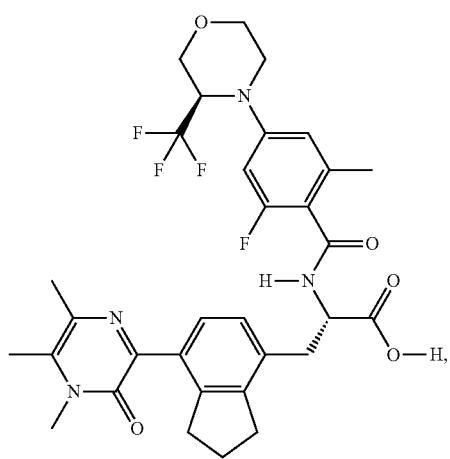
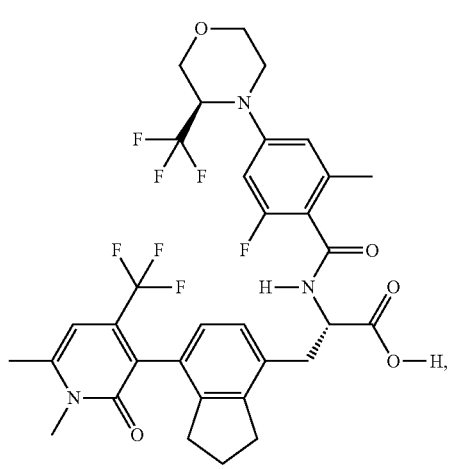
424
-continued
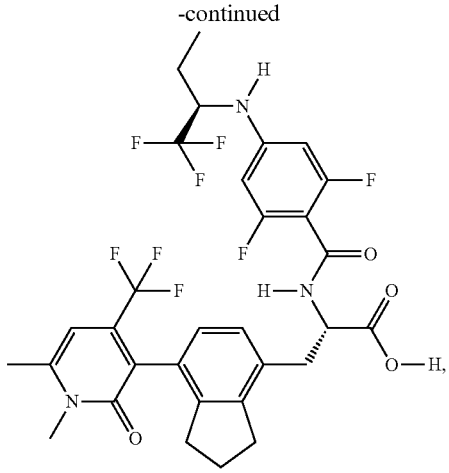
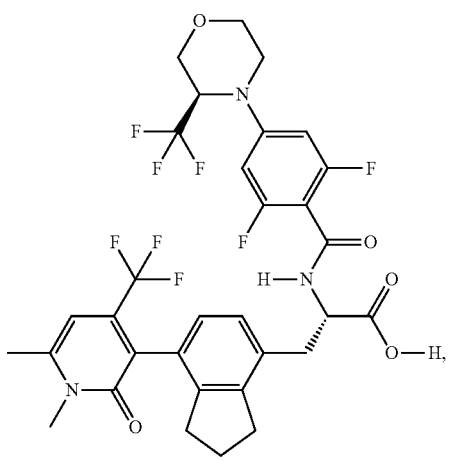
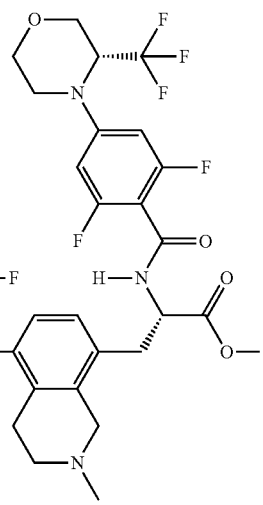

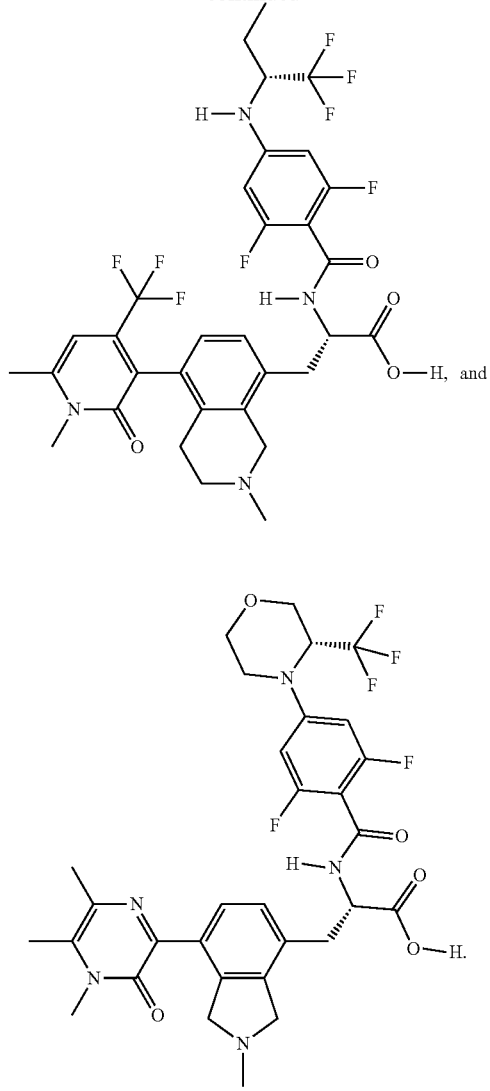

16. The compound of claim 1, or a pharmaceutically acceptable salt thereof, wherein the compound is selected from:

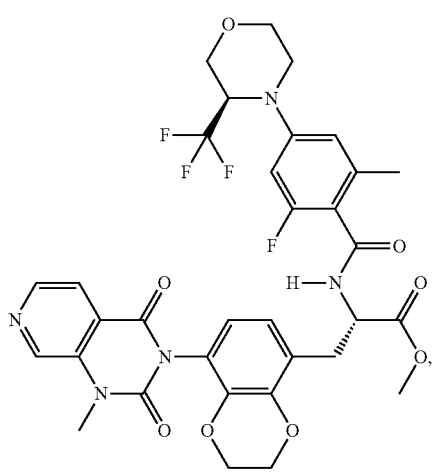

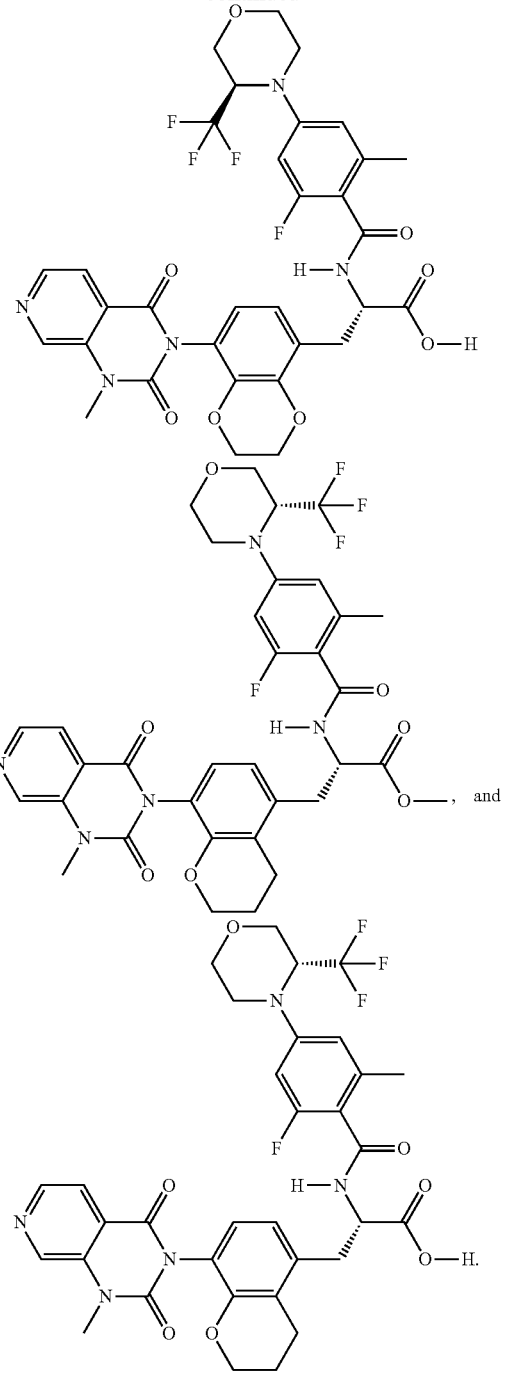

17. A pharmaceutical composition comprising a compound of claim 1, or a pharmaceutically acceptable salt thereof, and at least one pharmaceutically acceptable carrier.

18. The pharmaceutical composition of claim 17, further comprising at least one or more additional therapeutic agents.

19. A method for treating an inflammatory disease or condition mediated by α4β7 integrin comprising administrating to a subject an effective amount of the compound of claim 1, or a pharmaceutically acceptable salt thereof.

20. The pharmaceutical composition of claim 18, wherein the at least one or more additional therapeutic agents are independently selected from JAK tyrosine kinase inhibitors, Tumor Progression Locus 2 (TPL2) inhibitors, and IRAK4 inhibitors.

21. The pharmaceutical composition of claim 20, wherein the additional therapeutic agent is a JAK tyrosine kinase inhibitor, and wherein the JAK tyrosine kinase inhibitor is filgotinib.

* * * * *